(12) United States Patent
Holman et al.

(10) Patent No.: US 10,115,093 B2
(45) Date of Patent: Oct. 30, 2018

(54) FOOD PRINTING GOAL IMPLEMENTATION SUBSTRATE STRUCTURE INGESTIBLE MATERIAL PREPARATION SYSTEM AND METHOD

(71) Applicant: Elwha LLC, Bellevue, WA (US)

(72) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 649 days.

(21) Appl. No.: 14/753,907

(22) Filed: Jun. 29, 2015

(65) Prior Publication Data

US 2015/0296865 A1    Oct. 22, 2015

Related U.S. Application Data

(63) Continuation-in-part of application No. 13/317,979, filed on Oct. 31, 2011, now Pat. No. 9,111,256, and (Continued)

(51) Int. Cl.
  *A23P 1/08*    (2006.01)
  *G06Q 20/18*   (2012.01)
  (Continued)

(52) U.S. Cl.
  CPC .............. *G06Q 20/18* (2013.01); *A23P 20/00* (2016.08); *G06F 19/3475* (2013.01);
  (Continued)

(58) Field of Classification Search
  CPC ..................... G07F 17/0064; G06Q 30/0631; G06Q 20/18; G06Q 10/10; G06Q 50/12;
  (Continued)

(56) References Cited

U.S. PATENT DOCUMENTS 22,225 A * 12/1858 Berry .................... D05B 27/04
                                                        112/320
88,023 A *  3/1869 Estell ....................... B02C 1/02
                                                        241/262

(Continued)

FOREIGN PATENT DOCUMENTS

EP        1 469 431 B1    9/2009

OTHER PUBLICATIONS

McDonagh-Philp, Deana; "Using Focus Groups to Support New Product Development"; Institution of Engineering Designers Journal; Sep. 2000; pp. 1-6.

(Continued)

*Primary Examiner* — Eric Stapleton

(57) ABSTRACT

Prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus; and electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus. In addition to the foregoing, other method aspects are described in the claims, drawings, and text forming a part of the present disclosure.

76 Claims, 139 Drawing Sheets

Related U.S. Application Data a continuation-in-part of application No. 13/317,978, filed on Oct. 31, 2011, now Pat. No. 9,785,985, and a continuation-in-part of application No. 13/199,361, filed on Aug. 26, 2011, and a continuation-in-part of application No. 13/199,481, filed on Aug. 30, 2011, now Pat. No. 9,600,850, and a continuation-in-part of application No. 13/199,545, filed on Aug. 31, 2011, now Pat. No. 9,240,028, and a continuation-in-part of application No. 13/199,544, filed on Aug. 31, 2011, and a continuation-in-part of application No. 13/200,113, filed on Sep. 16, 2011, now Pat. No. 8,892,249, and a continuation-in-part of application No. 13/200,106, filed on Sep. 16, 2011, now Pat. No. 8,989,895, and a continuation-in-part of application No. 13/200,830, filed on Sep. 30, 2011, now abandoned, and a continuation-in-part of application No. 13/200,829, filed on Sep. 30, 2011, now abandoned, and a continuation-in-part of application No. 13/200,907, filed on Oct. 3, 2011, now Pat. No. 9,997,006, and a continuation-in-part of application No. 13/200,906, filed on Oct. 3, 2011, now Pat. No. 9,947,167, and a continuation-in-part of application No. 13/317,545, filed on Oct. 19, 2011, now abandoned, and a continuation-in-part of application No. 13/317,546, filed on Oct. 19, 2011, now Pat. No. 9,037,478, and a continuation-in-part of application No. 13/373,675, filed on Nov. 22, 2011, now Pat. No. 9,922,576, and a continuation-in-part of application No. 13/373,674, filed on Nov. 22, 2011, now abandoned, and a continuation-in-part of application No. 13/373,846, filed on Nov. 30, 2011, and a continuation-in-part of application No. 13/373,847, filed on Nov. 30, 2011, now abandoned, and a continuation-in-part of application No. 13/385,128, filed on Feb. 1, 2012, and a continuation-in-part of application No. 13/385,129, filed on Feb. 1, 2012, now abandoned, and a continuation-in-part of application No. 13/385,687, filed on Feb. 29, 2012, now abandoned, and a continuation-in-part of application No. 13/385,690, filed on Feb. 29, 2012, now abandoned, and a continuation-in-part of application No. 13/432,507, filed on Mar. 28, 2012, now abandoned, and a continuation-in-part of application No. 13/432,525, filed on Mar. 28, 2012, now abandoned, and a continuation-in-part of application No. 13/435,550, filed on Mar. 30, 2012, now abandoned, and a continuation-in-part of application No. 13/435,591, filed on Mar. 30, 2012, now abandoned, and a continuation-in-part of application No. 14/745,313, filed on Jun. 19, 2015, and a continuation-in-part of application No. 14/748,220, filed on Jun. 23, 2015, and a continuation-in-part of application No. 14/750,950, filed on Jun. 25, 2015.

(51) Int. Cl.

| | | |
|---|---|---|
| *G06Q 50/12* | (2012.01) | |
| *H04L 29/08* | (2006.01) | |
| *G06Q 10/10* | (2012.01) | |
| *G07F 17/00* | (2006.01) | |
| *G06Q 30/06* | (2012.01) | |
| *G06F 19/00* | (2018.01) | |
| *A23P 20/00* | (2016.01) | |

(52) U.S. Cl.
CPC ......... *G06Q 10/10* (2013.01); *G06Q 30/0631* (2013.01); *G07F 17/0064* (2013.01); *H04L 67/22* (2013.01); *H04L 67/306* (2013.01); *G06Q 50/12* (2013.01)

(58) Field of Classification Search
CPC ...... G06F 19/3475; A23P 20/00; H04L 67/22; H04L 67/306; B08B 1/003; B08B 1/002; B08B 3/00; B08B 3/08; B08B 3/12
USPC .......................... 99/485; 134/18, 57 R, 58 R
See application file for complete search history.

(56) References Cited

U.S. PATENT DOCUMENTS

| | | | | |
|---|---|---|---|---|
| 116,634 | A * | 7/1871 | Schwerin | A45C 13/26 |
| | | | | 16/410 |
| 260,918 | A * | 7/1882 | Yule et al. | A42C 1/02 |
| | | | | 19/148 |
| 249,129 | A | 2/1884 | Heffernan | |
| 294,129 | A * | 2/1884 | Heffernan | A43D 95/00 |
| | | | | 12/78 |
| 303,972 | A * | 8/1884 | Barton et al. | A63H 7/04 |
| | | | | 446/272 |
| 3,040,935 | A * | 6/1962 | Lopata | A21C 11/16 |
| | | | | 200/33 B |
| 3,702,583 | A * | 11/1972 | Rullman | A47J 37/04 |
| | | | | 221/69 |
| 4,127,232 | A * | 11/1978 | Gagliardo | G06K 7/14 |
| | | | | 235/419 |
| 4,452,132 | A * | 6/1984 | Miller | A47J 27/04 |
| | | | | 126/369 |
| 4,666,204 | A | 5/1987 | Reinholtz | |
| 4,723,614 | A * | 2/1988 | Lahti | G01G 7/06 |
| | | | | 177/120 |
| 4,796,182 | A * | 1/1989 | Duboff | G06F 19/3475 |
| | | | | 600/300 |
| 4,797,818 | A * | 1/1989 | Cotter | G06Q 10/087 |
| | | | | 379/912 |
| 4,974,747 | A * | 12/1990 | Ahlstrom | G07F 9/105 |
| | | | | 221/87 |
| 5,121,677 | A * | 6/1992 | Le Claire | A21C 9/04 |
| | | | | 118/18 |
| 5,132,914 | A * | 7/1992 | Cahlander | A47J 27/14 |
| | | | | 700/112 |
| 5,197,376 | A * | 3/1993 | Bird | A21B 5/00 |
| | | | | 99/330 |
| 5,228,382 | A * | 7/1993 | Hayashi | A47J 27/18 |
| | | | | 99/328 |
| 5,408,443 | A | 4/1995 | Weinberger | |
| 5,522,309 | A * | 6/1996 | Mizobuchi | A47J 27/14 |
| | | | | 700/239 |
| 5,522,310 | A * | 6/1996 | Black, Sr. | A47J 27/14 |
| | | | | 221/113 |
| 5,598,947 | A | 2/1997 | Smith | |
| 5,615,778 | A | 4/1997 | Kaiser et al. | |
| 5,736,940 | A * | 4/1998 | Burgener | G08G 1/123 |
| | | | | 340/991 |
| 6,032,574 | A * | 3/2000 | Brayton | E04H 5/02 |
| | | | | 99/486 |
| 6,112,182 | A | 8/2000 | Akers et al. | |
| 6,105,818 | A | 9/2000 | Speranza | |
| 6,137,686 | A * | 10/2000 | Saye | G06F 1/1626 |
| | | | | 361/679.43 |
| 6,202,923 | B1 | 3/2001 | Boyer et al. | |
| 6,280,784 | B1 * | 8/2001 | Yang | A21C 11/163 |
| | | | | 425/112 |
| 6,280,785 | B1 * | 8/2001 | Yang | A21C 11/163 |
| | | | | 425/112 |
| 6,317,686 | B1 * | 11/2001 | Ran | G01C 21/3691 |
| | | | | 701/117 |
| 6,359,239 | B1 * | 3/2002 | Missler | A47J 47/005 |
| | | | | 177/177 |

(56) References Cited

U.S. PATENT DOCUMENTS

| | | | |
|---|---|---|---|
| 6,415,555 B1 | 7/2002 | Montague | |
| 6,490,870 B1* | 12/2002 | Efremkine | B67D 1/0869 62/3.64 |
| 6,618,062 B1 | 9/2003 | Brown et al. | |
| 6,646,659 B1* | 11/2003 | Brown | G06Q 30/02 705/15 |
| 6,658,990 B1 | 12/2003 | Henning | A23B 4/28 99/352 |
| 6,660,317 B1* | 12/2003 | Akutagawa | A23G 1/205 425/130 |
| 6,660,982 B2* | 12/2003 | Thorneywork | H05B 6/6435 219/490 |
| 6,841,185 B2 | 1/2005 | Sargent et al. | |
| 6,843,166 B1* | 1/2005 | Li | A47J 27/14 99/327 |
| 6,859,215 B1 | 2/2005 | Brown et al. | |
| 6,865,261 B1 | 3/2005 | Rao et al. | |
| 7,027,996 B2* | 4/2006 | Levinson | G06Q 10/06311 705/7.26 |
| 7,110,964 B2 | 9/2006 | Tengler et al. | |
| 7,183,518 B2* | 2/2007 | Near | A47J 27/62 219/214 |
| 7,188,082 B2 | 3/2007 | Keane et al. | |
| 7,200,644 B1 | 4/2007 | Flanagan | |
| 7,231,917 B2 | 6/2007 | Frederiksen | |
| 7,286,258 B2* | 10/2007 | Schnoebelen | B44C 5/00 106/31.13 |
| 7,343,174 B2 | 3/2008 | Suryanarayana et al. | |
| 7,392,193 B2 | 6/2008 | Mault | |
| 7,415,375 B2 | 8/2008 | Shakman et al. | |
| 7,571,586 B1 | 8/2009 | Morales | |
| 7,680,690 B1* | 3/2010 | Catalano | G06Q 30/02 186/38 |
| 7,762,181 B2* | 7/2010 | Boland | A47J 31/40 99/321 |
| 7,858,136 B2 | 12/2010 | Park et al. | |
| 7,974,873 B2* | 7/2011 | Simmons | G06Q 10/06313 455/12.1 |
| 8,190,447 B2 | 5/2012 | Hungerford et al. | |
| 8,204,757 B2 | 6/2012 | Carlson et al. | |
| 8,321,364 B1 | 11/2012 | Gharpure et al. | |
| 8,594,838 B2 | 11/2013 | Selker et al. | |
| 8,688,277 B2* | 4/2014 | Studor | A47J 31/44 422/62 |
| 8,744,618 B2* | 6/2014 | Peters | B67D 1/0041 700/236 |
| 8,793,588 B2* | 7/2014 | DiPietro | G06F 3/0416 705/26.7 |
| 8,846,122 B2 | 9/2014 | Rumbaut et al. | |
| 9,165,117 B2* | 10/2015 | Teller | A61B 5/01 |
| 9,703,928 B2* | 7/2017 | Mochizuki | G16H 40/63 |
| 2001/0005830 A1 | 6/2001 | Kuroyanagi | |
| 2001/0028308 A1 | 10/2001 | De La Huerga | |
| 2002/0029149 A1 | 3/2002 | Nishina | |
| 2002/0035503 A1 | 3/2002 | Matsumoto | |
| 2002/0042726 A1* | 4/2002 | Mayaud | G06F 19/3456 705/2 |
| 2002/0050526 A1 | 5/2002 | Swartz et al. | |
| 2002/0055878 A1* | 5/2002 | Burton | G06Q 30/06 705/27.2 |
| 2002/0069097 A1 | 6/2002 | Conrath | |
| 2002/0116634 A1* | 8/2002 | Okubo | G06Q 10/06 726/26 |
| 2002/0165787 A1 | 11/2002 | Bates et al. | |
| 2003/0024946 A1* | 2/2003 | Severino | G07F 13/08 222/2 |
| 2003/0050854 A1* | 3/2003 | Showghi | G06Q 10/02 705/15 |
| 2003/0051606 A1* | 3/2003 | Cusenza | A47J 27/16 99/357 |
| 2003/0069745 A1 | 4/2003 | Zenko | |
| 2003/0071806 A1* | 4/2003 | Annand | G06Q 30/06 345/418 |
| 2003/0099157 A1 | 5/2003 | Quine | |
| 2003/0105555 A1 | 6/2003 | Lunak et al. | |
| 2003/0121929 A1 | 7/2003 | Liff et al. | |
| 2003/0125963 A1* | 7/2003 | Haken | G06Q 10/08 705/26.1 |
| 2003/0125986 A1 | 7/2003 | Collosi | |
| 2003/0197005 A1 | 10/2003 | Huegerich et al. | |
| 2003/0236682 A1* | 12/2003 | Heyer | G06F 19/324 705/2 |
| 2003/0236706 A1* | 12/2003 | Weiss | G06Q 30/06 705/15 |
| 2004/0015403 A1 | 1/2004 | Moskowitz et al. | |
| 2004/0025701 A1* | 2/2004 | Colston | A47J 31/3628 99/279 |
| 2004/0044469 A1* | 3/2004 | Bender | G01C 21/36 701/532 |
| 2004/0044489 A1* | 3/2004 | Jones | H04L 43/50 702/79 |
| 2004/0054554 A1* | 3/2004 | Barts | G06Q 10/063 705/7.11 |
| 2004/0073448 A1* | 4/2004 | Barts | G06Q 10/063 705/330 |
| 2004/0073449 A1* | 4/2004 | Yang | G06Q 10/08 705/330 |
| 2004/0091843 A1 | 5/2004 | Albro et al. | |
| 2004/0103033 A1* | 5/2004 | Reade | G06Q 20/20 705/16 |
| 2004/0143503 A1 | 7/2004 | Suthar | |
| 2004/0172169 A1* | 9/2004 | Wright, IV | A61J 3/074 700/265 |
| 2004/0183796 A1 | 9/2004 | Velde et al. | |
| 2004/0193495 A1 | 9/2004 | Kim | |
| 2004/0214597 A1* | 10/2004 | Suryanarayana | G06Q 20/20 455/552.1 |
| 2004/0226775 A1* | 11/2004 | Takatama | G06Q 30/06 186/53 |
| 2004/0238555 A1* | 12/2004 | Parks | G07F 9/105 221/80 |
| 2004/0246819 A1 | 12/2004 | Quine | |
| 2004/0263319 A1 | 12/2004 | Huomo | |
| 2005/0038719 A1 | 2/2005 | Young et al. | |
| 2005/0048461 A1* | 3/2005 | Lahteenmaki | A61J 3/002 435/3 |
| 2005/0059849 A1 | 3/2005 | Liu | |
| 2005/0060063 A1* | 3/2005 | Reichelt | G07F 5/18 700/244 |
| 2005/0065640 A1 | 3/2005 | Mallett et al. | |
| 2005/0080520 A1 | 4/2005 | Kline et al. | |
| 2005/0080650 A1 | 4/2005 | Noel | |
| 2005/0090425 A1* | 4/2005 | Reardan | G06F 19/328 514/1 |
| 2005/0098169 A1 | 5/2005 | Frederiksen | |
| 2005/0113968 A1* | 5/2005 | Williams | G07F 11/44 700/236 |
| 2005/0171663 A1 | 8/2005 | Mittelsteadt et al. | |
| 2005/0226975 A1* | 10/2005 | Drouillard | A23N 15/00 426/383 |
| 2005/0241497 A1 | 11/2005 | Cantu | |
| 2005/0267811 A1* | 12/2005 | Almblad | G06Q 30/06 705/15 |
| 2005/0280544 A1 | 12/2005 | Mishelevich | |
| 2006/0015289 A1 | 1/2006 | Shakman et al. | |
| 2006/0053184 A1 | 3/2006 | Grana | |
| 2006/0081653 A1* | 4/2006 | Boland | A47J 31/40 222/243 |
| 2006/0108415 A1* | 5/2006 | Thomas | B67D 1/0884 235/381 |
| 2006/0182240 A1* | 8/2006 | Schelberg, Jr. | G06Q 20/127 379/93.01 |
| 2006/0191885 A1* | 8/2006 | Near | A47J 27/62 219/214 |
| 2006/0224419 A1 | 10/2006 | Servizio et al. | |
| 2006/0260601 A1* | 11/2006 | Schedeler | F24C 7/082 126/30 |
| 2006/0263501 A1 | 11/2006 | Oghafua et al. | |
| 2006/0277066 A1 | 12/2006 | Hungerford et al. | |

(56) References Cited

U.S. PATENT DOCUMENTS

| | | | |
|---|---|---|---|
| 2006/0278093 A1* | 12/2006 | Biderman | A47J 31/40 99/282 |
| 2007/0027432 A1 | 2/2007 | Radford et al. | |
| 2007/0038727 A1 | 2/2007 | Bailey et al. | |
| 2007/0055550 A1 | 3/2007 | Courtney et al. | |
| 2007/0088624 A1 | 4/2007 | Vaughn et al. | |
| 2007/0150371 A1 | 6/2007 | Gangji | |
| 2007/0150375 A1* | 6/2007 | Yang | G06Q 10/08 705/339 |
| 2007/0168205 A1* | 7/2007 | Carlson | G06Q 10/02 705/15 |
| 2007/0170049 A1* | 7/2007 | Mansur | B01D 1/0017 202/160 |
| 2007/0170195 A1* | 7/2007 | Segiet | G07F 9/105 221/15 |
| 2007/0183633 A1* | 8/2007 | Hoffmann | G06K 9/00221 382/116 |
| 2007/0185785 A1* | 8/2007 | Carlson | G06F 17/3087 705/26.8 |
| 2007/0267441 A1* | 11/2007 | van Opstal | B67D 1/0025 222/129.4 |
| 2007/0271001 A1* | 11/2007 | Ratnakar | A61J 7/02 700/236 |
| 2007/0292573 A1* | 12/2007 | Smith | A23G 3/0097 426/383 |
| 2007/0294129 A1* | 12/2007 | Froseth | G06Q 10/08 705/7.32 |
| 2008/0114678 A1 | 5/2008 | Bennett et al. | |
| 2008/0141315 A1 | 6/2008 | Ogilvie | |
| 2008/0162181 A1 | 7/2008 | Ben-Haim et al. | |
| 2008/0163762 A1 | 7/2008 | Weiss | |
| 2008/0171967 A1* | 7/2008 | Blomquist | G06F 19/324 604/67 |
| 2008/0172261 A1* | 7/2008 | Albertson | G06K 9/00335 382/103 |
| 2008/0195247 A1 | 8/2008 | Mallett et al. | |
| 2008/0249859 A1* | 10/2008 | Angell | G06Q 30/02 705/14.39 |
| 2008/0260918 A1* | 10/2008 | Lai | A23P 10/00 426/231 |
| 2008/0281915 A1 | 11/2008 | Elad et al. | |
| 2008/0314918 A1 | 12/2008 | Nuriely | |
| 2009/0043176 A1 | 2/2009 | Nakajima et al. | |
| 2009/0087819 A1 | 4/2009 | Adachi et al. | |
| 2009/0094033 A1 | 4/2009 | Mazer et al. | |
| 2009/0099944 A1 | 4/2009 | Robinson et al. | |
| 2009/0106313 A1 | 4/2009 | Boldyga | |
| 2009/0106316 A1 | 4/2009 | Kubono et al. | |
| 2009/0106826 A1* | 4/2009 | Palestrant | G06F 21/35 726/7 |
| 2009/0112683 A1 | 4/2009 | Hamilton, II et al. | |
| 2009/0112782 A1 | 4/2009 | Cross et al. | |
| 2009/0142223 A1* | 6/2009 | Hyde | A61L 2/24 422/1 |
| 2009/0161907 A1* | 6/2009 | Healey | B65F 1/14 382/100 |
| 2009/0198547 A1 | 8/2009 | Sudak | |
| 2009/0199105 A1 | 8/2009 | Kamada et al. | |
| 2009/0209240 A1 | 8/2009 | Mahowald | |
| 2009/0234712 A1* | 9/2009 | Kolawa | G06Q 30/02 705/14.4 |
| 2009/0236333 A1* | 9/2009 | Ben-Shmuel | H05B 6/6402 219/702 |
| 2009/0236334 A1* | 9/2009 | Ben-Shmuel | B65D 81/3453 219/703 |
| 2009/0236335 A1* | 9/2009 | Ben-Shmuel | H05B 6/6402 219/710 |
| 2009/0254531 A1 | 10/2009 | Walker et al. | |
| 2009/0259559 A1* | 10/2009 | Carroll | G06Q 20/20 705/17 |
| 2009/0259688 A1* | 10/2009 | Do | G06F 3/016 |
| 2009/0261175 A1* | 10/2009 | Kauppinen | A47J 39/006 236/44 C |
| 2009/0271004 A1 | 10/2009 | Zecchin et al. | |
| 2009/0295575 A1 | 12/2009 | Kennedy | |
| 2009/0307139 A1 | 12/2009 | Mardikar et al. | |
| 2009/0313125 A1* | 12/2009 | Roh | G06Q 30/0224 705/14.66 |
| 2010/0017296 A1 | 1/2010 | Spignesi, Jr. et al. | |
| 2010/0038416 A1 | 2/2010 | Canora | |
| 2010/0038594 A1 | 2/2010 | Bohlig et al. | |
| 2010/0042427 A1 | 2/2010 | Graham et al. | |
| 2010/0043834 A1 | 2/2010 | Sheringer | |
| 2010/0045705 A1 | 2/2010 | Vertegaal et al. | |
| 2010/0052900 A1 | 3/2010 | Covannon et al. | |
| 2010/0062169 A1* | 3/2010 | Pierre | B05B 13/0221 427/388.1 |
| 2010/0063889 A1 | 3/2010 | Proctor, Jr. et al. | |
| 2010/0121669 A1* | 5/2010 | Madigan | G06Q 10/06 705/7.11 |
| 2010/0121722 A1 | 5/2010 | Vawter | |
| 2010/0125362 A1* | 5/2010 | Canora | G06Q 20/3278 700/236 |
| 2010/0136666 A1 | 6/2010 | Kobayashi et al. | |
| 2010/0160745 A1 | 6/2010 | Hills et al. | |
| 2010/0204676 A1 | 8/2010 | Cardullo | |
| 2010/0206765 A1 | 8/2010 | Fonte | |
| 2010/0250384 A1* | 9/2010 | Bhargava | G01C 21/343 705/26.1 |
| 2010/0268378 A1* | 10/2010 | Sharpley | G06Q 30/0603 700/233 |
| 2010/0268792 A1 | 10/2010 | Butler et al. | |
| 2010/0275625 A1 | 11/2010 | Lowenstein | |
| 2010/0291515 A1 | 11/2010 | Pinnisi et al. | |
| 2010/0303972 A1* | 12/2010 | Srivastava | A23L 5/10 426/233 |
| 2010/0305974 A1 | 12/2010 | Patch et al. | |
| 2010/0312601 A1 | 12/2010 | Lin | |
| 2010/0328099 A1 | 12/2010 | Wachman et al. | |
| 2010/0332140 A1 | 12/2010 | Joyce et al. | |
| 2011/0000923 A1 | 1/2011 | Morales | |
| 2011/0009715 A1 | 1/2011 | O'Reilly et al. | |
| 2011/0022225 A1* | 1/2011 | Rothschild | B67D 1/0041 700/233 |
| 2011/0022298 A1* | 1/2011 | Kronberg | G01C 21/3484 701/532 |
| 2011/0031236 A1* | 2/2011 | Ben-Shmuel | H05B 6/6402 219/620 |
| 2011/0035338 A1* | 2/2011 | Kagan | G01D 4/002 705/412 |
| 2011/0040660 A1 | 2/2011 | Allison et al. | |
| 2011/0054678 A1* | 3/2011 | Thompson | G06Q 30/06 700/237 |
| 2011/0055044 A1* | 3/2011 | Wiedl | G06Q 30/02 705/26.5 |
| 2011/0060457 A1 | 3/2011 | De Vrught et al. | |
| 2011/0080457 A1* | 4/2011 | Nagamine | B41J 2/085 347/93 |
| 2011/0133005 A1 | 6/2011 | Chesack | |
| 2011/0160902 A1 | 6/2011 | Postins | |
| 2011/0180441 A1* | 7/2011 | Bach | G06F 19/326 206/459.5 |
| 2011/0186624 A1 | 8/2011 | Wagner et al. | |
| 2011/0208617 A1 | 8/2011 | Weiland | |
| 2011/0218839 A1* | 9/2011 | Shamaiengar | G06Q 30/0203 705/7.32 |
| 2011/0231212 A1* | 9/2011 | Hurley | G06Q 10/02 705/5 |
| 2011/0300270 A1* | 12/2011 | Koppens | A47J 27/004 426/115 |
| 2011/0307316 A1* | 12/2011 | Peters | G06Q 30/0207 705/14.24 |
| 2011/0318717 A1 | 12/2011 | Adamowicz | |
| 2012/0016745 A1 | 1/2012 | Hendrickson | |
| 2012/0016754 A1* | 1/2012 | Jackson | G06Q 10/0631 705/15 |
| 2012/0041770 A1 | 2/2012 | Philippe | |
| 2012/0041778 A1 | 2/2012 | Kraft | |
| 2012/0088023 A1* | 4/2012 | Begun | A23G 1/0063 426/515 |

(56) References Cited

U.S. PATENT DOCUMENTS

| | | |
|---|---|---|
| 2012/0088212 A1 | 4/2012 | Knaan |
| 2012/0089249 A1 | 4/2012 | Rosenblum |
| 2012/0101914 A1 | 4/2012 | Kumar et al. |
| 2012/0131619 A1 | 5/2012 | Ogilvie |
| 2012/0136731 A1* | 5/2012 | Kidron ................ G06F 19/3475 705/15 |
| 2012/0137325 A1 | 5/2012 | Ogilvie |
| 2012/0173271 A1* | 7/2012 | Omidi ................ G06F 19/3418 705/2 |
| 2012/0232484 A1* | 9/2012 | Blomquist .......... G06F 19/3468 604/151 |
| 2012/0246004 A1 | 9/2012 | Book et al. |
| 2012/0262039 A1 | 10/2012 | Daugbjerg et al. |
| 2012/0268259 A1* | 10/2012 | Igel ........................ B60R 25/00 340/426.11 |
| 2012/0284126 A1 | 11/2012 | Giraud et al. |
| 2012/0310760 A1* | 12/2012 | Phillips .................. G06Q 40/02 705/26.1 |
| 2012/0323208 A1 | 12/2012 | Bochenko et al. |
| 2012/0323707 A1 | 12/2012 | Urban |
| 2013/0006415 A1 | 1/2013 | Paydar et al. |
| 2013/0018356 A1 | 1/2013 | Prince et al. |
| 2013/0048023 A1* | 2/2013 | Holman ................ B08B 1/003 134/18 |
| 2013/0048037 A1* | 2/2013 | Holman ................ B08B 1/003 134/58 R |
| 2013/0092033 A1* | 4/2013 | Murphy ................ F24C 7/086 99/342 |
| 2013/0151268 A1 | 6/2013 | Fletcher |
| 2013/0158705 A1 | 6/2013 | Levy et al. |
| 2015/0151050 A1* | 6/2015 | Estes ..................... A61M 5/172 604/500 |
| 2015/0216201 A1* | 8/2015 | Bruckner ............... A23G 9/283 700/233 |
| 2015/0296865 A1* | 10/2015 | Holman .............. G07F 17/0064 99/485 |
| 2015/0302375 A1* | 10/2015 | Holman .............. G06F 19/3462 705/15 |

OTHER PUBLICATIONS

Shimmura et al.; "Analysis of Eating Behavior in Restaurants Based on Leftover Food"; 2010; pp. 956-960; IEEE.

"Toddlers at the Table: Avoiding Power Struggles," located at https://web.archive.org/web/20101012173406/http://kidshealth.org/parent/nutrition_center/staying_fit/toddler_meals.html; KidsHealth; 2010; pp. 1-2; The Nemours Foundation.

Connors et al.; "Using a Visual Plate Waste Study to Monitor Menu Performance"; Journal of the American Dietetic Association; 2004; pp. 94-96; vol. 104; American Dietetic Association.

Poulter, Sean; "Medicine vending machines that dispense prescriptions 24 hours a day go on trial"; bearing a date of Jun. 22, 2010; created on Nov. 27, 2017; pp. 1-5; located at http://www.dailymail.co.uk/health/article-1288434/Medicine-vending-machine-dispenses-prescriptions-pharmacist-launched.html.

* cited by examiner

Method of Consumption/Delivery

10 ingestible product preparation system

- e1220 second vicinity housing elec circ arrange
- e1221 second vicinity building elec circ arrange
- e1222 second vicinity mall elec circ arrange
- e1223 second vicinity restaurant elec circ arrange
- e1224 second vicinity airplane elec circ arrange
- e1225 second vicinity vehicle elec circ arrange
- e1226 second vicinity territory elec circ arrange
- e1227 second vicinity region elec circ arrange
- e1228 acquisition conversation elec circ arrange
- e1229 acquisition gratuity elec circ arrange
- e1230 acquisition financial elec circ arrange
- e1231 acquisition leftovers elec circ arrange
- e1232 acquisition time elec circ arrange
- e1233 acquisition party elec circ arrange
- e1234 acquisition image elec circ arrange
- e1235 acquisition gesture elec circ arrange
- e1236 acquisition speech elec circ arrange
- e1237 acquisition keypad elec circ arrange
- e1238 acquisition input elec circ arrange
- e1239 acquisition restaurant elec circ arrange

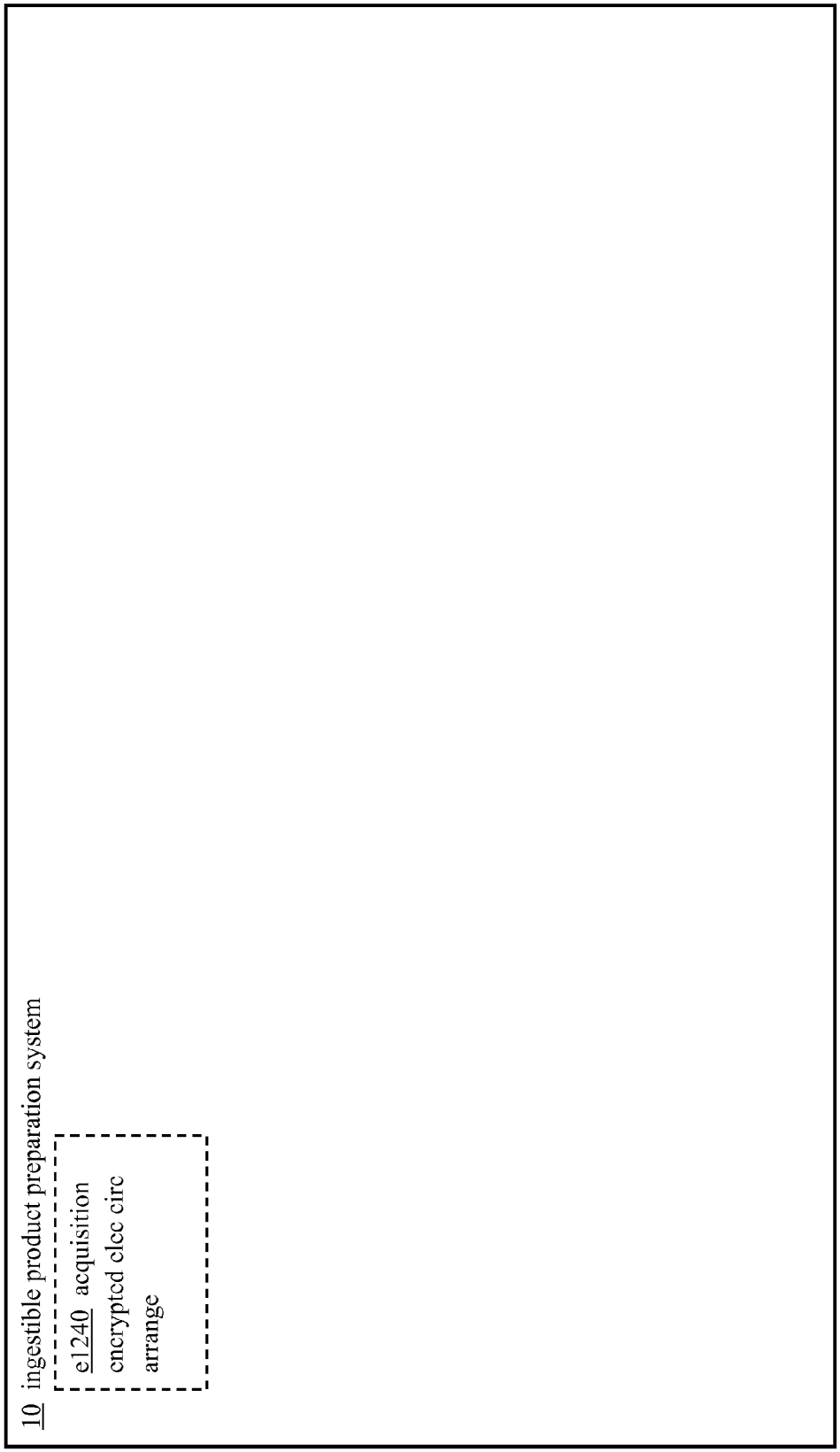

Fig. 82 o12 → electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus o1201 electronically directing control at least in part of the acquisition of the ingestion intelligence including the information related to the ingestion by the particular individual living being of at least one of the one or more selected ingestible products regarding occupant density associated with environs of the ingestion by the particular individual living being o1202 electronically directing control at least in part of the acquisition of the ingestion intelligence including the information related to the ingestion by the particular individual living being of at least one of the one or more selected ingestible products regarding furnishings associated with environs of the ingestion by the particular individual living being o1203 electronically directing control at least in part of the acquisition of the ingestion intelligence including the information related to the ingestion by the particular individual living being of at least one of the one or more selected ingestible products regarding air temperature associated with environs of the ingestion by the particular individual living being

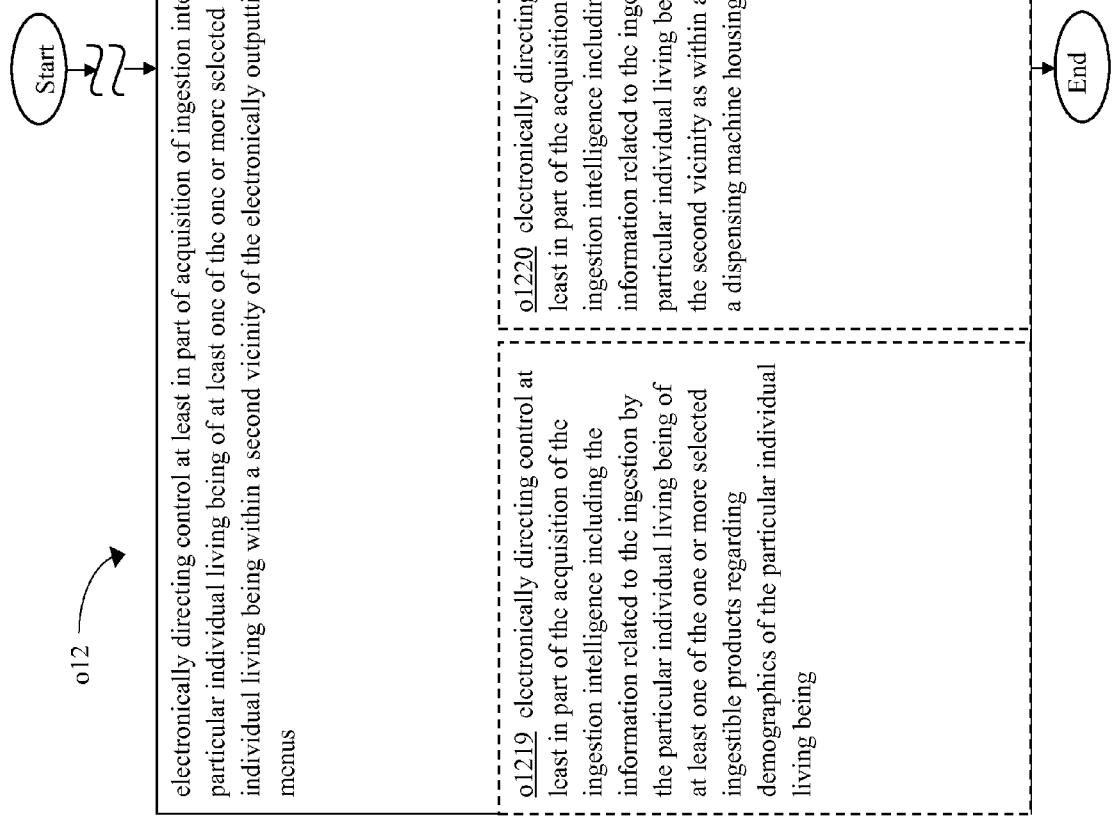

*Fig. 89*

o12

Start → ⟿ → electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus o1222 electronically directing control at least in part of the acquisition of the ingestion intelligence including the information related to the ingestion by the particular individual living being within the second vicinity as within a food court of a shopping mall o1223 electronically directing control at least in part of the acquisition of the ingestion intelligence including the information related to the ingestion by the particular individual living being within the second vicinity as within an interior of a restaurant o1224 electronically directing control at least in part of the acquisition of the ingestion intelligence including the information related to the ingestion by the particular individual living being within the second vicinity as within an interior of an airplane → End

Fig. 90 o12 electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus o1225 electronically directing control at least in part of the acquisition of the ingestion intelligence including the information related to the ingestion by the particular individual living being within the second vicinity as within an interior of a ground vehicle o1226 electronically directing control at least in part of the acquisition of the ingestion intelligence including the information related to the ingestion by the particular individual living being within the second vicinity as within a multi-state territory o1227 electronically directing control at least in part of the acquisition of the ingestion intelligence including the information related to the ingestion by the particular individual living being within the second vicinity as within an international region

*Fig. 91* o12 →

Start → 77 → electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus o1228 electronically directing control at least in part of the acquisition of the ingestion intelligence including the information related to the ingestion by the particular individual living being of at least one of the one or more selected ingestible products regarding one or more details of conversation by the particular individual living being o1229 electronically directing control at least in part of the acquisition of the ingestion intelligence including the information related to the ingestion by the particular individual living being of at least one of the one or more selected ingestible products regarding gratuity execution by the particular individual living being o1230 electronically directing control at least in part of the acquisition of the ingestion intelligence including the information related to the ingestion by the particular individual living being of at least one of the one or more selected ingestible products regarding one or more details regarding financial status of the particular individual living being End

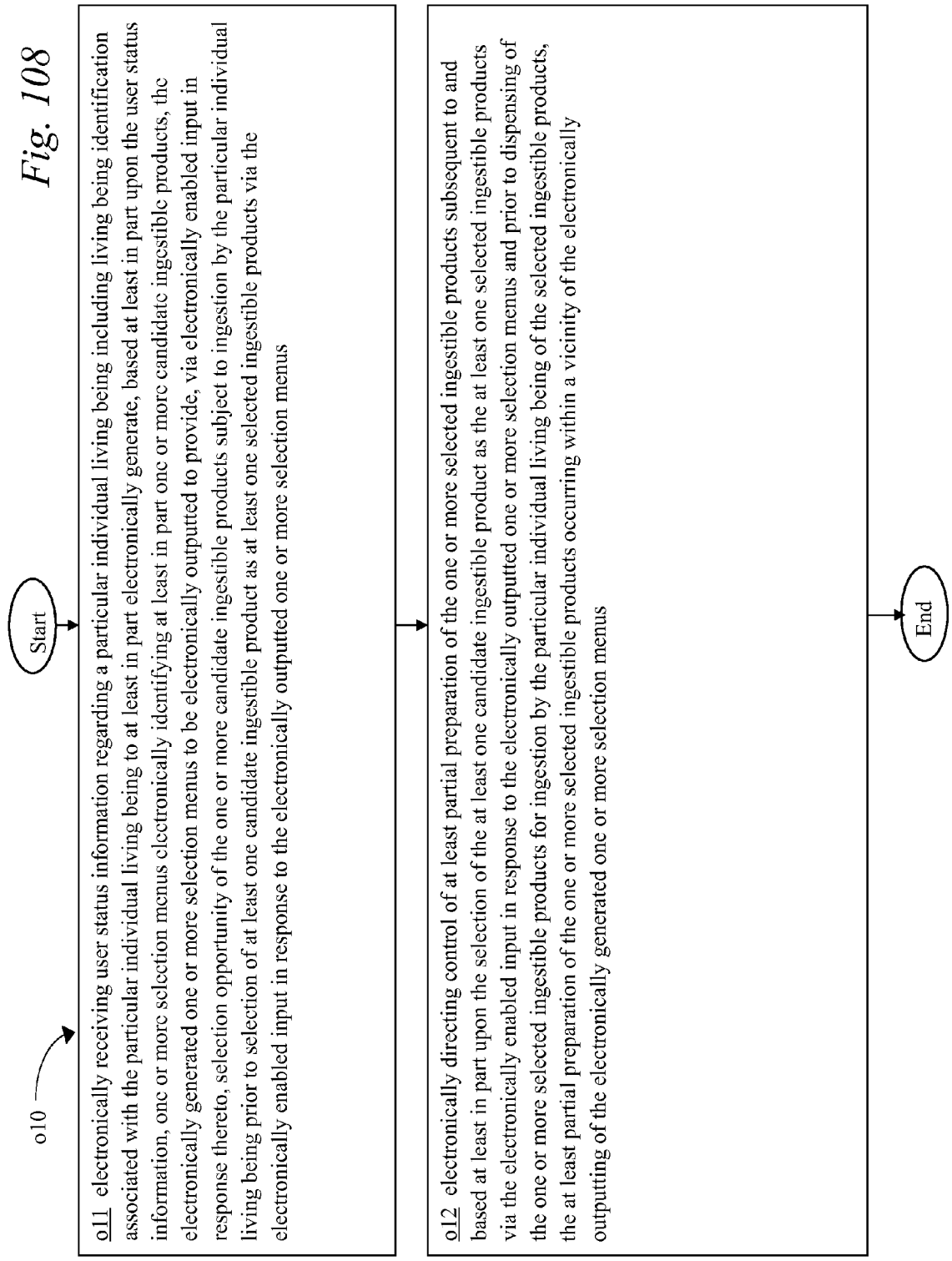

Fig. 108 o10 o11 electronically receiving user status information regarding a particular individual living being including living being identification associated with the particular individual living being to at least in part electronically generate, based at least in part upon the user status information, one or more selection menus electronically identifying at least in part one or more candidate ingestible products, the electronically generated one or more selection menus to be electronically outputted to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus o12 electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus

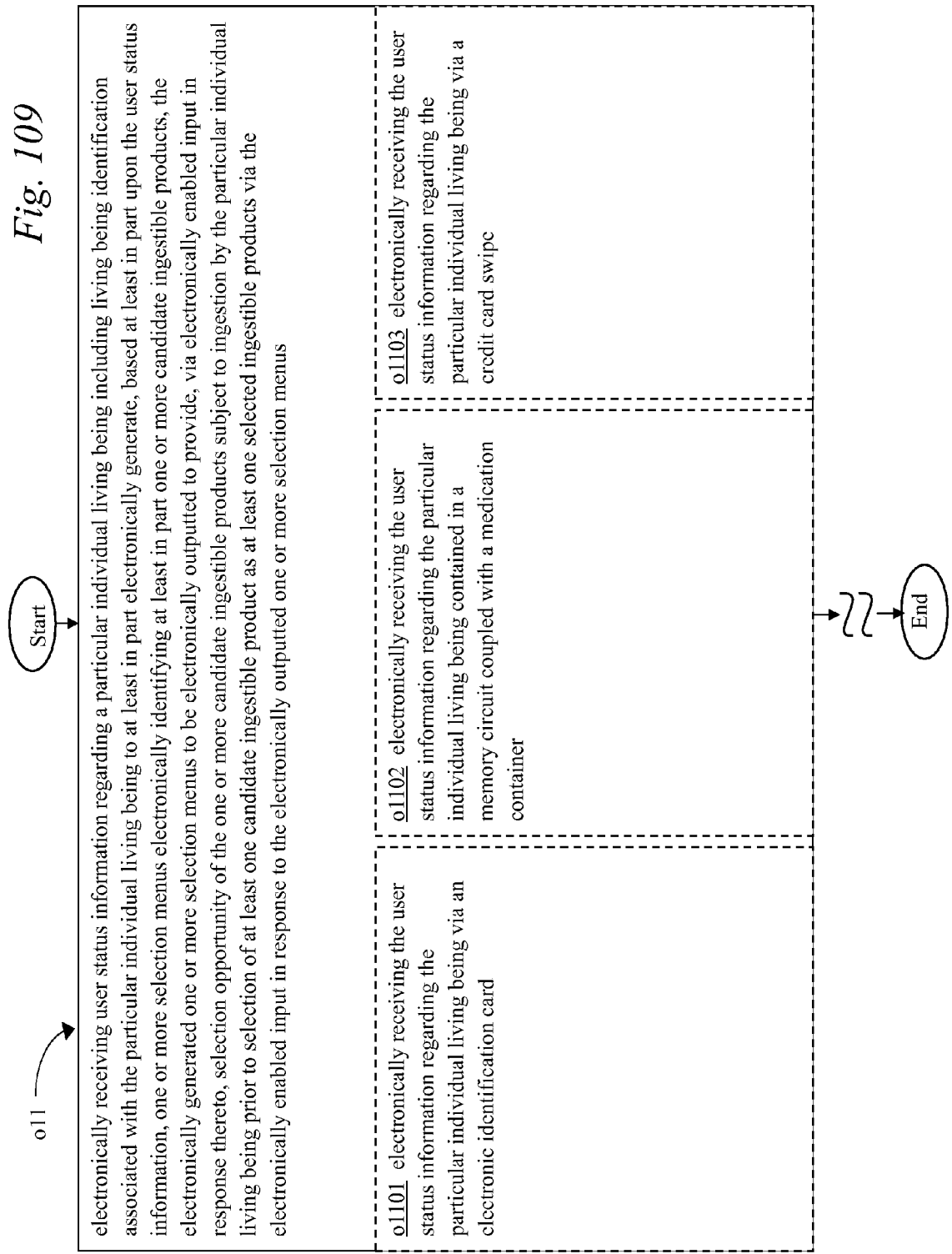

*Fig. 137* o12 →

Start → electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus o1207 electronically directing control of the at least partial preparation of the one or more selected ingestible products via controlling amount of ingredient mixing during preparation of the ingestible product o1208 electronically directing control of the at least partial preparation of the one or more selected ingestible products via control of radiation emitted within an enclosure containing ingredients to be used for preparation of the ingestible product o1209 electronically directing control of the at least partial preparation of the one or more selected ingestible products via control of sound emitted within an enclosure containing ingredients to be used for preparation of the ingestible product → End

*Fig. 138* o12

Start → electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus o1210 electronically directing control of the at least partial preparation of the one or more selected ingestible products via control of infrared radiation emitted within an enclosure containing ingredients to be used for preparation of the ingestible product o1211 electronically directing control of the at least partial preparation of the one or more selected ingestible products via control of microwave radiation emitted within an enclosure containing ingredients to be used for preparation of the ingestible product o1212 electronically directing control of the at least partial preparation of the one or more selected ingestible products via control of an outlet of an ingredient container holding an ingredient used for preparation of the ingestible product → End

*Fig. 139*

o12

(Start) → electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus o1213 electronically directing control of the at least partial preparation of the one or more selected ingestible products via control of an outlet of an ingredient syringe holding an ingredient used for preparation of the ingestible product o1214 electronically directing control of the at least partial preparation of the one or more selected ingestible products via control of mixing of at least some of the ingredients used to prepare the ingestible product before thermal treatment of the ingredients o1215 electronically directing control of the at least partial preparation of the one or more selected ingestible products via control of blending of at least some of the ingredients used to prepare the ingestible product after thermal treatment of the ingredients → (End)

FOOD PRINTING GOAL IMPLEMENTATION SUBSTRATE STRUCTURE INGESTIBLE MATERIAL PREPARATION SYSTEM AND METHOD

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

For purposes of the USPTO extra-statutory requirements, the present application constitutes a continuation-in-part of U.S. patent application Ser. No. 13/317,979, entitled SELECTION INFORMATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 31 Oct. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/317,978, entitled SELECTION INFORMATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 31 Oct. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,361, entitled CONTROLLED SUBSTANCE AUTHORIZATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 26 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,481, entitled CONTROLLED SUBSTANCE AUTHORIZATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,545, entitled REPORTING SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 31 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,544, entitled REPORTING SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 31 Aug. 2011, which is currently co-pending or is an application of which a currently co-pending application is entitled to the benefit of the filing date.

The present application claims benefit of priority of U.S. Pat. No. 8,892,249, entitled SUBSTANCE CONTROL SYSTEM AND METHOD FOR DISPENSING SYSTEMS, naming PAUL HOLMAN, ROYCE A. LEVIEN, MARK A. MALAMUD, NEAL STEPHENSON, AND CHRISTOPHER CHARLES YOUNG as inventors, filed 16 Sep. 2011, which was filed within the twelve months preceding the filing date of the present application or is an application of which a currently co-pending priority application is entitled to the benefit of the filing date.

The present application claims benefit of priority of U.S. Pat. No. 8,989,895, entitled SUBSTANCE CONTROL SYSTEM AND METHOD FOR DISPENSING SYSTEMS, naming PAUL HOLMAN, ROYCE A. LEVIEN, MARK A. MALAMUD, NEAL STEPHENSON, AND CHRISTOPHER CHARLES YOUNG as inventors, filed 16 Sep. 2011, which was filed within the twelve months preceding the filing date of the present application or is an application of which a currently co-pending priority application is entitled to the benefit of the filing date.

For purposes of the USPTO extra-statutory requirements, the present application constitutes a continuation-in-part of U.S. patent application Ser. No. 13/200,830, entitled CLEANING SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,829, entitled CLEANING SYSTEM AND METHOD FOR INGESTIBLE PRODUCT PREPARATION SYSTEM AND METHOD, naming PAUL HOLMAN, ROYCE A.

LEVIEN, MARK A. MALAMUD, NEAL STEPHENSON, AND CHRISTOPHER CHARLES YOUNG as inventors, filed 30 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,907, entitled TREATMENT SYSTEM AND METHOD FOR INGESTIBLE PRODUCT DISPENSING SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 3 Oct. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,906, entitled TREATMENT SYSTEM AND METHOD FOR INGESTIBLE PRODUCT DISPENSING SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 3 Oct. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/317,545, entitled SUBSTANCE ALLOCATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 19 Oct. 2011, which is currently co-pending or is an application of which a currently co-pending application is entitled to the benefit of the filing date.

The present application claims benefit of priority of U.S. Pat. No. 9,037,478, entitled SUBSTANCE ALLOCATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 19 Oct. 2011, which was filed within the twelve months preceding the filing date of the present application or is an application of which a currently co-pending priority application is entitled to the benefit of the filing date.

For purposes of the USPTO extra-statutory requirements, the present application constitutes a continuation-in-part of U.S. patent application Ser. No. 13/373,675, entitled INGESTION INTELLIGENCE ACQUISITION SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 22 Nov. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/373,674, entitled INGESTION INTELLIGENCE ACQUISITION SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 22 Nov. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/373,846, entitled REFUSE INTELLIGENCE ACQUISITION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Nov. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/373,847, entitled REFUSE INTELLIGENCE ACQUISITION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Nov. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/385,128, entitled ITINERARY INTEGRATION SYSTEM AND METHOD FOR VENDING NETWORK SYSTEMS, naming PAUL HOLMAN, ROYCE A. LEVIEN, MARK A. MALAMUD, NEAL STEPHENSON, AND CHRISTOPHER CHARLES YOUNG as inventors, filed 1 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/385,129, entitled ITINERARY INTEGRATION SYSTEM AND METHOD FOR VENDING NETWORK SYSTEMS, naming PAUL HOLMAN, ROYCE A. LEVIEN, MARK A. MALAMUD, NEAL STEPHENSON, AND CHRISTOPHER CHARLES YOUNG as inventors, filed 1 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/385,687, entitled SOCIAL NETWORK REPORTING SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 29 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/385,690, entitled SOCIAL NETWORK REPORTING SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 29 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/432,507, entitled SOCIAL NETWORK SELECTION SYSTEM AND METHOD FOR INGESTIBLE MATERIAL PREPARATION SYSTEM, naming PAUL HOLMAN, ROYCE A. LEVIEN, MARK A. MALAMUD, NEAL STEPHENSON, AND CHRISTOPHER CHARLES YOUNG as inventors, filed 28 Mar. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/432,525, entitled SOCIAL NETWORK SELECTION SYSTEM AND METHOD FOR INGESTIBLE MATERIAL PREPARATION SYSTEM, naming PAUL HOLMAN, ROYCE A. LEVIEN, MARK A. MALAMUD, NEAL STEPHENSON, AND CHRISTOPHER CHARLES YOUNG as inventors, filed 28 Mar. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/435,550, entitled STOCK SUPPLY BASED MODIFIABLE SELECTION SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Mar. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/435,591, entitled STOCK SUPPLY BASED MODIFIABLE SELECTION SYSTEM AND METHOD FOR INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 30 Mar. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 14/745,313 entitled 3D FOOD PRINTING SHOPPING HISTORY SUBSTRATE STRUCTURE INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 19 Jun. 2015, which is currently co-pending or is an application of which a currently co-pending application is entitled to the benefit of the filing date.

For purposes of the USPTO extra-statutory requirements, the present application constitutes a continuation-in-part of U.S. patent application Ser. No. 14/748,220 entitled FOOD PRINTING ADDITIVE MANUFACTURING SUBSTRATE STRUCTURE INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 23 Jun. 2015, which is currently co-pending or is an application of which a currently co-pending application is entitled to the benefit of the filing date.

For purposes of the USPTO extra-statutory requirements, the present application constitutes a continuation-in-part of U.S. patent application Ser. No. 14/750,950 entitled FOOD PRINTING ADDITIVE LAYERING SUBSTRATE STRUCTURE INGESTIBLE MATERIAL PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 25 Jun. 2015, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

A method includes, but is not limited to electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus; and electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus.

In one or more various aspects, related machines, compositions of matter, or manufactures of systems may include, but are not limited to, virtually any combination of hardware, software, and/or firmware configured to effect the herein-referenced method aspects depending upon the design choices of the system designer (limited to patentable subject matter under 35 USC 101).

A system includes, but is not limited to: means for electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus; and means for electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus. In addition to the foregoing, other system aspects are described in the claims, drawings, and text forming a part of the present disclosure.

A system includes, but is not limited to a receiving information electrical circuitry arrangement for electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus; and a controlling acquisition electrical circuitry arrangement for electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus. In addition to the foregoing, other system aspects are described in the claims, drawings, and text forming a part of the present disclosure.

An article of manufacture including a non-transitory signal-bearing storage medium bearing one or more instructions for electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus; and one or more instructions for electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 18 is a schematic diagram view depicting an information display associated with one or more ingestible product selection menus for the ingestible product preparation system 110 in FIG. 1.

FIG. 35 is a block diagram depicting one or more exemplary electrical circuitry arrangements of the ingestible product preparation system 10 of FIG. 1.

FIG. 36 is a block diagram depicting one or more exemplary electrical circuitry arrangements of the ingestible product preparation system 10 of FIG. 1.

FIG. 82 is a high-level flowchart including exemplary implementations of operation O12 of FIG. 46.

FIG. 88 is a high-level flowchart including exemplary implementations of operation O12 of FIG. 46.

FIG. 89 is a high-level flowchart including exemplary implementations of operation O12 of FIG. 46.

FIG. 90 is a high-level flowchart including exemplary implementations of operation O12 of FIG. 46.

FIG. 91 is a high-level flowchart including exemplary implementations of operation O12 of FIG. 46.

FIG. 108 is a high-level flowchart illustrating an operational flow o10 representing exemplary operations related to electronically receiving user status information regarding a particular individual living being including living being identification associated with the particular individual living being to at least in part electronically generate, based at least in part upon the user status information, one or more selection menus electronically identifying at least in part one or more candidate ingestible products, the electronically generated one or more selection menus to be electronically outputted to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus, and electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus at least associated with the depicted exemplary implementations of the system.

FIG. 109 is a high-level flowchart including exemplary implementations of operation p11 of FIG. 108.

FIG. 117 is a high-level flowchart including exemplary implementations of operation p11 of FIG. 108.

FIG. 118 is a high-level flowchart including exemplary implementations of operation p11 of FIG. 108.

FIG. 119 is a high-level flowchart including exemplary implementations of operation p11 of FIG. 108.

FIG. 120 is a high-level flowchart including exemplary implementations of operation p11 of FIG. 108.

FIG. 121 is a high-level flowchart including exemplary implementations of operation p11 of FIG. 108.

FIG. 122 is a high-level flowchart including exemplary implementations of operation p11 of FIG. 108.

FIG. 123 is a high-level flowchart including exemplary implementations of operation p11 of FIG. 108.

FIG. 124 is a high-level flowchart including exemplary implementations of operation p11 of FIG. 108.

FIG. 125 is a high-level flowchart including exemplary implementations of operation p11 of FIG. 108.

FIG. 126 is a high-level flowchart including exemplary implementations of operation p11 of FIG. 108.

FIG. 127 is a high-level flowchart including exemplary implementations of operation p11 of FIG. 108.

FIG. 128 is a high-level flowchart including exemplary implementations of operation p11 of FIG. 108.

Figure 129:
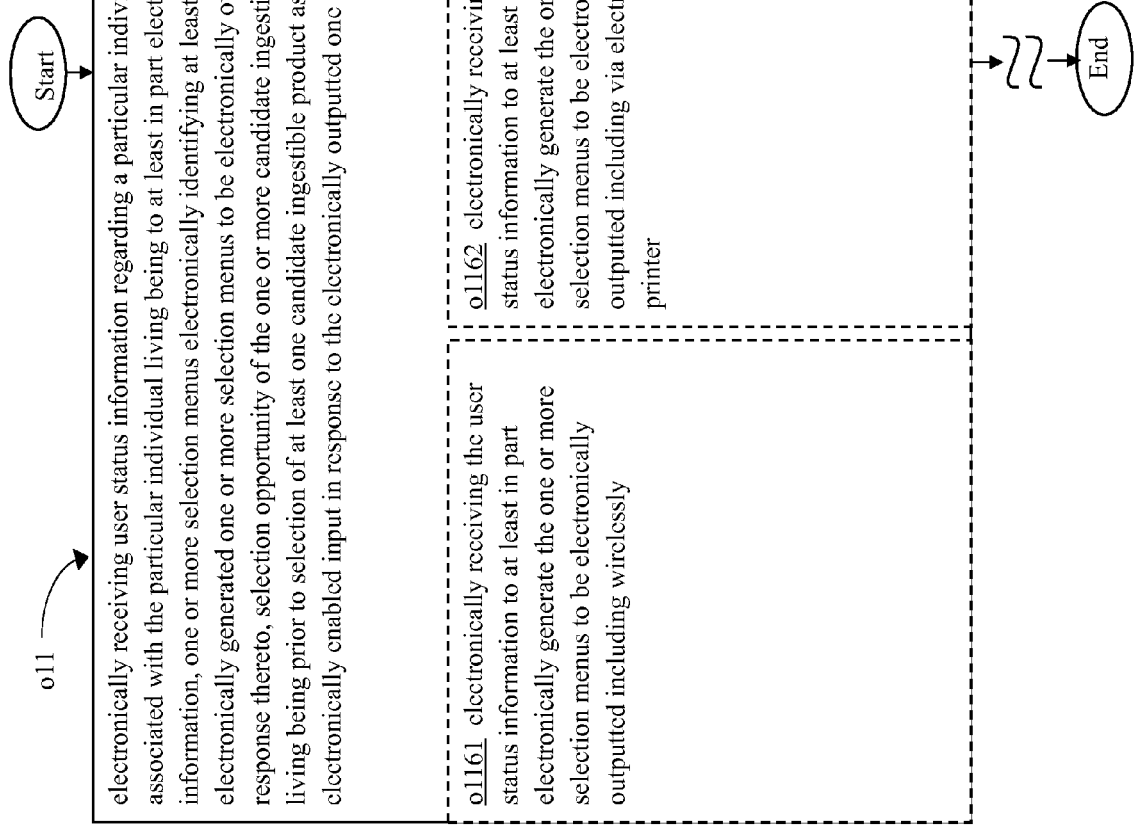

FIG. 129 is a high-level flowchart including exemplary implementations of operation p11 of FIG. 108.

Figure 130:
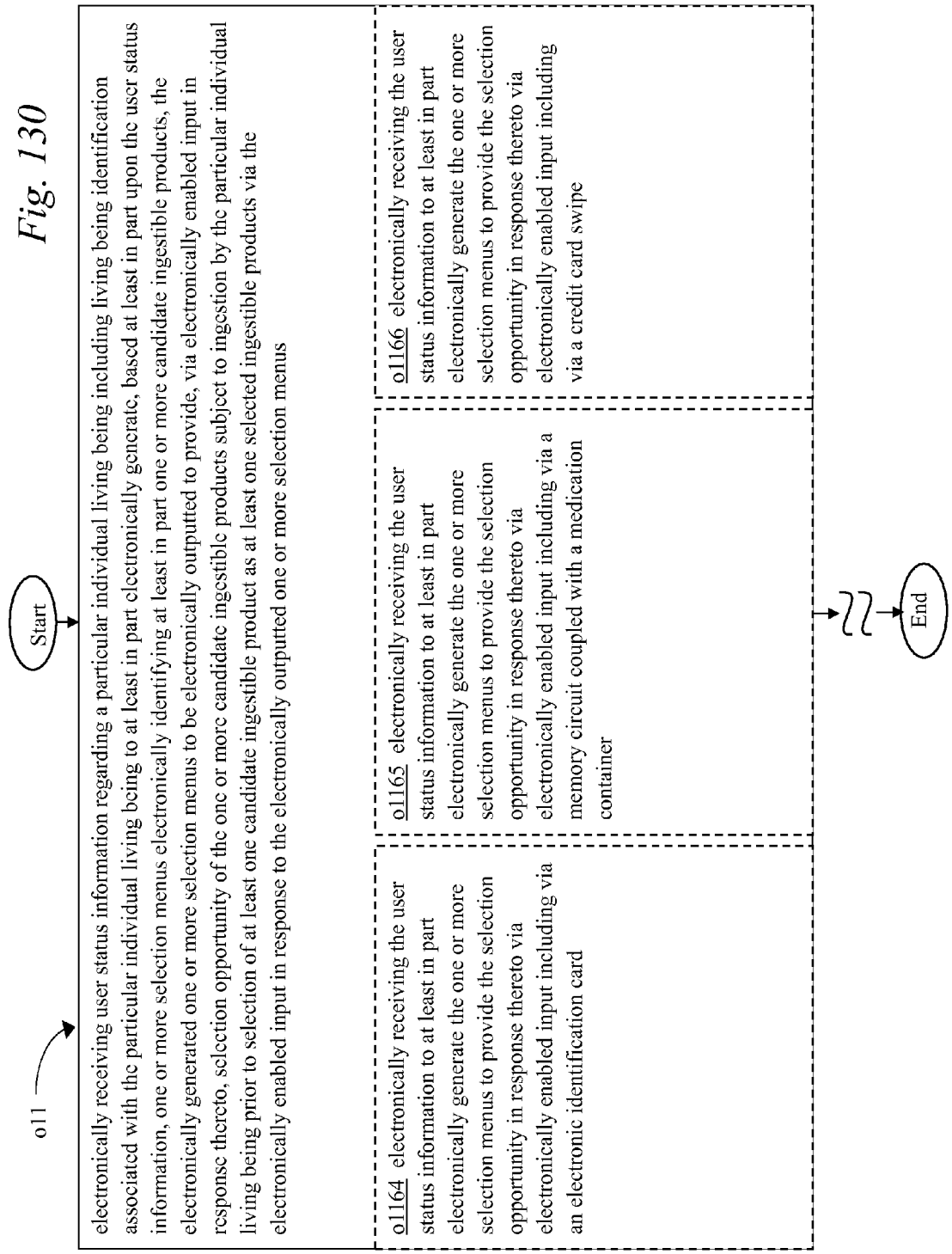

FIG. 130 is a high-level flowchart including exemplary implementations of operation p11 of FIG. 108.

Figure 131:
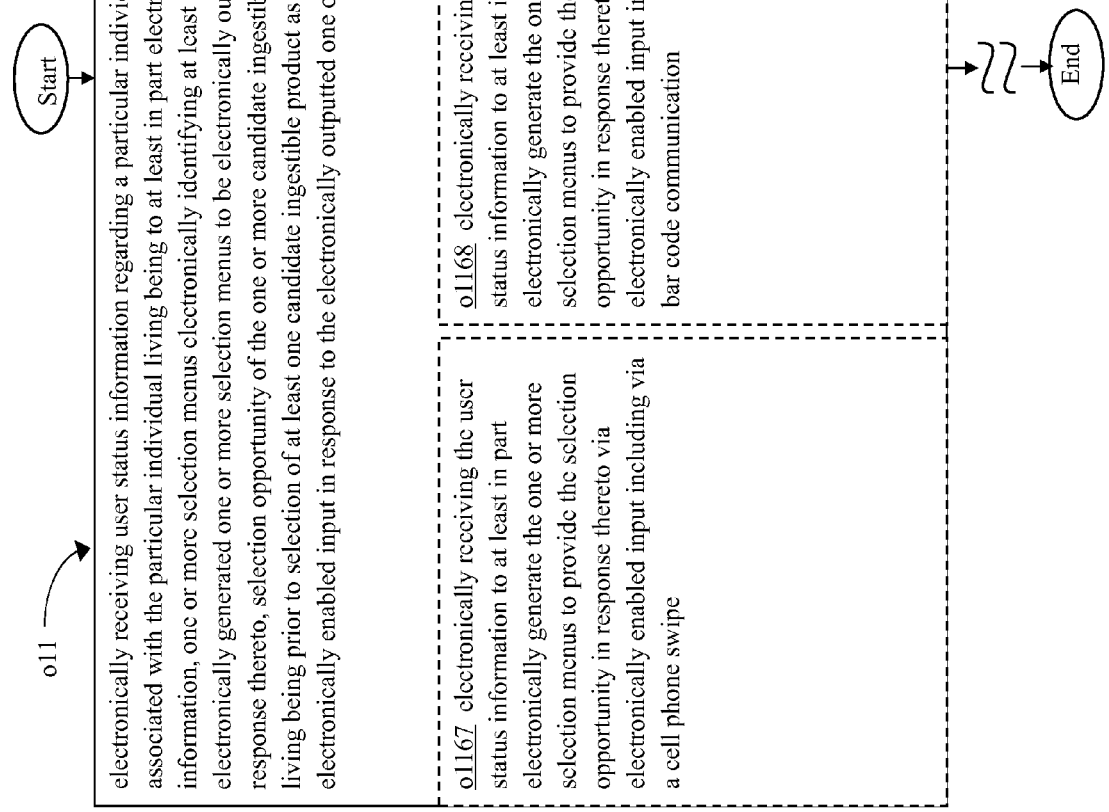

FIG. 131 is a high-level flowchart including exemplary implementations of operation p11 of FIG. 108.

Figure 132:
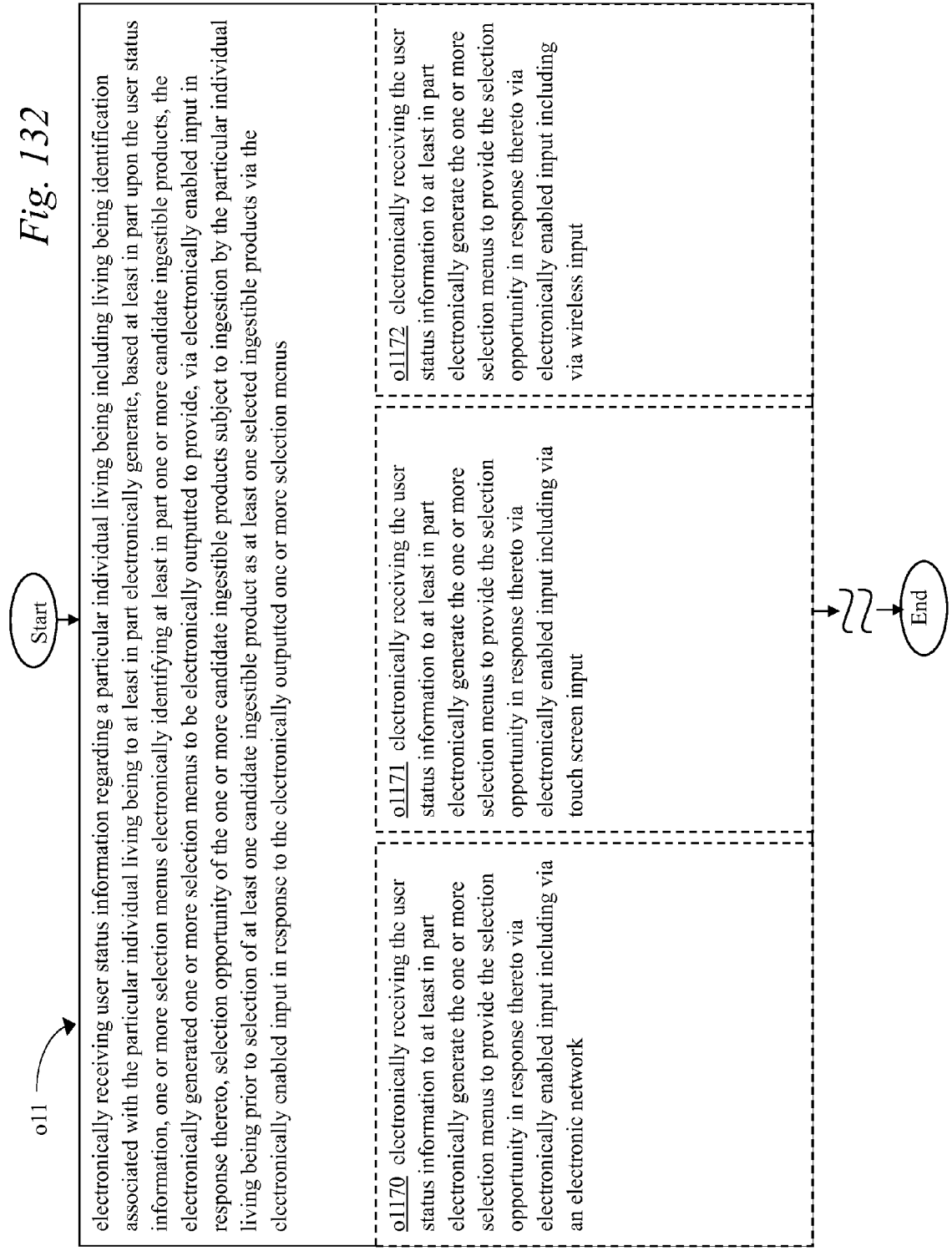

FIG. 132 is a high-level flowchart including exemplary implementations of operation p11 of FIG. 108.

Figure 133:
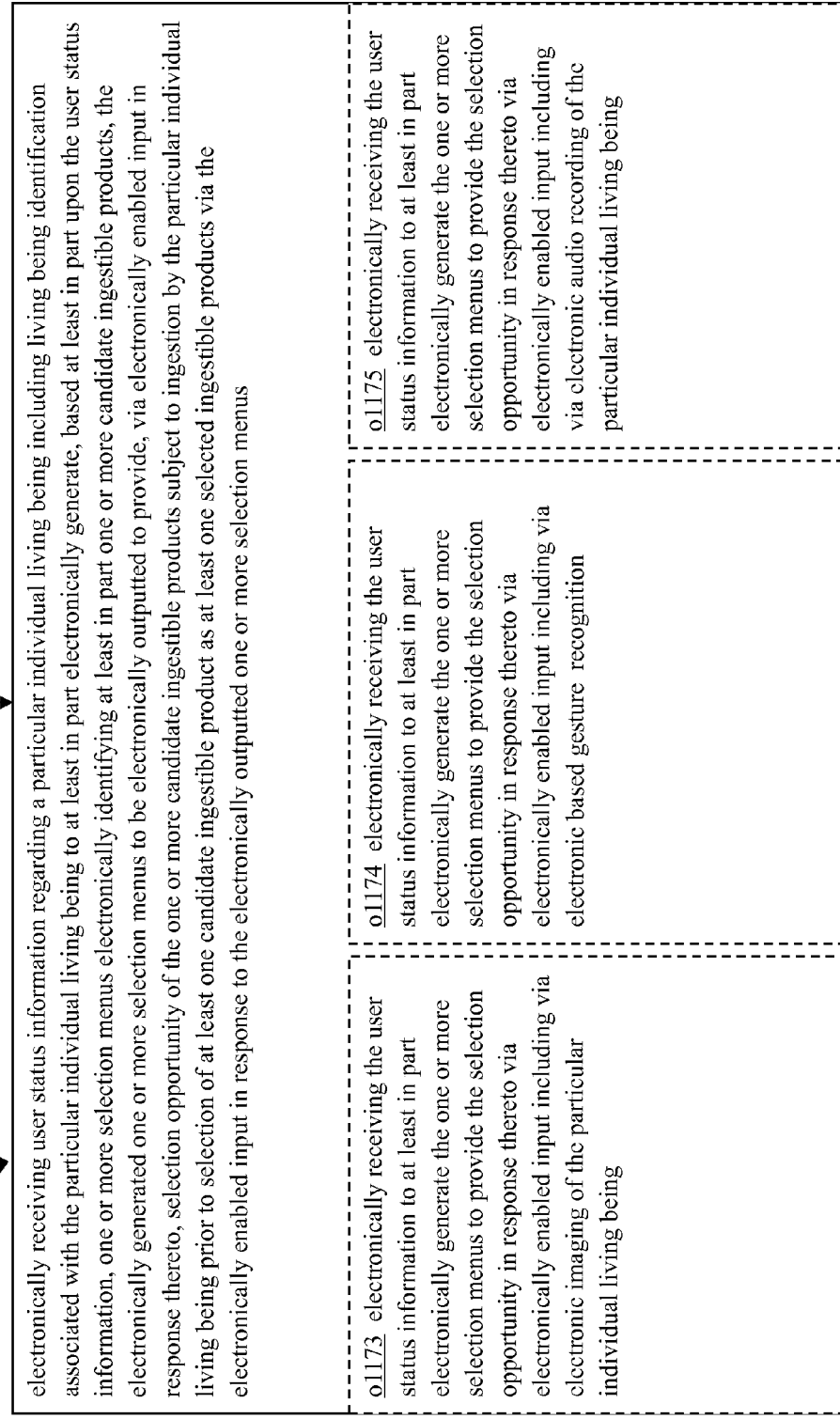

FIG. 133 is a high-level flowchart including exemplary implementations of operation p11 of FIG. 108.

Figure 134:
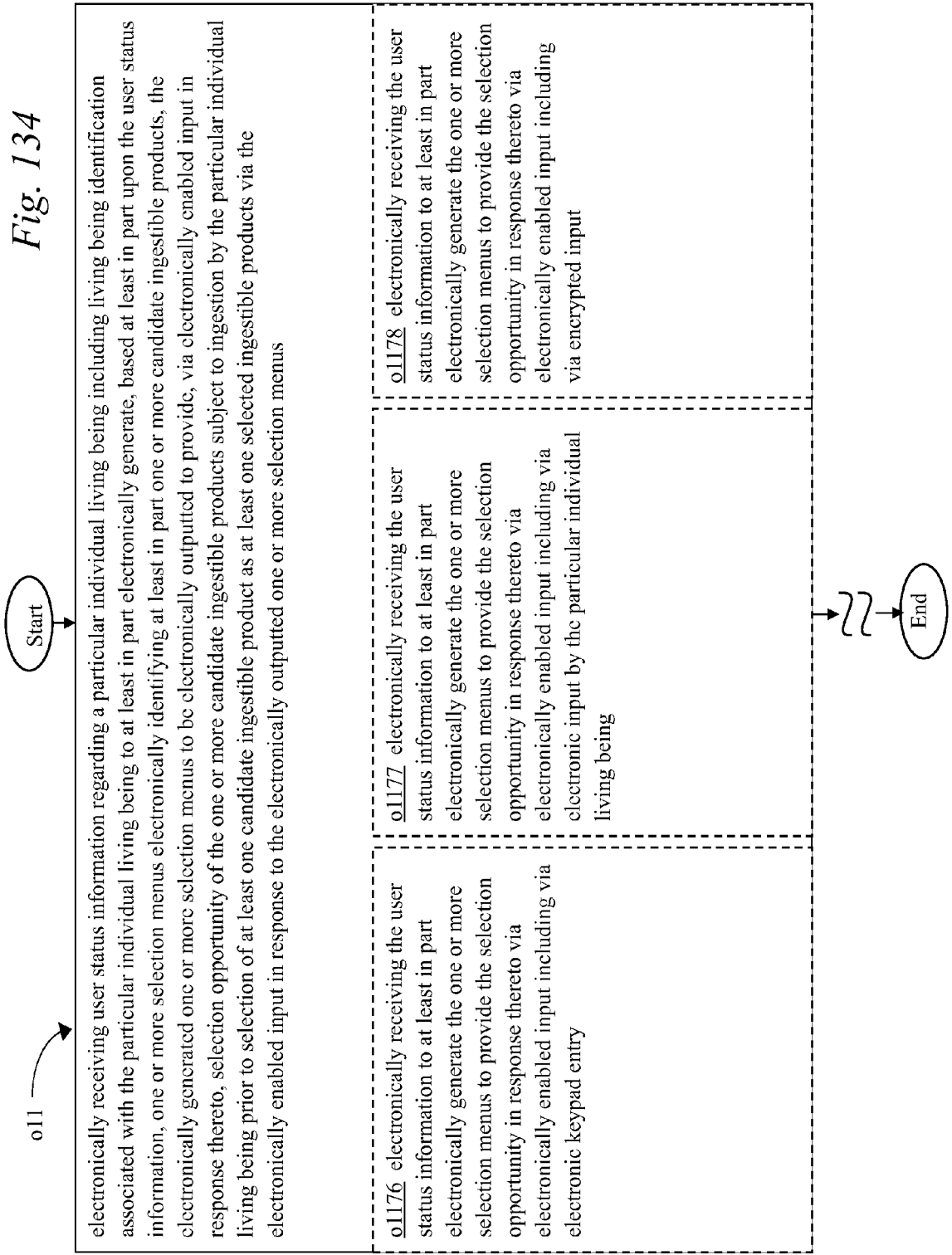

FIG. 134 is a high-level flowchart including exemplary implementations of operation p11 of FIG. 108.

Figure 135:
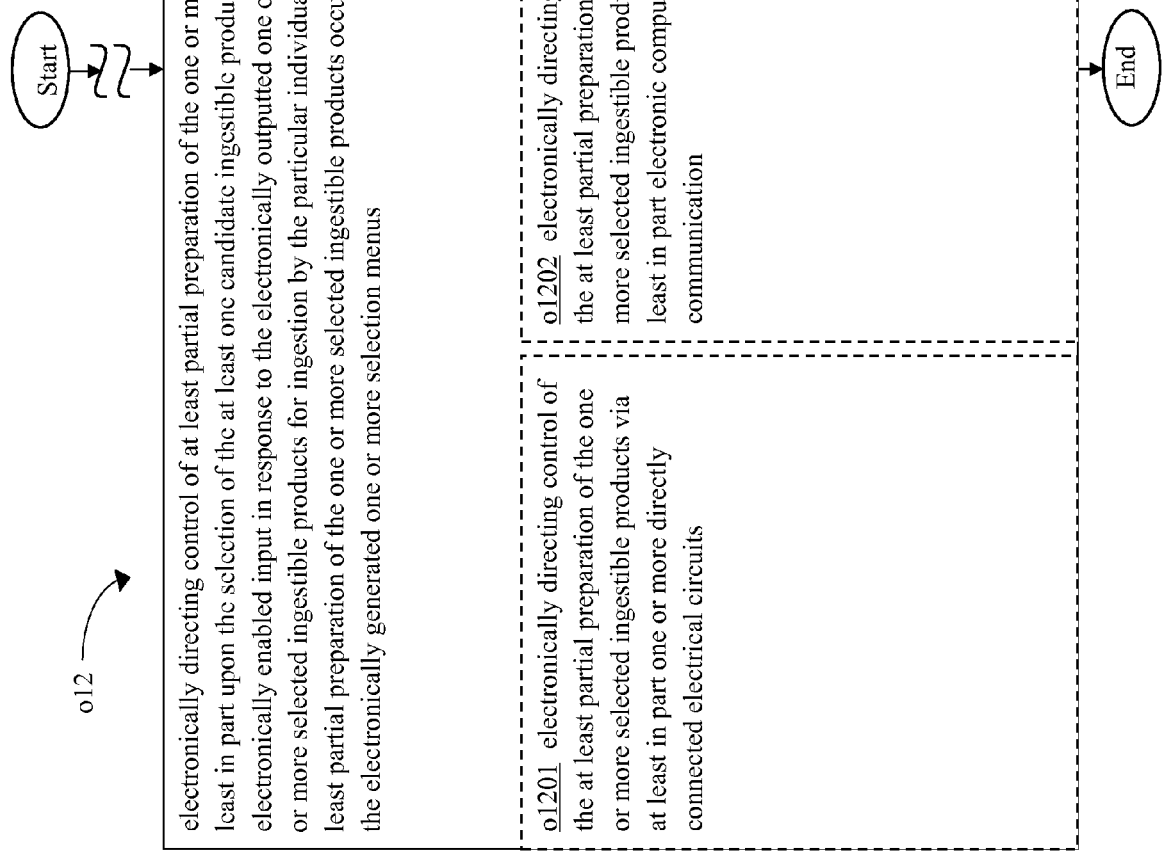

FIG. 135 is a high-level flowchart including exemplary implementations of operation p12 of FIG. 108.

Figure 136:
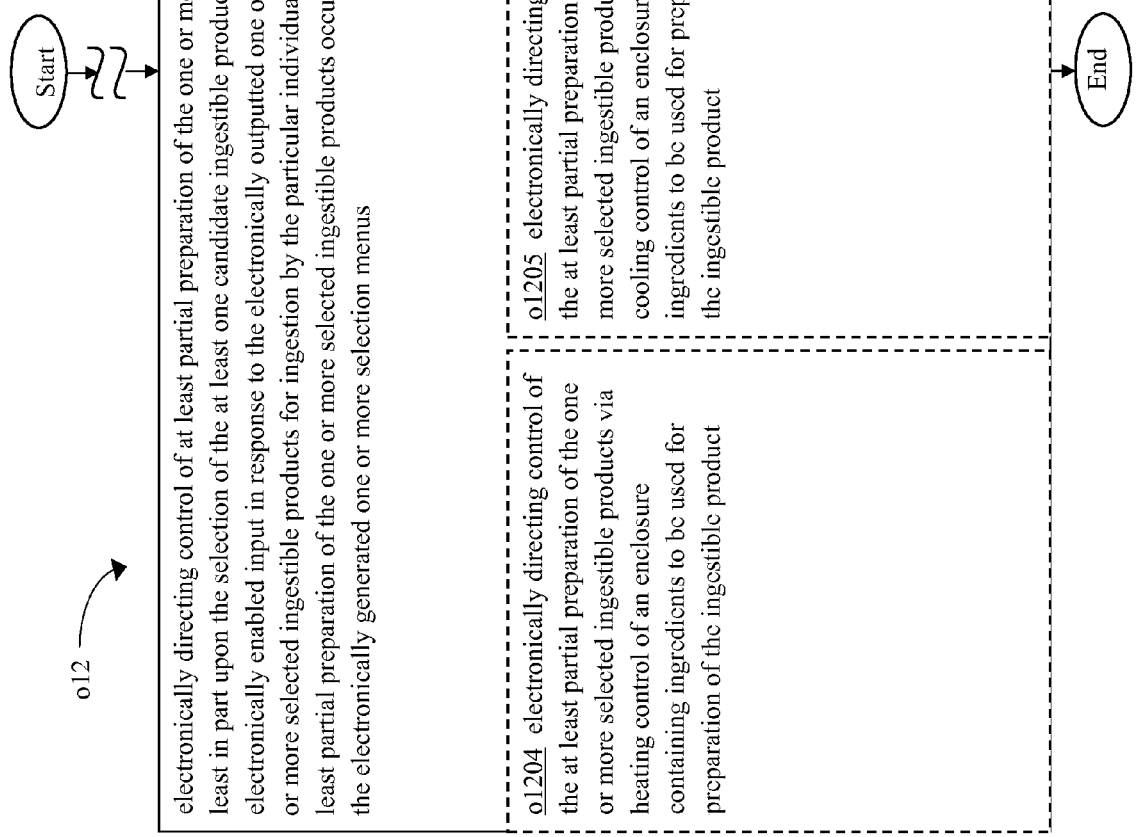

FIG. 136 is a high-level flowchart including exemplary implementations of operation p12 of FIG. 108.

FIG. 137 is a high-level flowchart including exemplary implementations of operation p12 of FIG. 108.

FIG. 138 is a high-level flowchart including exemplary implementations of operation p12 of FIG. 108.

FIG. 139 is a high-level flowchart including exemplary implementations of operation p12 of FIG. 108.

Figure 140:
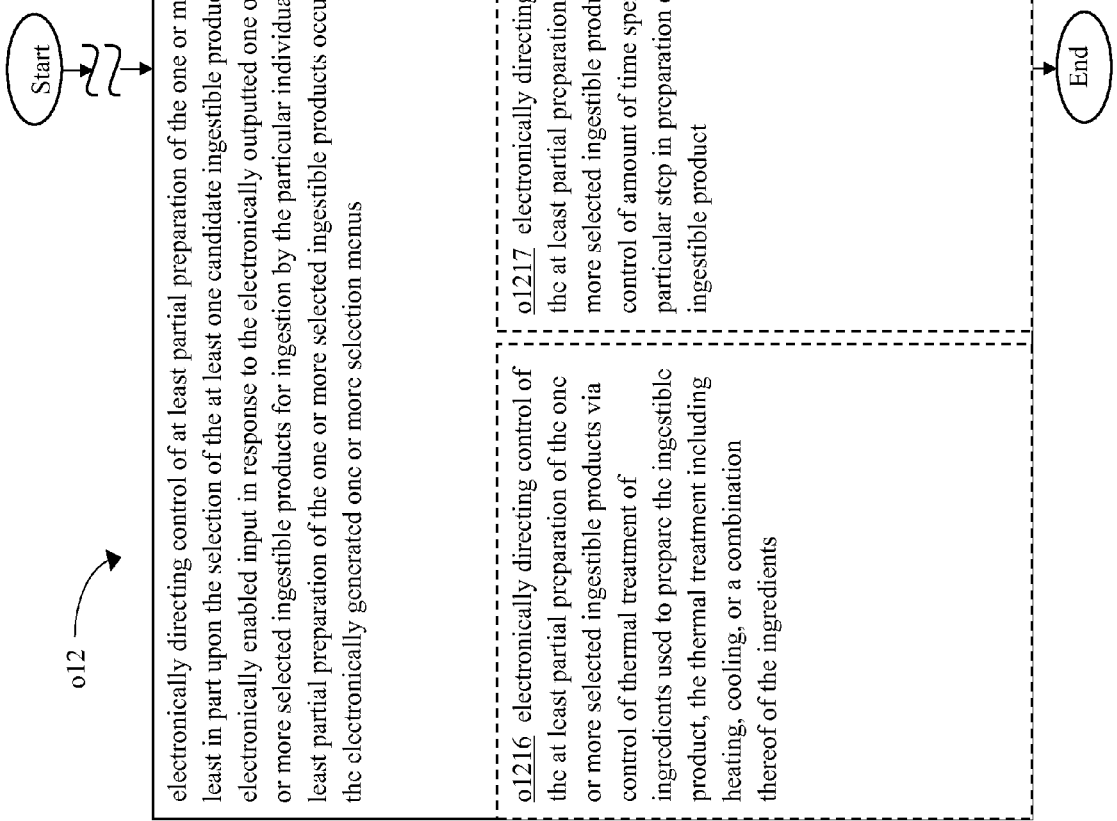

FIG. 140 is a high-level flowchart including exemplary implementations of operation p12 of FIG. 108.

Figure 141:
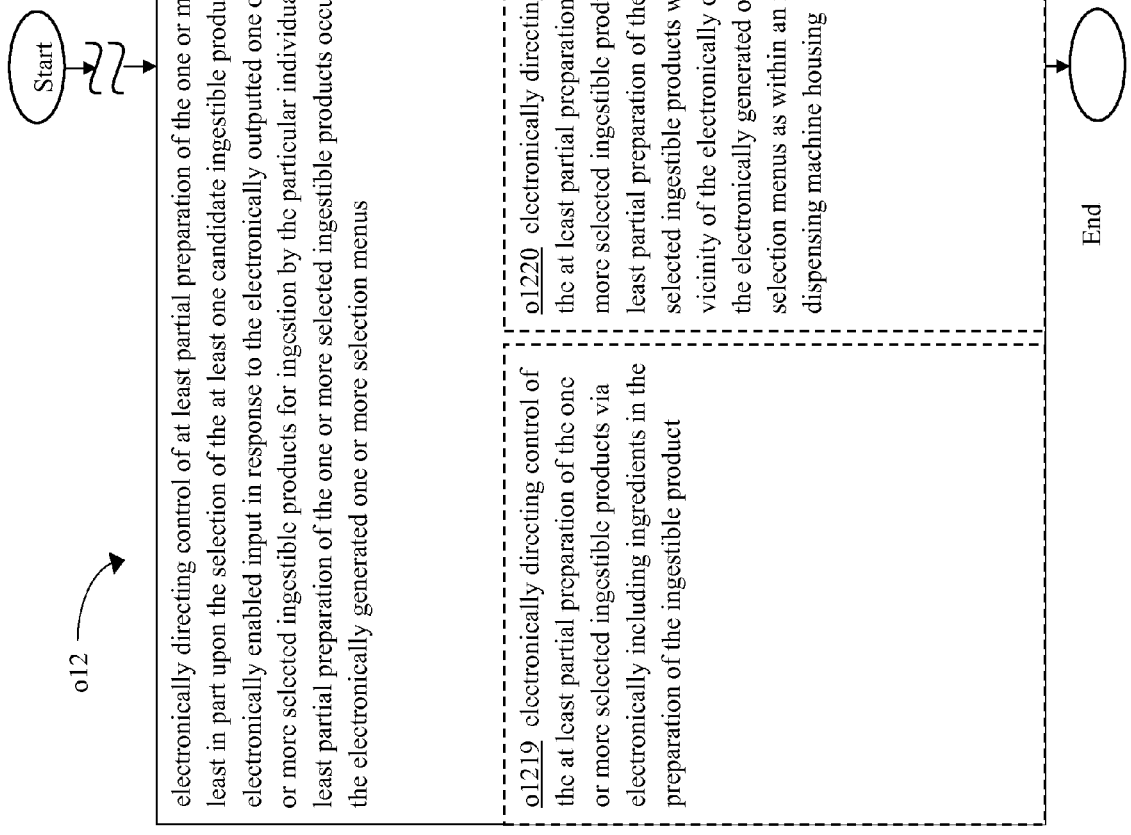

FIG. 141 is a high-level flowchart including exemplary implementations of operation p12 of FIG. 108.

Figure 142:
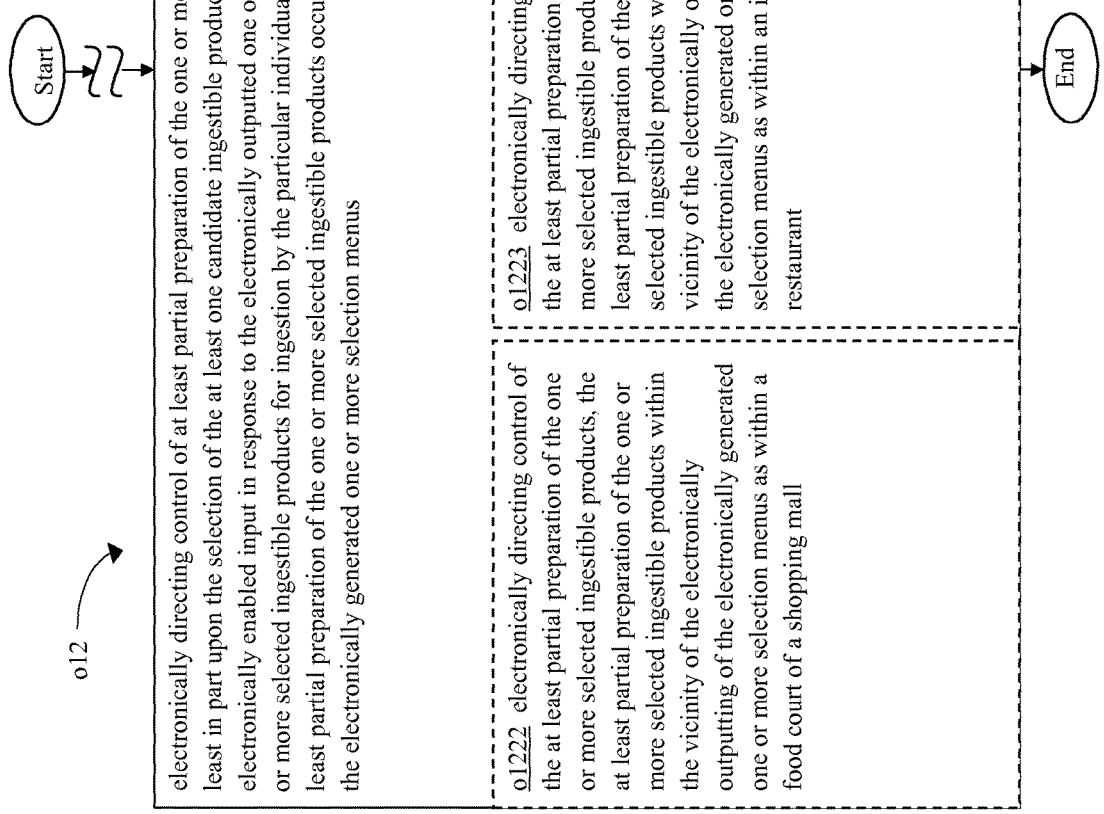

FIG. 142 is a high-level flowchart including exemplary implementations of operation p12 of FIG. 108.

Figure 143:
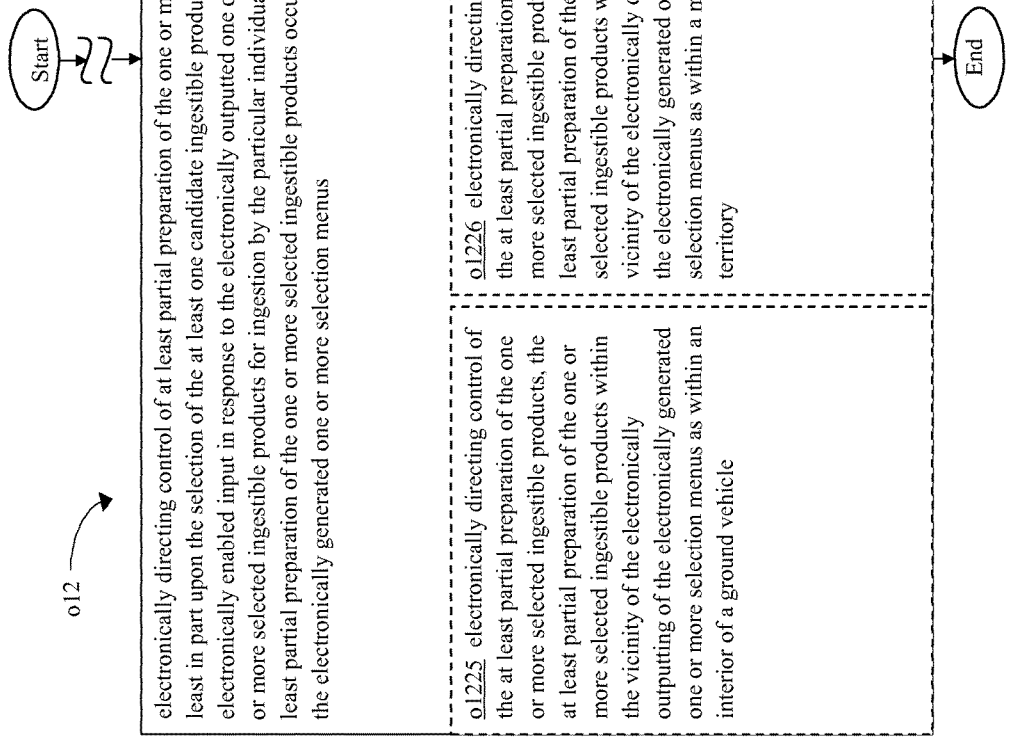

FIG. 143 is a high-level flowchart including exemplary implementations of operation p12 of FIG. 108.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare and/or dispense ingestible products to be ingested by living beings such as humans, animals, plants, etc are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared and/or dispensed by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Ingestion by the living beings can occur through many pathways including, but not limited to, oral ingestion, transdermal ingestion, peg-tube ingestion, nasal ingestion, anal ingestion, injectable ingestion, tear-duct ingestion, and respiratory ingestion.

Figure 1:
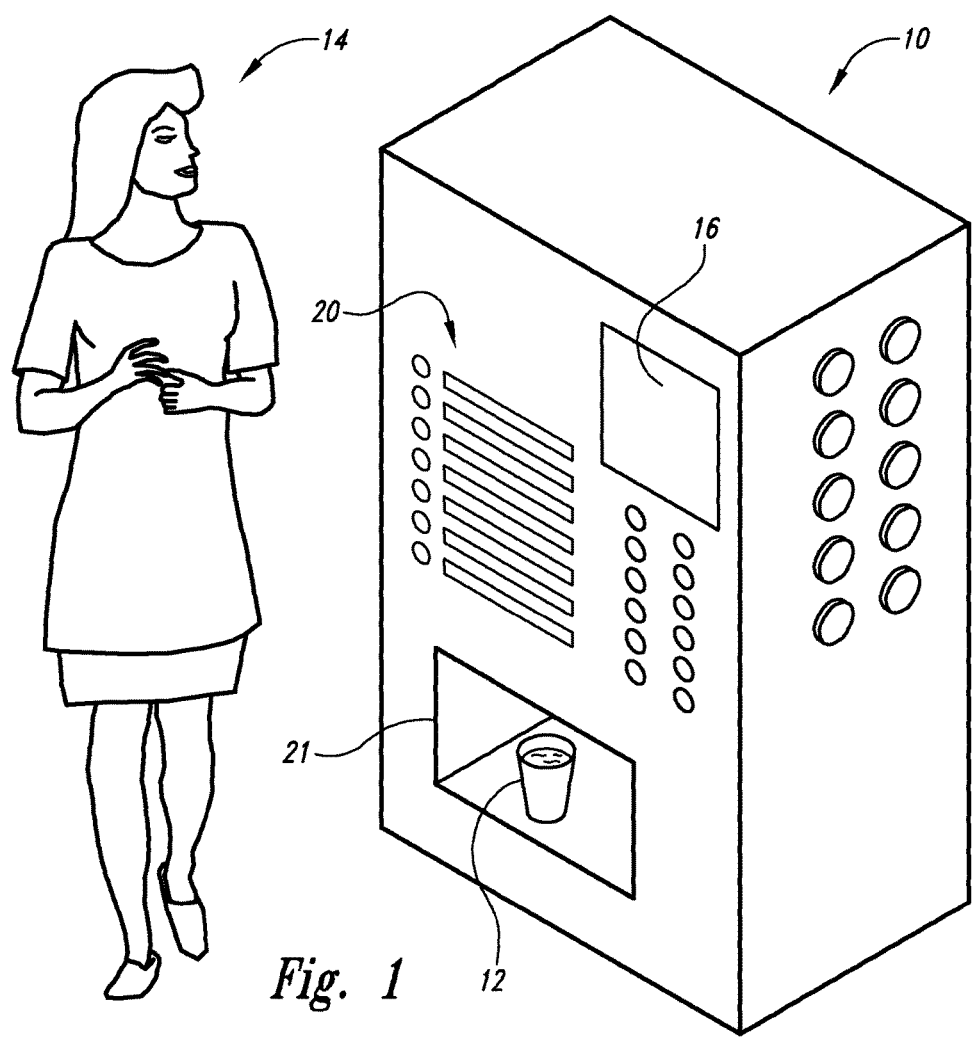
FIG. 1 is a schematic diagram depicting a first application of a first exemplary implementation of a ingestible product preparation system 10 including a selection information system.
Figure 1A:
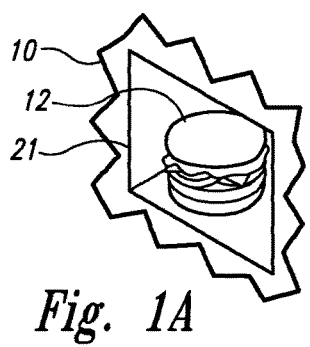
FIG. 1A is a fragmentary view depicting a second application of the first exemplary implementation of the ingestible product preparation system 10 of FIG. 1.
Figure 1B:
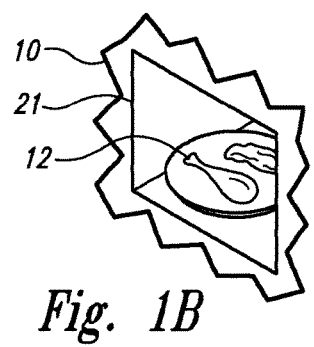
FIG. 1B is a fragmentary view depicting a third application of the first exemplary implementation of the ingestible product preparation system 10 of FIG. 1.
Figure 1C:
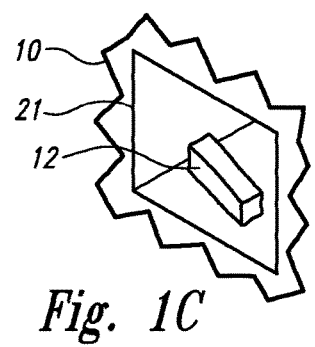
FIG. 1C is a fragmentary view depicting a fourth application of the first exemplary implementation of a ingestible product preparation system 10 including a substance allocation system therefor.
Figure 2:
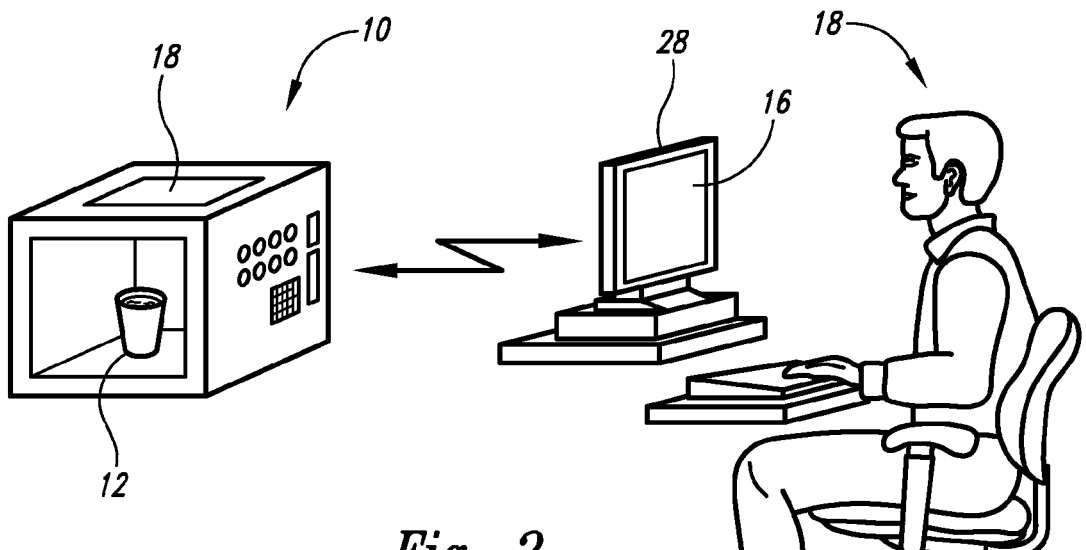
FIG. 2 is a schematic diagram depicting a first application of a second exemplary implementation of the ingestible product preparation system 10 of FIG. 1 including the selection information system.
Figure 3:
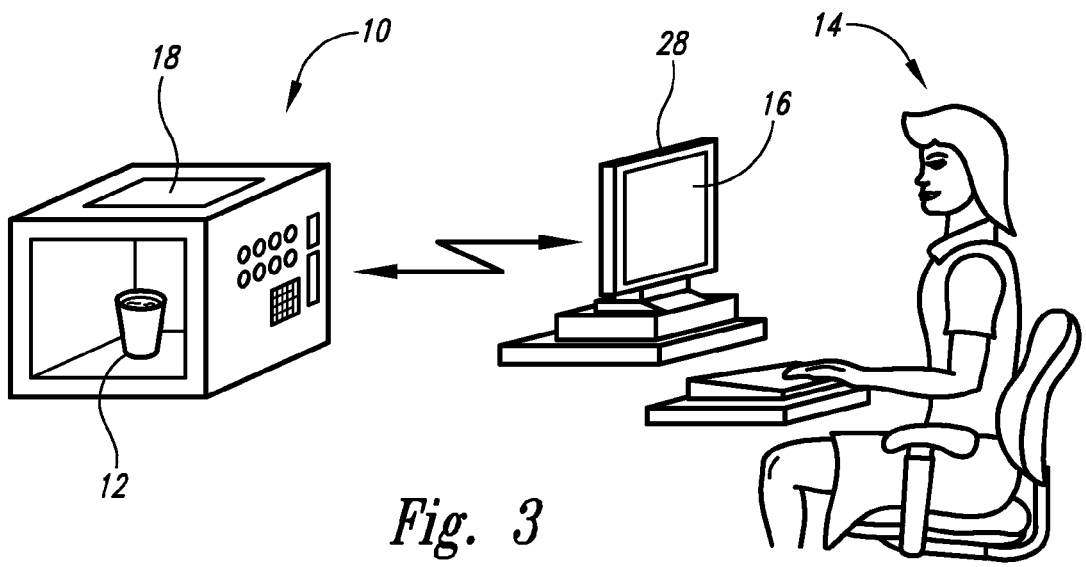
FIG. 3 is a schematic diagram depicting a second application of the second exemplary implementation of the ingestible product preparation system 10 of FIG. 1 including the selection information system.

As depicted in FIGS. 1-3, exemplary implementations of an ingestible product preparation system 10 are shown to prepare and dispense ingestible products such as a liquid drink 12 (shown in dispensing area 21) to be consumed by a particular individual living being, such as a human being 14 (such as a user, etc.) shown. Exemplary implementations determine selection menus to be generated and outputted, for instance, on display 16 and selections or other information can be inputted through user interfaces, for instance, user input 20 or other types of user input. For instance, input may be collected through active user input (e.g. keyboard, textual, audio, graphical user interface, etc.) or passive user input (e.g. image recognition of user behavior, refuse analysis of past dispensing such as quantity of wrappers, leftovers, audio analysis of collected unsolicited user comments, etc.). Selection menus can be generated that are unique to a particular individual living being, such as the human being 14, based upon such information as but not limited to identification of the individual and other information such as past selections, allergies, preferences, specials, holidays, location of preparation, location of dispensing, time of day, dislikes, recent ingestion, health goals, present illness, past illness, sports requirements, injuries, fads, hobbies, associated social organizations, etc. Other sorts of ingestible products can include but are not limited to sandwiches (FIG. 1A), full meals (FIG. 1B), food bars (FIG. 1C), meal replacements, snacks, plant and/or animal based products, nutraceuticals, pharmaceuticals, smoothies, etc.

The ingestible product preparation system 10 is further depicted in FIGS. 2 and 3 as communicating with the human being 14 an exemplary remotely located user or an exemplary advisor 18 (e.g. physician, nurse, nutritionist, health expert, sports coach, etc.) via a communication link (e.g. wireless or wired network or direct electronic communication, etc.) and display screen 28. The display screen 28 can include selection indicators configured to provide information described above by the users and advisors. The display screen 28 can also output generated selection menus based upon identification of the particular individual living being and other information including that described above. Selection menus can be furnished to suggest candidate ingestible products that once selected as selected ingestible products can be prepared and dispensed (in some implementations prepared such as from ingredient containers 22) and to provide other sorts of information discussed herein. The display screen 28 can display textual and graphic information such as including but not limited to menu screens allowing users to select various dispensing (including in some implementations preparation) options and information requests. Other implementations can include other devices and methods for information input and output including those further discussed below.

Figure 4:
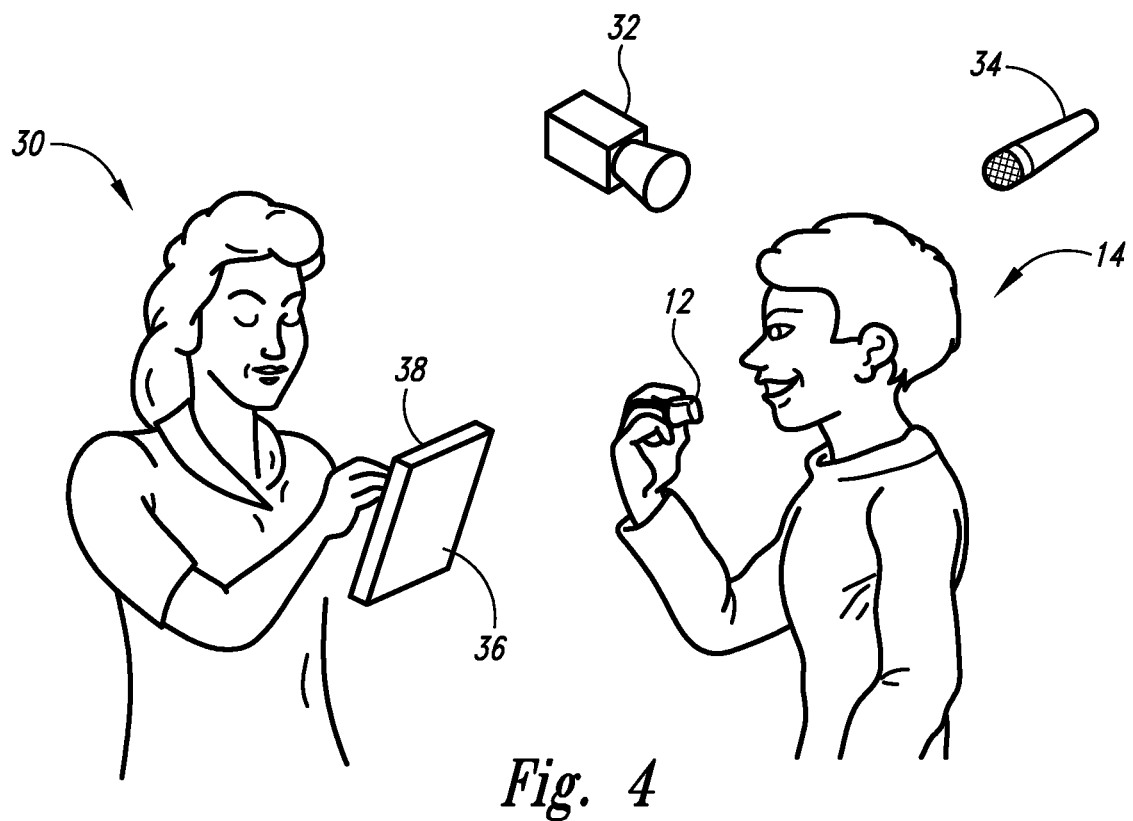
FIG. 4 is a schematic view depicting first implementations of acquisition of ingestion intelligence related to the ingestible product preparation system 10 in FIG. 1 displaying first content.
Figure 5:
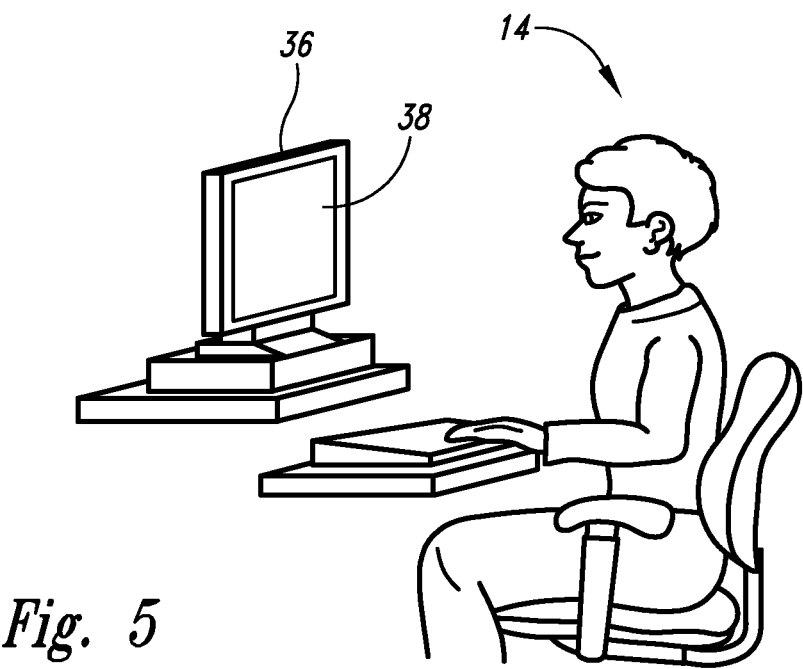
FIG. 5 is a schematic view depicting a second implementation of acquisition of ingestion intelligence related to the ingestible product preparation system 10 in FIG. 1 displaying second content.

Exemplary acquisition of ingestion intelligence information is depicted in FIG. 4 involving waitress 30 using electronic tablet 36 with interface screen 38, video camera 32, microphone 34 to collect information such as regarding topics of conversation, digestion rates, arrangement of tables, chairs, types of furnishings, types of clothing worn, types of tips left, etc. FIG. 5 depicts user 14 with monitor 36 and display screen 38 inputting other ingestion intelligence information such how the user feels about themselves and/or how the user feels about the ingested material such as a smoothie.

Figure 6:
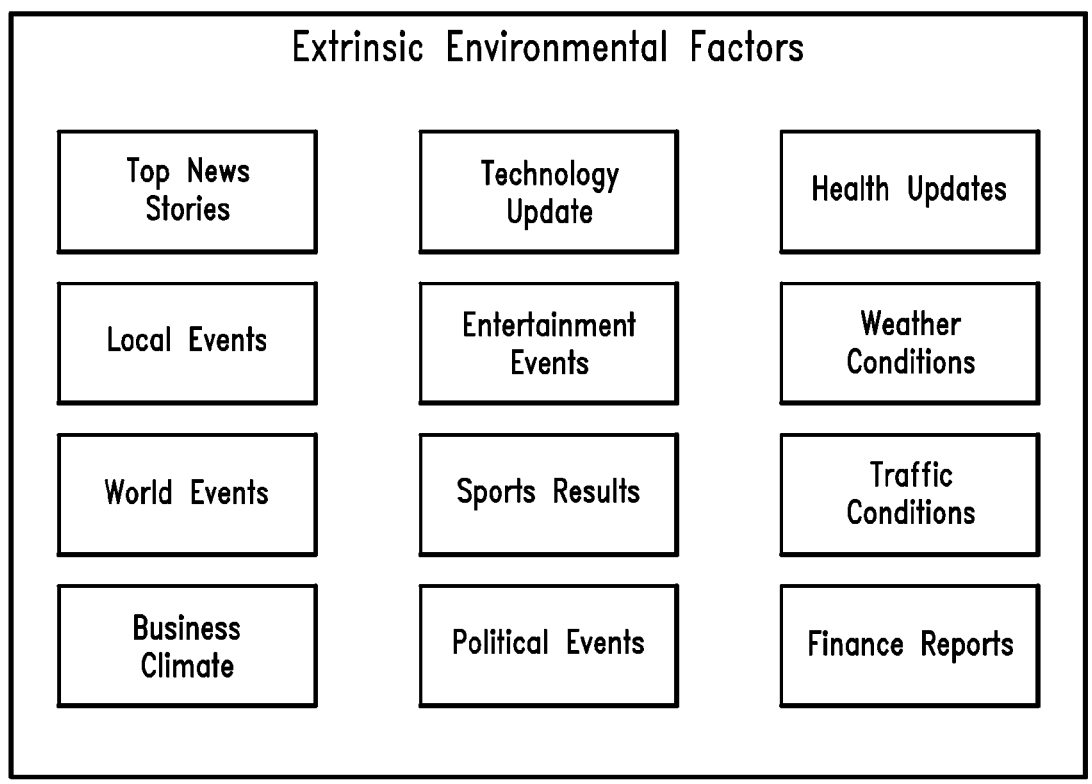
FIG. 6 is a schematic diagram depicting some acquired acquisition intelligence information of extrinsic environmental factors related to the ingestible product preparation system 10 in FIG. 1.

FIG. 6 depicts some extrinsic environmental factors that can be part of the ingestion intelligence information acquired such as top news stories, technology updates, health updates, local events, entertainment events, weather conditions, world events, sports results, traffic conditions, business climate, political events, finance reports, etc. as associated with ingestion by a particular individual living being of ingestible material prepared by the ingestible product preparation system 10.

Figure 7:
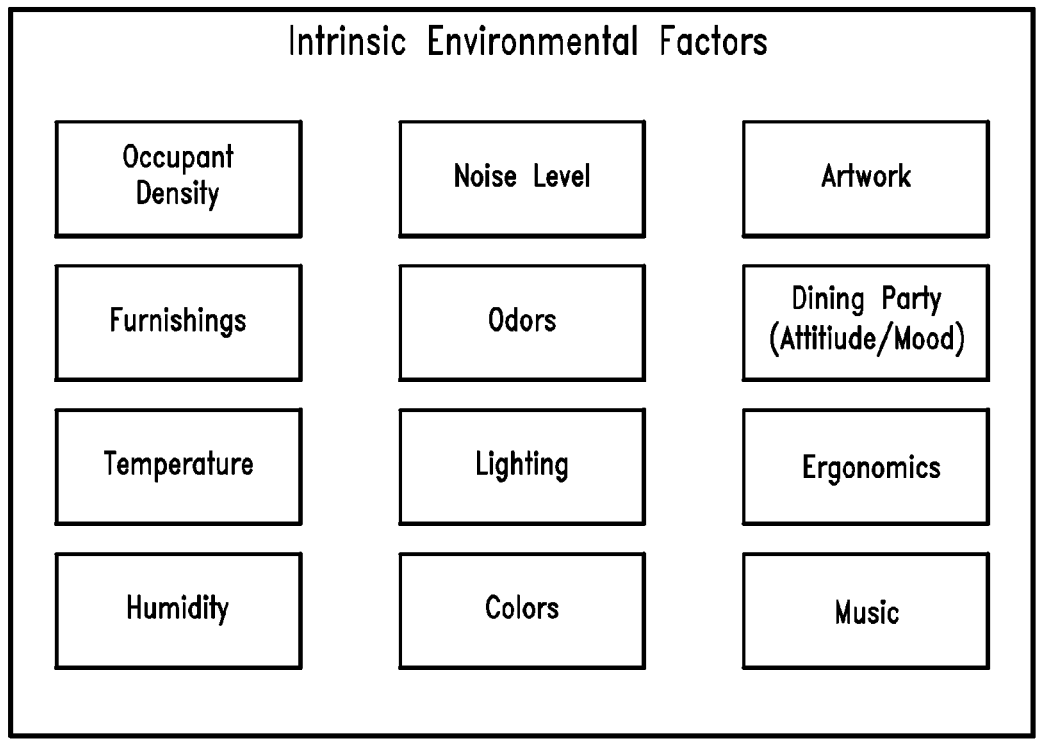
FIG. 7 is a schematic diagram depicting some acquired acquisition intelligence information of intrinsic environmental factors related to the ingestible product preparation system 10 in FIG. 1.

FIG. 7 depicts some intrinsic environmental factors that can be part of the ingestion intelligence information acquired such as occupant density, noise level, artwork, furnishings, olefactory factors such as odors, etc, dining party factors such as type, mood, size, etc, temperature and/or humidity level such as that of the air in contact with the particular individual living being, lighting factors such as intensity and/or spectrum, etc, ergonomics such as that of chairs, tables, arrangements of furniture involved, colors and/or music as associated with ingestion by a particular individual living being of ingestible material prepared by the ingestible product preparation system 10.

Figure 8:
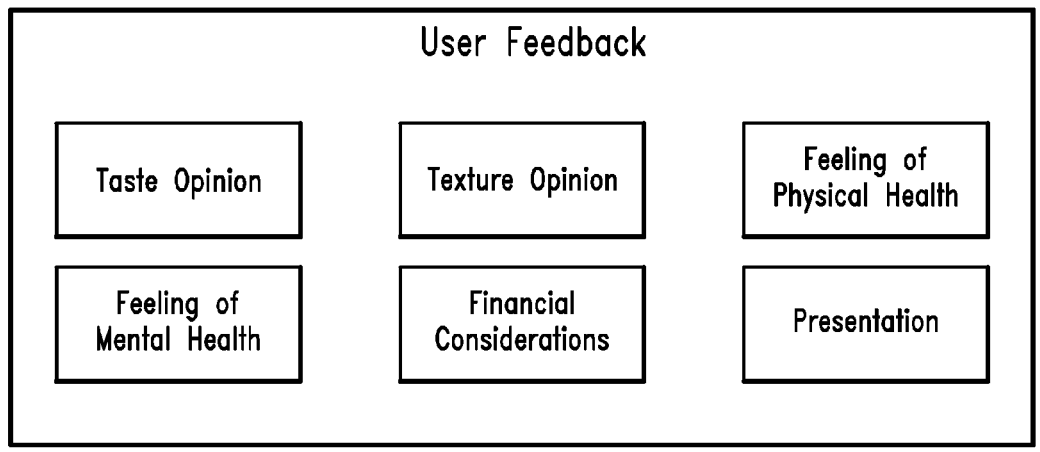
FIG. 8 is a schematic diagram depicting some acquired acquisition intelligence information of user feedback factors related to the ingestible product preparation system 10 in FIG. 1.

FIG. 8 depicts some user feedback factors that can be part of the ingestion intelligence information acquired such as taste opinion, texture opinion, feeling of physical health, feeling of mental health, financial considerations, and opinion on presentation of ingestible material, etc. as associated with ingestion by a particular individual living being of ingestible material prepared by the ingestible product preparation system 10.

Figure 9:
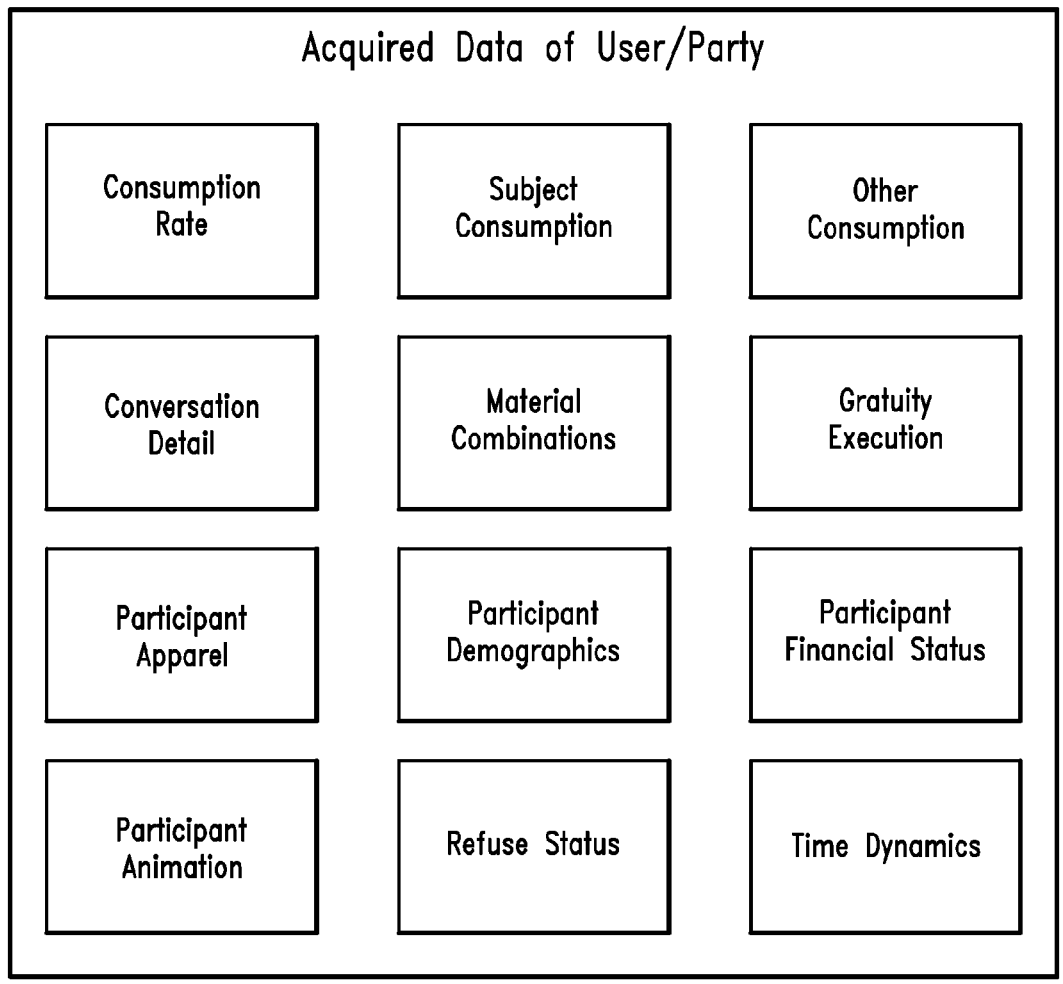
FIG. 9 is a schematic diagram depicting some acquired acquisition intelligence information of user/party factors related to the ingestible product preparation system 10 in FIG. 1.

FIG. 9 depicts some user (e.g. the particular individual living being) and/or dining party factors that can be part of the ingestion intelligence information acquired such as consumption rate that the user ingests the ingestible material, subject context of ingestion such as a special occasion or routine meal, other consumption or ingestion factors such as physical health of the user, conversation detail associated with discussion among members of a dining party including the user, material combinations that the ingestible product was combined with during ingestion, gratuity execution such as the amount of the tip left for the wait staff, participant apparel such as clothing worn by the user or other members of the dining party including the user, participant demographics of the user and/or others in the user's dining party, financial status of user and/or others in user's dining party, how animated the user or others in the user's dining party is, refuse status regarding what and how much of the ingestible material was not ingested by the user and/or the other members of the user's dining party, or time dynamics including amount of time taken to wait for a table, wait for the menus, wait for the order to be taken, wait for the food to be prepared and served, wait for the bill to delivered, wait for the bill to be paid, and amount of time taken to continue to occupy the dining space after the bill was paid as associated with ingestion by a user (e.g. particular individual living being) of ingestible material prepared by the ingestible product preparation system 10.

Figure 10:
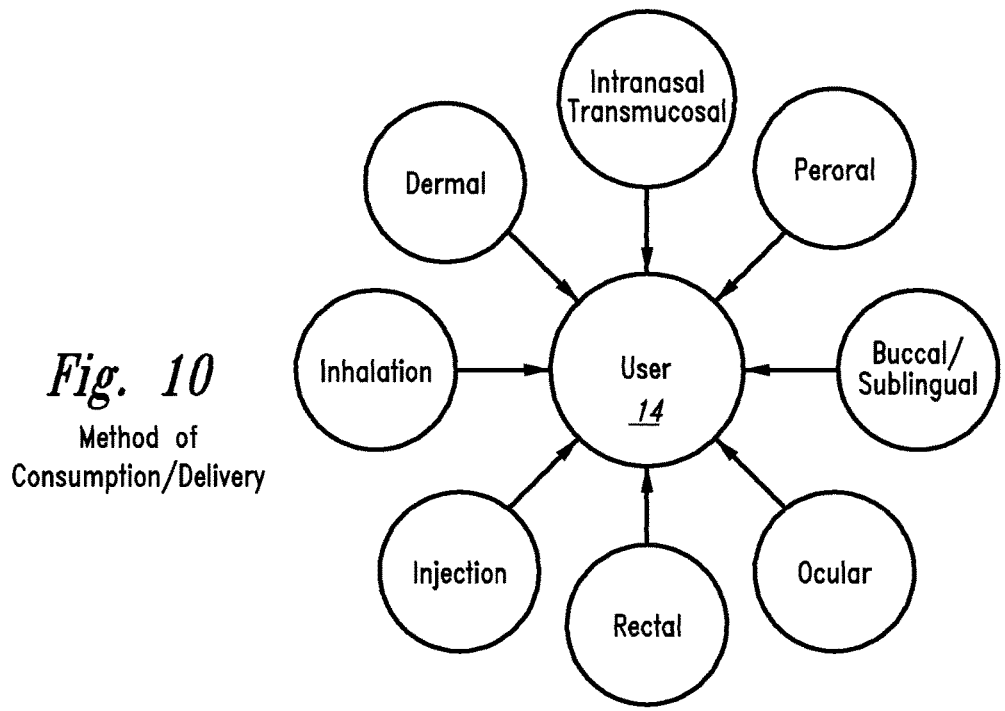
FIG. 10 is a schematic diagram depicting some acquired data of factors regarding methods of ingestion of ingestible products prepared by implementations of the ingestible product preparation system 10 in FIG. 1.

FIG. 10 depicts methods of ingestion by the user including consumption methods and delivery methods such as dermal, intranasal, transmucosal, peroral, buccal, sublingual, ocular, rectal, injection, and inhalation, etc. as associated with ingestion by a particular individual living being of ingestible material prepared by the ingestible product preparation system 10.

Figure 11:
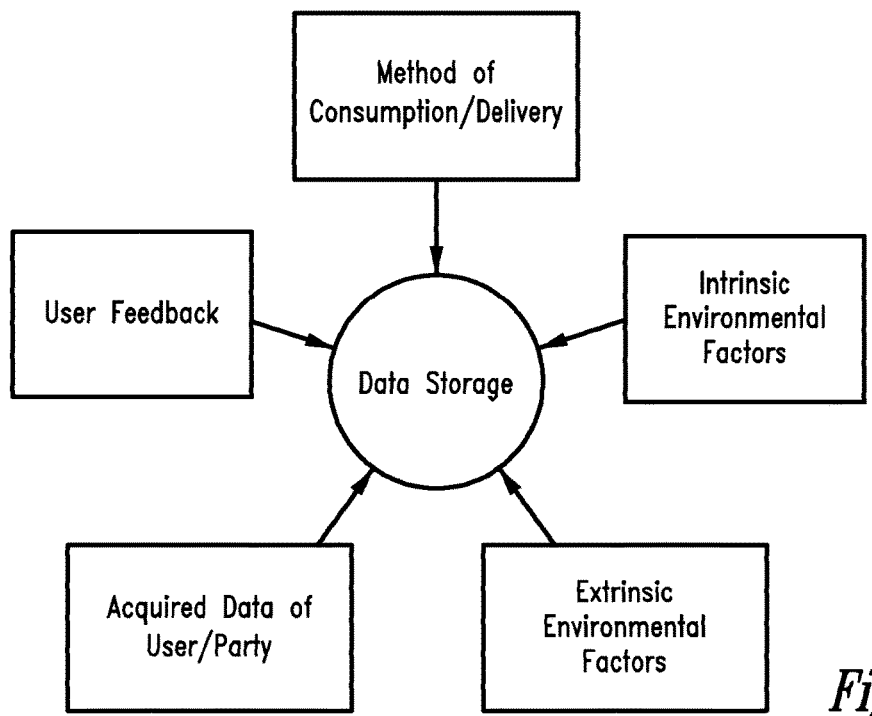
FIG. 11 is a schematic diagram depicting various acquisition types of ingestion intelligence information related to the ingestible product preparation system 10 in FIG. 1.

FIG. 11 depicts main modes and types of acquisition of ingestion intelligence such as methods of consumption and/or delivery, intrinsic environmental factors, extrinsic environmental factors, acquired data of user and/or party, and user feedback, etc. as associated with ingestion by a particular individual living being of ingestible material prepared by the ingestible product preparation system 10.

Figure 12:
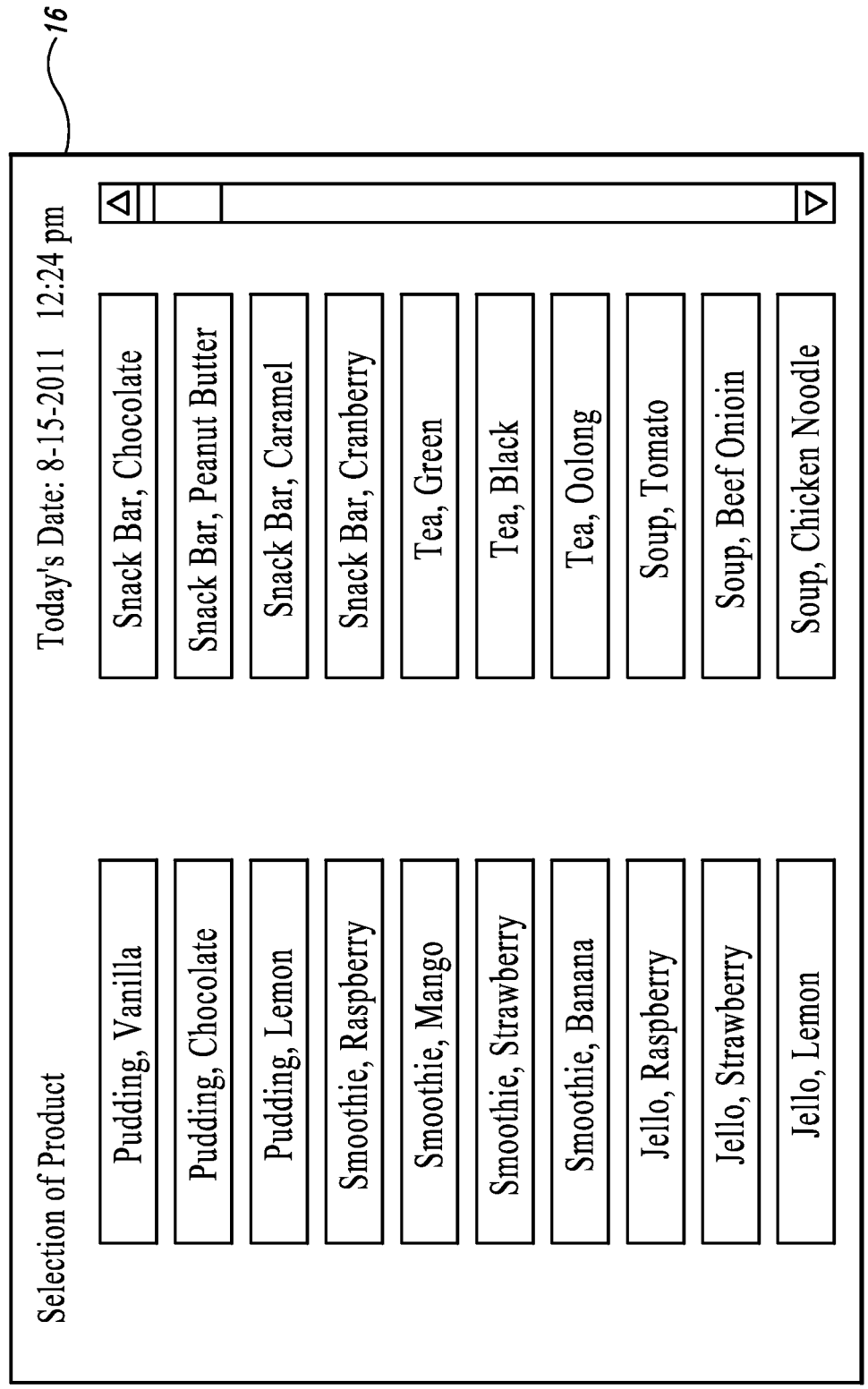
FIG. 12 is a schematic view of a display screen of the first exemplary implementation of the ingestible product preparation system 110 in FIG. 1 displaying first content.
Figure 13:
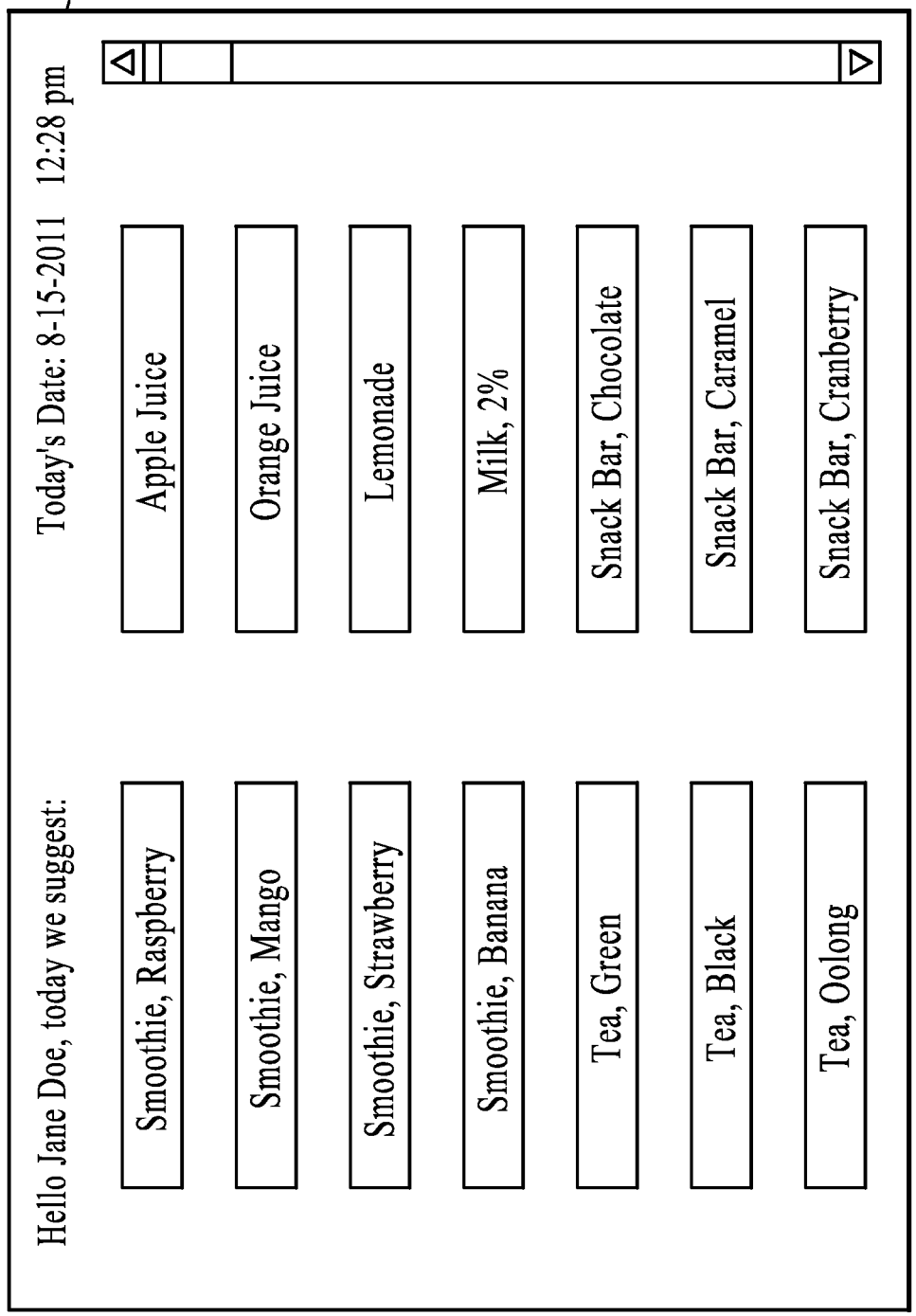
FIG. 13 is a schematic view of a display screen of the first exemplary implementation of the ingestible product preparation system 110 in FIG. 1 displaying second content.
Figure 14:
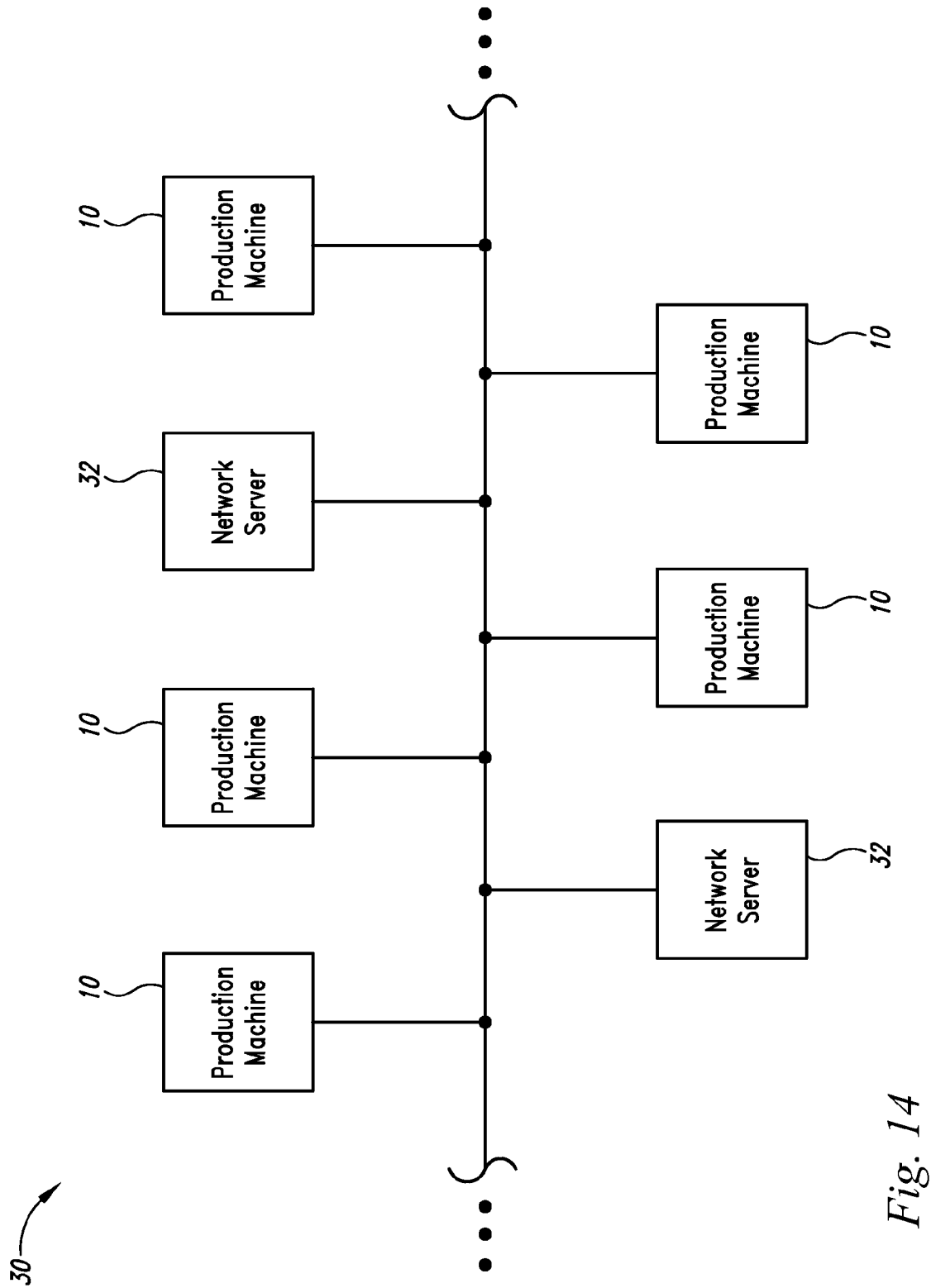
FIG. 14 is a schematic of an exemplary network implementation of the ingestible product preparation system 110 in FIG. 1.

Exemplary generated selection menus depicted in FIGS. 12 and 13 are in listed textual form, but other implementations can include but are not limited to graphical, audio, video, ingestible samples, maps of suggestions, hierarchical ordered arrangements and other sorts of arrangements, etc. As depicted in FIG. 14, information used to generate selection menus can be found on other machines networked, for example network 130, with the ingestible product preparation system (aka production machine) 110 such as being stored on network server 132.

Figure 15:
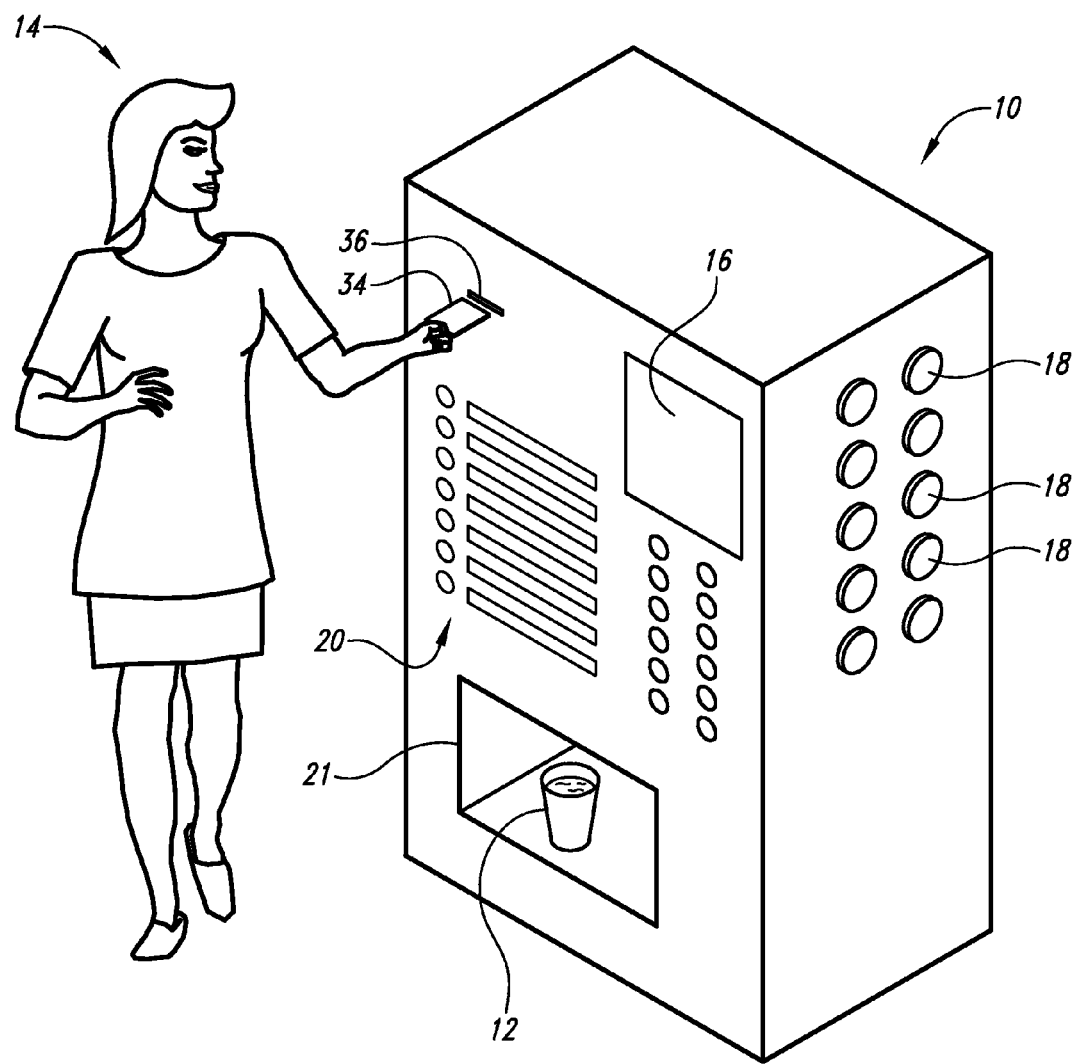
FIG. 15 is a schematic of an exemplary user identification implementation of the ingestible product preparation system 110 in FIG. 1.

Identification information and other information regarding the particular individual living being can be inputted directly to the ingestible product preparation system 110 or can be inputted through other devices to be stored apart from the ingestible product preparation system since in some implementations, the selection menus can be generated locally at the ingestible product preparation system whereas is other implementations the selection menus can be generated elsewhere to either be displayed elsewhere or to be sent to the digestible product preparation system to be displayed thereon. FIG. 15 depicts an exemplary implementation where at least some information such as identification information is inputted directly through a memory card 134 into receiving slot 136 to the ingestible product preparation system 110 to be used to generate selection menus either locally or remotely to then be displayed on the ingestible product preparation system. In other implementations, the memory card 134 can be inputted into a receiving slot found on another machine other than the ingestible product preparation system 110.

Figure 16:
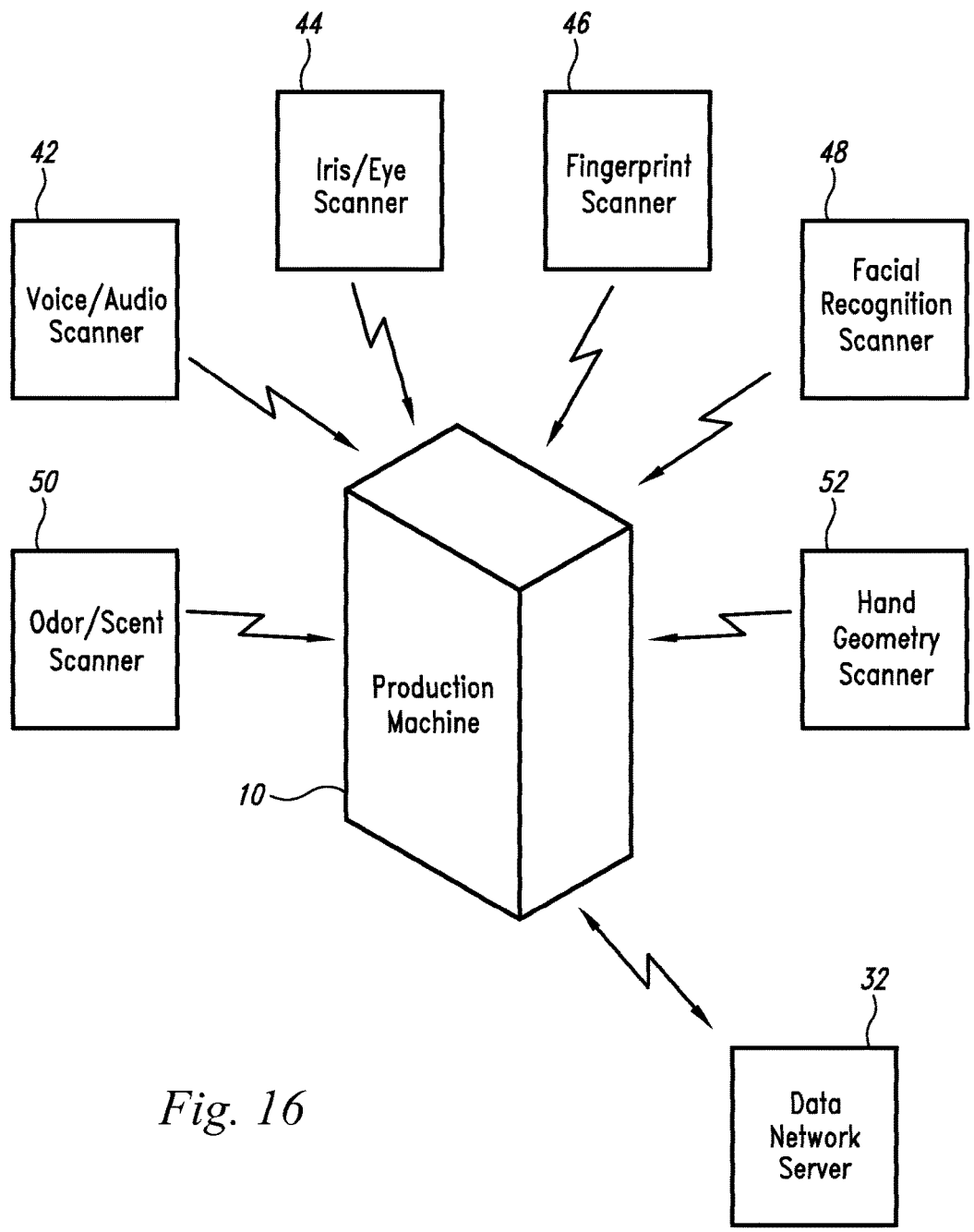
FIG. 16 is a schematic diagram depicting user identification implementations for the ingestible product preparation system 110 in FIG. 1.
Figure 17:
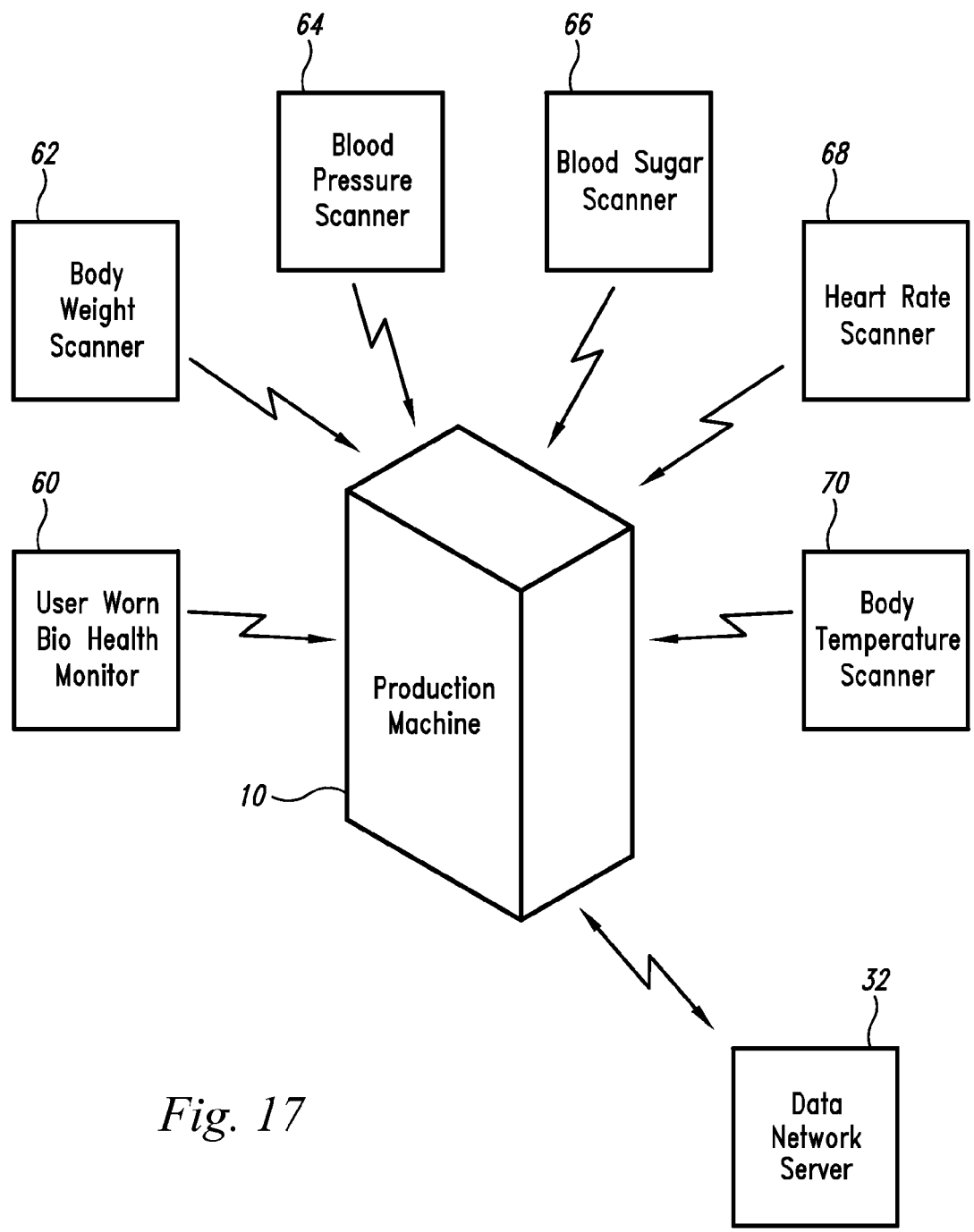
FIG. 17 is a schematic diagram depicting user identification implementations for the ingestible product preparation system 110 in FIG. 1.
Figure 18:
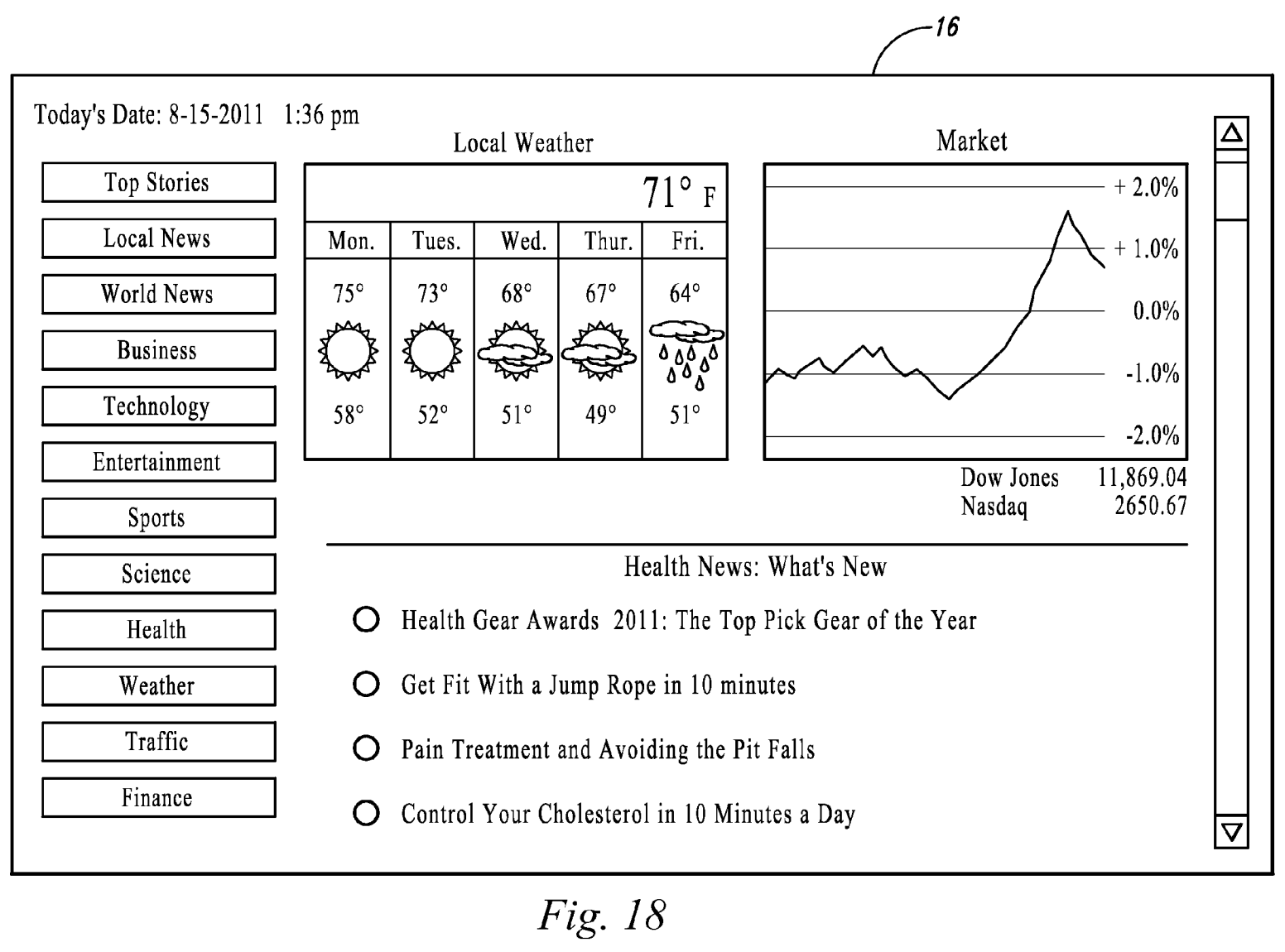

FIGS. 16 and 17 show other examples of various ways that information, such as identification information, can be inputted directly to the ingestible product preparation system 110. Alternatively, these depicted ways that information can be inputted and other ways can be inputted to other devices that are electronically linked to the ingestible product preparation system 110 so that selection menus can be generated directly by the ingestible product preparation system 110 or elsewhere, such as the network server 132, to be outputted at the ingestible product preparation system or elsewhere. The input ways depicted in FIG. 16 include voice/audio scanner 142, iris/eye scanner 144, fingerprint scanner 146, facial recognition scanner 148, odor/scent scanner 150, and hand geometry scanner 152. The input ways depicted in FIG. 17 include user worn bio health monitor 160 (for instance, tracking blood pressure, blood sugar, urea, temperature, activity, heart rate, EKG, ECG, hormone levels, nerve activity, other blood levels, etc), body weight scanner 162, blood pressure scanner 164, blood sugar scanner 166, heart rate scanner 168, and body temperature scanner 170. Other information can be displayed on other screens to complement the selection menus as depicted in FIG. 18.

Figure 19:
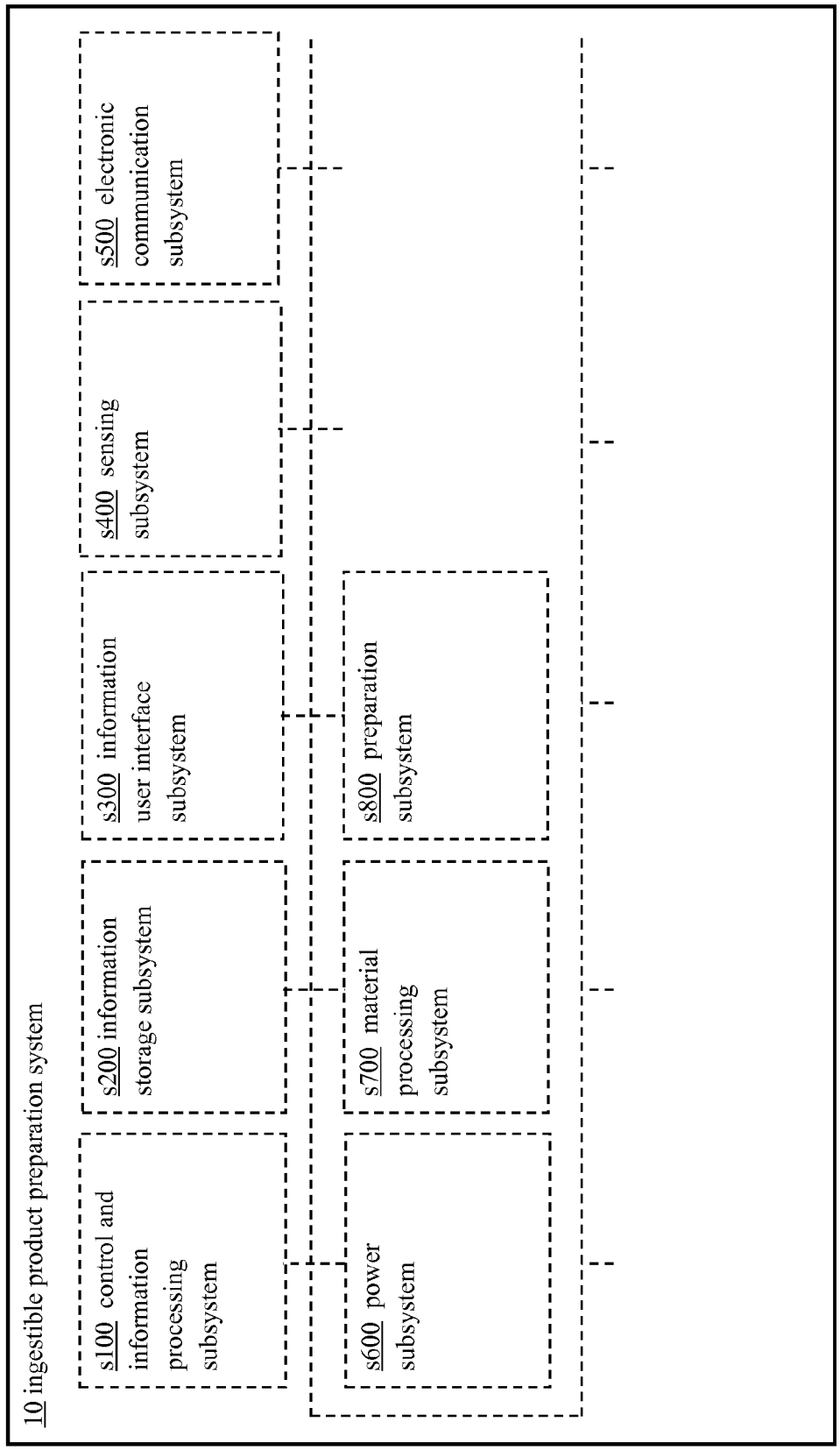
FIG. 19 is a block diagram depicting an exemplary implementation of the ingestible product preparation system 10 of FIG. 1 including exemplary subsystems.

An exemplary version of the ingestible product preparation system 10 is shown in FIG. 19 to optionally include various subsystems such as control and information processing subsystem s100, information storage subsystem s200, information user interface subsystem s300, sensing subsystem s400, electronic communication subsystem s500, power subsystem s600, material processing subsystem s700, and preparation subsystem s800.

Figure 20:
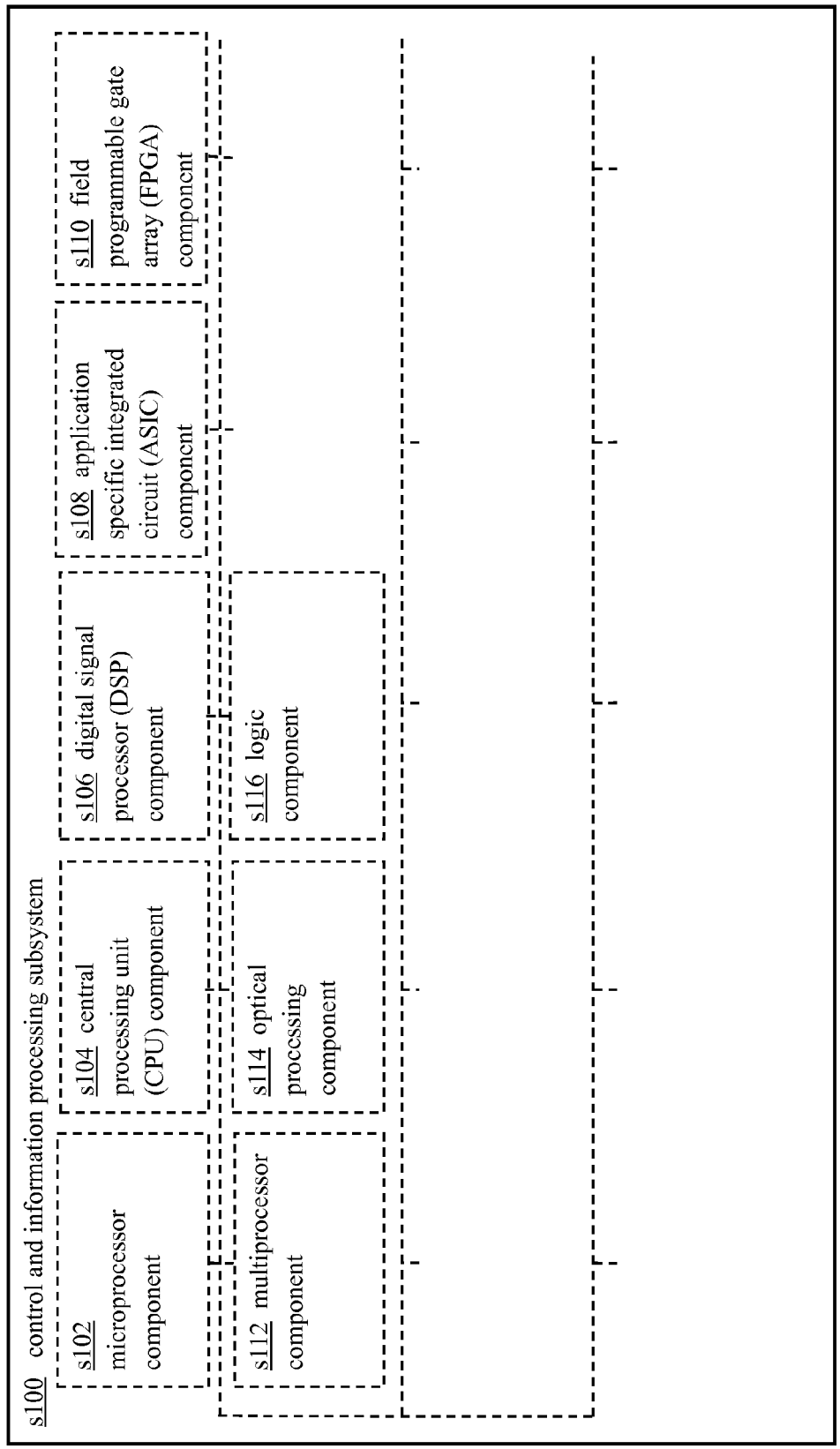
FIG. 20 is a block diagram depicting a control and information processing subsystem s100 of an exemplary implementation of the ingestible product preparation system 10 of FIG. 1.

An exemplary implementation of the control and information processing subsystem s100 is shown in FIG. 20 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, optical processing component s114, and logic component s116.

Figure 21:
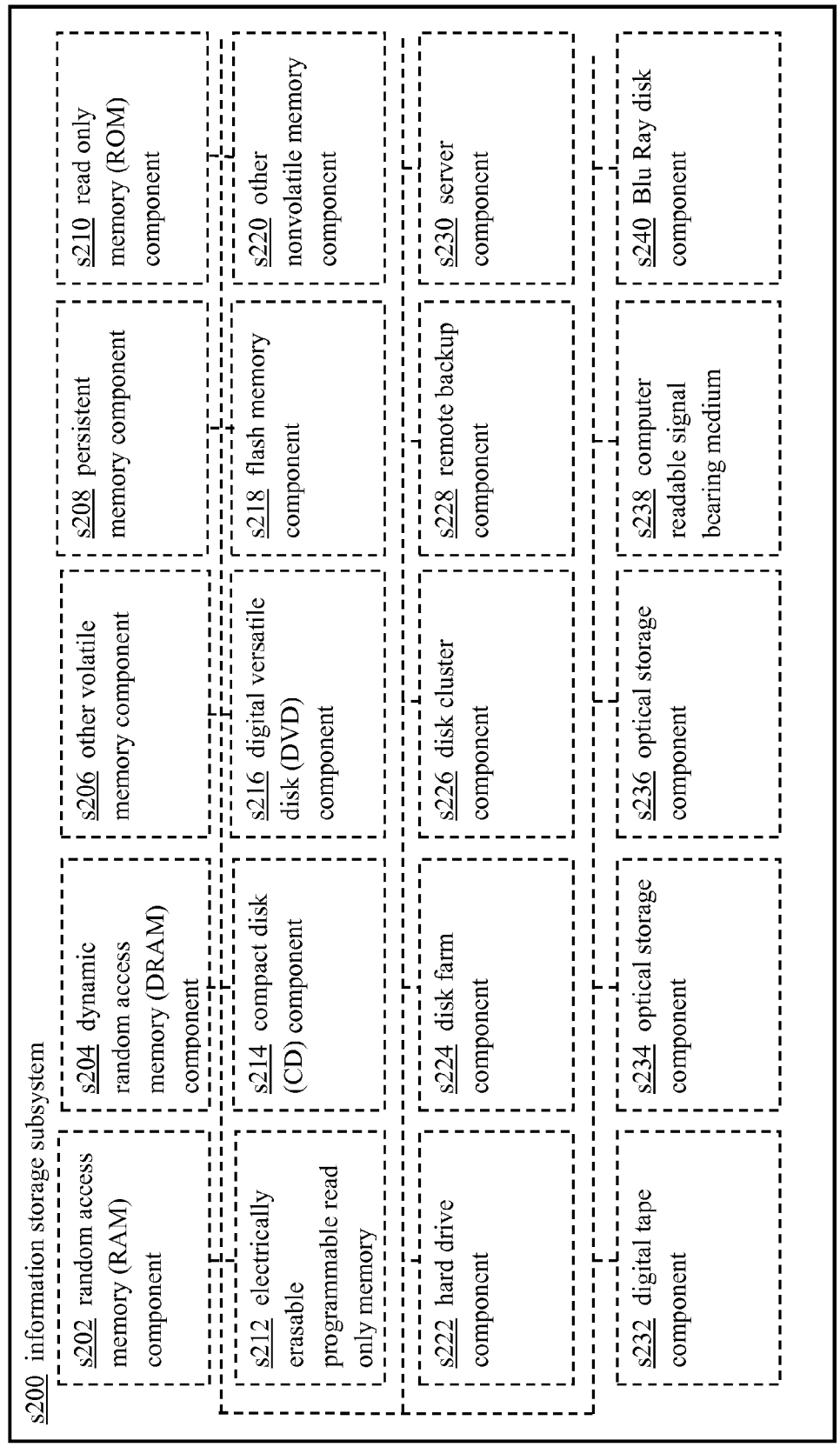
FIG. 21 is a block diagram depicting an information storage subsystem s200 of an exemplary implementation of the ingestible product preparation system 10 of FIG. 1.

An exemplary implementation of the information storage subsystem s200 is shown in FIG. 21 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, optical storage component s236, computer readable signal bearing medium s238, and Blu Ray disk component s240.

Figure 22:
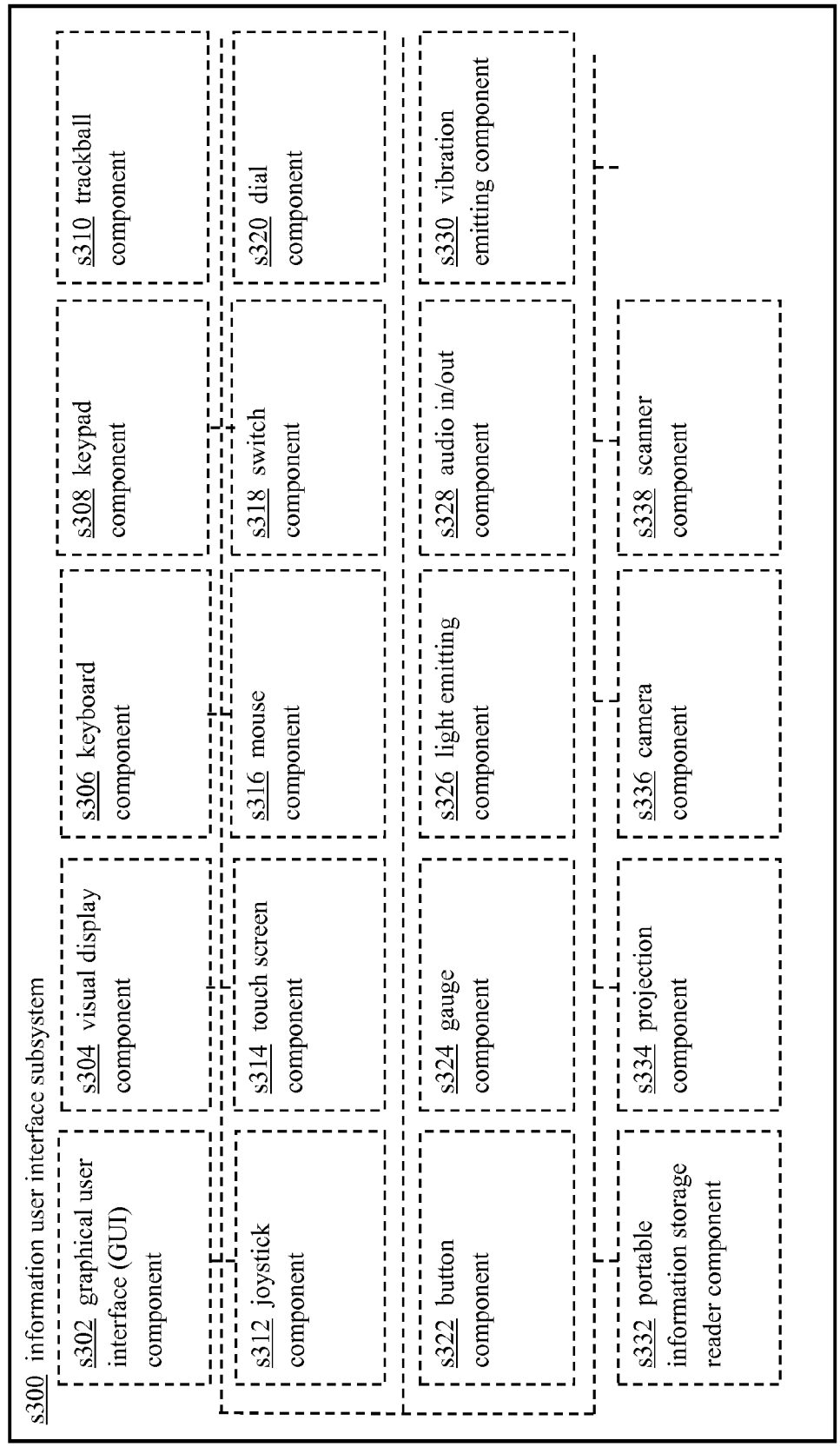
FIG. 22 is a block diagram depicting an information user interface subsystem s300 of an exemplary implementation of the ingestible product preparation system 10 of FIG. 1.

An exemplary implementation of the information user interface subsystem s300 is shown in FIG. 22 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, projection component s334, camera component s336, and scanner component s338.

Figure 23:
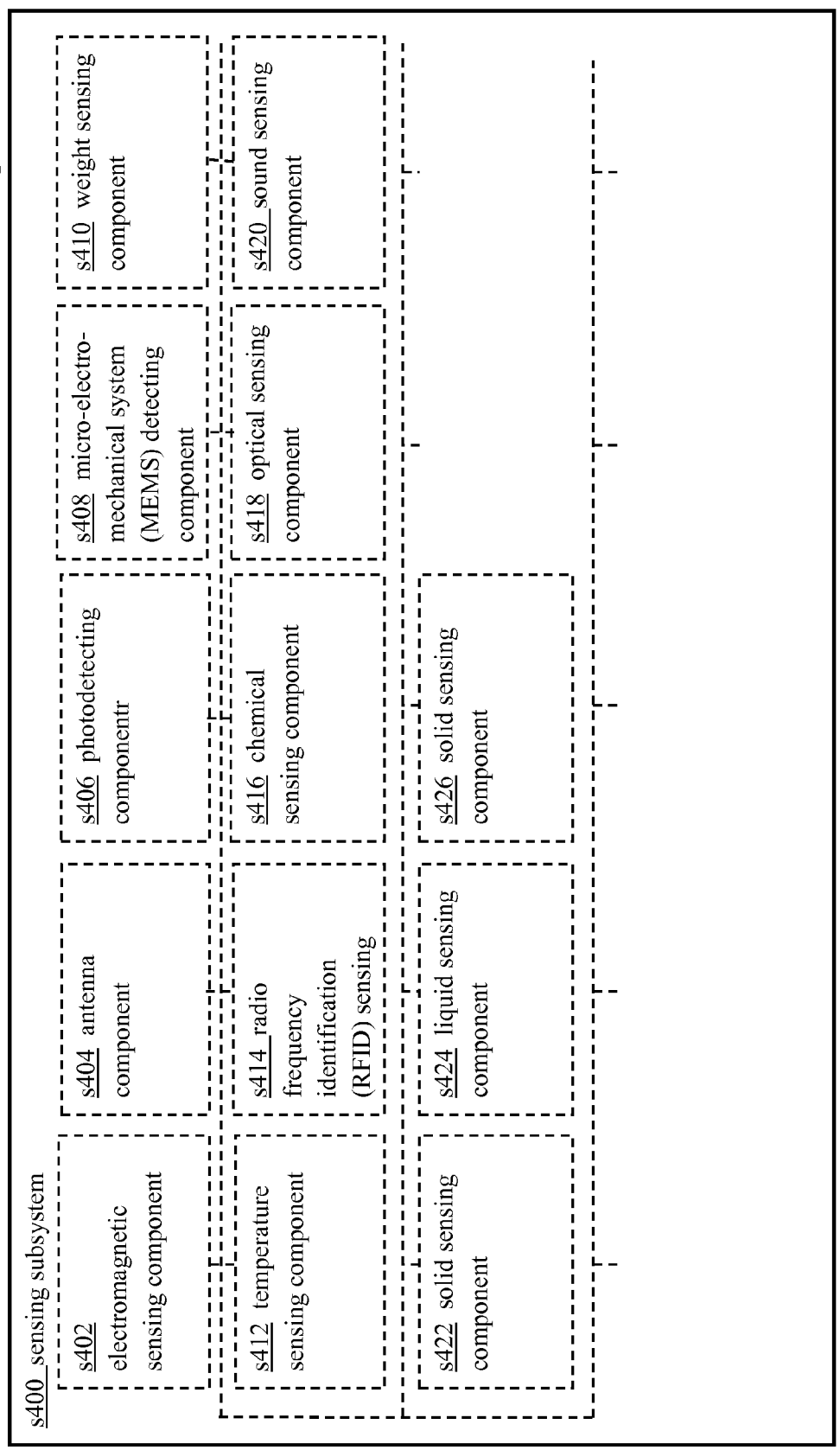
FIG. 23 is a block diagram depicting a sensing subsystem s400 of an exemplary implementation of the ingestible product preparation system 10 of FIG. 1.

An exemplary implementation of the sensing subsystem s400 is shown in FIG. 23 to optionally include various components such as electromagnetic sensing component s402, antenna component s404, photodetecting component s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 24:
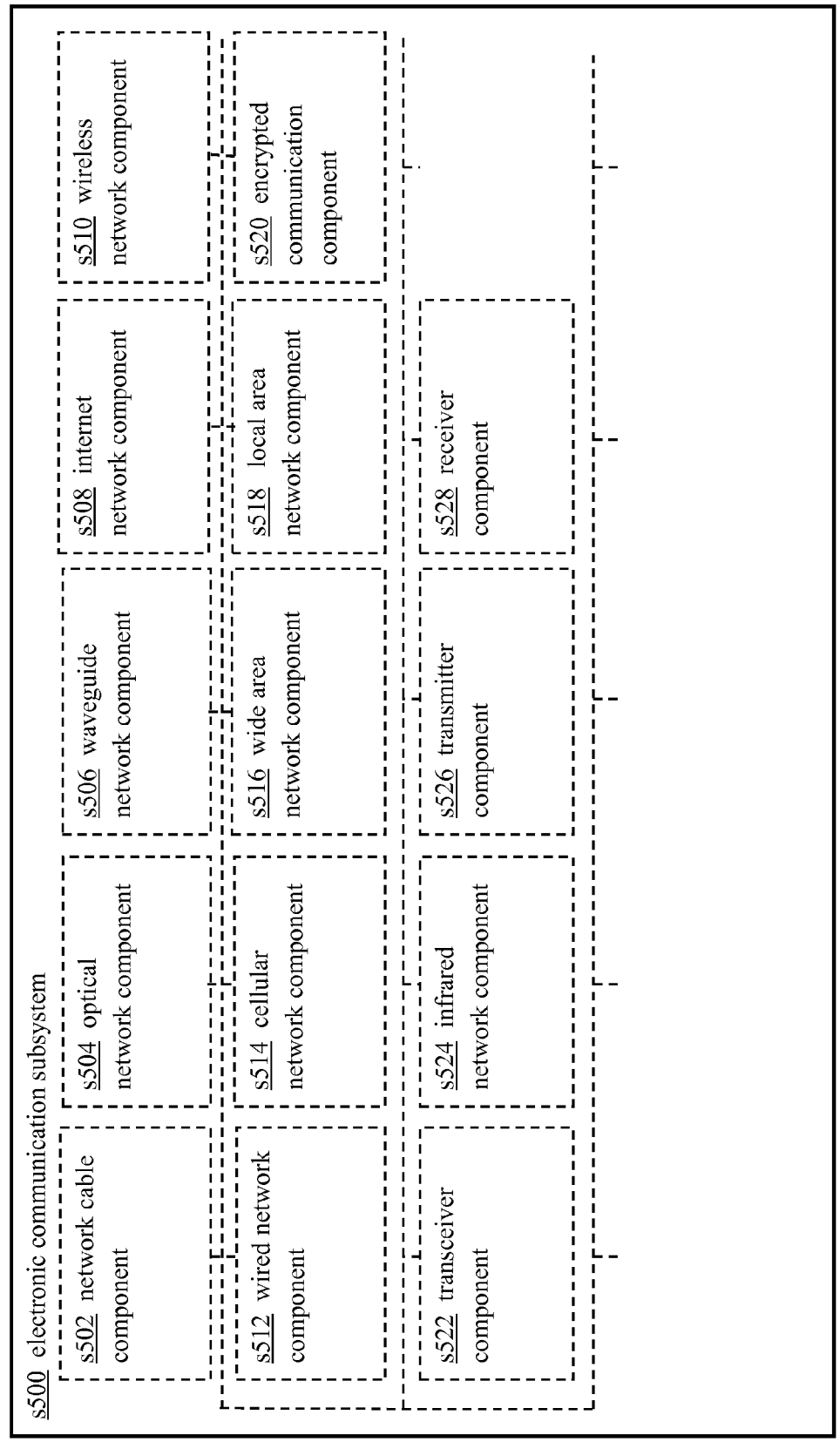
FIG. 24 is a block diagram depicting an electronic communication subsystem s500 of an exemplary implementation of the ingestible product preparation system 10 of FIG. 1.

An exemplary implementation of the electronic communication subsystem s500 is shown in FIG. 24 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 25:
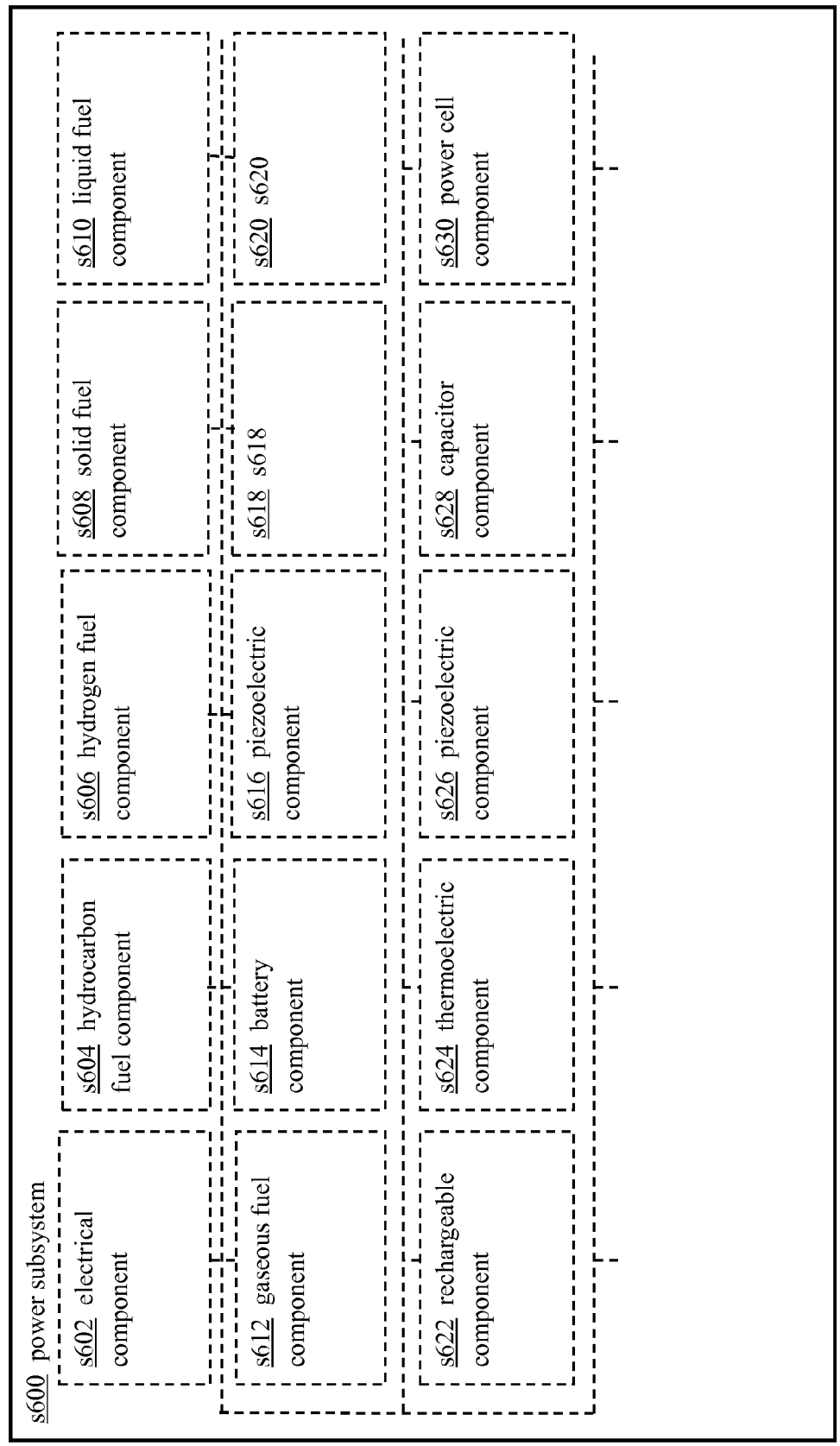
FIG. 25 is a block diagram depicting a power subsystem s600 of an exemplary implementation of the ingestible product preparation system 10 of FIG. 1.

An exemplary implementation of the power subsystem s600 is shown in FIG. 25 to optionally include various components such as electrical component s602, hydrocarbon fuel component s604, hydrogen fuel component s606, solid fuel component s608, liquid fuel component s610, gaseous fuel component s612, battery component s614, battery component s622, battery component s624, battery component s626, battery component s628, and power cell component s630.

Figure 26:
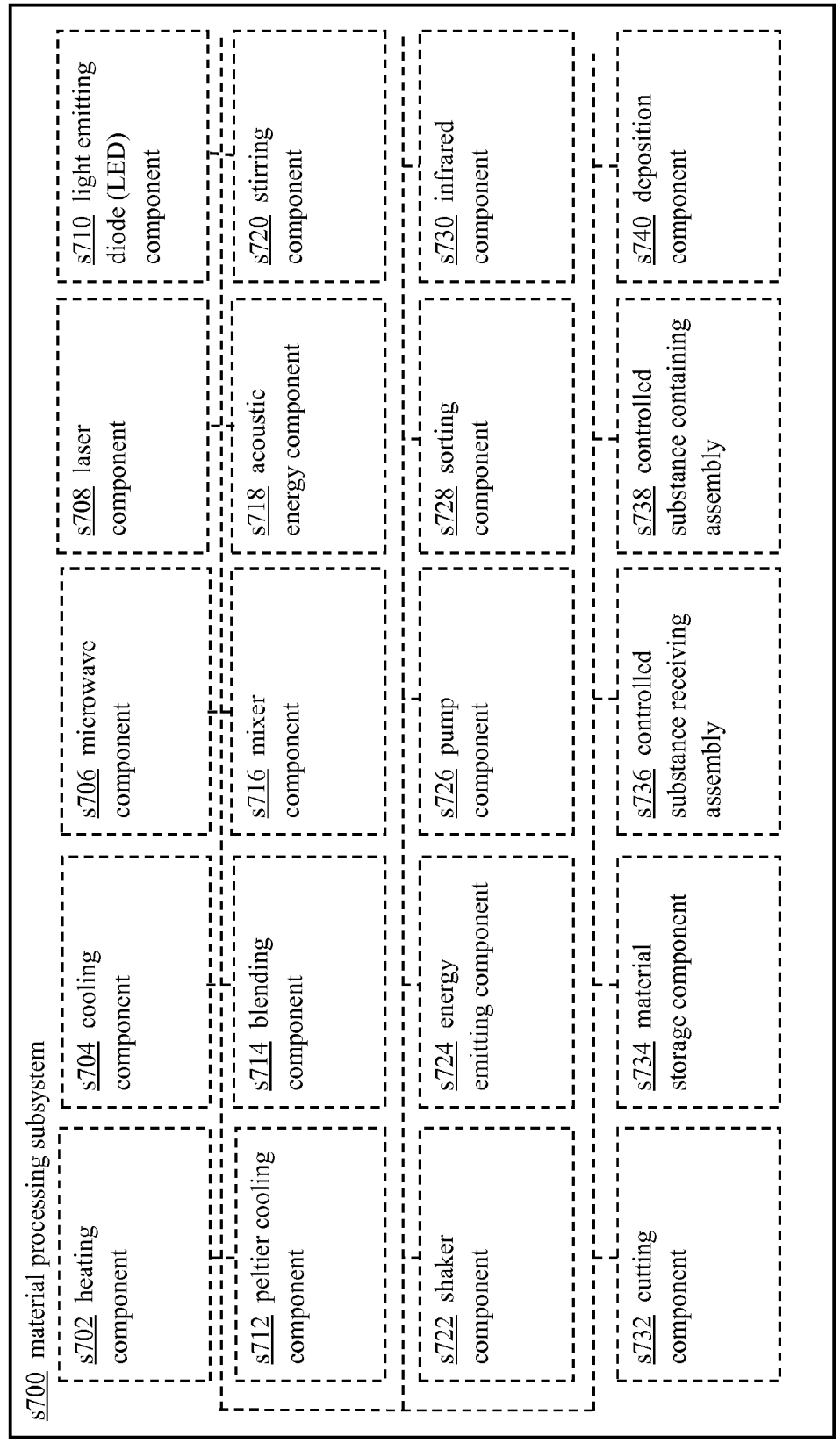
FIG. 26 is a block diagram depicting a material processing subsystem s700 of an exemplary implementation of the ingestible product preparation system 10 of FIG. 1.

An exemplary implementation of the material processing subsystem s700 is shown in FIG. 26 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, material storage component s734, controlled substance receiving assembly s736, controlled substance containing assembly s738, deposition component s740.

Figure 27:
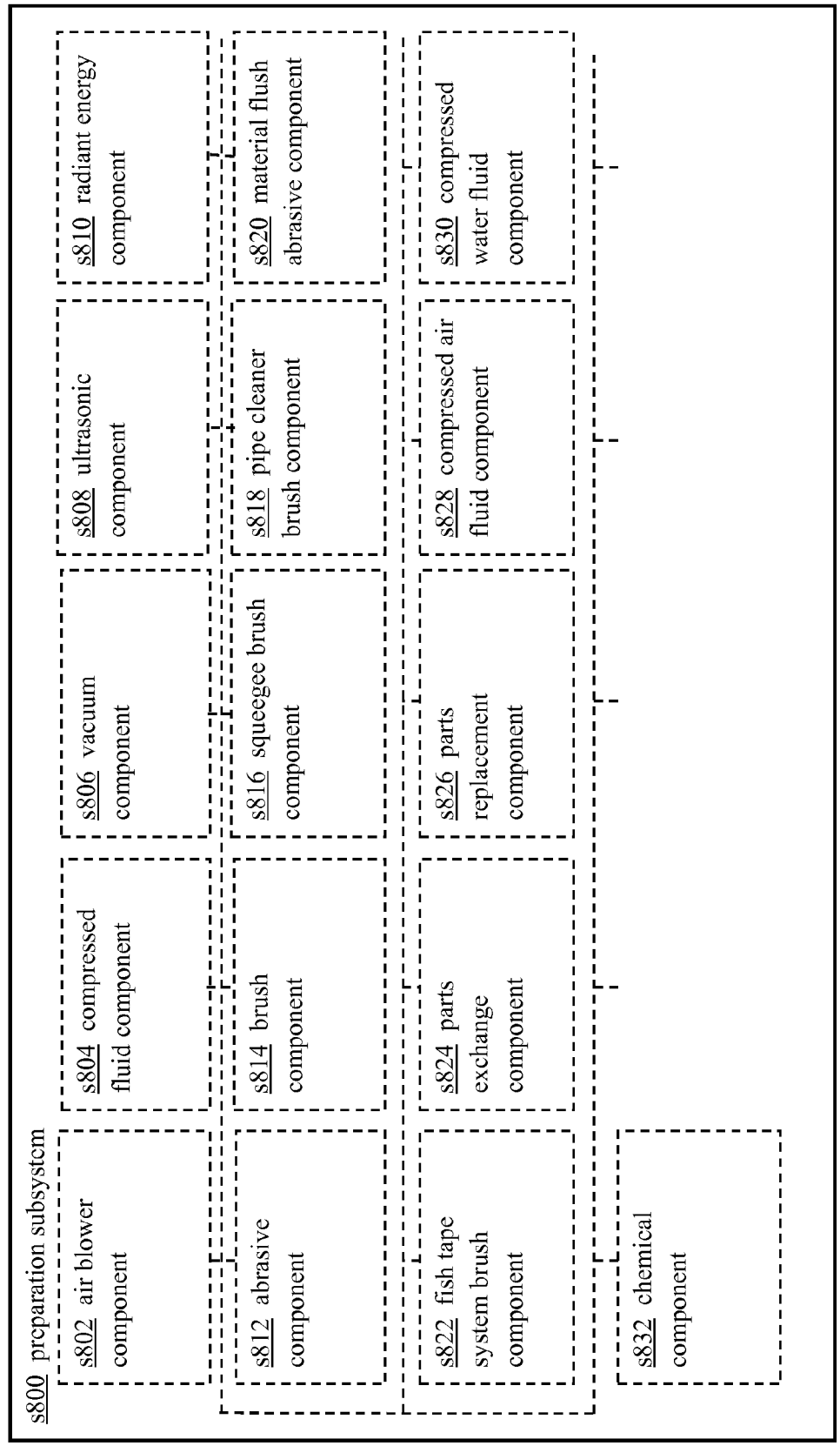
FIG. 27 is a block diagram depicting a preparation subsystem s800 of an exemplary implementation of the ingestible product preparation system 10 of FIG. 1.

An exemplary implementation of the preparation subsystem s800 is shown in FIG. 27 to optionally include various components such as air blower component s802, compressed fluid component s804, vacuum component s806, ultrasonic component s808, radiant energy component s810, abrasive component s812, brush component s814, squeegee brush component s816, pipe cleaner brush component s818, material flush abrasive component s820, fish tape system brush component s822, parts exchange component s824, parts replacement component s826, compressed air fluid component s828, compressed water fluid component s830, and chemical component s832.

Figure 28:
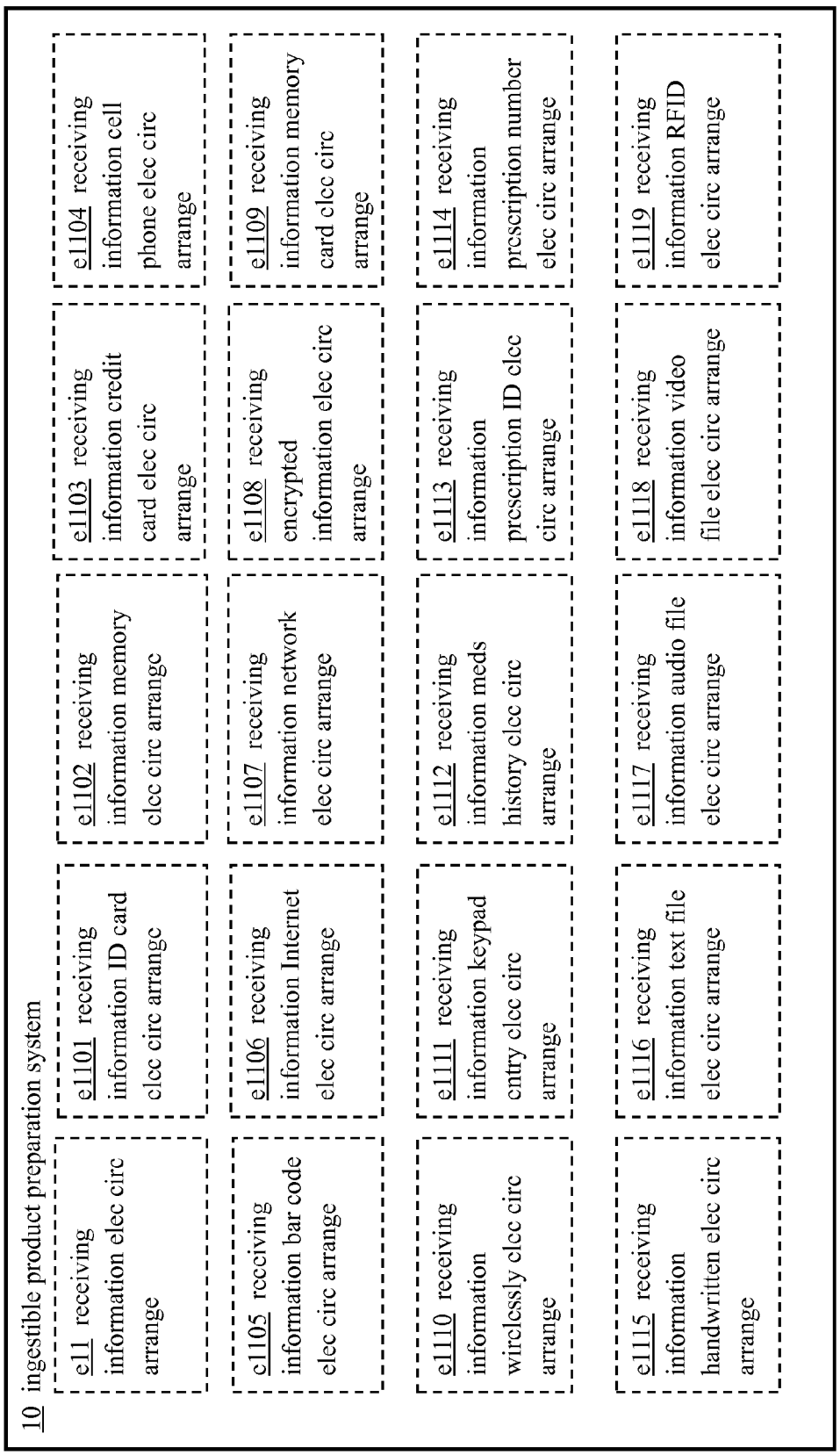
FIG. 28 is a block diagram depicting one or more exemplary electrical circuitry arrangements of the ingestible product preparation system 10 of FIG. 1.

Implementations involve different combinations (otherwise known as "electrical circuitry arrangements") of components from the subsystems of the ingestible product preparation system 10. Exemplary depictions of some of these electrical circuitry arrangements are shown in FIG. 28 to include receiving information electrical circuitry arrangement e11, receiving information ID card electrical circuitry arrangement e1101, receiving information memory electrical circuitry arrangement e1102, receiving information credit card electrical circuitry arrangement e1103, receiving information cell phone electrical circuitry arrangement e1104, receiving information bar code electrical circuitry arrangement e1105, receiving information Internet electrical circuitry arrangement e1106, receiving information network electrical circuitry arrangement e1107, receiving encrypted information electrical circuitry arrangement e1108, receiving information memory card electrical circuitry arrangement e1109, receiving information wirelessly electrical circuitry arrangement e1110, receiving information keypad entry electrical circuitry arrangement e1111, receiving information meds history electrical circuitry arrangement e1112, receiving information prescription ID electrical circuitry arrangement e1113, receiving information prescription number electrical circuitry arrangement e1114, receiving information handwritten electrical circuitry arrangement e1115, receiving information text file electrical circuitry arrangement e1116, receiving information audio file electrical circuitry arrangement e1117, receiving information video file electrical circuitry arrangement e1118, and receiving information RFID electrical circuitry arrangement e1119.

Figure 29:
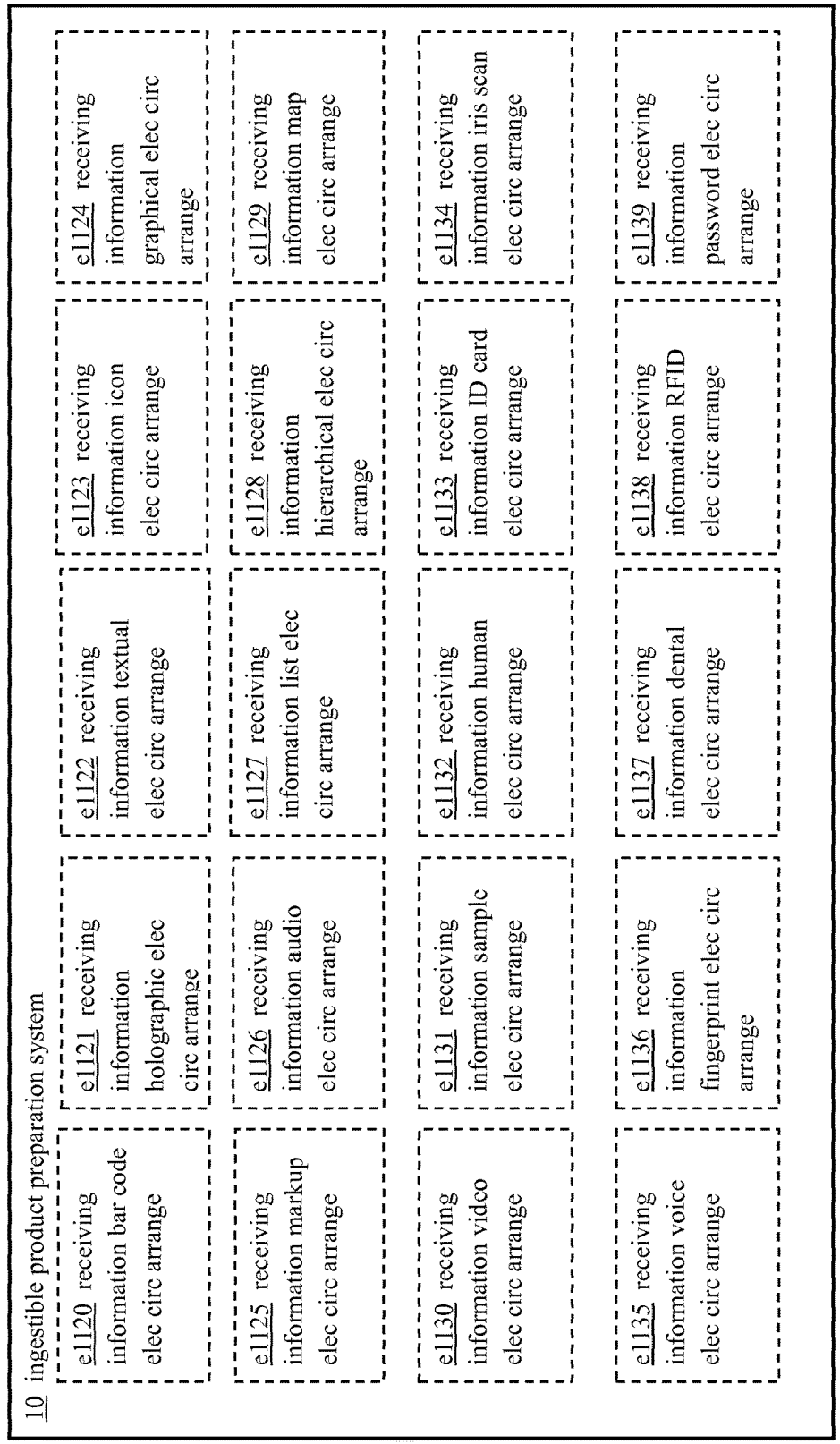
FIG. 29 is a block diagram depicting one or more exemplary electrical circuitry arrangements of the ingestible product preparation system 10 of FIG. 1.

Some of these electrical circuitry arrangements are depicted in FIG. 29 to include receiving information bar code electrical circuitry arrangement e1120, receiving information holographic electrical circuitry arrangement e1121, receiving information textual electrical circuitry arrangement e1122, receiving information icon electrical circuitry arrangement e1123, receiving information graphical electrical circuitry arrangement e1124, receiving information markup electrical circuitry arrangement e1125, receiving information audio electrical circuitry arrangement e1126, receiving information list electrical circuitry arrangement e1127, receiving information hierarchical electrical circuitry arrangement e1128, receiving information map electrical circuitry arrangement e1129, receiving information video electrical circuitry arrangement e1130, receiving information sample electrical circuitry arrangement e113, receiving information human electrical circuitry arrangement e1132, receiving information ID card electrical circuitry arrangement e1133, receiving information iris scan electrical circuitry arrangement e1134, receiving information voice electrical circuitry arrangement e1135, receiving information fingerprint electrical circuitry arrangement e1136, receiving information dental electrical circuitry arrangement e1137, receiving information RFID electrical circuitry arrangement e1138, and receiving information password electrical circuitry arrangement e1139.

Figure 30:
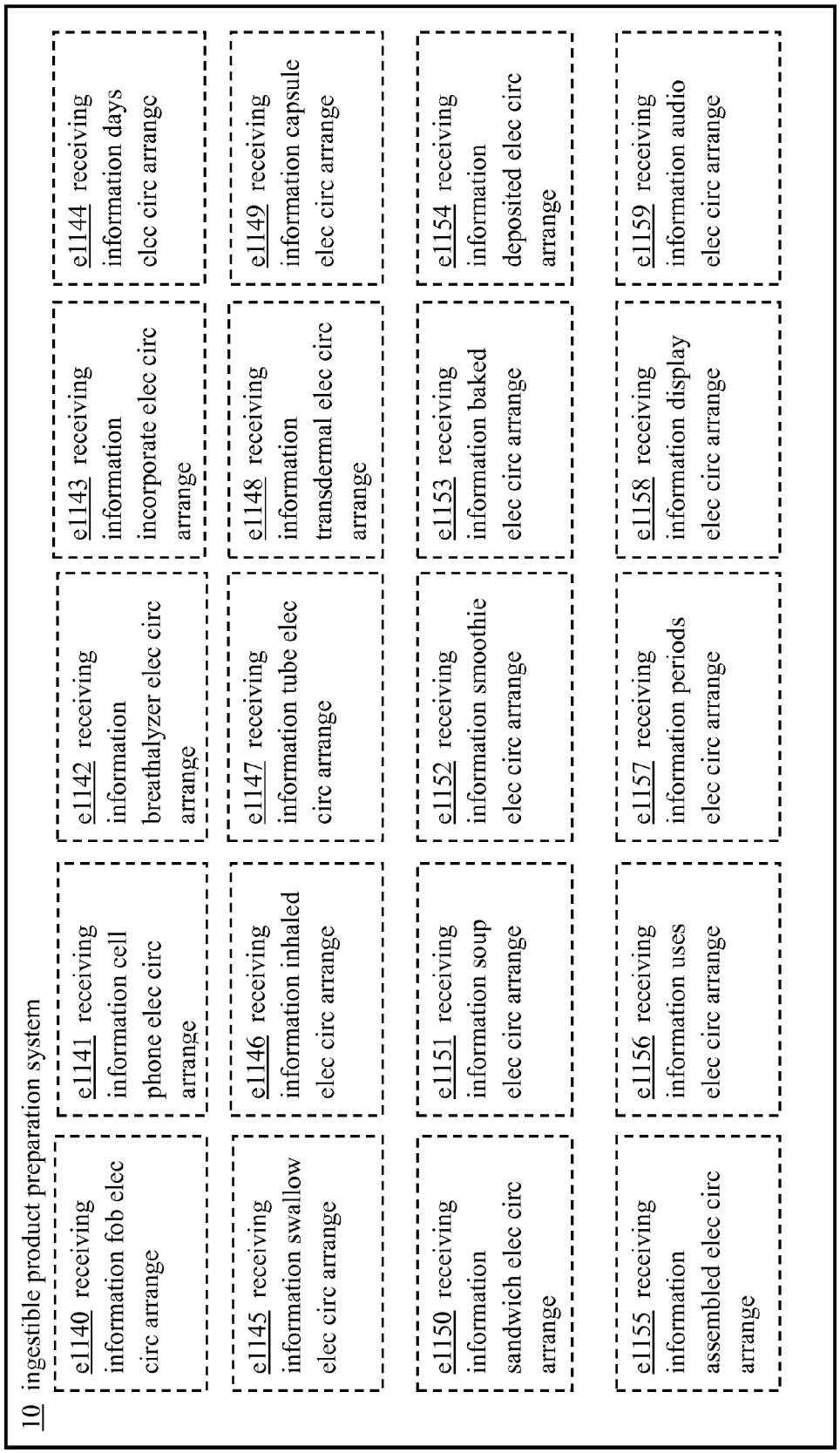
FIG. 30 is a block diagram depicting one or more exemplary electrical circuitry arrangements of the ingestible product preparation system 10 of FIG. 1.
Figure 31:
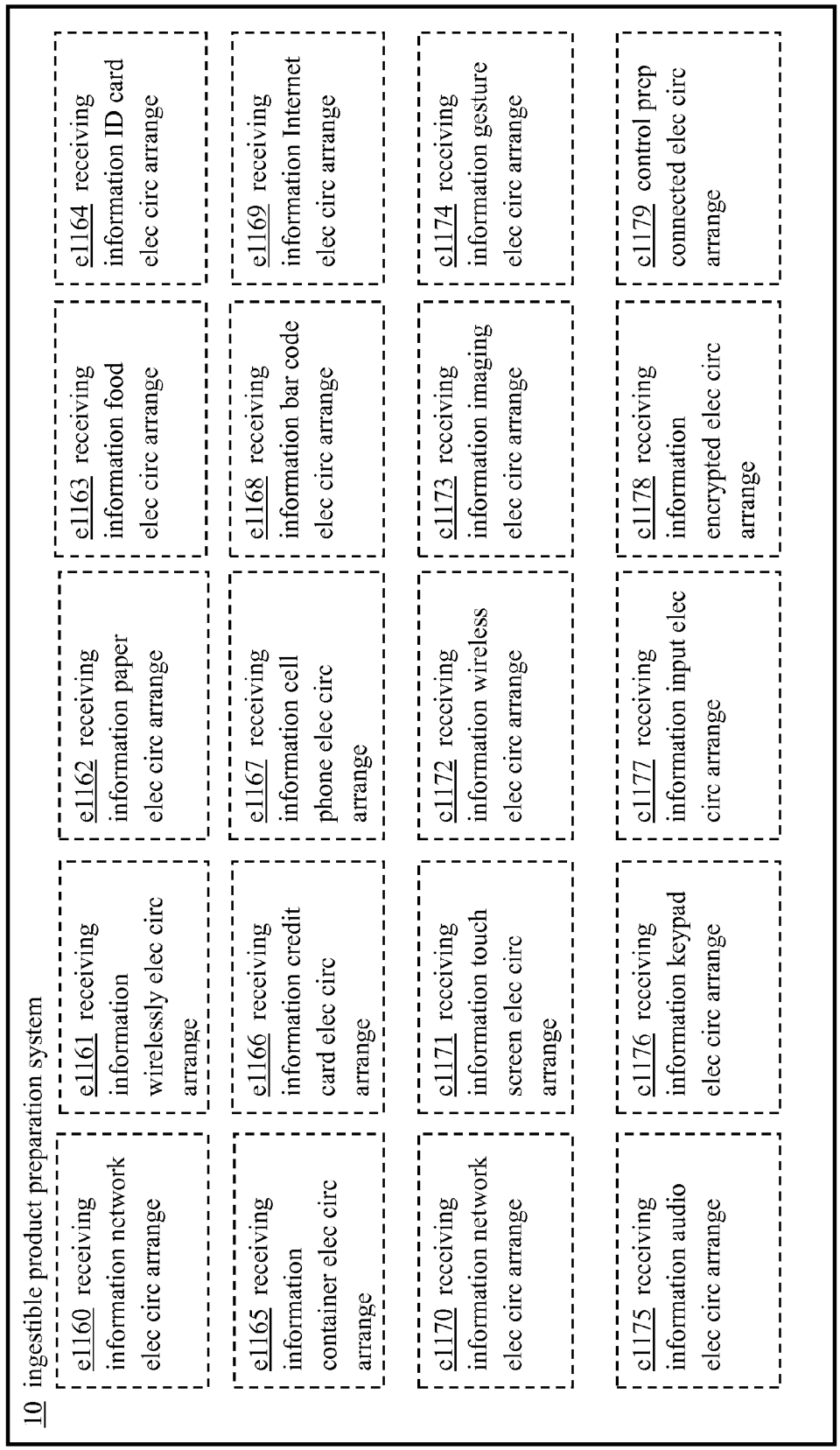
FIG. 31 is a block diagram depicting one or more exemplary electrical circuitry arrangements of the ingestible product preparation system 10 of FIG. 1.
Figure 32:
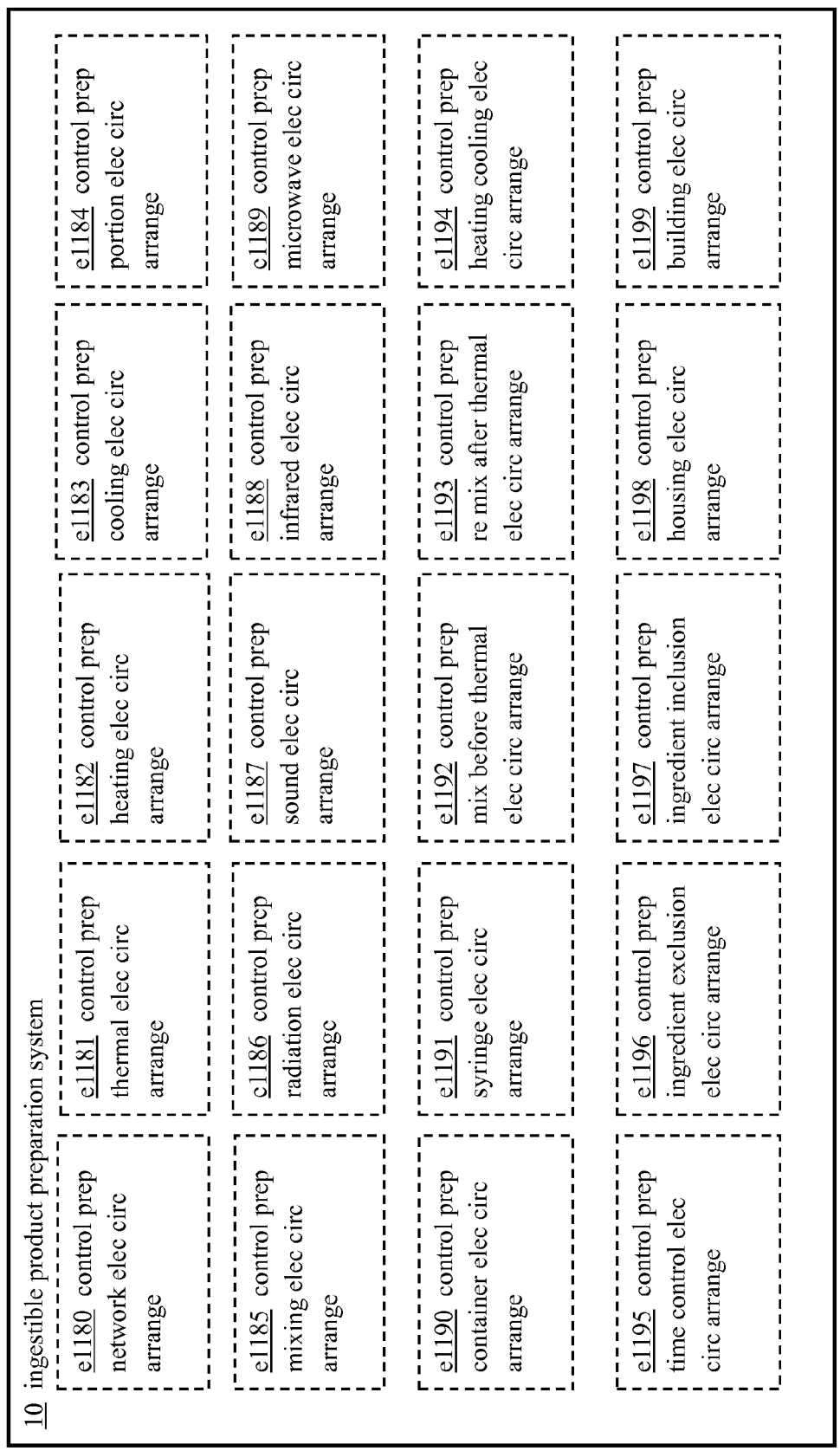
FIG. 32 is a block diagram depicting one or more exemplary electrical circuitry arrangements of the ingestible product preparation system 10 of FIG. 1.
Figure 33:
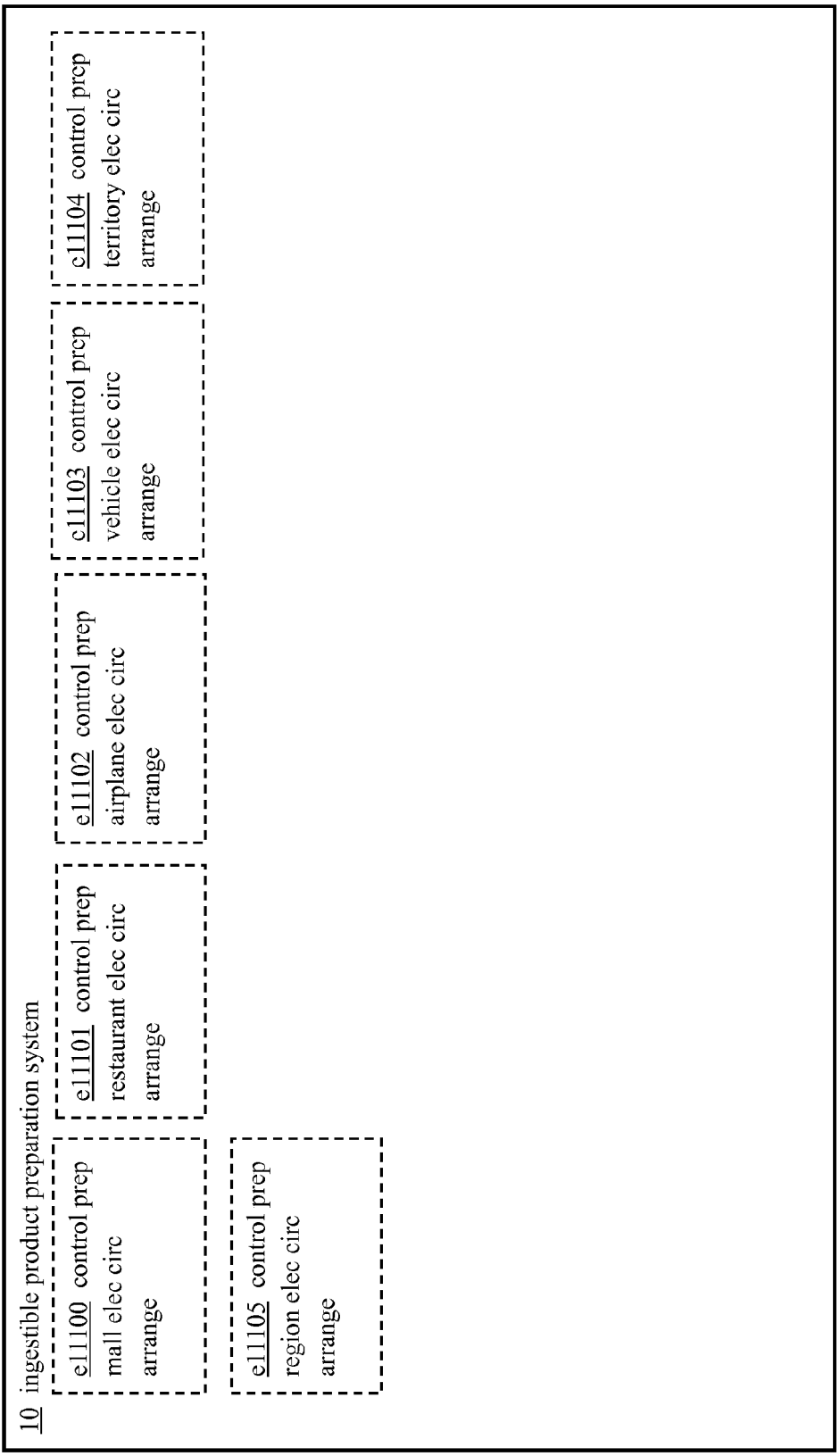
FIG. 33 is a block diagram depicting one or more exemplary electrical circuitry arrangements of the ingestible product preparation system 10 of FIG. 1.
Figure 34:
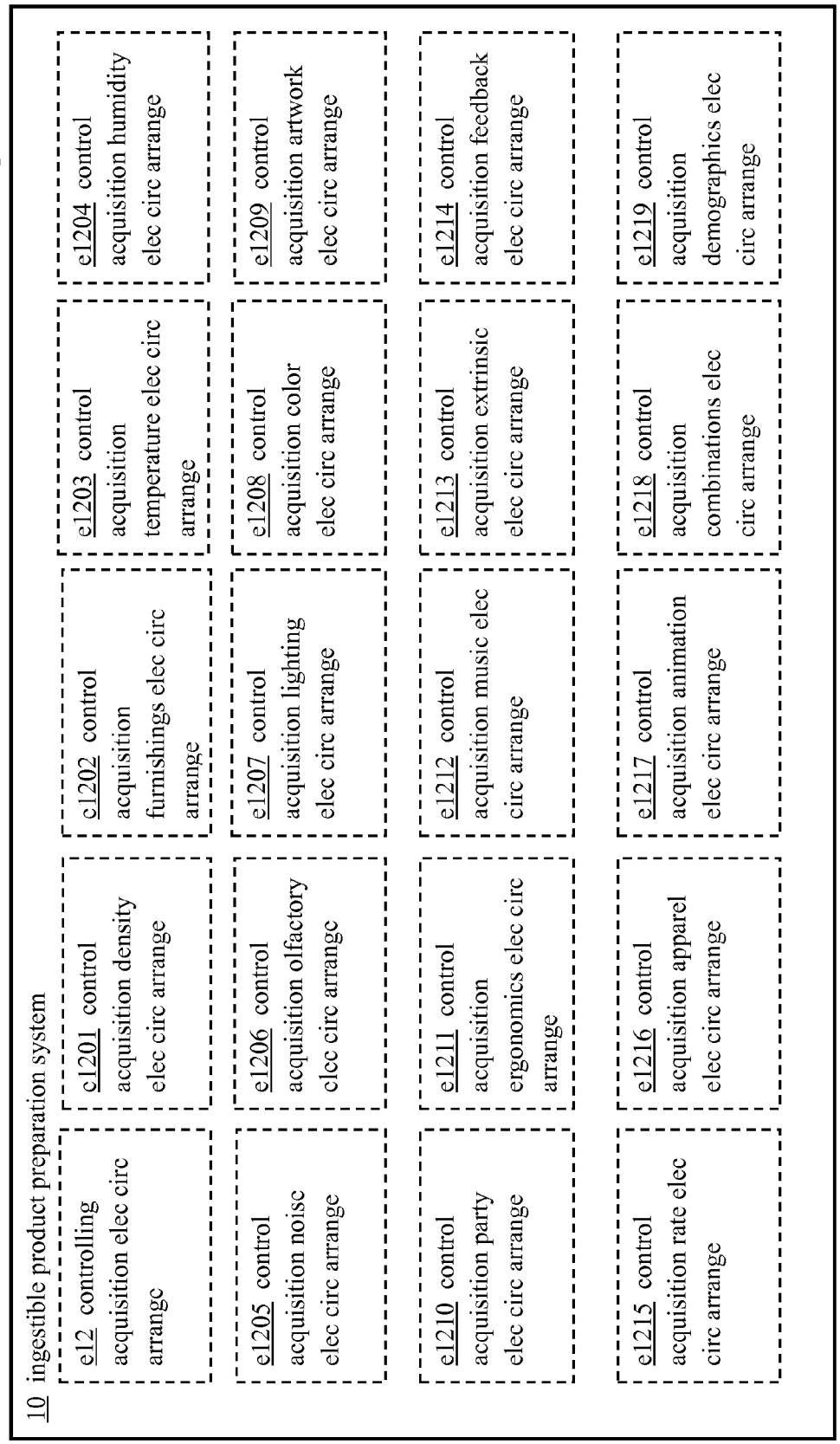
FIG. 34 is a block diagram depicting one or more exemplary electrical circuitry arrangements of the ingestible product preparation system 10 of FIG. 1.

Some of these electrical circuitry arrangements are depicted in FIG. 30 to include receiving information fob electrical circuitry arrangement e1140, receiving information cell phone electrical circuitry arrangement e1141, receiving information breathalyzer electrical circuitry arrangement e1142, receiving information incorporate electrical circuitry arrangement e1143, receiving information days electrical circuitry arrangement e1144, receiving information swallow electrical circuitry arrangement e1145, receiving information inhaled electrical circuitry arrangement e1146, receiving information tube electrical circuitry arrangement e1147, receiving information transdermal electrical circuitry arrangement e1148, receiving information capsule electrical circuitry arrangement e1149, receiving information sandwich electrical circuitry arrangement e1150, receiving information soup electrical circuitry arrangement e1151, receiving information smoothie electrical circuitry arrangement e1152, receiving information baked electrical circuitry arrangement e1153, receiving information deposited electrical circuitry arrangement e1154, receiving information assembled electrical circuitry arrangement e1155, receiving information uses electrical circuitry arrangement e1156, receiving information periods electrical circuitry arrangement e1157, receiving information display electrical circuitry arrangement e1158, and receiving information audio electrical circuitry arrangement e1159.

Some of these electrical circuitry arrangements are depicted in FIG. 31 to include receiving information network electrical circuitry arrangement e1160, receiving information wirelessly electrical circuitry arrangement e1161, receiving information paper electrical circuitry arrangement e1162, receiving information food electrical circuitry arrangement e1163, receiving information ID card electrical circuitry arrangement e1164, receiving information container electrical circuitry arrangement e1165, and receiving information credit card electrical circuitry arrangement e1166, receiving information cell phone electrical circuitry arrangement e1167, receiving information bar code electrical circuitry arrangement e1168, receiving information Internet electrical circuitry arrangement e1169, receiving information network electrical circuitry arrangement e1170, receiving information touch screen electrical circuitry arrangement e1171, receiving information wireless electrical circuitry arrangement e1172, receiving information imaging electrical circuitry arrangement e1173, receiving information gesture electrical circuitry arrangement e1174, receiving information audio electrical circuitry arrangement e1175, receiving information keypad electrical circuitry arrangement e1176, receiving information input electrical circuitry arrangement e1177, receiving information encrypted electrical circuitry arrangement e1178, and control prep connected electrical circuitry arrangement e1179.

Some of these electrical circuitry arrangements are depicted in FIG. 32 to include control prep network electrical circuitry arrangement e1180, control prep thermal electrical circuitry arrangement e1181, control prep heating electrical circuitry arrangement e1182, control prep cooling electrical circuitry arrangement e1183, control prep portion electrical circuitry arrangement e1184, control prep mixing electrical circuitry arrangement e1185, and control prep radiation electrical circuitry arrangement e1186, control prep sound electrical circuitry arrangement e1187, control prep infrared electrical circuitry arrangement e1188, control prep microwave electrical circuitry arrangement e1189, control prep container electrical circuitry arrangement e1190, control prep syringe electrical circuitry arrangement e1191, control prep mix before thermal electrical circuitry arrangement e1192, control prep re mix after thermal electrical circuitry arrangement e1193, control prep heating cooling electrical circuitry arrangement e1194, control prep time control electrical circuitry arrangement e1195, control prep ingredient exclusion electrical circuitry arrangement e1196, control prep ingredient inclusion electrical circuitry arrangement e1197, control prep housing electrical circuitry arrangement e1198, and control prep building electrical circuitry arrangement e1199.

Some of these electrical circuitry arrangements are depicted in FIG. 33 to include control prep mall electrical circuitry arrangement e11100, control prep restaurant electrical circuitry arrangement e11101, control prep airplane electrical circuitry arrangement e11102, control prep vehicle electrical circuitry arrangement e11103, control prep territory electrical circuitry arrangement e11104, and control prep region electrical circuitry arrangement e11105.

Some of these electrical circuitry arrangements are depicted in FIG. 34 to include controlling acquisition electrical circuitry arrangement e12, control acquisition density electrical circuitry arrangement e1201, control acquisition furnishings electrical circuitry arrangement e1202, control acquisition temperature electrical circuitry arrangement e1203, control acquisition humidity electrical circuitry arrangement e1204, control acquisition noise electrical circuitry arrangement e1205, control acquisition olfactory electrical circuitry arrangement e1206, control acquisition lighting electrical circuitry arrangement e1207, control acquisition color electrical circuitry arrangement e1208, control acquisition artwork electrical circuitry arrangement e1209, control acquisition party electrical circuitry arrangement e1210, control acquisition ergonomics electrical circuitry arrangement e1211, and control acquisition music electrical circuitry arrangement e1212, control acquisition extrinsic electrical circuitry arrangement e1213, control acquisition feedback electrical circuitry arrangement e1214, control acquisition rate electrical circuitry arrangement e1215, control acquisition apparel electrical circuitry arrangement e1216, control acquisition animation electrical circuitry arrangement e1217, control acquisition combinations electrical circuitry arrangement e1218, and control acquisition demographics electrical circuitry arrangement e1219.

Some of these electrical circuitry arrangements are depicted in FIG. 35 to include second vicinity housing electrical circuitry arrangement e12, second vicinity building electrical circuitry arrangement e1221, second vicinity mall electrical circuitry arrangement e1222, second vicinity restaurant electrical circuitry arrangement e1223, second vicinity airplane electrical circuitry arrangement e1224, second vicinity vehicle electrical circuitry arrangement e1225, second vicinity territory electrical circuitry arrangement e1226, second vicinity region electrical circuitry arrangement e1227, acquisition conversation electrical circuitry arrangement e1228, acquisition gratuity electrical circuitry arrangement e1229, acquisition financial electrical circuitry arrangement e1230, acquisition leftovers electrical circuitry arrangement e1231, and acquisition time electrical circuitry arrangement e1232, acquisition party electrical circuitry arrangement e1233, acquisition image electrical circuitry arrangement e1234, acquisition gesture electrical circuitry arrangement e1235, acquisition speech electrical circuitry arrangement e1236, acquisition keypad electrical circuitry arrangement e1237, acquisition input electrical circuitry arrangement e1238, and acquisition restaurant electrical circuitry arrangement e1239.

Some of these electrical circuitry arrangements are depicted in FIG. 36 to include acquisition encrypted electrical circuitry arrangement e1240.

Figure 37:
FIG. 37 is a block diagram depicting one or more exemplary instructions of the information storage subsystem s200 of the ingestible product preparation system 10 of FIG. 1.

In implementations one or more instructions are stored and/or otherwise borne in various subsystems, components, and/or accessories of the ingestible product preparation system 10 such as being borne in a non-transitory signal bearing medium of information storage subsystem s200. One or more exemplary instructions depicted in FIG. 37 as being borne in an exemplary version of a non-transitory signal bearing medium of information storage subsystem s200 include one or more receiving information instructions i11, one or more receiving information ID card instructions i1101, one or more receiving information memory instructions i1102, one or more receiving information credit card instructions i1103, one or more receiving information cell phone instructions i1104, one or more receiving information bar code instructions i1105, one or more receiving information Internet instructions i1106, one or more receiving information network instructions i1107, one or more receiving encrypted information instructions i1108, one or more receiving information memory card instructions i1109, one or more receiving information wirelessly instructions i1110, one or more receiving information keypad entry instructions i1111, one or more receiving information meds history instructions i1112, one or more receiving information prescription ID instructions i1113, one or more receiving information prescription number instructions i1114, one or more receiving information handwritten instructions i1115, one or more receiving information text file instructions i1116, one or more receiving information audio file instructions i1117, one or more receiving information video file instructions i1118, and one or more receiving information RFID instructions i1119.

Figure 38:
FIG. 38 is a block diagram depicting one or more exemplary instructions of the information storage subsystem s200 of the ingestible product preparation system 10 of FIG. 1.

One or more exemplary instructions depicted in FIG. 38 as being borne in an exemplary version of a non-transitory signal bearing medium of information storage subsystem s200 include one or more receiving information bar code instructions i1120, one or more receiving information holographic instructions i1121, one or more receiving information textual instructions i1122, one or more receiving information icon instructions i1123, one or more receiving information graphical instructions i1124, one or more receiving information markup instructions i1125, one or more receiving information audio instructions i1126, one or more receiving information list instructions i1127, one or more receiving information hierarchical instructions i1128, one or more receiving information map instructions i1129, one or more receiving information video instructions i1130, one or more receiving information sample instructions i1131, one or more receiving information human instructions i1132, one or more receiving information ID card instructions i1133, one or more receiving information iris scan instructions i1134, one or more receiving information voice instructions i1135, one or more receiving information fingerprint instructions i1136, one or more receiving information dental instructions i1137, one or more receiving information RFID instructions i1138, and one or more receiving information password instructions i1139.

Figure 39:
FIG. 39 is a block diagram depicting one or more exemplary instructions of the information storage subsystem s200 of the ingestible product preparation system 10 of FIG. 1.

One or more exemplary instructions depicted in FIG. 39 as being borne in an exemplary version of a non-transitory signal bearing medium of information storage subsystem s200 include one or more receiving information fob instructions i1140, one or more receiving information cell phone instructions i1141, one or more receiving information breathalyzer instructions i1142, one or more receiving information incorporate instructions i1143, one or more receiving information days instructions i1144, one or more receiving information swallow instructions i1145, one or more receiving information inhaled instructions i1146, one or more receiving information tube instructions i1147, one or more receiving information transdermal instructions i1148, one or more receiving information capsule instructions i1149, one or more receiving information sandwich instructions i1150, one or more receiving information soup instructions i1151, one or more receiving information smoothie instructions i1152, one or more receiving information baked instructions i1153, one or more receiving information deposited instructions i1154, one or more receiving information assembled instructions i1155, one or more receiving information uses instructions i1156, one or more receiving information periods instructions i1157, one or more receiving information display instructions i1158, and one or more receiving information audio instructions i1159.

Figure 40:
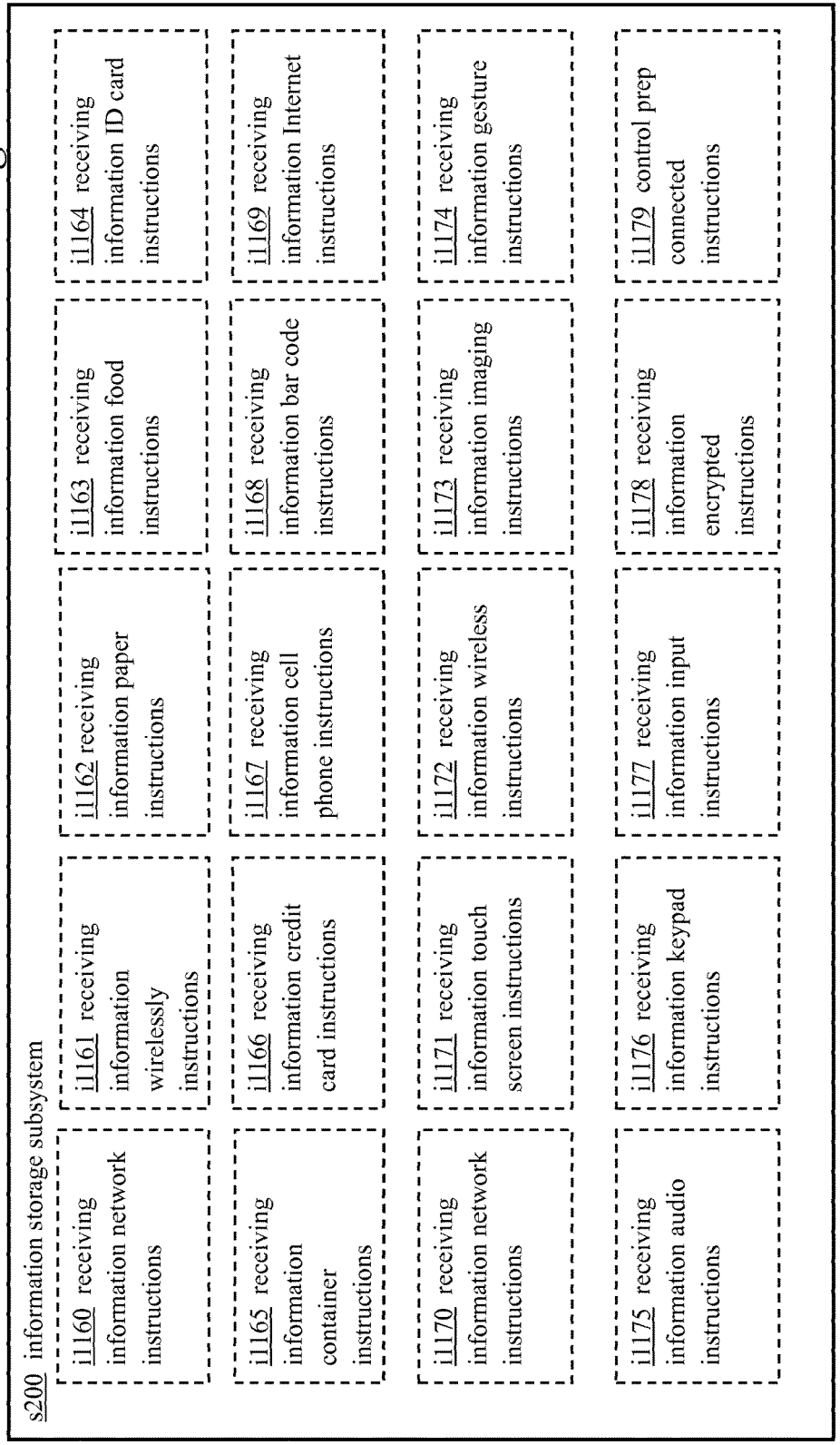
FIG. 40 is a block diagram depicting one or more exemplary instructions of the information storage subsystem s200 of the ingestible product preparation system 10 of FIG. 1.

One or more exemplary instructions depicted in FIG. 40 as being borne in an exemplary version of a non-transitory signal bearing medium of information storage subsystem s200 include one or more receiving information network instructions i1160, one or more receiving information wirelessly instructions i1161, one or more receiving information paper instructions i1162, one or more receiving information food instructions i1163, one or more receiving information ID card instructions i1164, one or more receiving information container instructions i1165, and one or more receiving information credit card instructions i1166, one or more receiving information cell phone instructions i1167, one or more receiving information bar code instructions i1168, one or more receiving information Internet instructions i1169, one or more receiving information network instructions i1170, one or more receiving information touch screen instructions i1171, one or more receiving information wireless instructions i1172, one or more receiving information imaging instructions i1173, one or more receiving information gesture instructions i1174, one or more receiving information audio instructions i1175, one or more receiving information keypad instructions i1176, one or more receiving information input instructions i1177, one or more receiving information encrypted instructions i1178, and one or more control prep connected instructions i1179.

Figure 41:
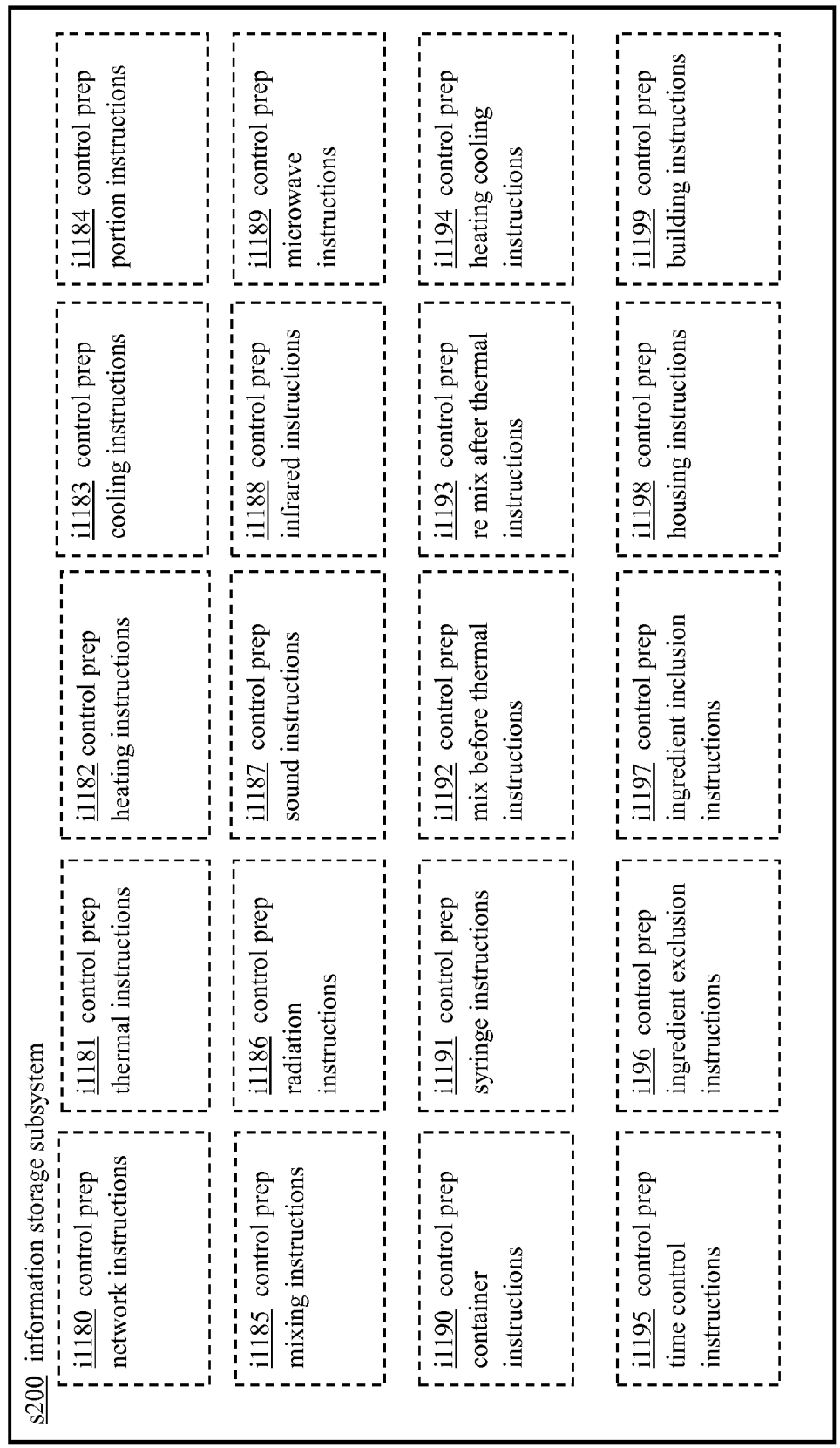
FIG. 41 is a block diagram depicting one or more exemplary instructions of the information storage subsystem s200 of the ingestible product preparation system 10 of FIG. 1.

One or more exemplary instructions depicted in FIG. 41 as being borne in an exemplary version of a non-transitory signal bearing medium of information storage subsystem s200 include one or more control prep network instructions i1180, one or more control prep thermal instructions i1181, one or more control prep heating instructions i1182, one or more control prep cooling instructions i1183, one or more control prep portion instructions i1184, one or more control prep mixing instructions i1185, and one or more control prep radiation instructions i1186, one or more control prep sound instructions i1187, one or more control prep infrared instructions i1188, one or more control prep microwave instructions i1189, one or more control prep container instructions i1190, one or more control prep syringe instructions i1191, one or more control prep mix before thermal instructions i1192, one or more control prep re mix after thermal instructions i1193, one or more control prep heating cooling instructions i1194, one or more control prep time control instructions i1195, one or more control prep ingredient exclusion instructions i1196, one or more control prep ingredient inclusion instructions i1197, one or more control prep housing instructions i1198, and one or more control prep building instructions i1199.

Figure 42:
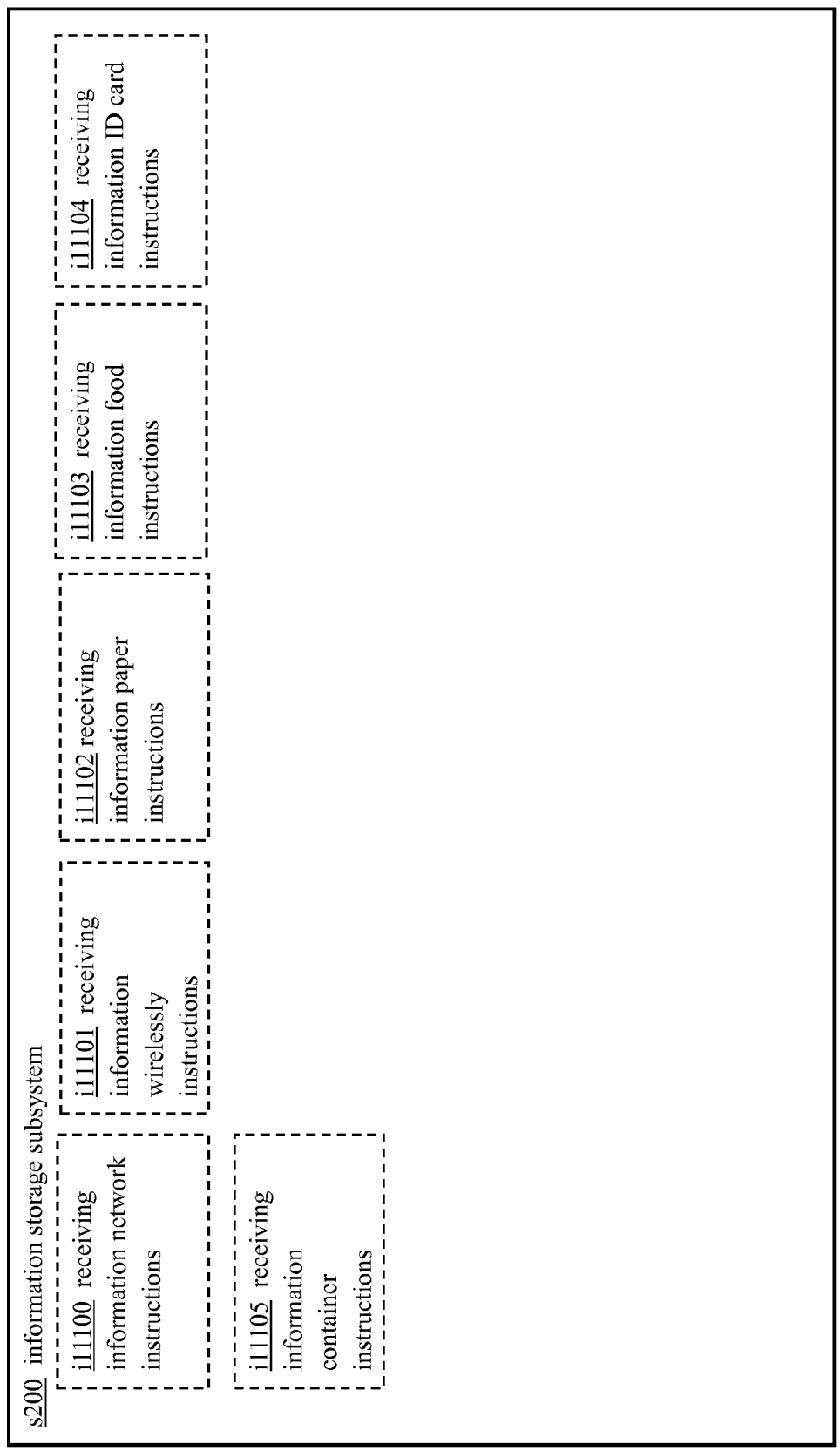
FIG. 42 is a block diagram depicting one or more exemplary instructions of the information storage subsystem s200 of the ingestible product preparation system 10 of FIG. 1.

One or more exemplary instructions depicted in FIG. 42 as being borne in an exemplary version of a non-transitory signal bearing medium of information storage subsystem s200 include one or more control prep mall instructions i11100, one or more control prep restaurant instructions i11101, one or more control prep airplane instructions i11102, one or more control prep vehicle instructions i11103, one or more control prep territory instructions i11104, and one or more control prep region instructions i11105.

Figure 43:
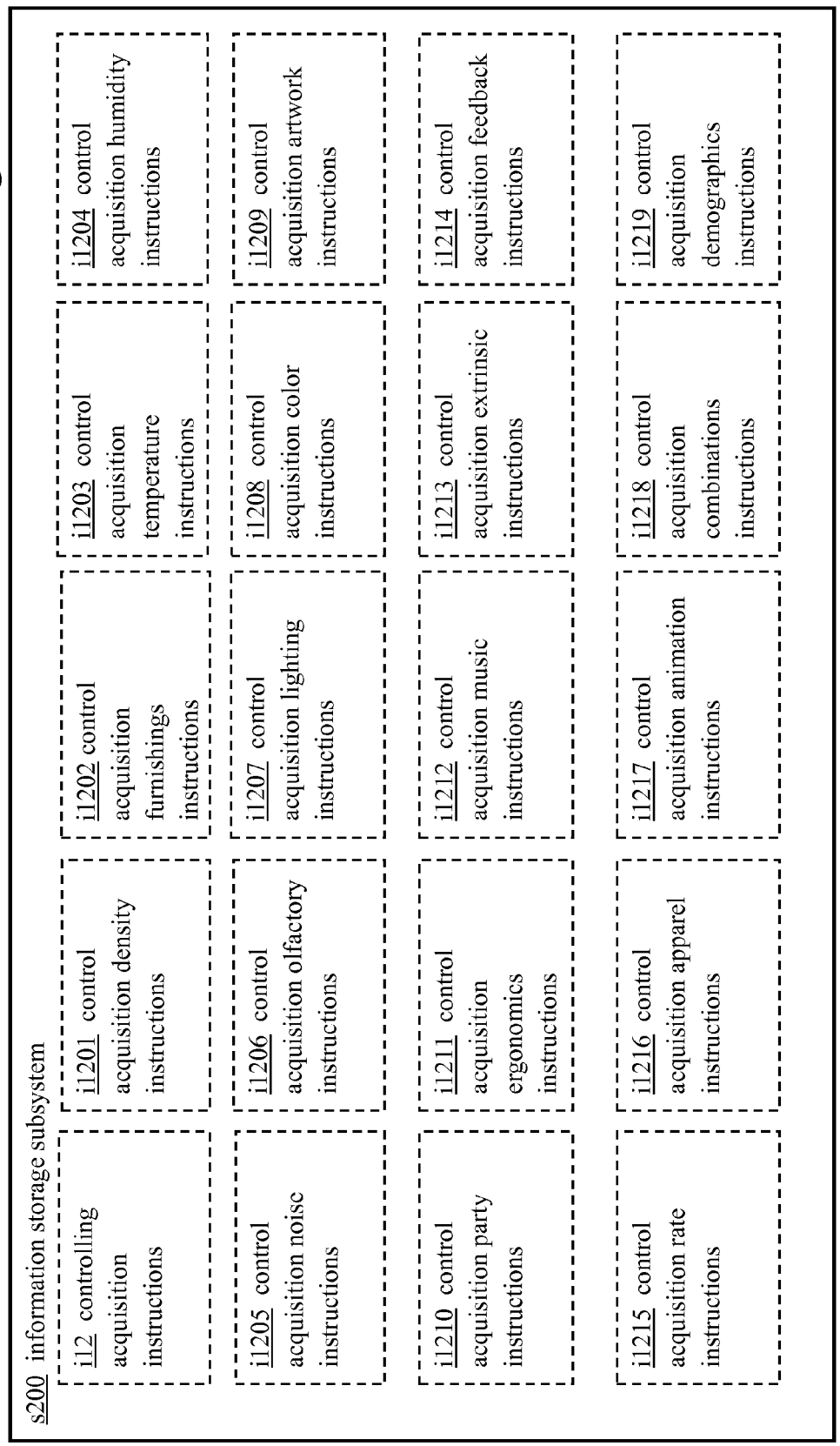
FIG. 43 is a block diagram depicting one or more exemplary instructions of the information storage subsystem s200 of the ingestible product preparation system 10 of FIG. 1.

One or more exemplary instructions depicted in FIG. 43 as being borne in an exemplary version of a non-transitory signal bearing medium of information storage subsystem s200 include one or more controlling acquisition instructions i12, one or more control acquisition density instructions i1201, one or more control acquisition furnishings instructions i1202, one or more control acquisition temperature instructions i1203, one or more control acquisition humidity instructions i1204, one or more control acquisition noise instructions i1205, one or more control acquisition olfactory instructions i1206, one or more control acquisition lighting instructions i1207, one or more control acquisition color instructions i1208, one or more control acquisition artwork instructions i1209, one or more control acquisition party instructions i1210, one or more control acquisition ergonomics instructions i1211, one or more control acquisition music instructions i1212, one or more control acquisition extrinsic instructions i1213, one or more control acquisition feedback instructions i1214, one or more control acquisition rate instructions i1215, one or more control acquisition apparel instructions i1216, one or more control acquisition animation instructions i1217, one or more control acquisition combinations instructions i1218, and one or more control acquisition demographics instructions i1219.

Figure 44:
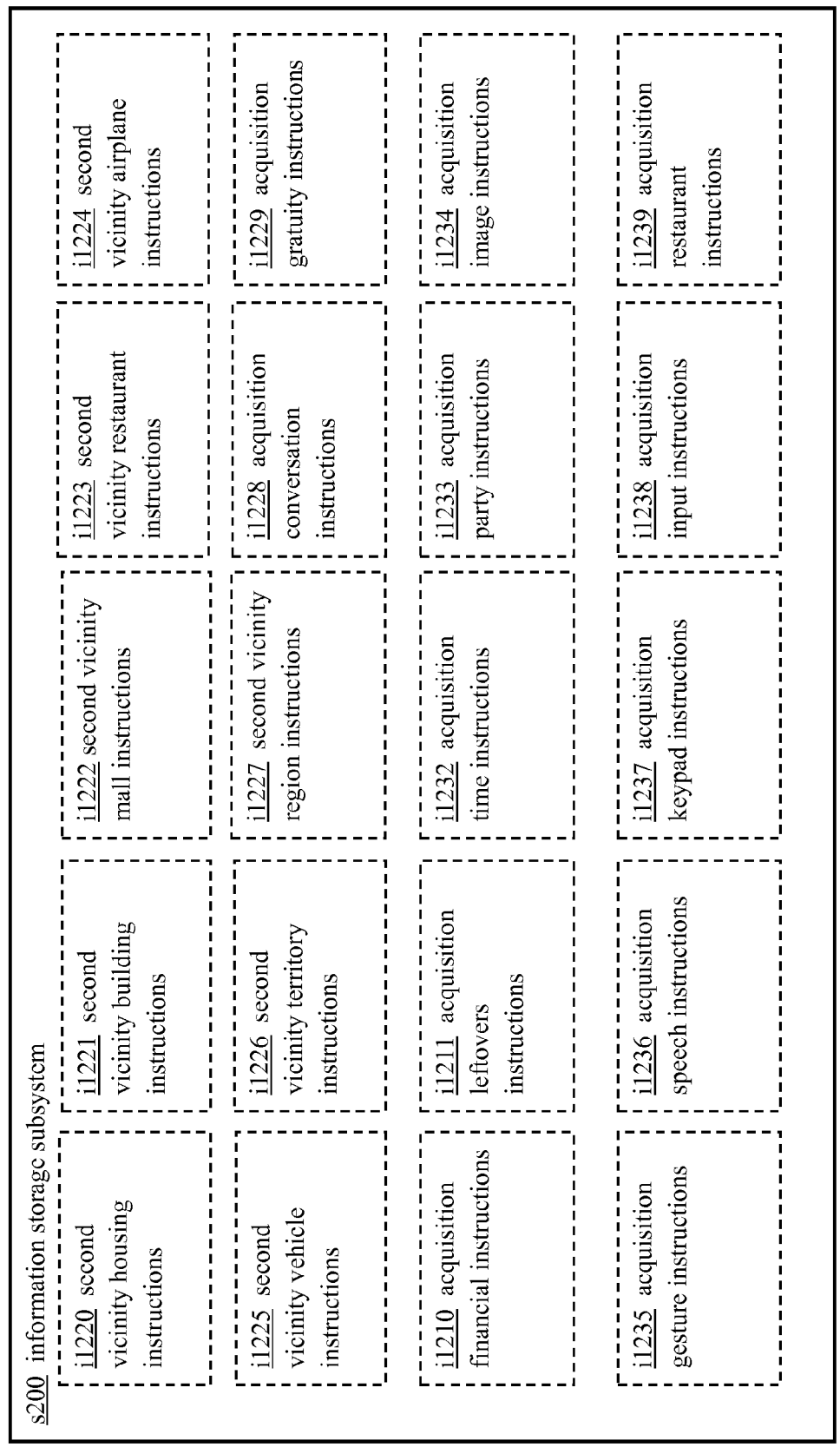
FIG. 44 is a block diagram depicting one or more exemplary instructions of the information storage subsystem s200 of the ingestible product preparation system 10 of FIG. 1.

One or more exemplary instructions depicted in FIG. 44 as being borne in an exemplary version of a non-transitory signal bearing medium of information storage subsystem s200 include one or more second vicinity housing instructions i1220, one or more second vicinity building instructions i1221, one or more second vicinity mall instructions i1222, one or more second vicinity restaurant instructions i1223, one or more second vicinity airplane instructions i1224, one or more second vicinity vehicle instructions i1225, one or more second vicinity territory instructions i1226, one or more second vicinity region instructions i1227, one or more acquisition conversation instructions i1228, one or more acquisition gratuity instructions i1229, one or more acquisition financial instructions i1230, one or more acquisition leftovers instructions i1231, one or more acquisition time instructions i1232, one or more acquisition party instructions i1233, one or more acquisition image instructions i1234, one or more acquisition gesture instructions i1235, one or more acquisition speech instructions i1236, one or more acquisition keypad instructions i1237, one or more acquisition input instructions i1238, and one or more acquisition restaurant instructions i1239.

Figure 45:
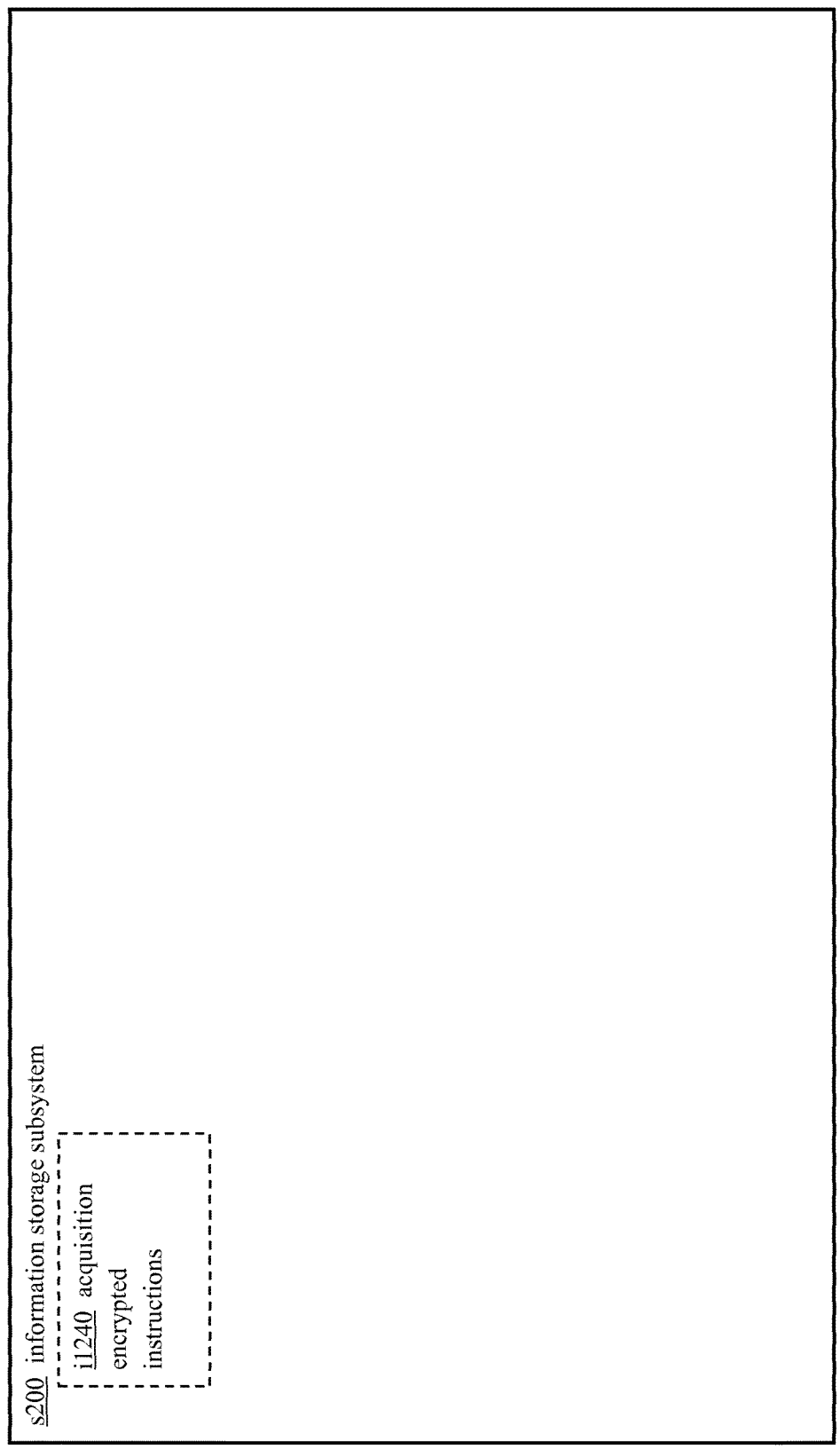
FIG. 45 is a block diagram depicting one or more exemplary instructions of the information storage subsystem s200 of the ingestible product preparation system 10 of FIG. 1.

One or more exemplary instructions depicted in FIG. 45 as being borne in an exemplary version of a non-transitory signal bearing medium of information storage subsystem s200 include one or more controlling acquisition instructions i1240.

Figure 46:
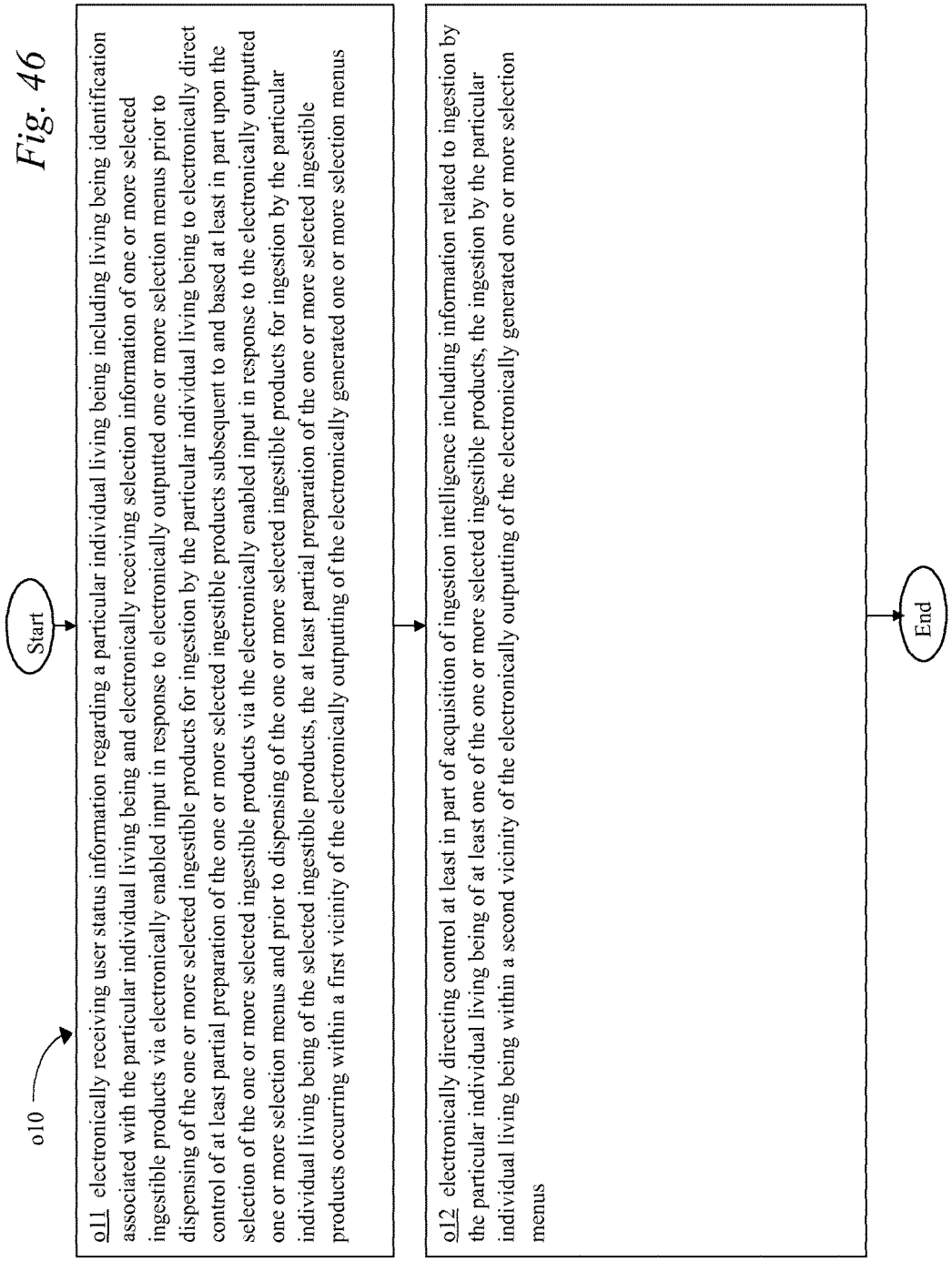
FIG. 46 is a high-level flowchart illustrating an operational flow o10 representing exemplary operations related to electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus, and electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus at least associated with the depicted exemplary implementations of the system.

An operational flow o10 as shown in FIG. 46 represents example operations related to electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus and electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus.

FIG. 46 and those figures that follow may have various examples of operational flows, and explanation may be provided with respect to the above-described examples of FIGS. 1-7 and/or with respect to other examples and contexts. Nonetheless, it should be understood that the operational flows may be executed in a number of other environments and contexts, and/or in modified versions of FIGS. 1-7. Furthermore, although the various operational flows are presented in the sequence(s) illustrated, it should be understood that the various operations may be performed in other orders than those which are illustrated, or may be performed concurrently.

In FIG. 46 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 46, the operational flow o10 proceeds to operation o11 for electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus. An exemplary version of a non-transitory signal bearing medium of information storage subsystem s200 is depicted as bearing one or more receiving information instructions i11 that when executed will direct performance of the operation o11. In an implementation, the one or more receiving information instructions i11 when executed direct electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) and electronically receiving (e.g. the network cable component s502 carries information to the transceiver component s522, etc.) selection information of one or more selected ingestible products via electronically enabled input (e.g. input using a keypad, voice commands, etc. to implement one or more selections, etc.) in response to electronically outputted (e.g. outputted on electronic display screens, etc.) one or more selection menus (e.g. textual, graphical, audio-visual or other sorts of menus, etc.) prior to dispensing of the one or more selected ingestible products for ingestion by the particular individual living being to electronically direct control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the one or more selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus (e.g. the graphical user interface s302 displaying the one or more selection menus is located within a room of a building that also houses the material processing subsystem 700 as the first vicinity used to prepare the selected fruit smoothie, etc.). Furthermore, the receiving information electrical circuitry arrangement ("elec circ arrange") e11 when activated will perform the operation o11. In an implementation, the receiving information electrical circuitry arrangement e11, when activated performs electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) and electronically receiving (e.g. the network cable component s502 carries information to the transceiver component s522, etc.) selection information of one or more selected ingestible products via electronically enabled input (e.g. input using a keypad, voice commands, etc. to implement one or more selections, etc.) in response to electronically outputted (e.g. outputted on electronic display screens, etc.) one or more selection menus (e.g. textual, graphical, audio-visual or other sorts of menus, etc.) prior to dispensing of the one or more selected ingestible products for ingestion by the particular individual living being to electronically direct control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the one or more selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus (e.g. the graphical user interface s302 displaying the one or more selection menus is located within a room of a building that also houses the material processing subsystem 700 as the first vicinity used to prepare the selected fruit smoothie, etc.). In an implementation, the electronically receiving user status information regarding a particular individual living being including living being identification associated with the particular individual living being and electronically receiving selection information of one or more selected ingestible products via electronically enabled input in response to electronically outputted one or more selection menus prior to dispensing of the one or more selected ingestible products for ingestion by the particular individual living being to electronically direct control of at least partial preparation of the one or more selected ingestible products subsequent to and based at least in part upon the selection of the one or more selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus is carried out by electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) and electronically receiving (e.g. the network cable component s502 carries information to the transceiver component s522, etc.) selection information of one or more selected ingestible products via electronically enabled input (e.g. input using a keypad, voice commands, etc. to implement one or more selections, etc.) in response to electronically outputted (e.g. outputted on electronic display screens, etc.) one or more selection menus (e.g. textual, graphical, audio-visual or other sorts of menus, etc.) prior to dispensing of the one or more selected ingestible products for ingestion by the particular individual living being to electronically direct control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the one or more selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a first vicinity of the electronically outputting of the electronically generated one or more selection menus (e.g. the graphical user interface s302 displaying the one or more selection menus is located within a room of a building that also houses the material processing subsystem 700 as the first vicinity used to prepare the selected fruit smoothie, etc.).

Figure 47:
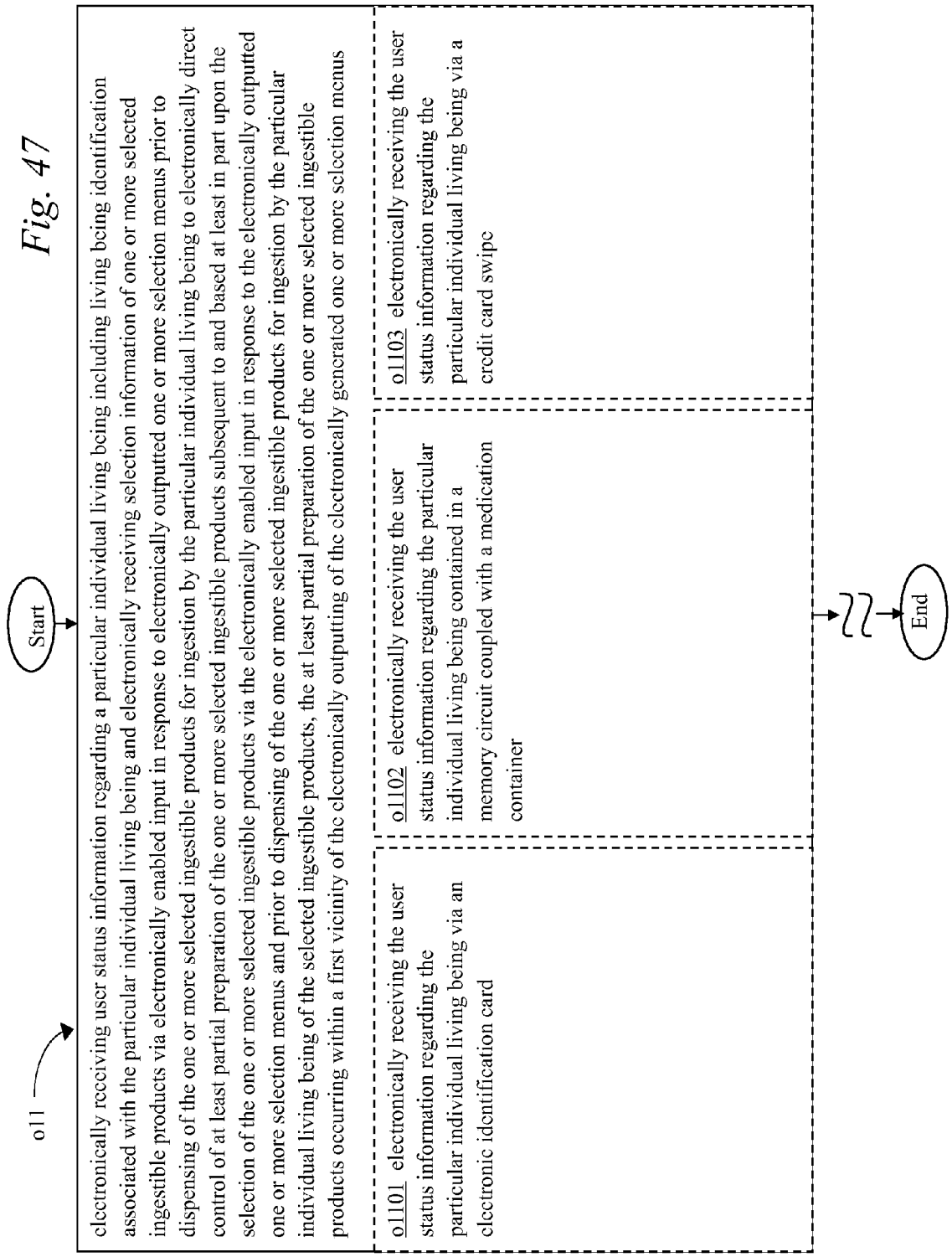
FIG. 47 is a high-level flowchart including exemplary implementations of operation O11 of FIG. 46.

In one or more implementations, as shown in FIG. 47, operation o11 includes an operation o1101 for electronically receiving the user status information regarding the particular individual living being via an electronic identification card. An exemplary version of a non-transitory signal bearing medium of information storage subsystem s200 is depicted as bearing one or more receiving information ID card instructions i1101 that when executed will direct performance of the operation o1101. In an implementation, the one or more receiving information ID card instructions i1101 when executed direct electronically receiving the user status information regarding the particular individual living being via an electronic identification card (e.g. an implementation of the receiver component s528 is configured to electronically engage with a card having memory storage holding the user status information, etc.). Furthermore, the receiving information ID card electrical circuitry arrangement ("elec circ arrange") e1101 when activated will perform the operation o1101. In an implementation, the receiving information ID card electrical circuitry arrangement e1101, when activated performs electronically receiving the user status information regarding the particular individual living being via an electronic identification card (e.g. an implementation of the receiver component s528 is configured to electronically engage with a card having memory storage holding the user status information, etc.). In an implementation, the electronically receiving the user status information regarding the particular individual living being via an electronic identification card is carried out by electronically receiving the user status information regarding the particular individual living being via an electronic identification card (e.g. an implementation of the receiver component s528 is configured to electronically engage with a card having memory storage holding the user status information, etc.).

In one or more implementations, operation o11 includes an operation o1102 for electronically receiving the user status information regarding the particular individual living being contained in a memory circuit coupled with a medication container. An exemplary version of a non-transitory signal bearing medium of information storage subsystem s200 is depicted as bearing one or more receiving information memory instructions i1102 that when executed will direct performance of the operation o1102. In an implementation, the one or more receiving information memory instructions i1102 when executed direct electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.). Furthermore, the receiving information memory electrical circuitry arrangement e1102 when activated will perform the operation o1102. In an implementation, the receiving information memory electrical circuitry arrangement e1102, when activated performs electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.). In an implementation, the electronically receiving the user status information regarding the particular individual living being contained in a memory circuit coupled with a medication container is carried out by electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.).

In one or more implementations, operation o11 includes an operation o1103 for electronically receiving the user status information regarding the particular individual living being via a credit card swipe. An exemplary version of a non-transitory signal bearing medium of information storage subsystem s200 is depicted as bearing one or more receiving information credit card instructions i1103 that when executed will direct performance of the operation o1103. In an implementation, the one or more receiving information credit card instructions i1103 when executed direct electronically receiving the user status information regarding the particular individual living being via a credit card swipe (e.g. an implementation of the receiver component s528 is configured to electronically engage with an electronic memory stripe integrated into a credit card to receive the user status information, etc.). Furthermore, the receiving information credit card electrical circuitry arrangement e1103 when activated will perform the operation o1103. In an implementation, the receiving information credit card electrical circuitry arrangement e1103, when activated performs electronically receiving the user status information regarding the particular individual living being via a credit card swipe (e.g. an implementation of the receiver component s528 is configured to electronically engage with an electronic memory stripe integrated into a credit card to receive the user status information, etc.). In an implementation, the is electronically receiving the user status information regarding the particular individual living being via a credit card swipe carried out by electronically receiving the user status information regarding the particular individual living being via a credit card swipe (e.g. an implementation of the receiver component s528 is configured to electronically engage with an electronic memory stripe integrated into a credit card to receive the user status information, etc.).

Figure 48:
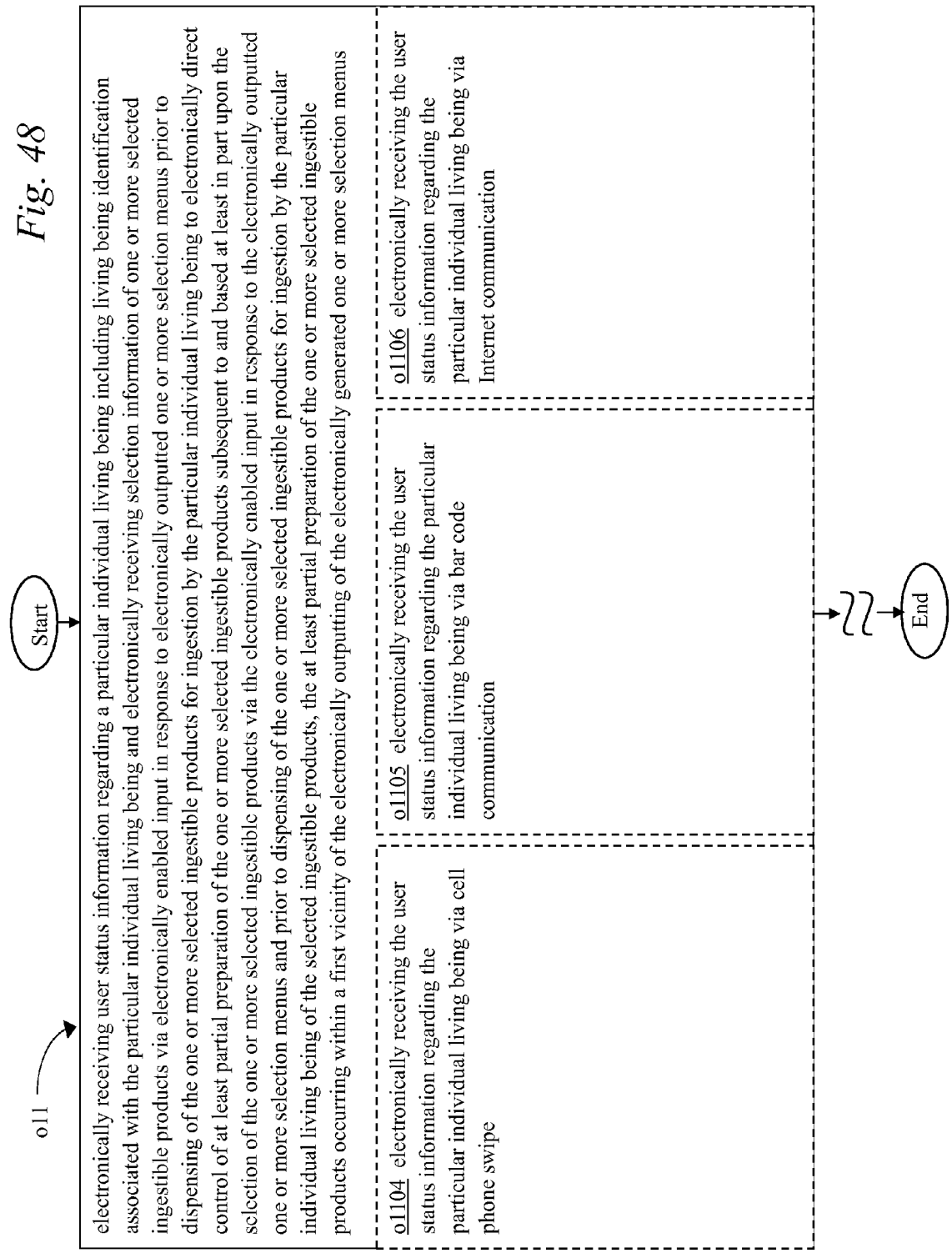
FIG. 48 is a high-level flowchart including exemplary implementations of operation O11 of FIG. 46.

In one or more implementations, as shown in FIG. 48, operation o11 includes an operation o1104 for electronically receiving the user status information regarding the particular individual living being via cell phone swipe. An exemplary version of a non-transitory signal bearing medium of information storage subsystem s200 is depicted as bearing one or more receiving information cell phone instructions i1104 that when executed will direct performance of the operation o1104. In an implementation, the one or more receiving information cell phone instructions i1104 when executed direct electronically receiving the user status information regarding the particular individual living being via cell phone swipe (e.g. an implementation of the receiver component s528 is configured to electronically engage with an electronic memory component integrated into a cell phone to receive the user status information, etc.). Furthermore, the receiving information cell phone electrical circuitry arrangement e1104 when activated will perform the operation o1104. In an implementation, the receiving information cell phone electrical circuitry arrangement e1104, when activated performs electronically receiving the user status information regarding the particular individual living being via cell phone swipe (e.g. an implementation of the receiver component s528 is configured to electronically engage with an electronic memory component integrated into a cell phone to receive the user status information, etc.). In an implementation, the is electronically receiving the user status information regarding the particular individual living being via cell phone swipe carried out by electronically receiving the user status information regarding the particular individual living being via cell phone swipe (e.g. an implementation of the receiver component s528 is configured to electronically engage with an electronic memory component integrated into a cell phone to receive the user status information, etc.).

In one or more implementations, operation o11 includes an operation o1105 for electronically receiving the user status information regarding the particular individual living being via bar code communication. An exemplary version of a non-transitory signal bearing medium of information storage subsystem s200 is depicted as bearing one or more receiving information bar code instructions i1105 that when executed will direct performance of the operation o1105. In an implementation, the one or more receiving information bar code instructions i1105 when executed direct electronically receiving the user status information regarding the particular individual living being via bar code communication (e.g. an implementation of the receiver component s528 is configured to electronically read a bar code label to receive the user status information, etc.). Furthermore, the receiving information bar code electrical circuitry arrangement e1105 when activated will perform the operation o1105. In an implementation, the receiving information bar code electrical circuitry arrangement e1105, when activated performs electronically receiving the user status information regarding the particular individual living being via bar code communication (e.g. an implementation of the receiver component s528 is configured to electronically read a bar code label to receive the user status information, etc.). In an implementation, the electronically receiving the user status information regarding the particular individual living being via bar code communication is carried out by electronically receiving the user status information regarding the particular individual living being via bar code communication (e.g. an implementation of the receiver component s528 is configured to electronically read a bar code label to receive the user status information, etc.).

In one or more implementations, operation o11 includes an operation o1106 for electronically receiving the user status information regarding the particular individual living being via Internet communication. An exemplary version of a non-transitory signal bearing medium of information storage subsystem s200 is depicted as bearing one or more receiving information Internet instructions i1106 that when executed will direct performance of the operation o1106. In an implementation, the one or more receiving information Internet instructions i1106 when executed direct electronically receiving the user status information regarding the particular individual living being via Internet communication (e.g. an implementation of the receiver component s528 is configured to electronically receive through the internet network component s508 the user status information, etc.). Furthermore, the receiving information Internet electrical circuitry arrangement e1106 when activated will perform the operation o1106. In an implementation, the receiving information Internet electrical circuitry arrangement e1106, when activated performs electronically receiving the user status information regarding the particular individual living being via Internet communication (e.g. an implementation of the receiver component s528 is configured to electronically receive through the internet network component s508 the user status information, etc.). In an implementation, the electronically receiving the user status information regarding the particular individual living being via Internet communication is carried out by electronically receiving the user status information regarding the particular individual living being via Internet communication (e.g. an implementation of the receiver component s528 is configured to electronically receive through the internet network component s508 the user status information, etc.).

Figure 49:
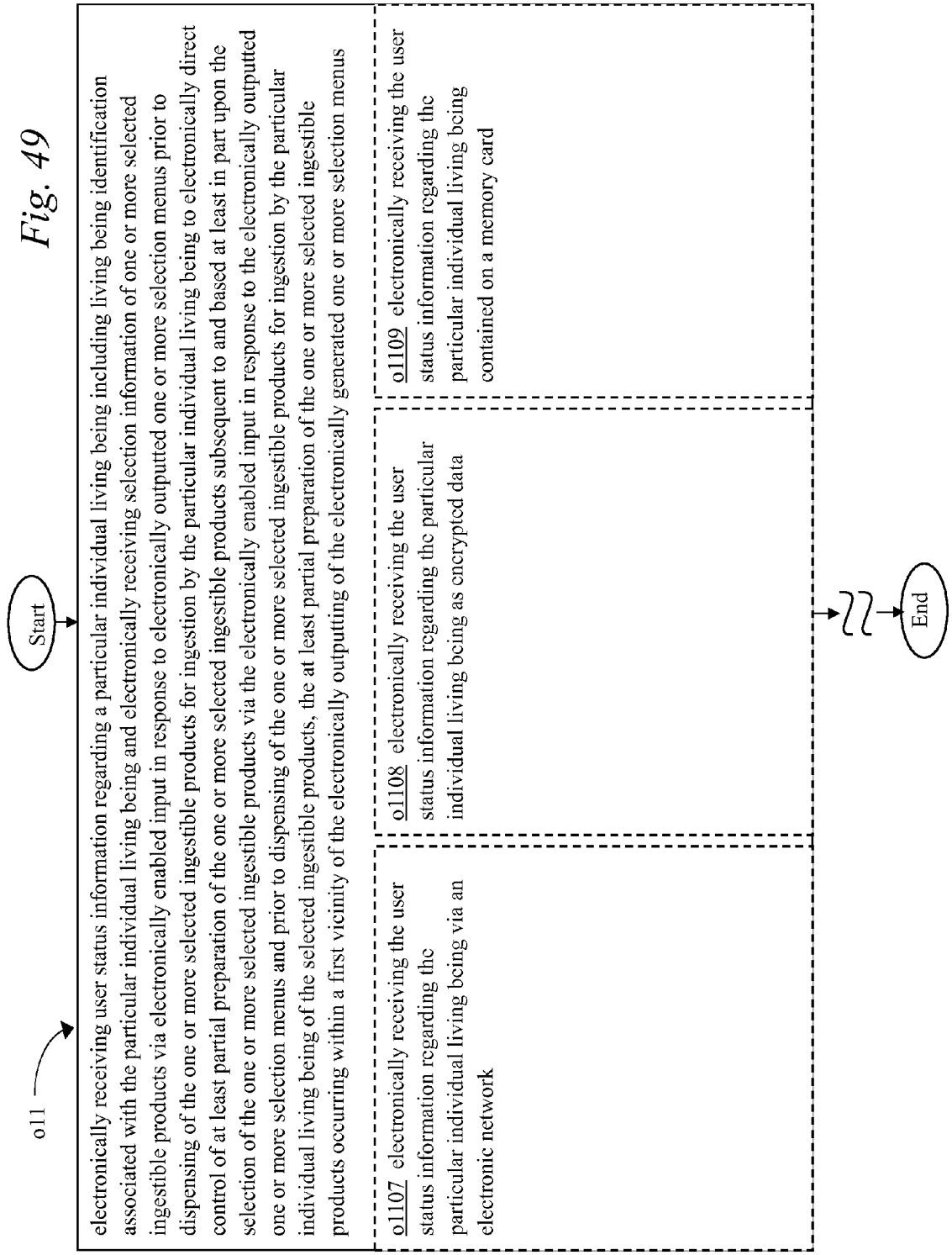
FIG. 49 is a high-level flowchart including exemplary implementations of operation O11 of FIG. 46.

In one or more implementations, as shown in FIG. 49, operation o11 includes an operation o1107 for electronically receiving the user status information regarding the particular individual living being via an electronic network. An exemplary version of a non-transitory signal bearing medium of information storage subsystem s200 is depicted as bearing one or more receiving information network instructions i1107 that when executed will direct performance of the operation o1107. In an implementation, the one or more receiving information network instructions i1107 when executed direct electronically receiving the user status information regarding the particular individual living being via an electronic network (e.g. an implementation of the receiver component s528 is configured to electronically engage with the network cable component s502 to receive the user status information, etc.). Furthermore, the receiving information network electrical circuitry arrangement e1107 when activated will perform the operation o1107. In an implementation, the receiving information network electrical circuitry arrangement e1107, when activated performs electronically receiving the user status information regarding the particular individual living being via an electronic network (e.g. an implementation of the receiver component s528 is configured to electronically engage with the network cable component s502 to receive the user status information, etc.). In an implementation, the electronically receiving the user status information regarding the particular individual living being via an electronic network is carried out by electronically receiving the user status information regarding the particular individual living being via an electronic network (e.g. an implementation of the receiver component s528 is configured to electronically engage with the network cable component s502 to receive the user status information, etc.).

In one or more implementations, operation o11 includes an operation o1108 for electronically receiving the user status information regarding the particular individual living being as encrypted data. An exemplary version of a non-transitory signal bearing medium of information storage subsystem s200 is depicted as bearing one or more receiving encrypted information instructions i1108 that when executed will direct performance of the operation o1108. In an implementation, the one or more receiving encrypted information instructions i1108 when executed direct electronically receiving the user status information as encrypted data (e.g. an implementation of the receiver component s528 is configured to electronically receive through the encrypted communication component s520 the user status information, etc.). Furthermore, the receiving encrypted information electrical circuitry arrangement e1108 when activated will perform the operation o1108. In an implementation, the receiving encrypted information electrical circuitry arrangement e1108, when activated performs electronically receiving the user status information as encrypted data (e.g. an implementation of the receiver component s528 is configured to electronically receive through the encrypted communication component s520 the user status information, etc.). In an implementation, the electronically receiving the user status information regarding the particular individual living being as encrypted data is carried out by electronically receiving the user status information as encrypted data (e.g. an implementation of the receiver component s528 is configured to electronically receive through the encrypted communication component s520 the user status information, etc.).

In one or more implementations, operation o11 includes an operation o1109 for electronically receiving the user status information regarding the particular individual living being contained on a memory card. An exemplary version of a non-transitory signal bearing medium of information storage subsystem s200 is depicted as bearing one or more receiving information memory card instructions i1109 that when executed will direct performance of the operation o1109. In an implementation, the one or more receiving information memory card instructions i1109 when executed direct electronically receiving the user status information contained on a memory card (e.g. an implementation of the receiver component s528 is configured to electronically engage with an electronic memory card to receive the user status information, etc.). Furthermore, the receiving information memory card electrical circuitry arrangement e1109 when activated will perform the operation o1109. In an implementation, the receiving information memory card electrical circuitry arrangement e1109, when activated performs electronically receiving the user status information contained on a memory card (e.g. an implementation of the receiver component s528 is configured to electronically engage with an electronic memory card to receive the user status information, etc.). In an implementation, the electronically receiving the user status information regarding the particular individual living being contained on a memory card is carried out by electronically receiving the user status information contained on a memory card (e.g. an implementation of the receiver component s528 is configured to electronically engage with an electronic memory card to receive the user status information, etc.).

Figure 50:
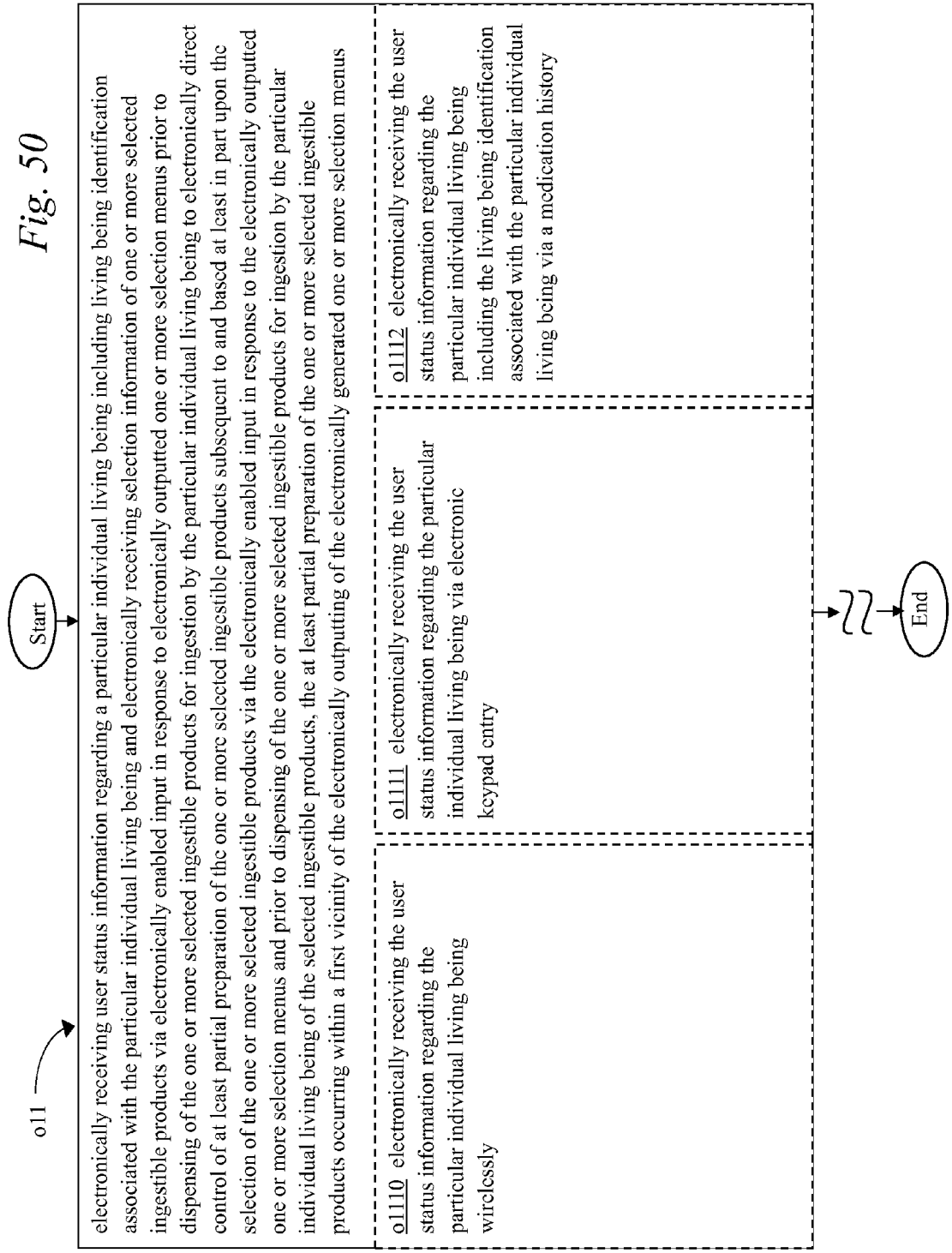
FIG. 50 is a high-level flowchart including exemplary implementations of operation O11 of FIG. 46.
Figure 51:
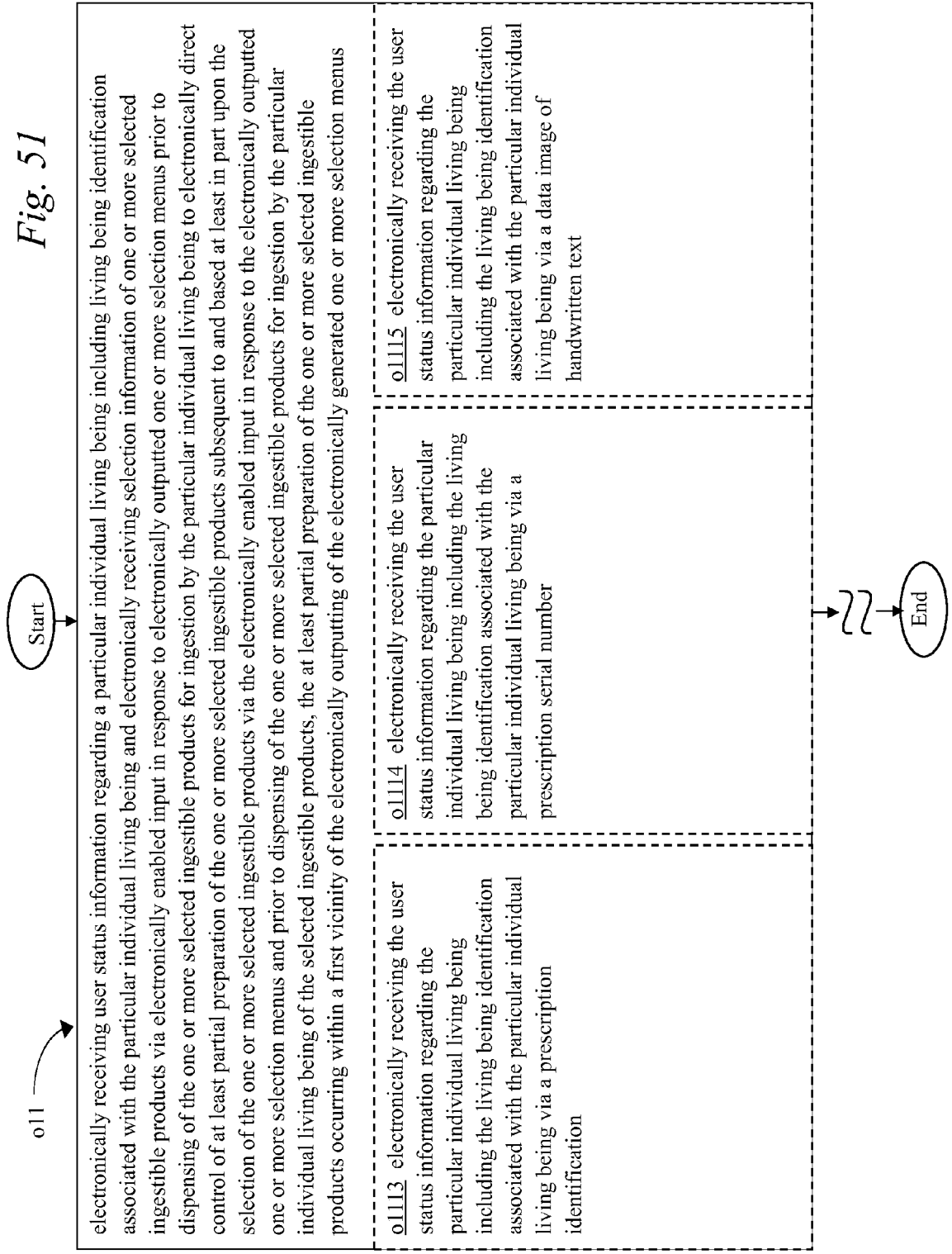
FIG. 51 is a high-level flowchart including exemplary implementations of operation O11 of FIG. 46.

In one or more implementations, as shown in FIG. 50, operation o11 includes an operation o1110 for electronically receiving the user status information regarding the particular individual living being wirelessly. An exemplary version of a non-transitory signal bearing medium of information storage subsystem s200 is depicted as bearing one or more receiving information wirelessly instructions i1110 that when executed will direct performance of the operation o1110. In an implementation, the one or more receiving information wirelessly instructions i1110 when executed direct electronically receiving the user status information wirelessly (e.g. an implementation of the receiver component s528 is configured to electronically receive through the wireless network component s512 the user status information, etc.). Furthermore, the receiving information wirelessly electrical circuitry arrangement e1110 when activated will perform the operation o1110. In an implementation, the receiving information wirelessly electrical circuitry arrangement e1110, when activated performs electronically receiving the user status information wirelessly (e.g. an implementation of the receiver component s528 is configured to electronically receive through the wireless network component s512 the user status information, etc.). In an implementation, the electronically receiving the user status information regarding the particular individual living being wirelessly is carried out by electronically receiving the user status information wirelessly (e.g. an implementation of the receiver component s528 is configured to electronically receive through the wireless network component s512 the user status information, etc.).

In one or more implementations, operation o11 includes an operation o1111 for electronically receiving the user status information regarding the particular individual living being via electronic keypad entry. An exemplary version of a non-transitory signal bearing medium of information storage subsystem s200 is depicted as bearing one or more receiving information keypad entry instructions i1111 that when executed will direct performance of the operation o1111. In an implementation, the one or more receiving information keypad entry instructions i1111 when executed direct electronically receiving the user status information regarding the particular individual living being via electronic keypad entry (e.g. an implementation of the receiver component s528 is configured to electronically engage with the keypad component s308 to receive the user status information as inputted by a user, etc.). Furthermore, the receiving information keypad entry electrical circuitry arrangement e1111 when activated will perform the operation o1111. In an implementation, the receiving information keypad entry electrical circuitry arrangement e1111, when activated performs electronically receiving the user status information regarding the particular individual living being via electronic keypad entry (e.g. an implementation of the receiver component s528 is configured to electronically engage with the keypad component s308 to receive the user status information as inputted by a user, etc.). In an implementation, the electronically receiving the user status information regarding the particular individual living being via electronic keypad entry is carried out by electronically receiving the user status information regarding the particular individual living being via electronic keypad entry (e.g. an implementation of the receiver component s528 is configured to electronically engage with the keypad component s308 to receive the user status information as inputted by a user, etc.).

In one or more implementations, operation o11 includes an operation o1112 for electronically receiving the user status information regarding the particular individual living being including the living being identification associated with the particular individual living being via a medication history. An exemplary version of a non-transitory signal bearing medium of information storage subsystem s200 is depicted as bearing one or more receiving information meds history instructions i1112 that when executed will direct performance of the operation o1112. In an implementation, the one or more receiving information meds history instructions i1112 when executed direct electronically receiving the user status information regarding the particular individual living being including the living being identification associated with the particular individual living being via a medication history (e.g. an implementation of the receiver component s528 is configured to electronically engage with the microprocessor component s102 to receive the user status information including the living being identification associated with the particular individual living being as determined by the microprocessor component to identify the name and control number of the medication history of the particular individual living being, etc.). Furthermore, the receiving information meds history electrical circuitry arrangement e1112 when activated will perform the operation o1112. In an implementation, the receiving information meds history electrical circuitry arrangement e1112, when activated performs electronically receiving the user status information regarding the particular individual living being including the living being identification associated with the particular individual living being via a medication history (e.g. an implementation of the receiver component s528 is configured to electronically engage with the microprocessor component s102 to receive the user status information including the living being identification associated with the particular individual living being as determined by the microprocessor component to identify the name and control number of the medication history of the particular individual living being, etc.). In an implementation, the electronically receiving the user status information regarding the particular individual living being including the living being identification associated with the particular individual living being via a medication history is carried out by electronically receiving the user status information regarding the particular individual living being including the living being identification associated with the particular individual living being via a medication history (e.g. an implementation of the receiver component s528 is configured to electronically engage with the microprocessor component s102 to receive the user status information including the living being identification associated with the particular individual living being as determined by the microprocessor component to identify the name and control number of the medication history of the particular individual living being, etc.).

In one or more implementations, as shown in FIG. 44, operation o11 includes an operation o1113 for electronically receiving the user status information regarding the particular individual living being including the living being identification associated with the particular individual living being via a prescription identification. An exemplary version of a non-transitory signal bearing medium of information storage subsystem s200 is depicted as bearing one or more receiving information prescription ID instructions i1113 that when executed will direct performance of the operation o1113. In an implementation, the one or more receiving information prescription ID instructions i1113 when executed direct electronically receiving the user status information regarding the particular individual living being including the living being identification associated with the particular individual living being via a prescription identification (e.g. an implementation of the receiver component s528 is configured to electronically engage with the microprocessor component s102 to receive the user status information including the living being identification associated with the particular individual living being as determined by the microprocessor component to include a prescription identification, etc.). Furthermore, the receiving information prescription ID electrical circuitry arrangement e1113 when activated will perform the operation o1113. In an implementation, the receiving information prescription ID electrical circuitry arrangement e1113, when activated performs electronically receiving the user status information regarding the particular individual living being including the living being identification associated with the particular individual living being via a prescription identification (e.g. an implementation of the receiver component s528 is configured to electronically engage with the microprocessor component s102 to receive the user status information including the living being identification associated with the particular individual living being as determined by the microprocessor component to include a prescription identification, etc.). In an implementation, the electronically receiving the user status information regarding the particular individual living being including the living being identification associated with the particular individual living being via a prescription identification is carried out by electronically receiving the user status information regarding the particular individual living being including the living being identification associated with the particular individual living being via a prescription identification (e.g. an implementation of the receiver component s528 is configured to electronically engage with the microprocessor component s102 to receive the user status information including the living being identification associated with the particular individual living being as determined by the microprocessor component to include a prescription identification, etc.).

In one or more implementations, operation o11 includes an operation o1114 for electronically receiving the user status information regarding the particular individual living being including the living being identification associated with the particular individual living being via a prescription serial number. An exemplary version of a non-transitory signal bearing medium of information storage subsystem s200 is depicted as bearing one or more receiving information prescription number instructions i1114 that when executed will direct performance of the operation o1114. In an implementation, the one or more receiving information prescription number instructions i1114 when executed direct electronically receiving the user status information regarding the particular individual living being including the living being identification associated with the particular individual living being via a prescription serial number (e.g. an implementation of the receiver component s528 is configured to electronically engage with the microprocessor component s102 to receive the user status information including the living being identification associated with the particular individual living being as determined by the microprocessor component to include a prescription serial number, etc.). Furthermore, the receiving information prescription number electrical circuitry arrangement e1114 when activated will perform the operation o1114. In an implementation, the receiving information prescription number electrical circuitry arrangement e1114, when activated performs electronically receiving the user status information regarding the particular individual living being including the living being identification associated with the particular individual living being via a prescription serial number (e.g. an implementation of the receiver component s528 is configured to electronically engage with the microprocessor component s102 to receive the user status information including the living being identification associated with the particular individual living being as determined by the microprocessor component to include a prescription serial number, etc.). In an implementation, the electronically receiving the user status information regarding the particular individual living being including the living being identification associated with the particular individual living being via a prescription serial number is carried out by electronically receiving the user status information regarding the particular individual living being including the living being identification associated with the particular individual living being via a prescription serial number (e.g. an implementation of the receiver component s528 is configured to electronically engage with the microprocessor component s102 to receive the user status information including the living being identification associated with the particular individual living being as determined by the microprocessor component to include a prescription serial number, etc.).

In one or more implementations, operation o11 includes an operation o1115 for electronically receiving the user status information regarding the particular individual living being including the living being identification associated with the particular individual living being via a data image of handwritten text. An exemplary version of a non-transitory signal bearing medium of information storage subsystem s200 is depicted as bearing one or more receiving information handwritten instructions i1115 that when executed will direct performance of the operation o1115. In an implementation, the one or more receiving information handwritten instructions i1115 when executed direct electronically receiving the user status information regarding the particular individual living being including the living being identification associated with the particular individual living being via a data image of handwritten text (e.g. an implementation of the receiver component s528 is configured to electronically engage with the microprocessor component s102 to receive the user status information regarding the particular individual living being including the living being identification associated with the particular individual living being as determined by the microprocessor component through electronic handwriting analysis of the data image of the handwritten text, etc.). Furthermore, the receiving information handwritten electrical circuitry arrangement e1115 when activated will perform the operation o1115. In an implementation, the receiving information handwritten electrical circuitry arrangement e1115, when activated performs electronically receiving the user status information regarding the particular individual living being including the living being identification associated with the particular individual living being via a data image of handwritten text (e.g. an implementation of the receiver component s528 is configured to electronically engage with the microprocessor component s102 to receive the user status information regarding the particular individual living being including the living being identification associated with the particular individual living being as determined by the microprocessor component through electronic handwriting analysis of the data image of the handwritten text, etc.). In an implementation, the electronically receiving the user status information regarding the particular individual living being including the living being identification associated with the particular individual living being via a data image of handwritten text is carried out by electronically receiving the user status information regarding the particular individual living being including the living being identification associated with the particular individual living being via a data image of handwritten text (e.g. an implementation of the receiver component s528 is configured to electronically engage with the microprocessor component s102 to receive the user status information regarding the particular individual living being including the living being identification associated with the particular individual living being as determined by the microprocessor component through electronic handwriting analysis of the data image of the handwritten text, etc.).

In one or more implementations, as shown in FIG. 45, operation o11 includes an operation o1116 for electronically receiving the user status information regarding the particular individual living being including the living being identification associated with the particular individual living being via a computer text file. An exemplary version of a non-transitory signal bearing medium of information storage subsystem s200 is depicted as bearing one or more receiving information text file instructions i1116 that when executed will direct performance of the operation o1116. In an implementation, the one or more receiving information text file instructions i1116 when executed direct electronically receiving the user status information regarding the particular individual living being including the living being identification associated with the particular individual living being via a computer text file (e.g. an implementation of the receiver component s528 is configured to electronically engage with the microprocessor component s102 to receive the user status information including the living being identification associated with the particular individual living being as determined by the microprocessor component through electronic reading of the computer text file, etc.). Furthermore, the receiving information text file electrical circuitry arrangement e1116 when activated will perform the operation o1116. In an implementation, the receiving information text file electrical circuitry arrangement e1116, when activated performs electronically receiving the user status information regarding the particular individual living being including the living being identification associated with the particular individual living being via a computer text file (e.g. an implementation of the receiver component s528 is configured to electronically engage with the microprocessor component s102 to receive the user status information including the living being identification associated with the particular individual living being as determined by the microprocessor component through electronic reading of the computer text file, etc.). In an implementation, the electronically receiving the user status information regarding the particular individual living being including the living being identification associated with the particular individual living being via a computer text file is carried out by electronically receiving the user status information regarding the particular individual living being including the living being identification associated with the particular individual living being via a computer text file (e.g. an implementation of the receiver component s528 is configured to electronically engage with the microprocessor component s102 to receive the user status information including the living being identification associated with the particular individual living being as determined by the microprocessor component through electronic reading of the computer text file, etc.).

In one or more implementations, operation o11 includes an operation o1117 for electronically receiving the user status information regarding the particular individual living being including the living being identification associated with the particular individual living being via a computer audio file. An exemplary version of a non-transitory signal bearing medium of information storage subsystem s200 is depicted as bearing one or more receiving information audio file instructions i1117 that when executed will direct performance of the operation o1117. In an implementation, the one or more receiving information audio file instructions i1117 when executed direct electronically receiving the user status information regarding the particular individual living being including the living being identification associated with the particular individual living being via a computer audio file (e.g. an implementation of the receiver component s528 is configured to electronically engage with the microprocessor component s102 to receive the user status information including the living being identification associated with the particular individual living being as determined by the microprocessor component through electronic reading of the computer audio file, etc.). Furthermore, the receiving information audio file electrical circuitry arrangement e1117 when activated will perform the operation o1117. In an implementation, the receiving information audio file electrical circuitry arrangement e1117, when activated performs electronically receiving the user status information regarding the particular individual living being including the living being identification associated with the particular individual living being via a computer audio file (e.g. an implementation of the receiver component s528 is configured to electronically engage with the microprocessor component s102 to receive the user status information including the living being identification associated with the particular individual living being as determined by the microprocessor component through electronic reading of the computer audio file, etc.). In an implementation, the electronically receiving the user status information regarding the particular individual living being including the living being identification associated with the particular individual living being via a computer audio file is carried out by electronically receiving the user status information regarding the particular individual living being including the living being identification associated with the particular individual living being via a computer audio file (e.g. an implementation of the receiver component s528 is configured to electronically engage with the microprocessor component s102 to receive the user status information including the living being identification associated with the particular individual living being as determined by the microprocessor component through electronic reading of the computer audio file, etc.).

In one or more implementations, operation o11 includes an operation o1118 for electronically receiving the user status information regarding the particular individual living being including the living being identification associated with the particular individual living being via a computer video file. An exemplary version of a non-transitory signal bearing medium of information storage subsystem s200 is depicted as bearing one or more receiving information video file instructions i1118 that when executed will direct performance of the operation o1118. In an implementation, the one or more receiving information video file instructions i1118 when executed direct electronically receiving the user status information regarding the particular individual living being including the living being identification associated with the particular individual living being via a computer video file (e.g. an implementation of the receiver component s528 is configured to electronically engage with the microprocessor component s102 to receive the user status information including the living being identification associated with the particular individual living being as determined by the microprocessor component through electronic reading of the computer video file, etc.). Furthermore, the receiving information video file electrical circuitry arrangement e1118 when activated will perform the operation o1118. In an implementation, the receiving information video file electrical circuitry arrangement e1118, when activated performs electronically receiving the user status information regarding the particular individual living being including the living being identification associated with the particular individual living being via a computer video file (e.g. an implementation of the receiver component s528 is configured to electronically engage with the microprocessor component s102 to receive the user status information including the living being identification associated with the particular individual living being as determined by the microprocessor component through electronic reading of the computer video file, etc.). In an implementation, the electronically receiving the user status information regarding the particular individual living being including the living being identification associated with the particular individual living being via a computer video file is carried out by electronically receiving the user status information regarding the particular individual living being including the living being identification associated with the particular individual living being via a computer video file (e.g. an implementation of the receiver component s528 is configured to electronically engage with the microprocessor component s102 to receive the user status information including the living being identification associated with the particular individual living being as determined by the microprocessor component through electronic reading of the computer video file, etc.).

In one or more implementations, as shown in FIG. 46, operation o11 includes an operation o1119 for electronically receiving the user status information regarding the particular individual living being including the living being identification associated with the particular individual living being via an RFID tag. An exemplary version of a non-transitory signal bearing medium of information storage subsystem s200 is depicted as bearing one or more receiving information RFID instructions i1119 that when executed will direct performance of the operation o1119. In an implementation, the one or more receiving information RFID instructions i1119 when executed direct electronically receiving the user status information regarding the particular individual living being including the living being identification associated with the particular individual living being via an RFID tag (e.g. an implementation of the receiver component s528 is configured to electronically engage with the microprocessor component s102 to receive the user status information including the living being identification associated with the particular individual living being as determined by the microprocessor component through electronic reading be the radio frequency identification (RFID) sensing component s414 of the RFID tag, etc.). Furthermore, the receiving information RFID electrical circuitry arrangement e1119 when activated will perform the operation o1119. In an implementation, the receiving information RFID electrical circuitry arrangement e1119, when activated performs electronically receiving the user status information regarding the particular individual living being including the living being identification associated with the particular individual living being via an RFID tag (e.g. an implementation of the receiver component s528 is configured to electronically engage with the microprocessor component s102 to receive the user status information including the living being identification associated with the particular individual living being as determined by the microprocessor component through electronic reading be the radio frequency identification (RFID) sensing component s414 of the RFID tag, etc.). In an implementation, the electronically receiving the user status information regarding the particular individual living being including the living being identification associated with the particular individual living being via an RFID tag is carried out by electronically receiving the user status information regarding the particular individual living being including the living being identification associated with the particular individual living being via an RFID tag (e.g. an implementation of the receiver component s528 is configured to electronically engage with the microprocessor component s102 to receive the user status information including the living being identification associated with the particular individual living being as determined by the microprocessor component through electronic reading be the radio frequency identification (RFID) sensing component s414 of the RFID tag, etc.).

In one or more implementations, operation o11 includes an operation o1120 for electronically receiving the user status information regarding the particular individual living being including the living being identification associated with the particular individual living being via a bar code. An exemplary version of a non-transitory signal bearing medium of information storage subsystem s200 is depicted as bearing one or more receiving information bar code instructions i1120 that when executed will direct performance of the operation o1120. In an implementation, the one or more receiving information bar code instructions i1120 when executed direct electronically receiving the user status information regarding the particular individual living being including the living being identification associated with the particular individual living being via a bar code (e.g. an implementation of the receiver component s528 is configured to electronically engage with the microprocessor component s102 to receive the user status information including the living being identification associated with the particular individual living being as determined by the microprocessor component through electronic reading of the bar code, etc.). Furthermore, the receiving information bar code electrical circuitry arrangement e1120 when activated will perform the operation electronically receiving the user status information regarding the particular individual living being including the living being identification associated with the particular individual living being via a bar code. In an implementation, the receiving information bar code electrical circuitry arrangement e1120, when activated performs electronically receiving the user status information regarding the particular individual living being including the living being identification associated with the particular individual living being via a bar code (e.g. an implementation of the receiver component s528 is configured to electronically engage with the microprocessor component s102 to receive the user status information including the living being identification associated with the particular individual living being as determined by the microprocessor component through electronic reading of the bar code, etc.). In an implementation, the electronically receiving the user status information regarding the particular individual living being including the living being identification associated with the particular individual living being via a bar code is carried out by electronically receiving the user status information regarding the particular individual living being including the living being identification associated with the particular individual living being via a bar code (e.g. an implementation of the receiver component s528 is configured to electronically engage with the microprocessor component s102 to receive the user status information including the living being identification associated with the particular individual living being as determined by the microprocessor component through electronic reading of the bar code, etc.).

In one or more implementations, operation o11 includes an operation o1121 for electronically receiving the user status information regarding the particular individual living being including the living being identification associated with the particular individual living being via a holographic image. An exemplary version of a non-transitory signal bearing medium of information storage subsystem s200 is depicted as bearing one or more receiving information holographic instructions i1121 that when executed will direct performance of the operation o1121. In an implementation, the one or more receiving information holographic instructions i1121 when executed direct electronically receiving the user status information regarding the particular individual living being including the living being identification associated with the particular individual living being via a holographic image (e.g. an implementation of the receiver component s528 is configured to electronically engage with the microprocessor component s102 to receive the user status information including the living being identification associated with the particular individual living being as determined by the microprocessor component through electronic reading of the holographic image, etc.). Furthermore, the receiving information holographic electrical circuitry arrangement e1121 when activated will perform the operation o1121. In an implementation, the receiving information holographic electrical circuitry arrangement e1121, when activated performs electronically receiving the user status information regarding the particular individual living being including the living being identification associated with the particular individual living being via a holographic image (e.g. an implementation of the receiver component s528 is configured to electronically engage with the microprocessor component s102 to receive the user status information including the living being identification associated with the particular individual living being as determined by the microprocessor component through electronic reading of the holographic image, etc.). In an implementation, the electronically receiving the user status information regarding the particular individual living being including the living being identification associated with the particular individual living being via a holographic image is carried out by electronically receiving the user status information regarding the particular individual living being including the living being identification associated with the particular individual living being via a holographic image (e.g. an implementation of the receiver component s528 is configured to electronically engage with the microprocessor component s102 to receive the user status information including the living being identification associated with the particular individual living being as determined by the microprocessor component through electronic reading of the holographic image, etc.).

In one or more implementations, as shown in FIG. 47, operation o11 includes an operation o1122 for electronically receiving the selection information of the one or more selected ingestible products via the electronically enabled input in response to the electronically outputted one or more selection menus in textual form. An exemplary version of a non-transitory signal bearing medium of information storage subsystem s200 is depicted as bearing one or more receiving information textual instructions i1122 that when executed will direct performance of the operation o1122. In an implementation, the one or more receiving information textual instructions i1122 when executed direct electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated allergies, one or more selection menus in textual form, such as a menu containing textual one or more descriptions of possible ingestible product to select from, etc.). Furthermore, the receiving information textual electrical circuitry arrangement e1122 when activated will perform the operation o1122. In an implementation, the receiving information textual electrical circuitry arrangement e1122, when activated performs electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated allergies, one or more selection menus in textual form, such as a menu containing textual one or more descriptions of possible ingestible product to select from, etc.). In an implementation, the electronically receiving the selection information of the one or more selected ingestible products via the electronically enabled input in response to the electronically outputted one or more selection menus in textual form is carried out by electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated allergies, one or more selection menus in textual form, such as a menu containing textual one or more descriptions of possible ingestible product to select from, etc.).

In one or more implementations, operation o11 includes an operation o1123 for electronically receiving the selection information of the one or more selected ingestible products via the electronically enabled input in response to the electronically outputted one or more selection menus in icon form. An exemplary version of a non-transitory signal bearing medium of information storage subsystem s200 is depicted as bearing one or more receiving information icon instructions i1123 that when executed will direct performance of the operation o1123. In an implementation, the one or more receiving information icon instructions i1123 when executed direct electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.). Furthermore, the receiving information icon electrical circuitry arrangement e1123 when activated will perform the operation o1123. In an implementation, the receiving information icon electrical circuitry arrangement e1123, when activated performs electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.). In an implementation, the electronically receiving the selection information of the one or more selected ingestible products via the electronically enabled input in response to the electronically outputted one or more selection menus in icon form is carried out by electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.).

In one or more implementations, operation o11 includes an operation o1124 for electronically receiving the selection information of the one or more selected ingestible products via the electronically enabled input in response to the electronically outputted one or more selection menus in graphical form. An exemplary version of a non-transitory signal bearing medium of information storage subsystem s200 is depicted as bearing one or more receiving information graphical instructions i1124 that when executed will direct performance of the operation o1124. In an implementation, the one or more receiving information graphical instructions i1124 when executed direct electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.). Furthermore, the receiving information graphical electrical circuitry arrangement e1124 when activated will perform the operation o1124. In an implementation, the receiving information graphical electrical circuitry arrangement e1124, when activated performs electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.). In an implementation, the electronically receiving the selection information of the one or more selected ingestible products via the electronically enabled input in response to the electronically outputted one or more selection menus in graphical form is carried out by electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.).

In one or more implementations, as shown in FIG. 48, operation o11 includes an operation o1125 for electronically receiving the selection information of the one or more selected ingestible products via the electronically enabled input in response to the electronically outputted one or more selection menus in markup language form. An exemplary version of a non-transitory signal bearing medium of information storage subsystem s200 is depicted as bearing one or more receiving information markup instructions i1125 that when executed will direct performance of the operation o1125. In an implementation, the one or more receiving information markup instructions i1125 when executed direct electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.). Furthermore, the receiving information markup electrical circuitry arrangement e1125 when activated will perform the operation o1125. In an implementation, the receiving information markup electrical circuitry arrangement e1125, when activated performs electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.). In an implementation, the electronically receiving the selection information of the one or more selected ingestible products via the electronically enabled input in response to the electronically outputted one or more selection menus in markup language form is carried out by electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.).

In one or more implementations, operation o11 includes an operation o1126 for electronically receiving the selection information of the one or more selected ingestible products via the electronically enabled input in response to the electronically outputted one or more selection menus in audio form. An exemplary version of a non-transitory signal bearing medium of information storage subsystem s200 is depicted as bearing one or more receiving information audio instructions i1126 that when executed will direct performance of the operation o1126. In an implementation, the one or more receiving information audio instructions i1126 when executed direct electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.). Furthermore, the receiving information audio electrical circuitry arrangement e1126 when activated will perform the operation o1126. In an implementation, the receiving information audio electrical circuitry arrangement e1126, when activated performs electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.). In an implementation, the electronically receiving the selection information of the one or more selected ingestible products via the electronically enabled input in response to the electronically outputted one or more selection menus in audio form is carried out by electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.).

In one or more implementations, operation o11 includes an operation o1127 for electronically receiving the selection information of the one or more selected ingestible products via the electronically enabled input in response to the electronically outputted one or more selection menus in list form. An exemplary version of a non-transitory signal bearing medium of information storage subsystem s200 is depicted as bearing one or more receiving information list instructions i1127 that when executed will direct performance of the operation o1127. In an implementation, the one or more receiving information list instructions i1127 when executed direct electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated dislikes, one or more selection menus in list form, such as a menu containing listed one or more descriptions of possible ingestible product to select from, etc.)l. Furthermore, the receiving information list electrical circuitry arrangement e1127 when activated will perform the operation o1127. In an implementation, the receiving information list electrical circuitry arrangement e1127, when activated performs electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated dislikes, one or more selection menus in list form, such as a menu containing listed one or more descriptions of possible ingestible product to select from, etc.)l. In an implementation, the electronically receiving the selection information of the one or more selected ingestible products via the electronically enabled input in response to the electronically outputted one or more selection menus in list form is carried out by electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated dislikes, one or more selection menus in list form, such as a menu containing listed one or more descriptions of possible ingestible product to select from, etc.).

Figure 56:
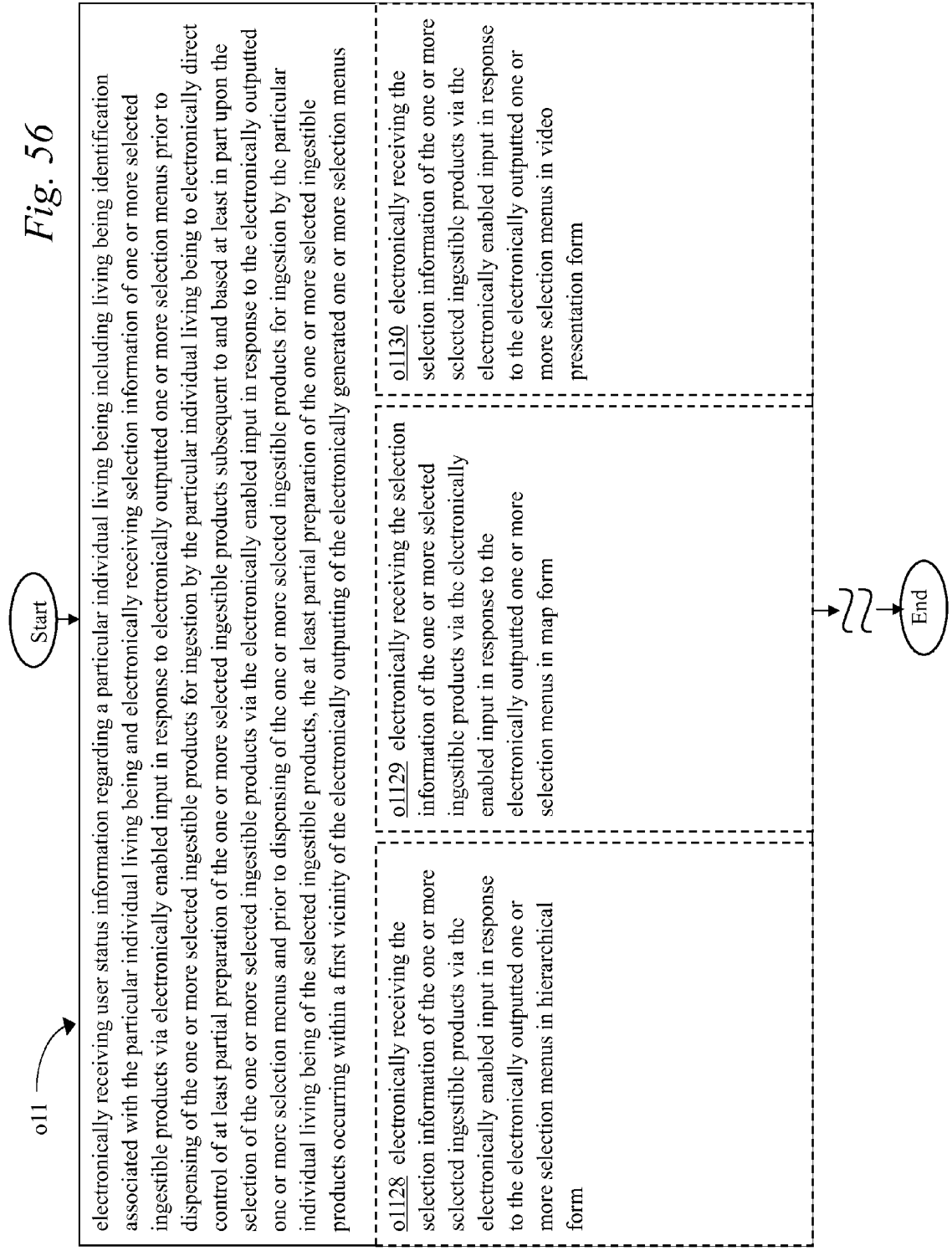
FIG. 56 is a high-level flowchart including exemplary implementations of operation O11 of FIG. 46.

In one or more implementations, as shown in FIG. 56, operation o11 includes an operation o1128 for electronically receiving the selection information of the one or more selected ingestible products via the electronically enabled input in response to the electronically outputted one or more selection menus in hierarchical form. An exemplary version of a non-transitory signal bearing medium of information storage subsystem s200 is depicted as bearing one or more receiving information hierarchical instructions i1128 that when executed will direct performance of the operation o1128. In an implementation, the one or more receiving information hierarchical instructions i1128 when executed direct electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.). Furthermore, the receiving information hierarchical electrical circuitry arrangement e1128 when activated will perform the operation o1128. In an implementation, the receiving information hierarchical electrical circuitry arrangement e1128, when activated performs electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.). In an implementation, the electronically receiving the selection information of the one or more selected ingestible products via the electronically enabled input in response to the electronically outputted one or more selection menus in hierarchical form is carried out by electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.).

In one or more implementations, operation o11 includes an operation o1129 for electronically receiving the selection information of the one or more selected ingestible products via the electronically enabled input in response to the electronically outputted one or more selection menus in map form. An exemplary version of a non-transitory signal bearing medium of information storage subsystem s200 is depicted as bearing one or more receiving information map instructions i1129 that when executed will direct performance of the operation o1129. In an implementation, the one or more receiving information map instructions i1129 when executed direct electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.). Furthermore, the receiving information map electrical circuitry arrangement e1129 when activated will perform the operation o1129. In an implementation, the receiving information map electrical circuitry arrangement e1129, when activated performs electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.). In an implementation, the electronically receiving the selection information of the one or more selected ingestible products via the electronically enabled input in response to the electronically outputted one or more selection menus in map form is carried out by electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.).

In one or more implementations, operation o11 includes an operation o1130 for electronically receiving the selection information of the one or more selected ingestible products via the electronically enabled input in response to the electronically outputted one or more selection menus in video presentation form. An exemplary version of a non-transitory signal bearing medium of information storage subsystem s200 is depicted as bearing one or more receiving information video instructions i1130 that when executed will direct performance of the operation o1130. In an implementation, the one or more receiving information video instructions i1130 when executed direct electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.). Furthermore, the receiving information video electrical circuitry arrangement e1130 when activated will perform the operation o1130. In an implementation, the receiving information video electrical circuitry arrangement e1130, when activated performs electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.). In an implementation, the electronically receiving the selection information of the one or more selected ingestible products via the electronically enabled input in response to the electronically outputted one or more selection menus in video presentation form is carried out by electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.).

Figure 57:
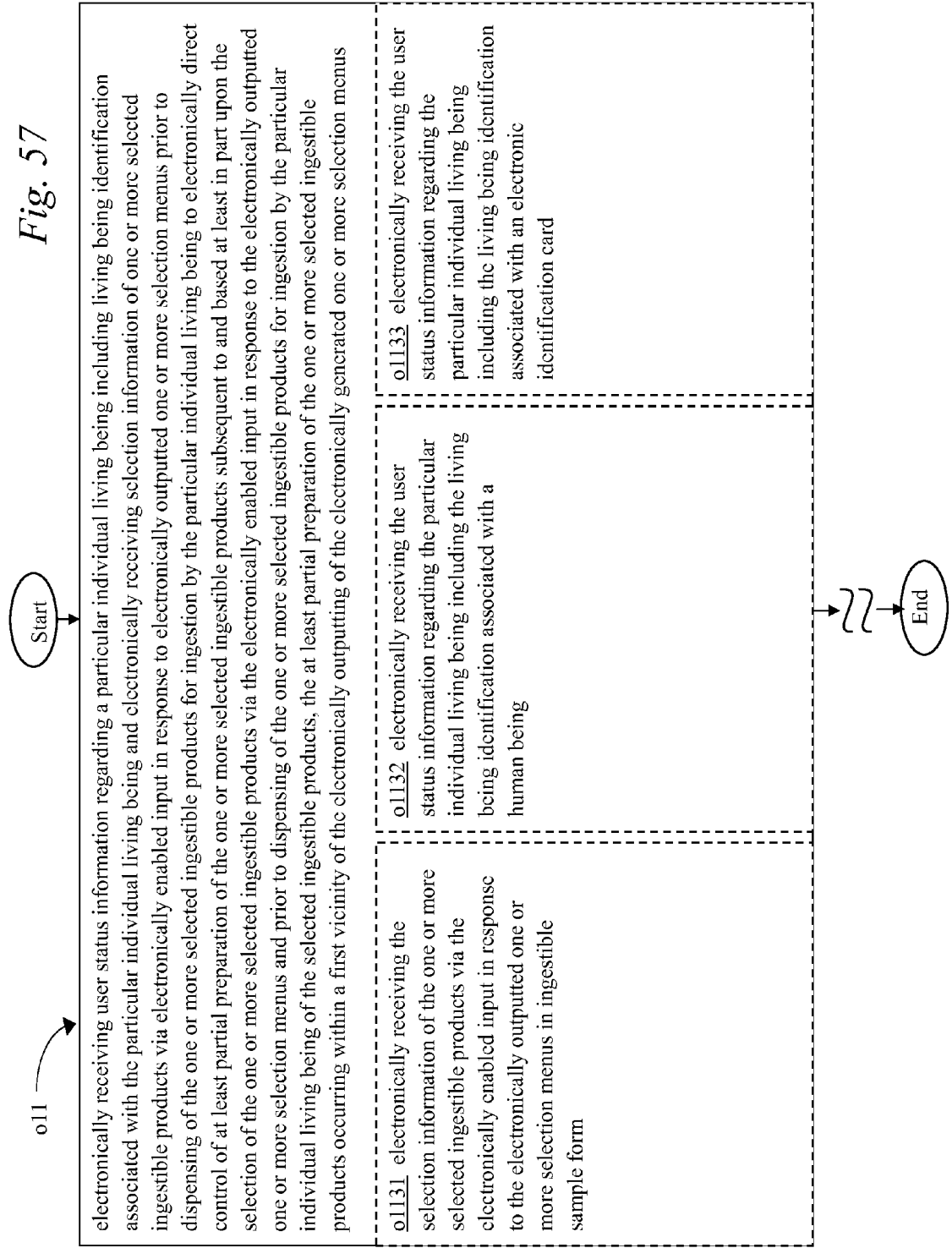
FIG. 57 is a high-level flowchart including exemplary implementations of operation O11 of FIG. 46.

In one or more implementations, as shown in FIG. 57, operation o11 includes an operation o1131 for electronically receiving the selection information of the one or more selected ingestible products via the electronically enabled input in response to the electronically outputted one or more selection menus in ingestible sample form. An exemplary version of a non-transitory signal bearing medium of information storage subsystem s200 is depicted as bearing one or more receiving information sample instructions i1131 that when executed will direct performance of the operation o1131. In an implementation, the one or more receiving information sample instructions i1131 when executed direct electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.). Furthermore, the receiving information sample electrical circuitry arrangement e1131 when activated will perform the operation o1131. In an implementation, the receiving information sample electrical circuitry arrangement e1131, when activated performs electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.). In an implementation, the electronically receiving the selection information of the one or more selected ingestible products via the electronically enabled input in response to the electronically outputted one or more selection menus in ingestible sample form is carried out by electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the microprocessor component s102 to receive the user status information including the living being identification associated with the particular individual living being for the microprocessor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.).

In one or more implementations, operation o11 includes an operation o1132 for electronically receiving the user status information regarding the particular individual living being including the living being identification associated with a human being. An exemplary version of a non-transitory signal bearing medium of information storage subsystem s200 is depicted as bearing one or more receiving information human instructions i1132 that when executed will direct performance of the operation o1132. In an implementation, the one or more receiving information human instructions i1132 when executed direct electronically receiving the user status information regarding the particular individual living being including living being identification associated with a human being (e.g. an implementation of the receiver component s528 is configured to electronically engage with the microprocessor component s102 to receive the user status information regarding the particular individual living being including living being identification as determined by the microprocessor component to be identifying a human being, etc.). Furthermore, the receiving information human electrical circuitry arrangement e1132 when activated will perform the operation o1132. In an implementation, the receiving information human electrical circuitry arrangement e1132, when activated performs electronically receiving the user status information regarding the particular individual living being including living being identification associated with a human being (e.g. an implementation of the receiver component s528 is configured to electronically engage with the microprocessor component s102 to receive the user status information regarding the particular individual living being including living being identification as determined by the microprocessor component to be identifying a human being, etc.). In an implementation, the electronically receiving the user status information regarding the particular individual living being including the living being identification associated with a human being is carried out by electronically receiving the user status information regarding the particular individual living being including living being identification associated with a human being (e.g. an implementation of the receiver component s528 is configured to electronically engage with the microprocessor component s102 to receive the user status information regarding the particular individual living being including living being identification as determined by the microprocessor component to be identifying a human being, etc.).

In one or more implementations, operation o11 includes an operation o1133 for electronically receiving the user status information regarding the particular individual living being including the living being identification associated with an electronic identification card. An exemplary version of a non-transitory signal bearing medium of information storage subsystem s200 is depicted as bearing one or more receiving information ID card instructions i1133 that when executed will direct performance of the operation o1133. In an implementation, the one or more receiving information ID card instructions i1133 when executed direct electronically receiving the user status information regarding the particular individual living being including living being identification associated with an electronic identification card (e.g. an implementation of the receiver component s528 is configured to electronically engage with the microprocessor component s102 to receive the user status information regarding the particular individual living being including living being identification as determined by the microprocessor component to be identifying a living being through the electronic identification card, etc.). Furthermore, the receiving information ID card electrical circuitry arrangement e1133 when activated will perform the operation o1133. In an implementation, the receiving information ID card electrical circuitry arrangement e1133, when activated performs electronically receiving the user status information regarding the particular individual living being including living being identification associated with an electronic identification card (e.g. an implementation of the receiver component s528 is configured to electronically engage with the microprocessor component s102 to receive the user status information regarding the particular individual living being including living being identification as determined by the microprocessor component to be identifying a living being through the electronic identification card, etc.). In an implementation, the electronically receiving the user status information regarding the particular individual living being including the living being identification associated with an electronic identification card is carried out by electronically receiving the user status information regarding the particular individual living being including living being identification associated with an electronic identification card (e.g. an implementation of the receiver component s528 is configured to electronically engage with the microprocessor component s102 to receive the user status information regarding the particular individual living being including living being identification as determined by the microprocessor component to be identifying a living being through the electronic identification card, etc.).

Figure 58:
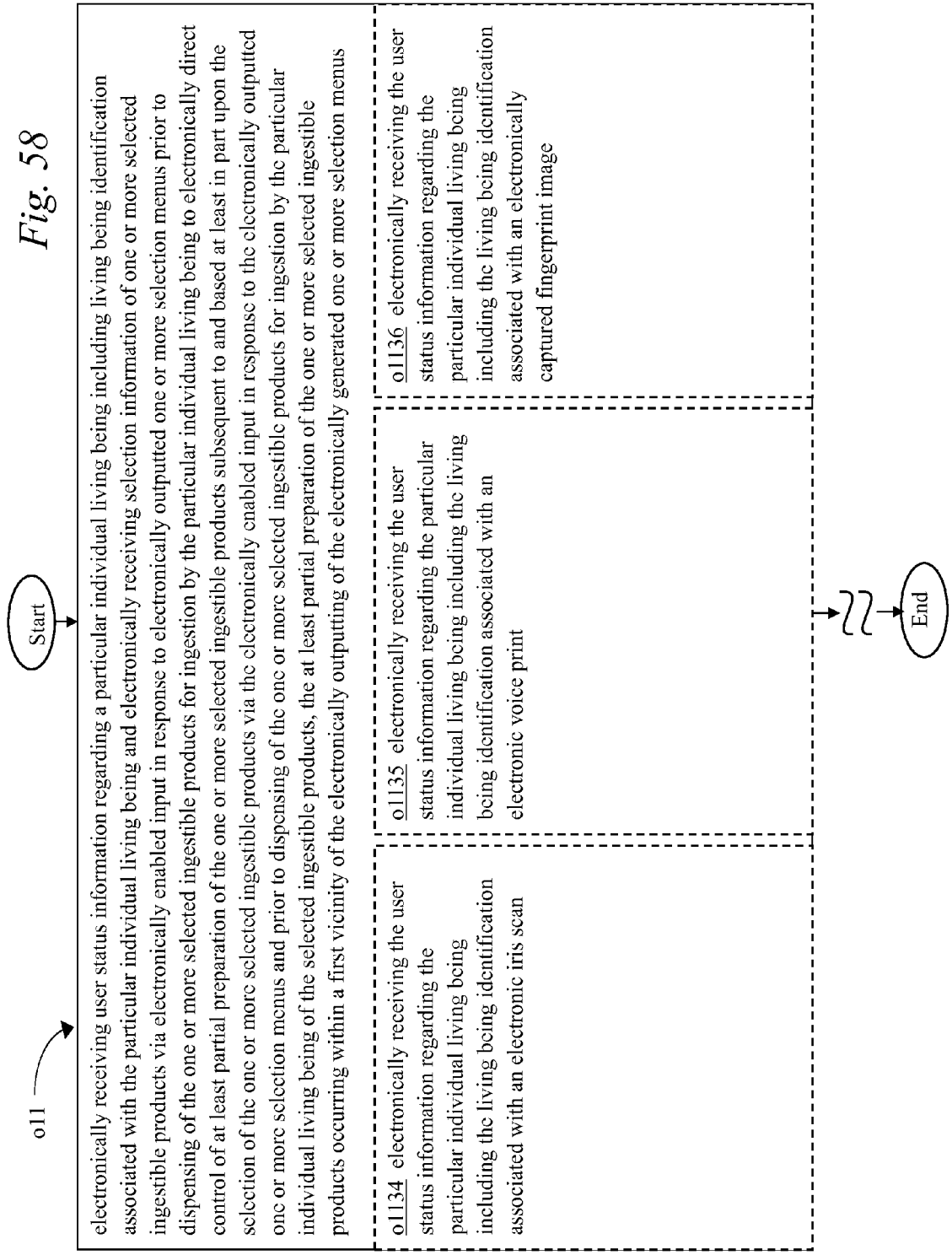
FIG. 58 is a high-level flowchart including exemplary implementations of operation O11 of FIG. 46.
Figure 59:
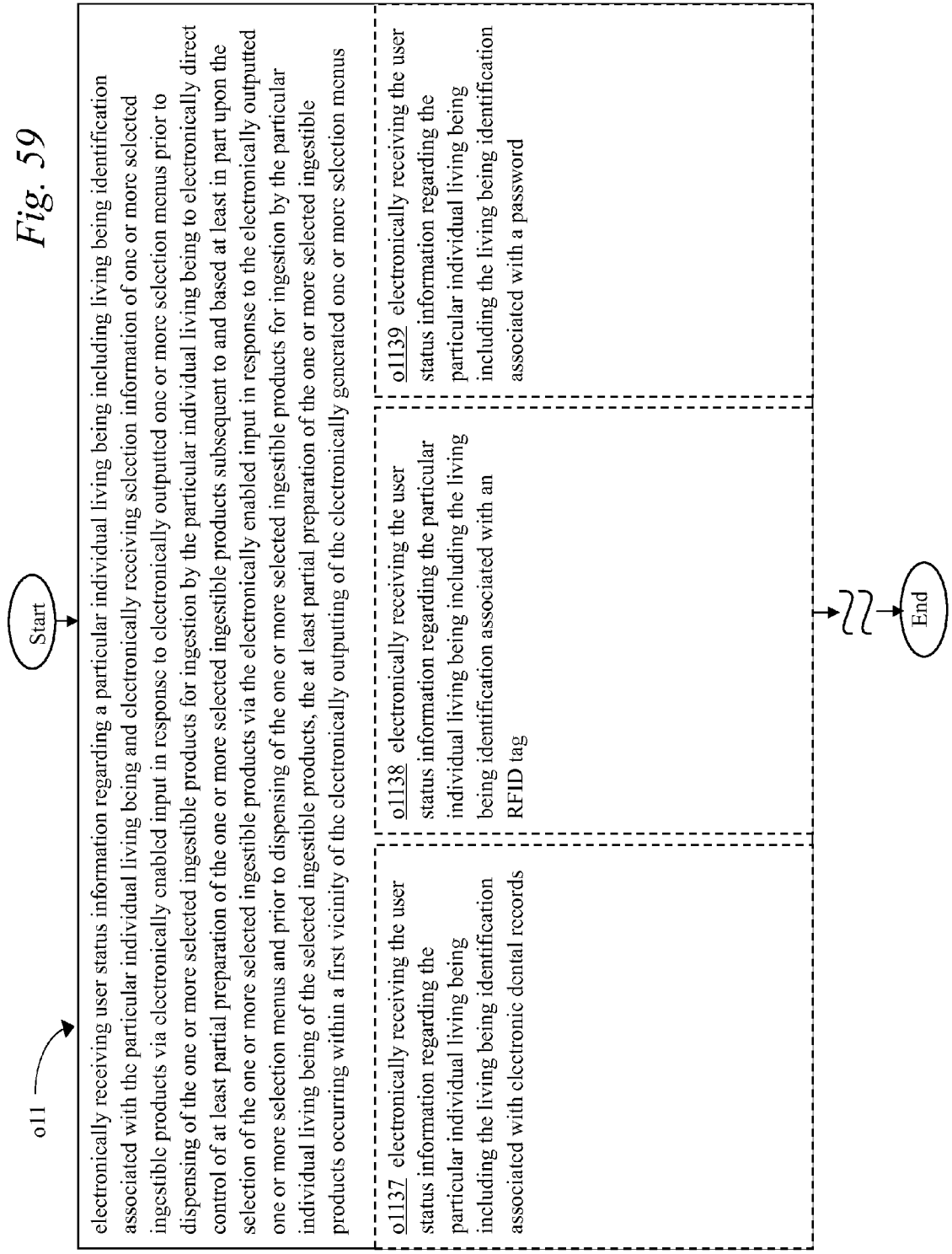
FIG. 59 is a high-level flowchart including exemplary implementations of operation O11 of FIG. 46.

In one or more implementations, as shown in FIG. 58, operation o11 includes an operation o1134 for electronically receiving the user status information regarding the particular individual living being including the living being identification associated with an electronic iris scan. An exemplary version of a non-transitory signal bearing medium of information storage subsystem s200 is depicted as bearing one or more receiving information iris scan instructions i1134 that when executed will direct performance of the operation o1134. In an implementation, the one or more receiving information iris scan instructions i1134 when executed direct electronically receiving the user status information regarding the particular individual living being including living being identification associated with an electronic iris scan (e.g. an implementation of the receiver component s528 is configured to electronically engage with the microprocessor component s102 to receive the user status information regarding the particular individual living being including living being identification as determined by the microprocessor component to be identifying the living being through the electronic iris scan, etc.). Furthermore, the receiving information iris scan electrical circuitry arrangement e1134 when activated will perform the operation o1134. In an implementation, the receiving information iris scan electrical circuitry arrangement e1134, when activated performs electronically receiving the user status information regarding the particular individual living being including living being identification associated with an electronic iris scan (e.g. an implementation of the receiver component s528 is configured to electronically engage with the microprocessor component s102 to receive the user status information regarding the particular individual living being including living being identification as determined by the microprocessor component to be identifying the living being through the electronic iris scan, etc.). In an implementation, the electronically receiving the user status information regarding the particular individual living being including the living being identification associated with an electronic iris scan is carried out by electronically receiving the user status information regarding the particular individual living being including living being identification associated with an electronic iris scan (e.g. an implementation of the receiver component s528 is configured to electronically engage with the microprocessor component s102 to receive the user status information regarding the particular individual living being including living being identification as determined by the microprocessor component to be identifying the living being through the electronic iris scan, etc.).

In one or more implementations, operation o11 includes an operation o1135 for electronically receiving the user status information regarding the particular individual living being including the living being identification associated with an electronic voice print. An exemplary version of a non-transitory signal bearing medium of information storage subsystem s200 is depicted as bearing one or more receiving information voice instructions i1135 that when executed will direct performance of the operation o1135. In an implementation, the one or more receiving information voice instructions i1135 when executed direct electronically receiving the user status information regarding the particular individual living being including living being identification associated with an electronic voice print (e.g. an implementation of the receiver component s528 is configured to electronically engage with the microprocessor component s102 to receive the user status information regarding the particular individual living being including living being identification as determined by the microprocessor component to be identifying the living being through the electronic voice print, etc.). Furthermore, the receiving information voice electrical circuitry arrangement e1135 when activated will perform the operation o1135. In an implementation, the receiving information voice electrical circuitry arrangement e1135, when activated performs electronically receiving the user status information regarding the particular individual living being including living being identification associated with an electronic voice print (e.g. an implementation of the receiver component s528 is configured to electronically engage with the microprocessor component s102 to receive the user status information regarding the particular individual living being including living being identification as determined by the microprocessor component to be identifying the living being through the electronic voice print, etc.). In an implementation, the electronically receiving the user status information regarding the particular individual living being including the living being identification associated with an electronic voice print is carried out by electronically receiving the user status information regarding the particular individual living being including living being identification associated with an electronic voice print (e.g. an implementation of the receiver component s528 is configured to electronically engage with the microprocessor component s102 to receive the user status information regarding the particular individual living being including living being identification as determined by the microprocessor component to be identifying the living being through the electronic voice print, etc.).

In one or more implementations, operation o11 includes an operation o1136 for electronically receiving the user status information regarding the particular individual living being including the living being identification associated with an electronically captured fingerprint image. An exemplary version of a non-transitory signal bearing medium of information storage subsystem s200 is depicted as bearing one or more receiving information fingerprint instructions i1136 that when executed will direct performance of the operation o1136. In an implementation, the one or more receiving information fingerprint instructions i1136 when executed direct electronically receiving the user status information regarding the particular individual living being including living being identification associated with an electronically captured fingerprint image (e.g. an implementation of the receiver component s528 is configured to electronically engage with the microprocessor component s102 to receive the user status information regarding the particular individual living being including living being identification as determined by the microprocessor component to be identifying the living being through the electronically captured fingerprint image, etc.). Furthermore, the receiving information fingerprint electrical circuitry arrangement e1136 when activated will perform the operation o1136. In an implementation, the receiving information fingerprint electrical circuitry arrangement e1136, when activated performs electronically receiving the user status information regarding the particular individual living being including living being identification associated with an electronically captured fingerprint image (e.g. an implementation of the receiver component s528 is configured to electronically engage with the microprocessor component s102 to receive the user status information regarding the particular individual living being including living being identification as determined by the microprocessor component to be identifying the living being through the electronically captured fingerprint image, etc.). In an implementation, the electronically receiving the user status information regarding the particular individual living being including the living being identification associated with an electronically captured fingerprint image is carried out by electronically receiving the user status information regarding the particular individual living being including living being identification associated with an electronically captured fingerprint image (e.g. an implementation of the receiver component s528 is configured to electronically engage with the microprocessor component s102 to receive the user status information regarding the particular individual living being including living being identification as determined by the microprocessor component to be identifying the living being through the electronically captured fingerprint image, etc.).

Figure 52:
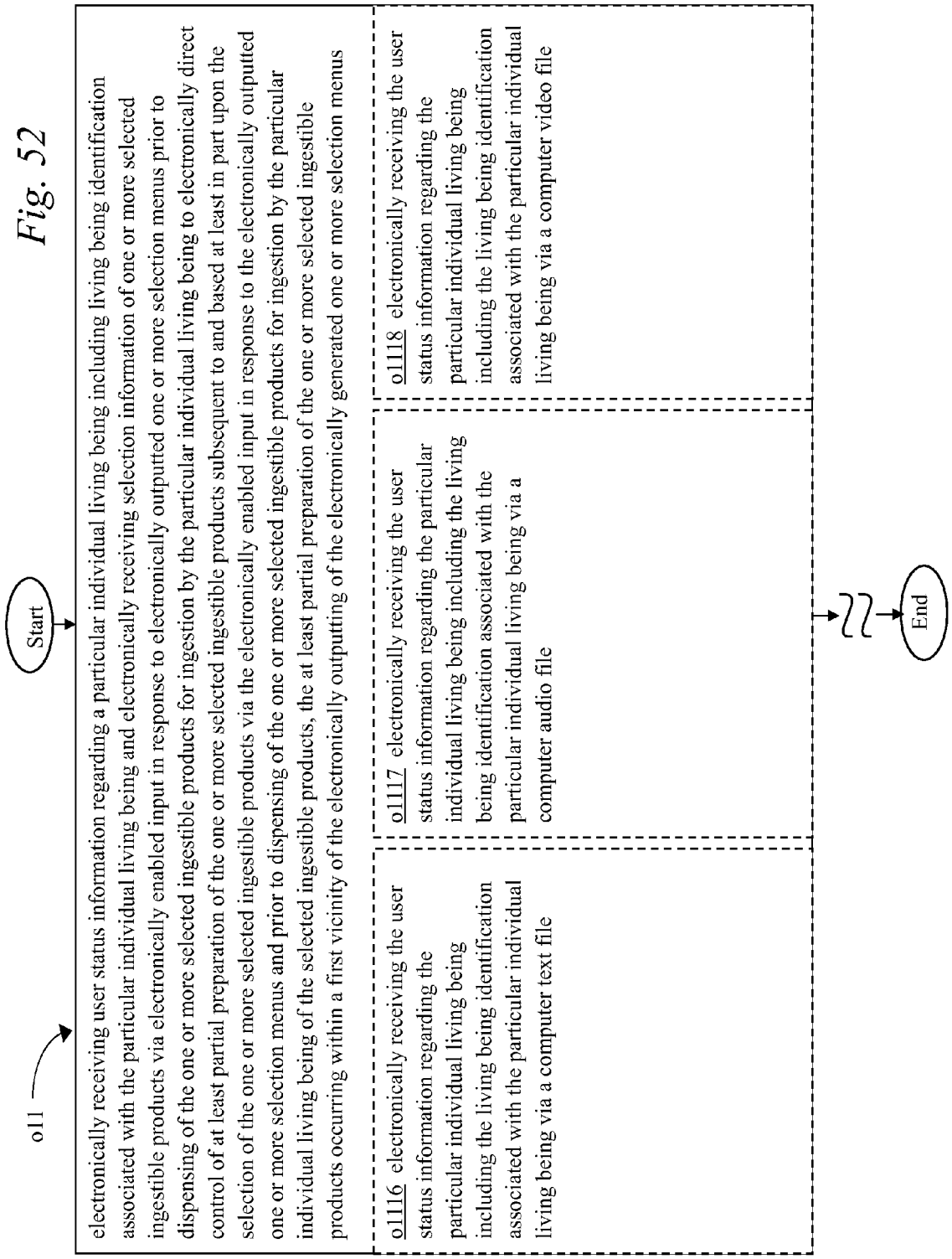
FIG. 52 is a high-level flowchart including exemplary implementations of operation O11 of FIG. 46.
Figure 53:
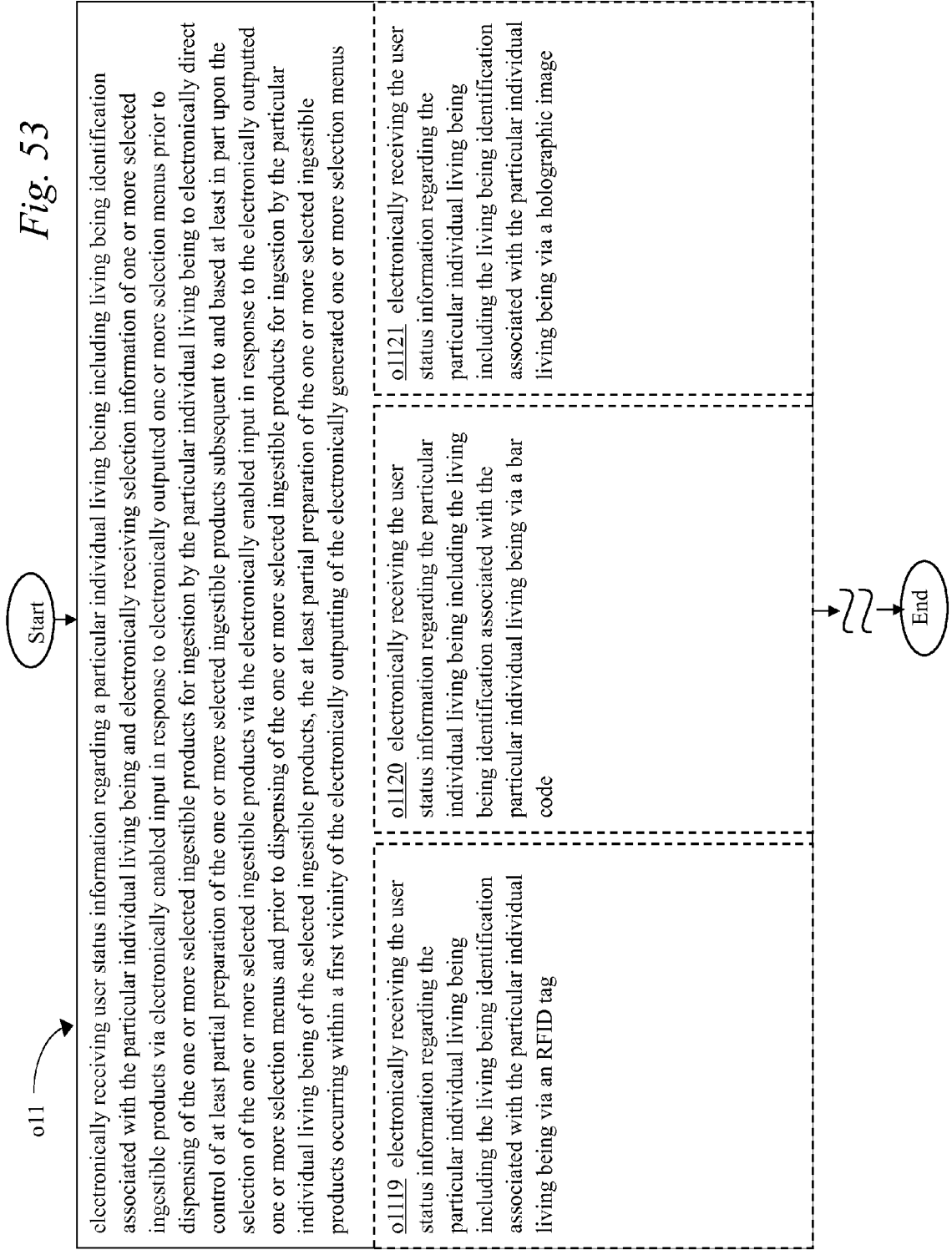
FIG. 53 is a high-level flowchart including exemplary implementations of operation O11 of FIG. 46.
Figure 54:
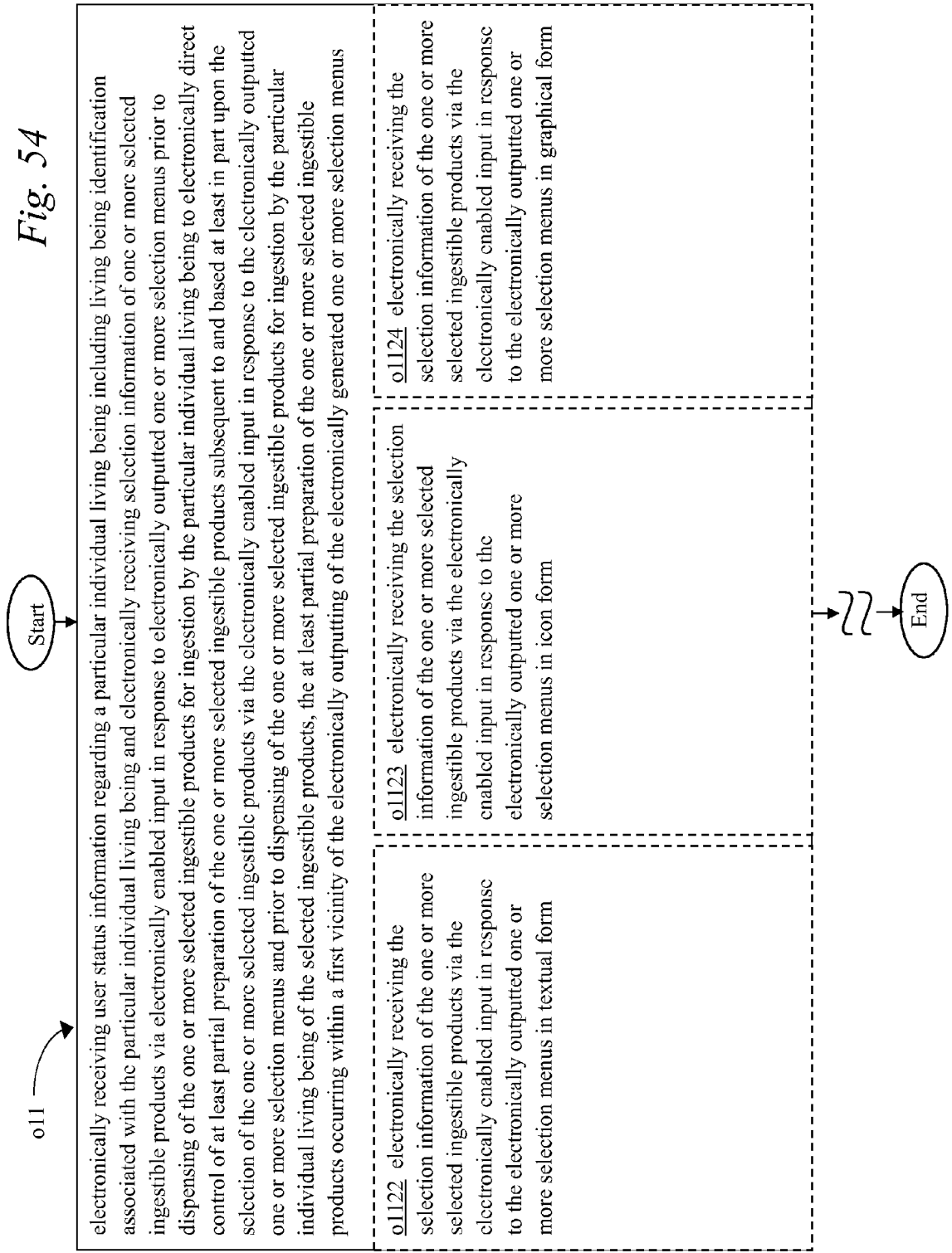
FIG. 54 is a high-level flowchart including exemplary implementations of operation O11 of FIG. 46.
Figure 55:
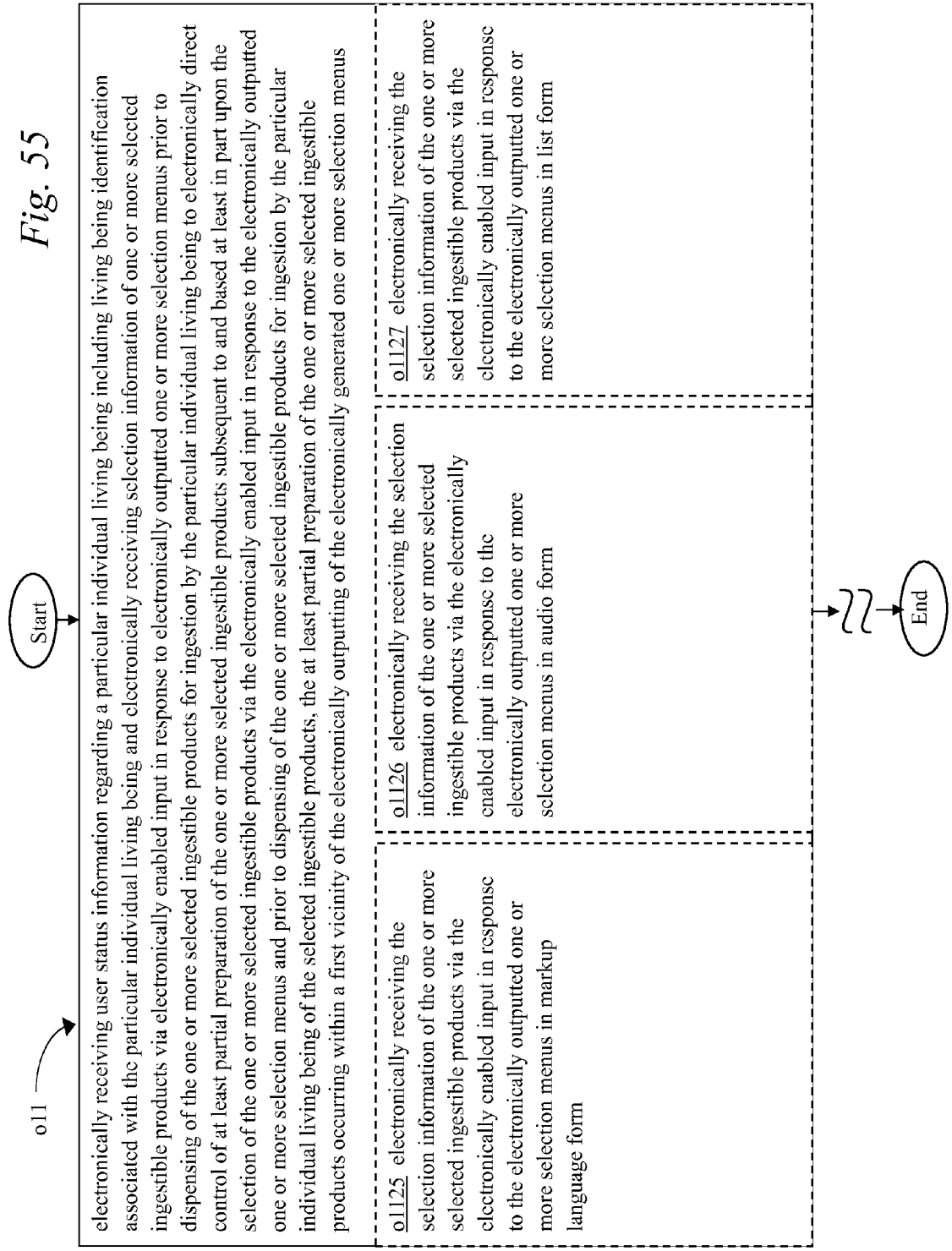
FIG. 55 is a high-level flowchart including exemplary implementations of operation O11 of FIG. 46.

In one or more implementations, as shown in FIG. 52, operation o11 includes an operation o1137 for electronically receiving the user status information regarding the particular individual living being including the living being identification associated with electronic dental records. An exemplary version of a non-transitory signal bearing medium of information storage subsystem s200 is depicted as bearing one or more receiving information dental instructions i1137 that when executed will direct performance of the operation o1137. In an implementation, the one or more receiving information dental instructions i1137 when executed direct electronically receiving the user status information regarding the particular individual living being including living being identification associated with electronic dental records (e.g. an implementation of the receiver component s528 is configured to electronically engage with the microprocessor component s102 to receive the user status information regarding the particular individual living being including living being identification as determined by the microprocessor component to be identifying the living being through the electronic dental records, etc.). Furthermore, the receiving information dental electrical circuitry arrangement e1137 when activated will perform the operation o1137. In an implementation, the receiving information dental electrical circuitry arrangement e1137, when activated performs electronically receiving the user status information regarding the particular individual living being including living being identification associated with electronic dental records (e.g. an implementation of the receiver component s528 is configured to electronically engage with the microprocessor component s102 to receive the user status information regarding the particular individual living being including living being identification as determined by the microprocessor component to be identifying the living being through the electronic dental records, etc.). In an implementation, the electronically receiving the user status information regarding the particular individual living being including the living being identification associated with electronic dental records is carried out by electronically receiving the user status information regarding the particular individual living being including living being identification associated with electronic dental records (e.g. an implementation of the receiver component s528 is configured to electronically engage with the microprocessor component s102 to receive the user status information regarding the particular individual living being including living being identification as determined by the microprocessor component to be identifying the living being through the electronic dental records, etc.).

In one or more implementations, operation o11 includes an operation o1138 for electronically receiving the user status information regarding the particular individual living being including the living being identification associated with an RFID tag. An exemplary version of a non-transitory signal bearing medium of information storage subsystem s200 is depicted as bearing one or more receiving information RFID instructions i1138 that when executed will direct performance of the operation o1138. In an implementation, the one or more receiving information RFID instructions i1138 when executed direct electronically receiving the user status information regarding the particular individual living being including living being identification associated with an RFID tag (e.g. an implementation of the receiver component s528 is configured to electronically engage with the microprocessor component s102 to receive the user status information regarding the particular individual living being including living being identification as determined by the microprocessor component to be identifying the living being through the RFID tag, etc.). Furthermore, the receiving information RFID electrical circuitry arrangement e1138 when activated will perform the operation o1138. In an implementation, the receiving information RFID electrical circuitry arrangement e1138, when activated performs electronically receiving the user status information regarding the particular individual living being including living being identification associated with an RFID tag (e.g. an implementation of the receiver component s528 is configured to electronically engage with the microprocessor component s102 to receive the user status information regarding the particular individual living being including living being identification as determined by the microprocessor component to be identifying the living being through the RFID tag, etc.). In an implementation, the electronically receiving the user status information regarding the particular individual living being including the living being identification associated with an RFID tag is carried out by electronically receiving the user status information regarding the particular individual living being including living being identification associated with an RFID tag (e.g. an implementation of the receiver component s528 is configured to electronically engage with the microprocessor component s102 to receive the user status information regarding the particular individual living being including living being identification as determined by the microprocessor component to be identifying the living being through the RFID tag, etc.).

In one or more implementations, operation o11 includes an operation o1139 for electronically receiving the user status information regarding the particular individual living being including the living being identification associated with a password. An exemplary version of a non-transitory signal bearing medium of information storage subsystem s200 is depicted as bearing one or more receiving information password instructions i1139 that when executed will direct performance of the operation o1139. In an implementation, the one or more receiving information password instructions i1139 when executed direct electronically receiving the user status information regarding the particular individual living being including living being identification associated with a password (e.g. an implementation of the receiver component s528 is configured to electronically engage with the microprocessor component s102 to receive the user status information regarding the particular individual living being including living being identification as determined by the microprocessor component to be identifying the living being through the password, etc.). Furthermore, the receiving information password electrical circuitry arrangement e1139 when activated will perform the operation o1139. In an implementation, the receiving information password electrical circuitry arrangement e1139, when activated performs electronically receiving the user status information regarding the particular individual living being including living being identification associated with a password (e.g. an implementation of the receiver component s528 is configured to electronically engage with the microprocessor component s102 to receive the user status information regarding the particular individual living being including living being identification as determined by the microprocessor component to be identifying the living being through the password, etc.). In an implementation, the electronically receiving the user status information regarding the particular individual living being including the living being identification associated with a password is carried out by electronically receiving the user status information regarding the particular individual living being including living being identification associated with a password (e.g. an implementation of the receiver component s528 is configured to electronically engage with the microprocessor component s102 to receive the user status information regarding the particular individual living being including living being identification as determined by the microprocessor component to be identifying the living being through the password, etc.).

Figure 60:
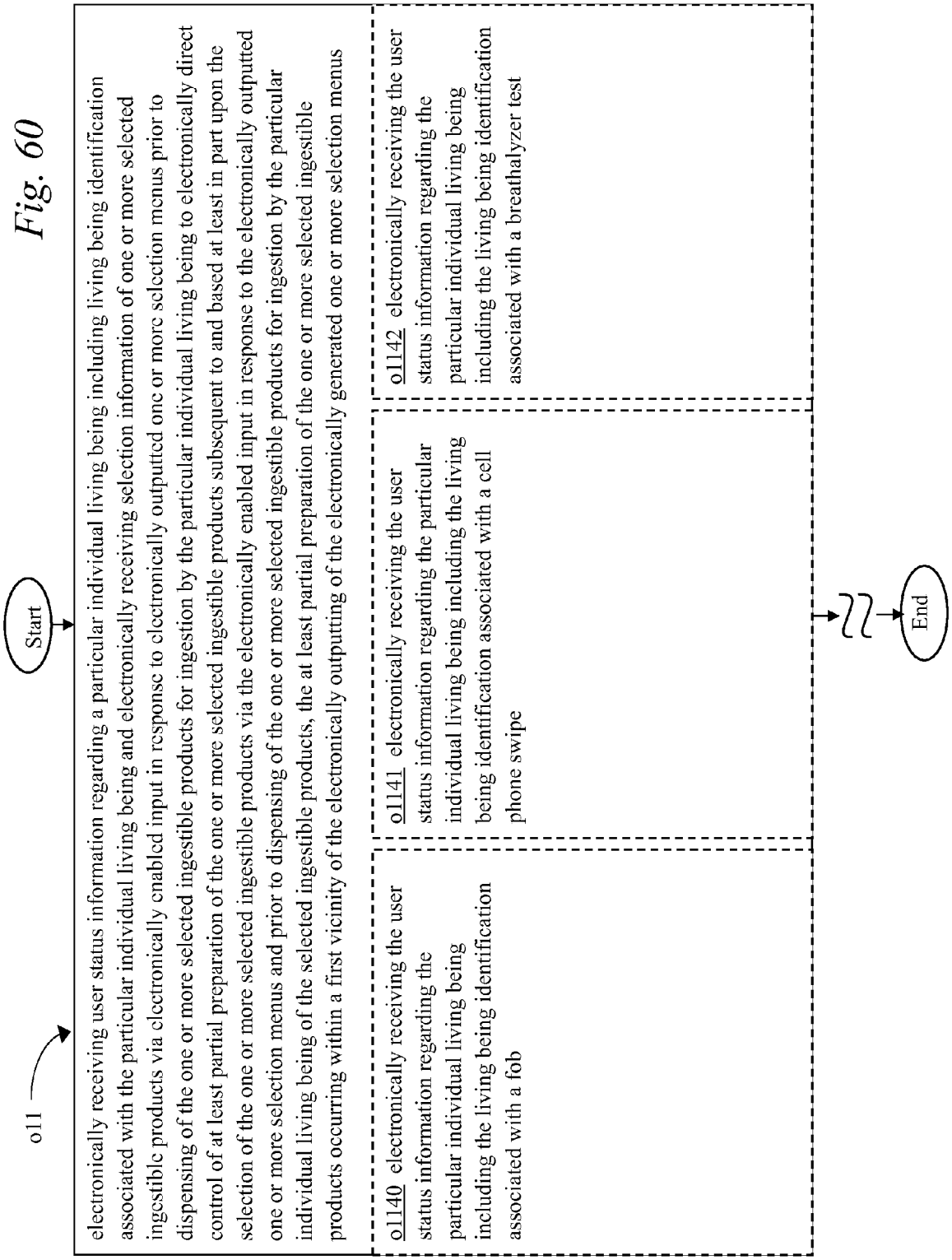
FIG. 60 is a high-level flowchart including exemplary implementations of operation O11 of FIG. 46.

In one or more implementations, as shown in FIG. 60, operation o11 includes an operation o1140 for electronically receiving the user status information regarding the particular individual living being including the living being identification associated with a fob. An exemplary version of a non-transitory signal bearing medium of information storage subsystem s200 is depicted as bearing one or more receiving information fob instructions i1140 that when executed will direct performance of the operation o1140. In an implementation, the one or more receiving information fob instructions i1140 when executed direct electronically receiving the user status information regarding the particular individual living being including living being identification associated with a fob (e.g. an implementation of the receiver component s528 is configured to electronically engage with the microprocessor component s102 to receive the user status information regarding the particular individual living being including living being identification as determined by the microprocessor component to be identifying the living being through electronic data contained on the fob, etc.). Furthermore, the receiving information fob electrical circuitry arrangement e1140 when activated will perform the operation o1140. In an implementation, the receiving information fob electrical circuitry arrangement e1140, when activated performs electronically receiving the user status information regarding the particular individual living being including living being identification associated with a fob (e.g. an implementation of the receiver component s528 is configured to electronically engage with the microprocessor component s102 to receive the user status information regarding the particular individual living being including living being identification as determined by the microprocessor component to be identifying the living being through electronic data contained on the fob, etc.). In an implementation, the electronically receiving the user status information regarding the particular individual living being including the living being identification associated with a fob is carried out by electronically receiving the user status information regarding the particular individual living being including living being identification associated with a fob (e.g. an implementation of the receiver component s528 is configured to electronically engage with the microprocessor component s102 to receive the user status information regarding the particular individual living being including living being identification as determined by the microprocessor component to be identifying the living being through electronic data contained on the fob, etc.).

In one or more implementations, operation o11 includes an operation o1141 for electronically receiving the user status information regarding the particular individual living being including the living being identification associated with a cell phone swipe. An exemplary version of a non-transitory signal bearing medium of information storage subsystem s200 is depicted as bearing one or more receiving information cell phone instructions i1141 that when executed will direct performance of the operation o1141. In an implementation, the one or more receiving information cell phone instructions i1141 when executed direct electronically receiving the user status information regarding the particular individual living being including living being identification associated with a cell phone swipe (e.g. an implementation of the receiver component s528 is configured to electronically engage with the microprocessor component s102 to receive the user status information regarding the particular individual living being including living being identification as determined by the microprocessor component to be identifying the living being through passing the cell phone in close proximity to the cell phone, etc.). Furthermore, the receiving information cell phone electrical circuitry arrangement e1141 when activated will perform the operation o1141. In an implementation, the receiving information cell phone electrical circuitry arrangement e1141, when activated performs electronically receiving the user status information regarding the particular individual living being including living being identification associated with a cell phone swipe (e.g. an implementation of the receiver component s528 is configured to electronically engage with the microprocessor component s102 to receive the user status information regarding the particular individual living being including living being identification as determined by the microprocessor component to be identifying the living being through passing the cell phone in close proximity to the cell phone, etc.). In an implementation, the electronically receiving the user status information regarding the particular individual living being including the living being identification associated with a cell phone swipe is carried out by electronically receiving the user status information regarding the particular individual living being including living being identification associated with a cell phone swipe (e.g. an implementation of the receiver component s528 is configured to electronically engage with the microprocessor component s102 to receive the user status information regarding the particular individual living being including living being identification as determined by the microprocessor component to be identifying the living being through passing the cell phone in close proximity to the cell phone, etc.).

In one or more implementations, operation o11 includes an operation o1142 for electronically receiving the user status information regarding the particular individual living being including the living being identification associated with a breathalyzer test. An exemplary version of a non-transitory signal bearing medium of information storage subsystem s200 is depicted as bearing one or more receiving information breathalyzer instructions i1142 that when executed will direct performance of the operation o1142. In an implementation, the one or more receiving information breathalyzer instructions i1142 when executed direct electronically receiving the user status information regarding the particular individual living being including living being identification associated with a breathalyzer test (e.g. an implementation of the receiver component s528 is configured to electronically engage with the microprocessor component s102 to receive the user status information regarding the particular individual living being including living being identification as determined by the microprocessor component to be identifying the living being through the breathalyzer test of the living being, etc.). Furthermore, the receiving information breathalyzer electrical circuitry arrangement e1142 when activated will perform the operation o1142. In an implementation, the receiving information breathalyzer electrical circuitry arrangement e1142, when activated performs electronically receiving the user status information regarding the particular individual living being including living being identification associated with a breathalyzer test (e.g. an implementation of the receiver component s528 is configured to electronically engage with the microprocessor component s102 to receive the user status information regarding the particular individual living being including living being identification as determined by the microprocessor component to be identifying the living being through the breathalyzer test of the living being, etc.). In an implementation, the electronically receiving the user status information regarding the particular individual living being including the living being identification associated with a breathalyzer test is carried out by electronically receiving the user status information regarding the particular individual living being including living being identification associated with a breathalyzer test (e.g. an implementation of the receiver component s528 is configured to electronically engage with the microprocessor component s102 to receive the user status information regarding the particular individual living being including living being identification as determined by the microprocessor component to be identifying the living being through the breathalyzer test of the living being, etc.).

Figure 61:
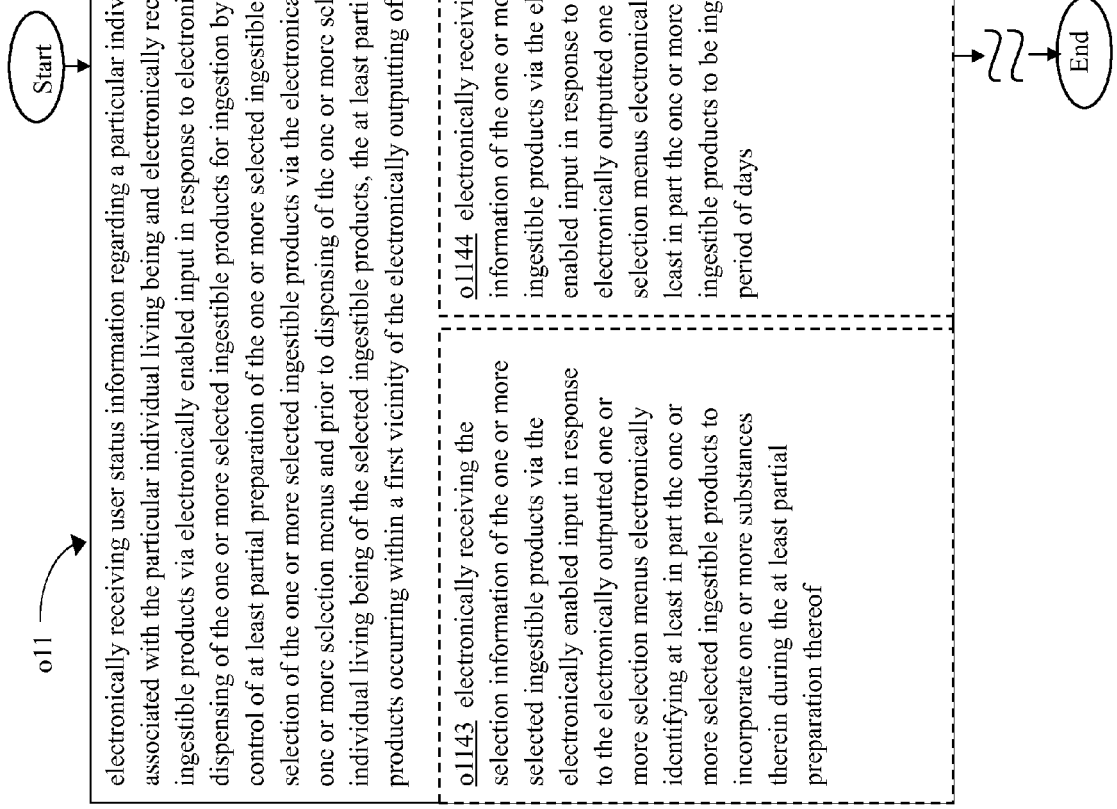
FIG. 61 is a high-level flowchart including exemplary implementations of operation O11 of FIG. 46.

In one or more implementations, as shown in FIG. 61, operation o11 includes an operation o1143 for electronically receiving the selection information of the one or more selected ingestible products via the electronically enabled input in response to the electronically outputted one or more selection menus electronically identifying at least in part the one or more selected ingestible products to incorporate one or more substances therein during the at least partial preparation thereof. An exemplary version of a non-transitory signal bearing medium of information storage subsystem s200 is depicted as bearing one or more receiving information incorporate instructions i1143 that when executed will direct performance of the operation o1143. In an implementation, the one or more receiving information incorporate instructions i1143 when executed direct electronically receiving the selection information of the one or more selected ingestible products via the electronically enabled input in response to the electronically outputted one or more selection menus electronically identifying at least in part the one or more selected ingestible products to incorporate one or more substances therein during the at least partial preparation thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to incorporate one or more substances therein during the at least partial preparation thereof such as a sandwich to include the substance as an amino acid incorporated into the sandwich, etc.). Furthermore, the receiving information incorporate electrical circuitry arrangement e1143 when activated will perform the operation o1143. In an implementation, the receiving information incorporate electrical circuitry arrangement e1143, when activated performs electronically receiving the selection information of the one or more selected ingestible products via the electronically enabled input in response to the electronically outputted one or more selection menus electronically identifying at least in part the one or more selected ingestible products to incorporate one or more substances therein during the at least partial preparation thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to incorporate one or more substances therein during the at least partial preparation thereof such as a sandwich to include the substance as an amino acid incorporated into the sandwich, etc.). In an implementation, the electronically receiving the selection information of the one or more selected ingestible products via the electronically enabled input in response to the electronically outputted one or more selection menus electronically identifying at least in part the one or more selected ingestible products to incorporate one or more substances therein during the at least partial preparation thereof is carried out by electronically receiving the selection information of the one or more selected ingestible products via the electronically enabled input in response to the electronically outputted one or more selection menus electronically identifying at least in part the one or more selected ingestible products to incorporate one or more substances therein during the at least partial preparation thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to incorporate one or more substances therein during the at least partial preparation thereof such as a sandwich to include the substance as an amino acid incorporated into the sandwich, etc.).

In one or more implementations, operation o11 includes an operation o1144 for electronically receiving the selection information of the one or more selected ingestible products via the electronically enabled input in response to the electronically outputted one or more selection menus electronically identifying at least in part the one or more selected ingestible products to be ingested over a period of days. An exemplary version of a non-transitory signal bearing medium of information storage subsystem s200 is depicted as bearing one or more receiving information days instructions i1144 that when executed will direct performance of the operation o1144. In an implementation, the one or more receiving information days instructions i1144 when executed direct electronically receiving the selection information of the one or more selected ingestible products via the electronically enabled input in response to the electronically outputted one or more selection menus electronically identifying at least in part the one or more selected ingestible products to be ingested over a period of days (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.). Furthermore, the receiving information days electrical circuitry arrangement e1144 when activated will perform the operation o1144. In an implementation, the receiving information days electrical circuitry arrangement e1144, when activated performs electronically receiving the selection information of the one or more selected ingestible products via the electronically enabled input in response to the electronically outputted one or more selection menus electronically identifying at least in part the one or more selected ingestible products to be ingested over a period of days (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.). In an implementation, the electronically receiving the selection information of the one or more selected ingestible products via the electronically enabled input in response to the electronically outputted one or more selection menus electronically identifying at least in part the one or more selected ingestible products to be ingested over a period of days is carried out by electronically receiving the selection information of the one or more selected ingestible products via the electronically enabled input in response to the electronically outputted one or more selection menus electronically identifying at least in part the one or more selected ingestible products to be ingested over a period of days (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.).

In one or more implementations, operation o11 includes an operation o1145 for electronically receiving the selection information of the one or more selected ingestible products via the electronically enabled input in response to the electronically outputted one or more selection menus electronically identifying at least in part the one or more selected ingestible products to be swallowed. An exemplary version of a non-transitory signal bearing medium of information storage subsystem s200 is depicted as bearing one or more receiving information swallow instructions i1145 that when executed will direct performance of the operation o1145. In an implementation, the one or more receiving information swallow instructions i1145 when executed direct electronically receiving the selection information of the one or more selected ingestible products via the electronically enabled input in response to the electronically outputted one or more selection menus electronically identifying at least in part the one or more selected ingestible products to be swallowed (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be swallowed such as a snack bar, etc.). Furthermore, the receiving information swallow electrical circuitry arrangement e1145 when activated will perform the operation o1145. In an implementation, the receiving information swallow electrical circuitry arrangement e1145, when activated performs electronically receiving the selection information of the one or more selected ingestible products via the electronically enabled input in response to the electronically outputted one or more selection menus electronically identifying at least in part the one or more selected ingestible products to be swallowed (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be swallowed such as a snack bar, etc.). In an implementation, the electronically receiving the selection information of the one or more selected ingestible products via the electronically enabled input in response to the electronically outputted one or more selection menus electronically identifying at least in part the one or more selected ingestible products to be swallowed is carried out by electronically receiving the selection information of the one or more selected ingestible products via the electronically enabled input in response to the electronically outputted one or more selection menus electronically identifying at least in part the one or more selected ingestible products to be swallowed (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be swallowed such as a snack bar, etc.).

Figure 62:
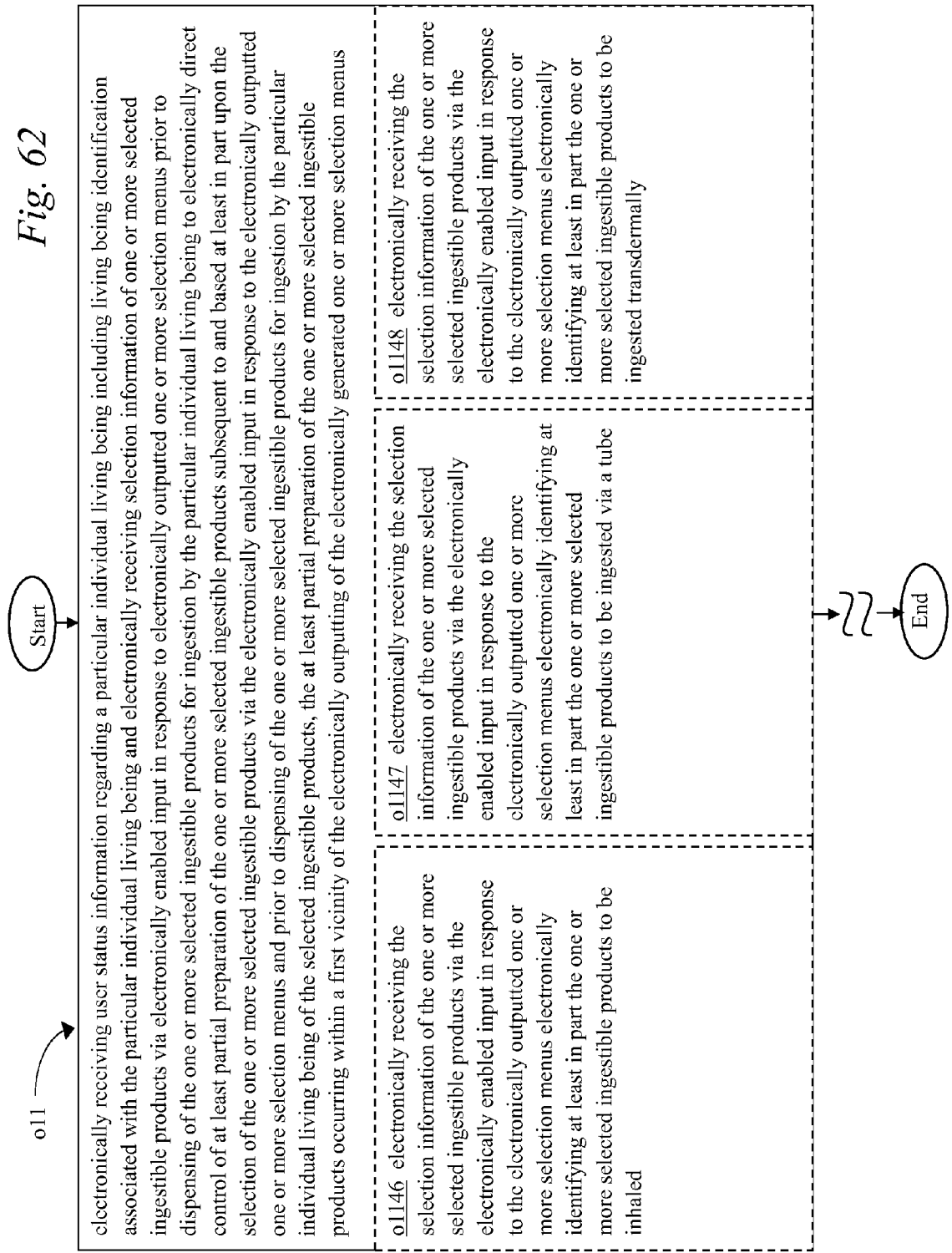
FIG. 62 is a high-level flowchart including exemplary implementations of operation O11 of FIG. 46.

In one or more implementations, as shown in FIG. 62, operation o11 includes an operation o1146 for electronically receiving the selection information of the one or more selected ingestible products via the electronically enabled input in response to the electronically outputted one or more selection menus electronically identifying at least in part the one or more selected ingestible products to be inhaled. An exemplary version of a non-transitory signal bearing medium of information storage subsystem s200 is depicted as bearing one or more receiving information inhaled instructions i1146 that when executed will direct performance of the operation o1146. In an implementation, the one or more receiving information inhaled instructions i1146 when executed direct electronically receiving the selection information of the one or more selected ingestible products via the electronically enabled input in response to the electronically outputted one or more selection menus electronically identifying at least in part the one or more selected ingestible products to be inhaled (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be inhaled such as a medicament dispensed through a nebulizer, etc.). Furthermore, the receiving information inhaled electrical circuitry arrangement e1146 when activated will perform the operation o1146. In an implementation, the receiving information inhaled electrical circuitry arrangement e1146, when activated performs electronically receiving the selection information of the one or more selected ingestible products via the electronically enabled input in response to the electronically outputted one or more selection menus electronically identifying at least in part the one or more selected ingestible products to be inhaled (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be inhaled such as a medicament dispensed through a nebulizer, etc.). In an implementation, the electronically receiving the selection information of the one or more selected ingestible products via the electronically enabled input in response to the electronically outputted one or more selection menus electronically identifying at least in part the one or more selected ingestible products to be inhaled is carried out by electronically receiving the selection information of the one or more selected ingestible products via the electronically enabled input in response to the electronically outputted one or more selection menus electronically identifying at least in part the one or more selected ingestible products to be inhaled (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be inhaled such as a medicament dispensed through a nebulizer, etc.).

In one or more implementations, operation o11 includes an operation o1147 for electronically receiving the selection information of the one or more selected ingestible products via the electronically enabled input in response to the electronically outputted one or more selection menus electronically identifying at least in part the one or more selected ingestible products to be ingested via a tube. An exemplary version of a non-transitory signal bearing medium of information storage subsystem s200 is depicted as bearing one or more receiving information tube instructions i1147 that when executed will direct performance of the operation o1147. In an implementation, the one or more receiving information tube instructions i1147 when executed direct electronically receiving the selection information of the one or more selected ingestible products via the electronically enabled input in response to the electronically outputted one or more selection menus electronically identifying at least in part the one or more selected ingestible products to be ingested via a tube (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested via a tube such as a liquid meal replacement, etc.). Furthermore, the receiving information tube electrical circuitry arrangement e1147 when activated will perform the operation o1147. In an implementation, the receiving information tube electrical circuitry arrangement e1147, when activated performs electronically receiving the selection information of the one or more selected ingestible products via the electronically enabled input in response to the electronically outputted one or more selection menus electronically identifying at least in part the one or more selected ingestible products to be ingested via a tube (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested via a tube such as a liquid meal replacement, etc.). In an implementation, the electronically receiving the selection information of the one or more selected ingestible products via the electronically enabled input in response to the electronically outputted one or more selection menus electronically identifying at least in part the one or more selected ingestible products to be ingested via a tube is carried out by electronically receiving the selection information of the one or more selected ingestible products via the electronically enabled input in response to the electronically outputted one or more selection menus electronically identifying at least in part the one or more selected ingestible products to be ingested via a tube (e.g., an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested via a tube such as a liquid meal replacement, etc.).

In one or more implementations, operation o11 includes an operation o1148 for electronically receiving the selection information of the one or more selected ingestible products via the electronically enabled input in response to the electronically outputted one or more selection menus electronically identifying at least in part the one or more selected ingestible products to be ingested transdermally. An exemplary version of a non-transitory signal bearing medium of information storage subsystem s200 is depicted as bearing one or more receiving information transdermal instructions i1148 that when executed will direct performance of the operation o1148. In an implementation, the one or more receiving information transdermal instructions i1148 when executed direct electronically receiving the selection information of the one or more selected ingestible products via the electronically enabled input in response to the electronically outputted one or more selection menus electronically identifying at least in part the one or more selected ingestible products to be ingested transdermally (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested transdermally such as a cream, etc.). Furthermore, the receiving information transdermal electrical circuitry arrangement e1148 when activated will perform the operation o1148. In an implementation, the receiving information transdermal electrical circuitry arrangement e1148, when activated performs electronically receiving the selection information of the one or more selected ingestible products via the electronically enabled input in response to the electronically outputted one or more selection menus electronically identifying at least in part the one or more selected ingestible products to be ingested transdermally (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested transdermally such as a cream, etc.). In an implementation, the electronically receiving the selection information of the one or more selected ingestible products via the electronically enabled input in response to the electronically outputted one or more selection menus electronically identifying at least in part the one or more selected ingestible products to be ingested transdermally is carried out by electronically receiving the selection information of the one or more selected ingestible products via the electronically enabled input in response to the electronically outputted one or more selection menus electronically identifying at least in part the one or more selected ingestible products to be ingested transdermally (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be ingested transdermally such as a cream, etc.).

Figure 63:
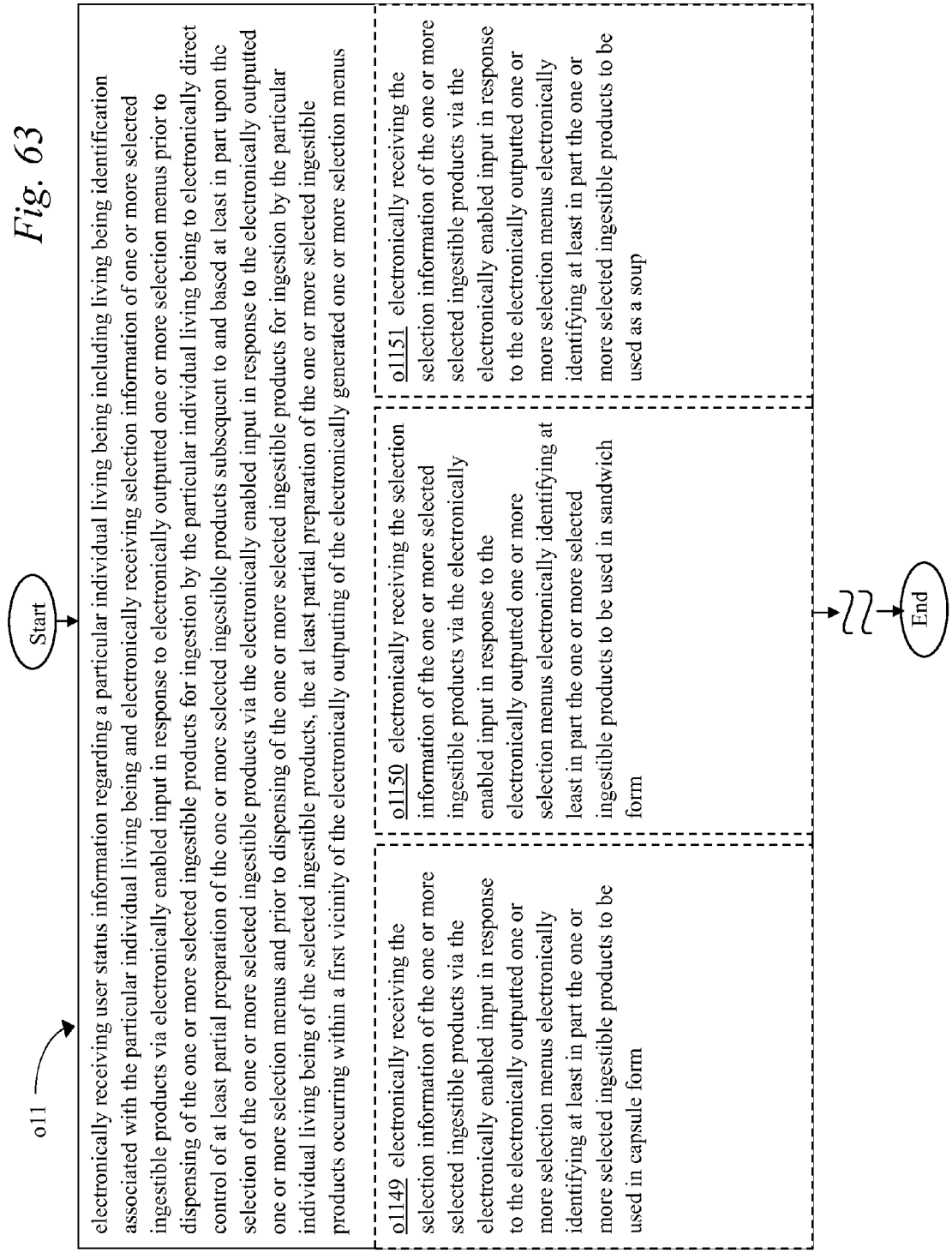
FIG. 63 is a high-level flowchart including exemplary implementations of operation O11 of FIG. 46.

In one or more implementations, as shown in FIG. 63, operation o11 includes an operation o1149 for electronically receiving the selection information of the one or more selected ingestible products via the electronically enabled input in response to the electronically outputted one or more selection menus electronically identifying at least in part the one or more selected ingestible products to be used in capsule form. An exemplary version of a non-transitory signal bearing medium of information storage subsystem s200 is depicted as bearing one or more receiving information capsule instructions i1149 that when executed will direct performance of the operation o1149. In an implementation, the one or more receiving information capsule instructions i1149 when executed direct electronically receiving the selection information of the one or more selected ingestible products via the electronically enabled input in response to the electronically outputted one or more selection menus electronically identifying at least in part the one or more selected ingestible products to be used in a capsule form (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used in capsule form, such as through capsules via encapsulation, etc.). Furthermore, the receiving information capsule electrical circuitry arrangement e1149 when activated will perform the operation o1149. In an implementation, the receiving information capsule electrical circuitry arrangement e1149, when activated performs electronically receiving the selection information of the one or more selected ingestible products via the electronically enabled input in response to the electronically outputted one or more selection menus electronically identifying at least in part the one or more selected ingestible products to be used in a capsule form (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used in capsule form, such as through capsules via encapsulation, etc.). In an implementation, the electronically receiving the selection information of the one or more selected ingestible products via the electronically enabled input in response to the electronically outputted one or more selection menus electronically identifying at least in part the one or more selected ingestible products to be used in capsule form is carried out by electronically receiving the selection information of the one or more selected ingestible products via the electronically enabled input in response to the electronically outputted one or more selection menus electronically identifying at least in part the one or more selected ingestible products to be used in a capsule form (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used in capsule form, such as through capsules via encapsulation, etc.).

In one or more implementations, operation o11 includes an operation o1150 for electronically receiving the selection information of the one or more selected ingestible products via the electronically enabled input in response to the electronically outputted one or more selection menus electronically identifying at least in part the one or more selected ingestible products to be used in sandwich form. An exemplary version of a non-transitory signal bearing medium of information storage subsystem s200 is depicted as bearing one or more receiving information sandwich instructions i1150 that when executed will direct performance of the operation o1150. In an implementation, the one or more receiving information sandwich instructions i1150 when executed direct electronically receiving the selection information of the one or more selected ingestible products via the electronically enabled input in response to the electronically outputted one or more selection menus electronically identifying at least in part the one or more selected ingestible products to be used in sandwich form (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products in sandwich form such as a hamburger, etc.). Furthermore, the receiving information sandwich electrical circuitry arrangement e1150 when activated will perform the operation o1150. In an implementation, the receiving information sandwich electrical circuitry arrangement e1150, when activated performs electronically receiving the selection information of the one or more selected ingestible products via the electronically enabled input in response to the electronically outputted one or more selection menus electronically identifying at least in part the one or more selected ingestible products to be used in sandwich form (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products in sandwich form such as a hamburger, etc.). In an implementation, the electronically receiving the selection information of the one or more selected ingestible products via the electronically enabled input in response to the electronically outputted one or more selection menus electronically identifying at least in part the one or more selected ingestible products to be used in sandwich form is carried out by electronically receiving the selection information of the one or more selected ingestible products via the electronically enabled input in response to the electronically outputted one or more selection menus electronically identifying at least in part the one or more selected ingestible products to be used in sandwich form (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products in sandwich form such as a hamburger, etc.).

In one or more implementations, operation o11 includes an operation o1151 for electronically receiving the selection information of the one or more selected ingestible products via the electronically enabled input in response to the electronically outputted one or more selection menus electronically identifying at least in part the one or more selected ingestible products to be used as a soup. An exemplary version of a non-transitory signal bearing medium of information storage subsystem s200 is depicted as bearing one or more receiving information soup instructions i1151 that when executed will direct performance of the operation o1151. In an implementation, the one or more receiving information soup instructions i1151 when executed direct electronically receiving the selection information of the one or more selected ingestible products via the electronically enabled input in response to the electronically outputted one or more selection menus electronically identifying at least in part the one or more selected ingestible products to be used as a soup (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a soup such as tomato soup, etc.). Furthermore, the receiving information soup electrical circuitry arrangement e1151 when activated will perform the operation o1151. In an implementation, the receiving information soup electrical circuitry arrangement e1151, when activated performs electronically receiving the selection information of the one or more selected ingestible products via the electronically enabled input in response to the electronically outputted one or more selection menus electronically identifying at least in part the one or more selected ingestible products to be used as a soup (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a soup such as tomato soup, etc.). In an implementation, the electronically receiving the selection information of the one or more selected ingestible products via the electronically enabled input in response to the electronically outputted one or more selection menus electronically identifying at least in part the one or more selected ingestible products to be used as a soup is carried out by electronically receiving the selection information of the one or more selected ingestible products via the electronically enabled input in response to the electronically outputted one or more selection menus electronically identifying at least in part the one or more selected ingestible products to be used as a soup (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a soup such as tomato soup, etc.).

Figure 64:
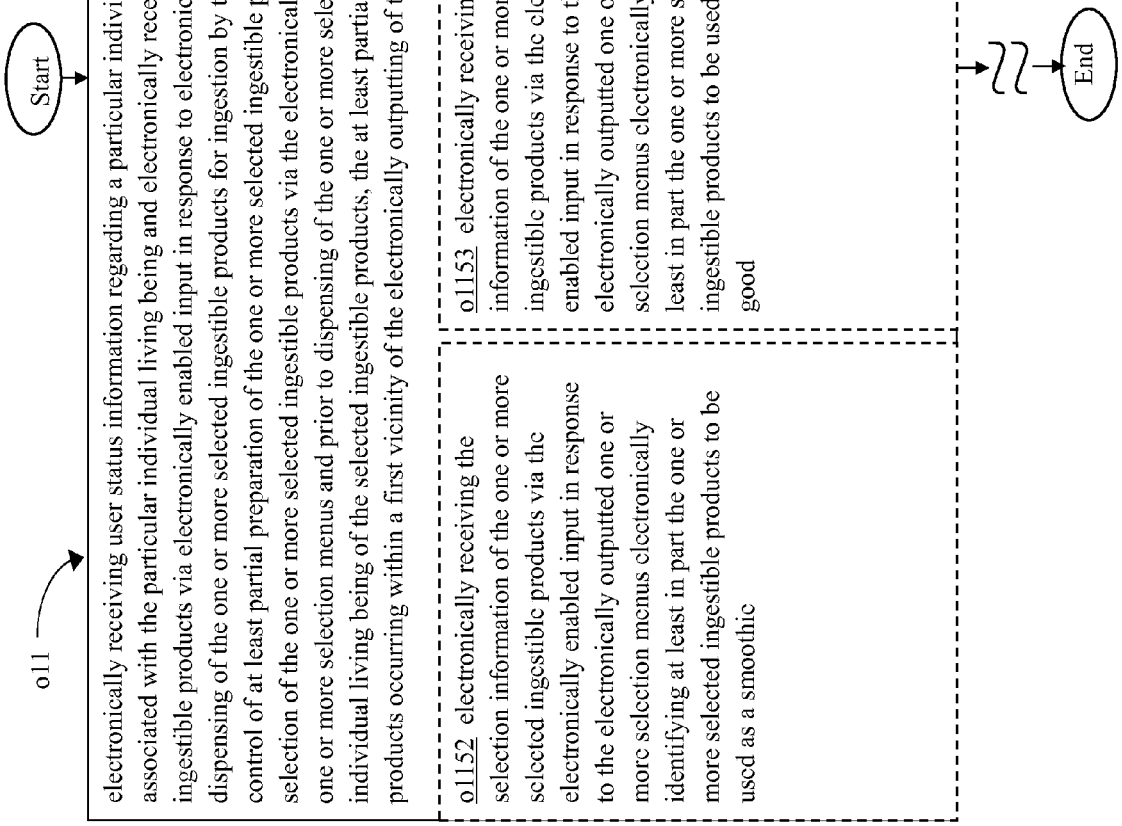
FIG. 64 is a high-level flowchart including exemplary implementations of operation O11 of FIG. 46.

In one or more implementations, as shown in FIG. 64, operation o11 includes an operation o1152 for electronically receiving the selection information of the one or more selected ingestible products via the electronically enabled input in response to the electronically outputted one or more selection menus electronically identifying at least in part the one or more selected ingestible products to be used as a smoothie. An exemplary version of a non-transitory signal bearing medium of information storage subsystem s200 is depicted as bearing one or more receiving information smoothie instructions i1152 that when executed will direct performance of the operation o1152. In an implementation, the one or more receiving information smoothie instructions i1152 when executed direct electronically receiving the selection information of the one or more selected ingestible products via the electronically enabled input in response to the electronically outputted one or more selection menus electronically identifying at least in part the one or more selected ingestible products to be used as a smoothie (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used a smoothie such as a fruit smoothie, etc.). Furthermore, the receiving information smoothie electrical circuitry arrangement e1152 when activated will perform the operation o1152. In an implementation, the receiving information smoothie electrical circuitry arrangement e1152, when activated performs electronically receiving the selection information of the one or more selected ingestible products via the electronically enabled input in response to the electronically outputted one or more selection menus electronically identifying at least in part the one or more selected ingestible products to be used as a smoothie (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used a smoothie such as a fruit smoothie, etc.). In an implementation, the electronically receiving the selection information of the one or more selected ingestible products via the electronically enabled input in response to the electronically outputted one or more selection menus electronically identifying at least in part the one or more selected ingestible products to be used as a smoothie is carried out by electronically receiving the selection information of the one or more selected ingestible products via the electronically enabled input in response to the electronically outputted one or more selection menus electronically identifying at least in part the one or more selected ingestible products to be used as a smoothie (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used a smoothie such as a fruit smoothie, etc.).

In one or more implementations, operation o11 includes an operation o1153 for electronically receiving the selection information of the one or more selected ingestible products via the electronically enabled input in response to the electronically outputted one or more selection menus electronically identifying at least in part the one or more selected ingestible products to be used as a baked good. An exemplary version of a non-transitory signal bearing medium of information storage subsystem s200 is depicted as bearing one or more receiving information baked instructions i1153 that when executed will direct performance of the operation o1153. In an implementation, the one or more receiving information baked instructions i1153 when executed direct electronically receiving the selection information of the one or more selected ingestible products via the electronically enabled input in response to the electronically outputted one or more selection menus electronically identifying at least in part the one or more selected ingestible products to be used as a baked good (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a baked good such as a muffin, etc.). Furthermore, the receiving information baked electrical circuitry arrangement e1153 when activated will perform the operation o1153. In an implementation, the receiving information baked electrical circuitry arrangement e1153, when activated performs electronically receiving the selection information of the one or more selected ingestible products via the electronically enabled input in response to the electronically outputted one or more selection menus electronically identifying at least in part the one or more selected ingestible products to be used as a baked good (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a baked good such as a muffin, etc.). In an implementation, the electronically receiving the selection information of the one or more selected ingestible products via the electronically enabled input in response to the electronically outputted one or more selection menus electronically identifying at least in part the one or more selected ingestible products to be used as a baked good is carried out by electronically receiving the selection information of the one or more selected ingestible products via the electronically enabled input in response to the electronically outputted one or more selection menus electronically identifying at least in part the one or more selected ingestible products to be used as a baked good (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a baked good such as a muffin, etc.).

In one or more implementations, operation o11 includes an operation o1154 for electronically receiving the selection information of the one or more selected ingestible products via the electronically enabled input in response to the electronically outputted one or more selection menus electronically identifying at least in part the one or more selected ingestible products to be used as a deposited material. An exemplary version of a non-transitory signal bearing medium of information storage subsystem s200 is depicted as bearing one or more receiving information deposited instructions i1154 that when executed will direct performance of the operation o1154. In an implementation, the one or more receiving information deposited instructions i1154 when executed direct electronically receiving the selection information of the one or more selected ingestible products via the electronically enabled input in response to the electronically outputted one or more selection menus electronically identifying at least in part the one or more selected ingestible products to be used as a deposited material (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as a deposited material such as a multi-layered cake, etc.). Furthermore, the receiving information deposited electrical circuitry arrangement e1154 when activated will perform the operation o1154. In an implementation, the receiving information deposited electrical circuitry arrangement e1154, when activated performs electronically receiving the selection information of the one or more selected ingestible products via the electronically enabled input in response to the electronically outputted one or more selection menus electronically identifying at least in part the one or more selected ingestible products to be used as a deposited material (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as a deposited material such as a multi-layered cake, etc.). In an implementation, the electronically receiving the selection information of the one or more selected ingestible products via the electronically enabled input in response to the electronically outputted one or more selection menus electronically identifying at least in part the one or more selected ingestible products to be used as a deposited material is carried out by electronically receiving the selection information of the one or more selected ingestible products via the electronically enabled input in response to the electronically outputted one or more selection menus electronically identifying at least in part the one or more selected ingestible products to be used as a deposited material (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as a deposited material such as a multi-layered cake, etc.).

Figure 65:
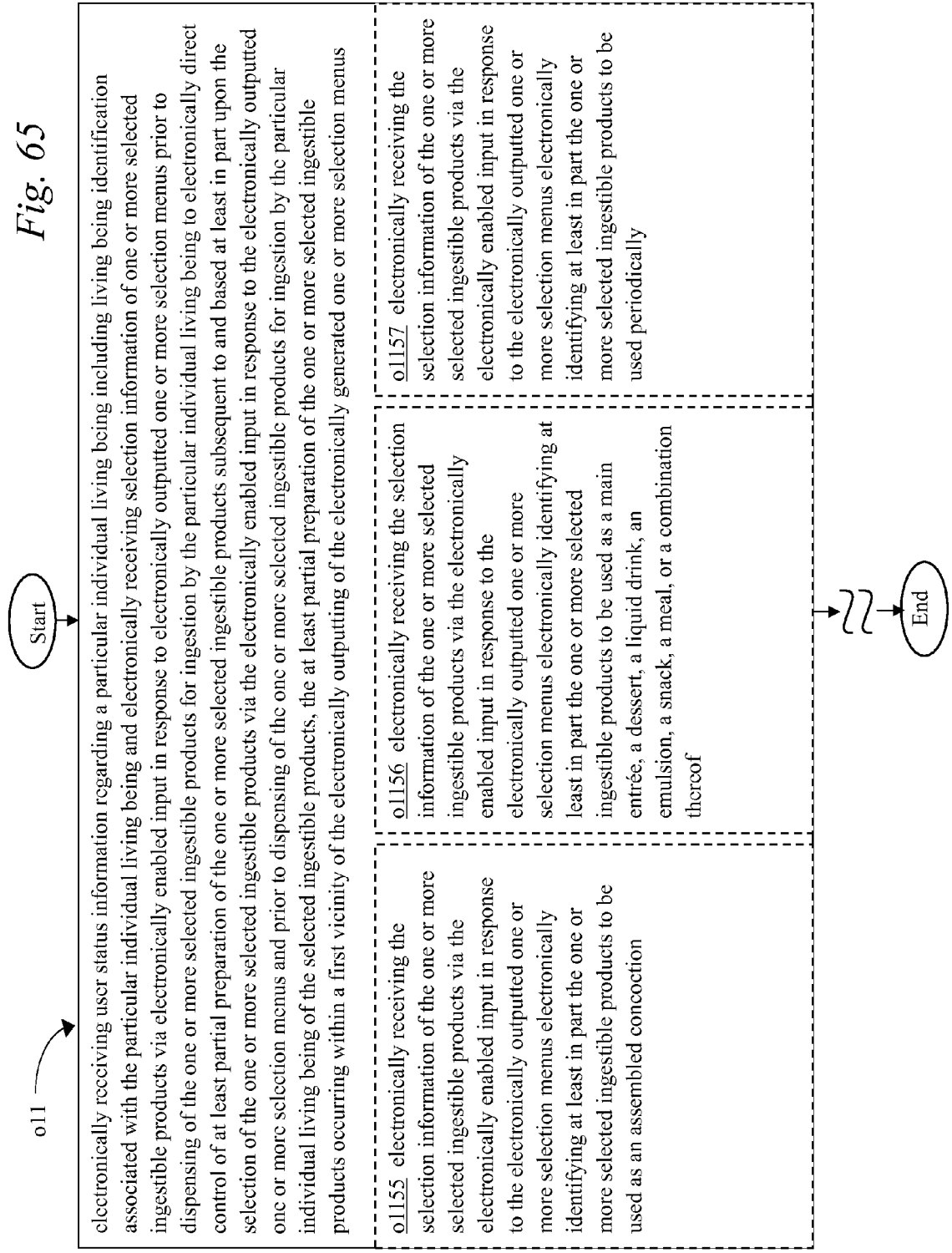
FIG. 65 is a high-level flowchart including exemplary implementations of operation O11 of FIG. 46.

In one or more implementations, as shown in FIG. 65, operation o11 includes an operation o1155 for electronically receiving the selection information of the one or more selected ingestible products via the electronically enabled input in response to the electronically outputted one or more selection menus electronically identifying at least in part the one or more selected ingestible products to be used as an assembled concoction. An exemplary version of a non-transitory signal bearing medium of information storage subsystem s200 is depicted as bearing one or more receiving information assembled instructions i1155 that when executed will direct performance of the operation o1155. In an implementation, the one or more receiving information assembled instructions i1155 when executed direct electronically receiving the selection information of the one or more selected ingestible products via the electronically enabled input in response to the electronically outputted one or more selection menus electronically identifying at least in part the one or more selected ingestible products to be used as an assembled concoction (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as an assembled concoction such as a decorated confection, etc.). Furthermore, the receiving information assembled electrical circuitry arrangement e1155 when activated will perform the operation o1155. In an implementation, the receiving information assembled electrical circuitry arrangement e1155, when activated performs electronically receiving the selection information of the one or more selected ingestible products via the electronically enabled input in response to the electronically outputted one or more selection menus electronically identifying at least in part the one or more selected ingestible products to be used as an assembled concoction (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as an assembled concoction such as a decorated confection, etc.). In an implementation, the electronically receiving the selection information of the one or more selected ingestible products via the electronically enabled input in response to the electronically outputted one or more selection menus electronically identifying at least in part the one or more selected ingestible products to be used as an assembled concoction is carried out by electronically receiving the selection information of the one or more selected ingestible products via the electronically enabled input in response to the electronically outputted one or more selection menus electronically identifying at least in part the one or more selected ingestible products to be used as an assembled concoction (e.g. an implementation of the receiver component s528 is configured to electronically receive the selection information of the one or more ingestible products and engage with the microprocessor component s102 to direct the material processing subsystem s700 in response to the electronically outputted one or more selection menus electronically identifying at least in part the one or more selected ingestible products to be used as an assembled concoction such as a decorated confection, etc.).

In one or more implementations, operation o11 includes an operation o1156 for electronically receiving the selection information of the one or more selected ingestible products via the electronically enabled input in response to the electronically outputted one or more selection menus electronically identifying at least in part the one or more selected ingestible products to be used as a main entrée, a dessert, a liquid drink, an emulsion, a snack, a meal, or a combination thereof. An exemplary version of a non-transitory signal bearing medium of information storage subsystem s200 is depicted as bearing one or more receiving information uses instructions i1156 that when executed will direct performance of the operation o1156. In an implementation, the one or more receiving information uses instructions i1156 when executed direct electronically receiving the selection information of the one or more selected ingestible products via the electronically enabled input in response to the electronically outputted one or more selection menus electronically identifying at least in part the one or more selected ingestible products to be used as a main entrée, a dessert, a liquid drink, an emulsion, a snack, a meal, or a combination thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a as a main entrée, a dessert, a liquid drink, an emulsion, a snack, a meal, or a combination thereof such as a steak dinner, etc.). Furthermore, the receiving information uses electrical circuitry arrangement e1156 when activated will perform the operation o1156. In an implementation, the receiving information uses electrical circuitry arrangement e1156, when activated performs electronically receiving the selection information of the one or more selected ingestible products via the electronically enabled input in response to the electronically outputted one or more selection menus electronically identifying at least in part the one or more selected ingestible products to be used as a main entrée, a dessert, a liquid drink, an emulsion, a snack, a meal, or a combination thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a as a main entrée, a dessert, a liquid drink, an emulsion, a snack, a meal, or a combination thereof such as a steak dinner, etc.). In an implementation, the electronically receiving the selection information of the one or more selected ingestible products via the electronically enabled input in response to the electronically outputted one or more selection menus electronically identifying at least in part the one or more selected ingestible products to be used as a main entrée, a dessert, a liquid drink, an emulsion, a snack, a meal, or a combination thereof is carried out by electronically receiving the selection information of the one or more selected ingestible products via the electronically enabled input in response to the electronically outputted one or more selection menus electronically identifying at least in part the one or more selected ingestible products to be used as a main entrée, a dessert, a liquid drink, an emulsion, a snack, a meal, or a combination thereof (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used as a as a main entrée, a dessert, a liquid drink, an emulsion, a snack, a meal, or a combination thereof such as a steak dinner, etc.).

In one or more implementations, operation o11 includes an operation o1157 for electronically receiving the selection information of the one or more selected ingestible products via the electronically enabled input in response to the electronically outputted one or more selection menus electronically identifying at least in part the one or more selected ingestible products to be used periodically. An exemplary version of a non-transitory signal bearing medium of information storage subsystem s200 is depicted as bearing one or more receiving information periods instructions i1157 that when executed will direct performance of the operation o1157. In an implementation, the one or more receiving information periods instructions i1157 when executed direct electronically receiving the selection information of the one or more selected ingestible products via the electronically enabled input in response to the electronically outputted one or more selection menus electronically identifying at least in part the one or more selected ingestible products to be used periodically (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used periodically such as once a week, etc.). Furthermore, the receiving information periods electrical circuitry arrangement e1157 when activated will perform the operation o1157. In an implementation, the receiving information periods electrical circuitry arrangement e1157, when activated performs electronically receiving the selection information of the one or more selected ingestible products via the electronically enabled input in response to the electronically outputted one or more selection menus electronically identifying at least in part the one or more selected ingestible products to be used periodically (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used periodically such as once a week, etc.). In an implementation, the electronically receiving the selection information of the one or more selected ingestible products via the electronically enabled input in response to the electronically outputted one or more selection menus electronically identifying at least in part the one or more selected ingestible products to be used periodically is carried out by electronically receiving the selection information of the one or more selected ingestible products via the electronically enabled input in response to the electronically outputted one or more selection menus electronically identifying at least in part the one or more selected ingestible products to be used periodically (e.g. an implementation of the receiver component s528 is configured to electronically receive the selection information of the one or more ingestible products and engage with the microprocessor component s102 in response to the electronically outputted one or more selection menus electronically identifying at least in part the one or more selected ingestible products to be used periodically such as once a week, etc.).

Figure 66:
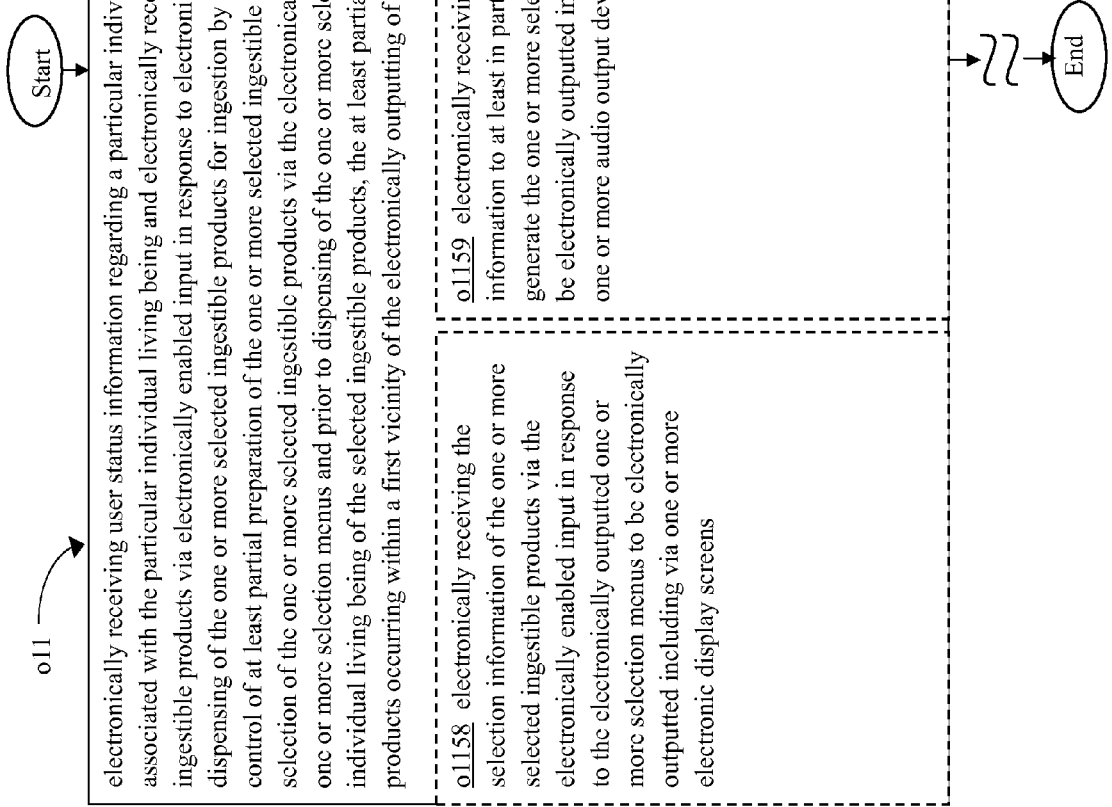
FIG. 66 is a high-level flowchart including exemplary implementations of operation O11 of FIG. 46.

In one or more implementations, as shown in FIG. 66, operation o11 includes an operation o1158 for electronically receiving the selection information of the one or more selected ingestible products via the electronically enabled input in response to the electronically outputted one or more selection menus to be electronically outputted including via one or more electronic display screens. An exemplary version of a non-transitory signal bearing medium of information storage subsystem s200 is depicted as bearing one or more receiving information display instructions i1158 that when executed will direct performance of the operation o1158. In an implementation, the one or more receiving information display instructions i1158 when executed direct electronically receiving the selection information of the one or more selected ingestible products via the electronically enabled input in response to the electronically outputted one or more selection menus to be electronically outputted including via one or more electronic display screens (e.g. an implementation of the receiver component s528 is configured to electronically receive the selection information of the one or more ingestible products in a format for the microprocessor component s102 in response to the electronically outputted one or more selection menus to be electronically outputted including via one or more display screens such as via graphical user interface (GUI) component s302, etc.). Furthermore, the receiving information display electrical circuitry arrangement e1158 when activated will perform the operation o1158. In an implementation, the receiving information display electrical circuitry arrangement e1158, when activated performs electronically receiving the selection information of the one or more selected ingestible products via the electronically enabled input in response to the electronically outputted one or more selection menus to be electronically outputted including via one or more electronic display screens (e.g. an implementation of the receiver component s528 is configured to electronically receive the selection information of the one or more ingestible products in a format for the microprocessor component s102 in response to the electronically outputted one or more selection menus to be electronically outputted including via one or more display screens such as via graphical user interface (GUI) component s302, etc.). In an implementation, the electronically receiving the selection information of the one or more selected ingestible products via the electronically enabled input in response to the electronically outputted one or more selection menus to be electronically outputted including via one or more electronic display screens is carried out by electronically receiving the selection information of the one or more selected ingestible products via the electronically enabled input in response to the electronically outputted one or more selection menus to be electronically outputted including via one or more electronic display screens (e.g. an implementation of the receiver component s528 is configured to electronically receive the selection information of the one or more ingestible products in a format for the microprocessor component s102 in response to the electronically outputted one or more selection menus to be electronically outputted including via one or more display screens such as via graphical user interface (GUI) component s302, etc.).

In one or more implementations, operation o11 includes an operation o1159 for electronically receiving user status information to at least in part electronically generate the one or more selection menus to be electronically outputted including via one or more audio output devices. An exemplary version of a non-transitory signal bearing medium of information storage subsystem s200 is depicted as bearing one or more receiving information audio instructions i1159 that when executed will direct performance of the operation o1159. In an implementation, the one or more receiving information audio instructions i1159 when executed direct electronically receiving the selection information of the one or more selected ingestible products via the electronically enabled input in response to the electronically outputted one or more selection menus to be electronically outputted including via one or more audio output devices (e.g. an implementation of the receiver component s528 is configured to electronically receive the selection information of the one or more ingestible products in a format for the microprocessor component s102 in response to the electronically outputted one or more selection menus to be electronically outputted including via one or more audio output devices such as via audio in/out component s328, etc.). Furthermore, the receiving information audio electrical circuitry arrangement e1159 when activated will perform the operation o1159. In an implementation, the receiving information audio electrical circuitry arrangement e1159, when activated performs electronically receiving the selection information of the one or more selected ingestible products via the electronically enabled input in response to the electronically outputted one or more selection menus to be electronically outputted including via one or more audio output devices (e.g. an implementation of the receiver component s528 is configured to electronically receive the selection information of the one or more ingestible products in a format for the microprocessor component s102 in response to the electronically outputted one or more selection menus to be electronically outputted including via one or more audio output devices such as via audio in/out component s328, etc.). In an implementation, the electronically receiving user status information to at least in part electronically generate the one or more selection menus to be electronically outputted including via one or more audio output devices is carried out by electronically receiving the selection information of the one or more selected ingestible products via the electronically enabled input in response to the electronically outputted one or more selection menus to be electronically outputted including via one or more audio output devices (e.g. an implementation of the receiver component s528 is configured to electronically receive the selection information of the one or more ingestible products in a format for the microprocessor component s102 in response to the electronically outputted one or more selection menus to be electronically outputted including via one or more audio output devices such as via audio in/out component s328, etc.).

In one or more implementations, operation o11 includes an operation o1160 for electronically receiving the selection information of the one or more selected ingestible products via the electronically enabled input in response to the electronically outputted one or more selection menus to be electronically outputted including via one or more network interfaces. An exemplary version of a non-transitory signal bearing medium of information storage subsystem s200 is depicted as bearing one or more receiving information network instructions i1160 that when executed will direct performance of the operation o1160. In an implementation, the one or more receiving information network instructions i1160 when executed direct electronically receiving the selection information of the one or more selected ingestible products via the electronically enabled input in response to the electronically outputted one or more selection menus to be electronically outputted including via one or more network interfaces (e.g. an implementation of the receiver component s528 is configured to electronically receive the selection information of the one or more ingestible products in a format for the microprocessor component s102 in response to the electronically outputted one or more selection menus to be electronically outputted including via one or more network interfaces such as via wide area network component s516, etc.). Furthermore, the receiving information network electrical circuitry arrangement e1160 when activated will perform the operation o1160. In an implementation, the receiving information network electrical circuitry arrangement e1160, when activated performs electronically receiving the selection information of the one or more selected ingestible products via the electronically enabled input in response to the electronically outputted one or more selection menus to be electronically outputted including via one or more network interfaces (e.g. an implementation of the receiver component s528 is configured to electronically receive the selection information of the one or more ingestible products in a format for the microprocessor component s102 in response to the electronically outputted one or more selection menus to be electronically outputted including via one or more network interfaces such as via wide area network component s516, etc.). In an implementation, the electronically receiving the selection information of the one or more selected ingestible products via the electronically enabled input in response to the electronically outputted one or more selection menus to be electronically outputted including via one or more network interfaces is carried out by electronically receiving the selection information of the one or more selected ingestible products via the electronically enabled input in response to the electronically outputted one or more selection menus to be electronically outputted including via one or more network interfaces (e.g. an implementation of the receiver component s528 is configured to electronically receive the selection information of the one or more ingestible products in a format for the microprocessor component s102 in response to the electronically outputted one or more selection menus to be electronically outputted including via one or more network interfaces such as via wide area network component s516, etc.).

Figure 67:
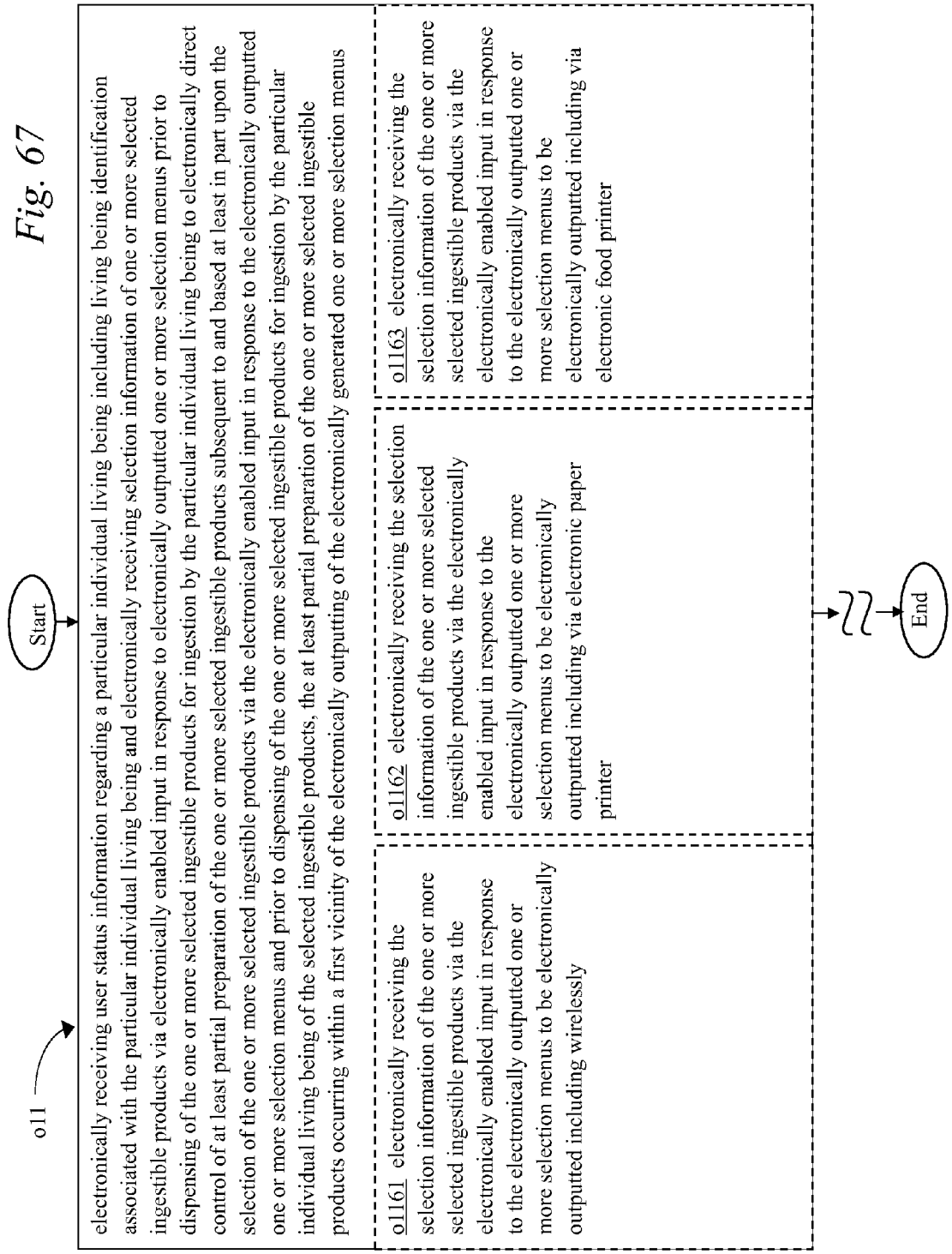
FIG. 67 is a high-level flowchart including exemplary implementations of operation O11 of FIG. 46.

In one or more implementations, as shown in FIG. 67, operation o11 includes an operation o1161 for electronically receiving the selection information of the one or more selected ingestible products via the electronically enabled input in response to the electronically outputted one or more selection menus to be electronically outputted including wirelessly. An exemplary version of a non-transitory signal bearing medium of information storage subsystem s200 is depicted as bearing one or more receiving information wirelessly instructions i1161 that when executed will direct performance of the operation o1161. In an implementation, the one or more receiving information wirelessly instructions i1161 when executed direct electronically receiving the selection information of the one or more selected ingestible products via the electronically enabled input in response to the electronically outputted one or more selection menus to be electronically outputted including wirelessly (e.g. an implementation of the receiver component s528 is configured to electronically receive the selection information of the one or more ingestible products in a format for the microprocessor component s102 in response to the electronically outputted one or more selection menus to be electronically outputted including wirelessly such as via wireless network component s510, etc.). Furthermore, the receiving information wirelessly electrical circuitry arrangement e1161 when activated will perform the operation o1161. In an implementation, the receiving information wirelessly electrical circuitry arrangement e1161, when activated performs electronically receiving the selection information of the one or more selected ingestible products via the electronically enabled input in response to the electronically outputted one or more selection menus to be electronically outputted including wirelessly (e.g. an implementation of the receiver component s528 is configured to electronically receive the selection information of the one or more ingestible products in a format for the microprocessor component s102 in response to the electronically outputted one or more selection menus to be electronically outputted including wirelessly such as via wireless network component s510, etc.). In an implementation, the electronically receiving the selection information of the one or more selected ingestible products via the electronically enabled input in response to the electronically outputted one or more selection menus to be electronically outputted including wirelessly is carried out by electronically receiving the selection information of the one or more selected ingestible products via the electronically enabled input in response to the electronically outputted one or more selection menus to be electronically outputted including wirelessly (e.g. an implementation of the receiver component s528 is configured to electronically receive the selection information of the one or more ingestible products in a format for the microprocessor component s102 in response to the electronically outputted one or more selection menus to be electronically outputted including wirelessly such as via wireless network component s510, etc.).

In one or more implementations, operation o11 includes an operation o1162 for electronically receiving the selection information of the one or more selected ingestible products via the electronically enabled input in response to the electronically outputted one or more selection menus to be electronically outputted including via electronic paper printer. An exemplary version of a non-transitory signal bearing medium of information storage subsystem s200 is depicted as bearing one or more receiving information paper instructions i1162 that when executed will direct performance of the operation o1162. In an implementation, the one or more receiving information paper instructions i1162 when executed direct electronically receiving the selection information of the one or more selected ingestible products via the electronically enabled input in response to the electronically outputted one or more selection menus to be electronically outputted including via electronic paper printer (e.g. an implementation of the receiver component s528 is configured to electronically receive the selection information of the one or more ingestible products in a format for the microprocessor component s102 in response to the electronically outputted one or more selection menus to be electronically outputted including via electronic paper printer such as via scanner component s338, etc.). Furthermore, the receiving information paper electrical circuitry arrangement e1162 when activated will perform the operation o1162. In an implementation, the receiving information paper electrical circuitry arrangement e1162, when activated performs electronically receiving the selection information of the one or more selected ingestible products via the electronically enabled input in response to the electronically outputted one or more selection menus to be electronically outputted including via electronic paper printer (e.g. an implementation of the receiver component s528 is configured to electronically receive the selection information of the one or more ingestible products in a format for the microprocessor component s102 in response to the electronically outputted one or more selection menus to be electronically outputted including via electronic paper printer such as via scanner component s338, etc.). In an implementation, the electronically receiving the selection information of the one or more selected ingestible products via the electronically enabled input in response to the electronically outputted one or more selection menus to be electronically outputted including via electronic paper printer is carried out by electronically receiving the selection information of the one or more selected ingestible products via the electronically enabled input in response to the electronically outputted one or more selection menus to be electronically outputted including via electronic paper printer (e.g. an implementation of the receiver component s528 is configured to electronically receive the selection information of the one or more ingestible products in a format for the microprocessor component s102 in response to the electronically outputted one or more selection menus to be electronically outputted including via electronic paper printer such as via scanner component s338, etc.).

In one or more implementations, operation o11 includes an operation o1163 for electronically receiving the selection information of the one or more selected ingestible products via the electronically enabled input in response to the electronically outputted one or more selection menus to be electronically outputted including via electronic food printer. An exemplary version of a non-transitory signal bearing medium of information storage subsystem s200 is depicted as bearing one or more receiving information food instructions i1163 that when executed will direct performance of the operation o1163. In an implementation, the one or more receiving information food instructions i1163 when executed direct electronically receiving the selection information of the one or more selected ingestible products via the electronically enabled input in response to the electronically outputted one or more selection menus to be electronically outputted including via electronic food printer (e.g. an implementation of the receiver component s528 is configured to electronically receive the selection information of the one or more ingestible products in a format for the microprocessor component s102 in response to the electronically outputted one or more selection menus to be electronically outputted including via electronic food printer such as via deposition component s740, etc.). Furthermore, the receiving information food electrical circuitry arrangement e1163 when activated will perform the operation o1163. In an implementation, the receiving information food electrical circuitry arrangement e1163, when activated performs electronically receiving the selection information of the one or more selected ingestible products via the electronically enabled input in response to the electronically outputted one or more selection menus to be electronically outputted including via electronic food printer (e.g. an implementation of the receiver component s528 is configured to electronically receive the selection information of the one or more ingestible products in a format for the microprocessor component s102 in response to the electronically outputted one or more selection menus to be electronically outputted including via electronic food printer such as via deposition component s740, etc.). In an implementation, the electronically receiving the selection information of the one or more selected ingestible products via the electronically enabled input in response to the electronically outputted one or more selection menus to be electronically outputted including via electronic food printer is carried out by electronically receiving the selection information of the one or more selected ingestible products via the electronically enabled input in response to the electronically outputted one or more selection menus to be electronically outputted including via electronic food printer (e.g. an implementation of the receiver component s528 is configured to electronically receive the selection information of the one or more ingestible products in a format for the microprocessor component s102 in response to the electronically outputted one or more selection menus to be electronically outputted including via electronic food printer such as via deposition component s740, etc.).

Figure 68:
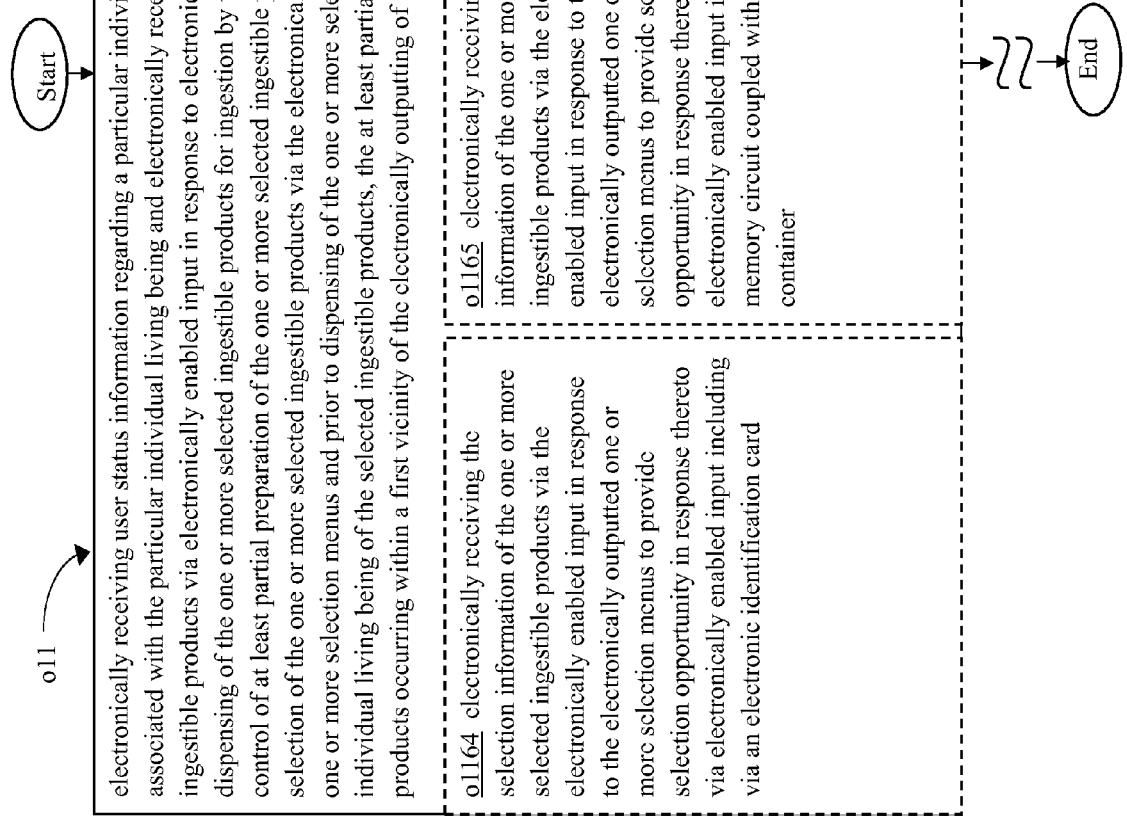
FIG. 68 is a high-level flowchart including exemplary implementations of operation O11 of FIG. 46.

In one or more implementations, as shown in FIG. 68, operation o11 includes an operation o1164 for electronically receiving the selection information of the one or more selected ingestible products via the electronically enabled input in response to the electronically outputted one or more selection menus to provide selection opportunity in response thereto via electronically enabled input including via an electronic identification card. An exemplary version of a non-transitory signal bearing medium of information storage subsystem s200 is depicted as bearing one or more receiving information ID card instructions i1164 that when executed will direct performance of the operation o1164. In an implementation, the one or more receiving information ID card instructions i1164 when executed direct electronically receiving the selection information of the one or more selected ingestible products via the electronically enabled input in response to the electronically outputted one or more selection menus to provide the selection opportunity in response thereto via electronically enabled input including via an electronic identification card (e.g. an implementation of the receiver component s528 is configured to electronically engage with a card having memory storage holding the user status information, etc.). Furthermore, the receiving information ID card electrical circuitry arrangement e1164 when activated will perform the operation o1164. In an implementation, the receiving information ID card electrical circuitry arrangement e1164, when activated performs electronically receiving the selection information of the one or more selected ingestible products via the electronically enabled input in response to the electronically outputted one or more selection menus to provide the selection opportunity in response thereto via electronically enabled input including via an electronic identification card (e.g. an implementation of the receiver component s528 is configured to electronically engage with a card having memory storage holding the user status information, etc.). In an implementation, the electronically receiving the selection information of the one or more selected ingestible products via the electronically enabled input in response to the electronically outputted one or more selection menus to provide selection opportunity in response thereto via electronically enabled input including via an electronic identification card is carried out by electronically receiving the selection information of the one or more selected ingestible products via the electronically enabled input in response to the electronically outputted one or more selection menus to provide the selection opportunity in response thereto via electronically enabled input including via an electronic identification card (e.g. an implementation of the receiver component s528 is configured to electronically engage with a card having memory storage holding the user status information, etc.).

In one or more implementations, operation o11 includes an operation o1165 for electronically receiving the selection information of the one or more selected ingestible products via the electronically enabled input in response to the electronically outputted one or more selection menus to provide selection opportunity in response thereto via electronically enabled input including via a memory circuit coupled with a medication container. A non-transitory signal bearing medium includes one or more receiving information container instructions i1165 that when executed will direct performance of the operation o1165. In an implementation, the one or more receiving information container instructions i1165 when executed direct electronically receiving the selection information of the one or more selected ingestible products via the electronically enabled input in response to the electronically outputted one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form, etc.). Furthermore, the receiving information container electrical circuitry arrangement e1165 when activated will perform the operation o1165. In an implementation, the receiving information container electrical circuitry arrangement e1165, when activated performs electronically receiving the selection information of the one or more selected ingestible products via the electronically enabled input in response to the electronically outputted one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form, etc.). In an implementation, the electronically receiving the selection information of the one or more selected ingestible products via the electronically enabled input in response to the electronically outputted one or more selection menus to provide selection opportunity in response thereto via electronically enabled input including via a memory circuit coupled with a medication container is carried out by electronically receiving the selection information of the one or more selected ingestible products via the electronically enabled input in response to the electronically outputted one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form, etc.).

In one or more implementations, operation o11 includes an operation o1166 for electronically receiving the selection information of the one or more selected ingestible products via the electronically enabled input in response to the electronically outputted one or more selection menus to provide selection opportunity in response thereto via electronically enabled input including via a credit card swipe. A non-transitory signal bearing medium includes one or more receiving information credit card instructions i1166 that when executed will direct performance of the operation o1166. In an implementation, the one or more receiving information credit card instructions i1166 when executed direct electronically receiving the selection information of the one or more selected ingestible products via the electronically enabled input in response to the electronically outputted one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input, etc.). Furthermore, the receiving information credit card electrical circuitry arrangement e1166 when activated will perform the operation o1166. In an implementation, the receiving information credit card electrical circuitry arrangement e1166, when activated performs electronically receiving the selection information of the one or more selected ingestible products via the electronically enabled input in response to the electronically outputted one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via a credit card swipe is carried out by electronically receiving the selection information of the one or more selected ingestible products via the electronically enabled input in response to the electronically outputted one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input, etc.).

Figure 69:
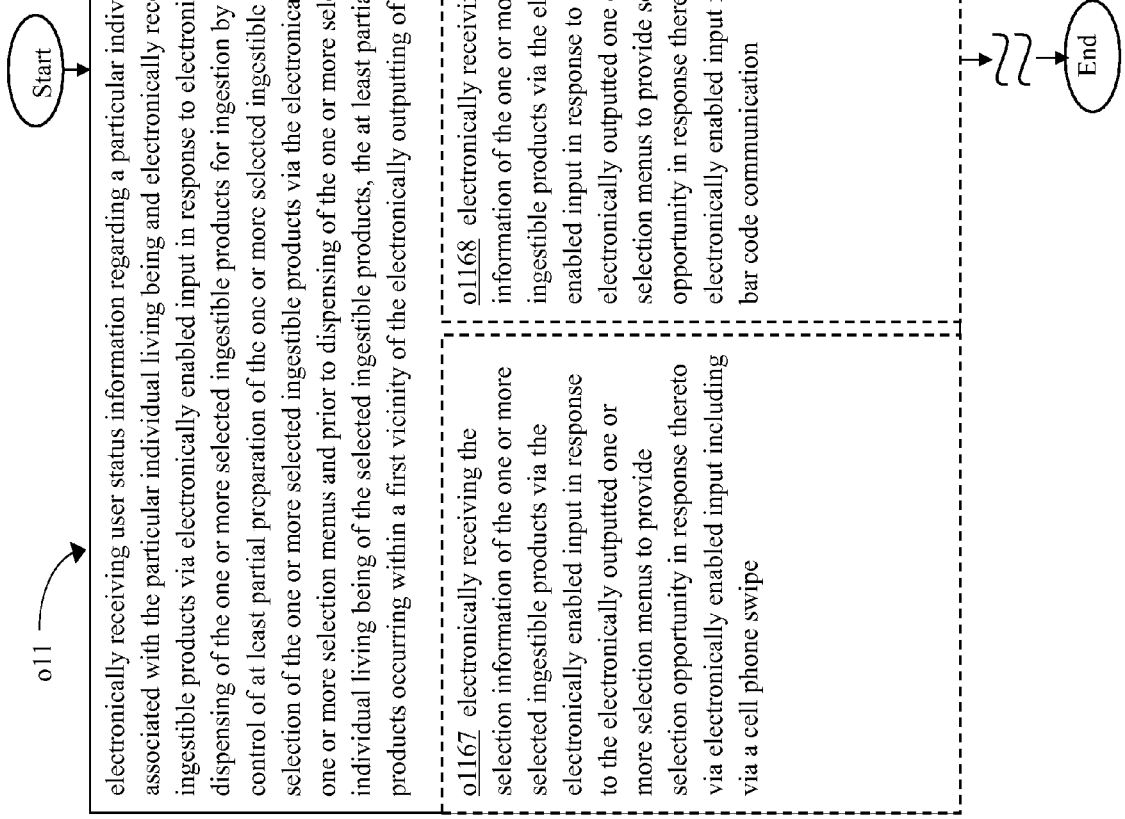
FIG. 69 is a high-level flowchart including exemplary implementations of operation O11 of FIG. 46.

In one or more implementations, as shown in FIG. 69, operation o11 includes an operation o1167 for electronically receiving the selection information of the one or more selected ingestible products via the electronically enabled input in response to the electronically outputted one or more selection menus to provide selection opportunity in response thereto via electronically enabled input including via a cell phone swipe. An exemplary version of a non-transitory signal bearing medium of information storage subsystem s200 is depicted as bearing one or more receiving information cell phone instructions i1167 that when executed will direct performance of the operation o1167. In an implementation, the one or more receiving information cell phone instructions i1167 when executed direct electronically receiving the selection information of the one or more selected ingestible products via the electronically enabled input in response to the electronically outputted one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input, etc.). Furthermore, the receiving information cell phone electrical circuitry arrangement e1167 when activated will perform the operation o1167. In an implementation, the receiving information cell phone electrical circuitry arrangement e1167, when activated performs electronically receiving the selection information of the one or more selected ingestible products via the electronically enabled input in response to the electronically outputted one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via a cell phone swipe is carried out by electronically receiving the selection information of the one or more selected ingestible products via the electronically enabled input in response to the electronically outputted one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input, etc.).

In one or more implementations, operation o11 includes an operation o1168 for electronically receiving the selection information of the one or more selected ingestible products via the electronically enabled input in response to the electronically outputted one or more selection menus to provide selection opportunity in response thereto via electronically enabled input including via a bar code communication. A non-transitory signal bearing medium includes one or more receiving information bar code instructions i1168 that when executed will direct performance of the operation o1168. In an implementation, the one or more receiving information bar code instructions i1168 when executed direct electronically receiving the selection information of the one or more selected ingestible products via the electronically enabled input in response to the electronically outputted one or more selection menus to provide the selection opportunity in response thereto via electronically enabled input including via bar code communication (e.g. an implementation of the receiver component s528 is configured to electronically read a bar code label to receive the electronically enabled input, etc.). Furthermore, the receiving information bar code electrical circuitry arrangement e1168 when activated will perform the operation o1168. In an implementation, the receiving information bar code electrical circuitry arrangement e1168, when activated performs electronically receiving the selection information of the one or more selected ingestible products via the electronically enabled input in response to the electronically outputted one or more selection menus to provide the selection opportunity in response thereto via electronically enabled input including via bar code communication (e.g. an implementation of the receiver component s528 is configured to electronically read a bar code label to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via a bar code communication is carried out by electronically receiving the selection information of the one or more selected ingestible products via the electronically enabled input in response to the electronically outputted one or more selection menus to provide the selection opportunity in response thereto via electronically enabled input including via bar code communication (e.g. an implementation of the receiver component s528 is configured to electronically read a bar code label to receive the electronically enabled input, etc.).

In one or more implementations, operation o11 includes an operation o1169 for electronically receiving the selection information of the one or more selected ingestible products via the electronically enabled input in response to the electronically outputted one or more selection menus to provide selection opportunity in response thereto via electronically enabled input including via an Internet communication. A non-transitory signal bearing medium includes one or more receiving information Internet instructions i1169 that when executed will direct performance of the operation o1169. In an implementation, the one or more receiving information Internet instructions i1169 when executed direct electronically receiving the selection information of the one or more selected ingestible products via the electronically enabled input in response to the electronically outputted one or more selection menus to provide the selection opportunity in response thereto via electronically enabled input including via Internet communication (e.g. an implementation of the receiver component s528 is configured to electronically receive through the internet network component s508 the user status information, etc.). Furthermore, the receiving information Internet electrical circuitry arrangement e1169 when activated will perform the operation o1169. In an implementation, the receiving information Internet electrical circuitry arrangement e1169, when activated performs electronically receiving the selection information of the one or more selected ingestible products via the electronically enabled input in response to the electronically outputted one or more selection menus to provide the selection opportunity in response thereto via electronically enabled input including via Internet communication (e.g. an implementation of the receiver component s528 is configured to electronically receive through the internet network component s508 the user status information, etc.). In an implementation, the electronically receiving the selection information of the one or more selected ingestible products via the electronically enabled input in response to the electronically outputted one or more selection menus to provide selection opportunity in response thereto via electronically enabled input including via an Internet communication is carried out by electronically receiving the selection information of the one or more selected ingestible products via the electronically enabled input in response to the electronically outputted one or more selection menus to provide the selection opportunity in response thereto via electronically enabled input including via Internet communication (e.g. an implementation of the receiver component s528 is configured to electronically receive through the internet network component s508 the user status information, etc.).

Figure 70:
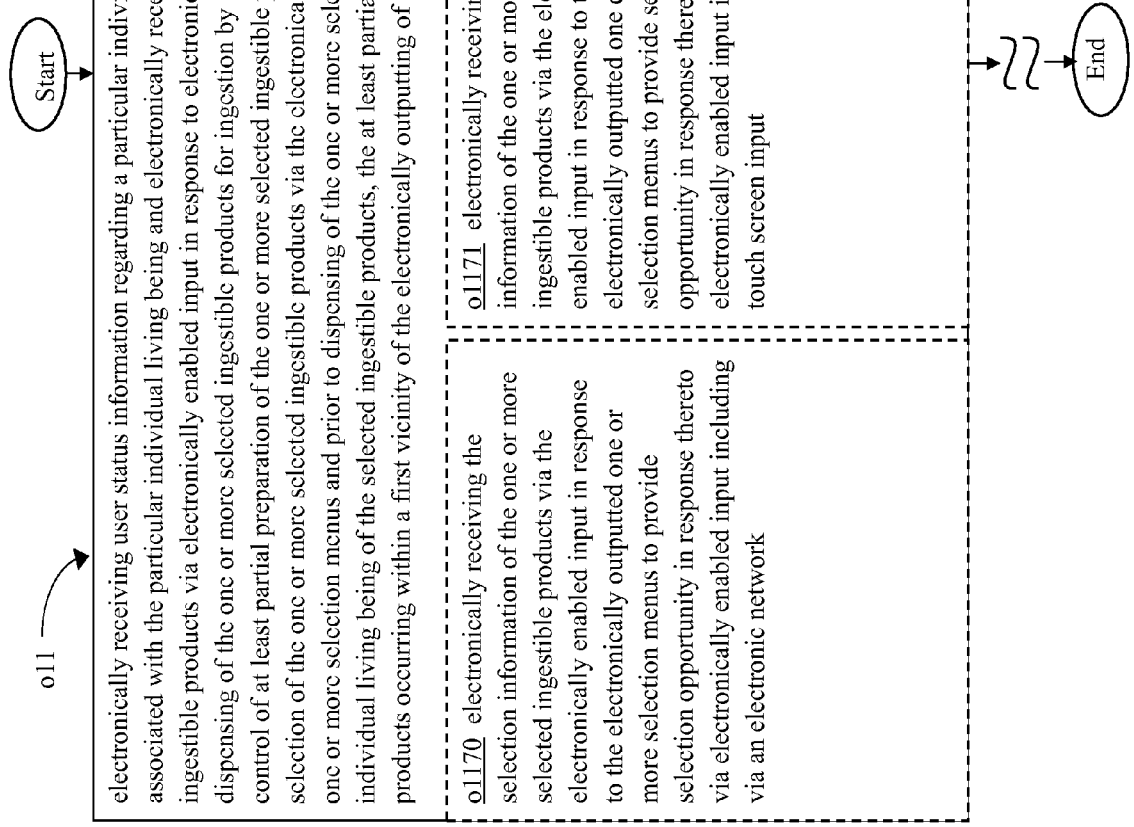
FIG. 70 is a high-level flowchart including exemplary implementations of operation O11 of FIG. 46.

In one or more implementations, as shown in FIG. 70, operation o11 includes an operation o1170 for electronically receiving the selection information of the one or more selected ingestible products via the electronically enabled input in response to the electronically outputted one or more selection menus to provide selection opportunity in response thereto via electronically enabled input including via an electronic network. An exemplary version of a non-transitory signal bearing medium of information storage subsystem s200 is depicted as bearing one or more receiving information network instructions i1170 that when executed will direct performance of the operation o1170. In an implementation, the one or more receiving information network instructions i1170 when executed direct electronically receiving the selection information of the one or more selected ingestible products via the electronically enabled input in response to the electronically outputted one or more selection menus to provide the selection opportunity in response thereto via electronically enabled input including via an electronic network (e.g. an implementation of the receiver component s528 is configured to electronically engage with the network cable component s502 to receive the electronically enabled input, etc.). Furthermore, the receiving information network electrical circuitry arrangement e1170 when activated will perform the operation o1170. In an implementation, the receiving information network electrical circuitry arrangement e1170, when activated performs electronically receiving the selection information of the one or more selected ingestible products via the electronically enabled input in response to the electronically outputted one or more selection menus to provide the selection opportunity in response thereto via electronically enabled input including via an electronic network (e.g. an implementation of the receiver component s528 is configured to electronically engage with the network cable component s502 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via an electronic network is carried out by electronically receiving the selection information of the one or more selected ingestible products via the electronically enabled input in response to the electronically outputted one or more selection menus to provide the selection opportunity in response thereto via electronically enabled input including via an electronic network (e.g. an implementation of the receiver component s528 is configured to electronically engage with the network cable component s502 to receive the electronically enabled input, etc.).

In one or more implementations, operation o11 includes an operation o1171 for electronically receiving the selection information of the one or more selected ingestible products via the electronically enabled input in response to the electronically outputted one or more selection menus to provide selection opportunity in response thereto via electronically enabled input including via touch screen input. A non-transitory signal bearing medium includes one or more receiving information touch screen instructions i1171 that when executed will direct performance of the operation o1171. In an implementation, the one or more receiving information touch screen instructions i1171 when executed direct electronically receiving the selection information of the one or more selected ingestible products via the electronically enabled input in response to the electronically outputted one or more selection menus to provide the selection opportunity in response thereto via electronically enabled input including via touch screen input (e.g. an implementation of the receiver component s528 is configured to electronically receive through the touch screen component s314 the user status information, etc.). Furthermore, the receiving information touch screen electrical circuitry arrangement e1171 when activated will perform the operation o1171. In an implementation, the receiving information touch screen electrical circuitry arrangement e1171, when activated performs electronically receiving the selection information of the one or more selected ingestible products via the electronically enabled input in response to the electronically outputted one or more selection menus to provide the selection opportunity in response thereto via electronically enabled input including via touch screen input (e.g. an implementation of the receiver component s528 is configured to electronically receive through the touch screen component s314 the user status information, etc.). In an implementation, the electronically receiving the selection information of the one or more selected ingestible products via the electronically enabled input in response to the electronically outputted one or more selection menus to provide selection opportunity in response thereto via electronically enabled input including via touch screen input is carried out by electronically receiving the selection information of the one or more selected ingestible products via the electronically enabled input in response to the electronically outputted one or more selection menus to provide the selection opportunity in response thereto via electronically enabled input including via touch screen input (e.g. an implementation of the receiver component s528 is configured to electronically receive through the touch screen component s314 the user status information, etc.).

In one or more implementations, operation o11 includes an operation o1172 for electronically receiving the selection information of the one or more selected ingestible products via the electronically enabled input in response to the electronically outputted one or more selection menus to provide selection opportunity in response thereto via electronically enabled input including via wireless input. A non-transitory signal bearing medium includes one or more receiving information wireless instructions i1172 that when executed will direct performance of the operation o1172. In an implementation, the one or more receiving information wireless instructions i1172 when executed direct electronically receiving the selection information of the one or more selected ingestible products via the electronically enabled input in response to the electronically outputted one or more selection menus to provide the selection opportunity in response thereto via electronically enabled input including via wireless input (e.g. an implementation of the receiver component s528 is configured to electronically receive through the wireless network component s510 to receive the electronically enabled input, etc.). Furthermore, the receiving information wireless electrical circuitry arrangement e1172 when activated will perform the operation o1172. In an implementation, the receiving information wireless electrical circuitry arrangement e1172, when activated performs electronically receiving the selection information of the one or more selected ingestible products via the electronically enabled input in response to the electronically outputted one or more selection menus to provide the selection opportunity in response thereto via electronically enabled input including via wireless input (e.g. an implementation of the receiver component s528 is configured to electronically receive through the wireless network component s510 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via wireless input is carried out by electronically receiving the selection information of the one or more selected ingestible products via the electronically enabled input in response to the electronically outputted one or more selection menus to provide the selection opportunity in response thereto via electronically enabled input including via wireless input (e.g. an implementation of the receiver component s528 is configured to electronically receive through the wireless network component s510 to receive the electronically enabled input, etc.).

Figure 71:
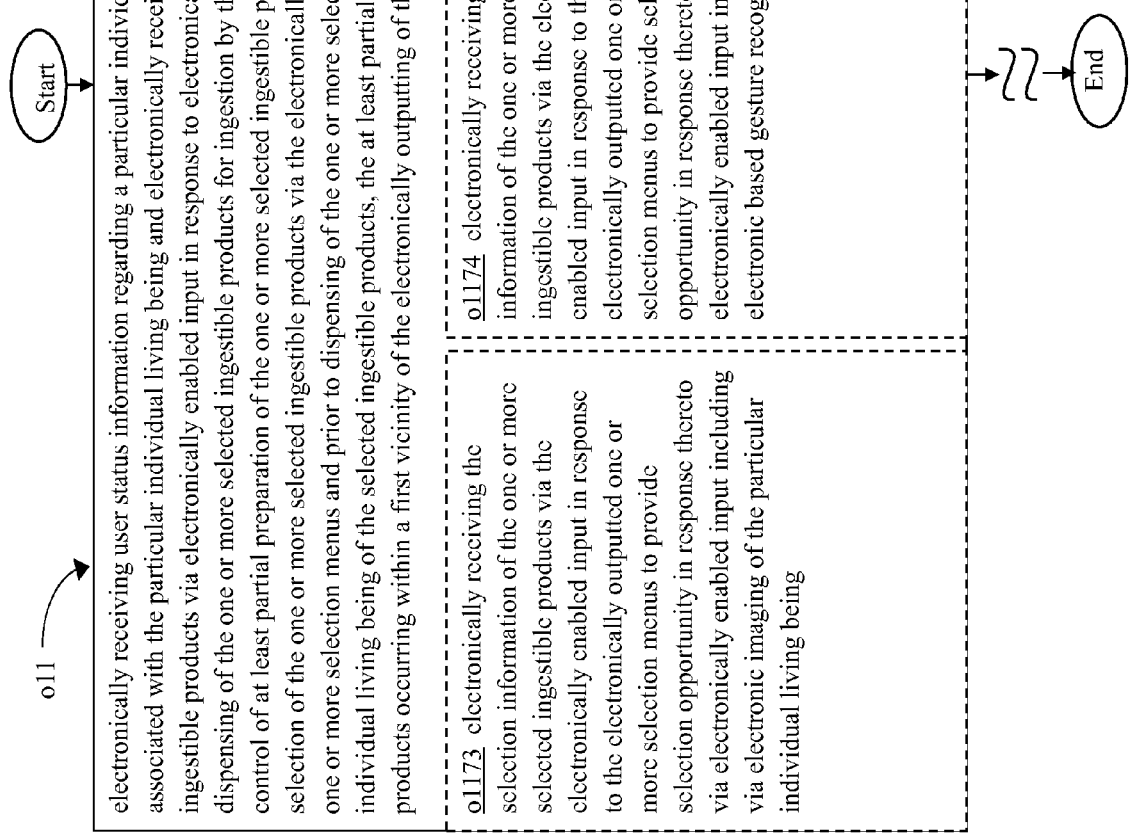
FIG. 71 is a high-level flowchart including exemplary implementations of operation O11 of FIG. 46.

In one or more implementations, as shown in FIG. 71, operation o11 includes an operation o1173 for electronically receiving the selection information of the one or more selected ingestible products via the electronically enabled input in response to the electronically outputted one or more selection menus to provide selection opportunity in response thereto via electronically enabled input including via electronic imaging of the particular individual living being. An exemplary version of a non-transitory signal bearing medium of information storage subsystem s200 is depicted as bearing one or more receiving information imaging instructions i1173 that when executed will direct performance of the operation o1173. In an implementation, the one or more receiving information imaging instructions i1173 when executed direct electronically receiving the selection information of the one or more selected ingestible products via the electronically enabled input in response to the electronically outputted one or more selection menus to provide the selection opportunity in response thereto via electronically enabled input including via electronic imaging of the particular individual living being (e.g. an implementation of the receiver component s528 is configured to electronically receive through the camera component s336 the user status information, etc.). Furthermore, the receiving information imaging electrical circuitry arrangement e1173 when activated will perform the operation o1173. In an implementation, the receiving information imaging electrical circuitry arrangement e1173, when activated performs electronically receiving the selection information of the one or more selected ingestible products via the electronically enabled input in response to the electronically outputted one or more selection menus to provide the selection opportunity in response thereto via electronically enabled input including via electronic imaging of the particular individual living being (e.g. an implementation of the receiver component s528 is configured to electronically receive through the camera component s336 the user status information, etc.). In an implementation, the electronically receiving the selection information of the one or more selected ingestible products via the electronically enabled input in response to the electronically outputted one or more selection menus to provide selection opportunity in response thereto via electronically enabled input including via electronic imaging of the particular individual living being is carried out by electronically receiving the selection information of the one or more selected ingestible products via the electronically enabled input in response to the electronically outputted one or more selection menus to provide the selection opportunity in response thereto via electronically enabled input including via electronic imaging of the particular individual living being (e.g. an implementation of the receiver component s528 is configured to electronically receive through the camera component s336 the user status information, etc.).

In one or more implementations, operation o11 includes an operation o1174 for electronically receiving the selection information of the one or more selected ingestible products via the electronically enabled input in response to the electronically outputted one or more selection menus to provide selection opportunity in response thereto via electronically enabled input including via electronic based gesture recognition. A non-transitory signal bearing medium includes one or more receiving information gesture instructions i1174 that when executed will direct performance of the operation o1174. In an implementation, the one or more receiving information gesture instructions i1174 when executed direct electronically receiving the selection information of the one or more selected ingestible products via the electronically enabled input in response to the electronically outputted one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user, etc.). Furthermore, the receiving information gesture electrical circuitry arrangement e1174 when activated will perform the operation o1174. In an implementation, the receiving information gesture electrical circuitry arrangement e1174, when activated performs electronically receiving the selection information of the one or more selected ingestible products via the electronically enabled input in response to the electronically outputted one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user, etc.). In an implementation, the electronically receiving the selection information of the one or more selected ingestible products via the electronically enabled input in response to the electronically outputted one or more selection menus to provide selection opportunity in response thereto via electronically enabled input including via electronic based gesture recognition is carried out by electronically receiving the selection information of the one or more selected ingestible products via the electronically enabled input in response to the electronically outputted one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user, etc.).

In one or more implementations, operation o11 includes an operation o1175 for electronically receiving the selection information of the one or more selected ingestible products via the electronically enabled input in response to the electronically outputted one or more selection menus to provide selection opportunity in response thereto via electronically enabled input including via electronic audio recording of the particular individual living being. A non-transitory signal bearing medium includes one or more receiving information audio instructions i1175 that when executed will direct performance of the operation o1175. In an implementation, the one or more receiving information audio instructions i1175 when executed direct electronically receiving the selection information of the one or more selected ingestible products via the electronically enabled input in response to the electronically outputted one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input, etc.). Furthermore, the receiving information audio electrical circuitry arrangement e1175 when activated will perform the operation o1175. In an implementation, the receiving information audio electrical circuitry arrangement e1175, when activated performs electronically receiving the selection information of the one or more selected ingestible products via the electronically enabled input in response to the electronically outputted one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via electronic audio recording of the particular individual living being is carried out by electronically receiving the selection information of the one or more selected ingestible products via the electronically enabled input in response to the electronically outputted one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input, etc.).

Figure 72:
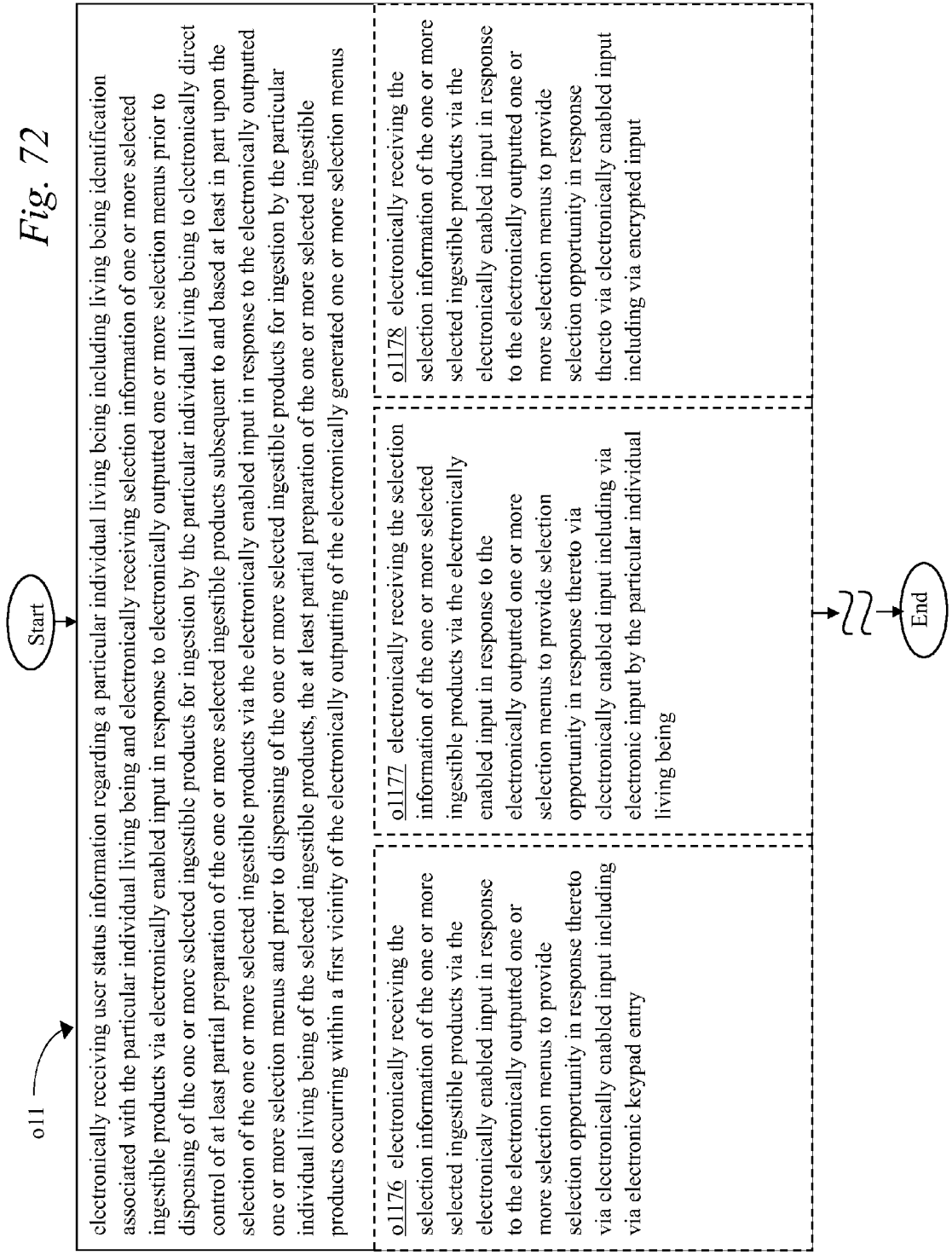
FIG. 72 is a high-level flowchart including exemplary implementations of operation O11 of FIG. 46.

In one or more implementations, as shown in FIG. 72, operation o11 includes an operation o1176 for electronically receiving the selection information of the one or more selected ingestible products via the electronically enabled input in response to the electronically outputted one or more selection menus to provide selection opportunity in response thereto via electronically enabled input including via electronic keypad entry. An exemplary version of a non-transitory signal bearing medium of information storage subsystem s200 is depicted as bearing one or more receiving information keypad instructions i1176 that when executed will direct performance of the operation o1176. In an implementation, the one or more receiving information keypad instructions i1176 when executed direct electronically receiving the selection information of the one or more selected ingestible products via the electronically enabled input in response to the electronically outputted one or more selection menus to provide the selection opportunity in response thereto via electronically enabled input including via electronic keypad entry (e.g. an implementation of the receiver component s528 is configured to electronically engage with the keypad component s308 to receive the electronically enabled input, etc.). Furthermore, the receiving information keypad electrical circuitry arrangement e1176 when activated will perform the operation o1176. In an implementation, the receiving information keypad electrical circuitry arrangement e1176, when activated performs electronically receiving the selection information of the one or more selected ingestible products via the electronically enabled input in response to the electronically outputted one or more selection menus to provide the selection opportunity in response thereto via electronically enabled input including via electronic keypad entry (e.g. an implementation of the receiver component s528 is configured to electronically engage with the keypad component s308 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via electronic keypad entry is carried out by electronically receiving the selection information of the one or more selected ingestible products via the electronically enabled input in response to the electronically outputted one or more selection menus to provide the selection opportunity in response thereto via electronically enabled input including via electronic keypad entry (e.g. an implementation of the receiver component s528 is configured to electronically engage with the keypad component s308 to receive the electronically enabled input, etc.).

In one or more implementations, operation o11 includes an operation o1177 for electronically receiving the selection information of the one or more selected ingestible products via the electronically enabled input in response to the electronically outputted one or more selection menus to provide selection opportunity in response thereto via electronically enabled input including via electronic input by the particular individual living being. A non-transitory signal bearing medium includes one or more receiving information input instructions i1177 that when executed will direct performance of the operation o1177. In an implementation, the one or more receiving information input instructions i1177 when executed direct electronically receiving the selection information of the one or more selected ingestible products via the electronically enabled input in response to the electronically outputted one or more selection menus to provide the selection opportunity in response thereto via electronically enabled input including via an electronic input by the particular individual living being (e.g. an implementation of the receiver component s528 is configured to electronically engage with the electromagnetic sensing component s402 to receive the electronically enabled input, etc.). Furthermore, the receiving information input electrical circuitry arrangement e1177 when activated will perform the operation o1177. In an implementation, the receiving information input electrical circuitry arrangement e1177, when activated performs electronically receiving the selection information of the one or more selected ingestible products via the electronically enabled input in response to the electronically outputted one or more selection menus to provide the selection opportunity in response thereto via electronically enabled input including via an electronic input by the particular individual living being (e.g. an implementation of the receiver component s528 is configured to electronically engage with the electromagnetic sensing component s402 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via electronic input by the particular individual living being is carried out by electronically receiving the selection information of the one or more selected ingestible products via the electronically enabled input in response to the electronically outputted one or more selection menus to provide the selection opportunity in response thereto via electronically enabled input including via an electronic input by the particular individual living being (e.g. an implementation of the receiver component s528 is configured to electronically engage with the electromagnetic sensing component s402 to receive the electronically enabled input, etc.).

In one or more implementations, operation o11 includes an operation o1178 for electronically receiving the selection information of the one or more selected ingestible products via the electronically enabled input in response to the electronically outputted one or more selection menus to provide selection opportunity in response thereto via electronically enabled input including via encrypted input. A non-transitory signal bearing medium includes one or more receiving information encrypted instructions i1178 that when executed will direct performance of the operation o1178. In an implementation, the one or more receiving information encrypted instructions i1178 when executed direct electronically receiving the selection information of the one or more selected ingestible products via the electronically enabled input in response to the electronically outputted one or more selection menus to provide the selection opportunity in response thereto via electronically enabled input including via encrypted input (e.g. an implementation of the receiver component s528 is configured to electronically engage with the encrypted communication component s520 to receive the electronically enabled input, etc.). Furthermore, the receiving information encrypted electrical circuitry arrangement e1178 when activated will perform the operation o1178. In an implementation, the receiving information encrypted electrical circuitry arrangement e1178, when activated performs electronically receiving the selection information of the one or more selected ingestible products via the electronically enabled input in response to the electronically outputted one or more selection menus to provide the selection opportunity in response thereto via electronically enabled input including via encrypted input (e.g. an implementation of the receiver component s528 is configured to electronically engage with the encrypted communication component s520 to receive the electronically enabled input, etc.). In an implementation, the electronically receiving the selection information of the one or more selected ingestible products via the electronically enabled input in response to the electronically outputted one or more selection menus to provide selection opportunity in response thereto via electronically enabled input including via encrypted input is carried out by electronically receiving the selection information of the one or more selected ingestible products via the electronically enabled input in response to the electronically outputted one or more selection menus to provide the selection opportunity in response thereto via electronically enabled input including via encrypted input (e.g. an implementation of the receiver component s528 is configured to electronically engage with the encrypted communication component s520 to receive the electronically enabled input, etc.).

Figure 73:
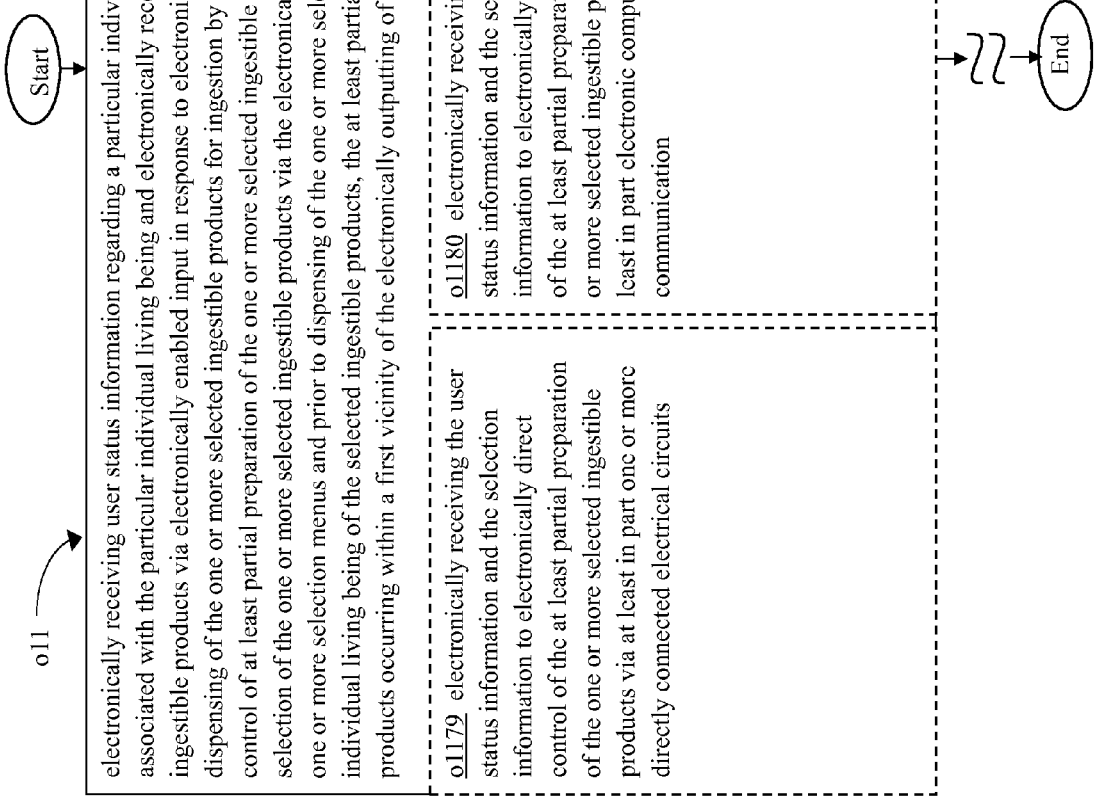
FIG. 73 is a high-level flowchart including exemplary implementations of operation O11 of FIG. 46.

In one or more implementations, as shown in FIG. 73, operation o11 includes an operation o1179 for electronically receiving the user status information and the selection information to electronically direct control of the at least partial preparation of the one or more selected ingestible products via at least in part one or more directly connected electrical circuits. An exemplary version of a non-transitory signal bearing medium of information storage subsystem s200 is depicted as bearing one or more control prep connected instructions i1179 that when executed will direct performance of the operation o1179. In an implementation, the one or more control prep connected instructions i1179 when executed direct electronically receiving the user status information and the selection information to electronically direct control of the at least partial preparation of the one or more selected ingestible products via at least in part one or more directly connected electrical circuits (e.g. an implementation of the microprocessor component s102 is configured to electronically receive the user status information end the selection information through receiver component s528 co-located within a common housing of the ingestible product preparation system 10 to control the material processing subsystem 700 in preparation of the one or more ingestible products, etc.). Furthermore, the control prep connected electrical circuitry arrangement e1179 when activated will perform the operation o1179. In an implementation, the control prep connected electrical circuitry arrangement e1179, when activated performs electronically receiving the user status information and the selection information to electronically direct control of the at least partial preparation of the one or more selected ingestible products via at least in part one or more directly connected electrical circuits (e.g. an implementation of the microprocessor component s102 is configured to electronically receive the user status information end the selection information through receiver component s528 co-located within a common housing of the ingestible product preparation system 10 to control the material processing subsystem 700 in preparation of the one or more ingestible products, etc.). In an implementation, the electronically receiving the user status information and the selection information to electronically direct control of the at least partial preparation of the one or more selected ingestible products via at least in part one or more directly connected electrical circuits is carried out by electronically receiving the user status information and the selection information to electronically direct control of the at least partial preparation of the one or more selected ingestible products via at least in part one or more directly connected electrical circuits (e.g. an implementation of the microprocessor component s102 is configured to electronically receive the user status information end the selection information through receiver component s528 co-located within a common housing of the ingestible product preparation system 10 to control the material processing subsystem 700 in preparation of the one or more ingestible products, etc.).

In one or more implementations, operation o11 includes an operation o1180 for electronically receiving the user status information and the selection information to electronically direct control of the at least partial preparation of the one or more selected ingestible products via at least in part electronic computer network communication. A non-transitory signal bearing medium includes one or more control prep network instructions i1180 that when executed will direct performance of the operation o1180. In an implementation, the one or more control prep network instructions i1180 when executed direct electronically receiving the user status information and the selection information to electronically direct control of the at least partial preparation of the one or more selected ingestible products via at least in part electronic computer network communication (e.g. an implementation of the microprocessor component s102 is configured to electronically receive the user status information end the selection information through internet network components s508 to control the material processing subsystem 700 in preparation of the one or more ingestible products, etc.). Furthermore, the control prep network electrical circuitry arrangement e1180 when activated will perform the operation o1180. In an implementation, the control prep network electrical circuitry arrangement e1180, when activated performs electronically receiving the user status information and the selection information to electronically direct control of the at least partial preparation of the one or more selected ingestible products via at least in part electronic computer network communication (e.g. an implementation of the microprocessor component s102 is configured to electronically receive the user status information end the selection information through internet network components s508 to control the material processing subsystem 700 in preparation of the one or more ingestible products, etc.). In an implementation, the electronically receiving the user status information and the selection information to electronically direct control of the at least partial preparation of the one or more selected ingestible products via at least in part electronic computer network communication is carried out by electronically receiving the user status information and the selection information to electronically direct control of the at least partial preparation of the one or more selected ingestible products via at least in part electronic computer network communication (e.g. an implementation of the microprocessor component s102 is configured to electronically receive the user status information end the selection information through internet network components s508 to control the material processing subsystem 700 in preparation of the one or more ingestible products, etc.).

In one or more implementations, operation o11 includes an operation o1181 for electronically receiving the user status information and the selection information to electronically direct control of the at least partial preparation of the one or more selected ingestible products via thermal control of an enclosure containing ingredients to be used for preparation of the ingestible product. A non-transitory signal bearing medium includes one or more control prep thermal instructions i1181 that when executed will direct performance of the operation o1181. In an implementation, the one or more control prep thermal instructions i1181 when executed direct electronically receiving the user status information and the selection information to electronically direct control of the at least partial preparation of the one or more selected ingestible products via thermal control of an enclosure containing ingredients to be used for preparation of the ingestible product (e.g. an implementation of the microprocessor component s102 is configured to electronically control the laser component s708 according to a temperature profile included in the user status information or the selection information received thereby, etc.). Furthermore, the control prep thermal electrical circuitry arrangement e1181 when activated will perform the operation o1181. In an implementation, the control prep thermal electrical circuitry arrangement e1181, when activated performs electronically receiving the user status information and the selection information to electronically direct control of the at least partial preparation of the one or more selected ingestible products via thermal control of an enclosure containing ingredients to be used for preparation of the ingestible product (e.g. an implementation of the microprocessor component s102 is configured to electronically control the laser component s708 according to a temperature profile included in the user status information or the selection information received thereby, etc.). In an implementation, the electronically receiving the user status information and the selection information to electronically direct control of the at least partial preparation of the one or more selected ingestible products via thermal control of an enclosure containing ingredients to be used for preparation of the ingestible product is carried out by electronically receiving the user status information and the selection information to electronically direct control of the at least partial preparation of the one or more selected ingestible products via thermal control of an enclosure containing ingredients to be used for preparation of the ingestible product (e.g. an implementation of the microprocessor component s102 is configured to electronically control the laser component s708 according to a temperature profile included in the user status information or the selection information received thereby, etc.).

Figure 74:
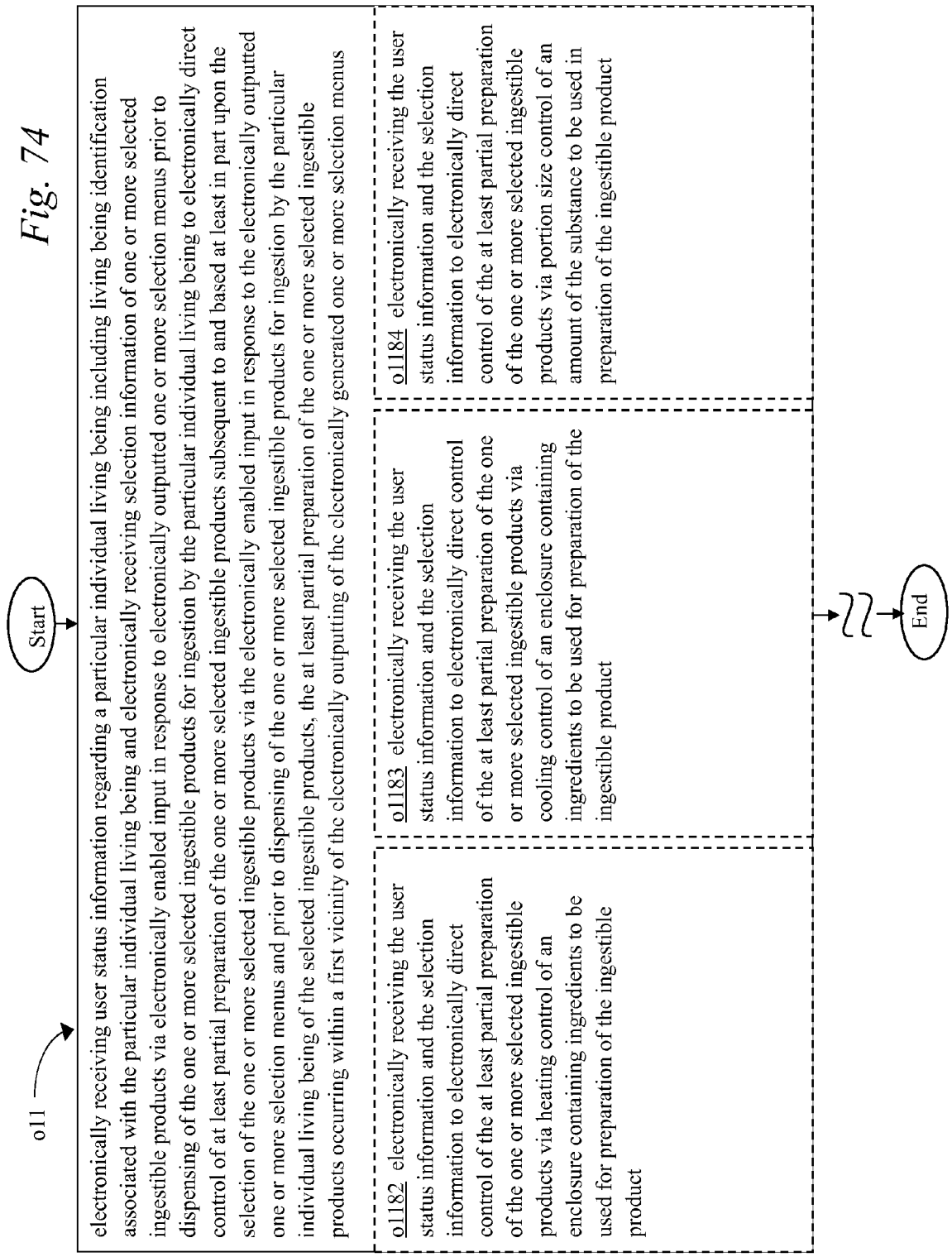
FIG. 74 is a high-level flowchart including exemplary implementations of operation O11 of FIG. 46.

In one or more implementations, as shown in FIG. 74, operation o11 includes an operation o1182 for electronically receiving the user status information and the selection information to electronically direct control of the at least partial preparation of the one or more selected ingestible products via heating control of an enclosure containing ingredients to be used for preparation of the ingestible product. An exemplary version of a non-transitory signal bearing medium of information storage subsystem s200 is depicted as bearing one or more control prep heating instructions i1182 that when executed will direct performance of the operation o1182. In an implementation, the one or more control prep heating instructions i1182 when executed direct electronically receiving the user status information and the selection information to electronically direct control of the at least partial preparation of the one or more selected ingestible products via heating control of an enclosure containing ingredients to be used for preparation of the ingestible product (e.g. an implementation of the microprocessor component s102 is configured to electronically control the heating component s702 according to a temperature profile included in the user status information or the selection information received thereby, etc.). Furthermore, the control prep heating electrical circuitry arrangement e1182 when activated will perform the operation o1182. In an implementation, the control prep heating electrical circuitry arrangement e1182, when activated performs electronically receiving the user status information and the selection information to electronically direct control of the at least partial preparation of the one or more selected ingestible products via heating control of an enclosure containing ingredients to be used for preparation of the ingestible product (e.g. an implementation of the microprocessor component s102 is configured to electronically control the heating component s702 according to a temperature profile included in the user status information or the selection information received thereby, etc.). In an implementation, the electronically receiving the user status information and the selection information to electronically direct control of the at least partial preparation of the one or more selected ingestible products via heating control of an enclosure containing ingredients to be used for preparation of the ingestible product is carried out by electronically receiving the user status information and the selection information to electronically direct control of the at least partial preparation of the one or more selected ingestible products via heating control of an enclosure containing ingredients to be used for preparation of the ingestible product (e.g. an implementation of the microprocessor component s102 is configured to electronically control the heating component s702 according to a temperature profile included in the user status information or the selection information received thereby, etc.).

In one or more implementations, operation o11 includes an operation o1183 for electronically receiving the user status information and the selection information to electronically direct control of the at least partial preparation of the one or more selected ingestible products via cooling control of an enclosure containing ingredients to be used for preparation of the ingestible product. A non-transitory signal bearing medium includes one or more control prep cooling instructions i1183 that when executed will direct performance of the operation o1183. In an implementation, the one or more control prep cooling instructions i1183 when executed direct electronically receiving the user status information and the selection information to electronically direct control of the at least partial preparation of the one or more selected ingestible products via cooling control of an enclosure containing ingredients to be used for preparation of the ingestible product (e.g. an implementation of the microprocessor component s102 is configured to electronically control the cooling component s704 according to a temperature profile included in the user status information or the selection information received thereby, etc.). Furthermore, the control prep cooling electrical circuitry arrangement e1183 when activated will perform the operation o1183. In an implementation, the control prep cooling electrical circuitry arrangement e1183, when activated performs electronically receiving the user status information and the selection information to electronically direct control of the at least partial preparation of the one or more selected ingestible products via cooling control of an enclosure containing ingredients to be used for preparation of the ingestible product (e.g. an implementation of the microprocessor component s102 is configured to electronically control the cooling component s704 according to a temperature profile included in the user status information or the selection information received thereby, etc.). In an implementation, the electronically receiving the user status information and the selection information to electronically direct control of the at least partial preparation of the one or more selected ingestible products via cooling control of an enclosure containing ingredients to be used for preparation of the ingestible product is carried out by electronically receiving the user status information and the selection information to electronically direct control of the at least partial preparation of the one or more selected ingestible products via cooling control of an enclosure containing ingredients to be used for preparation of the ingestible product (e.g. an implementation of the microprocessor component s102 is configured to electronically control the cooling component s704 according to a temperature profile included in the user status information or the selection information received thereby, etc.).

In one or more implementations, operation o11 includes an operation o1184 for electronically receiving the user status information and the selection information to electronically direct control of the at least partial preparation of the one or more selected ingestible products via portion size control of an amount of the substance to be used in preparation of the ingestible product. A non-transitory signal bearing medium includes one or more control prep portion instructions i1184 that when executed will direct performance of the operation o1184. In an implementation, the one or more control prep portion instructions i1184 when executed direct electronically receiving the user status information and the selection information to electronically direct control of the at least partial preparation of the one or more selected ingestible products via portion size control of an amount of the substance to be used in preparation of the ingestible product (e.g. an implementation of the microprocessor component s102 is configured to electronically control the sorting component s728 according to a ingredient size distribution profile included in the user status information or the selection information received thereby, etc.). Furthermore, the control prep portion electrical circuitry arrangement e1184 when activated will perform the operation o1184. In an implementation, the control prep portion electrical circuitry arrangement e1184, when activated performs electronically receiving the user status information and the selection information to electronically direct control of the at least partial preparation of the one or more selected ingestible products via portion size control of an amount of the substance to be used in preparation of the ingestible product (e.g. an implementation of the microprocessor component s102 is configured to electronically control the sorting component s728 according to a ingredient size distribution profile included in the user status information or the selection information received thereby, etc.). In an implementation, the electronically receiving the user status information and the selection information to electronically direct control of the at least partial preparation of the one or more selected ingestible products via portion size control of an amount of the substance to be used in preparation of the ingestible product is carried out by electronically receiving the user status information and the selection information to electronically direct control of the at least partial preparation of the one or more selected ingestible products via portion size control of an amount of the substance to be used in preparation of the ingestible product (e.g. an implementation of the microprocessor component s102 is configured to electronically control the sorting component s728 according to a ingredient size distribution profile included in the user status information or the selection information received thereby, etc.).

Figure 75:
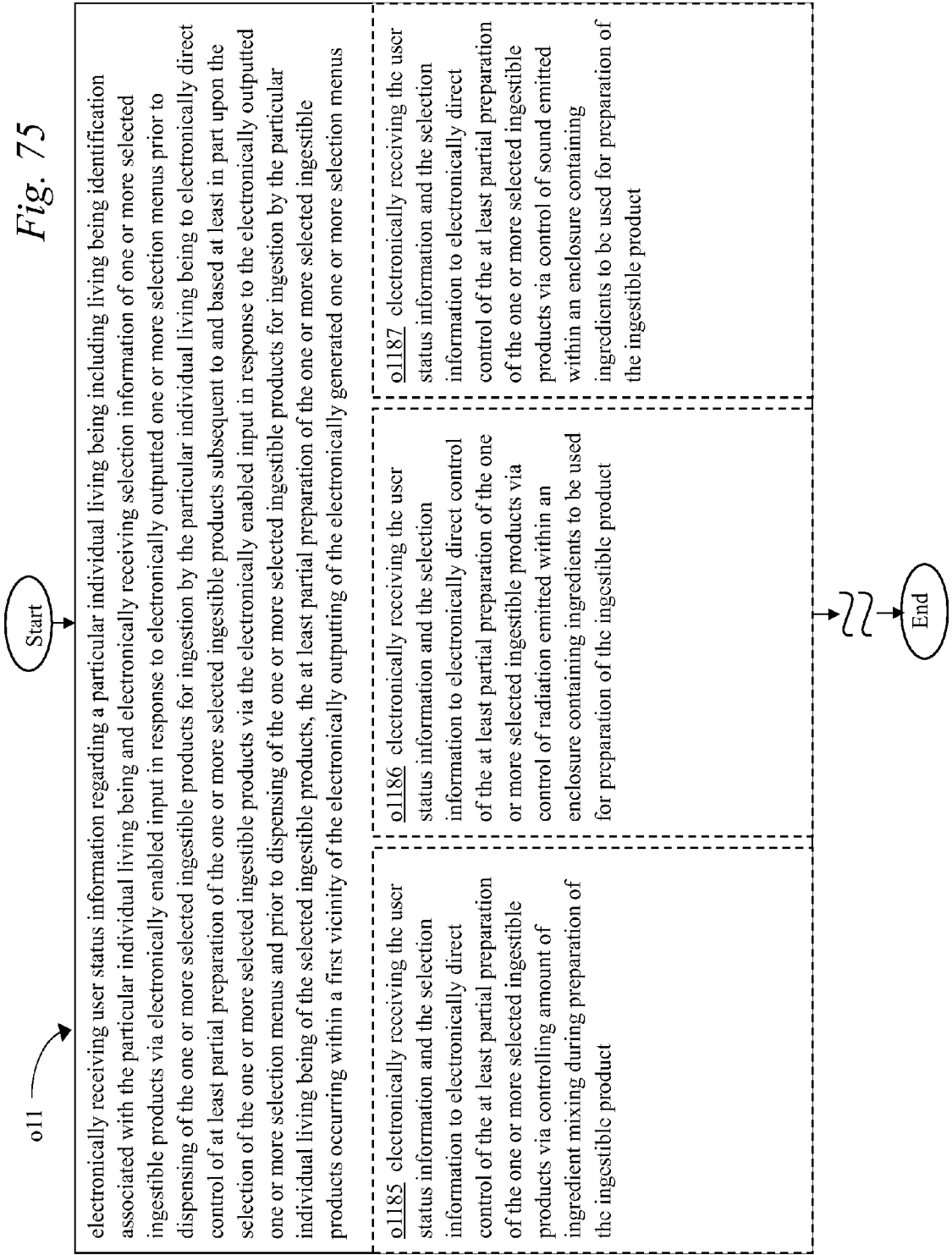
FIG. 75 is a high-level flowchart including exemplary implementations of operation O11 of FIG. 46.

In one or more implementations, as shown in FIG. 75, operation o11 includes an operation o1185 for electronically receiving the user status information and the selection information to electronically direct control of the at least partial preparation of the one or more selected ingestible products via controlling amount of ingredient mixing during preparation of the ingestible product. An exemplary version of a non-transitory signal bearing medium of information storage subsystem s200 is depicted as bearing one or more control prep mixing instructions i1185 that when executed will direct performance of the operation o1185. In an implementation, the one or more control prep mixing instructions i1185 when executed direct electronically receiving the user status information and the selection information to electronically direct control of the at least partial preparation of the one or more selected ingestible products via controlling amount of ingredient mixing during preparation of the ingestible product (e.g. an implementation of the microprocessor component s102 is configured to electronically control the mixer component s716 according to a mixing profile included in the user status information or the selection information received thereby, etc.). Furthermore, the control prep mixing electrical circuitry arrangement e1185 when activated will perform the operation o1185. In an implementation, the control prep mixing electrical circuitry arrangement e1185, when activated performs electronically receiving the user status information and the selection information to electronically direct control of the at least partial preparation of the one or more selected ingestible products via controlling amount of ingredient mixing during preparation of the ingestible product (e.g. an implementation of the microprocessor component s102 is configured to electronically control the mixer component s716 according to a mixing profile included in the user status information or the selection information received thereby, etc.). In an implementation, the electronically receiving the user status information and the selection information to electronically direct control of the at least partial preparation of the one or more selected ingestible products via controlling amount of ingredient mixing during preparation of the ingestible product is carried out by electronically receiving the user status information and the selection information to electronically direct control of the at least partial preparation of the one or more selected ingestible products via controlling amount of ingredient mixing during preparation of the ingestible product (e.g. an implementation of the microprocessor component s102 is configured to electronically control the mixer component s716 according to a mixing profile included in the user status information or the selection information received thereby, etc.).

In one or more implementations, operation o11 includes an operation o1186 for electronically receiving the user status information and the selection information to electronically direct control of the at least partial preparation of the one or more selected ingestible products via control of radiation emitted within an enclosure containing ingredients to be used for preparation of the ingestible product. A non-transitory signal bearing medium includes one or more control prep radiation instructions i1186 that when executed will direct performance of the operation o1186. In an implementation, the one or more control prep radiation instructions i1186 when executed direct electronically receiving the user status information and the selection information to electronically direct control of the at least partial preparation of the one or more selected ingestible products via control of radiation emitted within an enclosure containing ingredients to be used for preparation of the ingestible product (e.g. an implementation of the microprocessor component s102 is configured to electronically control the energy emitting component s724 configured to emit radiation according to a radiation profile included in the user status information or the selection information received thereby, etc.). Furthermore, the control prep radiation electrical circuitry arrangement e1186 when activated will perform the operation o1186. In an implementation, the control prep radiation electrical circuitry arrangement e1186, when activated performs electronically receiving the user status information and the selection information to electronically direct control of the at least partial preparation of the one or more selected ingestible products via control of radiation emitted within an enclosure containing ingredients to be used for preparation of the ingestible product (e.g. an implementation of the microprocessor component s102 is configured to electronically control the energy emitting component s724 configured to emit radiation according to a radiation profile included in the user status information or the selection information received thereby, etc.). In an implementation, the electronically receiving the user status information and the selection information to electronically direct control of the at least partial preparation of the one or more selected ingestible products via control of radiation emitted within an enclosure containing ingredients to be used for preparation of the ingestible product is carried out by electronically receiving the user status information and the selection information to electronically direct control of the at least partial preparation of the one or more selected ingestible products via control of radiation emitted within an enclosure containing ingredients to be used for preparation of the ingestible product (e.g. an implementation of the microprocessor component s102 is configured to electronically control the energy emitting component s724 configured to emit radiation according to a radiation profile included in the user status information or the selection information received thereby, etc.).

In one or more implementations, operation o11 includes an operation o1187 for electronically receiving the user status information and the selection information to electronically direct control of the at least partial preparation of the one or more selected ingestible products via control of sound emitted within an enclosure containing ingredients to be used for preparation of the ingestible product. A non-transitory signal bearing medium includes one or more control prep sound instructions i1187 that when executed will direct performance of the operation o1187. In an implementation, the one or more control prep sound instructions i1187 when executed direct electronically receiving the user status information and the selection information to electronically direct control of the at least partial preparation of the one or more selected ingestible products via control of sound emitted within an enclosure containing ingredients to be used for preparation of the ingestible product (e.g. an implementation of the microprocessor component s102 is configured to electronically control the acoustic energy component s718 according to an acoustic energy profile included in the user status information or the selection information received thereby, etc.). Furthermore, the control prep sound electrical circuitry arrangement e1187 when activated will perform the operation o1187. In an implementation, the control prep sound electrical circuitry arrangement e1187, when activated performs electronically receiving the user status information and the selection information to electronically direct control of the at least partial preparation of the one or more selected ingestible products via control of sound emitted within an enclosure containing ingredients to be used for preparation of the ingestible product (e.g. an implementation of the microprocessor component s102 is configured to electronically control the acoustic energy component s718 according to an acoustic energy profile included in the user status information or the selection information received thereby, etc.). In an implementation, the electronically receiving the user status information and the selection information to electronically direct control of the at least partial preparation of the one or more selected ingestible products via control of sound emitted within an enclosure containing ingredients to be used for preparation of the ingestible product is carried out by electronically receiving the user status information and the selection information to electronically direct control of the at least partial preparation of the one or more selected ingestible products via control of sound emitted within an enclosure containing ingredients to be used for preparation of the ingestible product (e.g. an implementation of the microprocessor component s102 is configured to electronically control the acoustic energy component s718 according to an acoustic energy profile included in the user status information or the selection information received thereby, etc.).

Figure 76:
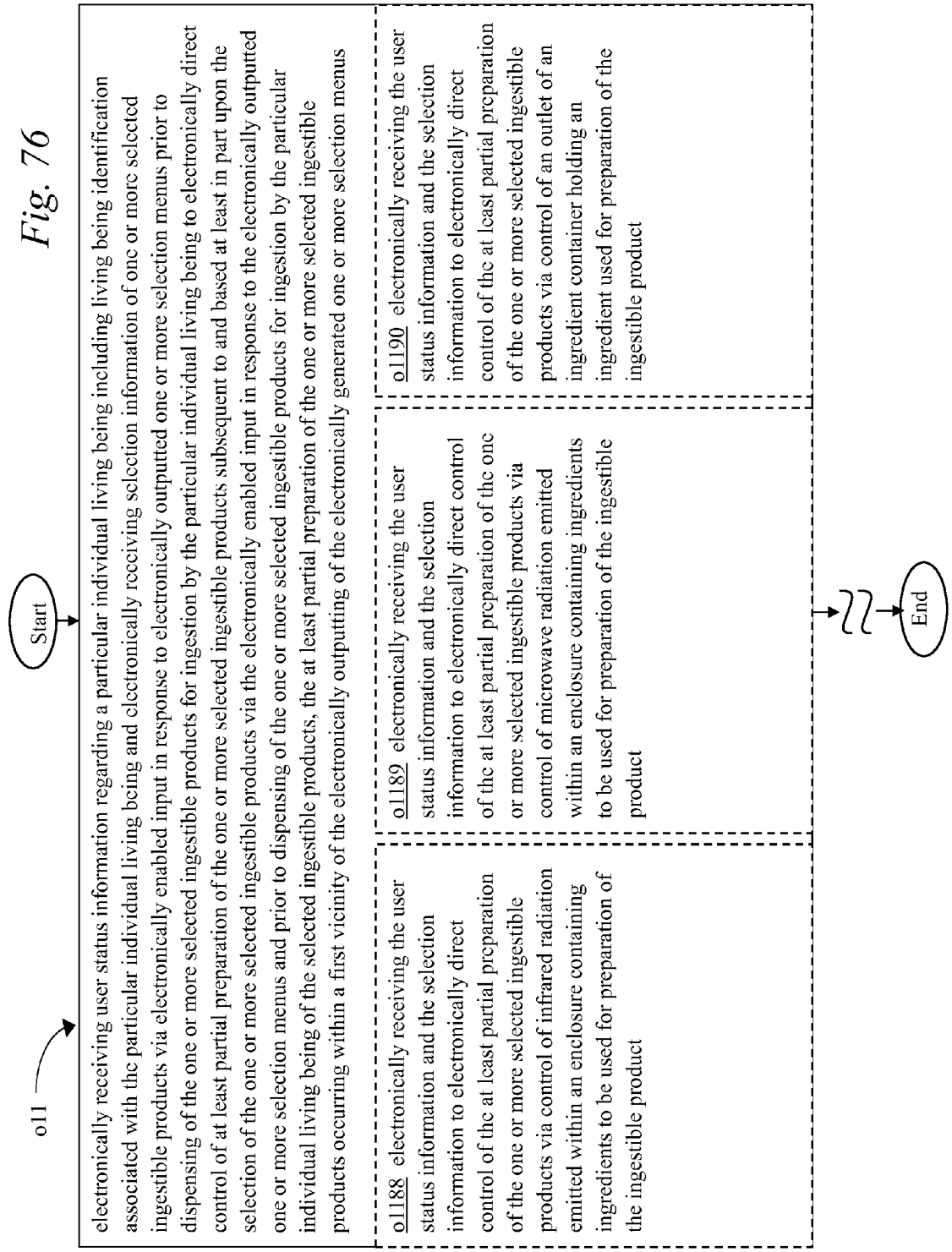
FIG. 76 is a high-level flowchart including exemplary implementations of operation O11 of FIG. 46.

In one or more implementations, as shown in FIG. 76, operation o11 includes an operation o1188 for electronically receiving the user status information and the selection information to electronically direct control of the at least partial preparation of the one or more selected ingestible products via control of infrared radiation emitted within an enclosure containing ingredients to be used for preparation of the ingestible product. An exemplary version of a non-transitory signal bearing medium of information storage subsystem s200 is depicted as bearing one or more control prep infrared instructions i1188 that when executed will direct performance of the operation o1188. In an implementation, the one or more control prep infrared instructions i1188 when executed direct electronically receiving the user status information and the selection information to electronically direct control of the at least partial preparation of the one or more selected ingestible products via control of infrared radiation emitted within an enclosure containing ingredients to be used for preparation of the ingestible product (e.g. an implementation of the microprocessor component s102 is configured to electronically control the infrared component s730 according to a temperature profile included in the user status information or the selection information received thereby, etc.). Furthermore, the control prep infrared electrical circuitry arrangement e1188 when activated will perform the operation o1188. In an implementation, the control prep infrared electrical circuitry arrangement e1188, when activated performs electronically receiving the user status information and the selection information to electronically direct control of the at least partial preparation of the one or more selected ingestible products via control of infrared radiation emitted within an enclosure containing ingredients to be used for preparation of the ingestible product (e.g. an implementation of the microprocessor component s102 is configured to electronically control the infrared component s730 according to a temperature profile included in the user status information or the selection information received thereby, etc.). In an implementation, the electronically receiving the user status information and the selection information to electronically direct control of the at least partial preparation of the one or more selected ingestible products via control of infrared radiation emitted within an enclosure containing ingredients to be used for preparation of the ingestible product is carried out by electronically receiving the user status information and the selection information to electronically direct control of the at least partial preparation of the one or more selected ingestible products via control of infrared radiation emitted within an enclosure containing ingredients to be used for preparation of the ingestible product (e.g. an implementation of the microprocessor component s102 is configured to electronically control the infrared component s730 according to a temperature profile included in the user status information or the selection information received thereby, etc.).

In one or more implementations, operation o11 includes an operation o1189 for electronically receiving the user status information and the selection information to electronically direct control of the at least partial preparation of the one or more selected ingestible products via control of microwave radiation emitted within an enclosure containing ingredients to be used for preparation of the ingestible product. A non-transitory signal bearing medium includes one or more control prep microwave instructions i1189 that when executed will direct performance of the operation o1189. In an implementation, the one or more control prep microwave instructions i1189 when executed direct electronically receiving the user status information and the selection information to electronically direct control of the at least partial preparation of the one or more selected ingestible products via control of microwave radiation emitted within an enclosure containing ingredients to be used for preparation of the ingestible product (e.g. an implementation of the microprocessor component s102 is configured to electronically control the microwave component s706 according to a temperature profile included in the user status information or the selection information received thereby, etc.). Furthermore, the control prep microwave electrical circuitry arrangement e1189 when activated will perform the operation o1189. In an implementation, the control prep microwave electrical circuitry arrangement e1189, when activated performs electronically receiving the user status information and the selection information to electronically direct control of the at least partial preparation of the one or more selected ingestible products via control of microwave radiation emitted within an enclosure containing ingredients to be used for preparation of the ingestible product (e.g. an implementation of the microprocessor component s102 is configured to electronically control the microwave component s706 according to a temperature profile included in the user status information or the selection information received thereby, etc.). In an implementation, the electronically receiving the user status information and the selection information to electronically direct control of the at least partial preparation of the one or more selected ingestible products via control of microwave radiation emitted within an enclosure containing ingredients to be used for preparation of the ingestible product is carried out by electronically receiving the user status information and the selection information to electronically direct control of the at least partial preparation of the one or more selected ingestible products via control of microwave radiation emitted within an enclosure containing ingredients to be used for preparation of the ingestible product (e.g. an implementation of the microprocessor component s102 is configured to electronically control the microwave component s706 according to a temperature profile included in the user status information or the selection information received thereby, etc.).

In one or more implementations, operation o11 includes an operation o1190 for electronically receiving the user status information and the selection information to electronically direct control of the at least partial preparation of the one or more selected ingestible products via control of an outlet of an ingredient container holding an ingredient used for preparation of the ingestible product. A non-transitory signal bearing medium includes one or more control prep container instructions i1190 that when executed will direct performance of the operation o1190. In an implementation, the one or more control prep container instructions i1190 when executed direct electronically receiving the user status information and the selection information to electronically direct control of the at least partial preparation of the one or more selected ingestible products via control of an outlet of an ingredient container holding an ingredient used for preparation of the ingestible product (e.g. an implementation of the microprocessor component s102 is configured to electronically control an outlet of the material storage component s734 configured as an ingredient container according to an access profile included in the user status information or the selection information received thereby, etc.). Furthermore, the control prep container electrical circuitry arrangement e1190 when activated will perform the operation o1190. In an implementation, the control prep container electrical circuitry arrangement e1190, when activated performs electronically receiving the user status information and the selection information to electronically direct control of the at least partial preparation of the one or more selected ingestible products via control of an outlet of an ingredient container holding an ingredient used for preparation of the ingestible product (e.g. an implementation of the microprocessor component s102 is configured to electronically control an outlet of the material storage component s734 configured as an ingredient container according to an access profile included in the user status information or the selection information received thereby, etc.). In an implementation, the electronically receiving the user status information and the selection information to electronically direct control of the at least partial preparation of the one or more selected ingestible products via control of an outlet of an ingredient container holding an ingredient used for preparation of the ingestible product is carried out by electronically receiving the user status information and the selection information to electronically direct control of the at least partial preparation of the one or more selected ingestible products via control of an outlet of an ingredient container holding an ingredient used for preparation of the ingestible product (e.g. an implementation of the microprocessor component s102 is configured to electronically control an outlet of the material storage component s734 configured as an ingredient container according to an access profile included in the user status information or the selection information received thereby, etc.).

Figure 77:
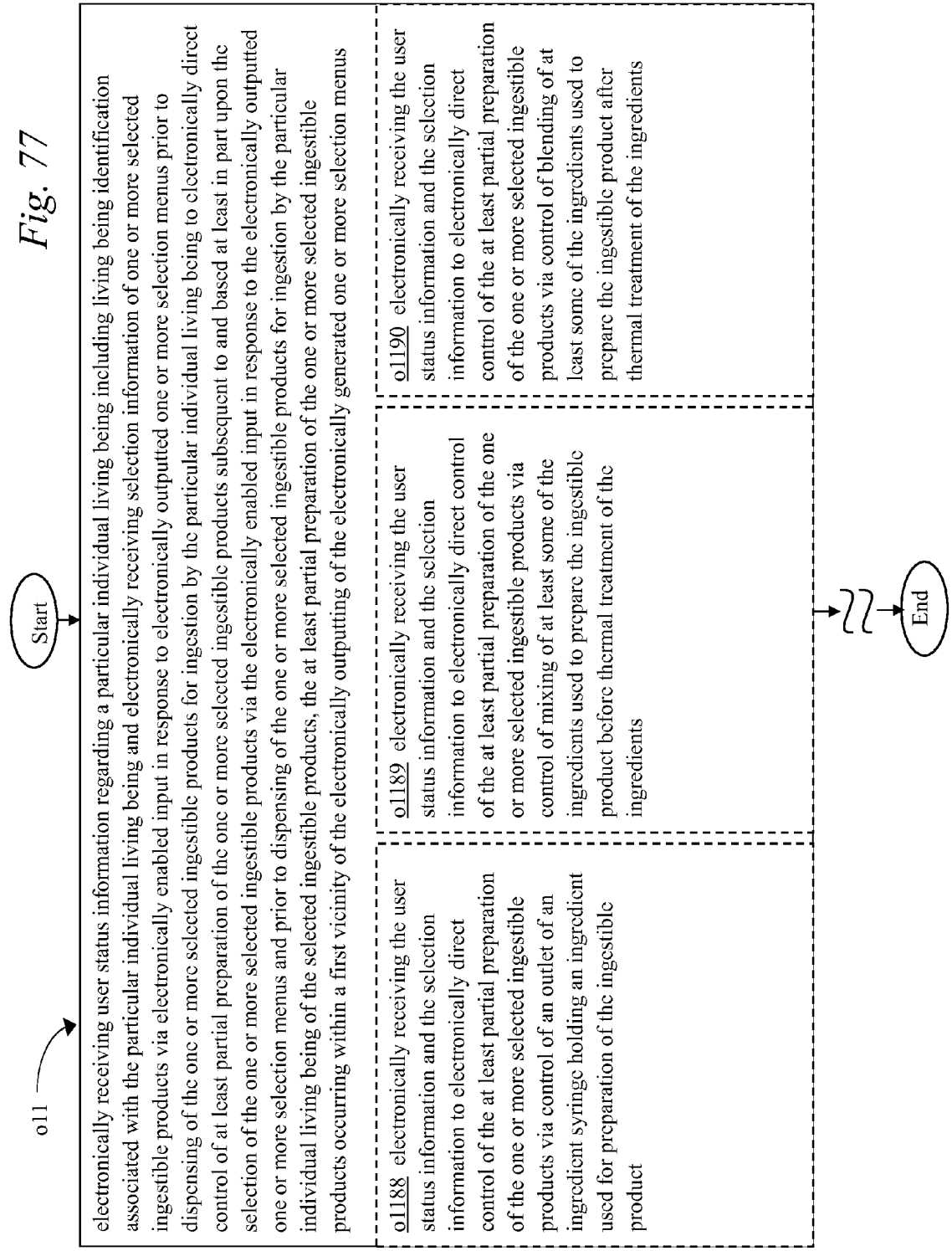
FIG. 77 is a high-level flowchart including exemplary implementations of operation O11 of FIG. 46.

In one or more implementations, as shown in FIG. 77, operation o11 includes an operation o1191 for electronically receiving the user status information and the selection information to electronically direct control of the at least partial preparation of the one or more selected ingestible products via control of an outlet of an ingredient syringe holding an ingredient used for preparation of the ingestible product. An exemplary version of a non-transitory signal bearing medium of information storage subsystem s200 is depicted as bearing one or more control prep syringe instructions i1191 that when executed will direct performance of the operation o1191. In an implementation, the one or more control prep syringe instructions i1191 when executed direct electronically receiving the user status information and the selection information to electronically direct control of the at least partial preparation of the one or more selected ingestible products via control of an outlet of an ingredient syringe holding an ingredient used for preparation of the ingestible product (e.g. an implementation of the microprocessor component s102 is configured to electronically control an outlet of the material storage component s734 configured as an ingredient syringe according to an access profile included in the user status information or the selection information received thereby, etc.). Furthermore, the control prep syringe electrical circuitry arrangement e1191 when activated will perform the operation o1191. In an implementation, the control prep syringe electrical circuitry arrangement e1191, when activated performs electronically receiving the user status information and the selection information to electronically direct control of the at least partial preparation of the one or more selected ingestible products via control of an outlet of an ingredient syringe holding an ingredient used for preparation of the ingestible product (e.g. an implementation of the microprocessor component s102 is configured to electronically control an outlet of the material storage component s734 configured as an ingredient syringe according to an access profile included in the user status information or the selection information received thereby, etc.). In an implementation, the electronically receiving the user status information and the selection information to electronically direct control of the at least partial preparation of the one or more selected ingestible products via control of an outlet of an ingredient syringe holding an ingredient used for preparation of the ingestible product is carried out by electronically receiving the user status information and the selection information to electronically direct control of the at least partial preparation of the one or more selected ingestible products via control of an outlet of an ingredient syringe holding an ingredient used for preparation of the ingestible product (e.g. an implementation of the microprocessor component s102 is configured to electronically control an outlet of the material storage component s734 configured as an ingredient syringe according to an access profile included in the user status information or the selection information received thereby, etc.).

In one or more implementations, operation o11 includes an operation o1192 for electronically receiving the user status information and the selection information to electronically direct control of the at least partial preparation of the one or more selected ingestible products via control of mixing of at least some of the ingredients used to prepare the ingestible product before thermal treatment of the ingredients. A non-transitory signal bearing medium includes one or more control prep mix before thermal instructions i1192 that when executed will direct performance of the operation o1192. In an implementation, the one or more control prep mix before thermal instructions i1192 when executed direct electronically receiving the user status information and the selection information to electronically direct control of the at least partial preparation of the one or more selected ingestible products via control of mixing of at least some of the ingredients used to prepare the ingestible product before thermal treatment of the ingredients (e.g. an implementation of the microprocessor component s102 is configured to electronically control the mixer component s716 according to a mixing profile included in the user status information or the selection information received thereby, etc.). Furthermore, the control prep mix before thermal electrical circuitry arrangement e1192 when activated will perform the operation o1192. In an implementation, the control prep mix before thermal electrical circuitry arrangement e1192, when activated performs electronically receiving the user status information and the selection information to electronically direct control of the at least partial preparation of the one or more selected ingestible products via control of mixing of at least some of the ingredients used to prepare the ingestible product before thermal treatment of the ingredients (e.g. an implementation of the microprocessor component s102 is configured to electronically control the mixer component s716 according to a mixing profile included in the user status information or the selection information received thereby, etc.). In an implementation, the electronically receiving the user status information and the selection information to electronically direct control of the at least partial preparation of the one or more selected ingestible products via control of mixing of at least some of the ingredients used to prepare the ingestible product before thermal treatment of the ingredients is carried out by electronically receiving the user status information and the selection information to electronically direct control of the at least partial preparation of the one or more selected ingestible products via control of mixing of at least some of the ingredients used to prepare the ingestible product before thermal treatment of the ingredients (e.g. an implementation of the microprocessor component s102 is configured to electronically control the mixer component s716 according to a mixing profile included in the user status information or the selection information received thereby, etc.).

In one or more implementations, operation o11 includes an operation o1193 for electronically receiving the user status information and the selection information to electronically direct control of the at least partial preparation of the one or more selected ingestible products via control of blending of at least some of the ingredients used to prepare the ingestible product after thermal treatment of the ingredients. A non-transitory signal bearing medium includes one or more control prep re mix after thermal instructions i1193 that when executed will direct performance of the operation o1193. In an implementation, the one or more control prep re mix after thermal instructions i1193 when executed direct electronically receiving the user status information and the selection information to electronically direct control of the at least partial preparation of the one or more selected ingestible products via control of blending of at least some of the ingredients used to prepare the ingestible product after thermal treatment of the ingredients (e.g. an implementation of the microprocessor component s102 is configured to electronically control the blending component s714 according to a blending profile involving some of the ingredients used to prepare the ingestible product included in the user status information, etc.). Furthermore, the control prep re mix after thermal electrical circuitry arrangement e1193 when activated will perform the operation o1193. In an implementation, the control prep re mix after thermal electrical circuitry arrangement e1193, when activated performs electronically receiving the user status information and the selection information to electronically direct control of the at least partial preparation of the one or more selected ingestible products via control of blending of at least some of the ingredients used to prepare the ingestible product after thermal treatment of the ingredients (e.g. an implementation of the microprocessor component s102 is configured to electronically control the blending component s714 according to a blending profile involving some of the ingredients used to prepare the ingestible product included in the user status information, etc.). In an implementation, the electronically receiving the user status information and the selection information to electronically direct control of the at least partial preparation of the one or more selected ingestible products via control of blending of at least some of the ingredients used to prepare the ingestible product after thermal treatment of the ingredients is carried out by electronically receiving the user status information and the selection information to electronically direct control of the at least partial preparation of the one or more selected ingestible products via control of blending of at least some of the ingredients used to prepare the ingestible product after thermal treatment of the ingredients (e.g. an implementation of the microprocessor component s102 is configured to electronically control the blending component s714 according to a blending profile involving some of the ingredients used to prepare the ingestible product included in the user status information, etc.).

Figure 78:
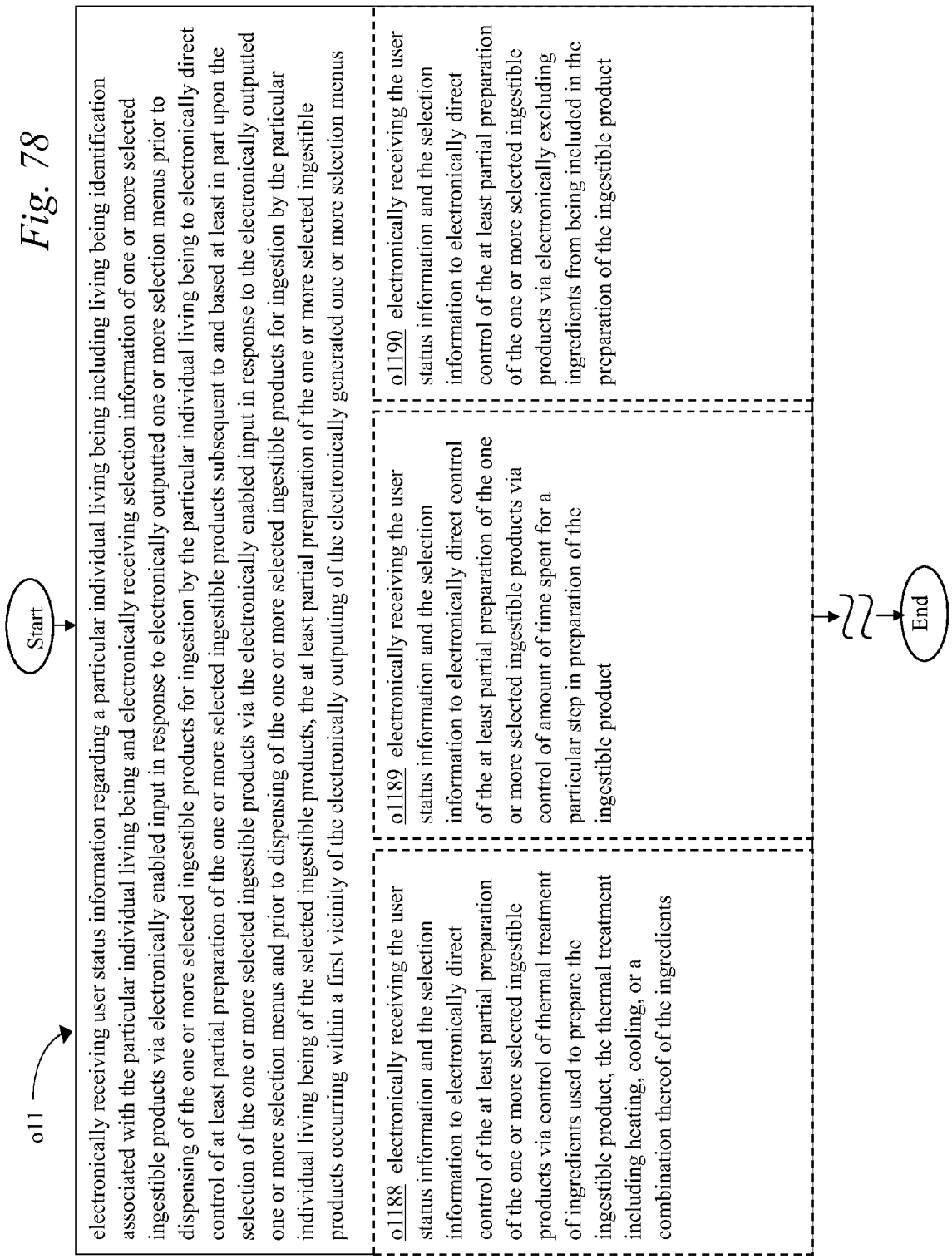
FIG. 78 is a high-level flowchart including exemplary implementations of operation O11 of FIG. 46.

In one or more implementations, as shown in FIG. 78, operation o11 includes an operation o1194 for electronically receiving the user status information and the selection information to electronically direct control of the at least partial preparation of the one or more selected ingestible products via control of thermal treatment of ingredients used to prepare the ingestible product, the thermal treatment including heating, cooling, or a combination thereof of the ingredients. An exemplary version of a non-transitory signal bearing medium of information storage subsystem s200 is depicted as bearing one or more control prep heating cooling instructions i1194 that when executed will direct performance of the operation o1194. In an implementation, the one or more control prep heating cooling instructions i1194 when executed direct electronically receiving the user status information and the selection information to electronically direct control of the at least partial preparation of the one or more selected ingestible products via control of thermal treatment of ingredients used to prepare the ingestible product, thermal treatment including heating, cooling, or a combination thereof of the ingredients (e.g. an implementation of the microprocessor component s102 is configured to electronically control the heating component s702 and/or the cooling component s704 according to a thermal profile included in the user status information or the selection information received thereby, etc.). Furthermore, the control prep heating cooling electrical circuitry arrangement e1194 when activated will perform the operation o1194. In an implementation, the control prep heating cooling electrical circuitry arrangement e1194, when activated performs electronically receiving the user status information and the selection information to electronically direct control of the at least partial preparation of the one or more selected ingestible products via control of thermal treatment of ingredients used to prepare the ingestible product, thermal treatment including heating, cooling, or a combination thereof of the ingredients (e.g. an implementation of the microprocessor component s102 is configured to electronically control the heating component s702 and/or the cooling component s704 according to a thermal profile included in the user status information or the selection information received thereby, etc.). In an implementation, the electronically receiving the user status information and the selection information to electronically direct control of the at least partial preparation of the one or more selected ingestible products via control of thermal treatment of ingredients used to prepare the ingestible product, the thermal treatment including heating, cooling, or a combination thereof of the ingredients is carried out by electronically receiving the user status information and the selection information to electronically direct control of the at least partial preparation of the one or more selected ingestible products via control of thermal treatment of ingredients used to prepare the ingestible product, thermal treatment including heating, cooling, or a combination thereof of the ingredients (e.g. an implementation of the microprocessor component s102 is configured to electronically control the heating component s702 and/or the cooling component s704 according to a thermal profile included in the user status information or the selection information received thereby, etc.).

In one or more implementations, operation o11 includes an operation o1195 for electronically receiving the user status information and the selection information to electronically direct control of the at least partial preparation of the one or more selected ingestible products via control of amount of time spent for a particular step in preparation of the ingestible product. A non-transitory signal bearing medium includes one or more control prep time control instructions i1195 that when executed will direct performance of the operation o1195. In an implementation, the one or more control prep time control instructions i1195 when executed direct electronically receiving the user status information and the selection information to electronically direct control of the at least partial preparation of the one or more selected ingestible products via control of amount of time spent for a particular step in preparation of the ingestible product (e.g. an implementation of the microprocessor component s102 is configured to electronically control components of the material processing subsystem s700 based upon an internal clock of the microprocessor according to a time profile included in the user status information or the selection information received thereby, etc.). Furthermore, the control prep time control electrical circuitry arrangement e1195 when activated will perform the operation o1195. In an implementation, the control prep time control electrical circuitry arrangement e1195, when activated performs electronically receiving the user status information and the selection information to electronically direct control of the at least partial preparation of the one or more selected ingestible products via control of amount of time spent for a particular step in preparation of the ingestible product (e.g. an implementation of the microprocessor component s102 is configured to electronically control components of the material processing subsystem s700 based upon an internal clock of the microprocessor according to a time profile included in the user status information or the selection information received thereby, etc.). In an implementation, the electronically receiving the user status information and the selection information to electronically direct control of the at least partial preparation of the one or more selected ingestible products via control of amount of time spent for a particular step in preparation of the ingestible product is carried out by electronically receiving the user status information and the selection information to electronically direct control of the at least partial preparation of the one or more selected ingestible products via control of amount of time spent for a particular step in preparation of the ingestible product (e.g. an implementation of the microprocessor component s102 is configured to electronically control components of the material processing subsystem s700 based upon an internal clock of the microprocessor according to a time profile included in the user status information or the selection information received thereby, etc.).

In one or more implementations, operation o11 includes an operation o1196 for electronically receiving the user status information and the selection information to electronically direct control of the at least partial preparation of the one or more selected ingestible products via electronically excluding ingredients from being included in the preparation of the ingestible product. A non-transitory signal bearing medium includes one or more control prep ingredient exclusion instructions i1196 that when executed will direct performance of the operation o1196. In an implementation, the one or more control prep ingredient exclusion instructions i1196 when executed direct electronically receiving the user status information and the selection information to electronically direct control of the at least partial preparation of the one or more selected ingestible products via electronically excluding ingredients from being included in the preparation of the ingestible product (e.g. an implementation of the microprocessor component s102 is configured to electronically control the sorting component s728 to exclude one or more ingredients from being included in the ingestible product according to an exclusion profile included in the user status information or the selection information received thereby, etc.). Furthermore, the control prep ingredient exclusion electrical circuitry arrangement e1196 when activated will perform the operation o1196. In an implementation, the control prep ingredient exclusion electrical circuitry arrangement e1196, when activated performs electronically receiving the user status information and the selection information to electronically direct control of the at least partial preparation of the one or more selected ingestible products via electronically excluding ingredients from being included in the preparation of the ingestible product (e.g. an implementation of the microprocessor component s102 is configured to electronically control the sorting component s728 to exclude one or more ingredients from being included in the ingestible product according to an exclusion profile included in the user status information or the selection information received thereby, etc.). In an implementation, the electronically receiving the user status information and the selection information to electronically direct control of the at least partial preparation of the one or more selected ingestible products via electronically excluding ingredients from being included in the preparation of the ingestible product is carried out by electronically receiving the user status information and the selection information to electronically direct control of the at least partial preparation of the one or more selected ingestible products via electronically excluding ingredients from being included in the preparation of the ingestible product (e.g. an implementation of the microprocessor component s102 is configured to electronically control the sorting component s728 to exclude one or more ingredients from being included in the ingestible product according to an exclusion profile included in the user status information or the selection information received thereby, etc.).

Figure 79:
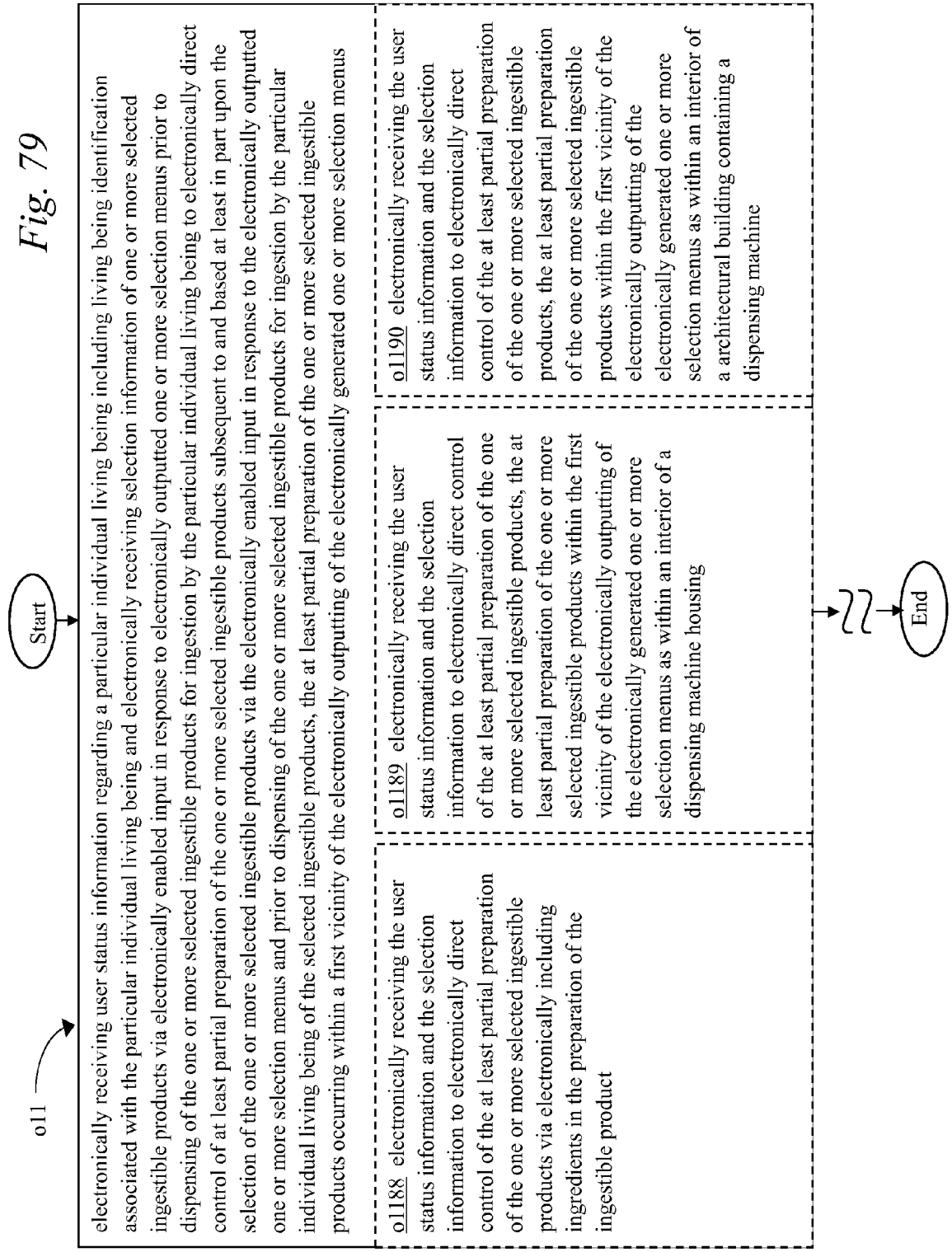
FIG. 79 is a high-level flowchart including exemplary implementations of operation O11 of FIG. 46.

In one or more implementations, as shown in FIG. 79, operation o11 includes an operation o1197 for electronically receiving the user status information and the selection information to electronically direct control of the at least partial preparation of the one or more selected ingestible products via electronically including ingredients in the preparation of the ingestible product. An exemplary version of a non-transitory signal bearing medium of information storage subsystem s200 is depicted as bearing one or more control prep ingredient inclusion instructions i1197 that when executed will direct performance of the operation o1197. In an implementation, the one or more control prep ingredient inclusion instructions i1197 when executed direct electronically receiving the user status information and the selection information to electronically direct control of the at least partial preparation of the one or more selected ingestible products via electronically including ingredients in the preparation of the ingestible product (e.g. an implementation of the microprocessor component s102 is configured to electronically control the sorting component s728 to include one or more ingredients in the ingestible product according to an inclusion profile included in the user status information or the selection information received thereby, etc.). Furthermore, the control prep ingredient inclusion electrical circuitry arrangement e1197 when activated will perform the operation o1197. In an implementation, the control prep ingredient inclusion electrical circuitry arrangement e1197, when activated performs electronically receiving the user status information and the selection information to electronically direct control of the at least partial preparation of the one or more selected ingestible products via electronically including ingredients in the preparation of the ingestible product (e.g. an implementation of the microprocessor component s102 is configured to electronically control the sorting component s728 to include one or more ingredients in the ingestible product according to an inclusion profile included in the user status information or the selection information received thereby, etc.). In an implementation, the electronically receiving the user status information and the selection information to electronically direct control of the at least partial preparation of the one or more selected ingestible products via electronically including ingredients in the preparation of the ingestible product is carried out by electronically receiving the user status information and the selection information to electronically direct control of the at least partial preparation of the one or more selected ingestible products via electronically including ingredients in the preparation of the ingestible product (e.g. an implementation of the microprocessor component s102 is configured to electronically control the sorting component s728 to include one or more ingredients in the ingestible product according to an inclusion profile included in the user status information or the selection information received thereby, etc.).

In one or more implementations, operation o11 includes an operation o1198 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a dispensing machine housing. A non-transitory signal bearing medium includes one or more control prep housing instructions i1198 that when executed will direct performance of the operation o1198. In an implementation, the one or more control prep housing instructions i1198 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a dispensing machine housing (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the digestible product preparation system 10 that uses for instance visual display component s304 to electronically output the electronically generated one or more selection menus, etc.). Furthermore, the control prep housing electrical circuitry arrangement e1198 when activated will perform the operation o1198. In an implementation, the control prep housing electrical circuitry arrangement e1198, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a dispensing machine housing (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the digestible product preparation system 10 that uses for instance visual display component s304 to electronically output the electronically generated one or more selection menus, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a dispensing machine housing is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a dispensing machine housing (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the digestible product preparation system 10 that uses for instance visual display component s304 to electronically output the electronically generated one or more selection menus, etc.).

In one or more implementations, operation o11 includes an operation o1199 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a architectural building containing a dispensing machine. A non-transitory signal bearing medium includes one or more control prep building instructions i1199 that when executed will direct performance of the operation o1199. In an implementation, the one or more control prep building instructions i1199 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a architectural building containing a dispensing machine (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of an airport wherein the digestible product preparation system 10 is located that communicates with for instance the visual display component s304 to electronically output the electronically generated one or more selection menus also within the airport, etc.). Furthermore, the control prep building electrical circuitry arrangement e1199 when activated will perform the operation o1199. In an implementation, the control prep building electrical circuitry arrangement e1199, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a architectural building containing a dispensing machine (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of an airport wherein the digestible product preparation system 10 is located that communicates with for instance the visual display component s304 to electronically output the electronically generated one or more selection menus also within the airport, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a architectural building containing a dispensing machine is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a architectural building containing a dispensing machine (e.g. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of an airport wherein the digestible product preparation system 10 is located that communicates with for instance the visual display component s304 to electronically output the electronically generated one or more selection menus also within the airport, etc.).

Figure 80:
FIG. 80 is a high-level flowchart including exemplary implementations of operation O11 of FIG. 46.

In one or more implementations, as shown in FIG. 80, operation o11 includes an operation o11100 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a food court of a shopping mall. An exemplary version of a non-transitory signal bearing medium of information storage subsystem s200 is depicted as bearing one or more control prep mall instructions i11100 that when executed will direct performance of the operation o11100. In an implementation, the one or more control prep mall instructions i11100 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a food court of a shopping mall (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the food court of the shopping mall wherein the digestible product preparation system 10 is located that communicates with for instance the visual display component s304 to electronically output the electronically generated one or more selection menus also within the food court of the shopping mall, etc.). Furthermore, the control prep mall electrical circuitry arrangement e11100 when activated will perform the operation o11100. In an implementation, the control prep mall electrical circuitry arrangement e11100, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a food court of a shopping mall (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the food court of the shopping mall wherein the digestible product preparation system 10 is located that communicates with for instance the visual display component s304 to electronically output the electronically generated one or more selection menus also within the food court of the shopping mall, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a food court of a shopping mall is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a food court of a shopping mall (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the food court of the shopping mall wherein the digestible product preparation system 10 is located that communicates with for instance the visual display component s304 to electronically output the electronically generated one or more selection menus also within the food court of the shopping mall, etc.).

In one or more implementations, operation o11 includes an operation o11101 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a restaurant. A non-transitory signal bearing medium includes one or more control prep restaurant instructions i11101 that when executed will direct performance of the operation o11101. In an implementation, the one or more control prep restaurant instructions i11101 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a restaurant (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the restaurant wherein the digestible product preparation system 10 is located that communicates with for instance the visual display component s304 to electronically output the electronically generated one or more selection menus also within the restaurant, etc.). Furthermore, the control prep restaurant electrical circuitry arrangement e11101 when activated will perform the operation o11101. In an implementation, the control prep restaurant electrical circuitry arrangement e11101, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a restaurant (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the restaurant wherein the digestible product preparation system 10 is located that communicates with for instance the visual display component s304 to electronically output the electronically generated one or more selection menus also within the restaurant, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a restaurant is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a restaurant (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the restaurant wherein the digestible product preparation system 10 is located that communicates with for instance the visual display component s304 to electronically output the electronically generated one or more selection menus also within the restaurant, etc.).

In one or more implementations, operation o11 includes an operation o11102 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of an airplane. A non-transitory signal bearing medium includes one or more control prep airplane instructions i11102 that when executed will direct performance of the operation o11102. In an implementation, the one or more control prep airplane instructions i11102 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of an airplane (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the airplane wherein the digestible product preparation system 10 is located that communicates with for instance the visual display component s304 to electronically output the electronically generated one or more selection menus also within the airplane, etc.). Furthermore, the control prep airplane electrical circuitry arrangement e11102 when activated will perform the operation o11102. In an implementation, the control prep airplane electrical circuitry arrangement e11102, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of an airplane (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the airplane wherein the digestible product preparation system 10 is located that communicates with for instance the visual display component s304 to electronically output the electronically generated one or more selection menus also within the airplane, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of an airplane is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of an airplane (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the airplane wherein the digestible product preparation system 10 is located that communicates with for instance the visual display component s304 to electronically output the electronically generated one or more selection menus also within the airplane, etc.).

Figure 81:
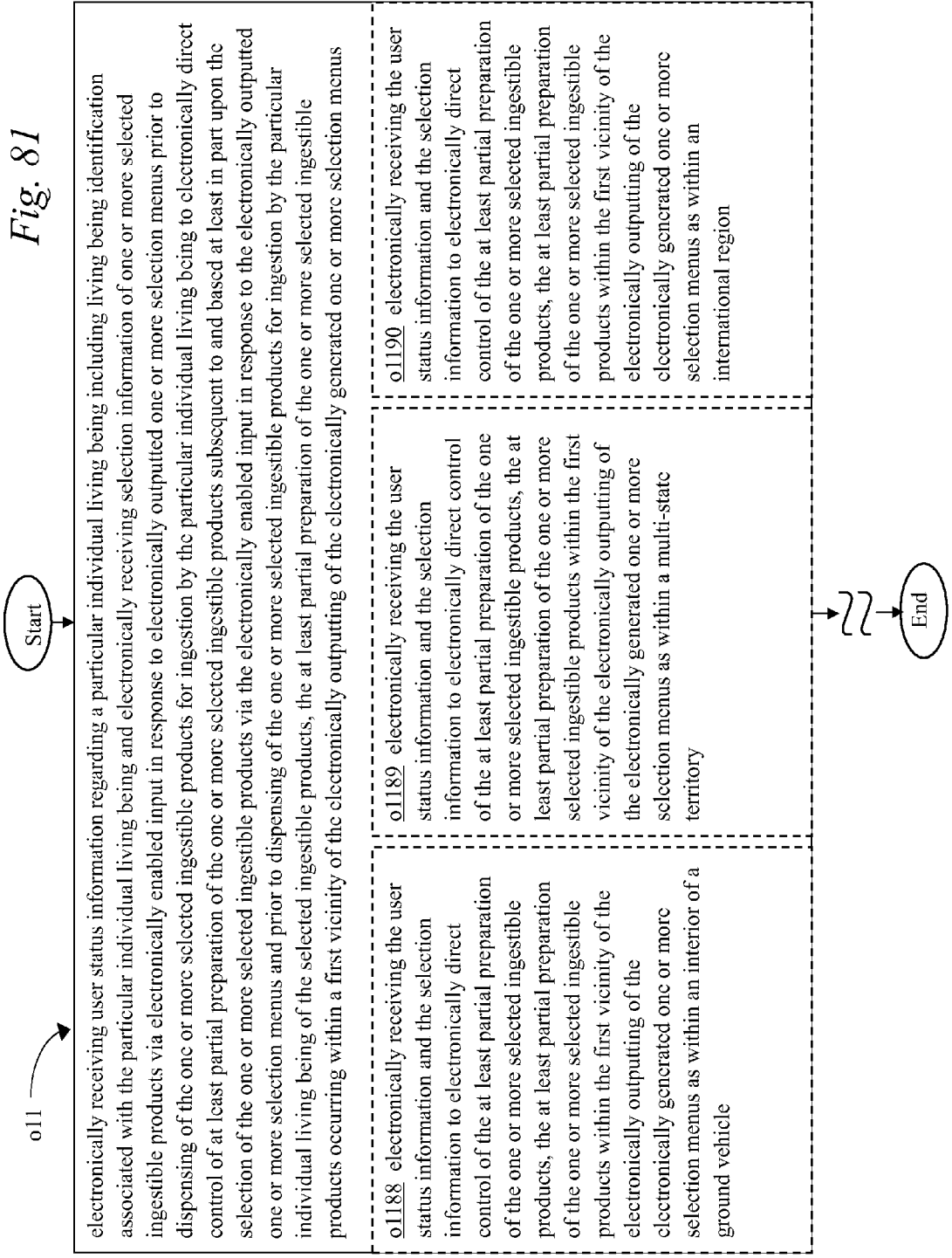
FIG. 81 is a high-level flowchart including exemplary implementations of operation O11 of FIG. 46.

In one or more implementations, as shown in FIG. 81, operation o11 includes an operation o11103 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a ground vehicle. An exemplary version of a non-transitory signal bearing medium of information storage subsystem s200 is depicted as bearing one or more control prep vehicle instructions i11103 that when executed will direct performance of the operation o11103. In an implementation, the one or more control prep vehicle instructions i11103 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a ground vehicle (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the ground vehicle wherein the digestible product preparation system 10 is located that communicates with for instance the visual display component s304 to electronically output the electronically generated one or more selection menus also within the ground vehicle, etc.). Furthermore, the control prep vehicle electrical circuitry arrangement e11103 when activated will perform the operation o11103. In an implementation, the control prep vehicle electrical circuitry arrangement e11103, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a ground vehicle (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the ground vehicle wherein the digestible product preparation system 10 is located that communicates with for instance the visual display component s304 to electronically output the electronically generated one or more selection menus also within the ground vehicle, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a ground vehicle is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an interior of a ground vehicle (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the ground vehicle wherein the digestible product preparation system 10 is located that communicates with for instance the visual display component s304 to electronically output the electronically generated one or more selection menus also within the ground vehicle, etc.).

In one or more implementations, operation o11 includes an operation o11104 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a multi-state territory. A non-transitory signal bearing medium includes one or more control prep territory instructions i11104 that when executed will direct performance of the operation o11104. In an implementation, the one or more control prep territory instructions i11104 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a multi-state territory (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). Furthermore, the control prep territory electrical circuitry arrangement e11104 when activated will perform the operation o11104. In an implementation, the control prep territory electrical circuitry arrangement e11104, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a multi-state territory (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a multi-state territory is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within a multi-state territory (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.).

In one or more implementations, operation o11 includes an operation o11105 for electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an international region. A non-transitory signal bearing medium includes one or more control prep region instructions i11105 that when executed will direct performance of the operation o11105. In an implementation, the one or more control prep region instructions i11105 when executed direct electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an international region (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.). Furthermore, the control prep region electrical circuitry arrangement e11105 when activated will perform the operation o11105. In an implementation, the control prep region electrical circuitry arrangement e11105, when activated performs electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an international region (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, France, Brazil, Russia, India, China, and the United States, etc.). In an implementation, the electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an international region is carried out by electronically receiving the user status information and the selection information to electronically direct control of the at least partial preparation of the one or more selected ingestible products, the at least partial preparation of the one or more selected ingestible products within the first vicinity of the electronically outputting of the electronically generated one or more selection menus as within an international region (i.e. an implementation of the microprocessor component s102 is configured to receive the user status information and the selection information through the electronic communication subsystem 500 to electronically direct control of the material processing subsystem 700 for at least partial preparation of the one or more selected ingestible products within the first vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.).

As shown in FIG. 46, the operational flow o10 proceeds to operation o12 for electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus. An exemplary version of a non-transitory signal bearing medium of information storage subsystem s200 is depicted as bearing one or more controlling acquisition instructions i12 that when executed will direct performance of the operation o12. In an implementation, the one or more controlling acquisition instructions i12 when executed direct electronically directing control (e.g. the microprocessor component s102 can direct control, etc.) at least in part of acquisition of ingestion intelligence including information related to ingestion (e.g. directing control of sensing system s400 including sound sensing component s410 along with recognition application implemented by microprocessor s102 to obtain topic of conversation of the party including the particular individual living being, etc.) by the particular individual living being of at least one of the one or more selected ingestible products (e.g. including fruit smoothies, etc.) the ingestion by the particular individual living being within a second vicinity of the electronically outputting of the electronically generated one or more selection menus (e.g. the graphical user interface s302 displaying the one or more selection menus is located within a room of a building as the second vicinity that also houses the sensing subsystem s400 used for acquisition of ingestion intelligence information such as use of the sound sensing component s420 along with recognition application implemented with the microprocessor s102 to determine topic of conversation of the dining party including the particular material processing subsystem 700 used to prepare the selected fruit smoothie, etc.). Furthermore, the controlling acquisition electrical circuitry arrangement e12 when activated will perform the operation o12. In an implementation, the controlling acquisition electrical circuitry arrangement e12, when activated performs electronically directing control (e.g. the microprocessor component s102 can direct control, etc.) at least in part of acquisition of ingestion intelligence including information related to ingestion (e.g. directing control of sensing system s400 including sound sensing component s410 along with recognition application implemented by microprocessor s102 to obtain topic of conversation of the party including the particular individual living being, etc.) by the particular individual living being of at least one of the one or more selected ingestible products (e.g. including fruit smoothies, etc.) the ingestion by the particular individual living being within a second vicinity of the electronically outputting of the electronically generated one or more selection menus (e.g. the graphical user interface s302 displaying the one or more selection menus is located within a room of a building as the second vicinity that also houses the sensing subsystem s400 used for acquisition of ingestion intelligence information such as use of the sound sensing component s420 along with recognition application implemented with the microprocessor s102 to determine topic of conversation of the dining party including the particular material processing subsystem 700 used to prepare the selected fruit smoothie, etc.). In an implementation, the electronically directing control at least in part of acquisition of ingestion intelligence including information related to ingestion by the particular individual living being of at least one of the one or more selected ingestible products, the ingestion by the particular individual living being within a second vicinity of the electronically outputting of the electronically generated one or more selection menus is carried out by electronically directing control (e.g. the microprocessor component s102 can direct control, etc.) at least in part of acquisition of ingestion intelligence including information related to ingestion (e.g. directing control of sensing system s400 including sound sensing component s410 along with recognition application implemented by microprocessor s102 to obtain topic of conversation of the party including the particular individual living being, etc.) by the particular individual living being of at least one of the one or more selected ingestible products (e.g. including fruit smoothies, etc.) the ingestion by the particular individual living being within a second vicinity of the electronically outputting of the electronically generated one or more selection menus (e.g. the graphical user interface s302 displaying the one or more selection menus is located within a room of a building as the second vicinity that also houses the sensing subsystem s400 used for acquisition of ingestion intelligence information such as use of the sound sensing component s420 along with recognition application implemented with the microprocessor s102 to determine topic of conversation of the dining party including the particular material processing subsystem 700 used to prepare the selected fruit smoothie, etc.).

In one or more implementations, as shown in FIG. 82, operation o12 includes an operation o1201 for electronically directing control at least in part of the acquisition of the ingestion intelligence including the information related to the ingestion by the particular individual living being of at least one of the one or more selected ingestible products regarding occupant density associated with environs of the ingestion by the particular individual living being. An exemplary version of a non-transitory signal bearing medium of information storage subsystem s200 is depicted as bearing one or more control acquisition density instructions i1201 that when executed will direct performance of the operation o1201. In an implementation, the one or more control acquisition density instructions i1201 when executed direct electronically directing control at least in part of the acquisition of the ingestion intelligence including the information related to the ingestion by the particular individual living being of at least one of the one or more selected ingestible products regarding occupant density associated with environs of the ingestion by the particular individual living being (e.g. an implementation of the microprocessor component s102 is configured to electronically direct control at least in part of the acquisition of the ingestion intelligence including the information related to the ingestion by the particular individual living being of at least one of the one or more selected ingestible products such as through transmitter component s526 regarding occupant density such as how many customers of a restaurant are occupying a certain designated area of the restaurant associated with environs such as the restaurant of the ingestion by the particular individual living being, etc.). Furthermore, the control acquisition density electrical circuitry arrangement e1201 when activated will perform the operation o1201. In an implementation, the control acquisition density electrical circuitry arrangement e1201, when activated performs electronically directing control at least in part of the acquisition of the ingestion intelligence including the information related to the ingestion by the particular individual living being of at least one of the one or more selected ingestible products regarding occupant density associated with environs of the ingestion by the particular individual living being (e.g. an implementation of the microprocessor component s102 is configured to electronically direct control at least in part of the acquisition of the ingestion intelligence including the information related to the ingestion by the particular individual living being of at least one of the one or more selected ingestible products such as through transmitter component s526 regarding occupant density such as how many customers of a restaurant are occupying a certain designated area of the restaurant associated with environs such as the restaurant of the ingestion by the particular individual living being, etc.). In an implementation, the electronically directing control at least in part of the acquisition of the ingestion intelligence including the information related to the ingestion by the particular individual living being of at least one of the one or more selected ingestible products regarding occupant density associated with environs of the ingestion by the particular individual living being is carried out by electronically directing control at least in part of the acquisition of the ingestion intelligence including the information related to the ingestion by the particular individual living being of at least one of the one or more selected ingestible products regarding occupant density associated with environs of the ingestion by the particular individual living being (e.g. an implementation of the microprocessor component s102 is configured to electronically direct control at least in part of the acquisition of the ingestion intelligence including the information related to the ingestion by the particular individual living being of at least one of the one or more selected ingestible products such as through transmitter component s526 regarding occupant density such as how many customers of a restaurant are occupying a certain designated area of the restaurant associated with environs such as the restaurant of the ingestion by the particular individual living being, etc.).

In one or more implementations, operation o12 includes an operation o1202 for electronically directing control at least in part of the acquisition of the ingestion intelligence including the information related to the ingestion by the particular individual living being of at least one of the one or more selected ingestible products regarding furnishings associated with environs of the ingestion by the particular individual living being. An exemplary version of a non-transitory signal bearing medium of information storage subsystem s200 is depicted as bearing one or more control acquisition furnishings instructions i1202 that when executed will direct performance of the operation o1202. In an implementation, the one or more control acquisition furnishings instructions i1202 when executed direct electronically directing control at least in part of the acquisition of the ingestion intelligence including the information related to the ingestion by the particular individual living being of at least one of the one or more selected ingestible products regarding furnishings associated with environs of the ingestion by the particular individual living being (e.g. an implementation of the microprocessor component s102 is configured to electronically direct control at least in part of the acquisition of the ingestion intelligence such as through other nonvolatile memory component s220 including the information related to the ingestion by the particular individual living being of at least one of the one or more selected ingestible products regarding furnishings such as interior design and decoration associated with environs such as a food court of the ingestion by the particular individual living being, etc.). Furthermore, the control acquisition furnishings electrical circuitry arrangement e1202 when activated will perform the operation o1202. In an implementation, the control acquisition furnishings electrical circuitry arrangement e1202, when activated performs electronically directing control at least in part of the acquisition of the ingestion intelligence including the information related to the ingestion by the particular individual living being of at least one of the one or more selected ingestible products regarding furnishings associated with environs of the ingestion by the particular individual living being (e.g. an implementation of the microprocessor component s102 is configured to electronically direct control at least in part of the acquisition of the ingestion intelligence such as through other nonvolatile memory component s220 including the information related to the ingestion by the particular individual living being of at least one of the one or more selected ingestible products regarding furnishings such as interior design and decoration associated with environs such as a food court of the ingestion by the particular individual living being, etc.). In an implementation, the electronically directing control at least in part of the acquisition of the ingestion intelligence including the information related to the ingestion by the particular individual living being of at least one of the one or more selected ingestible products regarding furnishings associated with environs of the ingestion by the particular individual living being is carried out by electronically directing control at least in part of the acquisition of the ingestion intelligence including the information related to the ingestion by the particular individual living being of at least one of the one or more selected ingestible products regarding furnishings associated with environs of the ingestion by the particular individual living being (e.g. an implementation of the microprocessor component s102 is configured to electronically direct control at least in part of the acquisition of the ingestion intelligence such as through other nonvolatile memory component s220 including the information related to the ingestion by the particular individual living being of at least one of the one or more selected ingestible products regarding furnishings such as interior design and decoration associated with environs such as a food court of the ingestion by the particular individual living being, etc.).

In one or more implementations, operation o12 includes an operation o1203 for electronically directing control at least in part of the acquisition of the ingestion intelligence including the information related to the ingestion by the particular individual living being of at least one of the one or more selected ingestible products regarding air temperature associated with environs of the ingestion by the particular individual living being. An exemplary version of a non-transitory signal bearing medium of information storage subsystem s200 is depicted as bearing one or more control acquisition temperature instructions i1203 that when executed will direct performance of the operation o1203. In an implementation, the one or more control acquisition temperature instructions i1203 when executed direct electronically directing control at least in part of the acquisition of the ingestion intelligence including the information related to the ingestion by the particular individual living being of at least one of the one or more selected ingestible products regarding air temperature associated with environs of the ingestion by the particular individual living being (e.g. an implementation of the microprocessor component s102 is configured to electronically control at least in part the acquisition of the ingestion intelligence such as through temperature sensing component s412 including the information related to the ingestion by the particular individual living being of at least one of the one or more selected ingestible products regarding air temperature associated with environs such as the outdoor temperature near a street vending machine of the ingestion by the particular individual living being, etc.). Furthermore, the control acquisition temperature electrical circuitry arrangement e1203 when activated will perform the operation o1203. In an implementation, the control acquisition temperature electrical circuitry arrangement e1203, when activated performs electronically directing control at least in part of the acquisition of the ingestion intelligence including the information related to the ingestion by the particular individual living being of at least one of the one or more selected ingestible products regarding air temperature associated with environs of the ingestion by the particular individual living being (e.g. an implementation of the microprocessor component s102 is configured to electronically control at least in part the acquisition of the ingestion intelligence such as through temperature sensing component s412 including the information related to the ingestion by the particular individual living being of at least one of the one or more selected ingestible products regarding air temperature associated with environs such as the outdoor temperature near a street vending machine of the ingestion by the particular individual living being, etc.). In an implementation, the electronically directing control at least in part of the acquisition of the ingestion intelligence including the information related to the ingestion by the particular individual living being of at least one of the one or more selected ingestible products regarding air temperature associated with environs of the ingestion by the particular individual living being is carried out by electronically directing control at least in part of the acquisition of the ingestion intelligence including the information related to the ingestion by the particular individual living being of at least one of the one or more selected ingestible products regarding air temperature associated with environs of the ingestion by the particular individual living being (e.g. an implementation of the microprocessor component s102 is configured to electronically control at least in part the acquisition of the ingestion intelligence such as through temperature sensing component s412 including the information related to the ingestion by the particular individual living being of at least one of the one or more selected ingestible products regarding air temperature associated with environs such as the outdoor temperature near a street vending machine of the ingestion by the particular individual living being, etc.).

Figure 83:
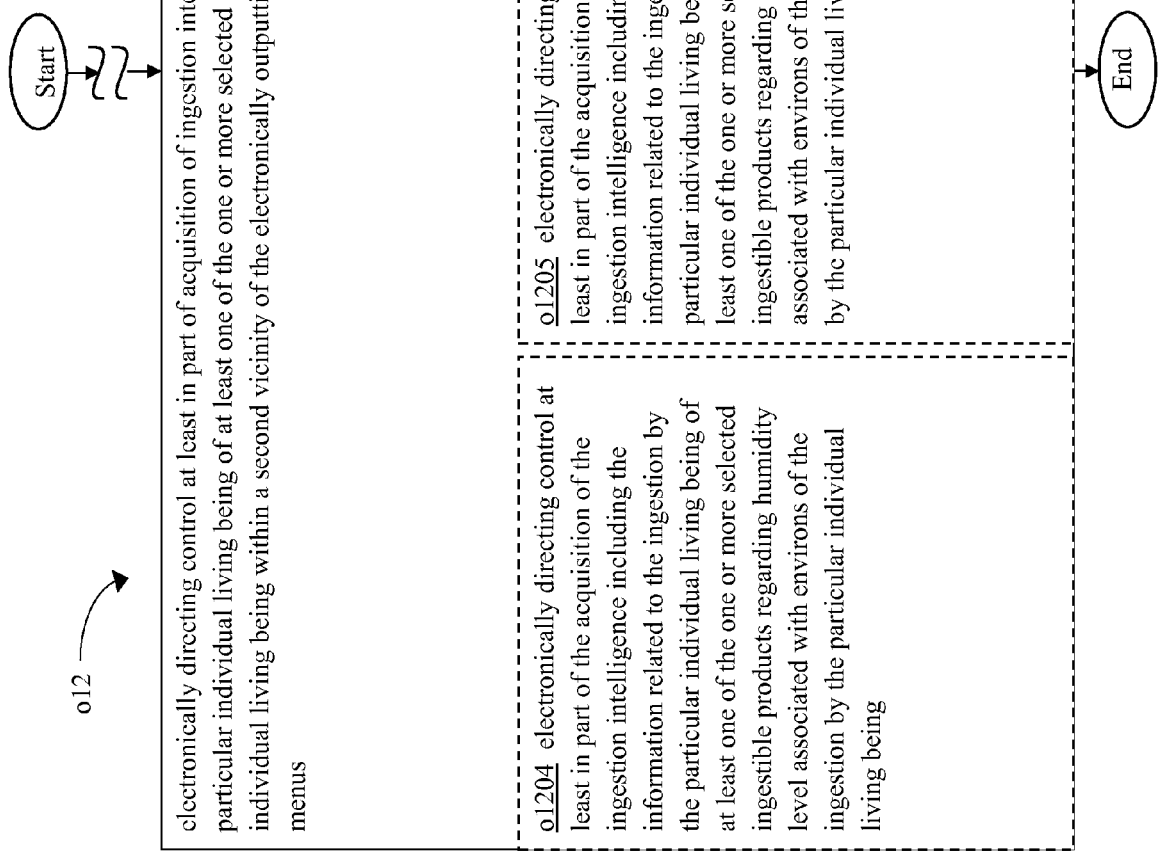
FIG. 83 is a high-level flowchart including exemplary implementations of operation O12 of FIG. 46.

In one or more implementations, as shown in FIG. 83, operation o12 includes an operation o1204 for electronically directing control at least in part of the acquisition of the ingestion intelligence including the information related to the ingestion by the particular individual living being of at least one of the one or more selected ingestible products regarding humidity level associated with environs of the ingestion by the particular individual living being. An exemplary version of a non-transitory signal bearing medium of information storage subsystem s200 is depicted as bearing one or more control acquisition humidity instructions i1204 that when executed will direct performance of the operation o1204. In an implementation, the one or more control acquisition humidity instructions i1204 when executed direct electronically directing control at least in part of the acquisition of the ingestion intelligence including the information related to the ingestion by the particular individual living being of at least one of the one or more selected ingestible products regarding humidity level associated with environs of the ingestion by the particular individual living being (e.g. an implementation of the microprocessor component s102 is configured to electronically control at least in part the acquisition of the ingestion intelligence such as through sensing subsystem s402 including the information related to the ingestion by the particular individual living being of at least one of the one or more selected ingestible products regarding humidity level associated with environs such as a street cafe of the ingestion by the particular individual living being, etc.). Furthermore, the control acquisition humidity electrical circuitry arrangement e1204 when activated will perform the operation o1204. In an implementation, the control acquisition humidity electrical circuitry arrangement e1204, when activated performs electronically directing control at least in part of the acquisition of the ingestion intelligence including the information related to the ingestion by the particular individual living being of at least one of the one or more selected ingestible products regarding humidity level associated with environs of the ingestion by the particular individual living being (e.g. an implementation of the microprocessor component s102 is configured to electronically control at least in part the acquisition of the ingestion intelligence such as through sensing subsystem s402 including the information related to the ingestion by the particular individual living being of at least one of the one or more selected ingestible products regarding humidity level associated with environs such as a street cafe of the ingestion by the particular individual living being, etc.). In an implementation, the electronically directing control at least in part of the acquisition of the ingestion intelligence including the information related to the ingestion by the particular individual living being of at least one of the one or more selected ingestible products regarding humidity level associated with environs of the ingestion by the particular individual living being is carried out by electronically directing control at least in part of the acquisition of the ingestion intelligence including the information related to the ingestion by the particular individual living being of at least one of the one or more selected ingestible products regarding humidity level associated with environs of the ingestion by the particular individual living being (e.g. an implementation of the microprocessor component s102 is configured to electronically control at least in part the acquisition of the ingestion intelligence such as through sensing subsystem s402 including the information related to the ingestion by the particular individual living being of at least one of the one or more selected ingestible products regarding humidity level associated with environs such as a street cafe of the ingestion by the particular individual living being, etc.).

In one or more implementations, operation o12 includes an operation o1205 for electronically directing control at least in part of the acquisition of the ingestion intelligence including the information related to the ingestion by the particular individual living being of at least one of the one or more selected ingestible products regarding noise level associated with environs of the ingestion by the particular individual living being. An exemplary version of a non-transitory signal bearing medium of information storage subsystem s200 is depicted as bearing one or more control acquisition noise instructions i1205 that when executed will direct performance of the operation o1205. In an implementation, the one or more control acquisition noise instructions i1205 when executed direct electronically directing control at least in part of the acquisition of the ingestion intelligence including the information related to the ingestion by the particular individual living being of at least one of the one or more selected ingestible products regarding noise level associated with environs of the ingestion by the particular individual living being (e.g. an implementation of the microprocessor component s102 is configured to electronically control at least in part the acquisition of the ingestion intelligence such as through sounding sensing component s420 including the information related to the ingestion by the particular individual living being of at least one of the one or more selected ingestible products regarding noise level associated with environs such as a restaurant of the ingestion by the particular individual living being, etc.). Furthermore, the control acquisition noise electrical circuitry arrangement e1205 when activated will perform the operation o1205. In an implementation, the control acquisition noise electrical circuitry arrangement e1205, when activated performs electronically directing control at least in part of the acquisition of the ingestion intelligence including the information related to the ingestion by the particular individual living being of at least one of the one or more selected ingestible products regarding noise level associated with environs of the ingestion by the particular individual living being (e.g. an implementation of the microprocessor component s102 is configured to electronically control at least in part the acquisition of the ingestion intelligence such as through sounding sensing component s420 including the information related to the ingestion by the particular individual living being of at least one of the one or more selected ingestible products regarding noise level associated with environs such as a restaurant of the ingestion by the particular individual living being, etc.). In an implementation, the electronically directing control at least in part of the acquisition of the ingestion intelligence including the information related to the ingestion by the particular individual living being of at least one of the one or more selected ingestible products regarding noise level associated with environs of the ingestion by the particular individual living being is carried out by electronically directing control at least in part of the acquisition of the ingestion intelligence including the information related to the ingestion by the particular individual living being of at least one of the one or more selected ingestible products regarding noise level associated with environs of the ingestion by the particular individual living being (e.g. an implementation of the microprocessor component s102 is configured to electronically control at least in part the acquisition of the ingestion intelligence such as through sounding sensing component s420 including the information related to the ingestion by the particular individual living being of at least one of the one or more selected ingestible products regarding noise level associated with environs such as a restaurant of the ingestion by the particular individual living being, etc.).

In one or more implementations, operation o12 includes an operation o1206 for electronically directing control at least in part of the acquisition of the ingestion intelligence including the information related to the ingestion by the particular individual living being of at least one of the one or more selected ingestible products regarding olfactory factors including at least one of smells, aromas, odors, or scents associated with environs of the ingestion by the particular individual living being. An exemplary version of a non-transitory signal bearing medium of information storage subsystem s200 is depicted as bearing one or more control acquisition olfactory instructions i1206 that when executed will direct performance of the operation o1206. In an implementation, the one or more control acquisition olfactory instructions i1206 when executed direct electronically directing control at least in part of the acquisition of the ingestion intelligence including the information related to the ingestion by the particular individual living being of at least one of the one or more selected ingestible products regarding olfactory factors including at least one of smells, aromas, odors, or scents associated with environs of the ingestion by the particular individual living being (e.g. an implementation of the microprocessor component s102 is configured to electronically control at least in part the acquisition such as through sensing subsystem s402 of the ingestion intelligence including the information related to the ingestion by the particular individual living being of at least one of the one or more selected ingestible products regarding olfactory factors including at least one of smells, aromas, odors, or scents associated with environs such as a cafeteria of the ingestion by the particular individual living being, etc.). Furthermore, the control acquisition olfactory electrical circuitry arrangement e1206 when activated will perform the operation o1205. In an implementation, the control acquisition olfactory electrical circuitry arrangement e1206, when activated performs electronically directing control at least in part of the acquisition of the ingestion intelligence including the information related to the ingestion by the particular individual living being of at least one of the one or more selected ingestible products regarding olfactory factors including at least one of smells, aromas, odors, or scents associated with environs of the ingestion by the particular individual living being (e.g. an implementation of the microprocessor component s102 is configured to electronically control at least in part the acquisition such as through sensing subsystem s402 of the ingestion intelligence including the information related to the ingestion by the particular individual living being of at least one of the one or more selected ingestible products regarding olfactory factors including at least one of smells, aromas, odors, or scents associated with environs such as a cafeteria of the ingestion by the particular individual living being, etc.). In an implementation, the electronically directing control at least in part of the acquisition of the ingestion intelligence including the information related to the ingestion by the particular individual living being of at least one of the one or more selected ingestible products regarding olfactory factors including at least one of smells, aromas, odors, or scents associated with environs of the ingestion by the particular individual living being is carried out by electronically directing control at least in part of the acquisition of the ingestion intelligence including the information related to the ingestion by the particular individual living being of at least one of the one or more selected ingestible products regarding olfactory factors including at least one of smells, aromas, odors, or scents associated with environs of the ingestion by the particular individual living being (e.g. an implementation of the microprocessor component s102 is configured to electronically control at least in part the acquisition such as through sensing subsystem s402 of the ingestion intelligence including the information related to the ingestion by the particular individual living being of at least one of the one or more selected ingestible products regarding olfactory factors including at least one of smells, aromas, odors, or scents associated with environs such as a cafeteria of the ingestion by the particular individual living being, etc.).

Figure 84:
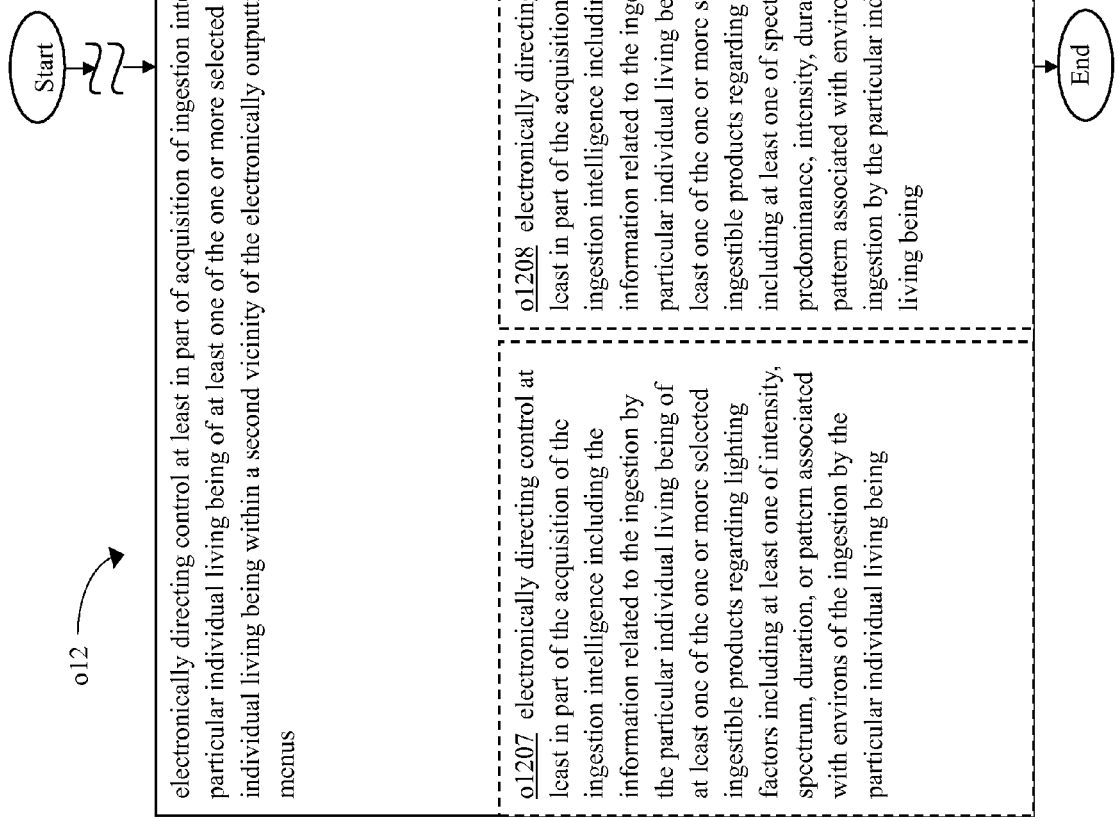
FIG. 84 is a high-level flowchart including exemplary implementations of operation O12 of FIG. 46.

In one or more implementations, as shown in FIG. 84, operation o12 includes an operation o1207 for electronically directing control at least in part of the acquisition of the ingestion intelligence including the information related to the ingestion by the particular individual living being of at least one of the one or more selected ingestible products regarding lighting factors including at least one of intensity, spectrum, duration, or pattern associated with environs of the ingestion by the particular individual living being. An exemplary version of a non-transitory signal bearing medium of information storage subsystem s200 is depicted as bearing one or more control acquisition lighting instructions i1207 that when executed will direct performance of the operation o1207. In an implementation, the one or more control acquisition lighting instructions i1207 when executed direct electronically directing control at least in part of the acquisition of the ingestion intelligence including the information related to the ingestion by the particular individual living being of at least one of the one or more selected ingestible products regarding lighting factors including at least one of intensity, spectrum, duration, or pattern associated with environs of the ingestion by the particular individual living being (e.g. an implementation of the microprocessor component s102 is configured to electronically control at least in part the acquisition of the ingestion intelligence such as through photodetecting components s406 including the information related to the ingestion by the particular individual living being of at least one of the one or more selected ingestible products regarding lighting factors including at least one of intensity, spectrum, duration, or pattern associated with environs such as a restaurant of the ingestion by the particular individual living being, etc.). Furthermore, the control acquisition lighting electrical circuitry arrangement e1207 when activated will perform the operation o1207. In an implementation, the control acquisition lighting electrical circuitry arrangement e1207, when activated performs electronically directing control at least in part of the acquisition of the ingestion intelligence including the information related to the ingestion by the particular individual living being of at least one of the one or more selected ingestible products regarding lighting factors including at least one of intensity, spectrum, duration, or pattern associated with environs of the ingestion by the particular individual living being (e.g. an implementation of the microprocessor component s102 is configured to electronically control at least in part the acquisition of the ingestion intelligence such as through photodetecting components s406 including the information related to the ingestion by the particular individual living being of at least one of the one or more selected ingestible products regarding lighting factors including at least one of intensity, spectrum, duration, or pattern associated with environs such as a restaurant of the ingestion by the particular individual living being, etc.). In an implementation, the electronically directing control at least in part of the acquisition of the ingestion intelligence including the information related to the ingestion by the particular individual living being of at least one of the one or more selected ingestible products regarding lighting factors including at least one of intensity, spectrum, duration, or pattern associated with environs of the ingestion by the particular individual living being is carried out by electronically directing control at least in part of the acquisition of the ingestion intelligence including the information related to the ingestion by the particular individual living being of at least one of the one or more selected ingestible products regarding lighting factors including at least one of intensity, spectrum, duration, or pattern associated with environs of the ingestion by the particular individual living being (e.g. an implementation of the microprocessor component s102 is configured to electronically control at least in part the acquisition of the ingestion intelligence such as through photodetecting components s406 including the information related to the ingestion by the particular individual living being of at least one of the one or more selected ingestible products regarding lighting factors including at least one of intensity, spectrum, duration, or pattern associated with environs such as a restaurant of the ingestion by the particular individual living being, etc.).

In one or more implementations, operation o12 includes an operation o1208 for electronically directing control at least in part of the acquisition of the ingestion intelligence including the information related to the ingestion by the particular individual living being of at least one of the one or more selected ingestible products regarding color including at least one of spectrum, predominance, intensity, duration, or pattern associated with environs of the ingestion by the particular individual living being. An exemplary version of a non-transitory signal bearing medium of information storage subsystem s200 is depicted as bearing one or more control acquisition color instructions i1208 that when executed will direct performance of the operation o1208. In an implementation, the one or more control acquisition color instructions i1208 when executed direct electronically directing control at least in part of the acquisition of the ingestion intelligence including the information related to the ingestion by the particular individual living being of at least one of the one or more selected ingestible products regarding color including at least one of spectrum, predominance, intensity, duration, or pattern associated with environs of the ingestion by the particular individual living being (e.g. an implementation of the microprocessor component s102 is configured to electronically control at least in part the acquisition of the ingestion intelligence such as through electromagnetic sensing component s402 including the information related to the ingestion by the particular individual living being of at least one of the one or more selected ingestible products regarding color including at least one of spectrum, predominance, intensity, duration, or pattern associated with environs such as colors used for interior of a restaurant of the ingestion by the particular individual living being, etc.). Furthermore, the control acquisition color electrical circuitry arrangement e1208 when activated will perform the operation o1208. In an implementation, the control acquisition color electrical circuitry arrangement e1208, when activated performs electronically directing control at least in part of the acquisition of the ingestion intelligence including the information related to the ingestion by the particular individual living being of at least one of the one or more selected ingestible products regarding color including at least one of spectrum, predominance, intensity, duration, or pattern associated with environs of the ingestion by the particular individual living being (e.g. an implementation of the microprocessor component s102 is configured to electronically control at least in part the acquisition of the ingestion intelligence such as through electromagnetic sensing component s402 including the information related to the ingestion by the particular individual living being of at least one of the one or more selected ingestible products regarding color including at least one of spectrum, predominance, intensity, duration, or pattern associated with environs such as colors used for interior of a restaurant of the ingestion by the particular individual living being, etc.). In an implementation, the electronically directing control at least in part of the acquisition of the ingestion intelligence including the information related to the ingestion by the particular individual living being of at least one of the one or more selected ingestible products regarding color including at least one of spectrum, predominance, intensity, duration, or pattern associated with environs of the ingestion by the particular individual living being is carried out by electronically directing control at least in part of the acquisition of the ingestion intelligence including the information related to the ingestion by the particular individual living being of at least one of the one or more selected ingestible products regarding color including at least one of spectrum, predominance, intensity, duration, or pattern associated with environs of the ingestion by the particular individual living being (e.g. an implementation of the microprocessor component s102 is configured to electronically control at least in part the acquisition of the ingestion intelligence such as through electromagnetic sensing component s402 including the information related to the ingestion by the particular individual living being of at least one of the one or more selected ingestible products regarding color including at least one of spectrum, predominance, intensity, duration, or pattern associated with environs such as colors used for interior of a restaurant of the ingestion by the particular individual living being, etc.).

In one or more implementations, operation o12 includes an operation o1209 for electronically directing control at least in part of the acquisition of the ingestion intelligence including the information related to the ingestion by the particular individual living being of at least one of the one or more selected ingestible products regarding artwork associated with environs of the ingestion by the particular individual living being. An exemplary version of a non-transitory signal bearing medium of information storage subsystem s200 is depicted as bearing one or more control acquisition artwork instructions i1209 that when executed will direct performance of the operation o1209. In an implementation, the one or more control acquisition artwork instructions i1209 when executed direct electronically directing control at least in part of the acquisition of the ingestion intelligence including the information related to the ingestion by the particular individual living being of at least one of the one or more selected ingestible products regarding artwork associated with environs of the ingestion by the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding artwork associated with environs regarding an eating establishment of the ingestion by the particular individual living being, etc.). Furthermore, the control acquisition artwork electrical circuitry arrangement e1209 when activated will perform the operation o1209. In an implementation, the control acquisition artwork electrical circuitry arrangement e1209, when activated performs electronically directing control at least in part of the acquisition of the ingestion intelligence including the information related to the ingestion by the particular individual living being of at least one of the one or more selected ingestible products regarding artwork associated with environs of the ingestion by the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding artwork associated with environs regarding an eating establishment of the ingestion by the particular individual living being, etc.). In an implementation, the electronically directing control at least in part of the acquisition of the ingestion intelligence including the information related to the ingestion by the particular individual living being of at least one of the one or more selected ingestible products regarding artwork associated with environs of the ingestion by the particular individual living being is carried out by electronically directing control at least in part of the acquisition of the ingestion intelligence including the information related to the ingestion by the particular individual living being of at least one of the one or more selected ingestible products regarding artwork associated with environs of the ingestion by the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding artwork associated with environs regarding an eating establishment of the ingestion by the particular individual living being, etc.).

Figure 85:
FIG. 85 is a high-level flowchart including exemplary implementations of operation O12 of FIG. 46.

In one or more implementations, as shown in FIG. 85, operation o12 includes an operation o1210 for electronically directing control at least in part of the acquisition of the ingestion intelligence including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member. An exemplary version of a non-transitory signal bearing medium of information storage subsystem s200 is depicted as bearing one or more control acquisition party instructions i1210 that when executed will direct performance of the operation o1210. In an implementation, the one or more control acquisition party instructions i1210 when executed direct electronically directing control at least in part of the acquisition of the ingestion intelligence including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member (e.g. an implementation of the microprocessor component s102 is configured to electronically control at least in part the acquisition of the ingestion intelligence such as through sound sensing component s420, camera component s336, and/or server component s230 along with recognition application implemented with the microprocessor component s102 including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member, etc.). Furthermore, the control acquisition party electrical circuitry arrangement e1210 when activated will perform the operation o1210. In an implementation, the control acquisition party electrical circuitry arrangement e1210, when activated performs electronically directing control at least in part of the acquisition of the ingestion intelligence including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member (e.g. an implementation of the microprocessor component s102 is configured to electronically control at least in part the acquisition of the ingestion intelligence such as through sound sensing component s420, camera component s336, and/or server component s230 along with recognition application implemented with the microprocessor component s102 including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member, etc.). In an implementation, the electronically directing control at least in part of the acquisition of the ingestion intelligence including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member is carried out by electronically directing control at least in part of the acquisition of the ingestion intelligence including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member (e.g. an implementation of the microprocessor component s102 is configured to electronically control at least in part the acquisition of the ingestion intelligence such as through sound sensing component s420, camera component s336, and/or server component s230 along with recognition application implemented with the microprocessor component s102 including the information related to the ingestion by the particular individual living being of at least one of the one or more selected ingestible products regarding dining party factors, the dining party including and having a relational association with the particular individual living being, the dining party factors including at least one of the following: number in party, demographics of at least one party member, attire of at least one party member, movement patterns of at least one party member, or topic of conversation of at least one party member, etc.).

In one or more implementations, operation o12 includes an operation o1211 for electronically directing control at least in part of the acquisition of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics. An exemplary version of a non-transitory signal bearing medium of information storage subsystem s200 is depicted as bearing one or more control acquisition ergonomics instructions i1211 that when executed will direct performance of the operation o1211. In an implementation, the one or more control acquisition ergonomics instructions i1211 when executed direct electronically directing control at least in part of the acquisition of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics (e.g. an implementation of the microprocessor component s102 is configured to electronically control at least in part the acquisition such as through camera component s336 and recognition application implemented through the microprocessor component of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics, etc.). Furthermore, the control acquisition ergonomics electrical circuitry arrangement e1211 when activated will perform the operation o1211. In an implementation, the control acquisition ergonomics electrical circuitry arrangement e1211, when activated performs electronically directing control at least in part of the acquisition of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics (e.g. an implementation of the microprocessor component s102 is configured to electronically control at least in part the acquisition such as through camera component s336 and recognition application implemented through the microprocessor component of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics is carried out by electronically directing control at least in part of the acquisition of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics (e.g. an implementation of the microprocessor component s102 is configured to electronically control at least in part the acquisition such as through camera component s336 and recognition application implemented through the microprocessor component of the ingestion intelligence including the information related to the ingestion by the particular individual living being of at least one of the one or more selected ingestible products regarding ergonomic factors including at least one of chair configuration ergonomics, table configuration ergonomics, utensil ergonomics, arrangement of dishware ergonomics, arrangement of surrounding chairs ergonomics, arrangement of surrounding tables ergonomics, arrangement of standing area ergonomics, counter ergonomics, or bench ergonomics, etc.).

In one or more implementations, operation o12 includes an operation o1212 for electronically directing control at least in part of the acquisition of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live. An exemplary version of a non-transitory signal bearing medium of information storage subsystem s200 is depicted as bearing one or more control acquisition music instructions i1212 that when executed will direct performance of the operation o1212. In an implementation, the one or more control acquisition music instructions i1212 when executed direct electronically directing control at least in part of the acquisition of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live (e.g. an implementation of the microprocessor component s102 is configured to electronically control at least in part the acquisition such as through sound sensing component s420 and recognition application implemented by the microprocessor component s102 of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live, etc.). Furthermore, the control acquisition music electrical circuitry arrangement e1212 when activated will perform the operation o1212. In an implementation, the control acquisition music electrical circuitry arrangement e1212, when activated performs electronically directing control at least in part of the acquisition of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live (e.g. an implementation of the microprocessor component s102 is configured to electronically control at least in part the acquisition such as through sound sensing component s420 and recognition application implemented by the microprocessor component s102 of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live, etc.). In an implementation, the electronically directing control at least in part of the acquisition of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live is carried out by electronically directing control at least in part of the acquisition of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live (e.g. an implementation of the microprocessor component s102 is configured to electronically control at least in part the acquisition such as through sound sensing component s420 and recognition application implemented by the microprocessor component s102 of the ingestion intelligence including the information related to the ingestion by the particular individual living being of at least one of the one or more selected ingestible products regarding background music factors including at least one of volume of music, genre of music, tempo of music, one or more vocalists involved, one or more musicians involved, or whether music is live, etc.).

Figure 86:
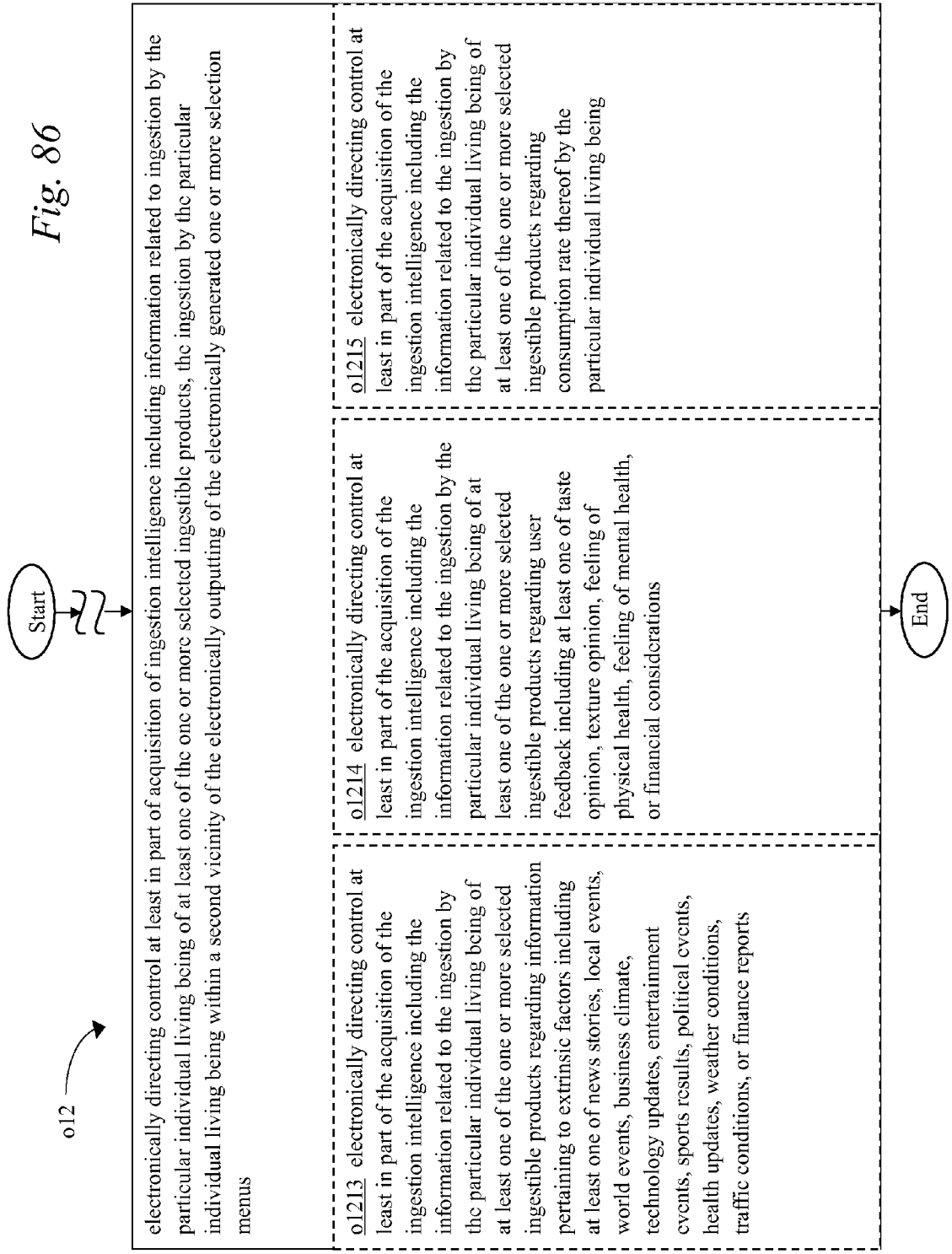
FIG. 86 is a high-level flowchart including exemplary implementations of operation O12 of FIG. 46.

In one or more implementations, as shown in FIG. 86, operation o12 includes an operation o1213 for electronically directing control at least in part of the acquisition of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports. An exemplary version of a non-transitory signal bearing medium of information storage subsystem s200 is depicted as bearing one or more control acquisition extrinsic instructions i1213 that when executed will direct performance of the operation o1213. In an implementation, the one or more control acquisition extrinsic instructions i1213 when executed direct electronically directing control at least in part of the acquisition of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports (e.g. an implementation of the microprocessor component s102 is configured to electronically control at least in part the acquisition such as through internet network component s508 of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports, etc.). Furthermore, the control acquisition extrinsic electrical circuitry arrangement e1213 when activated will perform the operation o1213. In an implementation, the control acquisition extrinsic electrical circuitry arrangement e1213, when activated performs electronically directing control at least in part of the acquisition of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports (e.g. an implementation of the microprocessor component s102 is configured to electronically control at least in part the acquisition such as through internet network component s508 of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports, etc.). In an implementation, the electronically directing control at least in part of the acquisition of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports is carried out by electronically directing control at least in part of the acquisition of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports (e.g. an implementation of the microprocessor component s102 is configured to electronically control at least in part the acquisition such as through internet network component s508 of the ingestion intelligence including the information related to the ingestion by the particular individual living being of at least one of the one or more selected ingestible products regarding information pertaining to extrinsic factors including at least one of news stories, local events, world events, business climate, technology updates, entertainment events, sports results, political events, health updates, weather conditions, traffic conditions, or finance reports, etc.).

In one or more implementations, operation o12 includes an operation o1214 for electronically directing control at least in part of the acquisition of the ingestion intelligence including the information related to the ingestion by the particular individual living being of at least one of the one or more selected ingestible products regarding user feedback including at least one of taste opinion, texture opinion, feeling of physical health, feeling of mental health, or financial considerations. An exemplary version of a non-transitory signal bearing medium of information storage subsystem s200 is depicted as bearing one or more control acquisition feedback instructions i1214 that when executed will direct performance of the operation o1214. In an implementation, the one or more control acquisition feedback instructions i1214 when executed direct electronically directing control at least in part of the acquisition of the ingestion intelligence including the information related to the ingestion by the particular individual living being of at least one of the one or more selected ingestible products regarding user feedback including at least one of taste opinion, texture opinion, feeling of physical health, feeling of mental health, or financial considerations (e.g. an implementation of the microprocessor component s102 is configured to electronically control at least in part the acquisition of the ingestion intelligence such as through touch screen component s314 including the information related to the ingestion by the particular individual living being of at least one of the one or more selected ingestible products regarding user feedback including at least one of taste opinion, texture opinion, feeling of physical health, feeling of mental health, or financial considerations, etc.). Furthermore, the control acquisition feedback electrical circuitry arrangement e1214 when activated will perform the operation o1214. In an implementation, the control acquisition feedback electrical circuitry arrangement e1214, when activated performs electronically directing control at least in part of the acquisition of the ingestion intelligence including the information related to the ingestion by the particular individual living being of at least one of the one or more selected ingestible products regarding user feedback including at least one of taste opinion, texture opinion, feeling of physical health, feeling of mental health, or financial considerations (e.g. an implementation of the microprocessor component s102 is configured to electronically control at least in part the acquisition of the ingestion intelligence such as through touch screen component s314 including the information related to the ingestion by the particular individual living being of at least one of the one or more selected ingestible products regarding user feedback including at least one of taste opinion, texture opinion, feeling of physical health, feeling of mental health, or financial considerations, etc.). In an implementation, the electronically directing control at least in part of the acquisition of the ingestion intelligence including the information related to the ingestion by the particular individual living being of at least one of the one or more selected ingestible products regarding user feedback including at least one of taste opinion, texture opinion, feeling of physical health, feeling of mental health, or financial considerations is carried out by electronically directing control at least in part of the acquisition of the ingestion intelligence including the information related to the ingestion by the particular individual living being of at least one of the one or more selected ingestible products regarding user feedback including at least one of taste opinion, texture opinion, feeling of physical health, feeling of mental health, or financial considerations (e.g. an implementation of the microprocessor component s102 is configured to electronically control at least in part the acquisition of the ingestion intelligence such as through touch screen component s314 including the information related to the ingestion by the particular individual living being of at least one of the one or more selected ingestible products regarding user feedback including at least one of taste opinion, texture opinion, feeling of physical health, feeling of mental health, or financial considerations, etc.).

In one or more implementations, operation o12 includes an operation o1215 for electronically directing control at least in part of the acquisition of the ingestion intelligence including the information related to the ingestion by the particular individual living being of at least one of the one or more selected ingestible products regarding consumption rate thereof by the particular individual living being. An exemplary version of a non-transitory signal bearing medium of information storage subsystem s200 is depicted as bearing one or more control acquisition rate instructions i1215 that when executed will direct performance of the operation o1215. In an implementation, the one or more control acquisition rate instructions i1215 when executed direct electronically directing control at least in part of the acquisition of the ingestion intelligence including the information related to the ingestion by the particular individual living being of at least one of the one or more selected ingestible products regarding consumption rate thereof by the particular individual living being (e.g. an implementation of the microprocessor component s102 is configured to electronically control at least in part the acquisition of the ingestion intelligence such as through camera component s336 and recognition application implemented by the microprocessor component s102 including the information related to the ingestion by the particular individual living being of at least one of the one or more selected ingestible products regarding consumption rate thereof by the particular individual living being, etc.). Furthermore, the control acquisition rate electrical circuitry arrangement e1215 when activated will perform the operation o1215. In an implementation, the control acquisition rate electrical circuitry arrangement e1215, when activated performs electronically directing control at least in part of the acquisition of the ingestion intelligence including the information related to the ingestion by the particular individual living being of at least one of the one or more selected ingestible products regarding consumption rate thereof by the particular individual living being (e.g. an implementation of the microprocessor component s102 is configured to electronically control at least in part the acquisition of the ingestion intelligence such as through camera component s336 and recognition application implemented by the microprocessor component s102 including the information related to the ingestion by the particular individual living being of at least one of the one or more selected ingestible products regarding consumption rate thereof by the particular individual living being, etc.). In an implementation, the electronically directing control at least in part of the acquisition of the ingestion intelligence including the information related to the ingestion by the particular individual living being of at least one of the one or more selected ingestible products regarding consumption rate thereof by the particular individual living being is carried out by electronically directing control at least in part of the acquisition of the ingestion intelligence including the information related to the ingestion by the particular individual living being of at least one of the one or more selected ingestible products regarding consumption rate thereof by the particular individual living being (e.g. an implementation of the microprocessor component s102 is configured to electronically control at least in part the acquisition of the ingestion intelligence such as through camera component s336 and recognition application implemented by the microprocessor component s102 including the information related to the ingestion by the particular individual living being of at least one of the one or more selected ingestible products regarding consumption rate thereof by the particular individual living being, etc.).

Figure 87:
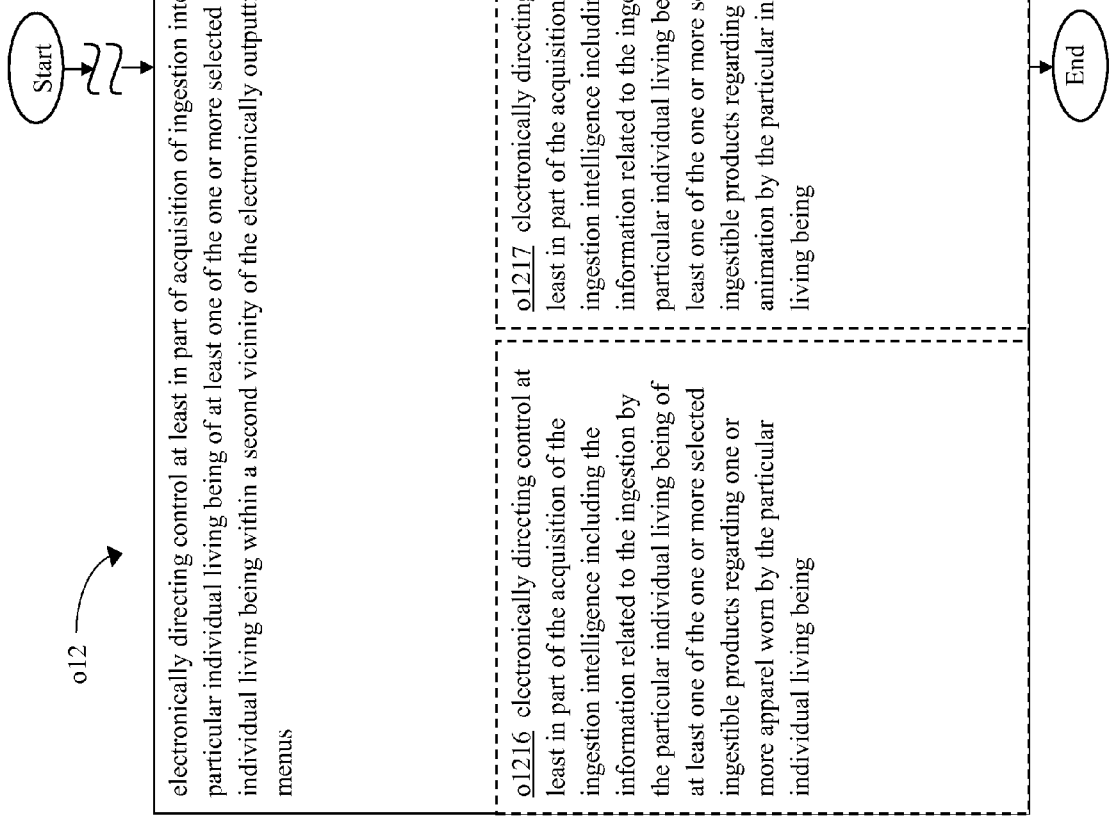
FIG. 87 is a high-level flowchart including exemplary implementations of operation O12 of FIG. 46.

In one or more implementations, as shown in FIG. 87, operation o12 includes an operation o1216 for electronically directing control at least in part of the acquisition of the ingestion intelligence including the information related to the ingestion by the particular individual living being of at least one of the one or more selected ingestible products regarding one or more apparel worn by the particular individual living being. An exemplary version of a non-transitory signal bearing medium of information storage subsystem s200 is depicted as bearing one or more control acquisition apparel instructions i1216 that when executed will direct performance of the operation o1216. In an implementation, the one or more control acquisition apparel instructions i1216 when executed direct electronically directing control at least in part of the acquisition of the ingestion intelligence including the information related to the ingestion by the particular individual living being of at least one of the one or more selected ingestible products regarding one or more apparel worn by the particular individual living being (e.g. an implementation of the microprocessor component s102 is configured to electronically control at least in part the acquisition such as through the camera component s336 and recognition application implemented by the microprocessor component s102 of the ingestion intelligence including the information related to the ingestion by the particular individual living being of at least one of the one or more selected ingestible products regarding one or more apparel worn by the particular individual living being, etc.). Furthermore, the control acquisition apparel electrical circuitry arrangement e1216 when activated will perform the operation o1216. In an implementation, the control acquisition apparel electrical circuitry arrangement e1216, when activated performs electronically directing control at least in part of the acquisition of the ingestion intelligence including the information related to the ingestion by the particular individual living being of at least one of the one or more selected ingestible products regarding one or more apparel worn by the particular individual living being (e.g. an implementation of the microprocessor component s102 is configured to electronically control at least in part the acquisition such as through the camera component s336 and recognition application implemented by the microprocessor component s102 of the ingestion intelligence including the information related to the ingestion by the particular individual living being of at least one of the one or more selected ingestible products regarding one or more apparel worn by the particular individual living being, etc.). In an implementation, the electronically directing control at least in part of the acquisition of the ingestion intelligence including the information related to the ingestion by the particular individual living being of at least one of the one or more selected ingestible products regarding one or more apparel worn by the particular individual living being is carried out by electronically directing control at least in part of the acquisition of the ingestion intelligence including the information related to the ingestion by the particular individual living being of at least one of the one or more selected ingestible products regarding one or more apparel worn by the particular individual living being (e.g. an implementation of the microprocessor component s102 is configured to electronically control at least in part the acquisition such as through the camera component s336 and recognition application implemented by the microprocessor component s102 of the ingestion intelligence including the information related to the ingestion by the particular individual living being of at least one of the one or more selected ingestible products regarding one or more apparel worn by the particular individual living being, etc.).

In one or more implementations, operation o12 includes an operation o1217 for electronically directing control at least in part of the acquisition of the ingestion intelligence including the information related to the ingestion by the particular individual living being of at least one of the one or more selected ingestible products regarding degree of animation by the particular individual living being. An exemplary version of a non-transitory signal bearing medium of information storage subsystem s200 is depicted as bearing one or more control acquisition animation instructions i1217 that when executed will direct performance of the operation o1217. In an implementation, the one or more control acquisition animation instructions i1217 when executed direct electronically directing control at least in part of the acquisition of the ingestion intelligence including the information related to the ingestion by the particular individual living being of at least one of the one or more selected ingestible products regarding degree of animation by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding degree of animation by the particular individual living being, etc.). Furthermore, the control acquisition animation electrical circuitry arrangement e1217 when activated will perform the operation o1217. In an implementation, the control acquisition animation electrical circuitry arrangement e1217, when activated performs electronically directing control at least in part of the acquisition of the ingestion intelligence including the information related to the ingestion by the particular individual living being of at least one of the one or more selected ingestible products regarding degree of animation by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding degree of animation by the particular individual living being, etc.). In an implementation, the electronically directing control at least in part of the acquisition of the ingestion intelligence including the information related to the ingestion by the particular individual living being of at least one of the one or more selected ingestible products regarding degree of animation by the particular individual living being is carried out by electronically directing control at least in part of the acquisition of the ingestion intelligence including the information related to the ingestion by the particular individual living being of at least one of the one or more selected ingestible products regarding degree of animation by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding degree of animation by the particular individual living being, etc.).

In one or more implementations, operation o12 includes an operation o1218 for electronically directing control at least in part of the acquisition of the ingestion intelligence including the information related to the ingestion by the particular individual living being of at least one of the one or more selected ingestible products regarding material combinations ingested by the particular individual living being. An exemplary version of a non-transitory signal bearing medium of information storage subsystem s200 is depicted as bearing one or more control acquisition combinations instructions i1218 that when executed will direct performance of the operation o1218. In an implementation, the one or more control acquisition combinations instructions i1218 when executed direct electronically directing control at least in part of the acquisition of the ingestion intelligence including the information related to the ingestion by the particular individual living being of at least one of the one or more selected ingestible products regarding material combinations ingested by the particular individual living being (e.g. an implementation of the microprocessor component s102 is configured to electronically control at least in part the acquisition such as through chemical sensing component s416 and recognition application implemented by the microprocessor component s102 of the ingestion intelligence including the information related to the ingestion by the particular individual living being of at least one of the one or more selected ingestible products regarding material combinations ingested by the particular individual living being, etc.). Furthermore, the control acquisition combinations electrical circuitry arrangement e1218 when activated will perform the operation o1218. In an implementation, the control acquisition combinations electrical circuitry arrangement e1218, when activated performs electronically directing control at least in part of the acquisition of the ingestion intelligence including the information related to the ingestion by the particular individual living being of at least one of the one or more selected ingestible products regarding material combinations ingested by the particular individual living being (e.g. an implementation of the microprocessor component s102 is configured to electronically control at least in part the acquisition such as through chemical sensing component s416 and recognition application implemented by the microprocessor component s102 of the ingestion intelligence including the information related to the ingestion by the particular individual living being of at least one of the one or more selected ingestible products regarding material combinations ingested by the particular individual living being, etc.). In an implementation, the electronically directing control at least in part of the acquisition of the ingestion intelligence including the information related to the ingestion by the particular individual living being of at least one of the one or more selected ingestible products regarding material combinations ingested by the particular individual living being is carried out by electronically directing control at least in part of the acquisition of the ingestion intelligence including the information related to the ingestion by the particular individual living being of at least one of the one or more selected ingestible products regarding material combinations ingested by the particular individual living being (e.g. an implementation of the microprocessor component s102 is configured to electronically control at least in part the acquisition such as through chemical sensing component s416 and recognition application implemented by the microprocessor component s102 of the ingestion intelligence including the information related to the ingestion by the particular individual living being of at least one of the one or more selected ingestible products regarding material combinations ingested by the particular individual living being, etc.).

In one or more implementations, as shown in FIG. 88, operation o12 includes an operation o1219 for electronically directing control at least in part of the acquisition of the ingestion intelligence including the information related to the ingestion by the particular individual living being of at least one of the one or more selected ingestible products regarding demographics of the particular individual living being. An exemplary version of a non-transitory signal bearing medium of information storage subsystem s200 is depicted as bearing one or more control acquisition demographics instructions i1219 that when executed will direct performance of the operation o1219. In an implementation, the one or more control acquisition demographics instructions i1219 when executed direct electronically directing control at least in part of the acquisition of the ingestion intelligence including the information related to the ingestion by the particular individual living being of at least one of the one or more selected ingestible products regarding demographics of the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding demographics of the particular individual living being, etc.). Furthermore, the control acquisition demographics electrical circuitry arrangement e1219 when activated will perform the operation o1219. In an implementation, the control acquisition demographics electrical circuitry arrangement e1219, when activated performs electronically directing control at least in part of the acquisition of the ingestion intelligence including the information related to the ingestion by the particular individual living being of at least one of the one or more selected ingestible products regarding demographics of the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding demographics of the particular individual living being, etc.). In an implementation, the electronically directing control at least in part of the acquisition of the ingestion intelligence including the information related to the ingestion by the particular individual living being of at least one of the one or more selected ingestible products regarding demographics of the particular individual living being is carried out by electronically directing control at least in part of the acquisition of the ingestion intelligence including the information related to the ingestion by the particular individual living being of at least one of the one or more selected ingestible products regarding demographics of the particular individual living being (e.g. an implementation of the microprocessor component s102 is configured to electronically control at least in part the acquisition of the ingestion intelligence such as through disk farm component s224 including the information related to the ingestion by the particular individual living being of at least one of the one or more selected ingestible products regarding demographics of the particular individual living being, etc.).

In one or more implementations, operation o12 includes an operation o1220 for electronically directing control at least in part of the acquisition of the ingestion intelligence including the information related to the ingestion by the particular individual living being within the second vicinity as within an interior of a dispensing machine housing. An exemplary version of a non-transitory signal bearing medium of information storage subsystem s200 is depicted as bearing one or more second vicinity housing instructions i1220 that when executed will direct performance of the operation o1220. In an implementation, the one or more second vicinity housing instructions i1220 when executed direct electronically directing control at least in part of the acquisition of the ingestion intelligence including the information related to the ingestion by the particular individual living being within the second vicinity as within an interior of a dispensing machine housing (e.g. an implementation of the microprocessor component s102 is configured through the electronic communication subsystem 500 to electronically direct control at least in part of the acquisition of the ingestion intelligence within the second vicinity as within the interior of the digestible product preparation system 10 that uses for instance visual display component s304 to electronically output the electronically generated one or more selection menus, etc.). Furthermore, the second vicinity housing electrical circuitry arrangement e1220 when activated will perform the operation o1220. In an implementation, the second vicinity housing electrical circuitry arrangement e1220, when activated performs electronically directing control at least in part of the acquisition of the ingestion intelligence including the information related to the ingestion by the particular individual living being within the second vicinity as within an interior of a dispensing machine housing (e.g. an implementation of the microprocessor component s102 is configured through the electronic communication subsystem 500 to electronically direct control at least in part of the acquisition of the ingestion intelligence within the second vicinity as within the interior of the digestible product preparation system 10 that uses for instance visual display component s304 to electronically output the electronically generated one or more selection menus, etc.). In an implementation, the electronically directing control at least in part of the acquisition of the ingestion intelligence including the information related to the ingestion by the particular individual living being within the second vicinity as within an interior of a dispensing machine housing is carried out by electronically directing control at least in part of the acquisition of the ingestion intelligence including the information related to the ingestion by the particular individual living being within the second vicinity as within an interior of a dispensing machine housing (e.g. an implementation of the microprocessor component s102 is configured through the electronic communication subsystem 500 to electronically direct control at least in part of the acquisition of the ingestion intelligence within the second vicinity as within the interior of the digestible product preparation system 10 that uses for instance visual display component s304 to electronically output the electronically generated one or more selection menus, etc.).

In one or more implementations, operation o12 includes an operation o1221 for electronically directing control at least in part of the acquisition of the ingestion intelligence including the information related to the ingestion by the particular individual living being within the second vicinity as within an interior of a architectural building containing a dispensing machine. An exemplary version of a non-transitory signal bearing medium of information storage subsystem s200 is depicted as bearing one or more second vicinity building instructions i1221 that when executed will direct performance of the operation o1221. In an implementation, the one or more second vicinity building instructions i1221 when executed direct electronically directing control at least in part of the acquisition of the ingestion intelligence including the information related to the ingestion by the particular individual living being within the second vicinity as within an interior of a architectural building containing a dispensing machine (e.g. an implementation of the microprocessor component s102 is configured through the electronic communication subsystem 500 to electronically direct control at least in part of the acquisition of the ingestion intelligence within the second vicinity as within the interior of an airport wherein the digestible product preparation system 10 is located that communicates with for instance the visual display component s304 to electronically output the electronically generated one or more selection menus also within the airport, etc.). Furthermore, the second vicinity building electrical circuitry arrangement e1221 when activated will perform the operation o1221. In an implementation, the second vicinity building electrical circuitry arrangement e1221, when activated performs electronically directing control at least in part of the acquisition of the ingestion intelligence including the information related to the ingestion by the particular individual living being within the second vicinity as within an interior of a architectural building containing a dispensing machine (e.g. an implementation of the microprocessor component s102 is configured through the electronic communication subsystem 500 to electronically direct control at least in part of the acquisition of the ingestion intelligence within the second vicinity as within the interior of an airport wherein the digestible product preparation system 10 is located that communicates with for instance the visual display component s304 to electronically output the electronically generated one or more selection menus also within the airport, etc.). In an implementation, the electronically directing control at least in part of the acquisition of the ingestion intelligence including the information related to the ingestion by the particular individual living being within the second vicinity as within an interior of a architectural building containing a dispensing machine is carried out by electronically directing control at least in part of the acquisition of the ingestion intelligence including the information related to the ingestion by the particular individual living being within the second vicinity as within an interior of a architectural building containing a dispensing machine (e.g. an implementation of the microprocessor component s102 is configured through the electronic communication subsystem 500 to electronically direct control at least in part of the acquisition of the ingestion intelligence within the second vicinity as within the interior of an airport wherein the digestible product preparation system 10 is located that communicates with for instance the visual display component s304 to electronically output the electronically generated one or more selection menus also within the airport, etc.).

In one or more implementations, as shown in FIG. 89, operation o12 includes an operation o1222 for electronically directing control at least in part of the acquisition of the ingestion intelligence including the information related to the ingestion by the particular individual living being within the second vicinity as within a food court of a shopping mall. An exemplary version of a non-transitory signal bearing medium of information storage subsystem s200 is depicted as bearing one or more second vicinity mall instructions i1222 that when executed will direct performance of the operation o1222. In an implementation, the one or more second vicinity mall instructions i1222 when executed direct electronically directing control at least in part of the acquisition of the ingestion intelligence including the information related to the ingestion by the particular individual living being within the second vicinity as within a food court of a shopping mall (i.e. an implementation of the microprocessor component s102 is configured through the electronic communication subsystem 500 to electronically direct control at least in part of the acquisition of the ingestion intelligence within the second vicinity as within the food court of the shopping mall wherein the digestible product preparation system 10 is located that communicates with for instance the visual display component s304 to electronically output the electronically generated one or more selection menus also within the food court of the shopping mall, etc.). Furthermore, the second vicinity mall electrical circuitry arrangement e1222 when activated will perform the operation o1222. In an implementation, the second vicinity mall electrical circuitry arrangement e1222, when activated performs electronically directing control at least in part of the acquisition of the ingestion intelligence including the information related to the ingestion by the particular individual living being within the second vicinity as within a food court of a shopping mall (i.e. an implementation of the microprocessor component s102 is configured through the electronic communication subsystem 500 to electronically direct control at least in part of the acquisition of the ingestion intelligence within the second vicinity as within the food court of the shopping mall wherein the digestible product preparation system 10 is located that communicates with for instance the visual display component s304 to electronically output the electronically generated one or more selection menus also within the food court of the shopping mall, etc.). In an implementation, the electronically directing control at least in part of the acquisition of the ingestion intelligence including the information related to the ingestion by the particular individual living being within the second vicinity as within a food court of a shopping mall is carried out by electronically directing control at least in part of the acquisition of the ingestion intelligence including the information related to the ingestion by the particular individual living being within the second vicinity as within a food court of a shopping mall (i.e. an implementation of the microprocessor component s102 is configured through the electronic communication subsystem 500 to electronically direct control at least in part of the acquisition of the ingestion intelligence within the second vicinity as within the food court of the shopping mall wherein the digestible product preparation system 10 is located that communicates with for instance the visual display component s304 to electronically output the electronically generated one or more selection menus also within the food court of the shopping mall, etc.)

In one or more implementations, operation o12 includes an operation o1223 for electronically directing control at least in part of the acquisition of the ingestion intelligence including the information related to the ingestion by the particular individual living being within the second vicinity as within an interior of a restaurant. An exemplary version of a non-transitory signal bearing medium of information storage subsystem s200 is depicted as bearing one or more second vicinity restaurant instructions i1223 that when executed will direct performance of the operation o1223. In an implementation, the one or more second vicinity restaurant instructions i1223 when executed direct electronically directing control at least in part of the acquisition of the ingestion intelligence including the information related to the ingestion by the particular individual living being within the second vicinity as within an interior of a restaurant (i.e. an implementation of the microprocessor component s102 is configured through the electronic communication subsystem 500 to electronically direct control at least in part of the acquisition of the ingestion intelligence within the second vicinity as within the interior of the restaurant wherein the digestible product preparation system 10 is located that communicates with for instance the visual display component s304 to electronically output the electronically generated one or more selection menus also within the restaurant, etc.). Furthermore, the second vicinity restaurant electrical circuitry arrangement e1223 when activated will perform the operation o1223. In an implementation, the second vicinity restaurant electrical circuitry arrangement e1223, when activated performs electronically directing control at least in part of the acquisition of the ingestion intelligence including the information related to the ingestion by the particular individual living being within the second vicinity as within an interior of a restaurant (i.e. an implementation of the microprocessor component s102 is configured through the electronic communication subsystem 500 to electronically direct control at least in part of the acquisition of the ingestion intelligence within the second vicinity as within the interior of the restaurant wherein the digestible product preparation system 10 is located that communicates with for instance the visual display component s304 to electronically output the electronically generated one or more selection menus also within the restaurant, etc.). In an implementation, the electronically directing control at least in part of the acquisition of the ingestion intelligence including the information related to the ingestion by the particular individual living being within the second vicinity as within an interior of a restaurant is carried out by electronically directing control at least in part of the acquisition of the ingestion intelligence including the information related to the ingestion by the particular individual living being within the second vicinity as within an interior of a restaurant (i.e. an implementation of the microprocessor component s102 is configured through the electronic communication subsystem 500 to electronically direct control at least in part of the acquisition of the ingestion intelligence within the second vicinity as within the interior of the restaurant wherein the digestible product preparation system 10 is located that communicates with for instance the visual display component s304 to electronically output the electronically generated one or more selection menus also within the restaurant, etc.).

In one or more implementations, operation o12 includes an operation o1224 for electronically directing control at least in part of the acquisition of the ingestion intelligence including the information related to the ingestion by the particular individual living being within the second vicinity as within an interior of an airplane. An exemplary version of a non-transitory signal bearing medium of information storage subsystem s200 is depicted as bearing one or more second vicinity airplane instructions i1224 that when executed will direct performance of the operation o1224. In an implementation, the one or more second vicinity airplane instructions i1224 when executed direct electronically directing control at least in part of the acquisition of the ingestion intelligence including the information related to the ingestion by the particular individual living being within the second vicinity as within an interior of an airplane (i.e. an implementation of the microprocessor component s102 is configured through the electronic communication subsystem 500 to electronically direct control at least in part of the acquisition of the ingestion intelligence within the second vicinity as within the interior of the airplane wherein the digestible product preparation system 10 is located that communicates with for instance the visual display component s304 to electronically output the electronically generated one or more selection menus also within the airplane, etc.). Furthermore, the second vicinity airplane electrical circuitry arrangement e1224 when activated will perform the operation o1224. In an implementation, the second vicinity airplane electrical circuitry arrangement e1224, when activated performs electronically directing control at least in part of the acquisition of the ingestion intelligence including the information related to the ingestion by the particular individual living being within the second vicinity as within an interior of an airplane (i.e. an implementation of the microprocessor component s102 is configured through the electronic communication subsystem 500 to electronically direct control at least in part of the acquisition of the ingestion intelligence within the second vicinity as within the interior of the airplane wherein the digestible product preparation system 10 is located that communicates with for instance the visual display component s304 to electronically output the electronically generated one or more selection menus also within the airplane, etc.). In an implementation, the electronically directing control at least in part of the acquisition of the ingestion intelligence including the information related to the ingestion by the particular individual living being within the second vicinity as within an interior of an airplane is carried out by electronically directing control at least in part of the acquisition of the ingestion intelligence including the information related to the ingestion by the particular individual living being within the second vicinity as within an interior of an airplane (i.e. an implementation of the microprocessor component s102 is configured through the electronic communication subsystem 500 to electronically direct control at least in part of the acquisition of the ingestion intelligence within the second vicinity as within the interior of the airplane wherein the digestible product preparation system 10 is located that communicates with for instance the visual display component s304 to electronically output the electronically generated one or more selection menus also within the airplane, etc.).

In one or more implementations, as shown in FIG. 90, operation o12 includes an operation o1225 for electronically directing control at least in part of the acquisition of the ingestion intelligence including the information related to the ingestion by the particular individual living being of at least one of the one or more selected ingestible products regarding air temperature associated with environs of the ingestion by the particular individual living being. An exemplary version of a non-transitory signal bearing medium of information storage subsystem s200 is depicted as bearing one or more second vicinity vehicle instructions i1225 that when executed will direct performance of the operation o1225. In an implementation, the one or more second vicinity vehicle instructions i1225 when executed direct electronically directing control at least in part of the acquisition of the ingestion intelligence including the information related to the ingestion by the particular individual living being within the second vicinity as within an interior of a ground vehicle (i.e. an implementation of the microprocessor component s102 is configured through the electronic communication subsystem 500 to electronically direct control at least in part of the acquisition of the ingestion intelligence within the second vicinity as within the interior of the ground vehicle wherein the digestible product preparation system 10 is located that communicates with for instance the visual display component s304 to electronically output the electronically generated one or more selection menus also within the ground vehicle, etc.). Furthermore, the second vicinity vehicle electrical circuitry arrangement e1225 when activated will perform the operation o1225. In an implementation, the second vicinity vehicle electrical circuitry arrangement e1225, when activated performs electronically directing control at least in part of the acquisition of the ingestion intelligence including the information related to the ingestion by the particular individual living being within the second vicinity as within an interior of a ground vehicle (i.e. an implementation of the microprocessor component s102 is configured through the electronic communication subsystem 500 to electronically direct control at least in part of the acquisition of the ingestion intelligence within the second vicinity as within the interior of the ground vehicle wherein the digestible product preparation system 10 is located that communicates with for instance the visual display component s304 to electronically output the electronically generated one or more selection menus also within the ground vehicle, etc.). In an implementation, the electronically directing control at least in part of the acquisition of the ingestion intelligence including the information related to the ingestion by the particular individual living being within the second vicinity as within an interior of a ground vehicle is carried out by electronically directing control at least in part of the acquisition of the ingestion intelligence including the information related to the ingestion by the particular individual living being within the second vicinity as within an interior of a ground vehicle (i.e. an implementation of the microprocessor component s102 is configured through the electronic communication subsystem 500 to electronically direct control at least in part of the acquisition of the ingestion intelligence within the second vicinity as within the interior of the ground vehicle wherein the digestible product preparation system 10 is located that communicates with for instance the visual display component s304 to electronically output the electronically generated one or more selection menus also within the ground vehicle, etc.)

In one or more implementations, operation o12 includes an operation o1226 for electronically directing control at least in part of the acquisition of the ingestion intelligence including the information related to the ingestion by the particular individual living being within the second vicinity as within a multi-state territory. An exemplary version of a non-transitory signal bearing medium of information storage subsystem s200 is depicted as bearing one or more second vicinity territory instructions i1226 that when executed will direct performance of the operation o1226. In an implementation, the one or more second vicinity territory instructions i1226 when executed direct electronically directing control at least in part of the acquisition of the ingestion intelligence including the information related to the ingestion by the particular individual living being within the second vicinity as within a multi-state territory (i.e. an implementation of the microprocessor component s102 is configured through the electronic communication subsystem 500 to electronically direct control at least in part of the acquisition of the ingestion intelligence within the second vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). Furthermore, the second vicinity territory electrical circuitry arrangement e1226 when activated will perform the operation o1226. In an implementation, the second vicinity territory electrical circuitry arrangement e1226, when activated performs electronically directing control at least in part of the acquisition of the ingestion intelligence including the information related to the ingestion by the particular individual living being within the second vicinity as within a multi-state territory (i.e. an implementation of the microprocessor component s102 is configured through the electronic communication subsystem 500 to electronically direct control at least in part of the acquisition of the ingestion intelligence within the second vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). In an implementation, the electronically directing control at least in part of the acquisition of the ingestion intelligence including the information related to the ingestion by the particular individual living being within the second vicinity as within a multi-state territory is carried out by electronically directing control at least in part of the acquisition of the ingestion intelligence including the information related to the ingestion by the particular individual living being within the second vicinity as within a multi-state territory (i.e. an implementation of the microprocessor component s102 is configured through the electronic communication subsystem 500 to electronically direct control at least in part of the acquisition of the ingestion intelligence within the second vicinity as within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.).

In one or more implementations, operation o12 includes an operation o1227 for electronically directing control at least in part of the acquisition of the ingestion intelligence including the information related to the ingestion by the particular individual living being within the second vicinity as within an international region. An exemplary version of a non-transitory signal bearing medium of information storage subsystem s200 is depicted as bearing one or more second vicinity region instructions i1227 that when executed will direct performance of the operation o1227. In an implementation, the one or more second vicinity region instructions i1227 when executed direct electronically directing control at least in part of the acquisition of the ingestion intelligence including the information related to the ingestion by the particular individual living being within the second vicinity as within an international region (i.e. an implementation of the microprocessor component s102 is configured through the electronic communication subsystem 500 to electronically direct control at least in part of the acquisition of the ingestion intelligence within the second vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.). Furthermore, the second vicinity region electrical circuitry arrangement e1227 when activated will perform the operation o1227. In an implementation, the second vicinity region electrical circuitry arrangement e1227, when activated performs electronically directing control at least in part of the acquisition of the ingestion intelligence including the information related to the ingestion by the particular individual living being within the second vicinity as within an international region (i.e. an implementation of the microprocessor component s102 is configured through the electronic communication subsystem 500 to electronically direct control at least in part of the acquisition of the ingestion intelligence within the second vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.). In an implementation, the electronically directing control at least in part of the acquisition of the ingestion intelligence including the information related to the ingestion by the particular individual living being within the second vicinity as within an international region is carried out by electronically directing control at least in part of the acquisition of the ingestion intelligence including the information related to the ingestion by the particular individual living being within the second vicinity as within an international region (i.e. an implementation of the microprocessor component s102 is configured through the electronic communication subsystem 500 to electronically direct control at least in part of the acquisition of the ingestion intelligence within the second vicinity as within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.).

In one or more implementations, as shown in FIG. 91, operation o12 includes an operation o1228 for electronically directing control at least in part of the acquisition of the ingestion intelligence including the information related to the ingestion by the particular individual living being of at least one of the one or more selected ingestible products regarding one or more details of conversation by the particular individual living being. An exemplary version of a non-transitory signal bearing medium of information storage subsystem s200 is depicted as bearing one or more acquisition conversation instructions i1228 that when executed will direct performance of the operation o1228. In an implementation, the one or more acquisition conversation instructions i1228 when executed direct electronically directing control at least in part of the acquisition of the ingestion intelligence including the information related to the ingestion by the particular individual living being of at least one of the one or more selected ingestible products regarding one or more details of conversation by the particular individual living being (e.g. an implementation of the microprocessor component s102 is configured to electronically control at least in part the acquisition such as through sound sensing component s420 and recognition application implemented by microprocessor component s102 of the ingestion intelligence including the information related to the ingestion by the particular individual living being of at least one of the one or more selected ingestible products regarding one or more details of conversation by the particular individual living being, etc.). Furthermore, the acquisition conversation electrical circuitry arrangement e1228 when activated will perform the operation o1228. In an implementation, the acquisition conversation electrical circuitry arrangement e1228, when activated performs electronically directing control at least in part of the acquisition of the ingestion intelligence including the information related to the ingestion by the particular individual living being of at least one of the one or more selected ingestible products regarding one or more details of conversation by the particular individual living being (e.g. an implementation of the microprocessor component s102 is configured to electronically control at least in part the acquisition such as through sound sensing component s420 and recognition application implemented by microprocessor component s102 of the ingestion intelligence including the information related to the ingestion by the particular individual living being of at least one of the one or more selected ingestible products regarding one or more details of conversation by the particular individual living being, etc.). In an implementation, the electronically directing control at least in part of the acquisition of the ingestion intelligence including the information related to the ingestion by the particular individual living being of at least one of the one or more selected ingestible products regarding one or more details of conversation by the particular individual living being is carried out by electronically directing control at least in part of the acquisition of the ingestion intelligence including the information related to the ingestion by the particular individual living being of at least one of the one or more selected ingestible products regarding one or more details of conversation by the particular individual living being (e.g. an implementation of the microprocessor component s102 is configured to electronically control at least in part the acquisition such as through sound sensing component s420 and recognition application implemented by microprocessor component s102 of the ingestion intelligence including the information related to the ingestion by the particular individual living being of at least one of the one or more selected ingestible products regarding one or more details of conversation by the particular individual living being, etc.)

In one or more implementations, operation o12 includes an operation o1229 for electronically directing control at least in part of the acquisition of the ingestion intelligence including the information related to the ingestion by the particular individual living being of at least one of the one or more selected ingestible products regarding gratuity execution by the particular individual living being. An exemplary version of a non-transitory signal bearing medium of information storage subsystem s200 is depicted as bearing one or more acquisition gratuity instructions i1229 that when executed will direct performance of the operation o1229. In an implementation, the one or more acquisition gratuity instructions i1229 when executed direct electronically directing control at least in part of the acquisition of the ingestion intelligence including the information related to the ingestion by the particular individual living being of at least one of the one or more selected ingestible products regarding gratuity execution by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding gratuity execution by the particular individual living being, etc.). Furthermore, the acquisition gratuity electrical circuitry arrangement e1229 when activated will perform the operation o1229. In an implementation, the acquisition gratuity electrical circuitry arrangement e1229, when activated performs electronically directing control at least in part of the acquisition of the ingestion intelligence including the information related to the ingestion by the particular individual living being of at least one of the one or more selected ingestible products regarding gratuity execution by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding gratuity execution by the particular individual living being, etc.). In an implementation, the electronically directing control at least in part of the acquisition of the ingestion intelligence including the information related to the ingestion by the particular individual living being of at least one of the one or more selected ingestible products regarding gratuity execution by the particular individual living being is carried out by electronically directing control at least in part of the acquisition of the ingestion intelligence including the information related to the ingestion by the particular individual living being of at least one of the one or more selected ingestible products regarding gratuity execution by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding gratuity execution by the particular individual living being, etc.).

In one or more implementations, operation o12 includes an operation o1230 for electronically directing control at least in part of the acquisition of the ingestion intelligence including the information related to the ingestion by the particular individual living being of at least one of the one or more selected ingestible products regarding one or more details regarding financial status of the particular individual living being. An exemplary version of a non-transitory signal bearing medium of information storage subsystem s200 is depicted as bearing one or more acquisition financial instructions i1230 that when executed will direct performance of the operation o1230. In an implementation, the one or more acquisition financial instructions i1230 when executed direct electronically directing control at least in part of the acquisition of the ingestion intelligence including the information related to the ingestion by the particular individual living being of at least one of the one or more selected ingestible products regarding one or more details regarding financial status of the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding financial status by the particular individual living being, etc.). Furthermore, the acquisition financial electrical circuitry arrangement e1230 when activated will perform the operation o1230. In an implementation, the acquisition financial electrical circuitry arrangement e1230, when activated performs electronically directing control at least in part of the acquisition of the ingestion intelligence including the information related to the ingestion by the particular individual living being of at least one of the one or more selected ingestible products regarding one or more details regarding financial status of the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding financial status by the particular individual living being, etc.). In an implementation, the electronically directing control at least in part of the acquisition of the ingestion intelligence including the information related to the ingestion by the particular individual living being of at least one of the one or more selected ingestible products regarding one or more details regarding financial status of the particular individual living being is carried out by electronically directing control at least in part of the acquisition of the ingestion intelligence including the information related to the ingestion by the particular individual living being of at least one of the one or more selected ingestible products regarding one or more details regarding financial status of the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding financial status by the particular individual living being, etc.).

Figure 92:
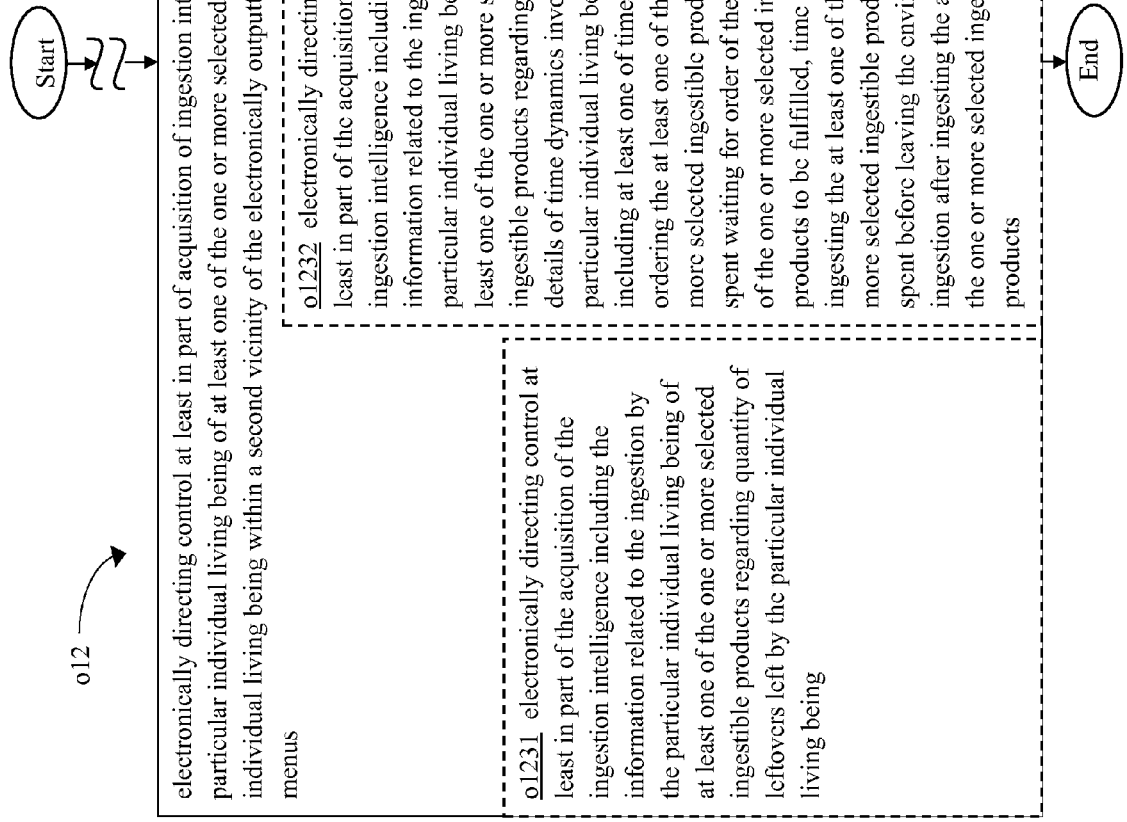
FIG. 92 is a high-level flowchart including exemplary implementations of operation O12 of FIG. 46.

In one or more implementations, as shown in FIG. 92, operation o12 includes an operation o1231 for electronically directing control at least in part of the acquisition of the ingestion intelligence including the information related to the ingestion by the particular individual living being of at least one of the one or more selected ingestible products regarding quantity of leftovers left by the particular individual living being. An exemplary version of a non-transitory signal bearing medium of information storage subsystem s200 is depicted as bearing one or more acquisition leftovers instructions i1231 that when executed will direct performance of the operation o1231. In an implementation, the one or more acquisition leftovers instructions i1231 when executed direct electronically directing control at least in part of the acquisition of the ingestion intelligence including the information related to the ingestion by the particular individual living being of at least one of the one or more selected ingestible products regarding quantity of leftovers left by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding quantity of leftovers left by the particular individual living being, etc.). Furthermore, the acquisition leftovers electrical circuitry arrangement e1231 when activated will perform the operation o1231. In an implementation, the acquisition leftovers electrical circuitry arrangement e1231, when activated performs electronically directing control at least in part of the acquisition of the ingestion intelligence including the information related to the ingestion by the particular individual living being of at least one of the one or more selected ingestible products regarding quantity of leftovers left by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding quantity of leftovers left by the particular individual living being, etc.). In an implementation, the electronically directing control at least in part of the acquisition of the ingestion intelligence including the information related to the ingestion by the particular individual living being of at least one of the one or more selected ingestible products regarding quantity of leftovers left by the particular individual living being is carried out by electronically directing control at least in part of the acquisition of the ingestion intelligence including the information related to the ingestion by the particular individual living being of at least one of the one or more selected ingestible products regarding quantity of leftovers left by the particular individual living being (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding quantity of leftovers left by the particular individual living being, etc.)

In one or more implementations, operation o12 includes an operation o1232 for electronically directing control at least in part of the acquisition of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs of ingestion after ingesting the at least one of the one or more selected ingestible products. An exemplary version of a non-transitory signal bearing medium of information storage subsystem s200 is depicted as bearing one or more acquisition time instructions i1232 that when executed will direct performance of the operation o1232. In an implementation, the one or more acquisition time instructions i1232 when executed direct electronically directing control at least in part of the acquisition of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs of ingestion after ingesting the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs such as a restaurant of ingestion after ingesting the at least one of the one or more selected ingestible products, etc.). Furthermore, the acquisition time electrical circuitry arrangement e1232 when activated will perform the operation o1232. In an implementation, the acquisition time electrical circuitry arrangement e1232, when activated performs electronically directing control at least in part of the acquisition of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs of ingestion after ingesting the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs such as a restaurant of ingestion after ingesting the at least one of the one or more selected ingestible products, etc.). In an implementation, the electronically directing control at least in part of the acquisition of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs of ingestion after ingesting the at least one of the one or more selected ingestible products is carried out by electronically directing control at least in part of the acquisition of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs of ingestion after ingesting the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding one or more details of time dynamics involving the particular individual living being including at least one of time spent ordering the at least one of the one or more selected ingestible products, time spent waiting for order of the at least one of the one or more selected ingestible products to be fulfilled, time spent ingesting the at least one of the one or more selected ingestible products, time spent before leaving the environs such as a restaurant of ingestion after ingesting the at least one of the one or more selected ingestible products, etc.).

In one or more implementations, operation o12 includes an operation o1233 for electronically directing control at least in part of the acquisition of the ingestion intelligence including the information related to the ingestion by the particular individual living being of at least one of the one or more selected ingestible products regarding one or more details regarding the type of dining party being attended by the particular individual living being during ingestion by the particular individual living being of the at least one of the one or more selected ingestible products. An exemplary version of a non-transitory signal bearing medium of information storage subsystem s200 is depicted as bearing one or more acquisition party instructions i1233 that when executed will direct performance of the operation o1233. In an implementation, the one or more acquisition party instructions i1233 when executed direct electronically directing control at least in part of the acquisition of the ingestion intelligence including the information related to the ingestion by the particular individual living being of at least one of the one or more selected ingestible products regarding one or more details regarding the type of dining party being attended by the particular individual living being during ingestion by the particular individual living being of the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding the type of dining party being attended, such as formal, business, casual, celebratory, etc., by the particular individual living being during ingestion by the particular individual living being of the at least one of the one or more selected ingestible products, etc.). Furthermore, the acquisition party electrical circuitry arrangement e1233 when activated will perform the operation o1233. In an implementation, the acquisition party electrical circuitry arrangement e1233, when activated performs electronically directing control at least in part of the acquisition of the ingestion intelligence including the information related to the ingestion by the particular individual living being of at least one of the one or more selected ingestible products regarding one or more details regarding the type of dining party being attended by the particular individual living being during ingestion by the particular individual living being of the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding the type of dining party being attended, such as formal, business, casual, celebratory, etc., by the particular individual living being during ingestion by the particular individual living being of the at least one of the one or more selected ingestible products, etc.). In an implementation, the electronically directing control at least in part of the acquisition of the ingestion intelligence including the information related to the ingestion by the particular individual living being of at least one of the one or more selected ingestible products regarding one or more details regarding the type of dining party being attended by the particular individual living being during ingestion by the particular individual living being of the at least one of the one or more selected ingestible products is carried out by electronically directing control at least in part of the acquisition of the ingestion intelligence including the information related to the ingestion by the particular individual living being of at least one of the one or more selected ingestible products regarding one or more details regarding the type of dining party being attended by the particular individual living being during ingestion by the particular individual living being of the at least one of the one or more selected ingestible products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products regarding the type of dining party being attended, such as formal, business, casual, celebratory, etc., by the particular individual living being during ingestion by the particular individual living being of the at least one of the one or more selected ingestible products, etc.).

Figure 93:
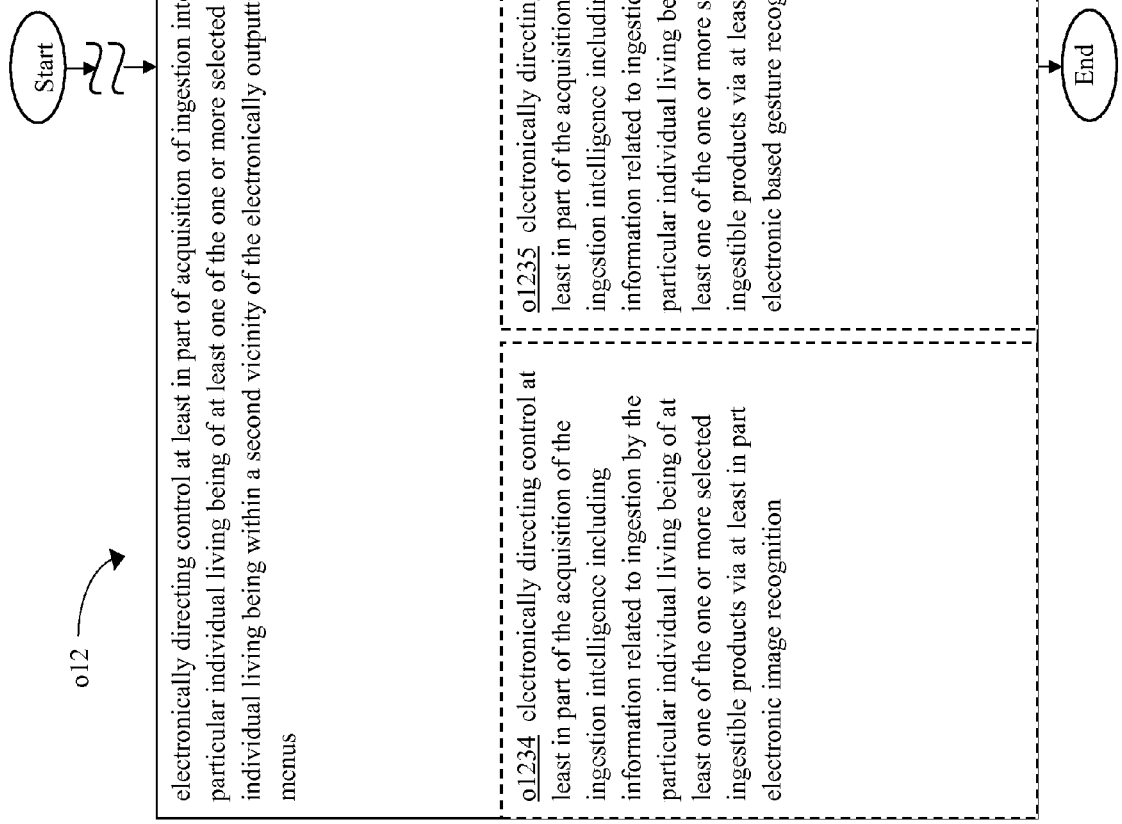
FIG. 93 is a high-level flowchart including exemplary implementations of operation O12 of FIG. 46.

In one or more implementations, as shown in FIG. 93, operation o12 includes an operation o1234 for electronically directing control at least in part of the acquisition of the ingestion intelligence including information related to ingestion by the particular individual living being of at least one of the one or more selected ingestible products via at least in part electronic image recognition. An exemplary version of a non-transitory signal bearing medium of information storage subsystem s200 is depicted as bearing one or more acquisition image instructions i1234 that when executed will direct performance of the operation o1234. In an implementation, the one or more acquisition image instructions i1234 when executed direct electronically directing control at least in part of the acquisition of the ingestion intelligence including information related to ingestion by the particular individual living being of at least one of the one or more selected ingestible products via at least in part electronic image recognition products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as the image recognition application implemented by the microprocessor component s102, etc.). Furthermore, the acquisition image electrical circuitry arrangement e1234 when activated will perform the operation o1234. In an implementation, the acquisition image electrical circuitry arrangement e1234, when activated performs electronically directing control at least in part of the acquisition of the ingestion intelligence including information related to ingestion by the particular individual living being of at least one of the one or more selected ingestible products via at least in part electronic image recognition products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as the image recognition application implemented by the microprocessor component s102, etc.). In an implementation, the electronically directing control at least in part of the acquisition of the ingestion intelligence including information related to ingestion by the particular individual living being of at least one of the one or more selected ingestible products via at least in part electronic image recognition is carried out by electronically directing control at least in part of the acquisition of the ingestion intelligence including information related to ingestion by the particular individual living being of at least one of the one or more selected ingestible products via at least in part electronic image recognition products (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as the image recognition application implemented by the microprocessor component s102, etc.)

In one or more implementations, operation o12 includes an operation o1235 for electronically directing control at least in part of the acquisition of the ingestion intelligence including information related to ingestion by the particular individual living being of at least one of the one or more selected ingestible products via at least in part electronic based gesture recognition. An exemplary version of a non-transitory signal bearing medium of information storage subsystem s200 is depicted as bearing one or more acquisition gesture instructions i1235 that when executed will direct performance of the operation o1235. In an implementation, the one or more acquisition gesture instructions i1235 when executed direct electronically directing control at least in part of the acquisition of the ingestion intelligence including information related to ingestion by the particular individual living being of at least one of the one or more selected ingestible products via at least in part electronic based gesture recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a gesture recognition application implemented by the microprocessor component s102, etc.). Furthermore, the acquisition gesture electrical circuitry arrangement e1235 when activated will perform the operation o1235. In an implementation, the acquisition gesture electrical circuitry arrangement e1235, when activated performs electronically directing control at least in part of the acquisition of the ingestion intelligence including information related to ingestion by the particular individual living being of at least one of the one or more selected ingestible products via at least in part electronic based gesture recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a gesture recognition application implemented by the microprocessor component s102, etc.). In an implementation, the electronically directing control at least in part of the acquisition of the ingestion intelligence including information related to ingestion by the particular individual living being of at least one of the one or more selected ingestible products via at least in part electronic based gesture recognition is carried out by electronically directing control at least in part of the acquisition of the ingestion intelligence including information related to ingestion by the particular individual living being of at least one of the one or more selected ingestible products via at least in part electronic based gesture recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a gesture recognition application implemented by the microprocessor component s102, etc.).

In one or more implementations, operation o12 includes an operation o1236 for electronically directing control at least in part of the acquisition of the ingestion intelligence including information related to ingestion by the particular individual living being of at least one of the one or more selected ingestible products via at least in part electronic speech recognition. An exemplary version of a non-transitory signal bearing medium of information storage subsystem s200 is depicted as bearing one or more acquisition speech instructions i1236 that when executed will direct performance of the operation o1236. In an implementation, the one or more acquisition speech instructions i1236 when executed direct electronically directing control at least in part of the acquisition of the ingestion intelligence including information related to ingestion by the particular individual living being of at least one of the one or more selected ingestible products via at least in part electronic speech recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a speech recognition application implemented by the microprocessor component s102, etc.). Furthermore, the acquisition speech electrical circuitry arrangement e1236 when activated will perform the operation o1236. In an implementation, the acquisition speech electrical circuitry arrangement e1236, when activated performs electronically directing control at least in part of the acquisition of the ingestion intelligence including information related to ingestion by the particular individual living being of at least one of the one or more selected ingestible products via at least in part electronic speech recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a speech recognition application implemented by the microprocessor component s102, etc.). In an implementation, the electronically directing control at least in part of the acquisition of the ingestion intelligence including information related to ingestion by the particular individual living being of at least one of the one or more selected ingestible products via at least in part electronic speech recognition is carried out by electronically directing control at least in part of the acquisition of the ingestion intelligence including information related to ingestion by the particular individual living being of at least one of the one or more selected ingestible products via at least in part electronic speech recognition (e.g. an implementation of the microprocessor component s102 is configured to electronically control at least in part the acquisition such as through camera component s336 and recognition application implemented by microprocessor component s102 of the ingestion intelligence including the information related to the ingestion by the particular individual living being of at least one of the one or more selected ingestible products via at least in part electronic image recognition products such as a speech recognition application implemented by the microprocessor component s102, etc.).

Figure 94:
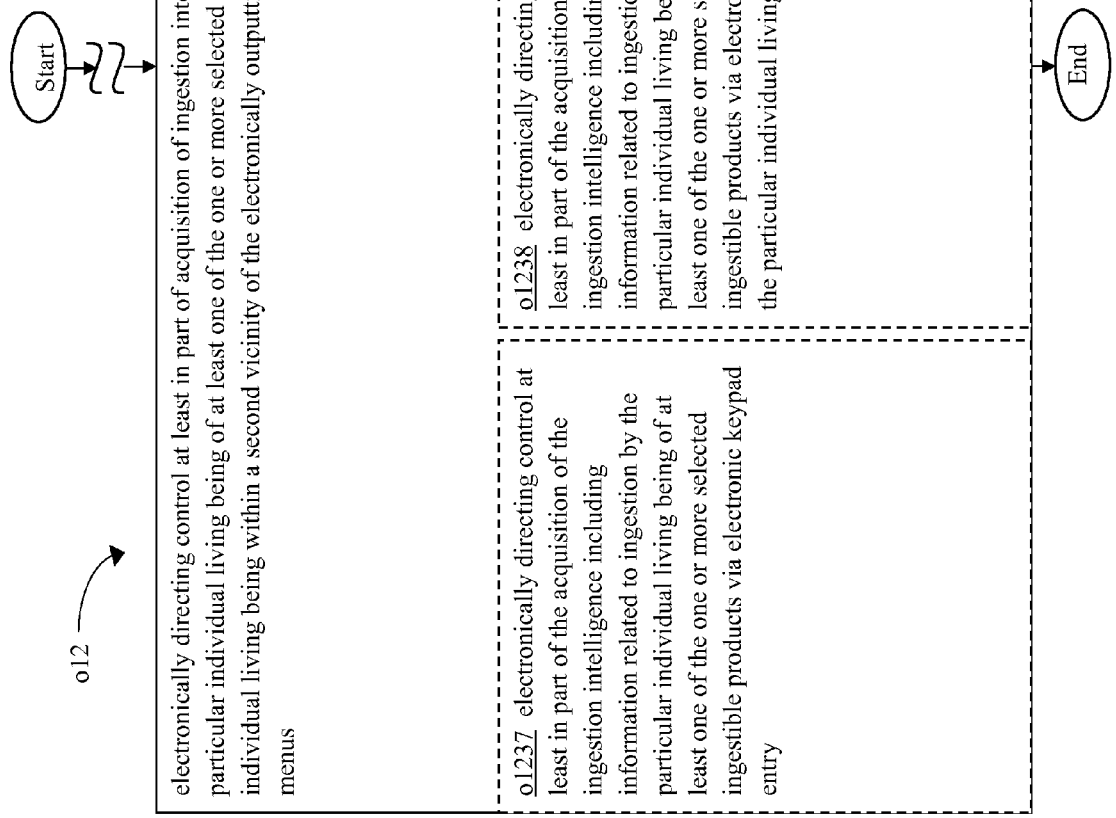
FIG. 94 is a high-level flowchart including exemplary implementations of operation O12 of FIG. 46.

In one or more implementations, as shown in FIG. 94, operation o12 includes an operation o1237 for electronically directing control at least in part of the acquisition of the ingestion intelligence including information related to ingestion by the particular individual living being of at least one of the one or more selected ingestible products via electronic keypad entry. An exemplary version of a non-transitory signal bearing medium of information storage subsystem s200 is depicted as bearing one or more acquisition keypad instructions i1237 that when executed will direct performance of the operation o1237. In an implementation, the one or more acquisition keypad instructions i1237 when executed direct electronically directing control at least in part of the acquisition of the ingestion intelligence including information related to ingestion by the particular individual living being of at least one of the one or more selected ingestible products via electronic keypad entry (e.g. an implementation of the microprocessor component s102 is configured to electronically control at least in part the acquisition of the ingestion intelligence including the information related to the ingestion by the particular individual living being of at least one of the one or more selected ingestible products via electronic keypad such as keypad component s308 communicatively linked to the microprocessor component s102, etc.). Furthermore, the acquisition keypad electrical circuitry arrangement e1237 when activated will perform the operation o1237. In an implementation, the acquisition keypad electrical circuitry arrangement e1237, when activated performs electronically directing control at least in part of the acquisition of the ingestion intelligence including information related to ingestion by the particular individual living being of at least one of the one or more selected ingestible products via electronic keypad entry (e.g. an implementation of the microprocessor component s102 is configured to electronically control at least in part the acquisition of the ingestion intelligence including the information related to the ingestion by the particular individual living being of at least one of the one or more selected ingestible products via electronic keypad such as keypad component s308 communicatively linked to the microprocessor component s102, etc.). In an implementation, the electronically directing control at least in part of the acquisition of the ingestion intelligence including information related to ingestion by the particular individual living being of at least one of the one or more selected ingestible products via electronic keypad entry is carried out by electronically directing control at least in part of the acquisition of the ingestion intelligence including information related to ingestion by the particular individual living being of at least one of the one or more selected ingestible products via electronic keypad entry (e.g. an implementation of the microprocessor component s102 is configured to electronically control at least in part the acquisition of the ingestion intelligence including the information related to the ingestion by the particular individual living being of at least one of the one or more selected ingestible products via electronic keypad such as keypad component s308 communicatively linked to the microprocessor component s102, etc.)

In one or more implementations, operation o12 includes an operation o1238 for electronically directing control at least in part of the acquisition of the ingestion intelligence including information related to ingestion by the particular individual living being of at least one of the one or more selected ingestible products via electronic input by the particular individual living being. An exemplary version of a non-transitory signal bearing medium of information storage subsystem s200 is depicted as bearing one or more acquisition input instructions i1238 that when executed will direct performance of the operation o1238. In an implementation, the one or more acquisition input instructions i1238 when executed direct electronically directing control at least in part of the acquisition of the ingestion intelligence including information related to ingestion by the particular individual living being of at least one of the one or more selected ingestible products via electronic input by the particular individual living being (e.g. an implementation of the microprocessor component s102 is configured to electronically control at least in part the acquisition of the ingestion intelligence including the information related to the ingestion by the particular individual living being of at least one of the one or more selected ingestible products via electronic input by the particular individual living being such as through use of the graphical user interface (GUI) component s302, etc.). Furthermore, the acquisition input electrical circuitry arrangement e1238 when activated will perform the operation o1238. In an implementation, the acquisition input electrical circuitry arrangement e1238, when activated performs electronically directing control at least in part of the acquisition of the ingestion intelligence including information related to ingestion by the particular individual living being of at least one of the one or more selected ingestible products via electronic input by the particular individual living being (e.g. an implementation of the microprocessor component s102 is configured to electronically control at least in part the acquisition of the ingestion intelligence including the information related to the ingestion by the particular individual living being of at least one of the one or more selected ingestible products via electronic input by the particular individual living being such as through use of the graphical user interface (GUI) component s302, etc.). In an implementation, the electronically directing control at least in part of the acquisition of the ingestion intelligence including information related to ingestion by the particular individual living being of at least one of the one or more selected ingestible products via electronic input by the particular individual living being is carried out by electronically directing control at least in part of the acquisition of the ingestion intelligence including information related to ingestion by the particular individual living being of at least one of the one or more selected ingestible products via electronic input by the particular individual living being (e.g. an implementation of the microprocessor component s102 is configured to electronically control at least in part the acquisition of the ingestion intelligence including the information related to the ingestion by the particular individual living being of at least one of the one or more selected ingestible products via electronic input by the particular individual living being such as through use of the graphical user interface (GUI) component s302, etc.).

In one or more implementations, operation o12 includes an operation o1239 for electronically directing control at least in part of the acquisition of the ingestion intelligence including information related to ingestion by the particular individual living being of at least one of the one or more selected ingestible products via electronic input by one or more restaurant staff. An exemplary version of a non-transitory signal bearing medium of information storage subsystem s200 is depicted as bearing one or more acquisition restaurant instructions i1239 that when executed will direct performance of the operation o1239. In an implementation, the one or more acquisition restaurant instructions i1239 when executed direct electronically directing control at least in part of the acquisition of the ingestion intelligence including information related to ingestion by the particular individual living being of at least one of the one or more selected ingestible products via electronic input by one or more restaurant staff (e.g. an implementation of the microprocessor component s102 is configured to electronically control at least in part the acquisition of the ingestion intelligence including the information related to the ingestion by the particular individual living being of at least one of the one or more selected ingestible products via electronic input by one or more restaurant staff such as a wait person using a touch screen component s314, etc.). Furthermore, the acquisition restaurant electrical circuitry arrangement e1239 when activated will perform the operation o1239. In an implementation, the acquisition restaurant electrical circuitry arrangement e1239, when activated performs electronically directing control at least in part of the acquisition of the ingestion intelligence including information related to ingestion by the particular individual living being of at least one of the one or more selected ingestible products via electronic input by one or more restaurant staff (e.g. an implementation of the microprocessor component s102 is configured to electronically control at least in part the acquisition of the ingestion intelligence including the information related to the ingestion by the particular individual living being of at least one of the one or more selected ingestible products via electronic input by one or more restaurant staff such as a wait person using a touch screen component s314, etc.). In an implementation, the electronically directing control at least in part of the acquisition of the ingestion intelligence including information related to ingestion by the particular individual living being of at least one of the one or more selected ingestible products via electronic input by one or more restaurant staff is carried out by electronically directing control at least in part of the acquisition of the ingestion intelligence including information related to ingestion by the particular individual living being of at least one of the one or more selected ingestible products via electronic input by one or more restaurant staff (e.g. an implementation of the microprocessor component s102 is configured to electronically control at least in part the acquisition of the ingestion intelligence including the information related to the ingestion by the particular individual living being of at least one of the one or more selected ingestible products via electronic input by one or more restaurant staff such as a wait person using a touch screen component s314, etc.).

Figure 95:
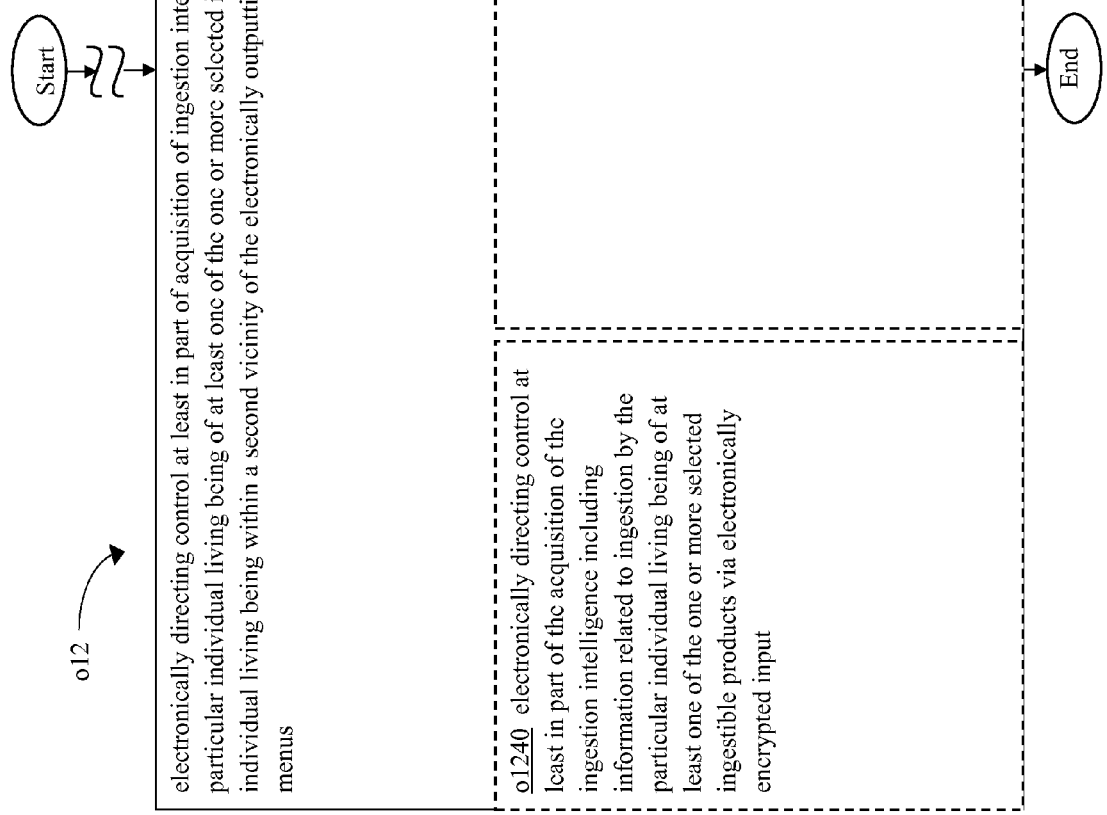
FIG. 95 is a high-level flowchart including exemplary implementations of operation O12 of FIG. 46.

In one or more implementations, as shown in FIG. 95, operation o12 includes an operation o1240 for electronically directing control at least in part of the acquisition of the ingestion intelligence including information related to ingestion by the particular individual living being of at least one of the one or more selected ingestible products via electronically encrypted input. An exemplary version of a non-transitory signal bearing medium of information storage subsystem s200 is depicted as bearing one or more acquisition encrypted instructions i1240 that when executed will direct performance of the operation o1240. In an implementation, the one or more acquisition encrypted instructions i1240 when executed direct electronically directing control at least in part of the acquisition of the ingestion intelligence including information related to ingestion by the particular individual living being of at least one of the one or more selected ingestible products via electronically encrypted input (e.g. an implementation of the microprocessor component s102 is configured to electronically control at least in part the acquisition of the ingestion intelligence including the information related to the ingestion by the particular individual living being of at least one of the one or more selected ingestible products via electronic encrypted input such as through an encrypted version of wireless network component s510, etc.). Furthermore, the acquisition encrypted electrical circuitry arrangement e1240 when activated will perform the operation o1240. In an implementation, the acquisition encrypted electrical circuitry arrangement e1240, when activated performs electronically directing control at least in part of the acquisition of the ingestion intelligence including information related to ingestion by the particular individual living being of at least one of the one or more selected ingestible products via electronically encrypted input (e.g. an implementation of the microprocessor component s102 is configured to electronically control at least in part the acquisition of the ingestion intelligence including the information related to the ingestion by the particular individual living being of at least one of the one or more selected ingestible products via electronic encrypted input such as through an encrypted version of wireless network component s510, etc.). In an implementation, the electronically directing control at least in part of the acquisition of the ingestion intelligence including information related to ingestion by the particular individual living being of at least one of the one or more selected ingestible products via electronically encrypted input is carried out by electronically directing control at least in part of the acquisition of the ingestion intelligence including information related to ingestion by the particular individual living being of at least one of the one or more selected ingestible products via electronically encrypted input (e.g. an implementation of the microprocessor component s102 is configured to electronically control at least in part the acquisition of the ingestion intelligence including the information related to the ingestion by the particular individual living being of at least one of the one or more selected ingestible products via electronic encrypted input such as through an encrypted version of wireless network component s510, etc.)

Figure 96:
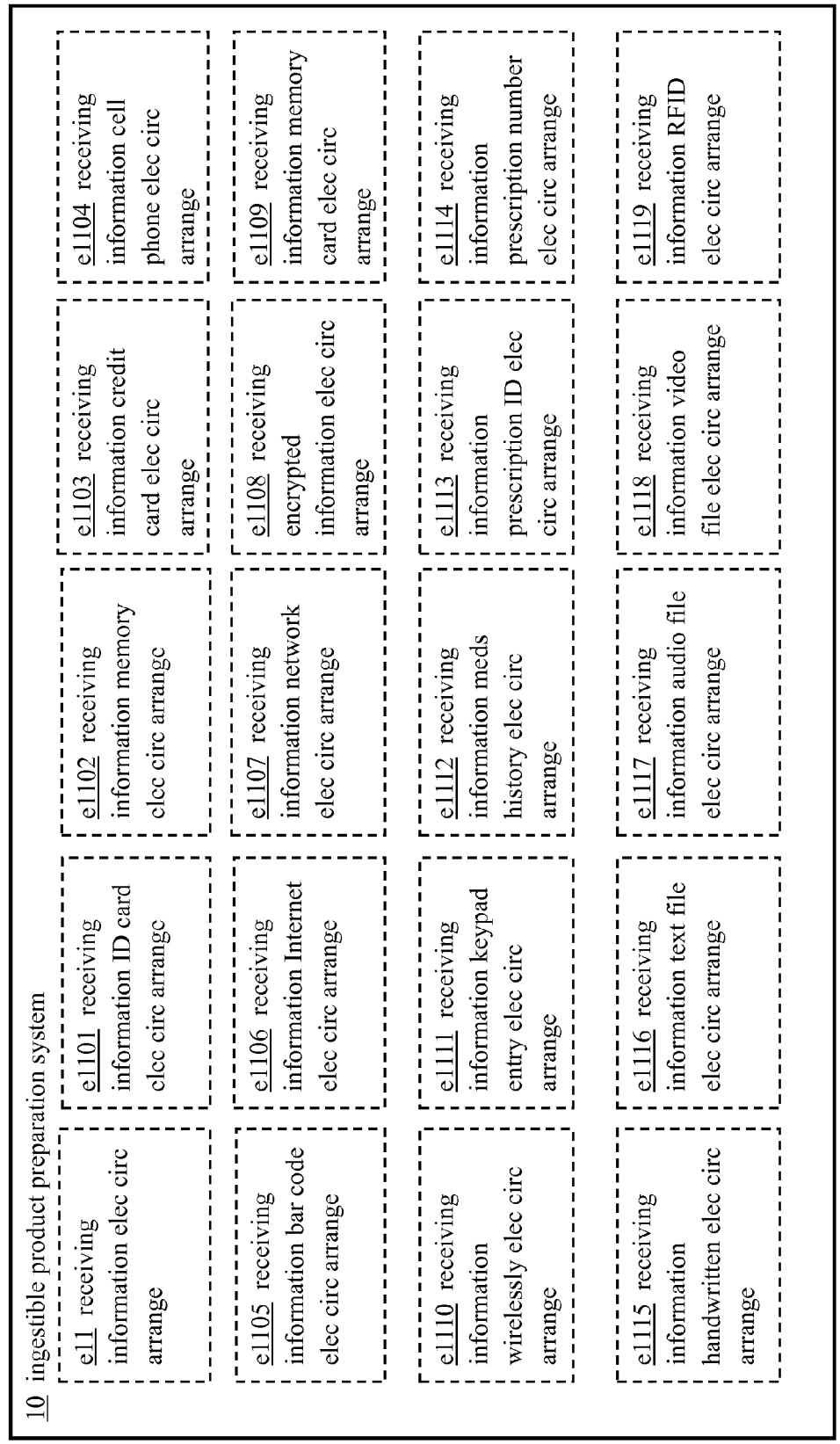
FIG. 96 is a block diagram depicting one or more exemplary electrical circuitry arrangements of the ingestible product preparation system 10 of FIG. 1.

Implementations involve different combinations (otherwise known as "electrical circuitry arrangements") of components from the subsystems of the ingestible product preparation system 10. Exemplary depictions of some of these electrical circuitry arrangements are shown in FIG. 96 to include receiving information electrical circuitry arrangement f11, receiving information ID card electrical circuitry arrangement f1101, receiving information memory electrical circuitry arrangement f1102, receiving information credit card electrical circuitry arrangement f1103, receiving information cell phone electrical circuitry arrangement f1104, receiving information bar code electrical circuitry arrangement f1105, receiving information Internet electrical circuitry arrangement f1106, receiving information network electrical circuitry arrangement f1107, receiving encrypted information electrical circuitry arrangement f1108, receiving information memory card electrical circuitry arrangement f1109, receiving information wirelessly electrical circuitry arrangement f1110, receiving information keypad entry electrical circuitry arrangement f1111, receiving information meds history electrical circuitry arrangement f1112, receiving information prescription ID electrical circuitry arrangement f1113, receiving information prescription number electrical circuitry arrangement f1114, receiving information handwritten electrical circuitry arrangement f1115, receiving information text file electrical circuitry arrangement f1116, receiving information audio file electrical circuitry arrangement f1117, receiving information video file electrical circuitry arrangement f1118, and receiving information RFID electrical circuitry arrangement f1119.

Figure 97:
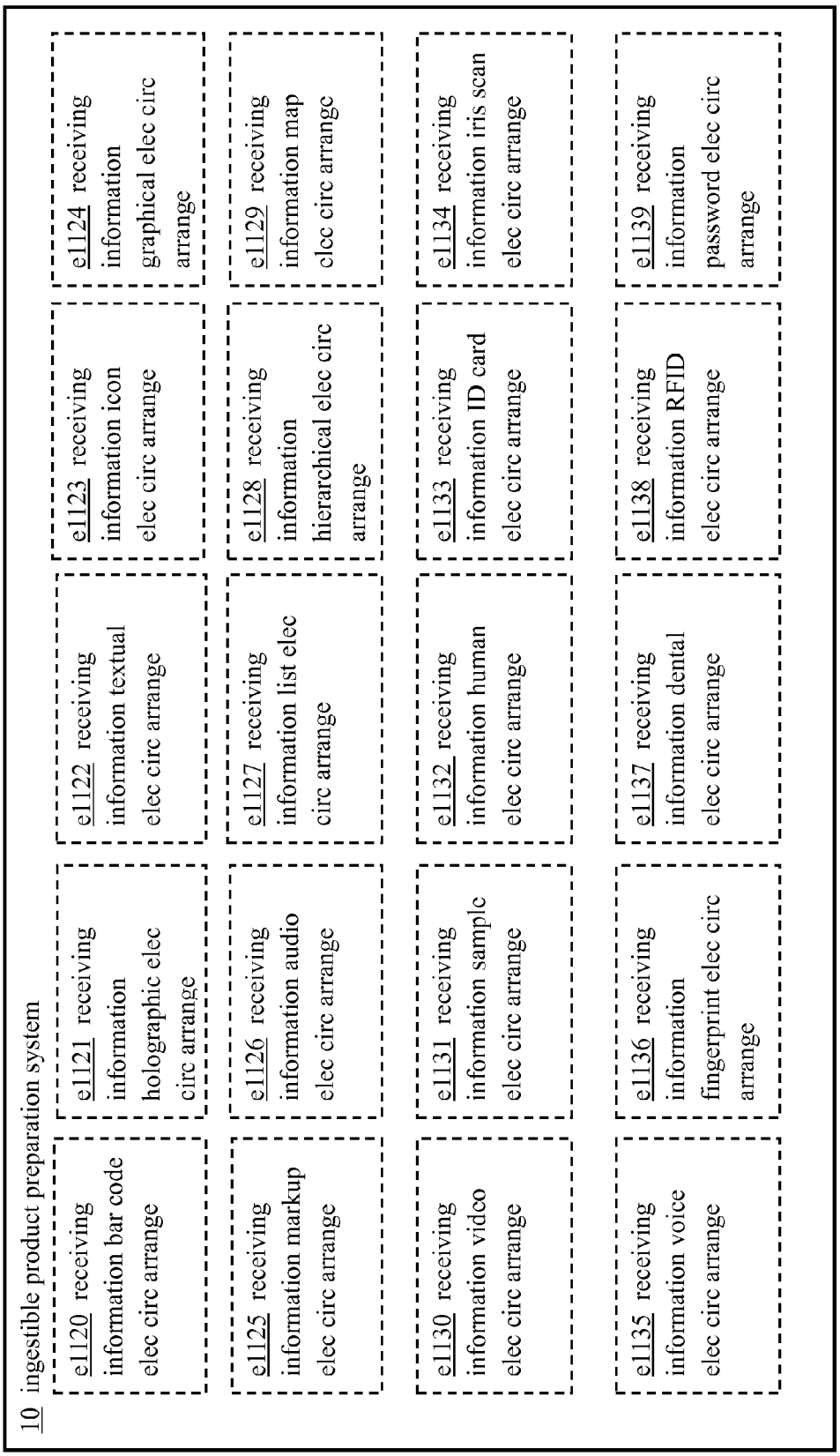
FIG. 97 is a block diagram depicting one or more exemplary electrical circuitry arrangements of the ingestible product preparation system 10 of FIG. 1.

Some of these electrical circuitry arrangements are depicted in FIG. 97 to include receiving information bar code electrical circuitry arrangement f1120, receiving information holographic electrical circuitry arrangement f1121, receiving information textual electrical circuitry arrangement f1122, receiving information icon electrical circuitry arrangement f1123, receiving information graphical electrical circuitry arrangement f1124, receiving information markup electrical circuitry arrangement f1125, receiving information audio electrical circuitry arrangement f1126, receiving information list electrical circuitry arrangement f1127, receiving information hierarchical electrical circuitry arrangement f1128, receiving information map electrical circuitry arrangement f1129, receiving information video electrical circuitry arrangement f1130, receiving information sample electrical circuitry arrangement f113, receiving information human electrical circuitry arrangement f1132, receiving information ID card electrical circuitry arrangement f1133, receiving information iris scan electrical circuitry arrangement f1134, receiving information voice electrical circuitry arrangement f1135, receiving information fingerprint electrical circuitry arrangement f1136, receiving information dental electrical circuitry arrangement f1137, receiving information RFID electrical circuitry arrangement f1138, and receiving information password electrical circuitry arrangement f1139.

Figure 98:
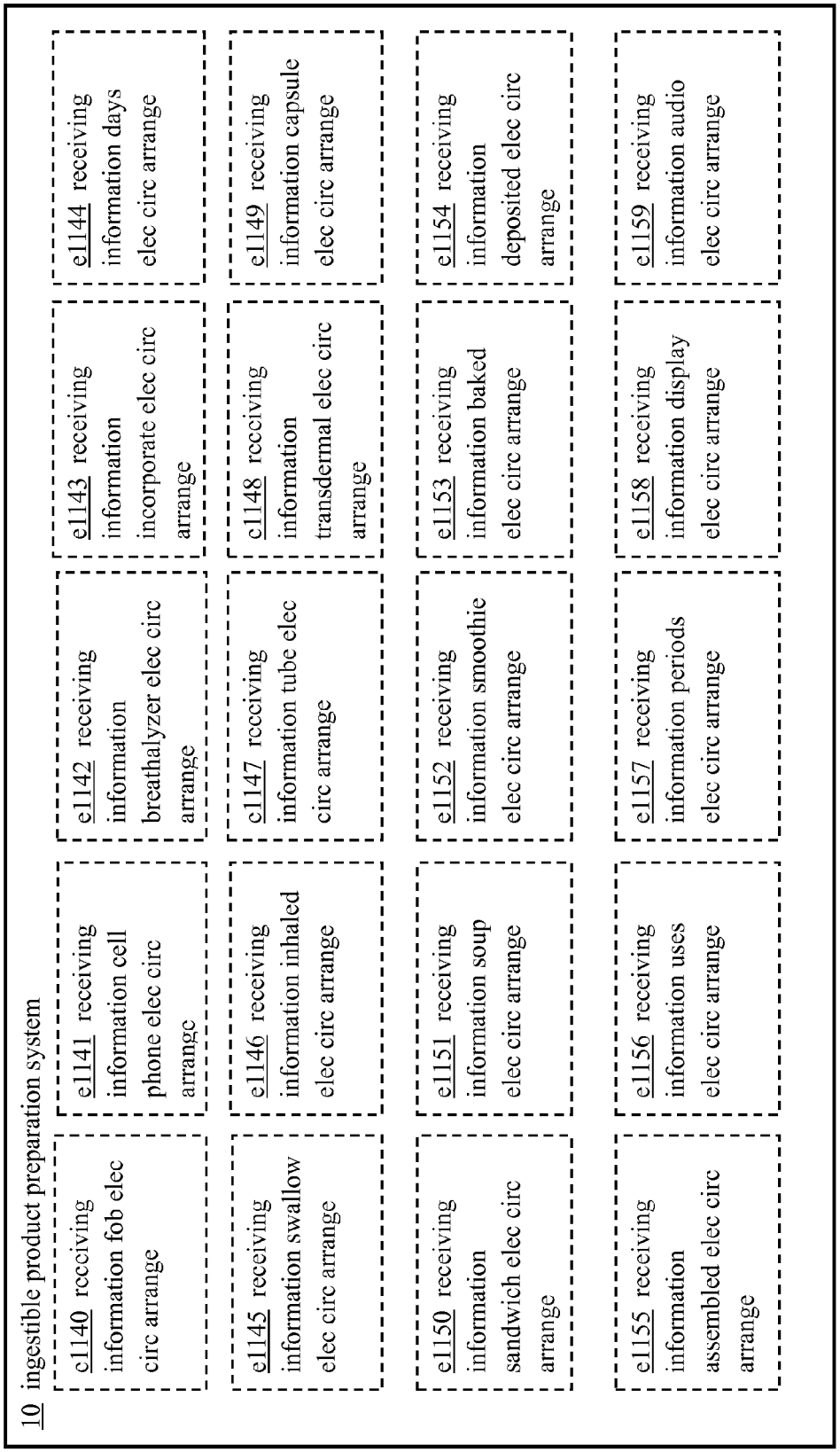
FIG. 98 is a block diagram depicting one or more exemplary electrical circuitry arrangements of the ingestible product preparation system 10 of FIG. 1.

Some of these electrical circuitry arrangements are depicted in FIG. 98 to include receiving information fob electrical circuitry arrangement f1140, receiving information cell phone electrical circuitry arrangement f1141, receiving information breathalyzer electrical circuitry arrangement f1142, receiving information incorporate electrical circuitry arrangement f1143, receiving information days electrical circuitry arrangement f1144, receiving information swallow electrical circuitry arrangement f1145, receiving information inhaled electrical circuitry arrangement f1146, receiving information tube electrical circuitry arrangement f1147, receiving information transdermal electrical circuitry arrangement f1148, receiving information capsule electrical circuitry arrangement f1149, receiving information sandwich electrical circuitry arrangement f1150, receiving information soup electrical circuitry arrangement f1151, receiving information smoothie electrical circuitry arrangement f1152, receiving information baked electrical circuitry arrangement f1153, receiving information deposited electrical circuitry arrangement f1154, receiving information assembled electrical circuitry arrangement f1155, receiving information uses electrical circuitry arrangement f1156, receiving information periods electrical circuitry arrangement f1157, receiving information display electrical circuitry arrangement f1158, and receiving information audio electrical circuitry arrangement f1159.

Figure 99:
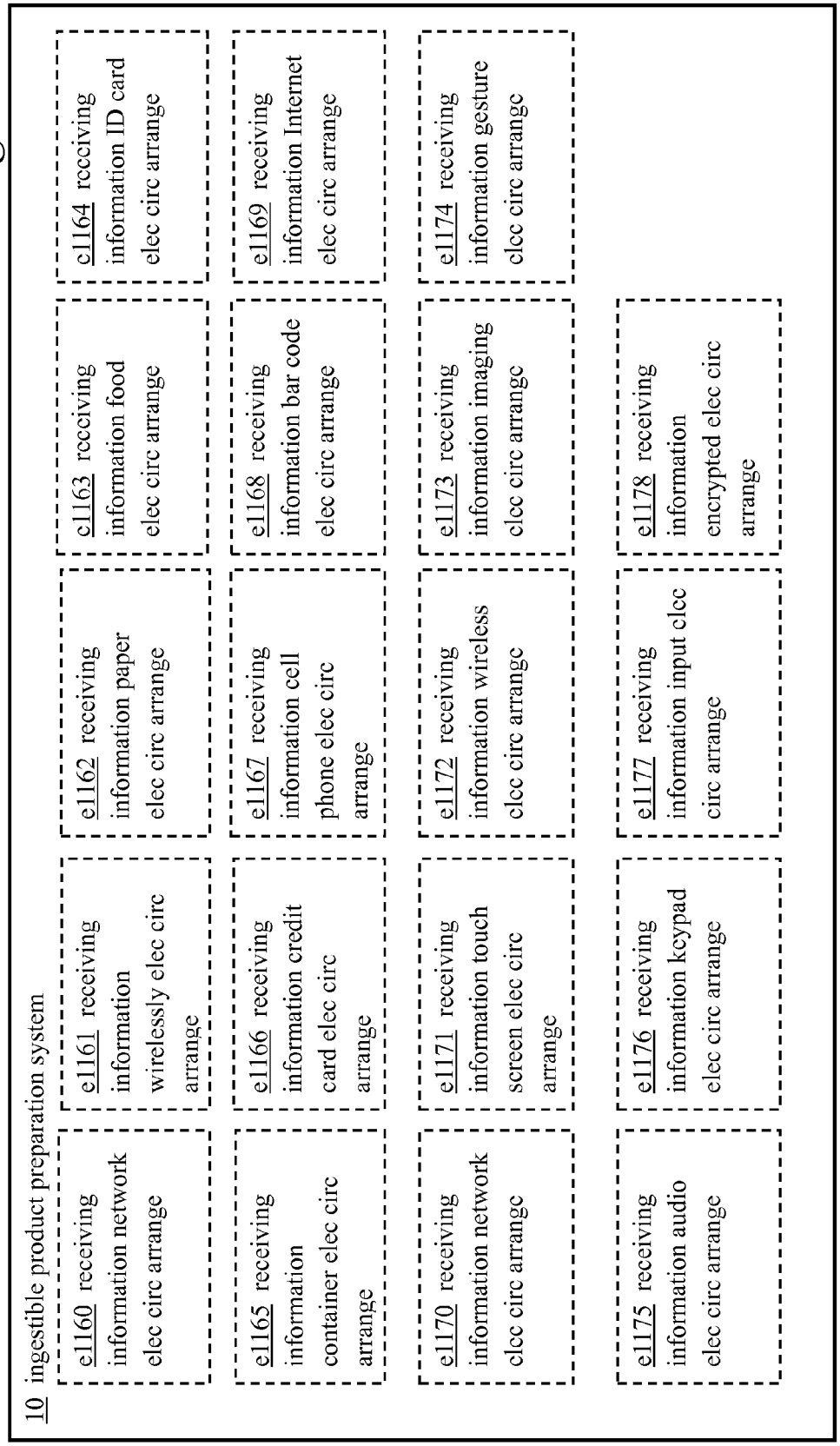
FIG. 99 is a block diagram depicting one or more exemplary electrical circuitry arrangements of the ingestible product preparation system 10 of FIG. 1.
Figure 100:
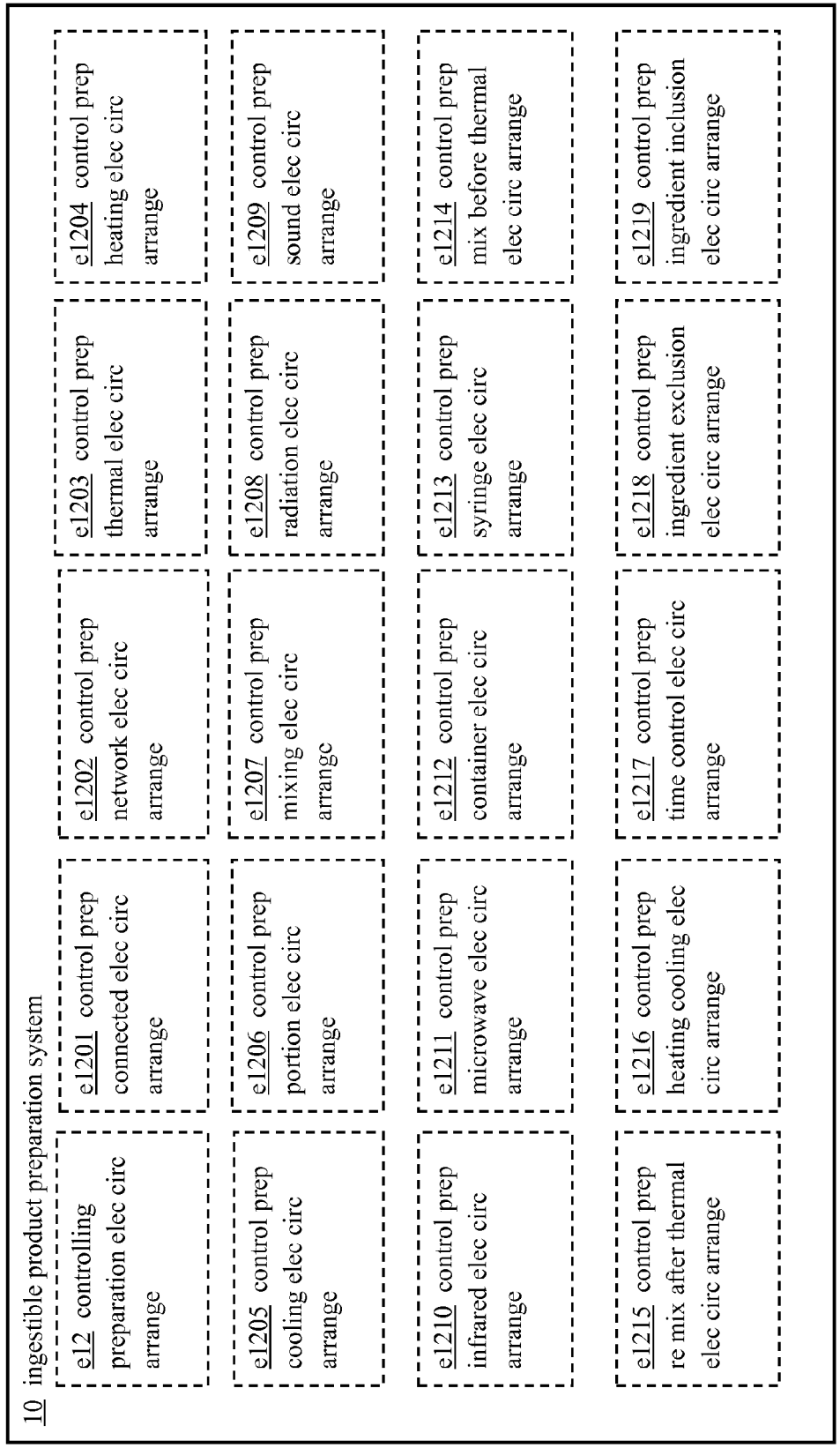
FIG. 100 is a block diagram depicting one or more exemplary electrical circuitry arrangements of the ingestible product preparation system 10 of FIG. 1.

Some of these electrical circuitry arrangements are depicted in FIG. 99 to include receiving information network electrical circuitry arrangement f1160, receiving information wirelessly electrical circuitry arrangement f1161, receiving information paper electrical circuitry arrangement f1162, receiving information food electrical circuitry arrangement f1163, receiving information ID card electrical circuitry arrangement f1164, receiving information container electrical circuitry arrangement f1165, and receiving information credit card electrical circuitry arrangement f1166, receiving information cell phone electrical circuitry arrangement f1167, receiving information bar code electrical circuitry arrangement f1168, receiving information Internet electrical circuitry arrangement f1169, receiving information network electrical circuitry arrangement f1170, receiving information touch screen electrical circuitry arrangement f1171, receiving information wireless electrical circuitry arrangement f1172, receiving information imaging electrical circuitry arrangement f1173, receiving information gesture electrical circuitry arrangement f1174, receiving information audio electrical circuitry arrangement f1175, receiving information keypad electrical circuitry arrangement f1176, receiving information input electrical circuitry arrangement f1177, and receiving information encrypted electrical circuitry arrangement f1178.

Some of these electrical circuitry arrangements are depicted in FIG. 200 to include controlling preparation electrical circuitry arrangement f12, control prep connected electrical circuitry arrangement f1201, control prep network electrical circuitry arrangement f1202, control prep thermal electrical circuitry arrangement f1203, control prep heating electrical circuitry arrangement f1204, control prep cooling electrical circuitry arrangement f1205, control prep portion electrical circuitry arrangement f1206, control prep mixing electrical circuitry arrangement f1207, control prep radiation electrical circuitry arrangement f1208, control prep sound electrical circuitry arrangement f1209, control prep infrared electrical circuitry arrangement f1210, control prep microwave electrical circuitry arrangement f1211, and control prep container electrical circuitry arrangement f1212, control prep syringe electrical circuitry arrangement f1213, control prep mix before thermal electrical circuitry arrangement f1214, control prep re mix after thermal electrical circuitry arrangement f1215, control prep heating cooling electrical circuitry arrangement f1216, control prep time control electrical circuitry arrangement f1217, control prep ingredient exclusion electrical circuitry arrangement f1218, and control prep ingredient inclusion electrical circuitry arrangement f1219.

Figure 101:
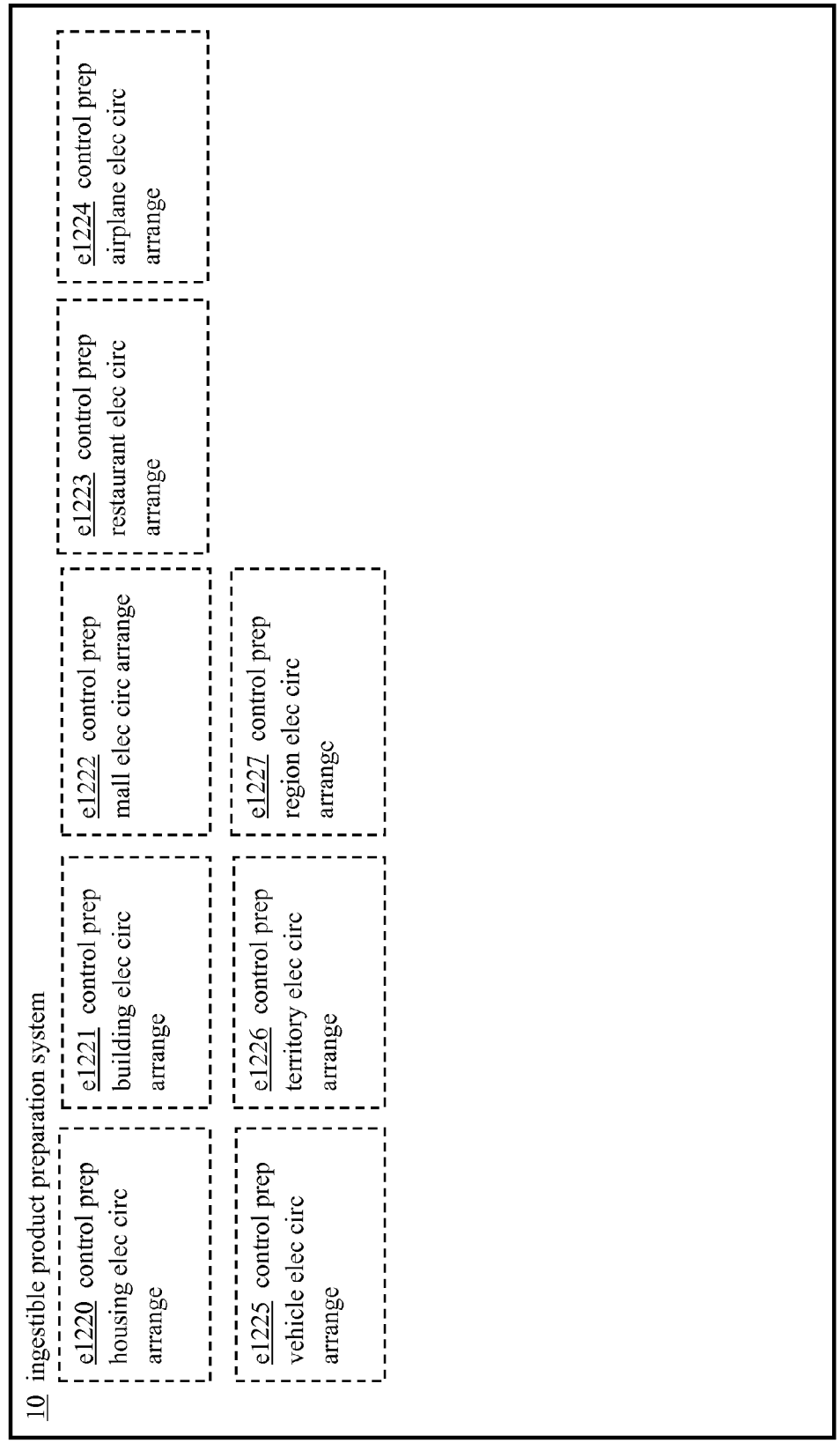
FIG. 101 is a block diagram depicting one or more exemplary electrical circuitry arrangements of the ingestible product preparation system 10 of FIG. 1.

Some of these electrical circuitry arrangements are depicted in FIG. 101 to include control prep housing electrical circuitry arrangement f1220, control prep building electrical circuitry arrangement f1221, control prep mall electrical circuitry arrangement f1222, control prep restaurant electrical circuitry arrangement f1223, control prep airplane electrical circuitry arrangement f1224, control prep vehicle electrical circuitry arrangement f1225, control prep territory electrical circuitry arrangement f1226, and control prep region electrical circuitry arrangement f1227.

Figure 102:
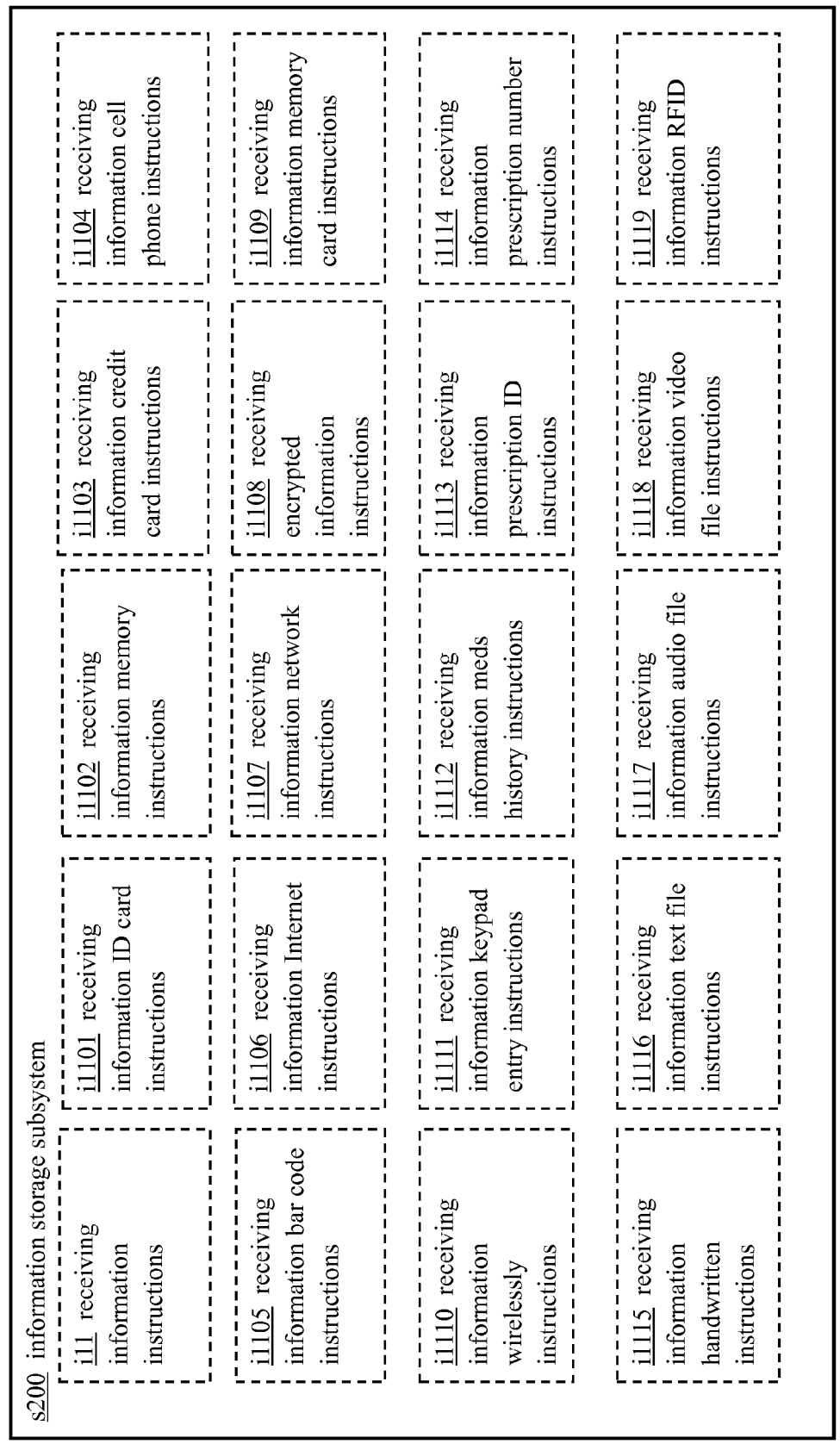
FIG. 102 is a block diagram depicting one or more exemplary instructions of the information storage subsystem s200 of the ingestible product preparation system 10 of FIG. 1.

In implementations one or more instructions are stored and/or otherwise borne in various subsystems, components, and/or accessories of the ingestible product preparation system 10 such as being borne in a non-transitory signal bearing medium of information storage subsystem s200. One or more exemplary instructions depicted in FIG. 102 as being borne in an exemplary version of a non-transitory signal bearing medium of information storage subsystem s200 include one or more receiving information instructions j11, one or more receiving information ID card instructions j1101, one or more receiving information memory instructions j1102, one or more receiving information credit card instructions j1103, one or more receiving information cell phone instructions j1104, one or more receiving information bar code instructions j1105, one or more receiving information Internet instructions j1106, one or more receiving information network instructions j1107, one or more receiving encrypted information instructions j1108, one or more receiving information memory card instructions j1109, one or more receiving information wirelessly instructions j1110, one or more receiving information keypad entry instructions j1111, one or more receiving information meds history instructions j1112, one or more receiving information prescription ID instructions j1113, one or more receiving information prescription number instructions j1114, one or more receiving information handwritten instructions j1115, one or more receiving information text file instructions j1116, one or more receiving information audio file instructions j1117, one or more receiving information video file instructions j1118, and one or more receiving information RFID instructions j1119.

Figure 103:
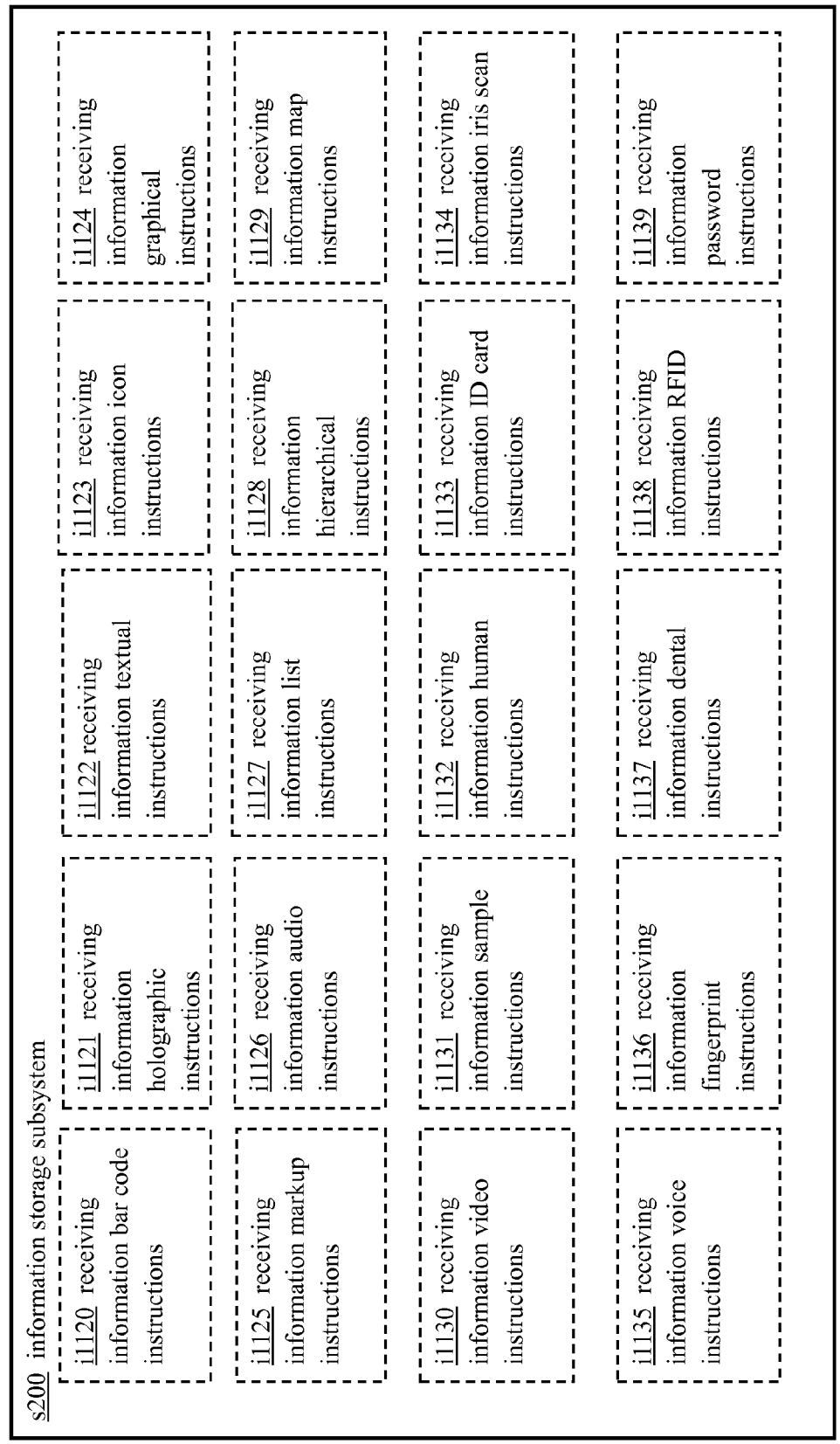
FIG. 103 is a block diagram depicting one or more exemplary instructions of the information storage subsystem s200 of the ingestible product preparation system 10 of FIG. 1.

One or more exemplary instructions depicted in FIG. 103 as being borne in an exemplary version of a non-transitory signal bearing medium of information storage subsystem s200 include one or more receiving information bar code instructions j1120, one or more receiving information holographic instructions j1121, one or more receiving information textual instructions j1122, one or more receiving information icon instructions j1123, one or more receiving information graphical instructions j1124, one or more receiving information markup instructions j1125, one or more receiving information audio instructions j1126, one or more receiving information list instructions j1127, one or more receiving information hierarchical instructions j1128, one or more receiving information map instructions j1129, one or more receiving information video instructions j1130, one or more receiving information sample instructions j1131, one or more receiving information human instructions j1132, one or more receiving information ID card instructions j1133, one or more receiving information iris scan instructions j1134, one or more receiving information voice instructions j1135, one or more receiving information fingerprint instructions j1136, one or more receiving information dental instructions j1137, one or more receiving information RFID instructions j1138, and one or more receiving information password instructions j1139.

Figure 104:
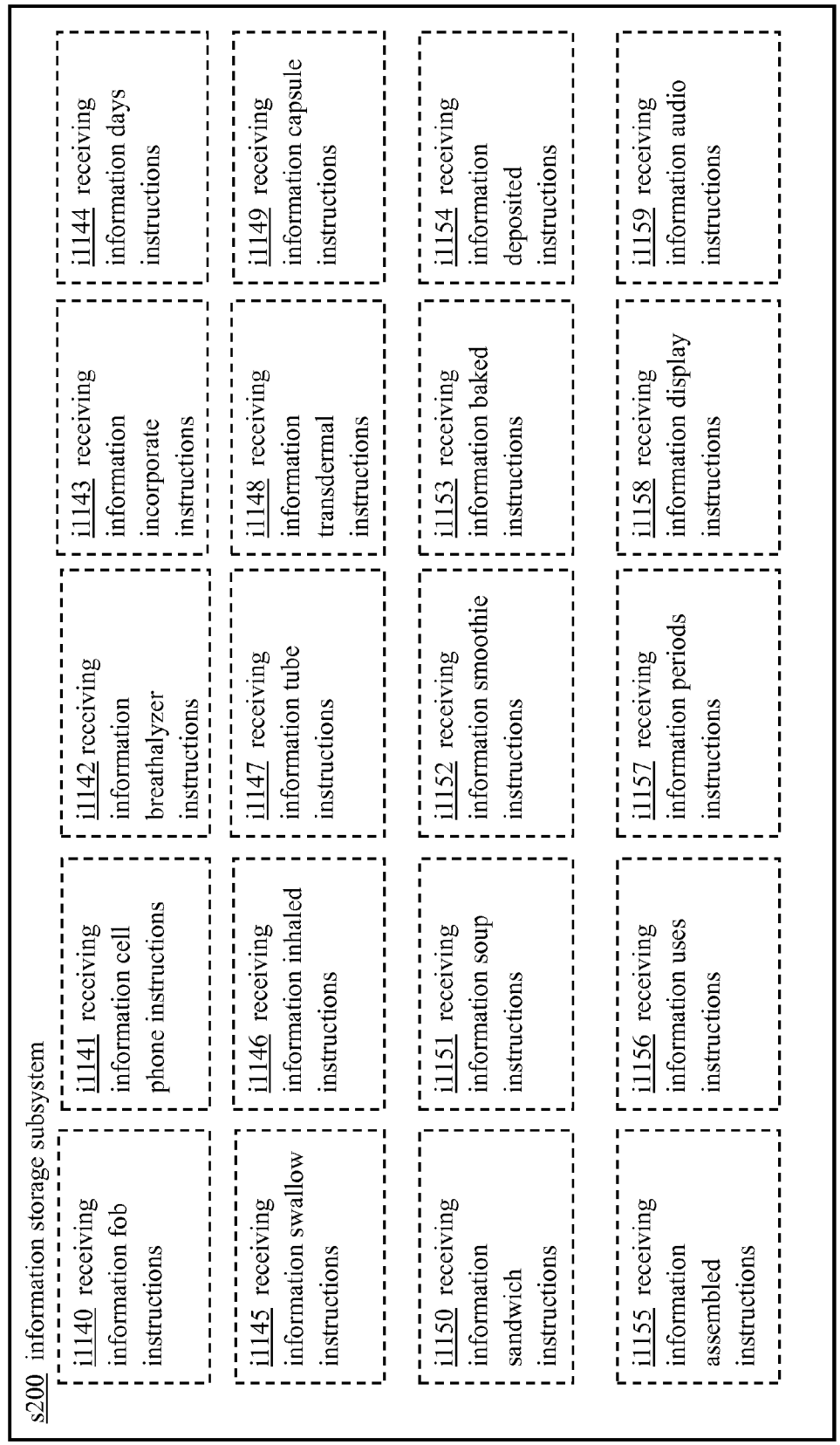
FIG. 104 is a block diagram depicting one or more exemplary instructions of the information storage subsystem s200 of the ingestible product preparation system 10 of FIG. 1.

One or more exemplary instructions depicted in FIG. 104 as being borne in an exemplary version of a non-transitory signal bearing medium of information storage subsystem s200 include one or more receiving information fob instructions j1140, one or more receiving information cell phone instructions j1141, one or more receiving information breathalyzer instructions j1142, one or more receiving information incorporate instructions j1143, one or more receiving information days instructions j1144, one or more receiving information swallow instructions j1145, one or more receiving information inhaled instructions j1146, one or more receiving information tube instructions j1147, one or more receiving information transdermal instructions j1148, one or more receiving information capsule instructions j1149, one or more receiving information sandwich instructions j1150, one or more receiving information soup instructions j1151, one or more receiving information smoothie instructions j1152, one or more receiving information baked instructions j1153, one or more receiving information deposited instructions j1154, one or more receiving information assembled instructions j1155, one or more receiving information uses instructions j1156, one or more receiving information periods instructions j1157, one or more receiving information display instructions j1158, and one or more receiving information audio instructions j1159.

Figure 105:
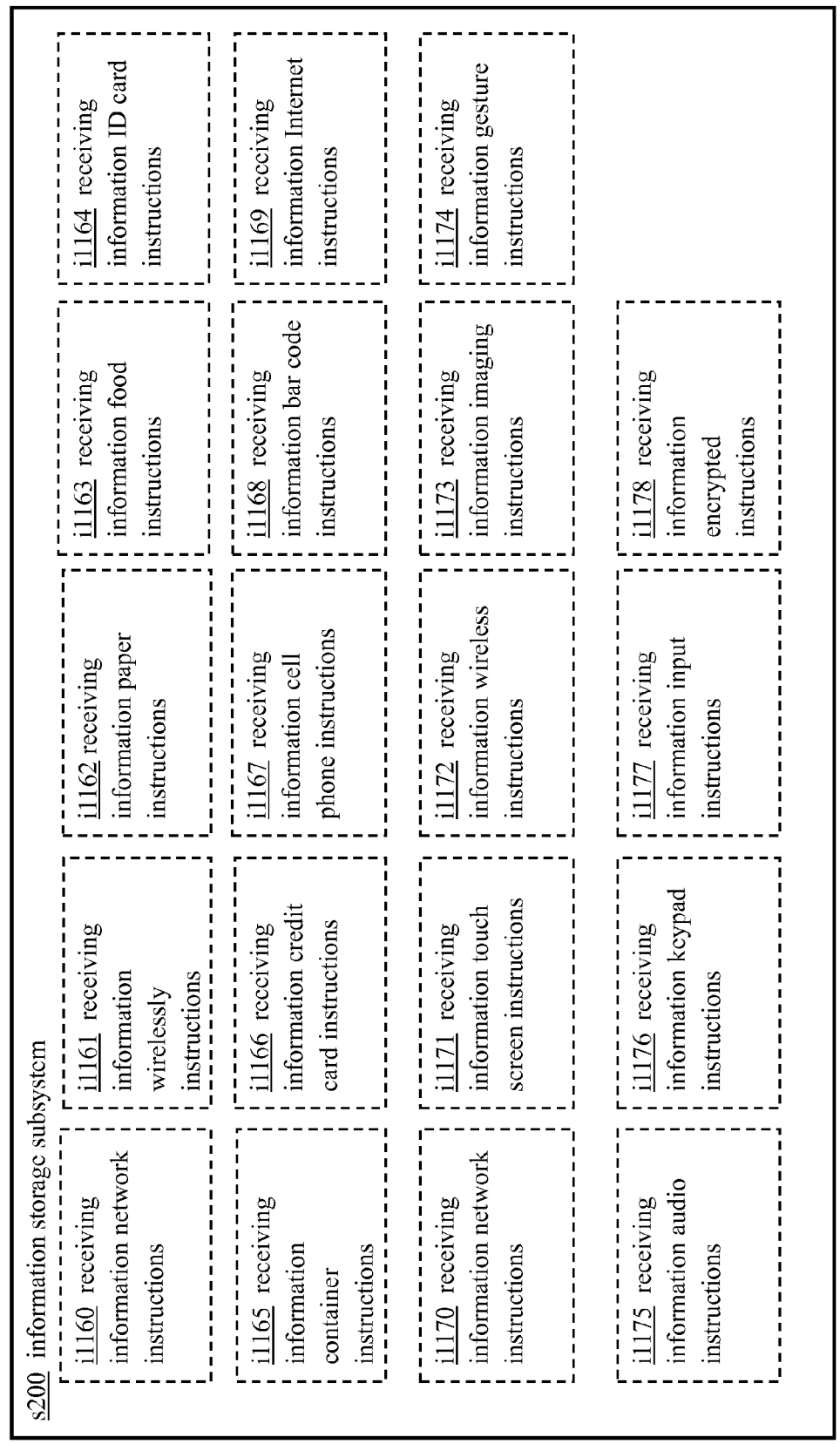
FIG. 105 is a block diagram depicting one or more exemplary instructions of the information storage subsystem s200 of the ingestible product preparation system 10 of FIG. 1.

One or more exemplary instructions depicted in FIG. 105 as being borne in an exemplary version of a non-transitory signal bearing medium of information storage subsystem s200 include one or more receiving information network instructions j1160, one or more receiving information wirelessly instructions j1161, one or more receiving information paper instructions j1162, one or more receiving information food instructions j1163, one or more receiving information ID card instructions j1164, one or more receiving information container instructions j1165, and one or more receiving information credit card instructions j1166, one or more receiving information cell phone instructions j1167, one or more receiving information bar code instructions j1168, one or more receiving information Internet instructions j1169, one or more receiving information network instructions j1170, one or more receiving information touch screen instructions j1171, one or more receiving information wireless instructions j1172, one or more receiving information imaging instructions j1173, one or more receiving information gesture instructions j1174, one or more receiving information audio instructions j1175, one or more receiving information keypad instructions j1176, one or more receiving information input instructions j1177, and one or more receiving information encrypted instructions j1178.

Figure 106:
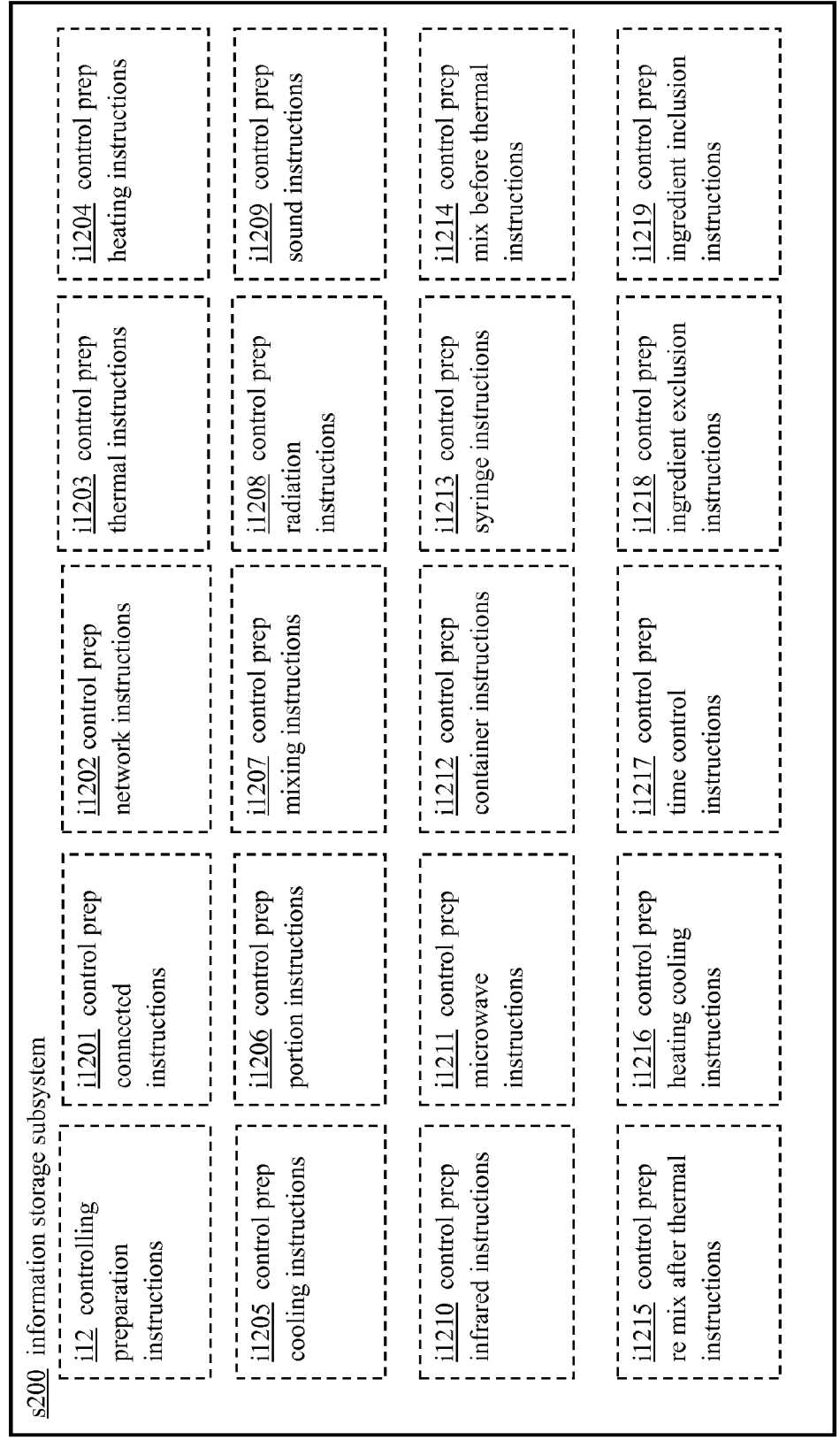
FIG. 106 is a block diagram depicting one or more exemplary instructions of the information storage subsystem s200 of the ingestible product preparation system 10 of FIG. 1.

One or more exemplary instructions depicted in FIG. 106 as being borne in an exemplary version of a non-transitory signal bearing medium of information storage subsystem s200 include one or more controlling preparation instructions j12, one or more control prep connected instructions j1201, one or more control prep network instructions j1202, one or more control prep thermal instructions j1203, one or more control prep heating instructions j1204, one or more control prep cooling instructions j1205, one or more control prep portion instructions j1206, one or more control prep mixing instructions j1207, one or more control prep radiation instructions j1208, one or more control prep sound instructions j1209, one or more control prep infrared instructions j1210, one or more control prep microwave instructions j1211, one or more control prep container instructions j1212, one or more control prep syringe instructions j1213, one or more control prep mix before thermal instructions j1214, one or more control prep re mix after thermal instructions j1215, one or more control prep heating cooling instructions j1216, one or more control prep time control instructions j1217, one or more control prep ingredient exclusion instructions j1218, and one or more control prep ingredient inclusion instructions j1219.

Figure 107:
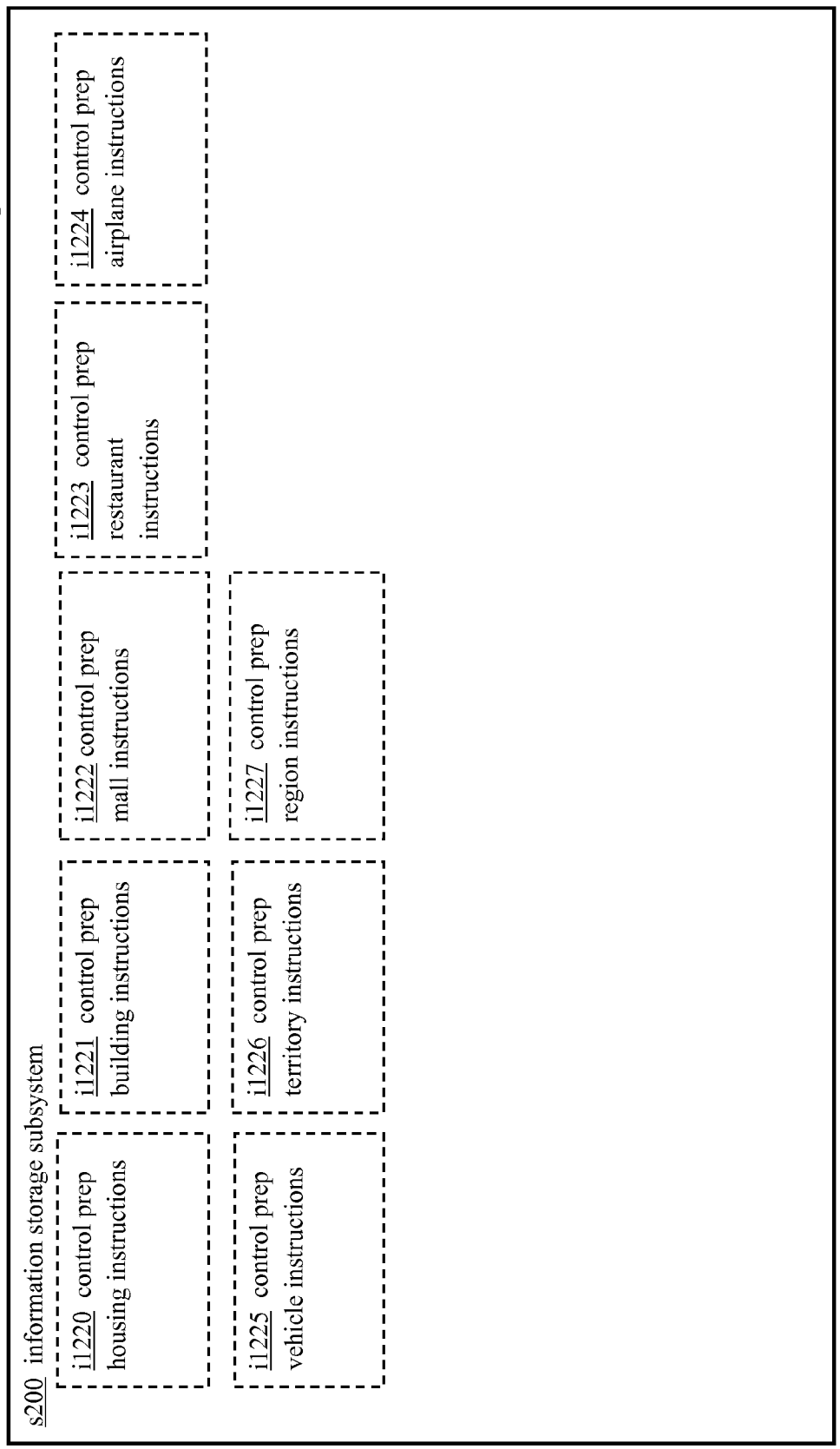
FIG. 107 is a block diagram depicting one or more exemplary instructions of the information storage subsystem s200 of the ingestible product preparation system 10 of FIG. 1.

One or more exemplary instructions depicted in FIG. 107 as being borne in an exemplary version of a non-transitory signal bearing medium of information storage subsystem s200 include one or more control prep housing instructions j1220, one or more control prep building instructions j1221, one or more control prep mall instructions j1222, one or more control prep restaurant instructions j1223, one or more control prep airplane instructions j1224, one or more control prep vehicle instructions j1225, one or more control prep territory instructions j1226, and one or more control prep region instructions j1227.

An operational flow p10 as shown in FIG. 108 represents example operations related to electronically receiving user status information regarding a particular individual living being including living being identification associated with the particular individual living being to at least in part electronically generate, based at least in part upon the user status information, one or more selection menus electronically identifying at least in part one or more candidate ingestible products, the electronically generated one or more selection menus to be electronically outputted to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus and electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus.

FIG. 108 and those figures that follow may have various examples of operational flows, and explanation may be provided with respect to the above-described examples of FIGS. 1-7 and/or with respect to other examples and contexts. Nonetheless, it should be understood that the operational flows may be executed in a number of other environments and contexts, and/or in modified versions of FIGS. 1-7. Furthermore, although the various operational flows are presented in the sequence(s) illustrated, it should be understood that the various operations may be performed in other orders than those which are illustrated, or may be performed concurrently.

In FIG. 108 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 108, the operational flow p10 proceeds to operation p11 for electronically receiving user status information regarding a particular individual living being including living being identification associated with the particular individual living being to at least in part electronically generate, based at least in part upon the user status information, one or more selection menus electronically identifying at least in part one or more candidate ingestible products, the electronically generated one or more selection menus to be electronically outputted to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus. An exemplary version of a non-transitory signal bearing medium of information storage subsystem s200 is depicted as bearing one or more receiving information instructions j11 that when executed will direct performance of the operation p11. In an implementation, the one or more receiving information instructions j11 when executed direct electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) to at least in part electronically generate (e.g. microprocessor component s102 uses the received user status information combined with database references to determine what to generate or otherwise be outputted), based at least in part upon the user status information (e.g. generating one or more menus based upon allergies, preferences, past selections, holidays, preparation and/or dispensing location, etc.) one or more selection menus (e.g. textual, graphical, audio-visual or other sorts of menus, etc.) electronically identifying at least in part one or more candidate ingestible products (e.g. textual descriptions on the menus of the one or more candidate ingestible products, etc.), the electronically generated one or more selection menus to be electronically outputted (e.g. outputted on electronic display screens, etc.) to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus (e.g. input using a keypad, voice commands, etc. to implement one or more selections, etc.). Furthermore, the receiving information electrical circuitry arrangement ("elec circ arrange") f11 when activated will perform the operation p11. In an implementation, the receiving information electrical circuitry arrangement f11, when activated performs electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) to at least in part electronically generate (e.g. microprocessor component s102 uses the received user status information combined with database references to determine what to generate or otherwise be outputted), based at least in part upon the user status information (e.g. generating one or more menus based upon allergies, preferences, past selections, holidays, preparation and/or dispensing location, etc.) one or more selection menus (e.g. textual, graphical, audio-visual or other sorts of menus, etc.) electronically identifying at least in part one or more candidate ingestible products (e.g. textual descriptions on the menus of the one or more candidate ingestible products, etc.), the electronically generated one or more selection menus to be electronically outputted (e.g. outputted on electronic display screens, etc.) to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus (e.g. input using a keypad, voice commands, etc. to implement one or more selections, etc.). In an implementation, the electronically receiving user status information regarding a particular individual living being including living being identification associated with the particular individual living being to at least in part electronically generate, based at least in part upon the user status information, one or more selection menus electronically identifying at least in part one or more candidate ingestible products, the electronically generated one or more selection menus to be electronically outputted to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus is carried out by electronically receiving (e.g. the network cable component s502 carries information to the transceiver component s522, etc.) user status information regarding a particular individual living being (e.g. a particular human being, animal, etc.) including living being identification associated with the particular individual living being (e.g. identification numbers, passwords, biometric data such as voice prints, stored in information storage subsystem 200) to at least in part electronically generate (e.g. microprocessor component s102 uses the received user status information combined with database references to determine what to generate or otherwise be outputted), based at least in part upon the user status information (e.g. generating one or more menus based upon allergies, preferences, past selections, holidays, preparation and/or dispensing location, etc.) one or more selection menus (e.g. textual, graphical, audio-visual or other sorts of menus, etc.) electronically identifying at least in part one or more candidate ingestible products (e.g. textual descriptions on the menus of the one or more candidate ingestible products, etc.), the electronically generated one or more selection menus to be electronically outputted (e.g. outputted on electronic display screens, etc.) to provide, via electronically enabled input in response thereto, selection opportunity of the one or more candidate ingestible products subject to ingestion by the particular individual living being prior to selection of at least one candidate ingestible product as at least one selected ingestible products via the electronically enabled input in response to the electronically outputted one or more selection menus (e.g. input using a keypad, voice commands, etc. to implement one or more selections, etc.).

In one or more implementations, as shown in FIG. 109, operation p11 includes an operation p1101 for electronically receiving the user status information regarding the particular individual living being via an electronic identification card. An exemplary version of a non-transitory signal bearing medium of information storage subsystem s200 is depicted as bearing one or more receiving information ID card instructions j1101 that when executed will direct performance of the operation p1101. In an implementation, the one or more receiving information ID card instructions j1101 when executed direct electronically receiving the user status information regarding the particular individual living being via an electronic identification card (e.g. an implementation of the receiver component s528 is configured to electronically engage with a card having memory storage holding the user status information, etc.). Furthermore, the receiving information ID card electrical circuitry arrangement ("elec circ arrange") f1101 when activated will perform the operation p1101. In an implementation, the receiving information ID card electrical circuitry arrangement f1101, when activated performs electronically receiving the user status information regarding the particular individual living being via an electronic identification card (e.g. an implementation of the receiver component s528 is configured to electronically engage with a card having memory storage holding the user status information, etc.). In an implementation, the electronically receiving the user status information regarding the particular individual living being via an electronic identification card is carried out by electronically receiving the user status information regarding the particular individual living being via an electronic identification card (e.g. an implementation of the receiver component s528 is configured to electronically engage with a card having memory storage holding the user status information, etc.).

In one or more implementations, operation p11 includes an operation p1102 for electronically receiving the user status information regarding the particular individual living being contained in a memory circuit coupled with a medication container. An exemplary version of a non-transitory signal bearing medium of information storage subsystem s200 is depicted as bearing one or more receiving information memory instructions j1102 that when executed will direct performance of the operation p1102. In an implementation, the one or more receiving information memory instructions j1102 when executed direct electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.). Furthermore, the receiving information memory electrical circuitry arrangement f1102 when activated will perform the operation p1102. In an implementation, the receiving information memory electrical circuitry arrangement f1102, when activated performs electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.). In an implementation, the electronically receiving the user status information regarding the particular individual living being contained in a memory circuit coupled with a medication container is carried out by electronically receiving the user status information regarding the particular individual living being contained in a memory circuit coupled with a medication container (e.g. an implementation of the receiver component s528 is configured to electronically engage with a memory storage coupled with a medication container to receive the user status information in electronic form, etc.).

In one or more implementations, operation p11 includes an operation p1103 for electronically receiving the user status information regarding the particular individual living being via a credit card swipe. An exemplary version of a non-transitory signal bearing medium of information storage subsystem s200 is depicted as bearing one or more receiving information credit card instructions j1103 that when executed will direct performance of the operation p1103. In an implementation, the one or more receiving information credit card instructions j1103 when executed direct electronically receiving the user status information regarding the particular individual living being via a credit card swipe (e.g. an implementation of the receiver component s528 is configured to electronically engage with an electronic memory stripe integrated into a credit card to receive the user status information, etc.). Furthermore, the receiving information credit card electrical circuitry arrangement f1103 when activated will perform the operation p1103. In an implementation, the receiving information credit card electrical circuitry arrangement f1103, when activated performs electronically receiving the user status information regarding the particular individual living being via a credit card swipe (e.g. an implementation of the receiver component s528 is configured to electronically engage with an electronic memory stripe integrated into a credit card to receive the user status information, etc.). In an implementation, the is electronically receiving the user status information regarding the particular individual living being via a credit card swipe carried out by electronically receiving the user status information regarding the particular individual living being via a credit card swipe (e.g. an implementation of the receiver component s528 is configured to electronically engage with an electronic memory stripe integrated into a credit card to receive the user status information, etc.).

Figure 110:
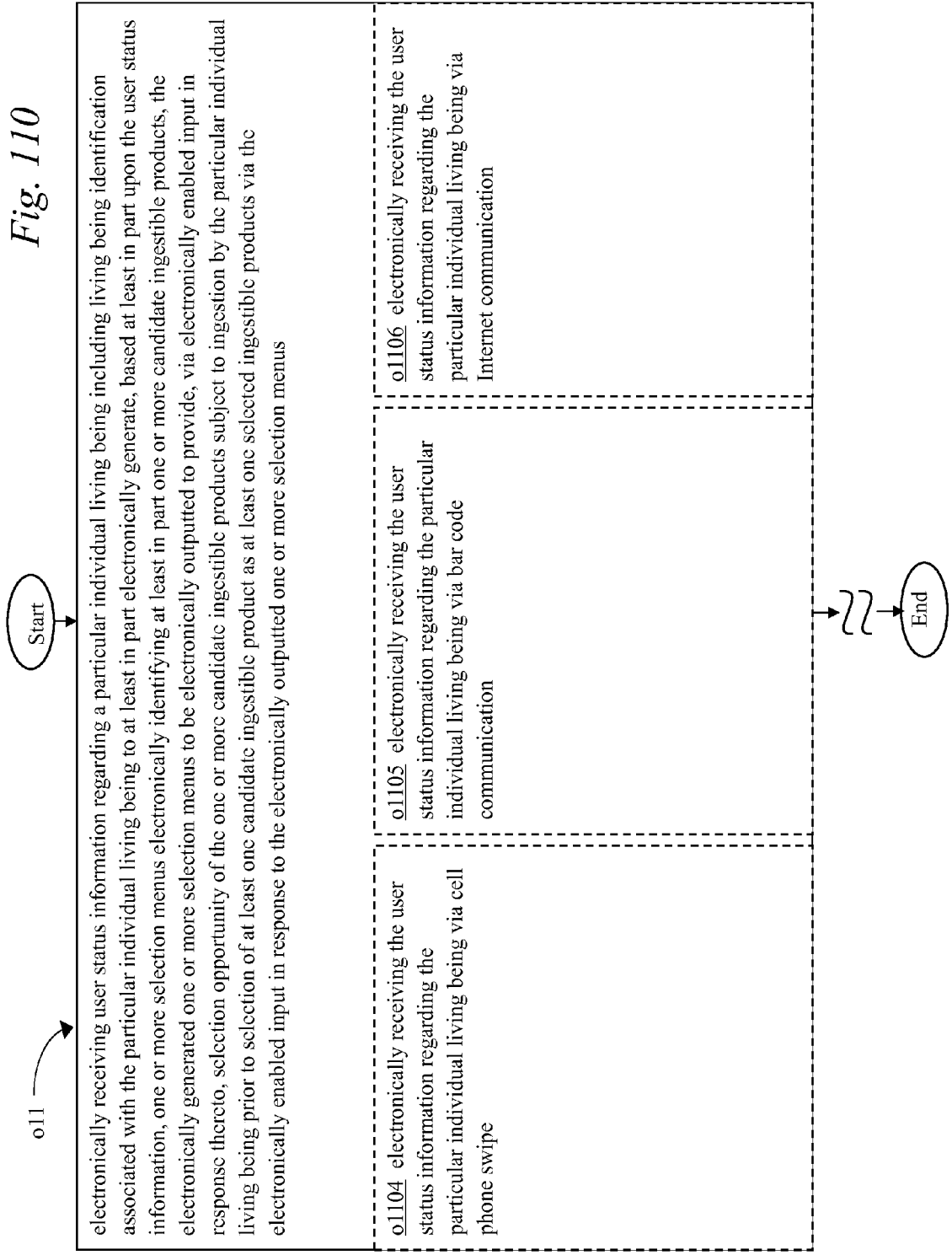
FIG. 110 is a high-level flowchart including exemplary implementations of operation p11 of FIG. 108.

In one or more implementations, as shown in FIG. 110, operation p11 includes an operation p1104 for electronically receiving the user status information regarding the particular individual living being via cell phone swipe. An exemplary version of a non-transitory signal bearing medium of information storage subsystem s200 is depicted as bearing one or more receiving information cell phone instructions j1104 that when executed will direct performance of the operation p1104. In an implementation, the one or more receiving information cell phone instructions j1104 when executed direct electronically receiving the user status information via cell phone swipe (e.g. an implementation of the receiver component s528 is configured to electronically engage with an electronic memory component integrated into a cell phone to receive the user status information, etc.). Furthermore, the receiving information cell phone electrical circuitry arrangement f1104 when activated will perform the operation p1104. In an implementation, the receiving information cell phone electrical circuitry arrangement f1104, when activated performs electronically receiving the user status information via cell phone swipe (e.g. an implementation of the receiver component s528 is configured to electronically engage with an electronic memory component integrated into a cell phone to receive the user status information, etc.). In an implementation, the is electronically receiving the user status information regarding the particular individual living being via cell phone swipe carried out by electronically receiving the user status information via cell phone swipe (e.g. an implementation of the receiver component s528 is configured to electronically engage with an electronic memory component integrated into a cell phone to receive the user status information, etc.).

In one or more implementations, operation p11 includes an operation p1105 for electronically receiving the user status information regarding the particular individual living being via bar code communication. An exemplary version of a non-transitory signal bearing medium of information storage subsystem s200 is depicted as bearing one or more receiving information bar code instructions j1105 that when executed will direct performance of the operation p1105. In an implementation, the one or more receiving information bar code instructions j1105 when executed direct electronically receiving the user status information via bar code communication (e.g. an implementation of the receiver component s528 is configured to electronically read a bar code label to receive the user status information, etc.). Furthermore, the receiving information bar code electrical circuitry arrangement f1105 when activated will perform the operation p1105. In an implementation, the receiving information bar code electrical circuitry arrangement f1105, when activated performs electronically receiving the user status information via bar code communication (e.g. an implementation of the receiver component s528 is configured to electronically read a bar code label to receive the user status information, etc.). In an implementation, the electronically receiving the user status information regarding the particular individual living being via bar code communication is carried out by electronically receiving the user status information via bar code communication (e.g. an implementation of the receiver component s528 is configured to electronically read a bar code label to receive the user status information, etc.).

In one or more implementations, operation p11 includes an operation p1106 for electronically receiving the user status information regarding the particular individual living being via Internet communication. An exemplary version of a non-transitory signal bearing medium of information storage subsystem s200 is depicted as bearing one or more receiving information Internet instructions j1106 that when executed will direct performance of the operation p1106. In an implementation, the one or more receiving information Internet instructions j1106 when executed direct electronically receiving the user status information via Internet communication (e.g. an implementation of the receiver component s528 is configured to electronically receive through the internet network component s508 the user status information, etc.). Furthermore, the receiving information Internet electrical circuitry arrangement f1106 when activated will perform the operation p1106. In an implementation, the receiving information Internet electrical circuitry arrangement f1106, when activated performs electronically receiving the user status information via Internet communication (e.g. an implementation of the receiver component s528 is configured to electronically receive through the internet network component s508 the user status information, etc.). In an implementation, the electronically receiving the user status information regarding the particular individual living being via Internet communication is carried out by electronically receiving the user status information via Internet communication (e.g. an implementation of the receiver component s528 is configured to electronically receive through the internet network component s508 the user status information, etc.).

Figure 111:
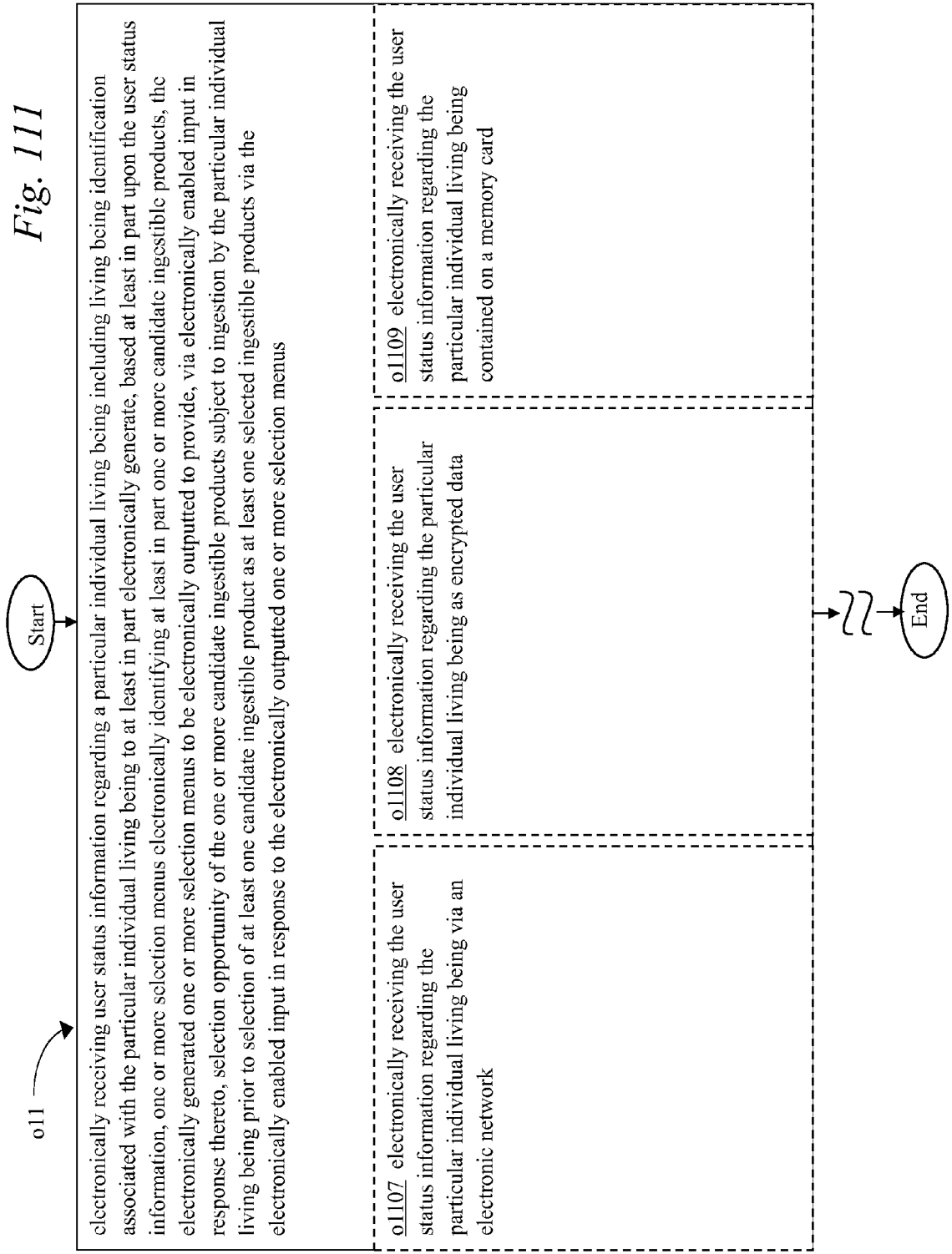
FIG. 111 is a high-level flowchart including exemplary implementations of operation p11 of FIG. 108.

In one or more implementations, as shown in FIG. 111, operation p11 includes an operation p1107 for electronically receiving the user status information regarding the particular individual living being via an electronic network. An exemplary version of a non-transitory signal bearing medium of information storage subsystem s200 is depicted as bearing one or more receiving information network instructions j1107 that when executed will direct performance of the operation p1107. In an implementation, the one or more receiving information network instructions j1107 when executed direct electronically receiving the user status information via an electronic network (e.g. an implementation of the receiver component s528 is configured to electronically engage with the network cable component s502 to receive the user status information, etc.). Furthermore, the receiving information network electrical circuitry arrangement f1107 when activated will perform the operation p1107. In an implementation, the receiving information network electrical circuitry arrangement f1107, when activated performs electronically receiving the user status information via an electronic network (e.g. an implementation of the receiver component s528 is configured to electronically engage with the network cable component s502 to receive the user status information, etc.). In an implementation, the electronically receiving the user status information regarding the particular individual living being via an electronic network is carried out by electronically receiving the user status information via an electronic network (e.g. an implementation of the receiver component s528 is configured to electronically engage with the network cable component s502 to receive the user status information, etc.).

In one or more implementations, operation p11 includes an operation p1108 for electronically receiving the user status information regarding the particular individual living being as encrypted data. An exemplary version of a non-transitory signal bearing medium of information storage subsystem s200 is depicted as bearing one or more receiving encrypted information instructions j1108 that when executed will direct performance of the operation p1108. In an implementation, the one or more receiving encrypted information instructions j1108 when executed direct electronically receiving the user status information as encrypted data (e.g. an implementation of the receiver component s528 is configured to electronically receive through the encrypted communication component s520 the user status information, etc.). Furthermore, the receiving encrypted information electrical circuitry arrangement f1108 when activated will perform the operation p1108. In an implementation, the receiving encrypted information electrical circuitry arrangement f1108, when activated performs electronically receiving the user status information as encrypted data (e.g. an implementation of the receiver component s528 is configured to electronically receive through the encrypted communication component s520 the user status information, etc.). In an implementation, the electronically receiving the user status information regarding the particular individual living being as encrypted data is carried out by electronically receiving the user status information as encrypted data (e.g. an implementation of the receiver component s528 is configured to electronically receive through the encrypted communication component s520 the user status information, etc.).

In one or more implementations, operation p11 includes an operation p1109 for electronically receiving the user status information regarding the particular individual living being contained on a memory card. An exemplary version of a non-transitory signal bearing medium of information storage subsystem s200 is depicted as bearing one or more receiving information memory card instructions j1109 that when executed will direct performance of the operation p1109. In an implementation, the one or more receiving information memory card instructions j1109 when executed direct electronically receiving the user status information contained on a memory card (e.g. an implementation of the receiver component s528 is configured to electronically engage with an electronic memory card to receive the user status information, etc.). Furthermore, the receiving information memory card electrical circuitry arrangement f1109 when activated will perform the operation p1109. In an implementation, the receiving information memory card electrical circuitry arrangement f1109, when activated performs electronically receiving the user status information contained on a memory card (e.g. an implementation of the receiver component s528 is configured to electronically engage with an electronic memory card to receive the user status information, etc.). In an implementation, the electronically receiving the user status information regarding the particular individual living being contained on a memory card is carried out by electronically receiving the user status information contained on a memory card (e.g. an implementation of the receiver component s528 is configured to electronically engage with an electronic memory card to receive the user status information, etc.).

Figure 112:
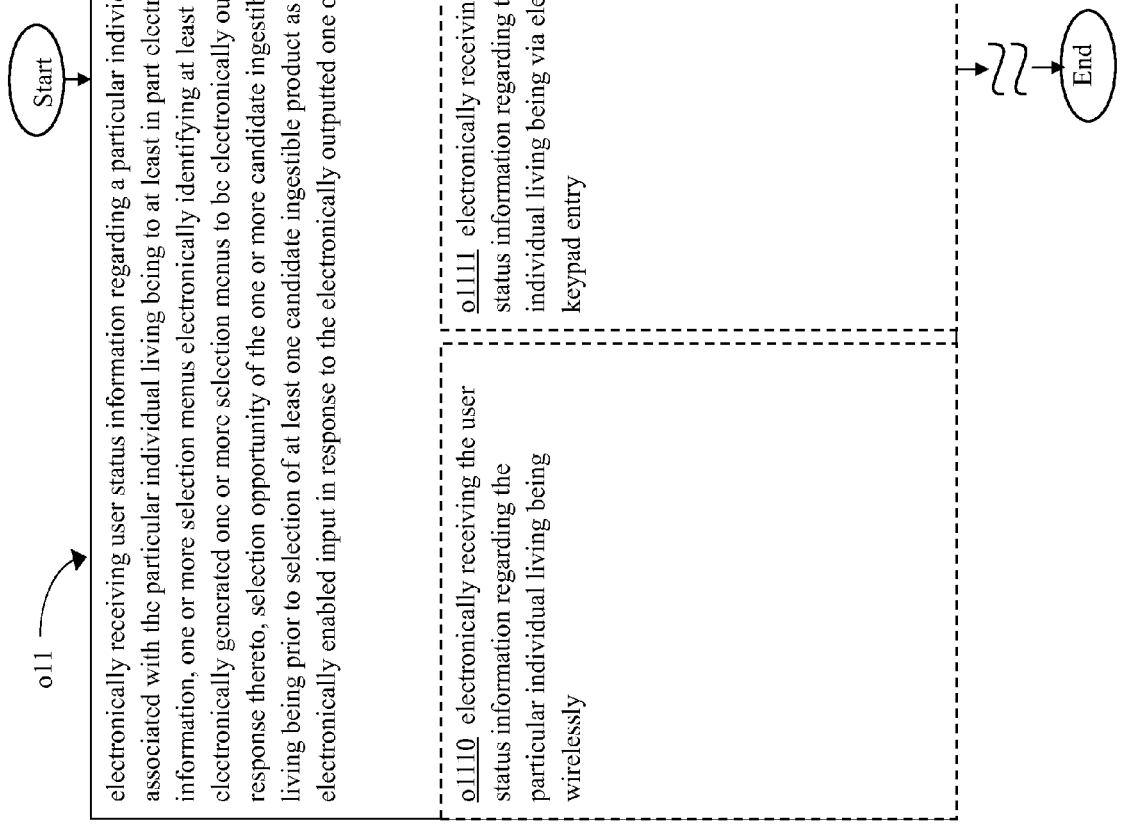
FIG. 112 is a high-level flowchart including exemplary implementations of operation p11 of FIG. 108.

In one or more implementations, as shown in FIG. 112, operation p11 includes an operation p1110 for electronically receiving the user status information regarding the particular individual living being wirelessly. An exemplary version of a non-transitory signal bearing medium of information storage subsystem s200 is depicted as bearing one or more receiving information wirelessly instructions j1110 that when executed will direct performance of the operation p1110. In an implementation, the one or more receiving information wirelessly instructions j1110 when executed direct electronically receiving the user status information wirelessly (e.g. an implementation of the receiver component s528 is configured to electronically receive through the wireless network component s512 the user status information, etc.). Furthermore, the receiving information wirelessly electrical circuitry arrangement f1110 when activated will perform the operation p1110. In an implementation, the receiving information wirelessly electrical circuitry arrangement f1110, when activated performs electronically receiving the user status information wirelessly (e.g. an implementation of the receiver component s528 is configured to electronically receive through the wireless network component s512 the user status information, etc.). In an implementation, the electronically receiving the user status information regarding the particular individual living being wirelessly is carried out by electronically receiving the user status information wirelessly (e.g. an implementation of the receiver component s528 is configured to electronically receive through the wireless network component s512 the user status information, etc.).

In one or more implementations, operation p11 includes an operation p1111 for electronically receiving the user status information regarding the particular individual living being via electronic keypad entry. An exemplary version of a non-transitory signal bearing medium of information storage subsystem s200 is depicted as bearing one or more receiving information keypad entry instructions j1111 that when executed will direct performance of the operation p1111. In an implementation, the one or more receiving information keypad entry instructions j1111 when executed direct electronically receiving the user status information via electronic keypad entry (e.g. an implementation of the receiver component s528 is configured to electronically engage with the keypad component s308 to receive the user status information as inputted by a user, etc.). Furthermore, the receiving information keypad entry electrical circuitry arrangement f1111 when activated will perform the operation p1111. In an implementation, the receiving information keypad entry electrical circuitry arrangement f1111, when activated performs electronically receiving the user status information via electronic keypad entry (e.g. an implementation of the receiver component s528 is configured to electronically engage with the keypad component s308 to receive the user status information as inputted by a user, etc.). In an implementation, the electronically receiving the user status information regarding the particular individual living being via electronic keypad entry is carried out by electronically receiving the user status information via electronic keypad entry (e.g. an implementation of the receiver component s528 is configured to electronically engage with the keypad component s308 to receive the user status information as inputted by a user, etc.).

In one or more implementations, operation p11 includes an operation p1112 for electronically receiving the user status information regarding the particular individual living being including the living being identification associated with the particular individual living being via a medication history. An exemplary version of a non-transitory signal bearing medium of information storage subsystem s200 is depicted as bearing one or more receiving information meds history instructions j1112 that when executed will direct performance of the operation p1112. In an implementation, the one or more receiving information meds history instructions j1112 when executed direct electronically receiving the user status information regarding the particular individual living being including the living being identification associated with the particular individual living being via a medication history (e.g. an implementation of the receiver component s528 is configured to electronically engage with the processor component s102 to receive the user status information including the living being identification associated with the particular individual living being as determined by the processor component to identify the name and control number of the medication history of the particular individual living being, etc.). Furthermore, the receiving information meds history electrical circuitry arrangement f1112 when activated will perform the operation p1112. In an implementation, the receiving information meds history electrical circuitry arrangement f1112, when activated performs electronically receiving the user status information regarding the particular individual living being including the living being identification associated with the particular individual living being via a medication history (e.g. an implementation of the receiver component s528 is configured to electronically engage with the processor component s102 to receive the user status information including the living being identification associated with the particular individual living being as determined by the processor component to identify the name and control number of the medication history of the particular individual living being, etc.). In an implementation, the electronically receiving the user status information regarding the particular individual living being including the living being identification associated with the particular individual living being via a medication history is carried out by electronically receiving the user status information regarding the particular individual living being including the living being identification associated with the particular individual living being via a medication history (e.g. an implementation of the receiver component s528 is configured to electronically engage with the processor component s102 to receive the user status information including the living being identification associated with the particular individual living being as determined by the processor component to identify the name and control number of the medication history of the particular individual living being, etc.).

Figure 113:
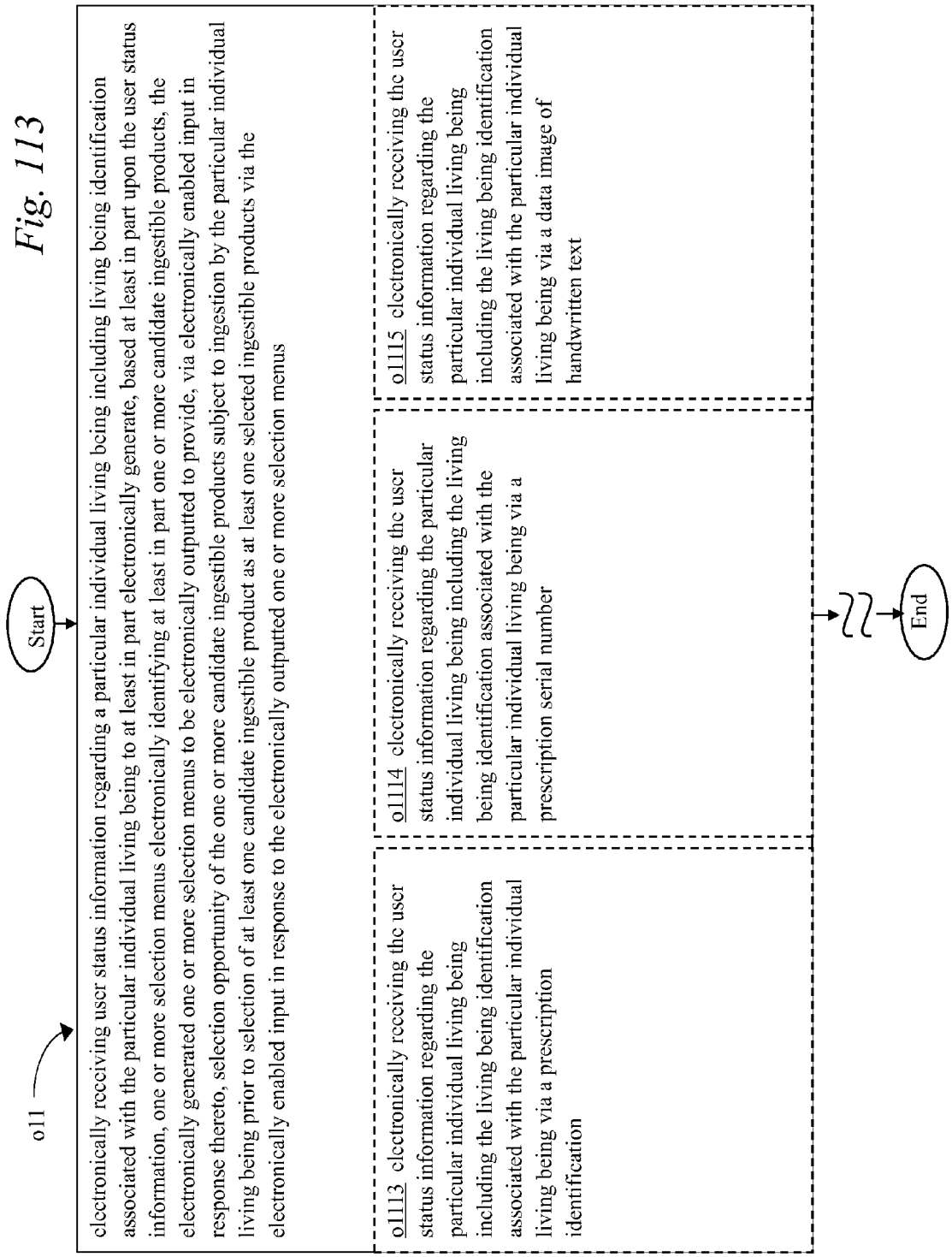
FIG. 113 is a high-level flowchart including exemplary implementations of operation p11 of FIG. 108.

In one or more implementations, as shown in FIG. 113, operation p11 includes an operation p1113 for electronically receiving the user status information regarding the particular individual living being including the living being identification associated with the particular individual living being via a prescription identification. An exemplary version of a non-transitory signal bearing medium of information storage subsystem s200 is depicted as bearing one or more receiving information prescription ID instructions j1113 that when executed will direct performance of the operation p1113. In an implementation, the one or more receiving information prescription ID instructions j1113 when executed direct electronically receiving the user status information regarding the particular individual living being including the living being identification associated with the particular individual living being via a prescription identification (e.g. an implementation of the receiver component s528 is configured to electronically engage with the processor component s102 to receive the user status information including the living being identification associated with the particular individual living being as determined by the processor component to include a prescription identification, etc.). Furthermore, the receiving information prescription ID electrical circuitry arrangement f1113 when activated will perform the operation p1113. In an implementation, the receiving information prescription ID electrical circuitry arrangement f1113, when activated performs electronically receiving the user status information regarding the particular individual living being including the living being identification associated with the particular individual living being via a prescription identification (e.g. an implementation of the receiver component s528 is configured to electronically engage with the processor component s102 to receive the user status information including the living being identification associated with the particular individual living being as determined by the processor component to include a prescription identification, etc.). In an implementation, the electronically receiving the user status information regarding the particular individual living being including the living being identification associated with the particular individual living being via a prescription identification is carried out by electronically receiving the user status information regarding the particular individual living being including the living being identification associated with the particular individual living being via a prescription identification (e.g. an implementation of the receiver component s528 is configured to electronically engage with the processor component s102 to receive the user status information including the living being identification associated with the particular individual living being as determined by the processor component to include a prescription identification, etc.).

In one or more implementations, operation p11 includes an operation p1114 for electronically receiving the user status information regarding the particular individual living being including the living being identification associated with the particular individual living being via a prescription serial number. An exemplary version of a non-transitory signal bearing medium of information storage subsystem s200 is depicted as bearing one or more receiving information prescription number instructions j1114 that when executed will direct performance of the operation p1114. In an implementation, the one or more receiving information prescription number instructions j1114 when executed direct electronically receiving the user status information regarding the particular individual living being including the living being identification associated with the particular individual living being via a prescription serial number (e.g. an implementation of the receiver component s528 is configured to electronically engage with the processor component s102 to receive the user status information including the living being identification associated with the particular individual living being as determined by the processor component to include a prescription serial number, etc.). Furthermore, the receiving information prescription number electrical circuitry arrangement f1114 when activated will perform the operation p1114. In an implementation, the receiving information prescription number electrical circuitry arrangement f1114, when activated performs electronically receiving the user status information regarding the particular individual living being including the living being identification associated with the particular individual living being via a prescription serial number (e.g. an implementation of the receiver component s528 is configured to electronically engage with the processor component s102 to receive the user status information including the living being identification associated with the particular individual living being as determined by the processor component to include a prescription serial number, etc.). In an implementation, the electronically receiving the user status information regarding the particular individual living being including the living being identification associated with the particular individual living being via a prescription serial number is carried out by electronically receiving the user status information regarding the particular individual living being including the living being identification associated with the particular individual living being via a prescription serial number (e.g. an implementation of the receiver component s528 is configured to electronically engage with the processor component s102 to receive the user status information including the living being identification associated with the particular individual living being as determined by the processor component to include a prescription serial number, etc.).

In one or more implementations, operation p11 includes an operation p1115 for electronically receiving the user status information regarding the particular individual living being including the living being identification associated with the particular individual living being via a data image of handwritten text. An exemplary version of a non-transitory signal bearing medium of information storage subsystem s200 is depicted as bearing one or more receiving information handwritten instructions j1115 that when executed will direct performance of the operation p1115. In an implementation, the one or more receiving information handwritten instructions j1115 when executed direct electronically receiving the user status information regarding the particular individual living being including the living being identification associated with the particular individual living being via a data image of handwritten text (e.g. an implementation of the receiver component s528 is configured to electronically engage with the processor component s102 to receive the user status information regarding the particular individual living being including the living being identification associated with the particular individual living being as determined by the processor component through electronic handwriting analysis of the data image of the handwritten text, etc.). Furthermore, the receiving information handwritten electrical circuitry arrangement f1115 when activated will perform the operation p1115. In an implementation, the receiving information handwritten electrical circuitry arrangement f1115, when activated performs electronically receiving the user status information regarding the particular individual living being including the living being identification associated with the particular individual living being via a data image of handwritten text (e.g. an implementation of the receiver component s528 is configured to electronically engage with the processor component s102 to receive the user status information regarding the particular individual living being including the living being identification associated with the particular individual living being as determined by the processor component through electronic handwriting analysis of the data image of the handwritten text, etc.). In an implementation, the electronically receiving the user status information regarding the particular individual living being including the living being identification associated with the particular individual living being via a data image of handwritten text is carried out by electronically receiving the user status information regarding the particular individual living being including the living being identification associated with the particular individual living being via a data image of handwritten text (e.g. an implementation of the receiver component s528 is configured to electronically engage with the processor component s102 to receive the user status information regarding the particular individual living being including the living being identification associated with the particular individual living being as determined by the processor component through electronic handwriting analysis of the data image of the handwritten text, etc.).

Figure 114:
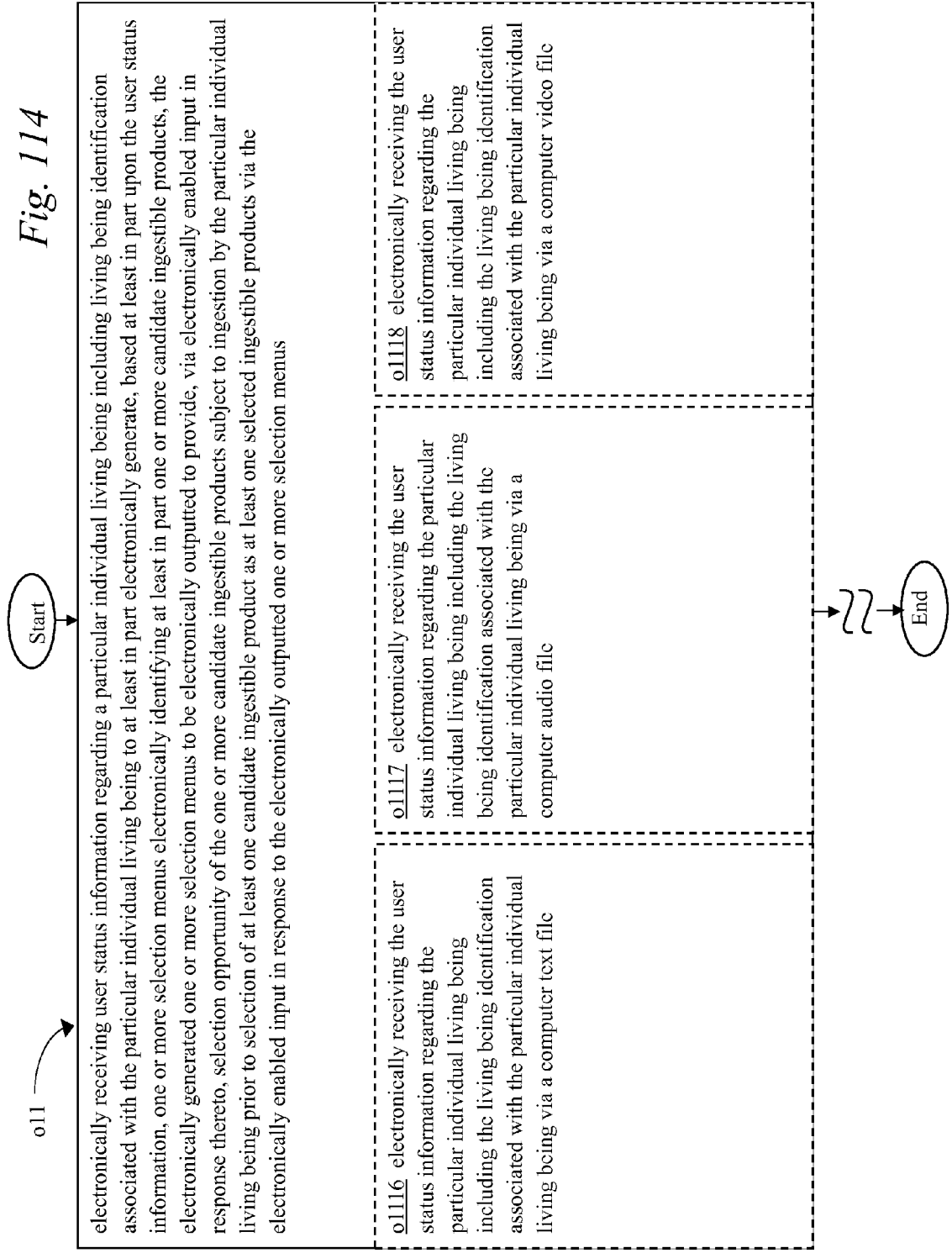
FIG. 114 is a high-level flowchart including exemplary implementations of operation p11 of FIG. 108.

In one or more implementations, as shown in FIG. 114, operation p11 includes an operation p1116 for electronically receiving the user status information regarding the particular individual living being including the living being identification associated with the particular individual living being via a computer text file. An exemplary version of a non-transitory signal bearing medium of information storage subsystem s200 is depicted as bearing one or more receiving information text file instructions j1116 that when executed will direct performance of the operation p1116. In an implementation, the one or more receiving information text file instructions j1116 when executed direct electronically receiving the user status information regarding the particular individual living being including the living being identification associated with the particular individual living being via a computer text file (e.g. an implementation of the receiver component s528 is configured to electronically engage with the processor component s102 to receive the user status information including the living being identification associated with the particular individual living being as determined by the processor component through electronic reading of the computer text file, etc.). Furthermore, the receiving information text file electrical circuitry arrangement f1116 when activated will perform the operation p1116. In an implementation, the receiving information text file electrical circuitry arrangement f1116, when activated performs electronically receiving the user status information regarding the particular individual living being including the living being identification associated with the particular individual living being via a computer text file (e.g. an implementation of the receiver component s528 is configured to electronically engage with the processor component s102 to receive the user status information including the living being identification associated with the particular individual living being as determined by the processor component through electronic reading of the computer text file, etc.). In an implementation, the electronically receiving the user status information regarding the particular individual living being including the living being identification associated with the particular individual living being via a computer text file is carried out by electronically receiving the user status information regarding the particular individual living being including the living being identification associated with the particular individual living being via a computer text file (e.g. an implementation of the receiver component s528 is configured to electronically engage with the processor component s102 to receive the user status information including the living being identification associated with the particular individual living being as determined by the processor component through electronic reading of the computer text file, etc.).

In one or more implementations, operation p11 includes an operation p1117 for electronically receiving the user status information regarding the particular individual living being including the living being identification associated with the particular individual living being via a computer audio file. An exemplary version of a non-transitory signal bearing medium of information storage subsystem s200 is depicted as bearing one or more receiving information audio file instructions j1117 that when executed will direct performance of the operation p1117. In an implementation, the one or more receiving information audio file instructions j1117 when executed direct electronically receiving the user status information regarding the particular individual living being including the living being identification associated with the particular individual living being via a computer audio file (e.g. an implementation of the receiver component s528 is configured to electronically engage with the processor component s102 to receive the user status information including the living being identification associated with the particular individual living being as determined by the processor component through electronic reading of the computer audio file, etc.). Furthermore, the receiving information audio file electrical circuitry arrangement f1117 when activated will perform the operation p1117. In an implementation, the receiving information audio file electrical circuitry arrangement f1117, when activated performs electronically receiving the user status information regarding the particular individual living being including the living being identification associated with the particular individual living being via a computer audio file (e.g. an implementation of the receiver component s528 is configured to electronically engage with the processor component s102 to receive the user status information including the living being identification associated with the particular individual living being as determined by the processor component through electronic reading of the computer audio file, etc.). In an implementation, the electronically receiving the user status information regarding the particular individual living being including the living being identification associated with the particular individual living being via a computer audio file is carried out by electronically receiving the user status information regarding the particular individual living being including the living being identification associated with the particular individual living being via a computer audio file (e.g. an implementation of the receiver component s528 is configured to electronically engage with the processor component s102 to receive the user status information including the living being identification associated with the particular individual living being as determined by the processor component through electronic reading of the computer audio file, etc.).

In one or more implementations, operation p11 includes an operation p1118 for electronically receiving the user status information regarding the particular individual living being including the living being identification associated with the particular individual living being via a computer video file. An exemplary version of a non-transitory signal bearing medium of information storage subsystem s200 is depicted as bearing one or more receiving information video file instructions j1118 that when executed will direct performance of the operation p1118. In an implementation, the one or more receiving information video file instructions j1118 when executed direct electronically receiving the user status information regarding the particular individual living being including the living being identification associated with the particular individual living being via a computer video file (e.g. an implementation of the receiver component s528 is configured to electronically engage with the processor component s102 to receive the user status information including the living being identification associated with the particular individual living being as determined by the processor component through electronic reading of the computer video file, etc.). Furthermore, the receiving information video file electrical circuitry arrangement f1118 when activated will perform the operation p1118. In an implementation, the receiving information video file electrical circuitry arrangement f1118, when activated performs electronically receiving the user status information regarding the particular individual living being including the living being identification associated with the particular individual living being via a computer video file (e.g. an implementation of the receiver component s528 is configured to electronically engage with the processor component s102 to receive the user status information including the living being identification associated with the particular individual living being as determined by the processor component through electronic reading of the computer video file, etc.). In an implementation, the electronically receiving the user status information regarding the particular individual living being including the living being identification associated with the particular individual living being via a computer video file is carried out by electronically receiving the user status information regarding the particular individual living being including the living being identification associated with the particular individual living being via a computer video file (e.g. an implementation of the receiver component s528 is configured to electronically engage with the processor component s102 to receive the user status information including the living being identification associated with the particular individual living being as determined by the processor component through electronic reading of the computer video file, etc.).

Figure 115:
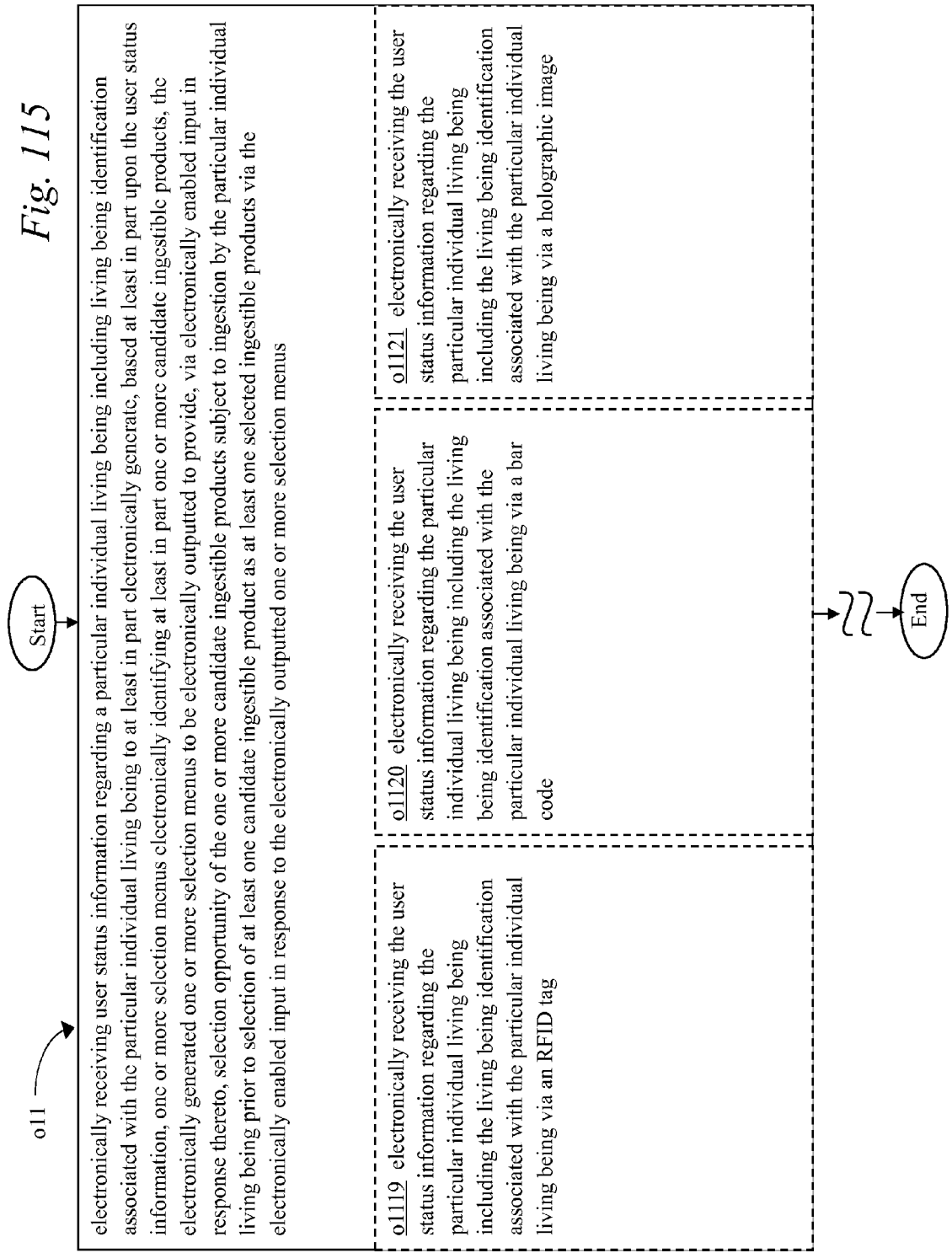
FIG. 115 is a high-level flowchart including exemplary implementations of operation p11 of FIG. 108.

In one or more implementations, as shown in FIG. 115, operation p11 includes an operation p1119 for electronically receiving the user status information regarding the particular individual living being including the living being identification associated with the particular individual living being via an RFID tag. An exemplary version of a non-transitory signal bearing medium of information storage subsystem s200 is depicted as bearing one or more receiving information RFID instructions j1119 that when executed will direct performance of the operation p1119. In an implementation, the one or more receiving information RFID instructions j1119 when executed direct electronically receiving the user status information regarding the particular individual living being including the living being identification associated with the particular individual living being via an RFID tag (e.g. an implementation of the receiver component s528 is configured to electronically engage with the processor component s102 to receive the user status information including the living being identification associated with the particular individual living being as determined by the processor component through electronic reading be the radio frequency identification (RFID) sensing component s414 of the RFID tag, etc.). Furthermore, the receiving information RFID electrical circuitry arrangement f1119 when activated will perform the operation p1119. In an implementation, the receiving information RFID electrical circuitry arrangement f1119, when activated performs electronically receiving the user status information regarding the particular individual living being including the living being identification associated with the particular individual living being via an RFID tag (e.g. an implementation of the receiver component s528 is configured to electronically engage with the processor component s102 to receive the user status information including the living being identification associated with the particular individual living being as determined by the processor component through electronic reading be the radio frequency identification (RFID) sensing component s414 of the RFID tag, etc.). In an implementation, the electronically receiving the user status information regarding the particular individual living being including the living being identification associated with the particular individual living being via an RFID tag is carried out by electronically receiving the user status information regarding the particular individual living being including the living being identification associated with the particular individual living being via an RFID tag (e.g. an implementation of the receiver component s528 is configured to electronically engage with the processor component s102 to receive the user status information including the living being identification associated with the particular individual living being as determined by the processor component through electronic reading be the radio frequency identification (RFID) sensing component s414 of the RFID tag, etc.).

In one or more implementations, operation p11 includes an operation p1120 for electronically receiving the user status information regarding the particular individual living being including the living being identification associated with the particular individual living being via a bar code. An exemplary version of a non-transitory signal bearing medium of information storage subsystem s200 is depicted as bearing one or more receiving information bar code instructions j1120 that when executed will direct performance of the operation p1120. In an implementation, the one or more receiving information bar code instructions j1120 when executed direct electronically receiving the user status information regarding the particular individual living being including the living being identification associated with the particular individual living being via a bar code (e.g. an implementation of the receiver component s528 is configured to electronically engage with the processor component s102 to receive the user status information including the living being identification associated with the particular individual living being as determined by the processor component through electronic reading of the bar code, etc.). Furthermore, the receiving information bar code electrical circuitry arrangement f1120 when activated will perform the operation electronically receiving the user status information regarding the particular individual living being including the living being identification associated with the particular individual living being via a bar code. In an implementation, the receiving information bar code electrical circuitry arrangement f1120, when activated performs electronically receiving the user status information regarding the particular individual living being including the living being identification associated with the particular individual living being via a bar code (e.g. an implementation of the receiver component s528 is configured to electronically engage with the processor component s102 to receive the user status information including the living being identification associated with the particular individual living being as determined by the processor component through electronic reading of the bar code, etc.). In an implementation, the electronically receiving the user status information regarding the particular individual living being including the living being identification associated with the particular individual living being via a bar code is carried out by electronically receiving the user status information regarding the particular individual living being including the living being identification associated with the particular individual living being via a bar code (e.g. an implementation of the receiver component s528 is configured to electronically engage with the processor component s102 to receive the user status information including the living being identification associated with the particular individual living being as determined by the processor component through electronic reading of the bar code, etc.).

In one or more implementations, operation p11 includes an operation p1121 for electronically receiving the user status information regarding the particular individual living being including the living being identification associated with the particular individual living being via a holographic image. An exemplary version of a non-transitory signal bearing medium of information storage subsystem s200 is depicted as bearing one or more receiving information holographic instructions j1121 that when executed will direct performance of the operation p1121. In an implementation, the one or more receiving information holographic instructions j1121 when executed direct electronically receiving the user status information regarding the particular individual living being including the living being identification associated with the particular individual living being via a holographic image (e.g. an implementation of the receiver component s528 is configured to electronically engage with the processor component s102 to receive the user status information including the living being identification associated with the particular individual living being as determined by the processor component through electronic reading of the holographic image, etc.). Furthermore, the receiving information holographic electrical circuitry arrangement f1121 when activated will perform the operation p1121. In an implementation, the receiving information holographic electrical circuitry arrangement f1121, when activated performs electronically receiving the user status information regarding the particular individual living being including the living being identification associated with the particular individual living being via a holographic image (e.g. an implementation of the receiver component s528 is configured to electronically engage with the processor component s102 to receive the user status information including the living being identification associated with the particular individual living being as determined by the processor component through electronic reading of the holographic image, etc.). In an implementation, the electronically receiving the user status information regarding the particular individual living being including the living being identification associated with the particular individual living being via a holographic image is carried out by electronically receiving the user status information regarding the particular individual living being including the living being identification associated with the particular individual living being via a holographic image (e.g. an implementation of the receiver component s528 is configured to electronically engage with the processor component s102 to receive the user status information including the living being identification associated with the particular individual living being as determined by the processor component through electronic reading of the holographic image, etc.).

Figure 116:
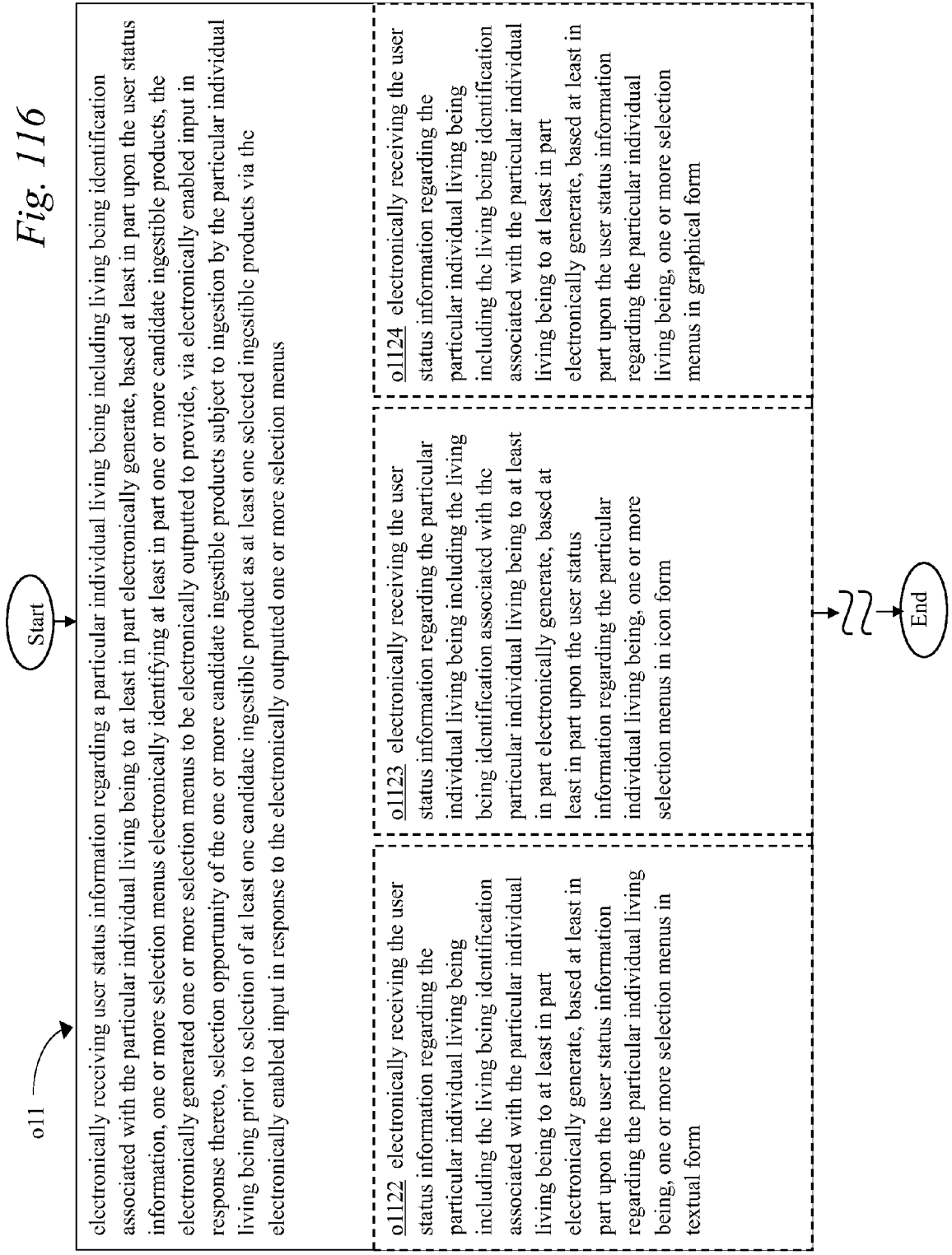
FIG. 116 is a high-level flowchart including exemplary implementations of operation p11 of FIG. 108.

In one or more implementations, as shown in FIG. 116, operation p11 includes an operation p1122 for electronically receiving the user status information regarding the particular individual living being including the living being identification associated with the particular individual living being to at least in part electronically generate, based at least in part upon the user status information regarding the particular individual living being, one or more selection menus in textual form. An exemplary version of a non-transitory signal bearing medium of information storage subsystem s200 is depicted as bearing one or more receiving information textual instructions j1122 that when executed will direct performance of the operation p1122. In an implementation, the one or more receiving information textual instructions j1122 when executed direct electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated allergies, one or more selection menus in textual form, such as a menu containing textual one or more descriptions of possible ingestible product to select from, etc.). Furthermore, the receiving information textual electrical circuitry arrangement f1122 when activated will perform the operation p1122. In an implementation, the receiving information textual electrical circuitry arrangement f1122, when activated performs electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated allergies, one or more selection menus in textual form, such as a menu containing textual one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in textual form is carried out by electronically receiving the user status information regarding the particular individual living being including the living being identification associated with the particular individual living being to at least in part electronically generate, based at least in part upon the user status information regarding the particular individual living being, one or more selection menus in textual form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated allergies, one or more selection menus in textual form, such as a menu containing textual one or more descriptions of possible ingestible product to select from, etc.).

In one or more implementations, operation p11 includes an operation p1123 for electronically receiving the user status information regarding the particular individual living being including the living being identification associated with the particular individual living being to at least in part electronically generate, based at least in part upon the user status information regarding the particular individual living being, one or more selection menus in icon form. An exemplary version of a non-transitory signal bearing medium of information storage subsystem s200 is depicted as bearing one or more receiving information icon instructions j1123 that when executed will direct performance of the operation p1123. In an implementation, the one or more receiving information icon instructions j1123 when executed direct electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.). Furthermore, the receiving information icon electrical circuitry arrangement f1123 when activated will perform the operation p1123. In an implementation, the receiving information icon electrical circuitry arrangement f1123, when activated performs electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in icon form is carried out by electronically receiving the user status information regarding the particular individual living being including the living being identification associated with the particular individual living being to at least in part electronically generate, based at least in part upon the user status information regarding the particular individual living being, one or more selection menus in icon form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated previous meals, one or more selection menus in icon form, such as a menu containing iconic one or more descriptions of possible ingestible product to select from, etc.).

In one or more implementations, operation p11 includes an operation p1124 for electronically receiving the user status information regarding the particular individual living being including the living being identification associated with the particular individual living being to at least in part electronically generate, based at least in part upon the user status information regarding the particular individual living being, one or more selection menus in graphical form. An exemplary version of a non-transitory signal bearing medium of information storage subsystem s200 is depicted as bearing one or more receiving information graphical instructions j1124 that when executed will direct performance of the operation p1124. In an implementation, the one or more receiving information graphical instructions j1124 when executed direct electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.). Furthermore, the receiving information graphical electrical circuitry arrangement f1124 when activated will perform the operation p1124. In an implementation, the receiving information graphical electrical circuitry arrangement f1124, when activated performs electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in graphical form is carried out by electronically receiving the user status information regarding the particular individual living being including the living being identification associated with the particular individual living being to at least in part electronically generate, based at least in part upon the user status information regarding the particular individual living being, one or more selection menus in graphical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated favorite foods as observed and recorded in a database, one or more selection menus in graphical form, such as a menu containing graphical one or more descriptions of possible ingestible product to select from, etc.).

Figure 117:
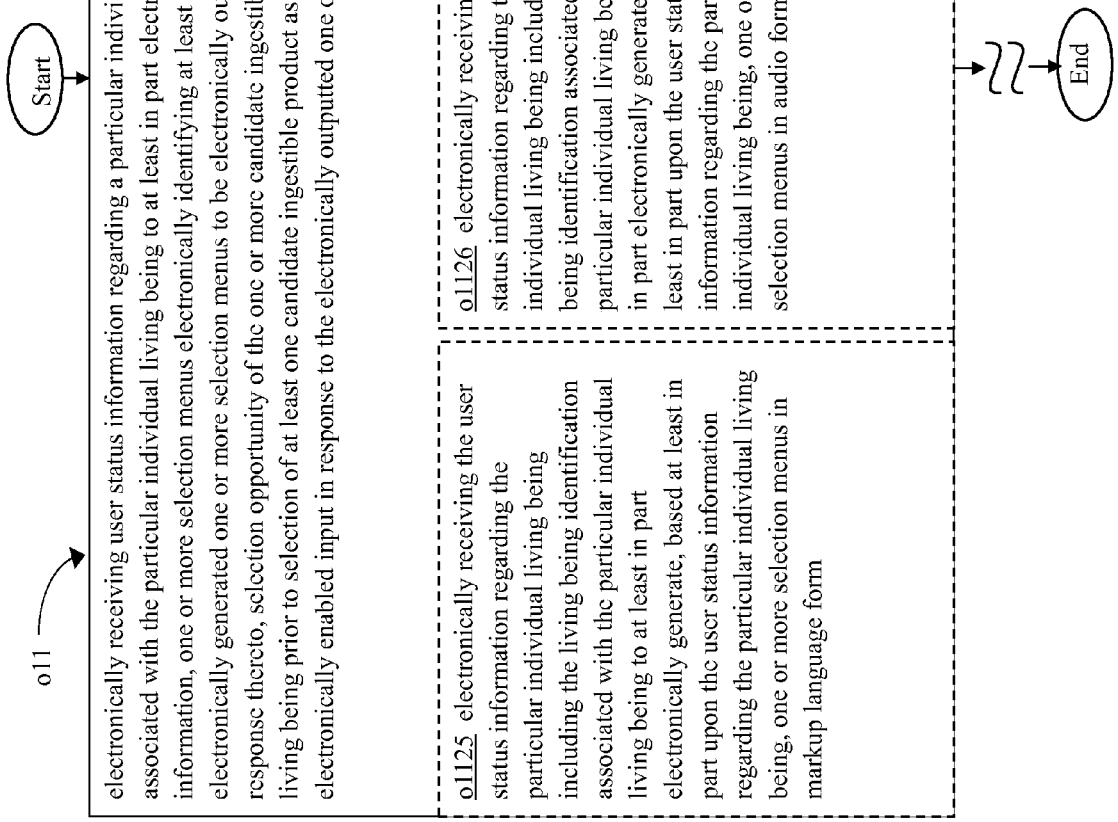

In one or more implementations, as shown in FIG. 117, operation p11 includes an operation p1125 for electronically receiving the user status information regarding the particular individual living being including the living being identification associated with the particular individual living being to at least in part electronically generate, based at least in part upon the user status information regarding the particular individual living being, one or more selection menus in markup language form. An exemplary version of a non-transitory signal bearing medium of information storage subsystem s200 is depicted as bearing one or more receiving information markup instructions j1125 that when executed will direct performance of the operation p1125. In an implementation, the one or more receiving information markup instructions j1125 when executed direct electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.). Furthermore, the receiving information markup electrical circuitry arrangement f1125 when activated will perform the operation p1125. In an implementation, the receiving information markup electrical circuitry arrangement f1125, when activated performs electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in markup language form is carried out by electronically receiving the user status information regarding the particular individual living being including the living being identification associated with the particular individual living being to at least in part electronically generate, based at least in part upon the user status information regarding the particular individual living being, one or more selection menus in markup language form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated health building goals, one or more selection menus in markup language form, such as a menu containing markup language one or more descriptions of possible ingestible product to select from, etc.).

In one or more implementations, operation p11 includes an operation p1126 for electronically receiving the user status information regarding the particular individual living being including the living being identification associated with the particular individual living being to at least in part electronically generate, based at least in part upon the user status information regarding the particular individual living being, one or more selection menus in audio form. An exemplary version of a non-transitory signal bearing medium of information storage subsystem s200 is depicted as bearing one or more receiving information audio instructions j1126 that when executed will direct performance of the operation p1126. In an implementation, the one or more receiving information audio instructions j1126 when executed direct electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.). Furthermore, the receiving information audio electrical circuitry arrangement f1126 when activated will perform the operation p1126. In an implementation, the receiving information audio electrical circuitry arrangement f1126, when activated performs electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in audio form is carried out by electronically receiving the user status information regarding the particular individual living being including the living being identification associated with the particular individual living being to at least in part electronically generate, based at least in part upon the user status information regarding the particular individual living being, one or more selection menus in audio form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated disease mitigating measures, one or more selection menus in audio form, such as a menu containing audio one or more descriptions of possible ingestible product to select from, etc.).

In one or more implementations, operation p11 includes an operation p1127 for electronically receiving the user status information regarding the particular individual living being including the living being identification associated with the particular individual living being to at least in part electronically generate, based at least in part upon the user status information regarding the particular individual living being, one or more selection menus in list form. An exemplary version of a non-transitory signal bearing medium of information storage subsystem s200 is depicted as bearing one or more receiving information list instructions j1127 that when executed will direct performance of the operation p1127. In an implementation, the one or more receiving information list instructions j1127 when executed direct electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated dislikes, one or more selection menus in list form, such as a menu containing listed one or more descriptions of possible ingestible product to select from, etc.)l. Furthermore, the receiving information list electrical circuitry arrangement f1127 when activated will perform the operation p1127. In an implementation, the receiving information list electrical circuitry arrangement f1127, when activated performs electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated dislikes, one or more selection menus in list form, such as a menu containing listed one or more descriptions of possible ingestible product to select from, etc.)l. In an implementation, the electronically receiving the user status information regarding the particular individual living being including the living being identification associated with the particular individual living being to at least in part electronically generate, based at least in part upon the user status information regarding the particular individual living being, one or more selection menus in list form is carried out by electronically receiving the user status information regarding the particular individual living being including the living being identification associated with the particular individual living being to at least in part electronically generate, based at least in part upon the user status information regarding the particular individual living being, one or more selection menus in list form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated dislikes, one or more selection menus in list form, such as a menu containing listed one or more descriptions of possible ingestible product to select from, etc.).

Figure 118:
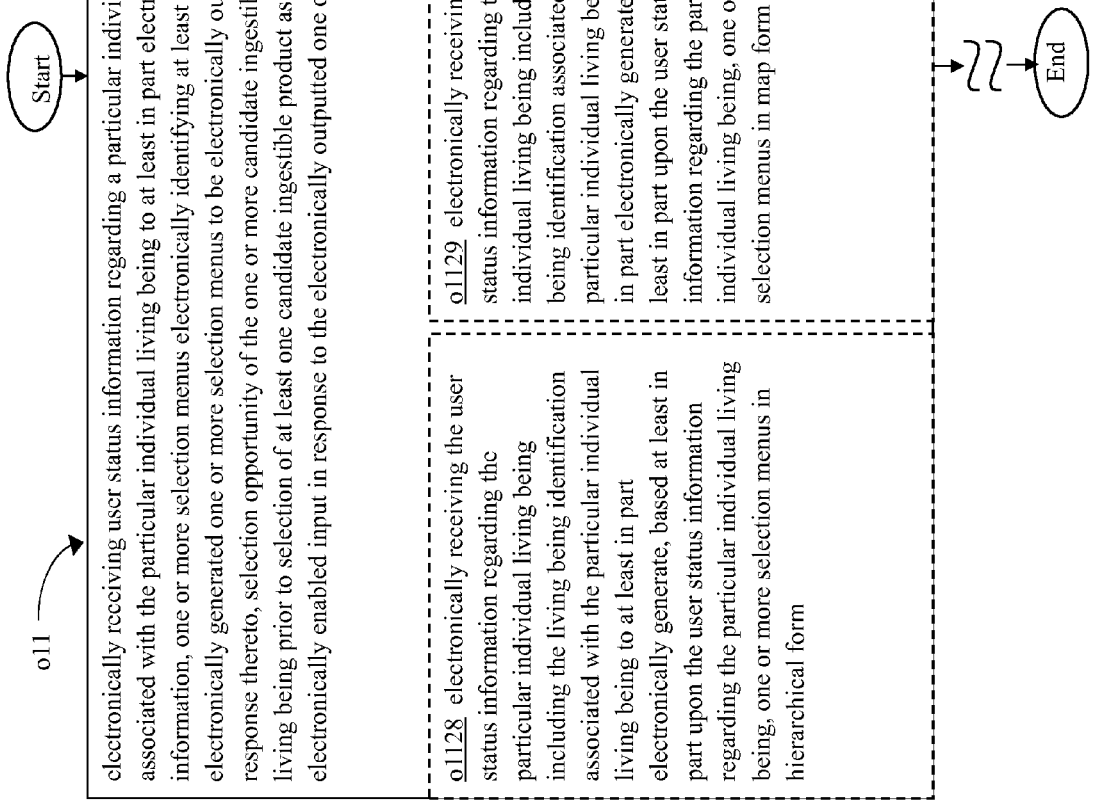

In one or more implementations, as shown in FIG. 118, operation p11 includes an operation p1128 for electronically receiving the user status information regarding the particular individual living being including the living being identification associated with the particular individual living being to at least in part electronically generate, based at least in part upon the user status information regarding the particular individual living being, one or more selection menus in hierarchical form. An exemplary version of a non-transitory signal bearing medium of information storage subsystem s200 is depicted as bearing one or more receiving information hierarchical instructions j1128 that when executed will direct performance of the operation p1128. In an implementation, the one or more receiving information hierarchical instructions j1128 when executed direct electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.). Furthermore, the receiving information hierarchical electrical circuitry arrangement f1128 when activated will perform the operation p1128. In an implementation, the receiving information hierarchical electrical circuitry arrangement f1128, when activated performs electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in hierarchical form is carried out by electronically receiving the user status information regarding the particular individual living being including the living being identification associated with the particular individual living being to at least in part electronically generate, based at least in part upon the user status information regarding the particular individual living being, one or more selection menus in hierarchical form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated past purchases, one or more selection menus in hierarchical form, such as a menu containing hierarchical one or more descriptions of possible ingestible product to select from, etc.).

In one or more implementations, operation p11 includes an operation p1129 for electronically receiving the user status information regarding the particular individual living being including the living being identification associated with the particular individual living being to at least in part electronically generate, based at least in part upon the user status information regarding the particular individual living being, one or more selection menus in map form. An exemplary version of a non-transitory signal bearing medium of information storage subsystem s200 is depicted as bearing one or more receiving information map instructions j1129 that when executed will direct performance of the operation p1129. In an implementation, the one or more receiving information map instructions j1129 when executed direct electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.). Furthermore, the receiving information map electrical circuitry arrangement f1129 when activated will perform the operation p1129. In an implementation, the receiving information map electrical circuitry arrangement f1129, when activated performs electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in map form is carried out by electronically receiving the user status information regarding the particular individual living being including the living being identification associated with the particular individual living being to at least in part electronically generate, based at least in part upon the user status information regarding the particular individual living being, one or more selection menus in map form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated food preferences determined from use history stored in one or more distributed databases, one or more selection menus in map form, such as a menu having arrangements resembling one or more maps containing one or more selections and one or more descriptions of possible ingestible product to select from, etc.).

In one or more implementations, operation p11 includes an operation p1130 for electronically receiving the user status information regarding the particular individual living being including the living being identification associated with the particular individual living being to at least in part electronically generate, based at least in part upon the user status information regarding the particular individual living being, one or more selection menus in video presentation form. An exemplary version of a non-transitory signal bearing medium of information storage subsystem s200 is depicted as bearing one or more receiving information video instructions j1130 that when executed will direct performance of the operation p1130. In an implementation, the one or more receiving information video instructions j1130 when executed direct electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.). Furthermore, the receiving information video electrical circuitry arrangement f1130 when activated will perform the operation p1130. In an implementation, the receiving information video electrical circuitry arrangement f1130, when activated performs electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in video presentation form is carried out by electronically receiving the user status information regarding the particular individual living being including the living being identification associated with the particular individual living being to at least in part electronically generate, based at least in part upon the user status information regarding the particular individual living being, one or more selection menus in video presentation form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more prescriptions, one or more selection menus in video presentation form, such as a menu containing one or more video presentations having one or more descriptions of possible ingestible product to select from, etc.).

Figure 119:
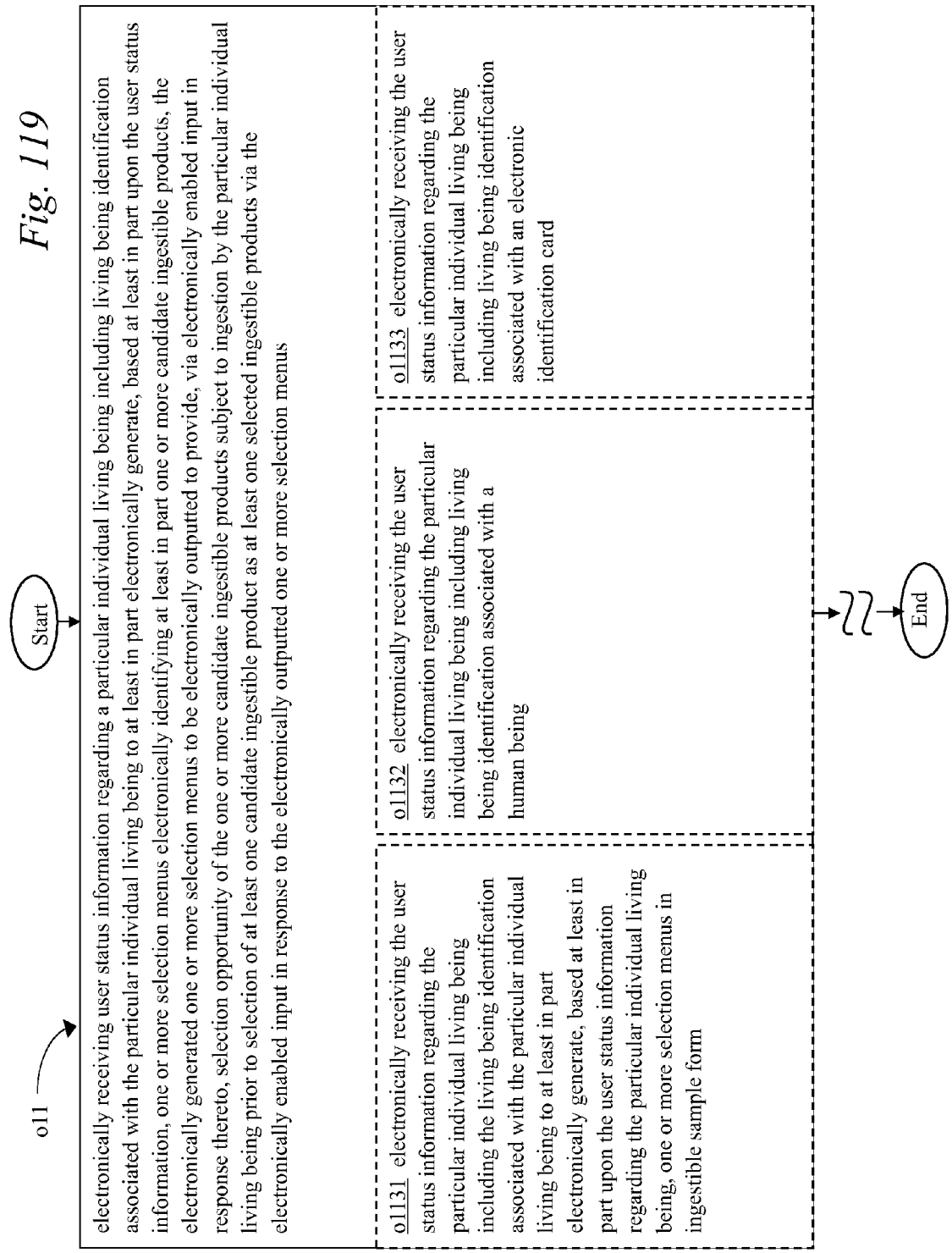

In one or more implementations, as shown in FIG. 119, operation p11 includes an operation p1131 for electronically receiving the user status information regarding the particular individual living being including the living being identification associated with the particular individual living being to at least in part electronically generate, based at least in part upon the user status information regarding the particular individual living being, one or more selection menus in ingestible sample form. An exemplary version of a non-transitory signal bearing medium of information storage subsystem s200 is depicted as bearing one or more receiving information sample instructions j1131 that when executed will direct performance of the operation p1131. In an implementation, the one or more receiving information sample instructions j1131 when executed direct electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.). Furthermore, the receiving information sample electrical circuitry arrangement f1131 when activated will perform the operation p1131. In an implementation, the receiving information sample electrical circuitry arrangement f1131, when activated performs electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.). In an implementation, the electronically receiving the user status information regarding the particular individual living being including the living being identification associated with the particular individual living being to at least in part electronically generate, based at least in part upon the user status information regarding the particular individual living being, one or more selection menus in ingestible sample form is carried out by electronically receiving the user status information regarding the particular individual living being including the living being identification associated with the particular individual living being to at least in part electronically generate, based at least in part upon the user status information regarding the particular individual living being, one or more selection menus in ingestible sample form (e.g. an implementation of the receiver component s528 is configured to electronically engage with the processor component s102 to receive the user status information including the living being identification associated with the particular individual living being for the processor component to at least in part electronically generate, based at least in part upon the user status information regarding the particular individual living being, such as based on associated one or more holidays stored in one or more databases, one or more selection menus in ingestible sample form, such as a menu containing ingestible samples that are either stored or produced in real time to serve as or otherwise complement one or more descriptions of possible ingestible product to select from, etc.).

In one or more implementations, operation p11 includes an operation p1132 for electronically receiving the user status information regarding the particular individual living being including living being identification associated with a human being. An exemplary version of a non-transitory signal bearing medium of information storage subsystem s200 is depicted as bearing one or more receiving information human instructions j1132 that when executed will direct performance of the operation p1132. In an implementation, the one or more receiving information human instructions j1132 when executed direct electronically receiving the user status information regarding the particular individual living being including living being identification associated with a human being (e.g. an implementation of the receiver component s528 is configured to electronically engage with the processor component s102 to receive the user status information regarding the particular individual living being including living being identification as determined by the processor component to be identifying a human being, etc.). Furthermore, the receiving information human electrical circuitry arrangement f1132 when activated will perform the operation p1132. In an implementation, the receiving information human electrical circuitry arrangement f1132, when activated performs electronically receiving the user status information regarding the particular individual living being including living being identification associated with a human being (e.g. an implementation of the receiver component s528 is configured to electronically engage with the processor component s102 to receive the user status information regarding the particular individual living being including living being identification as determined by the processor component to be identifying a human being, etc.). In an implementation, the electronically receiving the user status information regarding the particular individual living being including living being identification associated with a human being is carried out by electronically receiving the user status information regarding the particular individual living being including living being identification associated with a human being (e.g. an implementation of the receiver component s528 is configured to electronically engage with the processor component s102 to receive the user status information regarding the particular individual living being including living being identification as determined by the processor component to be identifying a human being, etc.).

In one or more implementations, operation p11 includes an operation p1133 for electronically receiving the user status information regarding the particular individual living being including living being identification associated with an electronic identification card. An exemplary version of a non-transitory signal bearing medium of information storage subsystem s200 is depicted as bearing one or more receiving information ID card instructions j1133 that when executed will direct performance of the operation p1133. In an implementation, the one or more receiving information ID card instructions j1133 when executed direct electronically receiving the user status information regarding the particular individual living being including living being identification associated with an electronic identification card (e.g. an implementation of the receiver component s528 is configured to electronically engage with the processor component s102 to receive the user status information regarding the particular individual living being including living being identification as determined by the processor component to be identifying a living being through the electronic identification card, etc.). Furthermore, the receiving information ID card electrical circuitry arrangement f1133 when activated will perform the operation p1133. In an implementation, the receiving information ID card electrical circuitry arrangement f1133, when activated performs electronically receiving the user status information regarding the particular individual living being including living being identification associated with an electronic identification card (e.g. an implementation of the receiver component s528 is configured to electronically engage with the processor component s102 to receive the user status information regarding the particular individual living being including living being identification as determined by the processor component to be identifying a living being through the electronic identification card, etc.). In an implementation, the electronically receiving the user status information regarding the particular individual living being including living being identification associated with an electronic identification card is carried out by electronically receiving the user status information regarding the particular individual living being including living being identification associated with an electronic identification card (e.g. an implementation of the receiver component s528 is configured to electronically engage with the processor component s102 to receive the user status information regarding the particular individual living being including living being identification as determined by the processor component to be identifying a living being through the electronic identification card, etc.).

Figure 120:
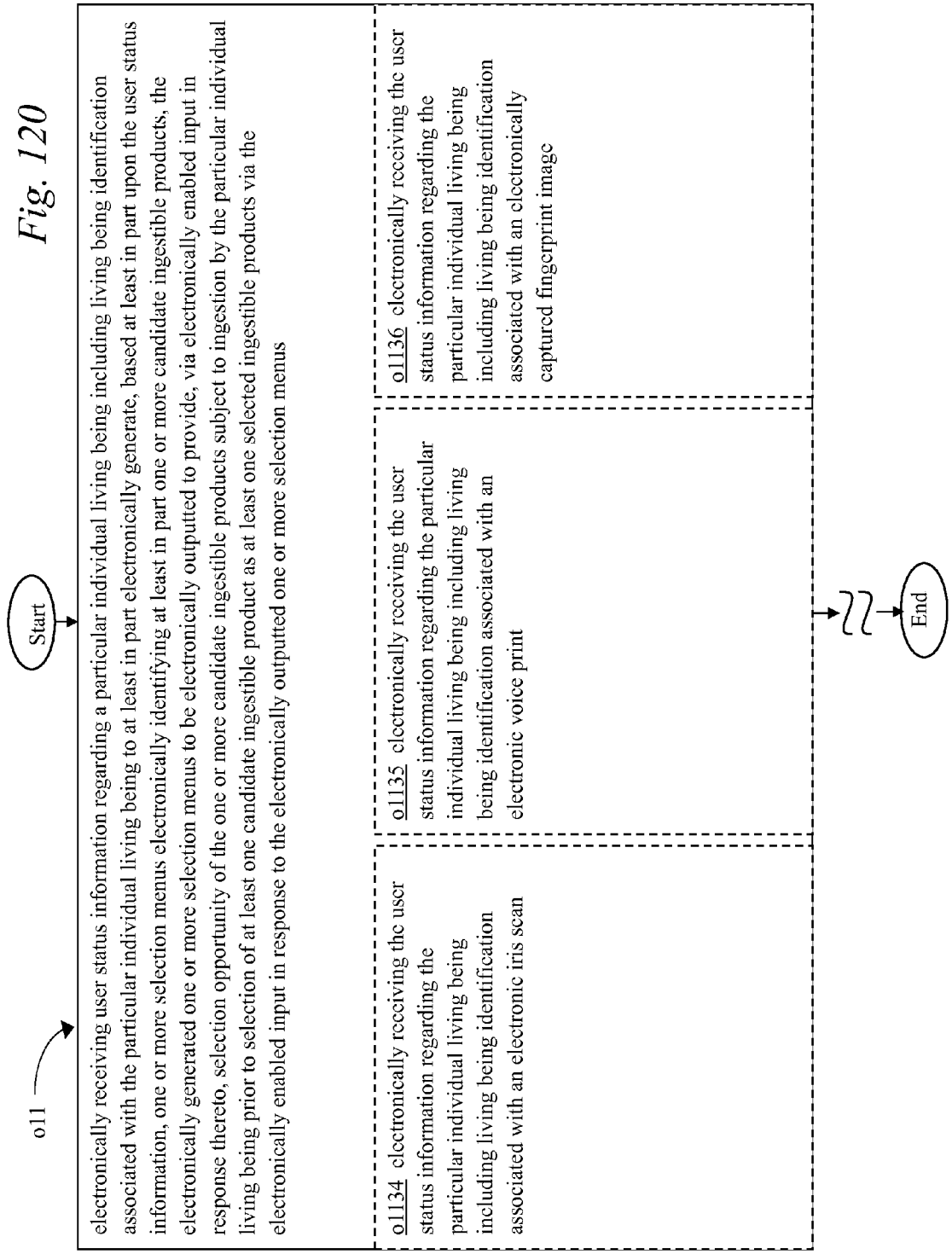

In one or more implementations, as shown in FIG. 120, operation p11 includes an operation p1134 for electronically receiving the user status information regarding the particular individual living being including living being identification associated with an electronic iris scan. An exemplary version of a non-transitory signal bearing medium of information storage subsystem s200 is depicted as bearing one or more receiving information iris scan instructions j1134 that when executed will direct performance of the operation p1134. In an implementation, the one or more receiving information iris scan instructions j1134 when executed direct electronically receiving the user status information regarding the particular individual living being including living being identification associated with an electronic iris scan (e.g. an implementation of the receiver component s528 is configured to electronically engage with the processor component s102 to receive the user status information regarding the particular individual living being including living being identification as determined by the processor component to be identifying the living being through the electronic iris scan, etc.). Furthermore, the receiving information iris scan electrical circuitry arrangement f1134 when activated will perform the operation p1134. In an implementation, the receiving information iris scan electrical circuitry arrangement f1134, when activated performs electronically receiving the user status information regarding the particular individual living being including living being identification associated with an electronic iris scan (e.g. an implementation of the receiver component s528 is configured to electronically engage with the processor component s102 to receive the user status information regarding the particular individual living being including living being identification as determined by the processor component to be identifying the living being through the electronic iris scan, etc.). In an implementation, the electronically receiving the user status information regarding the particular individual living being including living being identification associated with an electronic iris scan is carried out by electronically receiving the user status information regarding the particular individual living being including living being identification associated with an electronic iris scan (e.g. an implementation of the receiver component s528 is configured to electronically engage with the processor component s102 to receive the user status information regarding the particular individual living being including living being identification as determined by the processor component to be identifying the living being through the electronic iris scan, etc.).

In one or more implementations, operation p11 includes an operation p1135 for electronically receiving the user status information regarding the particular individual living being including living being identification associated with an electronic voice print. An exemplary version of a non-transitory signal bearing medium of information storage subsystem s200 is depicted as bearing one or more receiving information voice instructions j1135 that when executed will direct performance of the operation p1135. In an implementation, the one or more receiving information voice instructions j1135 when executed direct electronically receiving the user status information regarding the particular individual living being including living being identification associated with an electronic voice print (e.g. an implementation of the receiver component s528 is configured to electronically engage with the processor component s102 to receive the user status information regarding the particular individual living being including living being identification as determined by the processor component to be identifying the living being through the electronic voice print, etc.). Furthermore, the receiving information voice electrical circuitry arrangement f1135 when activated will perform the operation p1135. In an implementation, the receiving information voice electrical circuitry arrangement f1135, when activated performs electronically receiving the user status information regarding the particular individual living being including living being identification associated with an electronic voice print (e.g. an implementation of the receiver component s528 is configured to electronically engage with the processor component s102 to receive the user status information regarding the particular individual living being including living being identification as determined by the processor component to be identifying the living being through the electronic voice print, etc.). In an implementation, the electronically receiving the user status information regarding the particular individual living being including living being identification associated with an electronic voice print is carried out by electronically receiving the user status information regarding the particular individual living being including living being identification associated with an electronic voice print (e.g. an implementation of the receiver component s528 is configured to electronically engage with the processor component s102 to receive the user status information regarding the particular individual living being including living being identification as determined by the processor component to be identifying the living being through the electronic voice print, etc.).

In one or more implementations, operation p11 includes an operation p1136 for electronically receiving the user status information regarding the particular individual living being including living being identification associated with an electronically captured fingerprint image. An exemplary version of a non-transitory signal bearing medium of information storage subsystem s200 is depicted as bearing one or more receiving information fingerprint instructions j1136 that when executed will direct performance of the operation p1136. In an implementation, the one or more receiving information fingerprint instructions j1136 when executed direct electronically receiving the user status information regarding the particular individual living being including living being identification associated with an electronically captured fingerprint image (e.g. an implementation of the receiver component s528 is configured to electronically engage with the processor component s102 to receive the user status information regarding the particular individual living being including living being identification as determined by the processor component to be identifying the living being through the electronically captured fingerprint image, etc.). Furthermore, the receiving information fingerprint electrical circuitry arrangement f1136 when activated will perform the operation p1136. In an implementation, the receiving information fingerprint electrical circuitry arrangement f1136, when activated performs electronically receiving the user status information regarding the particular individual living being including living being identification associated with an electronically captured fingerprint image (e.g. an implementation of the receiver component s528 is configured to electronically engage with the processor component s102 to receive the user status information regarding the particular individual living being including living being identification as determined by the processor component to be identifying the living being through the electronically captured fingerprint image, etc.). In an implementation, the electronically receiving the user status information regarding the particular individual living being including living being identification associated with an electronically captured fingerprint image is carried out by electronically receiving the user status information regarding the particular individual living being including living being identification associated with an electronically captured fingerprint image (e.g. an implementation of the receiver component s528 is configured to electronically engage with the processor component s102 to receive the user status information regarding the particular individual living being including living being identification as determined by the processor component to be identifying the living being through the electronically captured fingerprint image, etc.).

Figure 121:
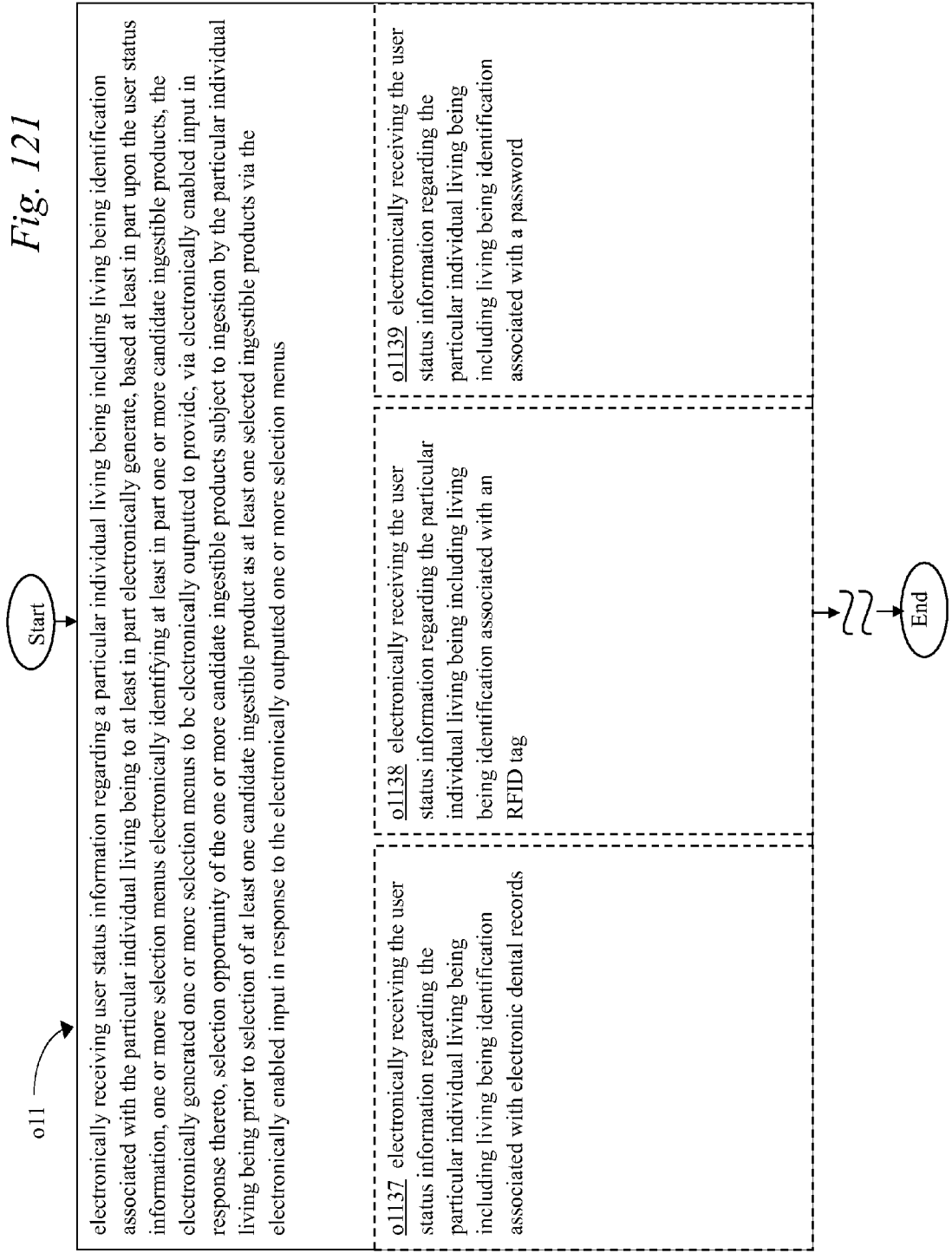

In one or more implementations, as shown in FIG. 121, operation p11 includes an operation p1137 for electronically receiving the user status information regarding the particular individual living being including living being identification associated with electronic dental records. An exemplary version of a non-transitory signal bearing medium of information storage subsystem s200 is depicted as bearing one or more receiving information dental instructions j1137 that when executed will direct performance of the operation p1137. In an implementation, the one or more receiving information dental instructions j1137 when executed direct electronically receiving the user status information regarding the particular individual living being including living being identification associated with electronic dental records (e.g. an implementation of the receiver component s528 is configured to electronically engage with the processor component s102 to receive the user status information regarding the particular individual living being including living being identification as determined by the processor component to be identifying the living being through the electronic dental records, etc.). Furthermore, the receiving information dental electrical circuitry arrangement f1137 when activated will perform the operation p1137. In an implementation, the receiving information dental electrical circuitry arrangement f1137, when activated performs electronically receiving the user status information regarding the particular individual living being including living being identification associated with electronic dental records (e.g. an implementation of the receiver component s528 is configured to electronically engage with the processor component s102 to receive the user status information regarding the particular individual living being including living being identification as determined by the processor component to be identifying the living being through the electronic dental records, etc.). In an implementation, the electronically receiving the user status information regarding the particular individual living being including living being identification associated with electronic dental records is carried out by electronically receiving the user status information regarding the particular individual living being including living being identification associated with electronic dental records (e.g. an implementation of the receiver component s528 is configured to electronically engage with the processor component s102 to receive the user status information regarding the particular individual living being including living being identification as determined by the processor component to be identifying the living being through the electronic dental records, etc.).

In one or more implementations, operation p11 includes an operation p1138 for electronically receiving the user status information regarding the particular individual living being including living being identification associated with an RFID tag. An exemplary version of a non-transitory signal bearing medium of information storage subsystem s200 is depicted as bearing one or more receiving information RFID instructions j1138 that when executed will direct performance of the operation p1138. In an implementation, the one or more receiving information RFID instructions j1138 when executed direct electronically receiving the user status information regarding the particular individual living being including living being identification associated with an RFID tag (e.g. an implementation of the receiver component s528 is configured to electronically engage with the processor component s102 to receive the user status information regarding the particular individual living being including living being identification as determined by the processor component to be identifying the living being through the RFID tag, etc.). Furthermore, the receiving information RFID electrical circuitry arrangement f1138 when activated will perform the operation p1138. In an implementation, the receiving information RFID electrical circuitry arrangement f1138, when activated performs electronically receiving the user status information regarding the particular individual living being including living being identification associated with an RFID tag (e.g. an implementation of the receiver component s528 is configured to electronically engage with the processor component s102 to receive the user status information regarding the particular individual living being including living being identification as determined by the processor component to be identifying the living being through the RFID tag, etc.). In an implementation, the electronically receiving the user status information regarding the particular individual living being including living being identification associated with an RFID tag is carried out by electronically receiving the user status information regarding the particular individual living being including living being identification associated with an RFID tag (e.g. an implementation of the receiver component s528 is configured to electronically engage with the processor component s102 to receive the user status information regarding the particular individual living being including living being identification as determined by the processor component to be identifying the living being through the RFID tag, etc.).

In one or more implementations, operation p11 includes an operation p1139 for electronically receiving the user status information regarding the particular individual living being including living being identification associated with a password. An exemplary version of a non-transitory signal bearing medium of information storage subsystem s200 is depicted as bearing one or more receiving information password instructions j1139 that when executed will direct performance of the operation p1139. In an implementation, the one or more receiving information password instructions j1139 when executed direct electronically receiving the user status information regarding the particular individual living being including living being identification associated with a password (e.g. an implementation of the receiver component s528 is configured to electronically engage with the processor component s102 to receive the user status information regarding the particular individual living being including living being identification as determined by the processor component to be identifying the living being through the password, etc.). Furthermore, the receiving information password electrical circuitry arrangement f1139 when activated will perform the operation p1139. In an implementation, the receiving information password electrical circuitry arrangement f1139, when activated performs electronically receiving the user status information regarding the particular individual living being including living being identification associated with a password (e.g. an implementation of the receiver component s528 is configured to electronically engage with the processor component s102 to receive the user status information regarding the particular individual living being including living being identification as determined by the processor component to be identifying the living being through the password, etc.). In an implementation, the electronically receiving the user status information regarding the particular individual living being including living being identification associated with a password is carried out by electronically receiving the user status information regarding the particular individual living being including living being identification associated with a password (e.g. an implementation of the receiver component s528 is configured to electronically engage with the processor component s102 to receive the user status information regarding the particular individual living being including living being identification as determined by the processor component to be identifying the living being through the password, etc.).

Figure 122:
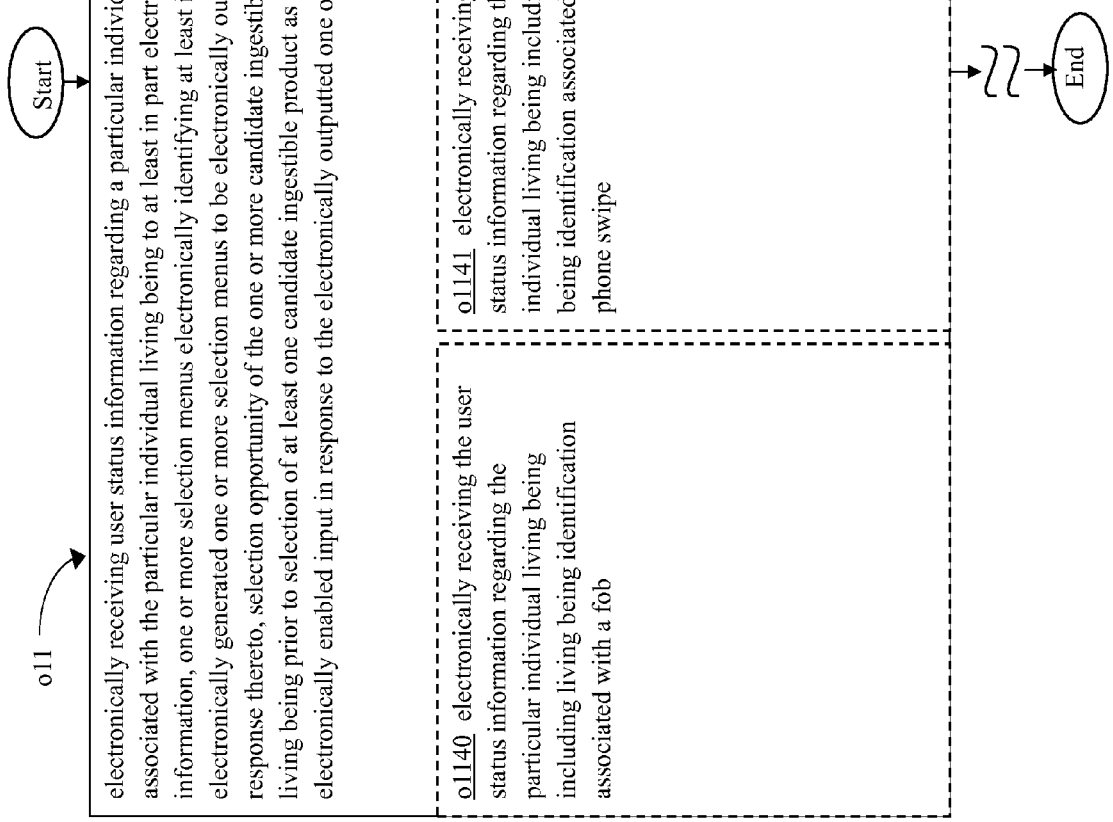

In one or more implementations, as shown in FIG. 122, operation p11 includes an operation p1140 for electronically receiving the user status information regarding the particular individual living being including living being identification associated with a fob. An exemplary version of a non-transitory signal bearing medium of information storage subsystem s200 is depicted as bearing one or more receiving information fob instructions j1140 that when executed will direct performance of the operation p1140. In an implementation, the one or more receiving information fob instructions j1140 when executed direct electronically receiving the user status information regarding the particular individual living being including living being identification associated with a fob (e.g. an implementation of the receiver component s528 is configured to electronically engage with the processor component s102 to receive the user status information regarding the particular individual living being including living being identification as determined by the processor component to be identifying the living being through electronic data contained on the fob, etc.). Furthermore, the receiving information fob electrical circuitry arrangement f1140 when activated will perform the operation p1140. In an implementation, the receiving information fob electrical circuitry arrangement f1140, when activated performs electronically receiving the user status information regarding the particular individual living being including living being identification associated with a fob (e.g. an implementation of the receiver component s528 is configured to electronically engage with the processor component s102 to receive the user status information regarding the particular individual living being including living being identification as determined by the processor component to be identifying the living being through electronic data contained on the fob, etc.). In an implementation, the electronically receiving the user status information regarding the particular individual living being including living being identification associated with a fob is carried out by electronically receiving the user status information regarding the particular individual living being including living being identification associated with a fob (e.g. an implementation of the receiver component s528 is configured to electronically engage with the processor component s102 to receive the user status information regarding the particular individual living being including living being identification as determined by the processor component to be identifying the living being through electronic data contained on the fob, etc.).

In one or more implementations, operation p11 includes an operation p1141 for electronically receiving the user status information regarding the particular individual living being including living being identification associated with a cell phone swipe. An exemplary version of a non-transitory signal bearing medium of information storage subsystem s200 is depicted as bearing one or more receiving information cell phone instructions j1141 that when executed will direct performance of the operation p1141. In an implementation, the one or more receiving information cell phone instructions j1141 when executed direct electronically receiving the user status information regarding the particular individual living being including living being identification associated with a cell phone swipe (e.g. an implementation of the receiver component s528 is configured to electronically engage with the processor component s102 to receive the user status information regarding the particular individual living being including living being identification as determined by the processor component to be identifying the living being through passing the cell phone in close proximity to the cell phone, etc.). Furthermore, the receiving information cell phone electrical circuitry arrangement f1141 when activated will perform the operation p1141. In an implementation, the receiving information cell phone electrical circuitry arrangement f1141, when activated performs electronically receiving the user status information regarding the particular individual living being including living being identification associated with a cell phone swipe (e.g. an implementation of the receiver component s528 is configured to electronically engage with the processor component s102 to receive the user status information regarding the particular individual living being including living being identification as determined by the processor component to be identifying the living being through passing the cell phone in close proximity to the cell phone, etc.). In an implementation, the electronically receiving the user status information regarding the particular individual living being including living being identification associated with a cell phone swipe is carried out by electronically receiving the user status information regarding the particular individual living being including living being identification associated with a cell phone swipe (e.g. an implementation of the receiver component s528 is configured to electronically engage with the processor component s102 to receive the user status information regarding the particular individual living being including living being identification as determined by the processor component to be identifying the living being through passing the cell phone in close proximity to the cell phone, etc.).

In one or more implementations, operation p11 includes an operation p1142 for electronically receiving the user status information regarding the particular individual living being including living being identification associated with a breathalyzer test. An exemplary version of a non-transitory signal bearing medium of information storage subsystem s200 is depicted as bearing one or more receiving information breathalyzer instructions j1142 that when executed will direct performance of the operation p1142. In an implementation, the one or more receiving information breathalyzer instructions j1142 when executed direct electronically receiving the user status information regarding the particular individual living being including living being identification associated with a breathalyzer test (e.g. an implementation of the receiver component s528 is configured to electronically engage with the processor component s102 to receive the user status information regarding the particular individual living being including living being identification as determined by the processor component to be identifying the living being through the breathalyzer test of the living being, etc.). Furthermore, the receiving information breathalyzer electrical circuitry arrangement f1142 when activated will perform the operation p1142. In an implementation, the receiving information breathalyzer electrical circuitry arrangement f1142, when activated performs electronically receiving the user status information regarding the particular individual living being including living being identification associated with a breathalyzer test (e.g. an implementation of the receiver component s528 is configured to electronically engage with the processor component s102 to receive the user status information regarding the particular individual living being including living being identification as determined by the processor component to be identifying the living being through the breathalyzer test of the living being, etc.). In an implementation, the electronically receiving the user status information regarding the particular individual living being including living being identification associated with a breathalyzer test is carried out by electronically receiving the user status information regarding the particular individual living being including living being identification associated with a breathalyzer test (e.g. an implementation of the receiver component s528 is configured to electronically engage with the processor component s102 to receive the user status information regarding the particular individual living being including living being identification as determined by the processor component to be identifying the living being through the breathalyzer test of the living being, etc.).

Figure 123:
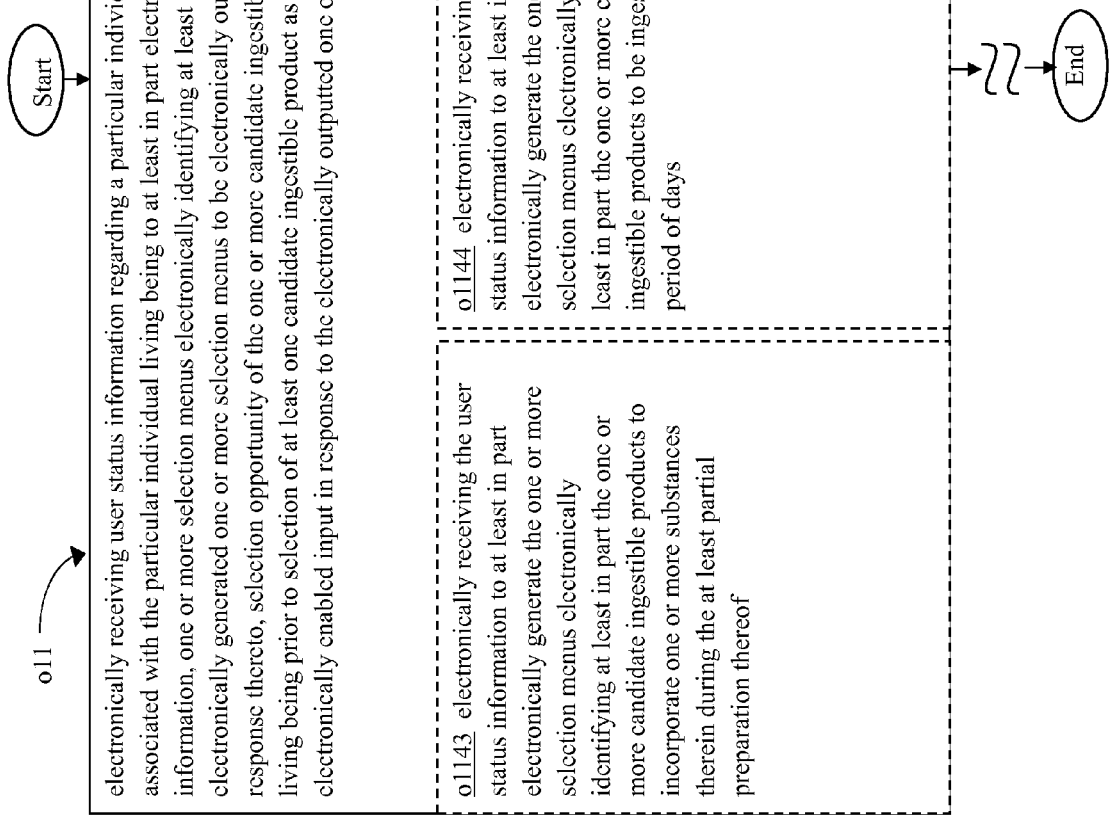

In one or more implementations, as shown in FIG. 123, operation p11 includes an operation p1143 for electronically receiving the user status information to at least in part electronically generate the one or more selection menus electronically identifying at least in part the one or more candidate ingestible products to incorporate one or more substances therein during the at least partial preparation thereof. An exemplary version of a non-transitory signal bearing medium of information storage subsystem s200 is depicted as bearing one or more receiving information incorporate instructions j1143 that when executed will direct performance of the operation p1143. In an implementation, the one or more receiving information incorporate instructions j1143 when executed direct electronically receiving the user status information to at least in part electronically generate the one or more selection menus electronically identifying at least in part the one or more candidate ingestible products to incorporate one or more substances therein during the at least partial preparation thereof (e.g. an implementation of the receiver component s528 is configured to electronically receive the user status information and engage with the processor component s102 to at least in part electronically generate the one or more selection menus electronically identifying at least in part the one or more candidate ingestible products to incorporate one or more substances therein during the at least partial preparation thereof such as a sandwich to include the substance as an amino acid incorporated into the sandwich, etc.). Furthermore, the receiving information incorporate electrical circuitry arrangement f1143 when activated will perform the operation p1143. In an implementation, the receiving information incorporate electrical circuitry arrangement f1143, when activated performs electronically receiving the user status information to at least in part electronically generate the one or more selection menus electronically identifying at least in part the one or more candidate ingestible products to incorporate one or more substances therein during the at least partial preparation thereof (e.g. an implementation of the receiver component s528 is configured to electronically receive the user status information and engage with the processor component s102 to at least in part electronically generate the one or more selection menus electronically identifying at least in part the one or more candidate ingestible products to incorporate one or more substances therein during the at least partial preparation thereof such as a sandwich to include the substance as an amino acid incorporated into the sandwich, etc.). In an implementation, the electronically receiving the user status information to at least in part electronically generate the one or more selection menus electronically identifying at least in part the one or more candidate ingestible products to incorporate one or more substances therein during the at least partial preparation thereof is carried out by electronically receiving the user status information to at least in part electronically generate the one or more selection menus electronically identifying at least in part the one or more candidate ingestible products to incorporate one or more substances therein during the at least partial preparation thereof (e.g. an implementation of the receiver component s528 is configured to electronically receive the user status information and engage with the processor component s102 to at least in part electronically generate the one or more selection menus electronically identifying at least in part the one or more candidate ingestible products to incorporate one or more substances therein during the at least partial preparation thereof such as a sandwich to include the substance as an amino acid incorporated into the sandwich, etc.).

In one or more implementations, operation p11 includes an operation p1144 for electronically receiving the user status information to at least in part electronically generate the one or more selection menus electronically identifying at least in part the one or more candidate ingestible products to be ingested over a period of days. An exemplary version of a non-transitory signal bearing medium of information storage subsystem s200 is depicted as bearing one or more receiving information days instructions j1144 that when executed will direct performance of the operation p1144. In an implementation, the one or more receiving information days instructions j1144 when executed direct electronically receiving the user status information to at least in part electronically generate the one or more selection menus electronically identifying at least in part the one or more candidate ingestible products to be ingested over a period of days (e.g. an implementation of the receiver component s528 is configured to electronically receive the user status information and engage with the processor component s102 to at least in part electronically generate the one or more selection menus electronically identifying at least in part the one or more candidate ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.). Furthermore, the receiving information days electrical circuitry arrangement f1144 when activated will perform the operation p1144. In an implementation, the receiving information days electrical circuitry arrangement f1144, when activated performs electronically receiving the user status information to at least in part electronically generate the one or more selection menus electronically identifying at least in part the one or more candidate ingestible products to be ingested over a period of days (e.g. an implementation of the receiver component s528 is configured to electronically receive the user status information and engage with the processor component s102 to at least in part electronically generate the one or more selection menus electronically identifying at least in part the one or more candidate ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.). In an implementation, the electronically receiving the user status information to at least in part electronically generate the one or more selection menus electronically identifying at least in part the one or more candidate ingestible products to be ingested over a period of days is carried out by electronically receiving the user status information to at least in part electronically generate the one or more selection menus electronically identifying at least in part the one or more candidate ingestible products to be ingested over a period of days (e.g. an implementation of the receiver component s528 is configured to electronically receive the user status information and engage with the processor component s102 to at least in part electronically generate the one or more selection menus electronically identifying at least in part the one or more candidate ingestible products to be ingested over a period of days such as a smoothie to contain an activator that is designed to interact with a substance, such as a pharmaceutical agent that is encapsulated in pill form to be ingested over a period of days by a living being, such as a boy, at the same time that the smoothie is being ingested by the boy, etc.).

In one or more implementations, operation p11 includes an operation p1145 for electronically receiving the user status information to at least in part electronically generate the one or more selection menus electronically identifying at least in part the one or more candidate ingestible products to be swallowed. An exemplary version of a non-transitory signal bearing medium of information storage subsystem s200 is depicted as bearing one or more receiving information swallow instructions j1145 that when executed will direct performance of the operation p1145. In an implementation, the one or more receiving information swallow instructions j1145 when executed direct electronically receiving the user status information to at least in part electronically generate the one or more selection menus electronically identifying at least in part the one or more candidate ingestible products to be swallowed (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be swallowed such as a snack bar, etc.). Furthermore, the receiving information swallow electrical circuitry arrangement f1145 when activated will perform the operation p1145. In an implementation, the receiving information swallow electrical circuitry arrangement f1145, when activated performs electronically receiving the user status information to at least in part electronically generate the one or more selection menus electronically identifying at least in part the one or more candidate ingestible products to be swallowed (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be swallowed such as a snack bar, etc.). In an implementation, the electronically receiving the user status information to at least in part electronically generate the one or more selection menus electronically identifying at least in part the one or more candidate ingestible products to be swallowed is carried out by electronically receiving the user status information to at least in part electronically generate the one or more selection menus electronically identifying at least in part the one or more candidate ingestible products to be swallowed (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be swallowed such as a snack bar, etc.).

Figure 124:
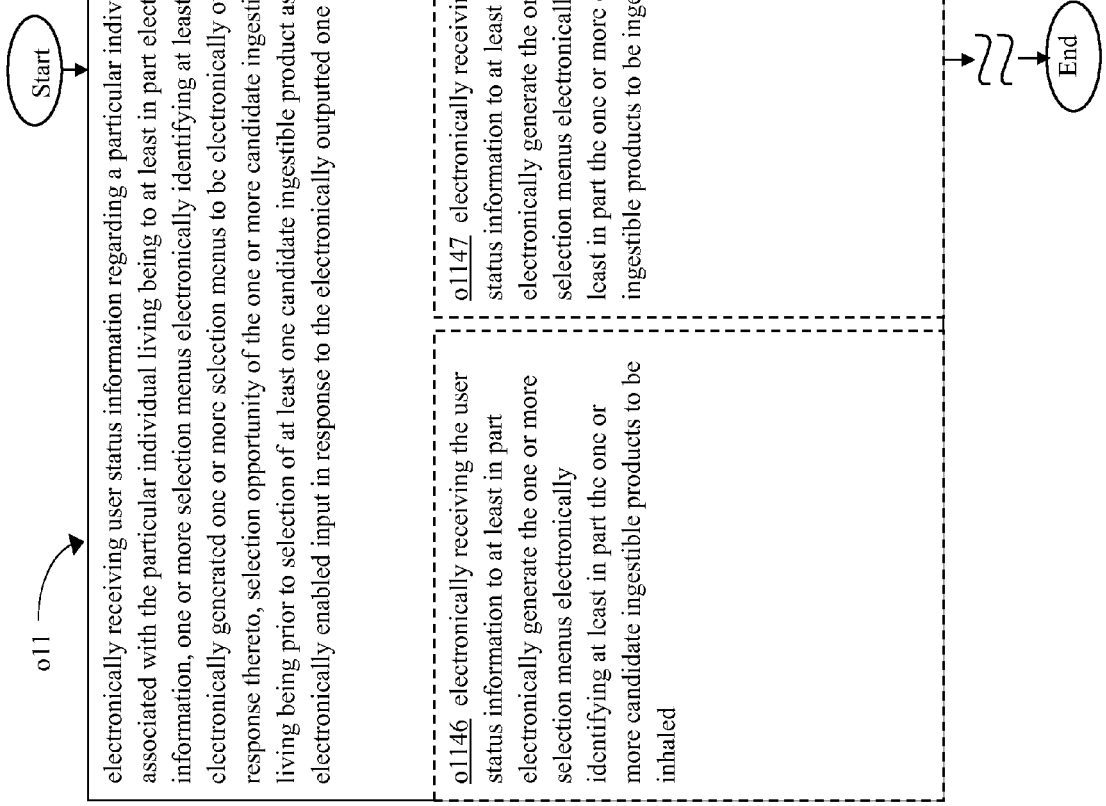

In one or more implementations, as shown in FIG. 124, operation p11 includes an operation p1146 for electronically receiving the user status information to at least in part electronically generate the one or more selection menus electronically identifying at least in part the one or more candidate ingestible products to be inhaled. An exemplary version of a non-transitory signal bearing medium of information storage subsystem s200 is depicted as bearing one or more receiving information inhaled instructions j1146 that when executed will direct performance of the operation p1146. In an implementation, the one or more receiving information inhaled instructions j1146 when executed direct electronically receiving the user status information to at least in part electronically generate the one or more selection menus electronically identifying at least in part the one or more candidate ingestible products to be inhaled (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be inhaled such as a medicament dispensed through a nebulizer, etc.). Furthermore, the receiving information inhaled electrical circuitry arrangement f1146 when activated will perform the operation p1146. In an implementation, the receiving information inhaled electrical circuitry arrangement f1146, when activated performs electronically receiving the user status information to at least in part electronically generate the one or more selection menus electronically identifying at least in part the one or more candidate ingestible products to be inhaled (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be inhaled such as a medicament dispensed through a nebulizer, etc.). In an implementation, the electronically receiving the user status information to at least in part electronically generate the one or more selection menus electronically identifying at least in part the one or more candidate ingestible products to be inhaled is carried out by electronically receiving the user status information to at least in part electronically generate the one or more selection menus electronically identifying at least in part the one or more candidate ingestible products to be inhaled (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be inhaled such as a medicament dispensed through a nebulizer, etc.).

In one or more implementations, operation p11 includes an operation p1147 for electronically receiving the user status information to at least in part electronically generate the one or more selection menus electronically identifying at least in part the one or more candidate ingestible products to be ingested via a tube. An exemplary version of a non-transitory signal bearing medium of information storage subsystem s200 is depicted as bearing one or more receiving information tube instructions j1147 that when executed will direct performance of the operation p1147. In an implementation, the one or more receiving information tube instructions j1147 when executed direct electronically receiving the user status information to at least in part electronically generate the one or more selection menus electronically identifying at least in part the one or more candidate ingestible products to be ingested thru a tube (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested via a tube such as a liquid meal replacement, etc.). Furthermore, the receiving information tube electrical circuitry arrangement f1147 when activated will perform the operation p1147. In an implementation, the receiving information tube electrical circuitry arrangement f1147, when activated performs electronically receiving the user status information to at least in part electronically generate the one or more selection menus electronically identifying at least in part the one or more candidate ingestible products to be ingested thru a tube (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested via a tube such as a liquid meal replacement, etc.). In an implementation, the electronically receiving the user status information to at least in part electronically generate the one or more selection menus electronically identifying at least in part the one or more candidate ingestible products to be ingested via a tube is carried out by electronically receiving the user status information to at least in part electronically generate the one or more selection menus electronically identifying at least in part the one or more candidate ingestible products to be ingested thru a tube (e.g., an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested via a tube such as a liquid meal replacement, etc.).

In one or more implementations, operation p11 includes an operation p1148 for electronically receiving the user status information to at least in part electronically generate the one or more selection menus electronically identifying at least in part the one or more candidate ingestible products to be ingested transdermally. An exemplary version of a non-transitory signal bearing medium of information storage subsystem s200 is depicted as bearing one or more receiving information transdermal instructions j1148 that when executed will direct performance of the operation p1148. In an implementation, the one or more receiving information transdermal instructions j1148 when executed direct electronically receiving the user status information to at least in part electronically generate the one or more selection menus electronically identifying at least in part the one or more candidate ingestible products to be ingested transdermally (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested transdermally such as a cream, etc.). Furthermore, the receiving information transdermal electrical circuitry arrangement f1148 when activated will perform the operation p1148. In an implementation, the receiving information transdermal electrical circuitry arrangement f1148, when activated performs electronically receiving the user status information to at least in part electronically generate the one or more selection menus electronically identifying at least in part the one or more candidate ingestible products to be ingested transdermally (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested transdermally such as a cream, etc.). In an implementation, the electronically receiving the user status information to at least in part electronically generate the one or more selection menus electronically identifying at least in part the one or more candidate ingestible products to be ingested transdermally is carried out by electronically receiving the user status information to at least in part electronically generate the one or more selection menus electronically identifying at least in part the one or more candidate ingestible products to be ingested transdermally (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be ingested transdermally such as a cream, etc.).

Figure 125:
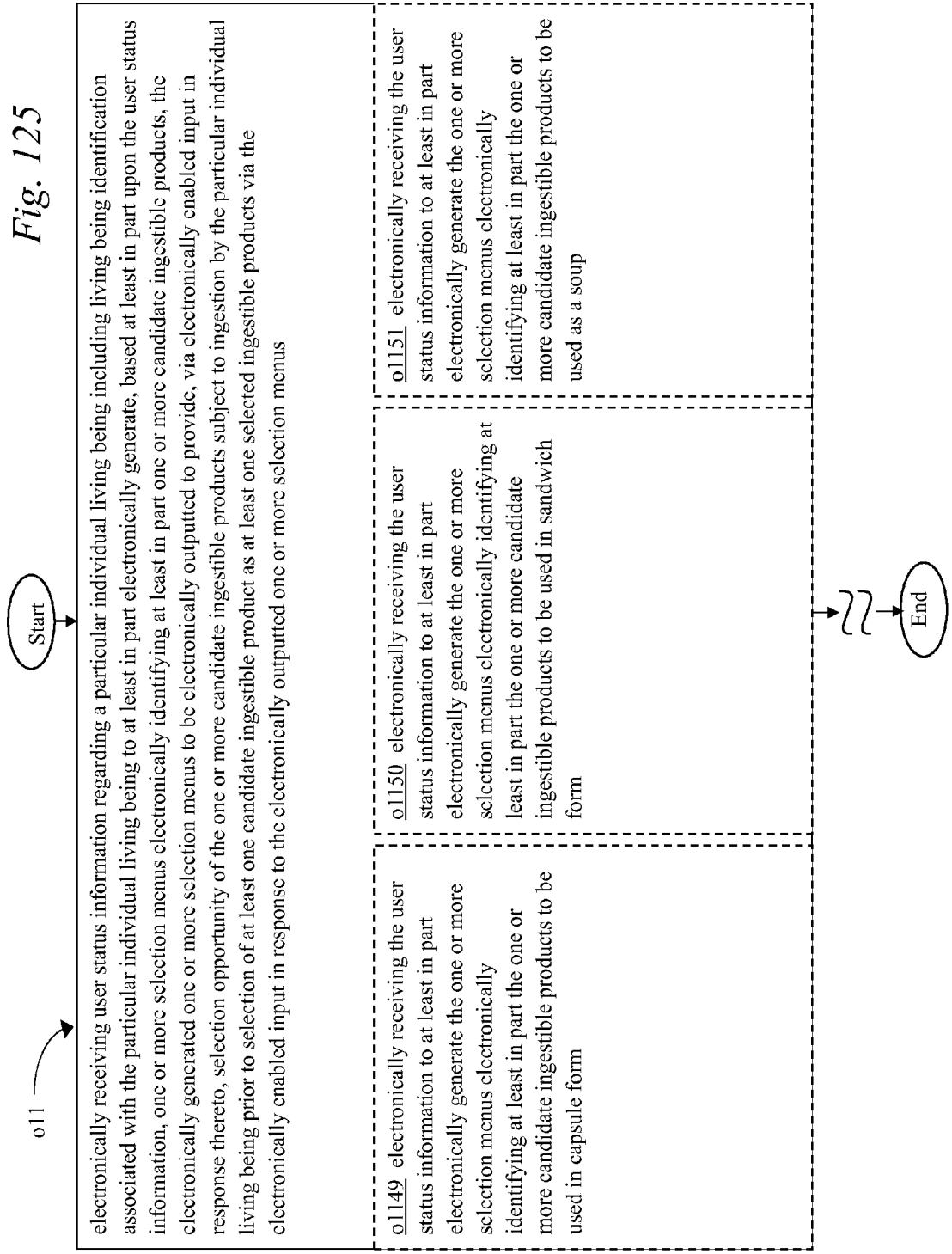

In one or more implementations, as shown in FIG. 125, operation p11 includes an operation p1149 for electronically receiving the user status information to at least in part electronically generate the one or more selection menus electronically identifying at least in part the one or more candidate ingestible products to be used in capsule form. An exemplary version of a non-transitory signal bearing medium of information storage subsystem s200 is depicted as bearing one or more receiving information capsule instructions j1149 that when executed will direct performance of the operation p1149. In an implementation, the one or more receiving information capsule instructions j1149 when executed direct electronically receiving the user status information to at least in part electronically generate the one or more selection menus electronically identifying at least in part the one or more candidate ingestible products to be used in a capsule form (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used in capsule form, such as through capsules via encapsulation, etc.). Furthermore, the receiving information capsule electrical circuitry arrangement f1149 when activated will perform the operation p1149. In an implementation, the receiving information capsule electrical circuitry arrangement f1149, when activated performs electronically receiving the user status information to at least in part electronically generate the one or more selection menus electronically identifying at least in part the one or more candidate ingestible products to be used in a capsule form (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used in capsule form, such as through capsules via encapsulation, etc.). In an implementation, the electronically receiving the user status information to at least in part electronically generate the one or more selection menus electronically identifying at least in part the one or more candidate ingestible products to be used in capsule form is carried out by electronically receiving the user status information to at least in part electronically generate the one or more selection menus electronically identifying at least in part the one or more candidate ingestible products to be used in a capsule form (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used in capsule form, such as through capsules via encapsulation, etc.).

In one or more implementations, operation p11 includes an operation p1150 for electronically receiving the user status information to at least in part electronically generate the one or more selection menus electronically identifying at least in part the one or more candidate ingestible products to be used in sandwich form. An exemplary version of a non-transitory signal bearing medium of information storage subsystem s200 is depicted as bearing one or more receiving information sandwich instructions j1150 that when executed will direct performance of the operation p1150. In an implementation, the one or more receiving information sandwich instructions j1150 when executed direct electronically receiving the user status information to at least in part electronically generate the one or more selection menus electronically identifying at least in part the one or more candidate ingestible products to be used in sandwich form (e.g. an implementation of the receiver component s528 is configured to electronically receive the user status information and engage with the processor component s102 to at least in part electronically generate the one or more selection menus electronically identifying at least in part the one or more candidate ingestible products in sandwich form such as a hamburger, etc.). Furthermore, the receiving information sandwich electrical circuitry arrangement f1150 when activated will perform the operation p1150. In an implementation, the receiving information sandwich electrical circuitry arrangement f1150, when activated performs electronically receiving the user status information to at least in part electronically generate the one or more selection menus electronically identifying at least in part the one or more candidate ingestible products to be used in sandwich form (e.g. an implementation of the receiver component s528 is configured to electronically receive the user status information and engage with the processor component s102 to at least in part electronically generate the one or more selection menus electronically identifying at least in part the one or more candidate ingestible products in sandwich form such as a hamburger, etc.). In an implementation, the electronically receiving the user status information to at least in part electronically generate the one or more selection menus electronically identifying at least in part the one or more candidate ingestible products to be used in sandwich form is carried out by electronically receiving the user status information to at least in part electronically generate the one or more selection menus electronically identifying at least in part the one or more candidate ingestible products to be used in sandwich form (e.g. an implementation of the receiver component s528 is configured to electronically receive the user status information and engage with the processor component s102 to at least in part electronically generate the one or more selection menus electronically identifying at least in part the one or more candidate ingestible products in sandwich form such as a hamburger, etc.).

In one or more implementations, operation p11 includes an operation p1151 for electronically receiving the user status information to at least in part electronically generate the one or more selection menus electronically identifying at least in part the one or more candidate ingestible products to be used as a soup. An exemplary version of a non-transitory signal bearing medium of information storage subsystem s200 is depicted as bearing one or more receiving information soup instructions j1151 that when executed will direct performance of the operation p1151. In an implementation, the one or more receiving information soup instructions j1151 when executed direct electronically receiving the user status information to at least in part electronically generate the one or more selection menus electronically identifying at least in part the one or more candidate ingestible products to be used as a soup (e.g. an implementation of the receiver component s528 is configured to electronically receive the user status information and engage with the processor component s102 to at least in part electronically generate the one or more selection menus electronically identifying at least in part the one or more candidate ingestible products to be used as a soup such as tomato soup, etc.). Furthermore, the receiving information soup electrical circuitry arrangement f1151 when activated will perform the operation p1151. In an implementation, the receiving information soup electrical circuitry arrangement f1151, when activated performs electronically receiving the user status information to at least in part electronically generate the one or more selection menus electronically identifying at least in part the one or more candidate ingestible products to be used as a soup (e.g. an implementation of the receiver component s528 is configured to electronically receive the user status information and engage with the processor component s102 to at least in part electronically generate the one or more selection menus electronically identifying at least in part the one or more candidate ingestible products to be used as a soup such as tomato soup, etc.). In an implementation, the electronically receiving the user status information to at least in part electronically generate the one or more selection menus electronically identifying at least in part the one or more candidate ingestible products to be used as a soup is carried out by electronically receiving the user status information to at least in part electronically generate the one or more selection menus electronically identifying at least in part the one or more candidate ingestible products to be used as a soup (e.g. an implementation of the receiver component s528 is configured to electronically receive the user status information and engage with the processor component s102 to at least in part electronically generate the one or more selection menus electronically identifying at least in part the one or more candidate ingestible products to be used as a soup such as tomato soup, etc.).

Figure 126:
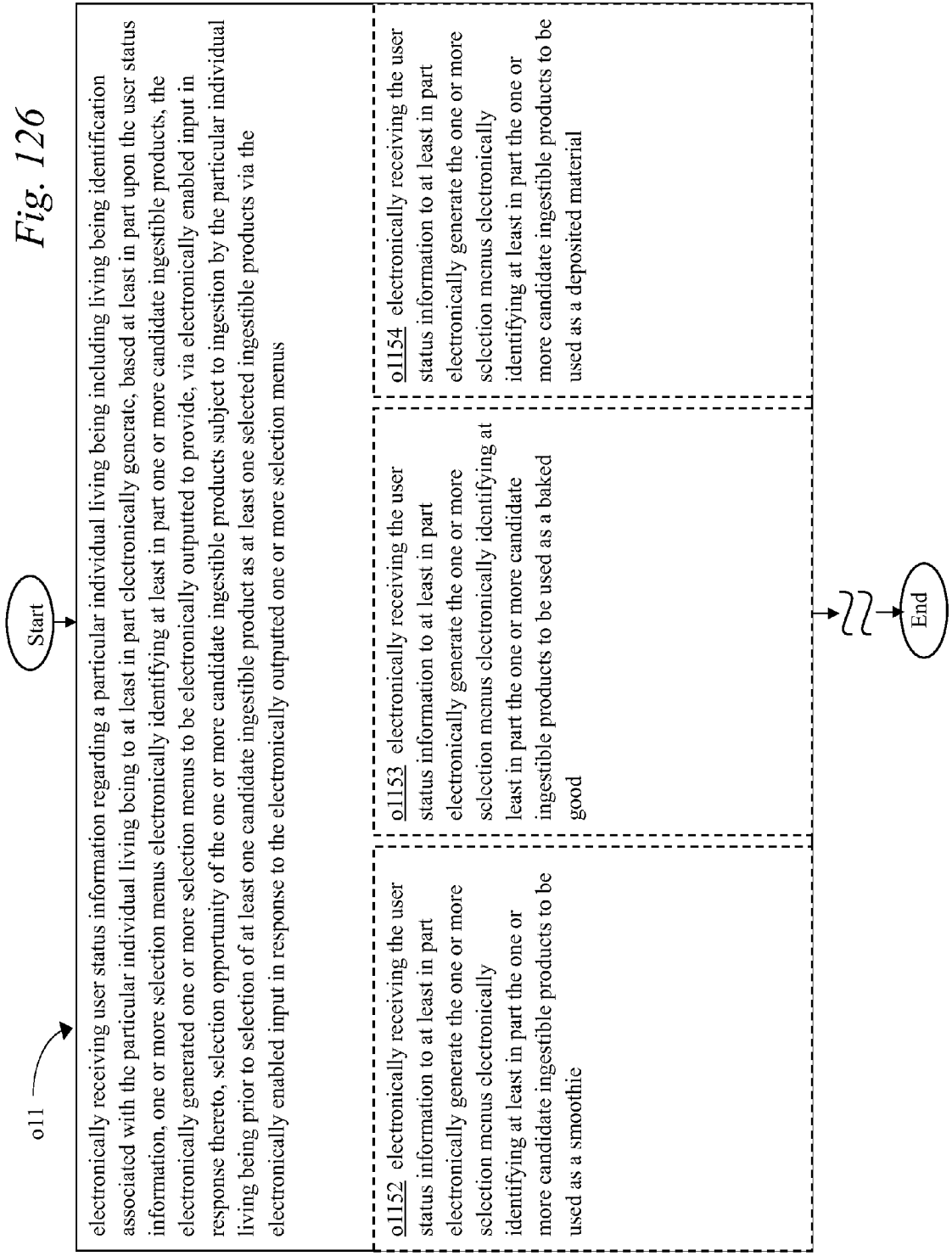

In one or more implementations, as shown in FIG. 126, operation p11 includes an operation p1152 for electronically receiving the user status information to at least in part electronically generate the one or more selection menus electronically identifying at least in part the one or more candidate ingestible products to be used as a smoothie. An exemplary version of a non-transitory signal bearing medium of information storage subsystem s200 is depicted as bearing one or more receiving information smoothie instructions j1152 that when executed will direct performance of the operation p1152. In an implementation, the one or more receiving information smoothie instructions j1152 when executed direct electronically receiving the user status information to at least in part electronically generate the one or more selection menus electronically identifying at least in part the one or more candidate ingestible products to be used as a smoothie (e.g. an implementation of the receiver component s528 is configured to electronically receive the user status information and engage with the processor component s102 to at least in part electronically generate the one or more selection menus electronically identifying at least in part the one or more candidate ingestible products to be used a smoothie such as a fruit smoothie, etc.). Furthermore, the receiving information smoothie electrical circuitry arrangement f1152 when activated will perform the operation p1152. In an implementation, the receiving information smoothie electrical circuitry arrangement f1152, when activated performs electronically receiving the user status information to at least in part electronically generate the one or more selection menus electronically identifying at least in part the one or more candidate ingestible products to be used as a smoothie (e.g. an implementation of the receiver component s528 is configured to electronically receive the user status information and engage with the processor component s102 to at least in part electronically generate the one or more selection menus electronically identifying at least in part the one or more candidate ingestible products to be used a smoothie such as a fruit smoothie, etc.). In an implementation, the electronically receiving the user status information to at least in part electronically generate the one or more selection menus electronically identifying at least in part the one or more candidate ingestible products to be used as a smoothie is carried out by electronically receiving the user status information to at least in part electronically generate the one or more selection menus electronically identifying at least in part the one or more candidate ingestible products to be used as a smoothie (e.g. an implementation of the receiver component s528 is configured to electronically receive the user status information and engage with the processor component s102 to at least in part electronically generate the one or more selection menus electronically identifying at least in part the one or more candidate ingestible products to be used a smoothie such as a fruit smoothie, etc.).

In one or more implementations, operation p11 includes an operation p1153 for electronically receiving the user status information to at least in part electronically generate the one or more selection menus electronically identifying at least in part the one or more candidate ingestible products to be used as a baked good. An exemplary version of a non-transitory signal bearing medium of information storage subsystem s200 is depicted as bearing one or more receiving information baked instructions j1153 that when executed will direct performance of the operation p1153. In an implementation, the one or more receiving information baked instructions j1153 when executed direct electronically receiving the user status information to at least in part electronically generate the one or more selection menus electronically identifying at least in part the one or more candidate ingestible products to be used as a baked good such as a muffin, etc.). Furthermore, the receiving information baked electrical circuitry arrangement f1153 when activated will perform the operation p1153. In an implementation, the receiving information baked electrical circuitry arrangement f1153, when activated performs electronically receiving the user status information to at least in part electronically generate the one or more selection menus electronically identifying at least in part the one or more candidate ingestible products to be used as a baked good (e.g. an implementation of the receiver component s528 is configured to electronically receive the user status information and engage with the processor component s102 to at least in part electronically generate the one or more selection menus electronically identifying at least in part the one or more candidate ingestible products to be used as a baked good such as a muffin, etc.). In an implementation, the electronically receiving the user status information to at least in part electronically generate the one or more selection menus electronically identifying at least in part the one or more candidate ingestible products to be used as a baked good is carried out by electronically receiving the user status information to at least in part electronically generate the one or more selection menus electronically identifying at least in part the one or more candidate ingestible products to be used as a baked good (e.g. an implementation of the receiver component s528 is configured to electronically receive the user status information and engage with the processor component s102 to at least in part electronically generate the one or more selection menus electronically identifying at least in part the one or more candidate ingestible products to be used as a baked good such as a muffin, etc.).

In one or more implementations, operation p11 includes an operation p1154 for electronically receiving the user status information to at least in part electronically generate the one or more selection menus electronically identifying at least in part the one or more candidate ingestible products to be used as a deposited material. An exemplary version of a non-transitory signal bearing medium of information storage subsystem s200 is depicted as bearing one or more receiving information deposited instructions j1154 that when executed will direct performance of the operation p1154. In an implementation, the one or more receiving information deposited instructions j1154 when executed direct electronically receiving the user status information to at least in part electronically generate the one or more selection menus electronically identifying at least in part the one or more candidate ingestible products to be used as a deposited material (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as a deposited material such as a multi-layered cake, etc.). Furthermore, the receiving information deposited electrical circuitry arrangement f1154 when activated will perform the operation p1154. In an implementation, the receiving information deposited electrical circuitry arrangement f1154, when activated performs electronically receiving the user status information to at least in part electronically generate the one or more selection menus electronically identifying at least in part the one or more candidate ingestible products to be used as a deposited material (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as a deposited material such as a multi-layered cake, etc.). In an implementation, the electronically receiving the user status information to at least in part electronically generate the one or more selection menus electronically identifying at least in part the one or more candidate ingestible products to be used as a deposited material is carried out by electronically receiving the user status information to at least in part electronically generate the one or more selection menus electronically identifying at least in part the one or more candidate ingestible products to be used as a deposited material (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as a deposited material such as a multi-layered cake, etc.).

Figure 127:
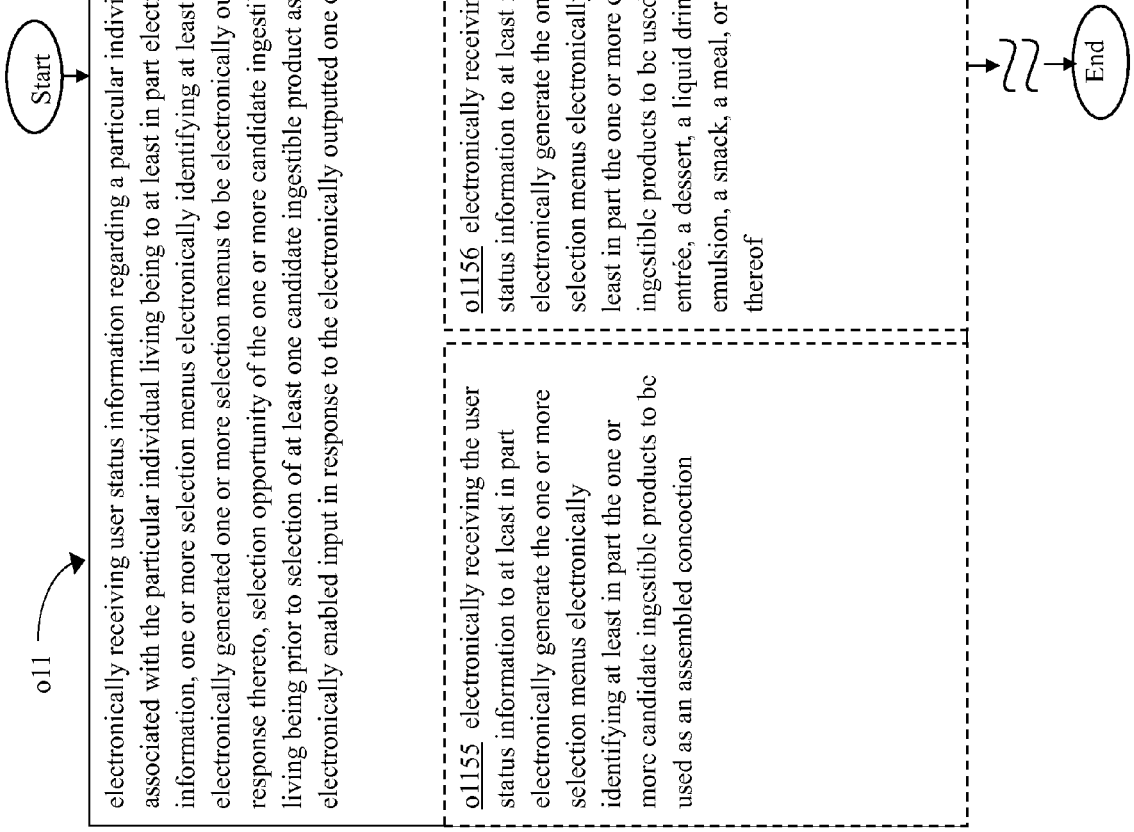

In one or more implementations, as shown in FIG. 127, operation p11 includes an operation p1155 for electronically receiving the user status information to at least in part electronically generate the one or more selection menus electronically identifying at least in part the one or more candidate ingestible products to be used as an assembled concoction. An exemplary version of a non-transitory signal bearing medium of information storage subsystem s200 is depicted as bearing one or more receiving information assembled instructions j1155 that when executed will direct performance of the operation p1155. In an implementation, the one or more receiving information assembled instructions j1155 when executed direct electronically receiving the user status information to at least in part electronically generate the one or more selection menus electronically identifying at least in part the one or more candidate ingestible products to be used as an assembled concoction (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as an assembled concoction such as a decorated confection, etc.). Furthermore, the receiving information assembled electrical circuitry arrangement f1155 when activated will perform the operation p1155. In an implementation, the receiving information assembled electrical circuitry arrangement f1155, when activated performs electronically receiving the user status information to at least in part electronically generate the one or more selection menus electronically identifying at least in part the one or more candidate ingestible products to be used as an assembled concoction (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as an assembled concoction such as a decorated confection, etc.). In an implementation, the electronically receiving the user status information to at least in part electronically generate the one or more selection menus electronically identifying at least in part the one or more candidate ingestible products to be used as an assembled concoction is carried out by electronically receiving the user status information to at least in part electronically generate the one or more selection menus electronically identifying at least in part the one or more candidate ingestible products to be used as an assembled concoction (e.g. an implementation of the receiver component s528 is configured to electronically receive the user status information and engage with the processor component s102 to direct the material processing subsystem s700 to at least in part electronically generate the one or more selection menus electronically identifying at least in part the one or more candidate ingestible products to be used as an assembled concoction such as a decorated confection, etc.).

In one or more implementations, operation p11 includes an operation p1156 for electronically receiving the user status information to at least in part electronically generate the one or more selection menus electronically identifying at least in part the one or more candidate ingestible products to be used as a main entrée, a dessert, a liquid drink, an emulsion, a snack, a meal, or a combination thereof. An exemplary version of a non-transitory signal bearing medium of information storage subsystem s200 is depicted as bearing one or more receiving information uses instructions j1156 that when executed will direct performance of the operation p1156. In an implementation, the one or more receiving information uses instructions j1156 when executed direct electronically receiving the user status information to at least in part electronically generate the one or more selection menus electronically identifying at least in part the one or more candidate ingestible products to be used as a main entrée, a dessert, a liquid drink, an emulsion, a snack, a meal, or a combination thereof (e.g. an implementation of the receiver component s528 is configured to electronically receive the user status information and engage with the processor component s102 to at least in part electronically generate the one or more selection menus electronically identifying at least in part the one or more candidate ingestible products to be used as a as a main entrée, a dessert, a liquid drink, an emulsion, a snack, a meal, or a combination thereof such as a steak dinner, etc.). Furthermore, the receiving information uses electrical circuitry arrangement f1156 when activated will perform the operation p1156. In an implementation, the receiving information uses electrical circuitry arrangement f1156, when activated performs electronically receiving the user status information to at least in part electronically generate the one or more selection menus electronically identifying at least in part the one or more candidate ingestible products to be used as a main entrée, a dessert, a liquid drink, an emulsion, a snack, a meal, or a combination thereof (e.g. an implementation of the receiver component s528 is configured to electronically receive the user status information and engage with the processor component s102 to at least in part electronically generate the one or more selection menus electronically identifying at least in part the one or more candidate ingestible products to be used as a as a main entrée, a dessert, a liquid drink, an emulsion, a snack, a meal, or a combination thereof such as a steak dinner, etc.). In an implementation, the electronically receiving the user status information to at least in part electronically generate the one or more selection menus electronically identifying at least in part the one or more candidate ingestible products to be used as a main entrée, a dessert, a liquid drink, an emulsion, a snack, a meal, or a combination thereof is carried out by electronically receiving the user status information to at least in part electronically generate the one or more selection menus electronically identifying at least in part the one or more candidate ingestible products to be used as a main entrée, a dessert, a liquid drink, an emulsion, a snack, a meal, or a combination thereof (e.g. an implementation of the receiver component s528 is configured to electronically receive the user status information and engage with the processor component s102 to at least in part electronically generate the one or more selection menus electronically identifying at least in part the one or more candidate ingestible products to be used as a as a main entrée, a dessert, a liquid drink, an emulsion, a snack, a meal, or a combination thereof such as a steak dinner, etc.).

In one or more implementations, operation p11 includes an operation p1157 for electronically receiving the user status information to at least in part electronically generate the one or more selection menus electronically identifying at least in part the one or more candidate ingestible products to be used periodically. An exemplary version of a non-transitory signal bearing medium of information storage subsystem s200 is depicted as bearing one or more receiving information periods instructions j1157 that when executed will direct performance of the operation p1157. In an implementation, the one or more receiving information periods instructions j1157 when executed direct electronically receiving the user status information to at least in part electronically generate the one or more selection menus electronically identifying at least in part the one or more candidate ingestible products to be used periodically (e.g. an implementation of the receiver component s528 is configured to electronically receive the user status information and engage with the processor component s102 to at least in part electronically generate the one or more selection menus electronically identifying at least in part the one or more candidate ingestible products to be used periodically such as once a week, etc.). Furthermore, the receiving information periods electrical circuitry arrangement f1157 when activated will perform the operation p1157. In an implementation, the receiving information periods electrical circuitry arrangement f1157, when activated performs electronically receiving the user status information to at least in part electronically generate the one or more selection menus electronically identifying at least in part the one or more candidate ingestible products to be used periodically (e.g. an implementation of the receiver component s528 is configured to electronically receive the user status information and engage with the processor component s102 to at least in part electronically generate the one or more selection menus electronically identifying at least in part the one or more candidate ingestible products to be used periodically such as once a week, etc.). In an implementation, the electronically receiving the user status information to at least in part electronically generate the one or more selection menus electronically identifying at least in part the one or more candidate ingestible products to be used periodically is carried out by electronically receiving the user status information to at least in part electronically generate the one or more selection menus electronically identifying at least in part the one or more candidate ingestible products to be used periodically (e.g. an implementation of the receiver component s528 is configured to electronically receive the user status information and engage with the processor component s102 to at least in part electronically generate the one or more selection menus electronically identifying at least in part the one or more candidate ingestible products to be used periodically such as once a week, etc.).

Figure 128:
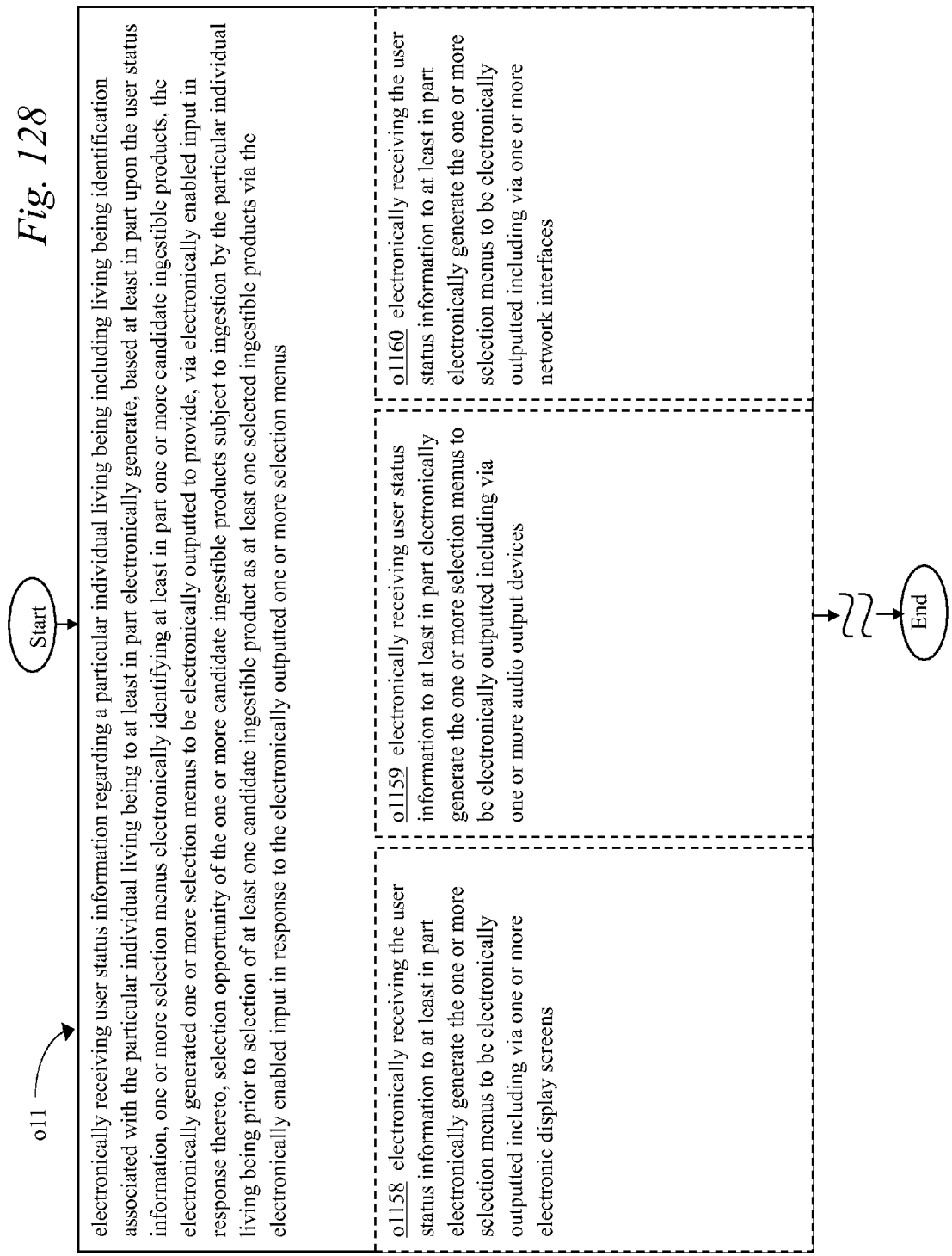

In one or more implementations, as shown in FIG. 128, operation p11 includes an operation p1158 for electronically receiving the user status information to at least in part electronically generate the one or more selection menus to be electronically outputted including via one or more electronic display screens. An exemplary version of a non-transitory signal bearing medium of information storage subsystem s200 is depicted as bearing one or more receiving information display instructions j1158 that when executed will direct performance of the operation p1158. In an implementation, the one or more receiving information display instructions j1158 when executed direct electronically receiving the user status information to at least in part electronically generate the one or more selection menus to be electronically outputted including via one or more electronic display screens (e.g. an implementation of the receiver component s528 is configured to electronically receive the user status information in a format for the processor component s102 to at least in part electronically generate the one or more selection menus to be electronically outputted including via one or more display screens such as via graphical user interface (GUI) component s302, etc.). Furthermore, the receiving information display electrical circuitry arrangement f1158 when activated will perform the operation p1158. In an implementation, the receiving information display electrical circuitry arrangement f1158, when activated performs electronically receiving the user status information to at least in part electronically generate the one or more selection menus to be electronically outputted including via one or more electronic display screens (e.g. an implementation of the receiver component s528 is configured to electronically receive the user status information in a format for the processor component s102 to at least in part electronically generate the one or more selection menus to be electronically outputted including via one or more display screens such as via graphical user interface (GUI) component s302, etc.). In an implementation, the electronically receiving the user status information to at least in part electronically generate the one or more selection menus to be electronically outputted including via one or more electronic display screens is carried out by electronically receiving the user status information to at least in part electronically generate the one or more selection menus to be electronically outputted including via one or more electronic display screens (e.g. an implementation of the receiver component s528 is configured to electronically receive the user status information in a format for the processor component s102 to at least in part electronically generate the one or more selection menus to be electronically outputted including via one or more display screens such as via graphical user interface (GUI) component s302, etc.).

In one or more implementations, operation p11 includes an operation p1159 for electronically receiving user status information to at least in part electronically generate the one or more selection menus to be electronically outputted including via one or more audio output devices. An exemplary version of a non-transitory signal bearing medium of information storage subsystem s200 is depicted as bearing one or more receiving information audio instructions j1159 that when executed will direct performance of the operation p1159. In an implementation, the one or more receiving information audio instructions j1159 when executed direct electronically receiving the user status information to at least in part electronically generate the one or more selection menus to be electronically outputted including via one or more audio output devices (e.g. an implementation of the receiver component s528 is configured to electronically receive the user status information in a format for the processor component s102 to at least in part electronically generate the one or more selection menus to be electronically outputted including via one or more audio output devices such as via audio in/out component s328, etc.). Furthermore, the receiving information audio electrical circuitry arrangement f1159 when activated will perform the operation p1159. In an implementation, the receiving information audio electrical circuitry arrangement f1159, when activated performs electronically receiving the user status information to at least in part electronically generate the one or more selection menus to be electronically outputted including via one or more audio output devices (e.g. an implementation of the receiver component s528 is configured to electronically receive the user status information in a format for the processor component s102 to at least in part electronically generate the one or more selection menus to be electronically outputted including via one or more audio output devices such as via audio in/out component s328, etc.). In an implementation, the electronically receiving user status information to at least in part electronically generate the one or more selection menus to be electronically outputted including via one or more audio output devices is carried out by electronically receiving the user status information to at least in part electronically generate the one or more selection menus to be electronically outputted including via one or more audio output devices (e.g. an implementation of the receiver component s528 is configured to electronically receive the user status information in a format for the processor component s102 to at least in part electronically generate the one or more selection menus to be electronically outputted including via one or more audio output devices such as via audio in/out component s328, etc.).

In one or more implementations, operation p11 includes an operation p1160 for electronically receiving the user status information to at least in part electronically generate the one or more selection menus to be electronically outputted including via one or more network interfaces. An exemplary version of a non-transitory signal bearing medium of information storage subsystem s200 is depicted as bearing one or more receiving information network instructions j1160 that when executed will direct performance of the operation p1160. In an implementation, the one or more receiving information network instructions j1160 when executed direct electronically receiving the user status information to at least in part electronically generate the one or more selection menus to be electronically outputted including via one or more network interfaces (e.g. an implementation of the receiver component s528 is configured to electronically receive the user status information in a format for the processor component s102 to at least in part electronically generate the one or more selection menus to be electronically outputted including via one or more network interfaces such as via wide area network component s516, etc.). Furthermore, the receiving information network electrical circuitry arrangement f1160 when activated will perform the operation p1160. In an implementation, the receiving information network electrical circuitry arrangement f1160, when activated performs electronically receiving the user status information to at least in part electronically generate the one or more selection menus to be electronically outputted including via one or more network interfaces (e.g. an implementation of the receiver component s528 is configured to electronically receive the user status information in a format for the processor component s102 to at least in part electronically generate the one or more selection menus to be electronically outputted including via one or more network interfaces such as via wide area network component s516, etc.). In an implementation, the electronically receiving the user status information to at least in part electronically generate the one or more selection menus to be electronically outputted including via one or more network interfaces is carried out by electronically receiving the user status information to at least in part electronically generate the one or more selection menus to be electronically outputted including via one or more network interfaces (e.g. an implementation of the receiver component s528 is configured to electronically receive the user status information in a format for the processor component s102 to at least in part electronically generate the one or more selection menus to be electronically outputted including via one or more network interfaces such as via wide area network component s516, etc.).

In one or more implementations, as shown in FIG. 129, operation p11 includes an operation p1161 for electronically receiving the user status information to at least in part electronically generate the one or more selection menus to be electronically outputted including wirelessly. An exemplary version of a non-transitory signal bearing medium of information storage subsystem s200 is depicted as bearing one or more receiving information wirelessly instructions j1161 that when executed will direct performance of the operation p1161. In an implementation, the one or more receiving information wirelessly instructions j1161 when executed direct electronically receiving the user status information to at least in part electronically generate the one or more selection menus to be electronically outputted including wirelessly (e.g. an implementation of the receiver component s528 is configured to electronically receive the user status information in a format for the processor component s102 to at least in part electronically generate the one or more selection menus to be electronically outputted including wirelessly such as via wireless network component s510, etc.). Furthermore, the receiving information wirelessly electrical circuitry arrangement f1161 when activated will perform the operation p1161. In an implementation, the receiving information wirelessly electrical circuitry arrangement f1161, when activated performs electronically receiving the user status information to at least in part electronically generate the one or more selection menus to be electronically outputted including wirelessly (e.g. an implementation of the receiver component s528 is configured to electronically receive the user status information in a format for the processor component s102 to at least in part electronically generate the one or more selection menus to be electronically outputted including wirelessly such as via wireless network component s510, etc.). In an implementation, the electronically receiving the user status information to at least in part electronically generate the one or more selection menus to be electronically outputted including wirelessly is carried out by electronically receiving the user status information to at least in part electronically generate the one or more selection menus to be electronically outputted including wirelessly (e.g. an implementation of the receiver component s528 is configured to electronically receive the user status information in a format for the processor component s102 to at least in part electronically generate the one or more selection menus to be electronically outputted including wirelessly such as via wireless network component s510, etc.).

In one or more implementations, operation p11 includes an operation p1162 for electronically receiving the user status information to at least in part electronically generate the one or more selection menus to be electronically outputted including via electronic paper printer. An exemplary version of a non-transitory signal bearing medium of information storage subsystem s200 is depicted as bearing one or more receiving information paper instructions j1162 that when executed will direct performance of the operation p1162. In an implementation, the one or more receiving information paper instructions j1162 when executed direct electronically receiving the user status information to at least in part electronically generate the one or more selection menus to be electronically outputted including via electronic paper printer (e.g. an implementation of the receiver component s528 is configured to electronically receive the user status information in a format for the processor component s102 to at least in part electronically generate the one or more selection menus to be electronically outputted including via electronic paper printer such as via scanner component s338, etc.). Furthermore, the receiving information paper electrical circuitry arrangement f1162 when activated will perform the operation p1162. In an implementation, the receiving information paper electrical circuitry arrangement f1162, when activated performs electronically receiving the user status information to at least in part electronically generate the one or more selection menus to be electronically outputted including via electronic paper printer (e.g. an implementation of the receiver component s528 is configured to electronically receive the user status information in a format for the processor component s102 to at least in part electronically generate the one or more selection menus to be electronically outputted including via electronic paper printer such as via scanner component s338, etc.). In an implementation, the electronically receiving the user status information to at least in part electronically generate the one or more selection menus to be electronically outputted including via electronic paper printer is carried out by electronically receiving the user status information to at least in part electronically generate the one or more selection menus to be electronically outputted including via electronic paper printer (e.g. an implementation of the receiver component s528 is configured to electronically receive the user status information in a format for the processor component s102 to at least in part electronically generate the one or more selection menus to be electronically outputted including via electronic paper printer such as via scanner component s338, etc.).

In one or more implementations, operation p11 includes an operation p1163 for electronically receiving the user status information to at least in part electronically generate the one or more selection menus to be electronically outputted including via electronic food printer. An exemplary version of a non-transitory signal bearing medium of information storage subsystem s200 is depicted as bearing one or more receiving information food instructions j1163 that when executed will direct performance of the operation p1163. In an implementation, the one or more receiving information food instructions j1163 when executed direct electronically receiving the user status information to at least in part electronically generate the one or more selection menus to be electronically outputted including via electronic food printer (e.g. an implementation of the receiver component s528 is configured to electronically receive the user status information in a format for the processor component s102 to at least in part electronically generate the one or more selection menus to be electronically outputted including via electronic food printer such as via deposition component s740, etc.). Furthermore, the receiving information food electrical circuitry arrangement f1163 when activated will perform the operation p1163. In an implementation, the receiving information food electrical circuitry arrangement f1163, when activated performs electronically receiving the user status information to at least in part electronically generate the one or more selection menus to be electronically outputted including via electronic food printer (e.g. an implementation of the receiver component s528 is configured to electronically receive the user status information in a format for the processor component s102 to at least in part electronically generate the one or more selection menus to be electronically outputted including via electronic food printer such as via deposition component s740, etc.). In an implementation, the electronically receiving the user status information to at least in part electronically generate the one or more selection menus to be electronically outputted including via electronic food printer is carried out by electronically receiving the user status information to at least in part electronically generate the one or more selection menus to be electronically outputted including via electronic food printer (e.g. an implementation of the receiver component s528 is configured to electronically receive the user status information in a format for the processor component s102 to at least in part electronically generate the one or more selection menus to be electronically outputted including via electronic food printer such as via deposition component s740, etc.).

In one or more implementations, as shown in FIG. 130, operation p11 includes an operation p1164 for electronically receiving the user status information to at least in part electronically generate the one or more selection menus to provide the selection opportunity in response thereto via electronically enabled input including via an electronic identification card. An exemplary version of a non-transitory signal bearing medium of information storage subsystem s200 is depicted as bearing one or more receiving information ID card instructions j1164 that when executed will direct performance of the operation p1164. In an implementation, the one or more receiving information ID card instructions j1164 when executed direct electronically receiving the user status information to at least in part electronically generate the one or more selection menus to provide the selection opportunity in response thereto via electronically enabled input including via an electronic identification card (e.g. an implementation of the receiver component s528 is configured to electronically engage with a card having memory storage holding the user status information to be used by the processor component s102 to generate the one or more selection menus, etc.). Furthermore, the receiving information ID card electrical circuitry arrangement f1164 when activated will perform the operation p1164. In an implementation, the receiving information ID card electrical circuitry arrangement f1164, when activated performs electronically receiving the user status information to at least in part electronically generate the one or more selection menus to provide the selection opportunity in response thereto via electronically enabled input including via an electronic identification card (e.g. an implementation of the receiver component s528 is configured to electronically engage with a card having memory storage holding the user status information to be used by the processor component s102 to generate the one or more selection menus, etc.). In an implementation, the electronically receiving the user status information to at least in part electronically generate the one or more selection menus to provide the selection opportunity in response thereto via electronically enabled input including via an electronic identification card is carried out by electronically receiving the user status information to at least in part electronically generate the one or more selection menus to provide the selection opportunity in response thereto via electronically enabled input including via an electronic identification card (e.g. an implementation of the receiver component s528 is configured to electronically engage with a card having memory storage holding the user status information to be used by the processor component s102 to generate the one or more selection menus, etc.).

In one or more implementations, operation p11 includes an operation p1165 for electronically receiving the user status information to at least in part electronically generate the one or more selection menus to provide the selection opportunity in response thereto via electronically enabled input including via a memory circuit coupled with a medication container. A non-transitory signal bearing medium includes one or more receiving information container instructions j1165 that when executed will direct performance of the operation p1165. In an implementation, the one or more receiving information container instructions j1165 when executed direct electronically receiving the user status information to at least in part electronically generate the one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form to be used by the processor component s102 to generate the one or more selection menus, etc.). Furthermore, the receiving information container electrical circuitry arrangement f1165 when activated will perform the operation p1165. In an implementation, the receiving information container electrical circuitry arrangement f1165, when activated performs electronically receiving the user status information to at least in part electronically generate the one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form to be used by the processor component s102 to generate the one or more selection menus, etc.). In an implementation, the electronically receiving the user status information to at least in part electronically generate the one or more selection menus to provide the selection opportunity in response thereto via electronically enabled input including via a memory circuit coupled with a medication container is carried out by electronically receiving the user status information to at least in part electronically generate the one or more selection menus to provide the selection opportunity in response thereto via electronically enabled input including via in a memory circuit coupled with a medication container (e.g. an implementation of the receiver component s528 is configured to electronically engage with a memory storage coupled with a medication container to receive the electronically enabled input in electronic form to be used by the processor component s102 to generate the one or more selection menus, etc.).

In one or more implementations, operation p11 includes an operation p1166 for electronically receiving the user status information to at least in part electronically generate the one or more selection menus to provide the selection opportunity in response thereto via electronically enabled input including via a credit card swipe. A non-transitory signal bearing medium includes one or more receiving information credit card instructions j1166 that when executed will direct performance of the operation p1166. In an implementation, the one or more receiving information credit card instructions j1166 when executed direct electronically receiving the user status information to at least in part electronically generate the one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input to be used by the processor component s102 to generate the one or more selection menus, etc.). Furthermore, the receiving information credit card electrical circuitry arrangement f1166 when activated will perform the operation p1166. In an implementation, the receiving information credit card electrical circuitry arrangement f1166, when activated performs electronically receiving the user status information to at least in part electronically generate the one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via a credit card swipe is carried out by electronically receiving the user status information to at least in part electronically generate the one or more selection menus to provide the selection opportunity in response thereto via electronically enabled input including via a credit card swipe (e.g. an implementation of the receiver component s528 is configured to electronically engage with an electronic memory stripe integrated into a credit card to receive the electronically enabled input to be used by the processor component s102 to generate the one or more selection menus, etc.).

In one or more implementations, as shown in FIG. 131, operation p11 includes an operation p1167 for electronically receiving the user status information to at least in part electronically generate the one or more selection menus to provide the selection opportunity in response thereto via electronically enabled input including via a cell phone swipe. An exemplary version of a non-transitory signal bearing medium of information storage subsystem s200 is depicted as bearing one or more receiving information cell phone instructions j1167 that when executed will direct performance of the operation p1167. In an implementation, the one or more receiving information cell phone instructions j1167 when executed direct electronically receiving the user status information to at least in part electronically generate the one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input to be used by the processor component s102 to generate the one or more selection menus, etc.). Furthermore, the receiving information cell phone electrical circuitry arrangement f1167 when activated will perform the operation p1167. In an implementation, the receiving information cell phone electrical circuitry arrangement f1167, when activated performs electronically receiving the user status information to at least in part electronically generate the one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via a cell phone swipe is carried out by electronically receiving the user status information to at least in part electronically generate the one or more selection menus to provide the selection opportunity in response thereto via electronically enabled input including via cell phone swipe (e.g. an implementation of the receiver component s528 is configured to electronically engage with an electronic memory component integrated into a cell phone to receive the electronically enabled input to be used by the processor component s102 to generate the one or more selection menus, etc.).

In one or more implementations, operation p11 includes an operation p1168 for electronically receiving the user status information to at least in part electronically generate the one or more selection menus to provide the selection opportunity in response thereto via electronically enabled input including via a bar code communication. A non-transitory signal bearing medium includes one or more receiving information bar code instructions j1168 that when executed will direct performance of the operation p1168. In an implementation, the one or more receiving information bar code instructions j1168 when executed direct electronically receiving the user status information to at least in part electronically generate the one or more selection menus to provide the selection opportunity in response thereto via electronically enabled input including via bar code communication (e.g. an implementation of the receiver component s528 is configured to electronically read a bar code label to receive the electronically enabled input to be used by the processor component s102 to generate the one or more selection menus, etc.). Furthermore, the receiving information bar code electrical circuitry arrangement f1168 when activated will perform the operation p1168. In an implementation, the receiving information bar code electrical circuitry arrangement f1168, when activated performs electronically receiving the user status information to at least in part electronically generate the one or more selection menus to provide the selection opportunity in response thereto via electronically enabled input including via bar code communication (e.g. an implementation of the receiver component s528 is configured to electronically read a bar code label to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via a bar code communication is carried out by electronically receiving the user status information to at least in part electronically generate the one or more selection menus to provide the selection opportunity in response thereto via electronically enabled input including via bar code communication (e.g. an implementation of the receiver component s528 is configured to electronically read a bar code label to receive the electronically enabled input to be used by the processor component s102 to generate the one or more selection menus, etc.).

In one or more implementations, operation p11 includes an operation p1169 for electronically receiving the user status information to at least in part electronically generate the one or more selection menus to provide the selection opportunity in response thereto via electronically enabled input including via an Internet communication. A non-transitory signal bearing medium includes one or more receiving information Internet instructions j1169 that when executed will direct performance of the operation p1169. In an implementation, the one or more receiving information Internet instructions j1169 when executed direct electronically receiving the user status information to at least in part electronically generate the one or more selection menus to provide the selection opportunity in response thereto via electronically enabled input including via Internet communication (e.g. an implementation of the receiver component s528 is configured to electronically receive through the internet network component s508 the user status information to be used by the processor component s102 to generate the one or more selection menus, etc.). Furthermore, the receiving information Internet electrical circuitry arrangement f1169 when activated will perform the operation p1169. In an implementation, the receiving information Internet electrical circuitry arrangement f1169, when activated performs electronically receiving the user status information to at least in part electronically generate the one or more selection menus to provide the selection opportunity in response thereto via electronically enabled input including via Internet communication (e.g. an implementation of the receiver component s528 is configured to electronically receive through the internet network component s508 the user status information to be used by the processor component s102 to generate the one or more selection menus, etc.). In an implementation, the electronically receiving the user status information to at least in part electronically generate the one or more selection menus to provide the selection opportunity in response thereto via electronically enabled input including via an Internet communication is carried out by electronically receiving the user status information to at least in part electronically generate the one or more selection menus to provide the selection opportunity in response thereto via electronically enabled input including via Internet communication (e.g. an implementation of the receiver component s528 is configured to electronically receive through the internet network component s508 the user status information to be used by the processor component s102 to generate the one or more selection menus, etc.).

In one or more implementations, as shown in FIG. 132, operation p11 includes an operation p1170 for electronically receiving the user status information to at least in part electronically generate the one or more selection menus to provide the selection opportunity in response thereto via electronically enabled input including via an electronic network. An exemplary version of a non-transitory signal bearing medium of information storage subsystem s200 is depicted as bearing one or more receiving information network instructions j1170 that when executed will direct performance of the operation p1170. In an implementation, the one or more receiving information network instructions j1170 when executed direct electronically receiving the user status information to at least in part electronically generate the one or more selection menus to provide the selection opportunity in response thereto via electronically enabled input including via an electronic network (e.g. an implementation of the receiver component s528 is configured to electronically engage with the network cable component s502 to receive the electronically enabled input to be used by the processor component s102 to generate the one or more selection menus, etc.). Furthermore, the receiving information network electrical circuitry arrangement f1170 when activated will perform the operation p1170. In an implementation, the receiving information network electrical circuitry arrangement f1170, when activated performs electronically receiving the user status information to at least in part electronically generate the one or more selection menus to provide the selection opportunity in response thereto via electronically enabled input including via an electronic network (e.g. an implementation of the receiver component s528 is configured to electronically engage with the network cable component s502 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via an electronic network is carried out by electronically receiving the user status information to at least in part electronically generate the one or more selection menus to provide the selection opportunity in response thereto via electronically enabled input including via an electronic network (e.g. an implementation of the receiver component s528 is configured to electronically engage with the network cable component s502 to receive the electronically enabled input to be used by the processor component s102 to generate the one or more selection menus, etc.).

In one or more implementations, operation p11 includes an operation p1171 for electronically receiving the user status information to at least in part electronically generate the one or more selection menus to provide the selection opportunity in response thereto via electronically enabled input including via touch screen input. A non-transitory signal bearing medium includes one or more receiving information touch screen instructions j1171 that when executed will direct performance of the operation p1171. In an implementation, the one or more receiving information touch screen instructions j1171 when executed direct electronically receiving the user status information to at least in part electronically generate the one or more selection menus to provide the selection opportunity in response thereto via electronically enabled input including via touch screen input (e.g. an implementation of the receiver component s528 is configured to electronically receive through the touch screen component s314 the user status information to be used by the processor component s102 to generate the one or more selection menus, etc.). Furthermore, the receiving information touch screen electrical circuitry arrangement f1171 when activated will perform the operation p1171. In an implementation, the receiving information touch screen electrical circuitry arrangement f1171, when activated performs electronically receiving the user status information to at least in part electronically generate the one or more selection menus to provide the selection opportunity in response thereto via electronically enabled input including via touch screen input (e.g. an implementation of the receiver component s528 is configured to electronically receive through the touch screen component s314 the user status information to be used by the processor component s102 to generate the one or more selection menus, etc.). In an implementation, the electronically receiving the user status information to at least in part electronically generate the one or more selection menus to provide the selection opportunity in response thereto via electronically enabled input including via touch screen input is carried out by electronically receiving the user status information to at least in part electronically generate the one or more selection menus to provide the selection opportunity in response thereto via electronically enabled input including via touch screen input (e.g. an implementation of the receiver component s528 is configured to electronically receive through the touch screen component s314 the user status information to be used by the processor component s102 to generate the one or more selection menus, etc.).

In one or more implementations, operation p11 includes an operation p1172 for electronically receiving the user status information to at least in part electronically generate the one or more selection menus to provide the selection opportunity in response thereto via electronically enabled input including via wireless input. A non-transitory signal bearing medium includes one or more receiving information wireless instructions j1172 that when executed will direct performance of the operation p1172. In an implementation, the one or more receiving information wireless instructions j1172 when executed direct electronically receiving the user status information to at least in part electronically generate the one or more selection menus to provide the selection opportunity in response thereto via electronically enabled input including via wireless input (e.g. an implementation of the receiver component s528 is configured to electronically receive through the wireless network component s510 to receive the electronically enabled input to be used by the processor component s102 to generate the one or more selection menus, etc.). Furthermore, the receiving information wireless electrical circuitry arrangement f1172 when activated will perform the operation p1172. In an implementation, the receiving information wireless electrical circuitry arrangement f1172, when activated performs electronically receiving the user status information to at least in part electronically generate the one or more selection menus to provide the selection opportunity in response thereto via electronically enabled input including via wireless input (e.g. an implementation of the receiver component s528 is configured to electronically receive through the wireless network component s510 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via wireless input is carried out by electronically receiving the user status information to at least in part electronically generate the one or more selection menus to provide the selection opportunity in response thereto via electronically enabled input including via wireless input (e.g. an implementation of the receiver component s528 is configured to electronically receive through the wireless network component s510 to receive the electronically enabled input to be used by the processor component s102 to generate the one or more selection menus, etc.).

In one or more implementations, as shown in FIG. 133, operation p11 includes an operation p1173 for electronically receiving the user status information to at least in part electronically generate the one or more selection menus to provide the selection opportunity in response thereto via electronically enabled input including via electronic imaging of the particular individual living being. An exemplary version of a non-transitory signal bearing medium of information storage subsystem s200 is depicted as bearing one or more receiving information imaging instructions j1173 that when executed will direct performance of the operation p1173. In an implementation, the one or more receiving information imaging instructions j1173 when executed direct electronically receiving the user status information to at least in part electronically generate the one or more selection menus to provide the selection opportunity in response thereto via electronically enabled input including via electronic imaging of the particular individual living being (e.g. an implementation of the receiver component s528 is configured to electronically receive through the camera component s336 the user status information to be used by the processor component s102 to generate the one or more selection menus, etc.). Furthermore, the receiving information imaging electrical circuitry arrangement f1173 when activated will perform the operation p1173. In an implementation, the receiving information imaging electrical circuitry arrangement f1173, when activated performs electronically receiving the user status information to at least in part electronically generate the one or more selection menus to provide the selection opportunity in response thereto via electronically enabled input including via electronic imaging of the particular individual living being (e.g. an implementation of the receiver component s528 is configured to electronically receive through the camera component s336 the user status information to be used by the processor component s102 to generate the one or more selection menus, etc.). In an implementation, the electronically receiving the user status information to at least in part electronically generate the one or more selection menus to provide the selection opportunity in response thereto via electronically enabled input including via electronic imaging of the particular individual living being is carried out by electronically receiving the user status information to at least in part electronically generate the one or more selection menus to provide the selection opportunity in response thereto via electronically enabled input including via electronic imaging of the particular individual living being (e.g. an implementation of the receiver component s528 is configured to electronically receive through the camera component s336 the user status information to be used by the processor component s102 to generate the one or more selection menus, etc.).

In one or more implementations, operation p11 includes an operation p1174 for electronically receiving the user status information to at least in part electronically generate the one or more selection menus to provide the selection opportunity in response thereto via electronically enabled input including via electronic based gesture recognition. A non-transitory signal bearing medium includes one or more receiving information gesture instructions j1174 that when executed will direct performance of the operation p1174. In an implementation, the one or more receiving information gesture instructions j1174 when executed direct electronically receiving the user status information to at least in part electronically generate the one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user to be used by the processor component s102 to generate the one or more selection menus, etc.). Furthermore, the receiving information gesture electrical circuitry arrangement f1174 when activated will perform the operation p1174. In an implementation, the receiving information gesture electrical circuitry arrangement f1174, when activated performs electronically receiving the user status information to at least in part electronically generate the one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user to be used by the processor component s102 to generate the one or more selection menus, etc.). In an implementation, the electronically receiving the user status information to at least in part electronically generate the one or more selection menus to provide the selection opportunity in response thereto via electronically enabled input including via electronic based gesture recognition is carried out by electronically receiving the user status information to at least in part electronically generate the one or more selection menus to provide the selection opportunity in response thereto via electronically enabled input including via electronic based gesture recognition (e.g. an implementation of the receiver component s528 is configured to electronically engage with the optical sensing component s418 to receive the electronically enabled input as inputted by a user to be used by the processor component s102 to generate the one or more selection menus, etc.).

In one or more implementations, operation p11 includes an operation p1175 for electronically receiving the user status information to at least in part electronically generate the one or more selection menus to provide the selection opportunity in response thereto via electronically enabled input including via electronic audio recording of the particular individual living being. A non-transitory signal bearing medium includes one or more receiving information audio instructions j1175 that when executed will direct performance of the operation p1175. In an implementation, the one or more receiving information audio instructions j1175 when executed direct electronically receiving the user status information to at least in part electronically generate the one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input to be used by the processor component s102 to generate the one or more selection menus, etc.). Furthermore, the receiving information audio electrical circuitry arrangement f1175 when activated will perform the operation p1175. In an implementation, the receiving information audio electrical circuitry arrangement f1175, when activated performs electronically receiving the user status information to at least in part electronically generate the one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via electronic audio recording of the particular individual living being is carried out by electronically receiving the user status information to at least in part electronically generate the one or more selection menus to provide the selection opportunity in response thereto via electronically enabled input including via an electronic audio recording of the particular individual living being (e.g. an implementation of the receiver component s528 is configured to electronically engage with the sound sensing component s420 to receive the electronically enabled input to be used by the processor component s102 to generate the one or more selection menus, etc.).

In one or more implementations, as shown in FIG. 134, operation p11 includes an operation p1176 for electronically receiving the user status information to at least in part electronically generate the one or more selection menus to provide the selection opportunity in response thereto via electronically enabled input including via electronic keypad entry. An exemplary version of a non-transitory signal bearing medium of information storage subsystem s200 is depicted as bearing one or more receiving information keypad instructions j1176 that when executed will direct performance of the operation p1176. In an implementation, the one or more receiving information keypad instructions j1176 when executed direct electronically receiving the user status information to at least in part electronically generate the one or more selection menus to provide the selection opportunity in response thereto via electronically enabled input including via electronic keypad entry (e.g. an implementation of the receiver component s528 is configured to electronically engage with the keypad component s308 to receive the electronically enabled input to be used by the processor component s102 to generate the one or more selection menus, etc.). Furthermore, the receiving information keypad electrical circuitry arrangement f1176 when activated will perform the operation p1176. In an implementation, the receiving information keypad electrical circuitry arrangement f1176, when activated performs electronically receiving the user status information to at least in part electronically generate the one or more selection menus to provide the selection opportunity in response thereto via electronically enabled input including via electronic keypad entry (e.g. an implementation of the receiver component s528 is configured to electronically engage with the keypad component s308 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via electronic keypad entry is carried out by electronically receiving the user status information to at least in part electronically generate the one or more selection menus to provide the selection opportunity in response thereto via electronically enabled input including via electronic keypad entry (e.g. an implementation of the receiver component s528 is configured to electronically engage with the keypad component s308 to receive the electronically enabled input to be used by the processor component s102 to generate the one or more selection menus, etc.).

In one or more implementations, operation p11 includes an operation p1177 for electronically receiving the user status information to at least in part electronically generate the one or more selection menus to provide the selection opportunity in response thereto via electronically enabled input including via electronic input by the particular individual living being. A non-transitory signal bearing medium includes one or more receiving information input instructions j1177 that when executed will direct performance of the operation p1177. In an implementation, the one or more receiving information input instructions j1177 when executed direct electronically receiving the user status information to at least in part electronically generate the one or more selection menus to provide the selection opportunity in response thereto via electronically enabled input including via an electronic input (e.g. an implementation of the receiver component s528 is configured to electronically engage with the electromagnetic sensing component s402 to receive the electronically enabled input to be used by the processor component s102 to generate the one or more selection menus, etc.). Furthermore, the receiving information input electrical circuitry arrangement f1177 when activated will perform the operation p1177. In an implementation, the receiving information input electrical circuitry arrangement f1177, when activated performs electronically receiving the user status information to at least in part electronically generate the one or more selection menus to provide the selection opportunity in response thereto via electronically enabled input including via an electronic input (e.g. an implementation of the receiver component s528 is configured to electronically engage with the electromagnetic sensing component s402 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via electronic input by the particular individual living being is carried out by electronically receiving the user status information to at least in part electronically generate the one or more selection menus to provide the selection opportunity in response thereto via electronically enabled input including via an electronic input (e.g. an implementation of the receiver component s528 is configured to electronically engage with the electromagnetic sensing component s402 to receive the electronically enabled input to be used by the processor component s102 to generate the one or more selection menus, etc.).

In one or more implementations, operation p11 includes an operation p1178 for electronically receiving the user status information to at least in part electronically generate the one or more selection menus to provide the selection opportunity in response thereto via electronically enabled input including via encrypted input. A non-transitory signal bearing medium includes one or more receiving information encrypted instructions j1178 that when executed will direct performance of the operation p1178. In an implementation, the one or more receiving information encrypted instructions j1178 when executed direct electronically receiving the user status information to at least in part electronically generate the one or more selection menus to provide the selection opportunity in response thereto via electronically enabled input including via encrypted input (e.g. an implementation of the receiver component s528 is configured to electronically engage with the encrypted communication component s520 to receive the electronically enabled input to be used by the processor component s102 to generate the one or more selection menus, etc.). Furthermore, the receiving information encrypted electrical circuitry arrangement f1178 when activated will perform the operation p1178. In an implementation, the receiving information encrypted electrical circuitry arrangement f1178, when activated performs electronically receiving the user status information to at least in part electronically generate the one or more selection menus to provide the selection opportunity in response thereto via electronically enabled input including via encrypted input (e.g. an implementation of the receiver component s528 is configured to electronically engage with the encrypted communication component s520 to receive the electronically enabled input to be used by the processor component s102 to generate the one or more selection menus, etc.). In an implementation, the electronically receiving the user status information to at least in part electronically generate the one or more selection menus to provide the selection opportunity in response thereto via electronically enabled input including via encrypted input is carried out by electronically receiving the user status information to at least in part electronically generate the one or more selection menus to provide the selection opportunity in response thereto via electronically enabled input including via encrypted input (e.g. an implementation of the receiver component s528 is configured to electronically engage with the encrypted communication component s520 to receive the electronically enabled input to be used by the processor component s102 to generate the one or more selection menus, etc.).

As shown in FIG. 108, the operational flow p10 proceeds to operation p12 for electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus. An exemplary version of a non-transitory signal bearing medium of information storage subsystem s200 is depicted as bearing one or more controlling preparation instructions j12 that when executed will direct performance of the operation p12. In an implementation, the one or more controlling preparation instructions j12 when executed direct electronically directing control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the at least one candidate ingestible product as the at least one selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus (e.g. the graphical user interface s302 displaying the one or more selection menus is located with a room of a building that also houses the material processing subsystem 700 used to prepare the selected fruit smoothie, etc.). Furthermore, the controlling preparation electrical circuitry arrangement f12 when activated will perform the operation p12. In an implementation, the controlling preparation electrical circuitry arrangement f12, when activated performs electronically directing control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the at least one candidate ingestible product as the at least one selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus (e.g. the graphical user interface s302 displaying the one or more selection menus is located with a room of a building that also houses the material processing subsystem 700 used to prepare the selected fruit smoothie, etc.). In an implementation, the electronically directing control of at least partial preparation of the one or more selected ingestible products subsequent to and based at least in part upon the selection of the at least one candidate ingestible product as the at least one selected ingestible products via the electronically enabled input in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus is carried out by electronically directing control (e.g. the microprocessor component s102 can direct control, etc.) of at least partial preparation (e.g. mixing and blending steps of making a smoothie, etc.) of the one or more selected ingestible products (e.g. a fruit smoothie, etc.) subsequent to and based at least in part upon the selection of the at least one candidate ingestible product as the at least one selected ingestible products via the electronically enabled input (e.g. graphical user interface s302 is used to input selection of a fruit smoothie to be prepared by the digestible product preparation system 10, etc.) in response to the electronically outputted one or more selection menus and prior to dispensing of the one or more selected ingestible products for ingestion by the particular individual living being of the selected ingestible products, the at least partial preparation of the one or more selected ingestible products occurring within a vicinity of the electronically outputting of the electronically generated one or more selection menus (e.g. the graphical user interface s302 displaying the one or more selection menus is located with a room of a building that also houses the material processing subsystem 700 used to prepare the selected fruit smoothie, etc.).

In one or more implementations, as shown in FIG. 135, operation p12 includes an operation p1201 for electronically directing control of the at least partial preparation of the one or more selected ingestible products via at least in part one or more directly connected electrical circuits. An exemplary version of a non-transitory signal bearing medium of information storage subsystem s200 is depicted as bearing one or more control prep connected instructions j1201 that when executed will direct performance of the operation p1201. In an implementation, the one or more control prep connected instructions j1201 when executed direct electronically directing control of the at least partial preparation of the one or more selected ingestible products via at least in part one or more directly connected electrical circuits (e.g. an implementation of the processor component s102 is configured to electronically receive directing control through receiver component s528 co-located within a common housing of the ingestible product preparation system 10 to control the material processing subsystem 700 in preparation of the one or more ingestible products, etc.). Furthermore, the control prep connected electrical circuitry arrangement f1201 when activated will perform the operation p1201. In an implementation, the control prep connected electrical circuitry arrangement f1201, when activated performs electronically directing control of the at least partial preparation of the one or more selected ingestible products via at least in part one or more directly connected electrical circuits (e.g. an implementation of the processor component s102 is configured to electronically receive directing control through receiver component s528 co-located within a common housing of the ingestible product preparation system 10 to control the material processing subsystem 700 in preparation of the one or more ingestible products, etc.). In an implementation, the electronically directing control of the at least partial preparation of the one or more selected ingestible products via at least in part one or more directly connected electrical circuits is carried out by electronically directing control of the at least partial preparation of the one or more selected ingestible products via at least in part one or more directly connected electrical circuits (e.g. an implementation of the processor component s102 is configured to electronically receive directing control through receiver component s528 co-located within a common housing of the ingestible product preparation system 10 to control the material processing subsystem 700 in preparation of the one or more ingestible products, etc.).

In one or more implementations, operation p12 includes an operation p1202 for electronically directing control of the at least partial preparation of the one or more selected ingestible products via at least in part electronic computer network communication. An exemplary version of a non-transitory signal bearing medium of information storage subsystem s200 is depicted as bearing one or more control prep network instructions j1202 that when executed will direct performance of the operation p1202. In an implementation, the one or more control prep network instructions j1202 when executed direct electronically directing control of the at least partial preparation of the one or more selected ingestible products via at least in part electronic computer network communication (e.g. an implementation of the processor component s102 is configured to electronically receive directing control through internet network components s508 to control the material processing subsystem 700 in preparation of the one or more ingestible products, etc.). Furthermore, the control prep network electrical circuitry arrangement f1202 when activated will perform the operation p1202. In an implementation, the control prep network electrical circuitry arrangement f1202, when activated performs electronically directing control of the at least partial preparation of the one or more selected ingestible products via at least in part electronic computer network communication (e.g. an implementation of the processor component s102 is configured to electronically receive directing control through internet network components s508 to control the material processing subsystem 700 in preparation of the one or more ingestible products, etc.). In an implementation, the electronically directing control of the at least partial preparation of the one or more selected ingestible products via at least in part electronic computer network communication is carried out by electronically directing control of the at least partial preparation of the one or more selected ingestible products via at least in part electronic computer network communication (e.g. an implementation of the processor component s102 is configured to electronically receive directing control through internet network components s508 to control the material processing subsystem 700 in preparation of the one or more ingestible products, etc.).

In one or more implementations, operation p12 includes an operation p1203 for electronically directing control of the at least partial preparation of the one or more selected ingestible products via thermal control of an enclosure containing ingredients to be used for preparation of the ingestible product. An exemplary version of a non-transitory signal bearing medium of information storage subsystem s200 is depicted as bearing one or more control prep thermal instructions j1203 that when executed will direct performance of the operation p1203. In an implementation, the one or more control prep thermal instructions j1203 when executed direct electronically directing control of the at least partial preparation of the one or more selected ingestible products via thermal control of an enclosure containing ingredients to be used for preparation of the ingestible product (e.g. an implementation of the processor component s102 is configured to electronically control the laser component s708 according to a temperature profile included in the user status information, etc.). Furthermore, the control prep thermal electrical circuitry arrangement f1203 when activated will perform the operation p1203. In an implementation, the control prep thermal electrical circuitry arrangement f1203, when activated performs electronically directing control of the at least partial preparation of the one or more selected ingestible products via thermal control of an enclosure containing ingredients to be used for preparation of the ingestible product (e.g. an implementation of the processor component s102 is configured to electronically control the laser component s708 according to a temperature profile included in the user status information, etc.). In an implementation, the electronically directing control of the at least partial preparation of the one or more selected ingestible products via thermal control of an enclosure containing ingredients to be used for preparation of the ingestible product is carried out by electronically directing control of the at least partial preparation of the one or more selected ingestible products via thermal control of an enclosure containing ingredients to be used for preparation of the ingestible product (e.g. an implementation of the processor component s102 is configured to electronically control the laser component s708 according to a temperature profile included in the user status information, etc.).

In one or more implementations, as shown in FIG. 136, operation p12 includes an operation p1204 for electronically directing control of the at least partial preparation of the one or more selected ingestible products via heating control of an enclosure containing ingredients to be used for preparation of the ingestible product. An exemplary version of a non-transitory signal bearing medium of information storage subsystem s200 is depicted as bearing one or more control prep heating instructions j1204 that when executed will direct performance of the operation p1204. In an implementation, the one or more control prep heating instructions j1204 when executed direct electronically directing control of the at least partial preparation of the one or more selected ingestible products via heating control of an enclosure containing ingredients to be used for preparation of the ingestible product (e.g. an implementation of the processor component s102 is configured to electronically control the heating component s702 according to a temperature profile included in the user status information, etc.). Furthermore, the control prep connected electrical circuitry arrangement f1204 when activated will perform the operation p1204. In an implementation, the control prep heating electrical circuitry arrangement f1204, when activated performs electronically directing control of the at least partial preparation of the one or more selected ingestible products via heating control of an enclosure containing ingredients to be used for preparation of the ingestible product (e.g. an implementation of the processor component s102 is configured to electronically control the heating component s702 according to a temperature profile included in the user status information, etc.). In an implementation, the electronically directing control of the at least partial preparation of the one or more selected ingestible products via heating control of an enclosure containing ingredients to be used for preparation of the ingestible product is carried out by electronically directing control of the at least partial preparation of the one or more selected ingestible products via heating control of an enclosure containing ingredients to be used for preparation of the ingestible product (e.g. an implementation of the processor component s102 is configured to electronically control the heating component s702 according to a temperature profile included in the user status information, etc.).

In one or more implementations, operation p12 includes an operation p1205 for electronically directing control of the at least partial preparation of the one or more selected ingestible products via cooling control of an enclosure containing ingredients to be used for preparation of the ingestible product. An exemplary version of a non-transitory signal bearing medium of information storage subsystem s200 is depicted as bearing one or more control prep cooling instructions j1205 that when executed will direct performance of the operation p1205. In an implementation, the one or more control prep cooling instructions j1205 when executed direct electronically directing control of the at least partial preparation of the one or more selected ingestible products via cooling control of an enclosure containing ingredients to be used for preparation of the ingestible product (e.g. an implementation of the processor component s102 is configured to electronically control the cooling component s704 according to a temperature profile included in the user status information, etc.). Furthermore, the control prep cooling electrical circuitry arrangement f1205 when activated will perform the operation p1205. In an implementation, the control prep cooling electrical circuitry arrangement f1205, when activated performs electronically directing control of the at least partial preparation of the one or more selected ingestible products via cooling control of an enclosure containing ingredients to be used for preparation of the ingestible product (e.g. an implementation of the processor component s102 is configured to electronically control the cooling component s704 according to a temperature profile included in the user status information, etc.). In an implementation, the electronically directing control of the at least partial preparation of the one or more selected ingestible products via cooling control of an enclosure containing ingredients to be used for preparation of the ingestible product is carried out by electronically directing control of the at least partial preparation of the one or more selected ingestible products via cooling control of an enclosure containing ingredients to be used for preparation of the ingestible product (e.g. an implementation of the processor component s102 is configured to electronically control the cooling component s704 according to a temperature profile included in the user status information, etc.).

In one or more implementations, operation p12 includes an operation p1206 for electronically directing control of the at least partial preparation of the one or more selected ingestible products via portion size control of an amount of the substance to be used in preparation of the ingestible product. An exemplary version of a non-transitory signal bearing medium of information storage subsystem s200 is depicted as bearing one or more control prep portion instructions j1206 that when executed will direct performance of the operation p1206. In an implementation, the one or more control prep portion instructions j1206 when executed direct electronically directing control of the at least partial preparation of the one or more selected ingestible products via portion size control of an amount of the substance to be used in preparation of the ingestible product (e.g. an implementation of the processor component s102 is configured to electronically control the sorting component s728 according to a ingredient size distribution profile included in the user status information, etc.). Furthermore, the control prep portion electrical circuitry arrangement f1206 when activated will perform the operation p1205. In an implementation, the control prep portion electrical circuitry arrangement f1206, when activated performs electronically directing control of the at least partial preparation of the one or more selected ingestible products via portion size control of an amount of the substance to be used in preparation of the ingestible product (e.g. an implementation of the processor component s102 is configured to electronically control the sorting component s728 according to a ingredient size distribution profile included in the user status information, etc.). In an implementation, the electronically directing control of the at least partial preparation of the one or more selected ingestible products via portion size control of an amount of the substance to be used in preparation of the ingestible product is carried out by electronically directing control of the at least partial preparation of the one or more selected ingestible products via portion size control of an amount of the substance to be used in preparation of the ingestible product (e.g. an implementation of the processor component s102 is configured to electronically control the sorting component s728 according to a ingredient size distribution profile included in the user status information, etc.).

In one or more implementations, as shown in FIG. 137, operation p12 includes an operation p1207 for electronically directing control of the at least partial preparation of the one or more selected ingestible products via controlling amount of ingredient mixing during preparation of the ingestible product. An exemplary version of a non-transitory signal bearing medium of information storage subsystem s200 is depicted as bearing one or more control prep mixing instructions j1207 that when executed will direct performance of the operation p1207. In an implementation, the one or more control prep mixing instructions j1207 when executed direct electronically directing control of the at least partial preparation of the one or more selected ingestible products via controlling amount of ingredient mixing during preparation of the ingestible product (e.g. an implementation of the processor component s102 is configured to electronically control the mixer component s716 according to a mixing profile included in the user status information, etc.). Furthermore, the control prep mixing electrical circuitry arrangement f1207 when activated will perform the operation p1207. In an implementation, the control prep mixing electrical circuitry arrangement f1207, when activated performs electronically directing control of the at least partial preparation of the one or more selected ingestible products via controlling amount of ingredient mixing during preparation of the ingestible product (e.g. an implementation of the processor component s102 is configured to electronically control the mixer component s716 according to a mixing profile included in the user status information, etc.). In an implementation, the electronically directing control of the at least partial preparation of the one or more selected ingestible products via controlling amount of ingredient mixing during preparation of the ingestible product is carried out by electronically directing control of the at least partial preparation of the one or more selected ingestible products via controlling amount of ingredient mixing during preparation of the ingestible product (e.g. an implementation of the processor component s102 is configured to electronically control the mixer component s716 according to a mixing profile included in the user status information, etc.).

In one or more implementations, operation p12 includes an operation p1208 for electronically directing control of the at least partial preparation of the one or more selected ingestible products via control of radiation emitted within an enclosure containing ingredients to be used for preparation of the ingestible product. An exemplary version of a non-transitory signal bearing medium of information storage subsystem s200 is depicted as bearing one or more control prep radiation instructions j1208 that when executed will direct performance of the operation p1208. In an implementation, the one or more control prep radiation instructions j1208 when executed direct electronically directing control of the at least partial preparation of the one or more selected ingestible products via control of radiation emitted within an enclosure containing ingredients to be used for preparation of the ingestible product (e.g. an implementation of the processor component s102 is configured to electronically control the energy emitting component s724 configured to emit radiation according to a radiation profile included in the user status information, etc.). Furthermore, the control prep radiation electrical circuitry arrangement f1208 when activated will perform the operation p1208. In an implementation, the control prep radiation electrical circuitry arrangement f1208, when activated performs electronically directing control of the one or more selected ingestible products via control of radiation emitted within an enclosure containing ingredients to be used for preparation of the ingestible product (e.g. an implementation of the processor component s102 is configured to electronically control the energy emitting component s724 configured to emit radiation according to a radiation profile included in the user status information, etc.). In an implementation, the electronically directing control of the at least partial preparation of the one or more selected ingestible products via control of radiation emitted within an enclosure containing ingredients to be used for preparation of the ingestible product is carried out by electronically directing control of the at least partial preparation of the one or more selected ingestible products via control of radiation emitted within an enclosure containing ingredients to be used for preparation of the ingestible product (e.g. an implementation of the processor component s102 is configured to electronically control the energy emitting component s724 configured to emit radiation according to a radiation profile included in the user status information, etc.).

In one or more implementations, operation p12 includes an operation p1209 for electronically directing control of the at least partial preparation of the one or more selected ingestible products via control of sound emitted within an enclosure containing ingredients to be used for preparation of the ingestible product. An exemplary version of a non-transitory signal bearing medium of information storage subsystem s200 is depicted as bearing one or more control prep sound instructions j1209 that when executed will direct performance of the operation p1209. In an implementation, the one or more control prep sound instructions j1209 when executed direct electronically directing control of the at least partial preparation of the one or more selected ingestible products via control of sound emitted within an enclosure containing ingredients to be used for preparation of the ingestible product (e.g. an implementation of the processor component s102 is configured to electronically control the acoustic energy component s718 according to an acoustic energy profile included in the user status information, etc.). Furthermore, the control prep sound electrical circuitry arrangement f1209 when activated will perform the operation p1209. In an implementation, the control prep sound electrical circuitry arrangement f1209, when activated performs electronically directing control of the at least partial preparation of the one or more selected ingestible products via control of sound emitted within an enclosure containing ingredients to be used for preparation of the ingestible product (e.g. an implementation of the processor component s102 is configured to electronically control the acoustic energy component s718 according to an acoustic energy profile included in the user status information, etc.). In an implementation, the electronically directing control of the at least partial preparation of the one or more selected ingestible products via control of sound emitted within an enclosure containing ingredients to be used for preparation of the ingestible product is carried out by electronically directing control of the at least partial preparation of the one or more selected ingestible products via control of sound emitted within an enclosure containing ingredients to be used for preparation of the ingestible product (e.g. an implementation of the processor component s102 is configured to electronically control the acoustic energy component s718 according to an acoustic energy profile included in the user status information, etc.).

In one or more implementations, as shown in FIG. 138, operation p12 includes an operation p1210 for electronically directing control of the at least partial preparation of the one or more selected ingestible products via control of infrared radiation emitted within an enclosure containing ingredients to be used for preparation of the ingestible product. An exemplary version of a non-transitory signal bearing medium of information storage subsystem s200 is depicted as bearing one or more control prep infrared instructions j1210 that when executed will direct performance of the operation p1210. In an implementation, the one or more control prep infrared instructions j1210 when executed direct electronically directing control of the at least partial preparation of the one or more selected ingestible products via control of infrared radiation emitted within an enclosure containing ingredients to be used for preparation of the ingestible product (e.g. an implementation of the processor component s102 is configured to electronically control the infrared component s730 according to a temperature profile included in the user status information, etc.). Furthermore, the control prep infrared electrical circuitry arrangement f1210 when activated will perform the operation p1210. In an implementation, the control prep infrared electrical circuitry arrangement f1210, when activated performs electronically directing control of the at least partial preparation of the one or more selected ingestible products via control of infrared radiation emitted within an enclosure containing ingredients to be used for preparation of the ingestible product (e.g. an implementation of the processor component s102 is configured to electronically control the infrared component s730 according to a temperature profile included in the user status information, etc.). In an implementation, the electronically directing control of the at least partial preparation of the one or more selected ingestible products via control of infrared radiation emitted within an enclosure containing ingredients to be used for preparation of the ingestible product is carried out by electronically directing control of the at least partial preparation of the one or more selected ingestible products via control of infrared radiation emitted within an enclosure containing ingredients to be used for preparation of the ingestible product (e.g. an implementation of the processor component s102 is configured to electronically control the infrared component s730 according to a temperature profile included in the user status information, etc.).

In one or more implementations, operation p12 includes an operation p1211 for electronically directing control of the at least partial preparation of the one or more selected ingestible products via control of microwave radiation emitted within an enclosure containing ingredients to be used for preparation of the ingestible product. An exemplary version of a non-transitory signal bearing medium of information storage subsystem s200 is depicted as bearing one or more control prep microwave instructions j1211 that when executed will direct performance of the operation p1211. In an implementation, the one or more control prep microwave instructions j1211 when executed direct electronically directing control of the at least partial preparation of the one or more selected ingestible products via control of microwave radiation emitted within an enclosure containing ingredients to be used for preparation of the ingestible product (e.g. an implementation of the processor component s102 is configured to electronically control the microwave component s706 according to a temperature profile included in the user status information, etc.). Furthermore, the control prep microwave electrical circuitry arrangement f1211 when activated will perform the operation p1211. In an implementation, the control prep microwave electrical circuitry arrangement f1211, when activated performs electronically directing control of the at least partial preparation of the one or more selected ingestible products via control of microwave radiation emitted within an enclosure containing ingredients to be used for preparation of the ingestible product (e.g. an implementation of the processor component s102 is configured to electronically control the microwave component s706 according to a temperature profile included in the user status information, etc.). In an implementation, the electronically directing control of the at least partial preparation of the one or more selected ingestible products via control of microwave radiation emitted within an enclosure containing ingredients to be used for preparation of the ingestible product is carried out by electronically directing control of the at least partial preparation of the one or more selected ingestible products via control of microwave radiation emitted within an enclosure containing ingredients to be used for preparation of the ingestible product (e.g. an implementation of the processor component s102 is configured to electronically control the microwave component s706 according to a temperature profile included in the user status information, etc.).

In one or more implementations, operation p12 includes an operation p1212 for electronically directing control of the at least partial preparation of the one or more selected ingestible products via control of an outlet of an ingredient container holding an ingredient used for preparation of the ingestible product. An exemplary version of a non-transitory signal bearing medium of information storage subsystem s200 is depicted as bearing one or more control prep container instructions j1212 that when executed will direct performance of the operation p1212. In an implementation, the one or more control prep container instructions j1212 when executed direct electronically directing control of the at least partial preparation of the one or more selected ingestible products via control of an outlet of an ingredient container holding an ingredient used for preparation of the ingestible product (e.g. an implementation of the processor component s102 is configured to electronically control an outlet of the material storage component s734 configured as an ingredient container according to an access profile included in the user status information, etc.). Furthermore, the control prep container electrical circuitry arrangement f1212 when activated will perform the operation p1212. In an implementation, the control prep container electrical circuitry arrangement f1212, when activated performs electronically directing control of the at least partial preparation of the one or more selected ingestible products via control of an outlet of an ingredient container holding an ingredient used for preparation of the ingestible product (e.g. an implementation of the processor component s102 is configured to electronically control an outlet of the material storage component s734 configured as an ingredient container according to an access profile included in the user status information, etc.). In an implementation, the electronically directing control of the at least partial preparation of the one or more selected ingestible products via control of an outlet of an ingredient container holding an ingredient used for preparation of the ingestible product is carried out by electronically directing control of the at least partial preparation of the one or more selected ingestible products via control of an outlet of an ingredient container holding an ingredient used for preparation of the ingestible product (e.g. an implementation of the processor component s102 is configured to electronically control an outlet of the material storage component s734 configured as an ingredient container according to an access profile included in the user status information, etc.).

In one or more implementations, as shown in FIG. 139, operation p12 includes an operation p1213 for electronically directing control of the at least partial preparation of the one or more selected ingestible products via control of an outlet of an ingredient syringe holding an ingredient used for preparation of the ingestible product. An exemplary version of a non-transitory signal bearing medium of information storage subsystem s200 is depicted as bearing one or more control prep syringe instructions j1213 that when executed will direct performance of the operation p1213. In an implementation, the one or more control prep syringe instructions j1213 when executed direct electronically directing control of the at least partial preparation of the one or more selected ingestible products via control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the user status information, etc.). Furthermore, the control prep syringe electrical circuitry arrangement f1213 when activated will perform the operation p1213. In an implementation, the control prep syringe electrical circuitry arrangement f1213, when activated performs electronically directing control of the at least partial preparation of the one or more selected ingestible products via control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the user status information, etc.). In an implementation, the electronically directing control of the at least partial preparation of the one or more selected ingestible products via control of an outlet of an ingredient syringe holding an ingredient used for preparation of the ingestible product is carried out by electronically directing control of the at least partial preparation of the one or more selected ingestible products via control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the user status information, etc.).

In one or more implementations, operation p12 includes an operation p1214 for electronically directing control of the at least partial preparation of the one or more selected ingestible products via control of mixing of at least some of the ingredients used to prepare the ingestible product before thermal treatment of the ingredients. An exemplary version of a non-transitory signal bearing medium of information storage subsystem s200 is depicted as bearing one or more control prep mix before thermal instructions j1214 that when executed will direct performance of the operation p1214. In an implementation, the one or more control prep mix before thermal instructions j1214 when executed direct electronically directing control of the at least partial preparation of the one or more selected ingestible products via control of mixing of at least some of the ingredients used to prepare the ingestible product before thermal treatment of the ingredients (e.g. an implementation of the processor component s102 is configured to electronically control the mixer component s716 according to a mixing profile included in the user status information, etc.). Furthermore, the control prep mix before thermal electrical circuitry arrangement f1214 when activated will perform the operation p1214. In an implementation, the control prep mix before thermal electrical circuitry arrangement f1214, when activated performs electronically directing control of the at least partial preparation of the one or more selected ingestible products via control of mixing of at least some of the ingredients used to prepare the ingestible product before thermal treatment of the ingredients (e.g. an implementation of the processor component s102 is configured to electronically control the mixer component s716 according to a mixing profile included in the user status information, etc.). In an implementation, the electronically directing control of the at least partial preparation of the one or more selected ingestible products via control of mixing of at least some of the ingredients used to prepare the ingestible product before thermal treatment of the ingredients is carried out by electronically directing control of the at least partial preparation of the one or more selected ingestible products via control of mixing of at least some of the ingredients used to prepare the ingestible product before thermal treatment of the ingredients (e.g. an implementation of the processor component s102 is configured to electronically control the mixer component s716 according to a mixing profile included in the user status information, etc.).

In one or more implementations, operation p12 includes an operation p1215 for electronically directing control of the at least partial preparation of the one or more selected ingestible products via control of blending of at least some of the ingredients used to prepare the ingestible product after thermal treatment of the ingredients. An exemplary version of a non-transitory signal bearing medium of information storage subsystem s200 is depicted as bearing one or more control prep re mix after thermal instructions j1215 that when executed will direct performance of the operation p1215. In an implementation, the one or more control prep re mix after thermal instructions j1215 when executed direct electronically directing control of the at least partial preparation of the one or more selected ingestible products via control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the user status information, etc.). Furthermore, the control prep re mix after thermal electrical circuitry arrangement f1215 when activated will perform the operation p1215. In an implementation, the control prep re mix after thermal electrical circuitry arrangement f1215, when activated performs electronically directing control of the at least partial preparation of the one or more selected ingestible products via control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the user status information, etc.). In an implementation, the electronically directing control of the at least partial preparation of the one or more selected ingestible products via control of blending of at least some of the ingredients used to prepare the ingestible product after thermal treatment of the ingredients is carried out by electronically directing control of the at least partial preparation of the one or more selected ingestible products via control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the user status information, etc.).

In one or more implementations, as shown in FIG. 140, operation p12 includes an operation p1216 for electronically directing control of the at least partial preparation of the one or more selected ingestible products via control of thermal treatment of ingredients used to prepare the ingestible product, the thermal treatment including heating, cooling, or a combination thereof of the ingredients. An exemplary version of a non-transitory signal bearing medium of information storage subsystem s200 is depicted as bearing one or more control prep heating cooling instructions j1216 that when executed will direct performance of the operation p1216. In an implementation, the one or more control prep heating cooling instructions j1216 when executed direct electronically directing control of the at least partial preparation of the one or more selected ingestible products via control of thermal treatment of ingredients used to prepare the ingestible product, the thermal treatment including heating, cooling, or a combination thereof of the ingredients (e.g.

an implementation of the processor component s102 is configured to electronically control the heating component s702 and/or the cooling component s704 according to a thermal profile included in the user status information, etc.). Furthermore, the control prep heating cooling electrical circuitry arrangement f1216 when activated will perform the operation p1216. In an implementation, the control prep heating cooling electrical circuitry arrangement f1216, when activated performs electronically directing control of the at least partial preparation of the one or more selected ingestible products via control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the user status information, etc.). In an implementation, the electronically directing control of the at least partial preparation of the one or more selected ingestible products via control of thermal treatment of ingredients used to prepare the ingestible product, the thermal treatment including heating, cooling, or a combination thereof of the ingredients is carried out by electronically directing control of the at least partial preparation of the one or more selected ingestible products via control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the user status information, etc.).

In one or more implementations, operation p12 includes an operation p1217 for electronically directing control of the at least partial preparation of the one or more selected ingestible products via control of amount of time spent for a particular step in preparation of the ingestible product. An exemplary version of a non-transitory signal bearing medium of information storage subsystem s200 is depicted as bearing one or more control prep time control instructions j1217 that when executed will direct performance of the operation p1217. In an implementation, the one or more control prep time control instructions j1217 when executed direct electronically directing control of the at least partial preparation of the one or more selected ingestible products via control of amount of time spent for a particular step in preparation of the ingestible product (e.g. an implementation of the processor component s102 is configured to electronically control components of the material processing subsystem s700 based upon an internal clock of the processor according to a time profile included in the user status information, etc.). Furthermore, the control prep time control electrical circuitry arrangement f1217 when activated will perform the operation p1217. In an implementation, the control prep time control electrical circuitry arrangement f1217, when activated performs electronically directing control of the at least partial preparation of the one or more selected ingestible products via control of amount of time spent for a particular step in preparation of the ingestible product (e.g. an implementation of the processor component s102 is configured to electronically control components of the material processing subsystem s700 based upon an internal clock of the processor according to a time profile included in the user status information, etc.). In an implementation, the electronically directing control of the at least partial preparation of the one or more selected ingestible products via control of amount of time spent for a particular step in preparation of the ingestible product is carried out by electronically directing control of the at least partial preparation of the one or more selected ingestible products via control of amount of time spent for a particular step in preparation of the ingestible product (e.g. an implementation of the processor component s102 is configured to electronically control components of the material processing subsystem s700 based upon an internal clock of the processor according to a time profile included in the user status information, etc.).

In one or more implementations, operation p12 includes an operation p1218 for electronically directing control of the at least partial preparation of the one or more selected ingestible products via electronically excluding ingredients from being included in the preparation of the ingestible product. An exemplary version of a non-transitory signal bearing medium of information storage subsystem s200 is depicted as bearing one or more control prep ingredient exclusion instructions j1218 that when executed will direct performance of the operation p1218. In an implementation, the one or more control prep ingredient exclusion instructions j1218 when executed direct electronically directing control of the at least partial preparation of the one or more selected ingestible products via electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the user status information, etc.). Furthermore, the control prep ingredient exclusion electrical circuitry arrangement f1218 when activated will perform the operation p1218. In an implementation, the control prep ingredient exclusion electrical circuitry arrangement f1218, when activated performs electronically directing control of the at least partial preparation of the one or more selected ingestible products via electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the user status information, etc.). In an implementation, the electronically directing control of the at least partial preparation of the one or more selected ingestible products via electronically excluding ingredients from being included in the preparation of the ingestible product is carried out by electronically directing control of the at least partial preparation of the one or more selected ingestible products via electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the user status information, etc.).

In one or more implementations, as shown in FIG. 141, operation p12 includes an operation p1219 for electronically directing control of the at least partial preparation of the one or more selected ingestible products via electronically including ingredients in the preparation of the ingestible product. An exemplary version of a non-transitory signal bearing medium of information storage subsystem s200 is depicted as bearing one or more control prep ingredient inclusion instructions j1219 that when executed will direct performance of the operation p1219. In an implementation, the one or more control prep ingredient inclusion instructions j1219 when executed direct electronically directing control of the at least partial preparation of the one or more selected ingestible products via electronically including ingredients in the preparation of the ingestible product (e.g. an implementation of the processor component s102 is configured to electronically control the sorting component s728 to include one or more ingredients in the ingestible product according to an inclusion profile included in the user status information, etc.). Furthermore, the control prep ingredient inclusion electrical circuitry arrangement f1219 when activated will perform the operation p1219. In an implementation, the control prep ingredient inclusion electrical circuitry arrangement f1219, when activated performs electronically directing control of the at least partial preparation of the one or more selected ingestible products via electronically including ingredients in the preparation of the ingestible product (e.g. an implementation of the processor component s102 is configured to electronically control the sorting component s728 to include one or more ingredients in the ingestible product according to an inclusion profile included in the user status information, etc.). In an implementation, the electronically directing control of the at least partial preparation of the one or more selected ingestible products via electronically including ingredients in the preparation of the ingestible product is carried out by electronically directing control of the at least partial preparation of the one or more selected ingestible products via electronically including ingredients in the preparation of the ingestible product (e.g. an implementation of the processor component s102 is configured to electronically control the sorting component s728 to include one or more ingredients in the ingestible product according to an inclusion profile included in the user status information, etc.).

In one or more implementations, operation p12 includes an operation p1220 for electronically directing control of the at least partial preparation of the one or more selected ingestible products, the at least partial preparation of the one or more selected ingestible products within the vicinity of the electronically outputting of the electronically generated one or more selection menus as within an interior of a dispensing machine housing. An exemplary version of a non-transitory signal bearing medium of information storage subsystem s200 is depicted as bearing one or more control prep housing instructions j1220 that when executed will direct performance of the operation p1220. In an implementation, the one or more control prep housing instructions j1220 when executed direct electronically directing control of the at least partial preparation of the one or more selected ingestible products, the at least partial preparation of the one or more selected ingestible products within the vicinity of the electronically outputting of the electronically generated one or more selection menus as within an interior of a dispensing machine housing (e.g. an implementation of the processor component s102 is configured to receive through the electronic communication subsystem 500 directing control to electronically control the material processing subsystem 700 for at least partial preparation of the one or more selected ingestible products within the interior of the digestible product preparation system 10 that uses for instance visual display component s304 to electronically output the electronically generated one or more selection menus, etc.). Furthermore, the control prep housing electrical circuitry arrangement f1220 when activated will perform the operation p1220. In an implementation, the control prep housing electrical circuitry arrangement f1220, when activated performs electronically directing control of the at least partial preparation of the one or more selected ingestible products, the at least partial preparation of the one or more selected ingestible products within the vicinity of the electronically outputting of the electronically generated one or more selection menus as within an interior of a dispensing machine housing (e.g. an implementation of the processor component s102 is configured to receive through the electronic communication subsystem 500 directing control to electronically control the material processing subsystem 700 for at least partial preparation of the one or more selected ingestible products within the interior of the digestible product preparation system 10 that uses for instance visual display component s304 to electronically output the electronically generated one or more selection menus, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an interior of a dispensing machine housing is carried out by electronically directing control of the at least partial preparation of the one or more selected ingestible products, the at least partial preparation of the one or more selected ingestible products within the vicinity of the electronically outputting of the electronically generated one or more selection menus as within an interior of a dispensing machine housing (e.g. an implementation of the processor component s102 is configured to receive through the electronic communication subsystem 500 directing control to electronically control the material processing subsystem 700 for at least partial preparation of the one or more selected ingestible products within the interior of the digestible product preparation system 10 that uses for instance visual display component s304 to electronically output the electronically generated one or more selection menus, etc.).

In one or more implementations, operation p12 includes an operation p1221 for electronically directing control of the at least partial preparation of the one or more selected ingestible products, the at least partial preparation of the one or more selected ingestible products within the vicinity of the electronically outputting of the electronically generated one or more selection menus as within an interior of a architectural building containing a dispensing machine. An exemplary version of a non-transitory signal bearing medium of information storage subsystem s200 is depicted as bearing one or more control prep building instructions j1221 that when executed will direct performance of the operation p1221. In an implementation, the one or more control prep building instructions j1221 when executed direct electronically directing control of the at least partial preparation of the one or more selected ingestible products, the at least partial preparation of the one or more selected ingestible products within the vicinity of the electronically outputting of the electronically generated one or more selection menus as within an interior of a architectural building containing a dispensing machine (e.g. an implementation of the processor component s102 is configured to receive through the electronic communication subsystem 500 directing control to electronically control the material processing subsystem 700 for at least partial preparation of the one or more selected ingestible products within the interior of an airport wherein the digestible product preparation system 10 is located that communicates with for instance the visual display component s304 to electronically output the electronically generated one or more selection menus also within the airport, etc.). Furthermore, the control prep building electrical circuitry arrangement f1221 when activated will perform the operation p1221. In an implementation, the control prep building electrical circuitry arrangement f1221, when activated performs electronically directing control of the at least partial preparation of the one or more selected ingestible products, the at least partial preparation of the one or more selected ingestible products within the vicinity of the electronically outputting of the electronically generated one or more selection menus as within an interior of a architectural building containing a dispensing machine (e.g. an implementation of the processor component s102 is configured to receive through the electronic communication subsystem 500 directing control to electronically control the material processing subsystem 700 for at least partial preparation of the one or more selected ingestible products within the interior of an airport wherein the digestible product preparation system 10 is located that communicates with for instance the visual display component s304 to electronically output the electronically generated one or more selection menus also within the airport, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an interior of a architectural building containing a dispensing machine is carried out by electronically directing control of the at least partial preparation of the one or more selected ingestible products, the at least partial preparation of the one or more selected ingestible products within the vicinity of the electronically outputting of the electronically generated one or more selection menus as within an interior of a architectural building containing a dispensing machine (e.g. an implementation of the processor component s102 is configured to receive through the electronic communication subsystem 500 directing control to electronically control the material processing subsystem 700 for at least partial preparation of the one or more selected ingestible products within the interior of an airport wherein the digestible product preparation system 10 is located that communicates with for instance the visual display component s304 to electronically output the electronically generated one or more selection menus also within the airport, etc.).

In one or more implementations, as shown in FIG. 142, operation p12 includes an operation p1222 for electronically directing control of the at least partial preparation of the one or more selected ingestible products, the at least partial preparation of the one or more selected ingestible products within the vicinity of the electronically outputting of the electronically generated one or more selection menus as within a food court of a shopping mall. An exemplary version of a non-transitory signal bearing medium of information storage subsystem s200 is depicted as bearing one or more control prep mall instructions j1222 that when executed will direct performance of the operation p1222. In an implementation, the one or more control prep mall instructions j1222 when executed direct electronically directing control of the at least partial preparation of the one or more selected ingestible products, the at least partial preparation of the one or more selected ingestible products within the vicinity of the electronically outputting of the electronically generated one or more selection menus as within a food court of a shopping mall (i.e. an implementation of the processor component s102 is configured to receive through the electronic communication subsystem 500 directing control to electronically control the material processing subsystem 700 for at least partial preparation of the one or more selected ingestible products within the food court of the shopping mall wherein the digestible product preparation system 10 is located that communicates with for instance the visual display component s304 to electronically output the electronically generated one or more selection menus also within the food court of the shopping mall, etc.). Furthermore, the control prep mall electrical circuitry arrangement f1222 when activated will perform the operation p1222. In an implementation, the control prep mall electrical circuitry arrangement f1222, when activated performs electronically directing control of the at least partial preparation of the one or more selected ingestible products, the at least partial preparation of the one or more selected ingestible products within the vicinity of the electronically outputting of the electronically generated one or more selection menus as within a food court of a shopping mall (i.e. an implementation of the processor component s102 is configured to receive through the electronic communication subsystem 500 directing control to electronically control the material processing subsystem 700 for at least partial preparation of the one or more selected ingestible products within the food court of the shopping mall wherein the digestible product preparation system 10 is located that communicates with for instance the visual display component s304 to electronically output the electronically generated one or more selection menus also within the food court of the shopping mall, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within a food court of a shopping mall is carried out by electronically directing control of the at least partial preparation of the one or more selected ingestible products, the at least partial preparation of the one or more selected ingestible products within the vicinity of the electronically outputting of the electronically generated one or more selection menus as within a food court of a shopping mall (i.e. an implementation of the processor component s102 is configured to receive through the electronic communication subsystem 500 directing control to electronically control the material processing subsystem 700 for at least partial preparation of the one or more selected ingestible products within the food court of the shopping mall wherein the digestible product preparation system 10 is located that communicates with for instance the visual display component s304 to electronically output the electronically generated one or more selection menus also within the food court of the shopping mall, etc.)

In one or more implementations, operation p12 includes an operation p1223 for electronically directing control of the at least partial preparation of the one or more selected ingestible products, the at least partial preparation of the one or more selected ingestible products within the vicinity of the electronically outputting of the electronically generated one or more selection menus as within an interior of a restaurant. An exemplary version of a non-transitory signal bearing medium of information storage subsystem s200 is depicted as bearing one or more control prep restaurant instructions j1223 that when executed will direct performance of the operation p1223. In an implementation, the one or more control prep restaurant instructions j1223 when executed direct electronically directing control of the at least partial preparation of the one or more selected ingestible products, the at least partial preparation of the one or more selected ingestible products within the vicinity of the electronically outputting of the electronically generated one or more selection menus as within an interior of a restaurant (i.e. an implementation of the processor component s102 is configured to receive through the electronic communication subsystem 500 directing control to electronically control the material processing subsystem 700 for at least partial preparation of the one or more selected ingestible products within the interior of the restaurant wherein the digestible product preparation system 10 is located that communicates with for instance the visual display component s304 to electronically output the electronically generated one or more selection menus also within the restaurant, etc.). Furthermore, the control prep restaurant electrical circuitry arrangement f1223 when activated will perform the operation p1223. In an implementation, the control prep restaurant electrical circuitry arrangement f1223, when activated performs electronically directing control of the at least partial preparation of the one or more selected ingestible products, the at least partial preparation of the one or more selected ingestible products within the vicinity of the electronically outputting of the electronically generated one or more selection menus as within an interior of a restaurant (i.e. an implementation of the processor component s102 is configured to receive through the electronic communication subsystem 500 directing control to electronically control the material processing subsystem 700 for at least partial preparation of the one or more selected ingestible products within the interior of the restaurant wherein the digestible product preparation system 10 is located that communicates with for instance the visual display component s304 to electronically output the electronically generated one or more selection menus also within the restaurant, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an interior of a restaurant is carried out by electronically directing control of the at least partial preparation of the one or more selected ingestible products, the at least partial preparation of the one or more selected ingestible products within the vicinity of the electronically outputting of the electronically generated one or more selection menus as within an interior of a restaurant (i.e. an implementation of the processor component s102 is configured to receive through the electronic communication subsystem 500 directing control to electronically control the material processing subsystem 700 for at least partial preparation of the one or more selected ingestible products within the interior of the restaurant wherein the digestible product preparation system 10 is located that communicates with for instance the visual display component s304 to electronically output the electronically generated one or more selection menus also within the restaurant, etc.).

In one or more implementations, operation p12 includes an operation p1224 for electronically directing control of the at least partial preparation of the one or more selected ingestible products, the at least partial preparation of the one or more selected ingestible products within the vicinity of the electronically outputting of the electronically generated one or more selection menus as within an interior of an airplane. An exemplary version of a non-transitory signal bearing medium of information storage subsystem s200 is depicted as bearing one or more control prep airplane instructions j1224 that when executed will direct performance of the operation p1224. In an implementation, the one or more control prep airplane instructions j1224 when executed direct electronically directing control of the at least partial preparation of the one or more selected ingestible products, the at least partial preparation of the one or more selected ingestible products within the vicinity of the electronically outputting of the electronically generated one or more selection menus as within an interior of an airplane (i.e. an implementation of the processor component s102 is configured to receive through the electronic communication subsystem 500 directing control to electronically control the material processing subsystem 700 for at least partial preparation of the one or more selected ingestible products within the interior of the airplane wherein the digestible product preparation system 10 is located that communicates with for instance the visual display component s304 to electronically output the electronically generated one or more selection menus also within the airplane, etc.). Furthermore, the control prep airplane electrical circuitry arrangement f1224 when activated will perform the operation p1224. In an implementation, the control prep airplane electrical circuitry arrangement f1224, when activated performs electronically directing control of the at least partial preparation of the one or more selected ingestible products, the at least partial preparation of the one or more selected ingestible products within the vicinity of the electronically outputting of the electronically generated one or more selection menus as within an interior of an airplane (i.e. an implementation of the processor component s102 is configured to receive through the electronic communication subsystem 500 directing control to electronically control the material processing subsystem 700 for at least partial preparation of the one or more selected ingestible products within the interior of the airplane wherein the digestible product preparation system 10 is located that communicates with for instance the visual display component s304 to electronically output the electronically generated one or more selection menus also within the airplane, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an interior of an airplane is carried out by electronically directing control of the at least partial preparation of the one or more selected ingestible products, the at least partial preparation of the one or more selected ingestible products within the vicinity of the electronically outputting of the electronically generated one or more selection menus as within an interior of an airplane (i.e. an implementation of the processor component s102 is configured to receive through the electronic communication subsystem 500 directing control to electronically control the material processing subsystem 700 for at least partial preparation of the one or more selected ingestible products within the interior of the airplane wherein the digestible product preparation system 10 is located that communicates with for instance the visual display component s304 to electronically output the electronically generated one or more selection menus also within the airplane, etc.).

In one or more implementations, as shown in FIG. 143, operation p12 includes an operation p1225 for electronically directing control of the at least partial preparation of the one or more selected ingestible products via thermal control of an enclosure containing ingredients to be used for preparation of the ingestible product. An exemplary version of a non-transitory signal bearing medium of information storage subsystem s200 is depicted as bearing one or more control prep vehicle instructions j1225 that when executed will direct performance of the operation p1225. In an implementation, the one or more control prep vehicle instructions j1225 when executed direct electronically directing control of the at least partial preparation of the one or more selected ingestible products, the at least partial preparation of the one or more selected ingestible products within the vicinity of the electronically outputting of the electronically generated one or more selection menus as within an interior of a ground vehicle (i.e. an implementation of the processor component s102 is configured to receive through the electronic communication subsystem 500 directing control to electronically control the material processing subsystem 700 for at least partial preparation of the one or more selected ingestible products within the interior of the ground vehicle wherein the digestible product preparation system 10 is located that communicates with for instance the visual display component s304 to electronically output the electronically generated one or more selection menus also within the ground vehicle, etc.). Furthermore, the control prep vehicle electrical circuitry arrangement f1225 when activated will perform the operation p1225. In an implementation, the control prep vehicle electrical circuitry arrangement f1225, when activated performs electronically directing control of the at least partial preparation of the one or more selected ingestible products, the at least partial preparation of the one or more selected ingestible products within the vicinity of the electronically outputting of the electronically generated one or more selection menus as within an interior of a ground vehicle (i.e. an implementation of the processor component s102 is configured to receive through the electronic communication subsystem 500 directing control to electronically control the material processing subsystem 700 for at least partial preparation of the one or more selected ingestible products within the interior of the ground vehicle wherein the digestible product preparation system 10 is located that communicates with for instance the visual display component s304 to electronically output the electronically generated one or more selection menus also within the ground vehicle, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an interior of a ground vehicle is carried out by electronically directing control of the at least partial preparation of the one or more selected ingestible products, the at least partial preparation of the one or more selected ingestible products within the vicinity of the electronically outputting of the electronically generated one or more selection menus as within an interior of a ground vehicle (i.e. an implementation of the processor component s102 is configured to receive through the electronic communication subsystem 500 directing control to electronically control the material processing subsystem 700 for at least partial preparation of the one or more selected ingestible products within the interior of the ground vehicle wherein the digestible product preparation system 10 is located that communicates with for instance the visual display component s304 to electronically output the electronically generated one or more selection menus also within the ground vehicle, etc.)

In one or more implementations, operation p12 includes an operation p1226 for electronically directing control of the at least partial preparation of the one or more selected ingestible products, the at least partial preparation of the one or more selected ingestible products within the vicinity of the electronically outputting of the electronically generated one or more selection menus as within a multi-state territory. An exemplary version of a non-transitory signal bearing medium of information storage subsystem s200 is depicted as bearing one or more control prep territory instructions j1226 that when executed will direct performance of the operation p1226. In an implementation, the one or more control prep territory instructions j1226 when executed direct electronically directing control of the at least partial preparation of the one or more selected ingestible products, the at least partial preparation of the one or more selected ingestible products within the vicinity of the electronically outputting of the electronically generated one or more selection menus as within a multi-state territory (i.e. an implementation of the processor component s102 is configured to receive through the electronic communication subsystem 500 directing control to electronically control the material processing subsystem 700 for at least partial preparation of the one or more selected ingestible products within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). Furthermore, the control prep territory electrical circuitry arrangement f1226 when activated will perform the operation p1226. In an implementation, the control prep territory electrical circuitry arrangement f1226, when activated performs electronically directing control of the at least partial preparation of the one or more selected ingestible products, the at least partial preparation of the one or more selected ingestible products within the vicinity of the electronically outputting of the electronically generated one or more selection menus as within a multi-state territory (i.e. an implementation of the processor component s102 is configured to receive through the electronic communication subsystem 500 directing control to electronically control the material processing subsystem 700 for at least partial preparation of the one or more selected ingestible products within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within a multi-state territory is carried out by electronically directing control of the at least partial preparation of the one or more selected ingestible products, the at least partial preparation of the one or more selected ingestible products within the vicinity of the electronically outputting of the electronically generated one or more selection menus as within a multi-state territory (i.e. an implementation of the processor component s102 is configured to receive through the electronic communication subsystem 500 directing control to electronically control the material processing subsystem 700 for at least partial preparation of the one or more selected ingestible products within the interior of the multi-state territory of Colorado, Wyoming, Montana, Utah, New Mexico, and Texas wherein the digestible product preparation system 10 is located that communicates with for instance the visual display component s304 to electronically output the electronically generated one or more selection menus also within the multi-state territory of Colorado, Wyoming, Montana, Utah, New Mexico, and Texas, etc.).

In one or more implementations, operation p12 includes an operation p1227 for electronically directing control of the at least partial preparation of the one or more selected ingestible products, the at least partial preparation of the one or more selected ingestible products within the vicinity of the electronically outputting of the electronically generated one or more selection menus as within an international region. An exemplary version of a non-transitory signal bearing medium of information storage subsystem s200 is depicted as bearing one or more control prep region instructions j1227 that when executed will direct performance of the operation p1227. In an implementation, the one or more control prep region instructions j1227 when executed direct electronically directing control of the at least partial preparation of the one or more selected ingestible products, the at least partial preparation of the one or more selected ingestible products within the vicinity of the electronically outputting of the electronically generated one or more selection menus as within an international region (i.e. an implementation of the processor component s102 is configured to receive through the electronic communication subsystem 500 directing control to electronically control the material processing subsystem 700 for at least partial preparation of the one or more selected ingestible products within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.). Furthermore, the control prep region electrical circuitry arrangement f1227 when activated will perform the operation p1227. In an implementation, the control prep region electrical circuitry arrangement f1227, when activated performs electronically directing control of the at least partial preparation of the one or more selected ingestible products, the at least partial preparation of the one or more selected ingestible products within the vicinity of the electronically outputting of the electronically generated one or more selection menus as within an international region (i.e. an implementation of the processor component s102 is configured to receive through the electronic communication subsystem 500 directing control to electronically control the material processing subsystem 700 for at least partial preparation of the one or more selected ingestible products within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.). In an implementation, the electronically directing control of the at least partial preparation of the one or more selected ingestible products, the at least partial preparation of the one or more selected ingestible products within the vicinity of the electronically outputting of the electronically generated one or more selection menus as within an international region is carried out by electronically directing control of the at least partial preparation of the one or more selected ingestible products, the at least partial preparation of the one or more selected ingestible products within the vicinity of the electronically outputting of the electronically generated one or more selection menus as within an international region (i.e. an implementation of the processor component s102 is configured to receive through the electronic communication subsystem 500 directing control to electronically control the material processing subsystem 700 for at least partial preparation of the one or more selected ingestible products within the international region of England, Germany, France, Brazil, Russia, India, China, and the United States wherein the digestible product preparation system 10 is located that communicates with for instance the visual display component s304 to electronically output the electronically generated one or more selection menus also within the international region of England, Germany, France, Brazil, Russia, India, China, and the United States, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture (limited to patentable subject matter under 35 USC 101). Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware_in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure (limited to patentable subject matter under 35 USC 101). In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (limited to patentable subject matter under 35 U.S.C. 101) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
   inputter electronic machine circuitry configured for involvement with inputting user identifying data;
   presenter electronic machine circuitry configured for involvement with presenting food selection options to the user based at least in part on the user identifying data;
   selector electronic machine circuitry configured for involvement with receiving user food selection of the presented food selection options;
   retriever electronic machine circuitry configured for involvement with retrieving food consumption history data of the user; and
   food printer electronic machine circuitry configured for involvement with printing food of the user food selection with one or more ingredient levels based at least in part on the food consumption history of the user and based at least in part on one or more goals of the user.

2. The system of claim 1, wherein the food printer electronic machine circuitry configured for involvement with printing food of the user food selection with one or more ingredient levels based at least in part on the food consumption history of the user and based at least in part on one or more goals of the user further comprises:
   retriever electronic machine circuitry configured for involvement with electronically retrieving the one or more goals of the user from one or more electronic databases.

3. The system of claim 2, wherein the retriever electronic machine circuitry configured for involvement with electronically retrieving the one or more goals of the user from one or more electronic databases comprises:
   the retriever electronic machine circuitry configured for involvement with electronically retrieving the one or more goals as one or more user health goals.

4. The system of claim 2, wherein the food printer electronic machine circuitry configured for involvement with printing food of the user food selection with one or more ingredient levels based at least in part on the food consumption history of the user and based at least in part on one or more goals of the user comprises:
   the retriever electronic machine circuitry configured for involvement with electronically retrieving the one or more goals including condiment use goals.

5. The system of claim 2, wherein the retriever electronic machine circuitry configured for involvement with electronically retrieving the one or more goals of the user from one or more electronic databases comprises:
   the retriever electronic machine circuitry configured for involvement with electronically retrieving the one or more goals including condiment use goals.

6. The system of claim 1, wherein the food printer electronic machine circuitry configured for involvement with printing food of the user food selection with one or more ingredient levels based at least in part on the food consumption history of the user and based at least in part on one or more goals of the user further comprising:
   feedback electronic machine circuitry configured for involvement with modification of the one or more goals based upon electronic reception of feedback information regarding food consumption.

7. The system of claim 6, wherein the feedback electronic machine circuitry configured for involvement with modification of the one or more goals based upon electronic reception of feedback information regarding food consumption comprises:
   post-consumption electronic machine circuitry configured for involvement with electronic reception of feedback information from electronic analysis of post-consumption activity of the user.

8. The system of claim 1, wherein the food printer electronic machine circuitry configured for involvement with printing food of the user food selection with one or more ingredient levels based at least in part on the food consumption history of the user and based at least in part on one or more goals of the user comprises:
   the food printer electronic machine circuitry configured for involvement with printing food based on a goal of increasing a nutrient level intake by the user over a series of instances of food printing.

9. The system of claim 8, wherein the food printer electronic machine circuitry configured for involvement with printing food based on a goal of increasing a nutrient level intake by the user over a series of instances of food printing comprises:
   capsaicin electronic machine circuitry configured for involvement with printing food based on a goal of increasing capsaicin intake of a user over a series of instances of food printing.

10. The system of claim 1, wherein the food printer electronic machine circuitry configured for involvement with printing food of the user food selection with one or more ingredient levels based at least in part on the food consumption history of the user and based at least in part on one or more goals of the user further comprising:
    the food printer electronic machine circuitry configured for involvement with printing food based on a goal of reducing ingredient concentration of the food of the user food selection over a series of instances of food printing.

11. The system of claim 10, wherein the food printer electronic machine circuitry configured for involvement with printing food based on a goal of reducing ingredient concentration of the food of the user food selection over a series of instances of food printing comprises:
   salt reduction electronic machine circuitry configured for involvement with printing the food of the user food selection with a reduction of salt concentration over a series of instances of food printing.

12. The system of claim 1, wherein the food printer electronic machine circuitry configured for involvement with printing food of the user food selection with one or more ingredient levels based at least in part on the food consumption history of the user and based at least in part on one or more goals of the user comprises:
   disease treatment electronic machine circuitry configured for involvement with printing food for treatment of a disease of the user.

13. The system of claim 1, wherein the retriever electronic machine circuitry configured for involvement with retrieving food consumption history data of the user comprises:
   nutrient consumption history electronic machine circuitry configured for involvement with retrieving food consumption history data of the user regarding presence of a particular nutrient in food being consumed.

14. The system of claim 1, wherein the retriever electronic machine circuitry configured for involvement with retrieving food consumption history data of the user comprises:
   toxin consumption history electronic machine circuitry configured for involvement with retrieving food consumption history data of the user regarding presence of a particular toxin in food being consumed.

15. The system of claim 1, wherein the food printer electronic machine circuitry configured for involvement with printing food of the user food selection with one or more ingredient levels based at least in part on the food consumption history of the user and based at least in part on one or more goals of the user comprises:
   smoothie electronic machine circuitry configured for involvement with printing food as a smoothie.

16. The system of claim 1, wherein the inputter electronic machine circuitry configured for involvement with inputting user identifying data comprises:
   smart-card electronic machine circuitry configured for involvement with inputting user identifying data via smart-card.

17. The system of claim 1, wherein the inputter electronic machine circuitry configured for involvement with inputting user identifying data comprises:
   smart-card electronic machine circuitry configured for involvement with inputting user identifying data via container memory circuitry.

18. The system of claim 1, wherein the inputter electronic machine circuitry configured for involvement with inputting user identifying data comprises:
   cell phone electronic machine circuitry configured for involvement with inputting user identifying data via electronic cell phone swipe.

19. The system of claim 1, wherein the retriever electronic machine circuitry configured for involvement with retrieving food consumption history data of the user comprises:
   period electronic machine circuitry configured for involvement with retrieving food consumption history regarding a span of one or more days.

20. The system of claim 1, wherein the food printer electronic machine circuitry configured for involvement with printing food of the user food selection with one or more ingredient levels based at least in part on the food consumption history of the user and based at least in part on one or more goals of the user comprises:
   deposition treatment electronic machine circuitry configured for involvement with printing food by deposition of food materials.

21. A system comprising:
   a first circuitry arrangement operable for:
      electronically receiving direction for storing of first preparation information into preparation history information storage,
      wherein the first preparation information is associated with at least one first preparation of at least one first ingestible product by automated preparation equipment,
      wherein the at least one first ingestible product includes at least one first substance having a first, a second, and a third portion, and
      electronically receiving direction for storing of first cleaning information, if existent, into cleaning history information storage,
      wherein the first cleaning information is associated with at least one first automated cleaning operation, if existent,
      wherein the at least one first automated cleaning operation is subsequent to the at least one first preparation,
      wherein the at least one first automated cleaning operation, if existent, uses at least one automated device to remove the second portion of the at least one first substance from at least a portion of the automated preparation equipment; and
   a second electrical circuitry arrangement operable for:
      electronically receiving direction for at least one second automated cleaning operation of the at least one automated device to remove the third portion of the at least one first substance from at least a portion of the preparation equipment prior to at least one second preparation of at least one second ingestible product,
      wherein the at least one second preparation is electronically initiated via electronically receiving first input associated with a particular individual living being, and
      wherein the electronically receiving direction for at least one second automated cleaning operation of the at least one automated device is electronically initiated based at least in part upon status associated with information stored in the preparation history information storage, associated with information stored in the cleaning history information storage, and associated with the electronically received first input associated with the particular individual living being.

22. The system of claim 21, wherein the first electrical circuitry arrangement comprises:
   a store memory card electrical circuitry arrangement operable for electronically receiving direction to store the first preparation information into one or more electronic memory cards.

23. The system of claim 21, wherein the first electrical circuitry arrangement comprises:
   a store electrical circuitry arrangement operable for electronically receiving direction to store preparation information into the preparation history information storage associated with a preparation by the automated preparation equipment of an ingestible product prior to the at least one first preparation.

24. The system of claim 21, wherein the first electrical circuitry arrangement comprises:
an equipment cooling electrical circuitry arrangement operable for electronically receiving direction to store the first preparation information involving one or more cooling components.

25. The system of claim 21, wherein the first electrical circuitry arrangement comprises:
an equipment microwave electrical circuitry arrangement operable for electronically receiving direction to store the first preparation information involving one or more microwave components.

26. The system of claim 21, wherein the first electrical circuitry arrangement comprises:
an equipment LED electrical circuitry arrangement operable for electronically receiving direction to store the first preparation information involving one or more light emitting diode (LED) components.

27. The system of claim 21, wherein the first electrical circuitry arrangement comprises:
an equipment blending electrical circuitry arrangement operable for electronically receiving direction to store the first preparation information involving one or more blending components.

28. The system of claim 21, wherein the first electrical circuitry arrangement comprises:
an equipment acoustic electrical circuitry arrangement operable for electronically receiving direction to store the first preparation information involving one or more acoustic energy components.

29. The system of claim 21, wherein the first electrical circuitry arrangement comprises:
an equipment stirring electrical circuitry arrangement operable for electronically receiving direction to store the first preparation information involving one or more stirring components.

30. The system of claim 21, wherein the first electrical circuitry arrangement comprises:
an equipment shaker electrical circuitry arrangement operable for electronically receiving direction to store the first preparation information involving one or more shaker components.

31. The system of claim 21, wherein the first electrical circuitry arrangement comprises:
an equipment energy electrical circuitry arrangement operable for electronically receiving direction to store the first preparation information involving one or more energy emitting components.

32. The system of claim 21, wherein the first electrical circuitry arrangement comprises:
an equipment sorting electrical circuitry arrangement operable for electronically receiving direction to store the first preparation information involving one or more sorting components.

33. The system of claim 21, wherein the first electrical circuitry arrangement comprises:
an equipment cutting electrical circuitry arrangement operable for electronically receiving direction to store the first preparation information involving one or more cutting components.

34. The system of claim 21, wherein the first electrical circuitry arrangement comprises:
an equipment receiving electrical circuitry arrangement operable for electronically receiving direction to store the first preparation information involving one or more controlled substance receiving components.

35. The system of claim 21, wherein the first electrical circuitry arrangement comprises:
an equipment containing electrical circuitry arrangement operable for electronically receiving direction to store the first preparation information involving one or more controlled substance containing components.

36. The system of claim 21, wherein the first electrical circuitry arrangement comprises:
a composition fluids electrical circuitry arrangement operable for electronically receiving direction to store the first preparation information involving one or more fluids.

37. The system of claim 21, wherein the first electrical circuitry arrangement comprises:
a combination powders electrical circuitry arrangement operable for electronically receiving direction to store the first preparation information involving at least one combination of one or more powders.

38. The system of claim 21, wherein the first electrical circuitry arrangement comprises:
an excluding allergens electrical circuitry arrangement operable for electronically receiving direction to store the first preparation information to exclude one or more allergens.

39. The system of claim 21, wherein the first electrical circuitry arrangement comprises:
a geographic regions electrical circuitry arrangement operable for electronically receiving direction to store the first preparation information involving the at least one first ingestible product as originating from one or more geographic regions.

40. The system of claim 21, wherein the first electrical circuitry arrangement comprises:
a designated users electrical circuitry arrangement operable for electronically receiving direction to store the first preparation information to prepare the at least one first ingestible product as being endorsed by one or more designated users.

41. The system of claim 21, wherein the first electrical circuitry arrangement comprises:
a substance liquids electrical circuitry arrangement operable for electronically receiving direction to store the first preparation information involving one or more liquids.

42. The system of claim 21, wherein the first electrical circuitry arrangement comprises:
a cleaning network electrical circuitry arrangement operable for electronically receiving direction to store the first cleaning information via one or more computer networks.

43. The system of claim 21, wherein the first electrical circuitry arrangement comprises:
a cleaning microprocessor electrical circuitry arrangement operable for electronically receiving direction to store the first cleaning information via one or more microprocessors.

44. The system of claim 21, wherein the first electrical circuitry arrangement comprises:
a cleaning memory electrical circuitry arrangement operable for electronically receiving direction to store the first cleaning information in one or more memory circuits of the automated preparation equipment.

45. The system of claim 21, wherein the first electrical circuitry arrangement comprises:

a cleaning card electrical circuitry arrangement operable for electronically receiving direction to store the first cleaning information in one or more electronic memory cards.

46. The system of claim 21, wherein the first electrical circuitry arrangement comprises:
a cleaning blowing electrical circuitry arrangement operable for electronically receiving direction to store the first cleaning information using the at least one automated device to remove the second portion of the at least one first substance via blowing air.

47. The system of claim 21, wherein the first electrical circuitry arrangement comprises:
a cleaning ultrasonic electrical circuitry arrangement operable for electronically receiving direction to store the first cleaning information to remove the second portion of the at least one first substance via emitting ultrasonic waves.

48. The system of claim 21, wherein the first electrical circuitry arrangement comprises:
a cleaning electromagnetic electrical circuitry arrangement operable for electronically receiving direction to store the first cleaning information to remove the second portion of the at least one first substance via emitting electromagnetic energy.

49. The system of claim 21, wherein the first electrical circuitry arrangement comprises:
a cleaning brush electrical circuitry arrangement operable for electronically receiving direction to store the first cleaning information to remove the second portion of the at least one first substance via brush contact.

50. The system of claim 21, wherein the first electrical circuitry arrangement comprises:
a cleaning tubes electrical circuitry arrangement operable for electronically receiving direction to store the first cleaning information to remove the second portion of the at least one first substance from at least a portion of one or more manifolds of tubes.

51. The system of claim 21, wherein the first electrical circuitry arrangement comprises:
a cleaning blender electrical circuitry arrangement operable for electronically receiving direction to store the first cleaning information to remove the second portion of the at least one first substance from at least a portion of one or more blender compartments.

52. The system of claim 21, wherein the first electrical circuitry arrangement comprises:
a cleaning syringe electrical circuitry arrangement operable for electronically receiving direction to store the first cleaning information to remove the second portion of the at least one first substance from at least a portion of one or more syringes.

53. The system of claim 21, wherein the first electrical circuitry arrangement comprises:
a cleaning replacement electrical circuitry arrangement operable for electronically receiving direction to store the first cleaning information to remove the second portion of the at least one first substance via replacement of one or more portions of the automated preparation equipment.

54. The system of claim 21, wherein the second electrical circuitry arrangement comprises:
a cleaning network electrical circuitry arrangement operable for electronically receiving direction to control at least one second automated cleaning operation via one or more computer networks.

55. The system of claim 21, wherein the second electrical circuitry arrangement comprises:
a cleaning cellular electrical circuitry arrangement operable for electronically receiving direction to control at least one second automated cleaning operation via one or more cellular networks.

56. The system of claim 21, wherein the second electrical circuitry arrangement comprises:
a cleaning microprocessors electrical circuitry arrangement operable for electronically receiving direction to control at least one second automated cleaning operation via one or more microprocessors.

57. The system of claim 21, wherein the second electrical circuitry arrangement comprises:
a cleaning server electrical circuitry arrangement operable for electronically receiving direction to control at least one second automated cleaning operation via one or more networked servers.

58. The system of claim 21, wherein the second electrical circuitry arrangement comprises:
a cleaning compressed electrical circuitry arrangement operable for electronically receiving direction to control the at least one second automated cleaning operation to remove the third portion of the at least one first substance via injecting compressed fluid.

59. The system of claim 21, wherein the second electrical circuitry arrangement comprises:
a cleaning vacuum electrical circuitry arrangement operable for electronically receiving direction to control the at least one second automated cleaning operation to remove the third portion of the at least one first substance via a vacuum.

60. The system of claim 21, wherein the second electrical circuitry arrangement comprises:
a cleaning ultrasonic electrical circuitry arrangement operable for electronically receiving direction to control the at least one second automated cleaning operation to remove the third portion of the at least one first substance via emitting ultrasonic waves.

61. The system of claim 21, wherein the second electrical circuitry arrangement comprises:
a cleaning abrasives electrical circuitry arrangement operable for electronically receiving direction to control the at least one second automated cleaning operation to remove the third portion of the at least one first substance via fluid flow of one or more abrasives.

62. The system of claim 21, wherein the second electrical circuitry arrangement comprises:
a cleaning tubes electrical circuitry arrangement operable for electronically receiving direction to control the at least one second automated cleaning operation to remove the third portion of the at least one first substance from at least a portion of the preparation equipment having one or more manifolds of tubes.

63. The system of claim 21, wherein the second electrical circuitry arrangement comprises:
a cleaning blender electrical circuitry arrangement operable for electronically receiving direction to control the at least one second automated cleaning operation to remove the third portion of the at least one first substance from at least a portion of the preparation equipment having one or more blender compartments.

64. The system of claim 21, wherein the second electrical circuitry arrangement comprises:
a cleaning cooling electrical circuitry arrangement operable for electronically receiving direction to control the at least one second automated cleaning operation to remove the third portion of the at least one first substance from at least a portion of the preparation equipment having one or more cooling chambers.

65. The system of claim 21, wherein the second electrical circuitry arrangement comprises:
a cleaning exchange electrical circuitry arrangement operable for electronically receiving direction to control the at least one second automated cleaning operation to remove the third portion of the at least one first substance via exchange of one or more portions of the automated preparation equipment with one or more other portions of the automated preparation equipment.

66. The system of claim 21, wherein the second electrical circuitry arrangement comprises:
a cleaning other electrical circuitry arrangement operable for electronically receiving direction to control the at least one second automated cleaning operation to remove the third portion of the at least one first substance from at least a portion of the preparation equipment prior to the at least one second preparation of the least one second ingestible product.

67. The system of claim 21, wherein the second electrical circuitry arrangement comprises:
a cleaning fluids electrical circuitry arrangement operable for electronically receiving direction to control the at least one second automated cleaning operation to remove the third portion of the at least one first substance from at least a portion of the preparation equipment prior to the at least one second preparation of the at least one second ingestible product including one or more fluids.

68. The system of claim 21, wherein the second electrical circuitry arrangement comprises:
a cleaning allergens electrical circuitry arrangement operable for electronically receiving direction to control the at least one second automated cleaning operation to remove the third portion of the at least one first substance to exclude one or more allergens found in the at least one first ingestible product from the at least one second preparation.

69. The system of claim 21, wherein the second electrical circuitry arrangement comprises:
a cleaning regions electrical circuitry arrangement operable for electronically receiving direction to control the at least one second automated cleaning operation to remove the third portion of the at least one first substance from at least a portion of the preparation equipment prior to the at least one second preparation occurrence of the at least one second ingestible product as originating from one or more geographic regions.

70. The system of claim 21, wherein the second electrical circuitry arrangement comprises:
a cleaning designated electrical circuitry arrangement operable for electronically receiving direction to control the at least one second automated cleaning operation to remove the third portion of the at least one first substance from at least a portion of the preparation equipment prior to the at least one second preparation occurrence of the at least one second ingestible product as being endorsed by one or more designated users.

71. The system of claim 21, wherein the second electrical circuitry arrangement comprises:
a cleaning reactive electrical circuitry arrangement operable for electronically receiving direction to remove the third portion of the at least one first substance from at least a portion of the preparation equipment prior to the at least one second preparation of the at least one second ingestible product, wherein the second ingestible product is-chemically reactive with the at least one first substance of the at least one first ingestible product.

72. The system of claim 21, wherein the second electrical circuitry arrangement comprises:
a cleaning keyboard electrical circuitry arrangement operable for electronically receiving direction to control the at least one second preparation electronically initiated via electronically receiving first input via one or more keyboard components.

73. The system of claim 21, wherein the second electrical circuitry arrangement comprises:
a cleaning screen electrical circuitry arrangement operable for electronically receiving direction to control the at least one second preparation electronically initiated via electronically receiving first input via one or more touch screen components.

74. The system of claim 21, wherein the second electrical circuitry arrangement comprises:
a cleaning cellular electrical circuitry arrangement operable for electronically receiving direction to control the at least one second preparation electronically initiated via electronically receiving first input via one or more cellular networks.

75. The system of claim 21, wherein the second electrical circuitry arrangement comprises:
a cleaning menu electrical circuitry arrangement operable for electronically receiving direction to control the at least one second preparation occurrence electronically initiated via electronically receiving first input associated with a particular individual living being including menu selections by the particular individual living being regarding the at least one second ingestible product to be consumed by the particular individual living being.

76. The system of claim 21, wherein the second electrical circuitry arrangement comprises:
a cleaning preferences electrical circuitry arrangement operable for electronically receiving direction to electronically initiate the at least one second preparation via electronically receiving first input associated with a particular individual living being including cleaning preferences of the particular individual living being.

* * * * *